US008592194B2

(12) United States Patent
Aehle et al.

(10) Patent No.: US 8,592,194 B2
(45) Date of Patent: Nov. 26, 2013

(54) GLUCOAMYLASE VARIANTS WITH ALTERED PROPERTIES

(75) Inventors: Wolfgang Aehle, Zwingenberg (NL);
Richard R. Bott, Burlingame, CA (US);
Igor Nikolaev, Noordwijk (NL);
Martijn Scheffers, Leiden (NL); Piet Van Solingen, Naaldwijk (NL); Casper Vroemen, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 236 days.

(21) Appl. No.: 12/681,612

(22) PCT Filed: Apr. 8, 2008

(86) PCT No.: PCT/US2008/004574
§ 371 (c)(1),
(2), (4) Date: Oct. 1, 2010

(87) PCT Pub. No.: WO2009/048488
PCT Pub. Date: Apr. 16, 2009

(65) Prior Publication Data
US 2011/0020899 A1    Jan. 27, 2011

(30) Foreign Application Priority Data
Oct. 9, 2007  (WO) ................ PCT/US2007/021683

(51) Int. Cl.
C12N 9/00      (2006.01)
C12N 9/34      (2006.01)
C12N 1/20      (2006.01)
C12N 15/00     (2006.01)
C07H 21/04     (2006.01)

(52) U.S. Cl.
USPC ..... 435/205; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 4,247,637 A | 1/1981 | Tamura et al. |
| 4,514,496 A | 4/1985 | Yoshizumi |
| 4,618,579 A | 10/1986 | Dwiggins |
| 4,794,175 A | 12/1988 | Nunberg |
| 4,863,864 A | 9/1989 | Ashikari |
| 5,024,941 A | 6/1991 | Maine |
| 5,246,853 A | 9/1993 | Clarkson |
| 5,475,101 A | 12/1995 | Ward |
| 5,874,276 A | 2/1999 | Fowler et al. |
| 6,022,725 A | 2/2000 | Fowler |
| 6,254,914 B1 | 7/2001 | Singh |
| 6,255,084 B1 | 7/2001 | Nielsen |
| 6,268,328 B1 | 7/2001 | Mitchinson |
| 6,352,851 B1 | 3/2002 | Nielsen |
| 6,537,792 B1 | 3/2003 | Allen |
| 6,582,914 B1 | 6/2003 | Caldwell |
| 6,620,924 B2 | 9/2003 | Nielsen |
| 6,777,589 B1 | 8/2004 | Lundquist |
| 6,803,499 B1 | 10/2004 | Anderson |
| 6,899,910 B2 | 5/2005 | Johnston |
| 7,037,704 B2 | 5/2006 | Dunn-Coleman |
| 7,354,753 B2 | 4/2008 | Nielsen et al. |
| 7,494,685 B2 | 2/2009 | Dunn-Coleman et al. |
| 8,058,033 B2 | 11/2011 | Aehle et al. |
| 2006/0094080 A1 | 5/2006 | Dunn-Coleman et al. |

FOREIGN PATENT DOCUMENTS

| | | |
|---|---|---|
| EP | 0215594 | 3/1987 |
| EP | 0238023 | 9/1987 |
| EP | 0244234 | 11/1987 |
| WO | WO 88/09795 | 12/1988 |
| WO | WO 92/06184 | 4/1992 |
| WO | WO 92/06209 | 4/1992 |
| WO | WO 96/00787 | 1/1996 |
| WO | WO 00/04136 | 1/2000 |
| WO | WO 02/14490 | 2/2002 |
| WO | WO 02/46429 | 6/2002 |
| WO | WO 03/029449 | 4/2003 |
| WO | WO03029449 * | 4/2003 |
| WO | WO 03/049550 | 6/2003 |
| WO | WO 2004/080923 | 9/2004 |
| WO | WO 2004/081193 | 9/2004 |
| WO | WO 2005/001036 | 1/2005 |
| WO | WO 2005/052148 | 6/2005 |
| WO | WO 2005/117756 A2 | 12/2005 |
| WO | WO 2006/043178 | 4/2006 |
| WO | WO 2006/060062 | 6/2006 |
| WO | WO2006060062 * | 6/2006 |

OTHER PUBLICATIONS

Accession Q599K8, Apr. 26, 2005.*
Chica et al. Curr Opin Biotechnol. Aug. 2005;16(4):378-84.*
Sen et al. Appl Biochem Biotechnol. Dec. 2007;143(3):212-23.*
Accession Q12623, Berka, et al., "Glucoamylase", (2006) http://www.ncbi.nlm.nih.gov/protein/Q12623.
Aleshin, et al., "Refined crystal structures of glucoamylase from Aspergi I I us awamori var. XIOO", J Mol Biol, (1994), 238:575-91.
Aleshin, et al., "Crystal Structure of Glucoamylase from *Aspergillus awamori* var. X100 to 2.2-A Resolution", J Biol Chem, (1992), 267:19291-8.
Altschul et al., "Local Alignment Statistics", Methods Enzymol, (1996), 266:460-80.
Altschul, et al., "Basic local alignment search tool", J. Mol. Biol., (1990), 215:403-10.
Anagnostopoulos, et al., "Requirements for Transformation in *Bacillus subtilis*", J Bacteriol, (1961), 81:741-6.
Ashikari et al., "Direct fermentation of raw corn to ethanol by yeast transformants containing a modified *Rhizopus* glucoamylase gene", App. Microbiol. and Biotech., (1989), 32:129-33.

(Continued)

Primary Examiner — Christian Fronda
(74) Attorney, Agent, or Firm — Danisco US Inc.

(57) ABSTRACT

The present invention relates to variant glucoamylases wherein the variant has altered properties (e.g., improved thermostability and/or specific activity) compared to a corresponding parent glucoamylase. The present invention also relates to enzyme compositions comprising a variant glucoamylase (e.g., starch hydrolyzing compositions); DNA constructs comprising polynucleotides encoding the variants and methods of producing the variant glucoamylases in host cells.

28 Claims, 11 Drawing Sheets

(56) References Cited

OTHER PUBLICATIONS

Ashikari et al., "*Rhizopus* raw-starch-degrading glucoamylase: its cloning and expression in yeast", Agric Biol Chem, (1986), 50:957-64.

Ausubel, et al., "Introduction of DNA into mammalian cells", Current Protocols in Molecular Biology, (1987), 2(9):9.01-9.17.3.

Bajar, et al., "Identification of a fungal cutinase promoter that is inducible by a plant signal via a phosphorylated trans-acting factor", Proc. Natl. Acad. Sci, (1991), 88:8208-12.

Bennett and Lasure, More Gene Manipulations in Fungi, Academic Press, San Diego, pp. 70-76. Timberlake, "Cloning and Analysis of Fungi Genes," Chapter 3, (1991).

Berges, "Isolation of uridine auxotrophs from *Trichoderma reesei* and efficient transformation with the cloned ura3 and ura5 genes", Curr. Genet., (1991), 19:359-65.

Berka, et al., "*Aspergillus niger* var. awamori as a Host for the Expression of Heterologous Genes", Kelly and Baldwin (eds.), Applications of Enzyme Biotechnology, (1991), 273-92.

Boel, E. et al., "Two different types of intervening sequences in the glucoamylase gene from *Aspergillus niger*", The EMBO Journal, (1984), 3:1581-5.

Boel, et al., "Glucoamylases G1 and G2 from *Aspergillus niger* are synthesized from two different but closely related mRNAs", The EMBO Journal, (1984), 3:1097-1102.

Brunger, et al., "Free R value: a novel statistical quantity for assessing the accuracy of crystal structures", Nature, (1992), 355:472-5.

Campbell, et al., "Improved transformation efficiency of *Aspergillus niger* using the homologous niaD gene for nitrate reductase", Current Genetics, (1989), 16:53-6.

Cao, et al., "Penicillopepsin-JT2, a recombinant enzyme from *Penicillium janthinellum* and the contribution of a hydrogen bond in subsite $S_3$ to $k_{cat}$", Protein Science, (2000), 9:991-1001.

Chen, et al., "Effect of replacing helical glycine residues with alanines on reversible and irreversible stability and production of *Aspergillus awamori* glucoamylase", Protein Engineering, (1996), 9:499-505.

Chen, et al., "Identification and elimination by site-directed mutagenesis of thermolabile aspartyl bonds in *Aspergillus awamori* glucoamylase", Protein Engineering, (1995), 8:575-82.

Chica, et al., "Semi-rational approaches to engineering enzyme activity: combining the benefits of directed evolution and rational design", Cum Opin. Biotechnol, (2005), 16:378-84.

Coutinho et al., "Structural similarities in glucoamylases by hydrophobic cluster analysis", Protein Eng., (1994), 7:749- 60.

Coutinho, et al., "Structure-function relationships in the catalytic and starch binding domains of glucoamylase", Protein Eng., (1994), 7:393-400.

Database EMBLl [Online] Feb. 2, 2001, "*Talaromyces emersonii* ga gene for glucoamylase, exons 1-5" XP002495030 retrieved from EBI accession No. EMBL1:AJ304803 Database accession No. AJ304803.

De Groot, et al., "*Agrobacterium tumefaciens*-mediated transformation of filamentous fungi", Nature Biotechnology, (1998), 16:839-42.

Devereux et al., "A Comprehensive set of sequence analysis programs for the VAX", Nuel. Acids Res., (1984) 12:387-95.

Elder, et al., "Glucoamylase activity in industrial enzyme preparations using colorimetric enzymatic method", Journal of AOAC International, (1995), 78:398-401.

Emsley, et al., "Coot: model-building tools for molecular graphics", Acta Crystallogr D Biol Crystallogr, (2004), 60:2126-32.

Fagerstrom, et al., "Characterization, sub site mapping and partial amino acid sequence of glucoamylase from the filamentous fungus *Trichoderma reesei*", Biotechnol Appl Biochem, (1995), 21:223-31.

Feng et al., "Progressive Sequence Alignment as a Prerequisite to Correct Phylogenetic Tress", J. Mol Evol., (1987), 25:351-60.

Fierobe, et al., "Mutational Modulation of Substrate Bond-Type Specificity and Thermostability of Glucoamylase from Aspergillus awamori by Replacement with Short Homologue Active Site Sequences and Thiol/Disulfide Engineering", Biochemistry, (1996), 35:8696-8704.

Finkelstein, et al., "Transformation", Biotechnology of Filamentous Fungi, (1992), (6):113-56.

Fromm, et al., "Inheritance and Expression of Chimeric Genes in the Progeny of Transcgenic Maize Plants", Biotechnology, (1990). 8:833-9.

Goedegebuur, et al., "Cloning and relational analysis of 15 novel fungal endoglucanases from family 12 glycosyl hydrolase", Current Genetics, (2002), 41:89-98.

Goto, et al., "The Mechanism of Binding of Glucoamylase I from *Aspergillus awamori* var. kawachi to Cyclodextrins and Raw Starch", Biosci. Biotech. Biochem., (1994), 58:49-54.

Harkki, et al., "A Novel Fungal Expression System: Secretion of Active Calf Chymosin from the Filamentous Fungus *Trichoderma Reesei*", Bio Technol, (1989), 7:596-603.

Harkki, et al., "Genetic engineering of *Trichoderma* to produce strains with novel cellulase profiles", Enzyme Microb. Technol., (1991), 13:227-33.

Hartingseldt, et al., "Development of a homologous transformation system for *Aspergillus niger* based on the pyrG gene", Mol. Gen. Genet., (1987), 206:71-5.

Hayashida, et al., "Molecular Cloning of the Glucoamylase I Gene of *Aspergillus awamori* var. kawachi for Localization of the Raw-starch-affinity Site", Agric. Biol. Chem., (1989), 53:923-9.

Higgins, et al., "Fast and sensitive multiple sequence alignments on microcomputer", CABIOS, (1989), 5:151-3.

Houghton-Larsen, et al., "Cloning and characterisation of a glucoamylase gene (G1aM) from the dimorphic zygomycete Mucor circinelloides", Appl. Microbiol. Biotechnol., (2003), 62:210-7.

Ilmen, et al., "Regulation of Cellulase Gene Expression in the Filamentous Fungus *Trichoderma reesei*", Appl Environ Microbiol, (1997), 63:1298-306.

Innis, et al., "Expression, Glycosylation, and Secretion of an *Aspergillus* Glucoamylase by *Saccharomyces cerevisiae*", Science, (1985), 228:21-6.

Jones, et al., "Improved methods for building protein models in electron density maps and the location of errors in these models", Acta Crystallogr A., (1991), 47:110-9.

Karlin, et al., "Applications and statistics for multiple high-scoring segments in molecular sequences", Proc. Natl. Acad. Sci., (1993), 90:5873-7.

Kelly, et al., "Transformation of *Aspergillus niger* by the amdS gene of *Aspergillus nidulans*", The EMBO Journal, (1985), 4:475-9.

Li, et al., "Effect of introducing proline residues on the stability of *Aspergillus awamori*", Protein Eng., (1997), 10:1199-1204.

Matthews, "Solvent Content of Protein Crystals", J Mol Biol, (1968), 33:491-7.

Minshull J. et al., "Engineered protein function by selective amino acid diversification", Methods, (2004), 32:416-27.

Murshudov, et al. "Refinement of macromolecular structures by the maximum-likelihood method", Acta Crystallogr D Biol Crystallogr., (1997), 53:240-55.

Needleman, Saul B., "A General Method Applicable to the Search for Similarities in the Amino Acid Sequence of Two Proteins," J. Mol. Biol., (1970), 48:443-53.

Nevalainen, et al., "The Molecular Biology of *Trichoderma* and its Application to the Expression of Both Homologous and Heterologous Genes", Molecular Industrial Mycology, (1992), 6:129-48.

Nielsen Bjarne, et al., "Cloning, heterologous expression, and enzymatic characterization of a thermostable glucoamylase from *Talaromyces emersonii*", Pretein Expr Purif, (2002), 26:1-8.

Nunberg, et al., "Molecular Cloning and Characterization of the Glucoamylase Gene of *Aspergillus awamori*", Molecular and Cellular Biology, pp. 2306-2315, Nov. 1984.

Pearson, et al., "Improved tools for biological sequence comparison," Proc. Natl. Acad. Sci. USA, vol. 85, pp. 2444-2448, Apr. 1988.

Pentilla et al., "A versatile transformation system for the cellulolytic filamentous fungus *Trichoderma reesei*," Gene, vol. 61, pp. 155-164, 1987.

Potrykus et al., "Molecular and general genetics of a hybrid foreign gene introduced into tobacco by direct gene transfer," Mol. Gen. Genet., V. 199 :169-177 (1985).

(56) References Cited

OTHER PUBLICATIONS

Pourquie, et al., "Scale Up of Cellulase Production and Utilization," Biochemistry and Genetics of Cellulose Degradation, Academic Press Ltd., pp. 71-86, 1988.

Punt et al., "Transformation of *Asperghillus* based on the hygromycin B resistance marker from *Escherichia coli*," Gene 56:117-124, 1987.

Ally, "Protein engineering of glucoamylase to improve industrial performance a review", STARCH/STAERKE, (1999), 51:269-74.

Saver Jorgen, et al., "Glucoamylase: Structure/function relationships, and protein engineering", Biochimica Et Biophysica Acta, vol. 1543, No. 2, Dec. 29, 2000, pp. 275-293, XP004279110 ISSN: 0006-3002 abstract p. 288, paragraph 4.6.

Sen et al., "Developments in directed evolution for improving enzyme functions", Appl. Biochem. Biotechnol. 143(3): 212-223, 2007.

Sheir-Neiss, et al., "Characterization of the secreted cellulases of *Trichoderma reesei* wild type and mutants during controlled fermentations," Appl. Microbiol. Biotechnol., vol. 20, pp. 46-53, 1984.

Smith, et al., "Comparison of Biosequences," Advances in Applied Mathematics, vol. 2, pp. 482-489, 1981.

Svensson et al., "Amino Acid Sequence Studies of a Novel Subtilisin," Carlsberg Res. Commun., 48:583-591, 1983.

Van den Hondel et al., "Heterologous Gene Expression in Filamentous Fungi," More Gene Manipulations in Fungi, Chapter 18, pp. 396-428, 1991, Academic Press, Inc.

van Hartingsveldt, et al., "Development of a homologous transformation system for *Aspergillus niger* based on the pyrG gene," Mol. Gen. Genet., 206:71-75, 1987.

Ward, et al., "Use of *Aspergillus* overproducing mutants, cured for integrated plasmid, to overproduce heterologous proteins," Appl. Microbiol. Biotechnol., vol. 39, pp. 738-743, 1993.

Yelton, et al, "Transformation of *Aspergillus nidulans* by using a trpC plasmid," Proc. Natl. Acad. Sci., vol. 81, pp. 1470-1474, 1984.

\* cited by examiner

FIG. 1A

TrGA parent protein (632 amino acids) (SEQ ID NO: 1)

```
  1 MHVLSTAVLL GSVAVQKVLG RPGSSGLSDV TKRSVDDFIS TETPIALNNL
 51 LCNVGPDGCR AFGTSAGAVI ASPSTIDPDY YYMWTRDSAL VFKNLIDRFT
101 ETYDAGLQRR IEQYITAQVT LQGLSNPSGS LADGSGLGEP KFELTLKPFT
151 GNWGRPQRDG PALRAIALIG YSKWLINNNY QSTVSNVIWP IVRNDLNYVA
201 QYWNQTGFDL WEEVNGSSFF TVANQHRALV EGATLAATLG QSGSAYSSVA
251 PQVLCFLQRF WVSSGGYVDS NINTNEGRTG KDVNSVLTSI HTFDPNLGCD
301 AGTFQPCSDK ALSNLKVVVD SFRSIYGVNK GIPAGAAVAI GRYAEDVYYN
351 GNPWYLATFA AAEQLYDAIY VWKKTGSITV TATSLAFFQE LVPGVTAGTY
401 SSSSSTFTNI INAVSTYADG FLSEAAKYVP ADGSLAEQFD RNSGTPLSAL
451 HLTWSYASFL TATARRAGIV PPSWANSSAS TIPSTCSGAS VVGSYSRPTA
501 TSFPPSQTPK PGVPSGTPYT PLPCATPTSV AVTFHELVST QFGQTVKVAG
551 NAAALGNWST SAAVALDAVN YADNHPLWIG TVNLEAGDVV EYKYINVGQD
601 GSVTWESDPN HTYTVPAVAC VTQVVKEDTW QS
```

FIG. 1B

DNA coding sequence of TrGA (1899 bp) (SEQ ID NO: 4)

```
   1 ATGCACGTCC TGTCGACTGC GGTGCTGCTC GGCTCCGTTG CCGTTCAAAA
  51 GGTCCTGGGA AGACCAGGAT CAAGCGGTCT GTCCGACGTC ACCAAGAGGT
 101 CTGTTGACGA CTTCATCAGC ACCGAGACGC CTATTGCACT GAACAATCTT
 151 CTTTGCAATG TTGGTCCTGA TGGATGCCGT GCATTCGGCA CATCAGCTGG
 201 TGCGGTGATT GCATCTCCCA GCACAATTGA CCCGGACTAC TATTACATGT
 251 GGACGCGAGA TAGCGCTCTT GTCTTCAAGA ACCTCATCGA CCGCTTCACC
 301 GAAACGTACG ATGCGGGCCT GCAGCGCCGC ATCGAGCAGT ACATTACTGC
 351 CCAGGTCACT CTCCAGGGCC TCTCTAACCC CTCGGGCTCC CTCGCGGACG
 401 GCTCTGGTCT CGGCGAGCCC AAGTTTGAGT TGACCCTGAA GCCTTTCACC
 451 GGCAACTGGG GTCGACCGCA GCGGGATGGC CCAGCTCTGC GAGCCATTGC
 501 CTTGATTGGA TACTCAAAGT GGCTCATCAA CAACAACTAT CAGTCGACTG
 551 TGTCCAACGT CATCTGGCCT ATTGTGCGCA ACGACCTCAA CTATGTTGCC
 601 CAGTACTGGA ACCAAACCGG CTTTGACCTC TGGGAAGAAG TCAATGGGAG
 651 CTCATTCTTT ACTGTTGCCA ACCAGCACCG AGCACTTGTC GAGGGCGCCA
 701 CTCTTGCTGC CACTCTTGGC CAGTCGGGAA GCGCTTATTC ATCTGTTGCT
 751 CCCCAGGTTT TGTGCTTTCT CCAACGATTC TGGGTGTCGT CTGGTGGATA
 801 CGTCGACTCC AACATCAACA CCAACGAGGG CAGGACTGGC AAGGATGTCA
 851 ACTCCGTCCT GACTTCCATC CACACCTTCG ATCCCAACCT TGGCTGTGAC
 901 GCAGGCACCT TCCAGCCATG CAGTGACAAA GCGCTCTCCA ACCTCAAGGT
 951 TGTTGTCGAC TCCTTCCGCT CCATCTACGG CGTGAACAAG GGCATTCCTG
1001 CCGGTGCTGC CGTCGCCATT GGCCGGTATG CAGAGGATGT GTACTACAAC
1051 GGCAACCCTT GGTATCTTGC TACATTTGCT GCTGCCGAGC AGCTGTACGA
1101 TGCCATCTAC GTCTGGAAGA AGACGGGCTC CATCACGGTG ACCGCCACCT
1151 CCCTGGCCTT CTTCCAGGAG CTTGTTCCTG GCGTGACGGC CGGGACCTAC
1201 TCCAGCAGCT CTTCGACCTT TACCAACATC ATCAACGCCG TCTCGACATA
1251 CGCCGATGGC TTCCTCAGCG AGGCTGCCAA GTACGTCCCC GCCGACGGTT
1301 CGCTGGCCGA GCAGTTTGAC CGCAACAGCG GCACTCCGCT GTCTGCGCTT
1351 CACCTGACGT GGTCGTACGC CTCGTTCTTG ACAGCCACGG CCCGTCGGGC
1401 TGGCATCGTG CCCCCCTCGT GGGCCAACAG CAGCGCTAGC ACGATCCCCT
1451 CGACGTGCTC CGGCGCGTCC GTGGTCGGAT CCTACTCGCG TCCCACCGCC
1501 ACGTCATTCC CTCCGTCGCA GACGCCCAAG CCTGGCGTGC CTTCCGGTAC
1551 TCCCTACACG CCCCTGCCCT GCGCGACCCC AACCTCCGTG GCCGTCACCT
1601 TCCACGAGCT CGTGTCGACA CAGTTTGGCC AGACGGTCAA GGTGGCGGGC
1651 AACGCCGCGG CCCTGGGCAA CTGGAGCACG AGCGCCGCCG TGGCTCTGGA
1701 CGCCGTCAAC TATGCCGATA ACCACCCCCT GTGGATTGGG ACGGTCAACC
1751 TCGAGGCTGG AGACGTCGTG GAGTACAAGT ACATCAATGT GGGCCAAGAT
1801 GGCTCCGTGA CCTGGGAGAG TGATCCCAAC CACACTTACA CGGTTCCTGC
1851 GGTGGCTTGT GTGACGCAGG TTGTCAAGGA GGACACCTGG CAGTCGTAA
```

FIG. 5A

```
AaGA    (1)   -ATLDSWLSNEATVARTAILNNIGADGAWVSGADSGIVVASPSTDNPDYF
AnGA    (1)   -ATLDSWLSNEATVARTAILNNIGADGAWVSGADSGIVVASPSTDNPDYF
AoGA    (1)   QSDLNAFIEAQTPIAKQGYLNNIGADGKLVEGAAAGIVYASPSKSNPDYF
HgGA    (1)   -AAVDTFINTEKPIAWNKLLANIGPNGKAAPGAAAGVVIASPSRTDPPYF
HvGA    (1)   --SVDDFINTQTPIALNNLLCNVGPDGCRAFGTSAGAVIASPSTTDPDYY
TrGA    (1)   --SVDDFISTETPIALNNLLCNVGPDGCRAFGTSAGAVIASPSTIDPDYY
                       *    *  *  *    *   *  * * ****   *  *

AaGA    (50)  YTWTRDSGLVIKTLVDLFRNGDTD-LLSTIENYISSQAIVQGISNPSGDL
AnGA    (50)  YTWTRDSGLVLKTLVDLFRNGDTS-LLSTIENYISAQAIVQGISNPSGDL
AoGA    (51)  YTWTRDAGLTMEEYIEQFIGGDAT-LESTIQNYVDSQANEQAVSNPSGGL
HgGA    (50)  FTWTPDAALVLTGIIESLGHNYNT--------------TLQQVSNPSGTF
HvGA    (49)  YMWTRDSALVFKNIVDRFTQQYDAGLQRRIEQYISAQVTLQGISNPSGSL
TrGA    (49)  YMWTRDSALVFKNLIDRFTETYDAGLQRRIEQYITAQVTLQGLSNPSGSL
               ** *  *                                *  *****

AaGA    (99)  SSGG-LGEPKFNVDETAYTGSWGRPQRDGPALRATAMIGFRQWLLDNGYT
AnGA    (99)  SSGAGLGEPKFNVDETAYTGSWGRPQRDGPALRATAMIGFGQWLLDNGYT
AoGA    (100) SDGSGLAEPKFYYNISQFTDSWGRPQRDGPALRASALIAYGNSLISSDKQ
HgGA    (86)  ADGSGLGEAKFNVDLTAFTGEWGRPQRDGPPLRAIALIQYAKWLIANGYK
HvGA    (99)  SDGSGLGEPKFELTLSQFTGNWGRPQRDGPALRAIALIGYSKWLINNNYQ
TrGA    (99)  ADGSGLGEPKFELTLKPFTGNWGRPQRDGPALRAIALIGYSKWLINNNYQ
               *   *  **      *  ********* *** *  *         *

AaGA    (148) SAATEIVWPLVRNDLSYVAQYWNQTGYDLWEEVNGSSFFTIAVQHRALVE
AnGA    (149) STATDIVWPLVRNDLSYVAQYWNQTGYDLWEEVNGSSFFTIAVQHRALVE
AoGA    (150) SVVKANIWPIYQNDLSYVGQYWNQTGFDLWEEVQGSSFFTVAVQHKALVE
HgGA    (136) STAKSVVWPVVKNDLAYTAQYWNETGFDLWEEVPGSSFFTIASSHRALTE
HvGA    (149) STVSNIIWPIVRNDLNYVAQYWNQTGFDLWEEVNGSSFFTVANQHRALVE
TrGA    (149) STVSNVIWPIVRNDLNYVAQYWNQTGFDLWEEVNGSSFFTVANQHRALVE
               *     **  *** *  ****  ** ****** ****** *   ** *

AaGA    (198) GSAFATAVGSSCSWCDSQAPQILCYLQSFWTG--EYILANFDSS--RSGK
AnGA    (199) GSAFATAVGSSCSWCDSQAPEILCYLQSFWTG--SFILANFDSS--RSGK
AoGA    (200) GDAFAKALGEECQACS-VAPQILCHLQDFWNG--SAVLSNLPTNG-RSGL
HgGA    (186) GAYLAAQLDTECPPCTTVAPQVLCFQQAFWNSKGNYVVSTSTAGEYRSGK
HvGA    (199) GATLAATLGQSGSTYSSVAPQILCFLQRFWVS-GGYIDSNINTNEGRTGK
TrGA    (199) GATLAATLGQSGSAYSSVAPQVLCFLQRFWVSSGGYVDSNINTNEGRTGK
                *     *              **  **   *  **           * *

AaGA    (244) DTNTLLGSIHTFDPEAGCDDSTFQPCSPRALANHKEVVDSFRSIYTLNDG
AnGA    (245) DANTLLGSIHTFDPEAACDDSTFQPCSPRALANHKEVVDSFRSIYTLNDG
AoGA    (246) DTNSLLGSIHTFDPAAACDDTTFQPCSSRALSNHKLVVDSFRSVYGINNG
HgGA    (236) DANSILASIHNFDPEAGCDNLTFQPCSERALANHKAYVDSFRNLYAINKG
HvGA    (248) DANSLLASIHTFDPSLGCDASTFQPCSDKALSNLKVVVDSFRSIYGVNKG
TrGA    (249) DVNSVLTSIHTFDPNLGCDAGTFQPCSDKALSNLKVVVDSFRSIYGVNKG
              *  *  *** ***   **  ******  ** *     *****   *  *

AaGA    (294) LSDSEAVAVGRYPKDSYYNGNPWFLCTLAAAEQLYDALYQWDKQGSLEIT
AnGA    (295) LSDSEAVAVGRYPEDTYYNGNPWFLCTLAAAEQLYDALYQWDKQGSLEVT
AoGA    (296) RGAGKAAAVGPYAEDTYQGGNPWYLTTLVAAELLYDALYQWDKQGQVNVT
HgGA    (286) IAQGKAVAVGRYSEDVYYNGNPWYLANFAAAEQLYDAIYVWNKQGSITVT
HvGA    (298) IPAGSAVAIGRYPEDVYFNGNPWYLATFAAAEQLYDSVYWWKKTGSITVT
TrGA    (299) IPAGAAVAIGRYAEDVYYNGNPWYLATFAAAEQLYDAIYWWKKTGSITVT
                 *  *   * *   *  ****  *  ***  ***    *    *
```

FIG. 5B

```
AaGA  (344)  DVSLDFFQALYSDAATGTYSSSSSTYSSIVDAVKTFADGFVSIVETHAAS
AnGA  (345)  DVSLDFFKALYSDAATGTYSSSSSTYSSIVDAVKTFADGFVSIVETHAAS
AoGA  (346)  ETSLPFFKDLSSNVTTGSYAKSSSAYESLTSAVKTYADGFISVVQEYTPD
HgGA  (336)  SVSLPFFRDLVSSVSTGTYSKSSSTFTNIVNAVKAYADGFIEVAAKYTPS
HvGA  (348)  STSSAFFQELVPGVAAGTYSSSQSTFTSIINAISTYADGFLSEAAKYVPA
TrGA  (349)  ATSLAFFQELVPGVTAGTYSSSSSTFTNIINAVSTYADGFLSEAAKYVPA
                *  **  *        *  *  *      *    ****

AaGA  (394)  NGSLSEQYDKSDGDELSARDLTWSYAALLTANNRRNSVMPPSWGETSAS-
AnGA  (395)  NGSMSEQYDKSDGEQLSARDLTWSYAALLTANNRRNSVVPASWGETSAS-
AoGA  (396)  GGALAEQYSRDQGTPVSASDLTWSYAAFLSAVGRRNGTVPASWGSSTAN-
HgGA  (386)  NGALAEQYDRNTGKPDSAADLTWSYSAFLSAIDRRAGLVPPSWRASVAKS
HvGA  (398)  DGSLAEQFDRNTGTPLSAVHLTWSYASFLTAAARRAGVVPPSWASSGAN-
TrGA  (399)  DGSLAEQFDRNSGTPLSALHLTWSYASFLTATARRAGIVPPSWANSSAS-
                *  **     *   **  *****  *  *  **   *  **    *

AaGA  (443)  SVPGTC
AnGA  (444)  SVPGTC
AoGA  (445)  AVPSQC
HgGA  (436)  QLPSTC
HvGA  (447)  TVPSSC
TrGA  (448)  TIPSTC
                •  *
```

FIG. 5C gsldsflatetpialqgvlnnigpngadvagasagivvaspsrsdpdyfyswtrdaaltakylvdafia
gnkdleqtiqeyisaqaqvqtisnpsgdlstgglgepkfnvnetaftgpwgrpqrdgpalrataliaya
nylidngqastadeiiwpivqndlsyvtqywnsstfdlweevegssffttavqhralvegnalatrlnh
tcpncvsqapqvlcflqsywtgsyvlanfggsgrsgkdvnsilgsihtfdpaggcddstfqpcsarala
nhkvvtdsfrsvyavnsgiaegsavavgrypedvyqggnpwylataaaaeqlydaiyqwnkigsisitd
vslaffqdiypsaavgtynsgsstfndiisavqtyadgylsiiekytpsdgslteqfsrsdgtplsasg
ltwsyaslltaaarrqsivpaswgessassvpavcsatsatgpystatntawpssgsgpstttsvpctt
ptsvavtfdeivsttygetiylagsipelgnwspssaiplradaytssnplwyvtlnlpagtsfeykff
kketdgtivweddpnrsytvpaycgqttailddswq

SEQUENCE LISTING

<160> NUMBER OF SEQ ID NOS: 308

<210> SEQ ID NO 1
<211> LENGTH: 632
<212> TYPE: PRT
<213> ORGANISM: Trichoderma reesei

<400> SEQUENCE: 1

```
Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320
```

Ser Phe Arg Ser Ile Tyr Gly Val Asn Lys Gly Ile Pro Ala Gly Ala
              325                 330                 335

Ala Val Ala Ile Gly Arg Tyr Ala Glu Asp Val Tyr Tyr Asn Gly Asn
              340                 345                 350

Pro Trp Tyr Leu Ala Thr Phe Ala Ala Glu Gln Leu Tyr Asp Ala
              355                 360                 365

Ile Tyr Val Trp Lys Lys Thr Gly Ser Ile Thr Val Thr Ala Thr Ser
370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                    405                 410                 415

Tyr Ala Asp Gly Phe Leu Ser Glu Ala Ala Lys Tyr Val Pro Ala Asp
              420                 425                 430

Gly Ser Leu Ala Glu Gln Phe Asp Arg Asn Ser Gly Thr Pro Leu Ser
              435                 440                 445

Ala Leu His Leu Thr Trp Ser Tyr Ala Ser Phe Leu Thr Ala Thr Ala
450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                    485                 490                 495

Arg Pro Thr Ala Thr Ser Phe Pro Pro Ser Gln Thr Pro Lys Pro Gly
              500                 505                 510

Val Pro Ser Gly Thr Pro Tyr Thr Pro Leu Pro Cys Ala Thr Pro Thr
              515                 520                 525

Ser Val Ala Val Thr Phe His Glu Leu Val Ser Thr Gln Phe Gly Gln
              530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                    565                 570                 575

Leu Trp Ile Gly Thr Val Asn Leu Glu Ala Gly Asp Val Val Glu Tyr
              580                 585                 590

Lys Tyr Ile Asn Val Gly Gln Asp Gly Ser Val Thr Trp Glu Ser Asp
              595                 600                 605

Pro Asn His Thr Tyr Thr Val Pro Ala Val Ala Cys Val Thr Gln Val
              610                 615                 620

Val Lys Glu Asp Thr Trp Gln Ser
625                 630

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
              35                  40                  45

Tyr Met Trp Thr Arg Asp Ser Ala Leu Val Phe Lys Asn Leu Ile Asp
50                  55                  60

```
Arg Phe Thr Glu Thr Tyr Asp Ala Gly Leu Gln Arg Arg Ile Glu Gln
 65                  70                  75                  80

Tyr Ile Thr Ala Gln Val Thr Leu Gln Gly Leu Ser Asn Pro Ser Gly
                 85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys Ser Gly Ala Ser Val Val Gly Ser Tyr Ser Arg
450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
```

```
                        485                 490                 495
Val Ala Val Thr Phe His Glu Leu Val Ser Thr Gln Phe Gly Gln Thr
            500                 505                 510

Val Lys Val Ala Gly Asn Ala Ala Leu Gly Asn Trp Ser Thr Ser
        515                 520                 525

Ala Ala Val Ala Leu Asp Ala Val Asn Tyr Ala Asp Asn His Pro Leu
        530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 3
<211> LENGTH: 453
<212> TYPE: PRT
<213> ORGANISM: Trichoderma reesei

<400> SEQUENCE: 3

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
```

```
                260                 265                 270
Pro Cys Ser Asp Lys Ala Leu Ser Asn Leu Lys Val Val Asp Ser
            275                 280                 285

Phe Arg Ser Ile Tyr Gly Val Asn Lys Gly Ile Pro Ala Gly Ala
        290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys
    450

<210> SEQ ID NO 4
<211> LENGTH: 1899
<212> TYPE: DNA
<213> ORGANISM: Trichoderma reesei

<400> SEQUENCE: 4
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc     120
accgagacgc ctattgcact gaacaatctt ctttgcaatg ttggtcctga tggatgccgt     180
gcattcggca catcagctgg tgcggtgatt gcatctccca gcacaattga cccggactac     240
tattacatgt ggacgcgaga tagcgctctt gtcttcaaga acctcatcga ccgcttcacc     300
gaaacgtacg atgcgggcct gcagcgccgc atcgagcagt acattactgc ccaggtcact     360
ctccagggcc tctctaaccc ctcgggctcc ctcgcggacg gctctggtct cggcgagccc     420
aagtttgagt gaccctgaa gcctttcacc ggcaactggg tcgaccgca gcggatggc       480 ccagctctgc gagccattgc cttgattgga tactcaaagt ggctcatcaa caacaactat     540
cagtcgactg tgtccaacgt catctggcct attgtgcgca acgacctcaa ctatgttgcc     600
cagtactgga accaaaccgg ctttgacctc tgggaagaag tcaatgggag ctcattcttt     660
actgttgcca accagcaccg agcacttgtc gagggcgcca ctcttgctgc cactcttggc     720
cagtcgggaa gcgcttattc atctgttgct ccccaggttt tgtgctttct ccaacgattc     780
tgggtgtcgt ctggtggata cgtcgactcc aacatcaaca ccaacgaggg caggactggc     840
aaggatgtca actccgtcct gacttccatc acacccttcg atcccaacct tggctgtgac     900
gcaggcacct tccagccatg cagtgacaaa gcgctctcca acctcaaggt tgttgtcgac     960
tccttccgct ccatctacgg cgtgaacaag ggcattcctg ccggtgctgc cgtcgccatt    1020
```

```
ggccggtatg cagaggatgt gtactacaac ggcaacccct tggtatcttgc tacatttgct   1080 gctgccgagc agctgtacga tgccatctac gtctggaaga gacgggctc catcacggtg    1140 accgccacct ccctggcctt cttccaggag cttgttcctg cgtgacggc cgggacctac    1200 tccagcagct cttcgacctt taccaacatc atcaacgccg tctcgacata cgccgatggc   1260
ttcctcagcg aggctgccaa gtacgtcccc gccgacggtt cgctggccga gcagtttgac   1320
cgcaacagcg gcactccgct gtctgcgctt cacctgacgt ggtcgtacgc ctcgttcttg   1380
acagccacgg cccgtcgggc tggcatcgtg cccccctcgt gggccaacag cagcgctagc   1440
acgatcccct cgacgtgctc cggcgcgtcc gtggtcggat cctactcgcg tcccaccgcc   1500
acgtcattcc ctccgtcgca gacgcccaag cctggcgtgc cttccggtac tccctacacg   1560
cccctgccct gcgcgacccc aacctccgtg gccgtcacct ccacgagct cgtgtcgaca   1620 cagtttggcc agacggtcaa ggtggcgggc aacgccgcgg ccctgggcaa ctggagcacg   1680
agcgccgccg tggctctgga cgccgtcaac tatgccgata accacccccct gtggattggg   1740 acggtcaacc tcgaggctgg agacgtcgtg gagtacaagt acatcaatgt gggccaagat   1800
ggctccgtga cctgggagag tgatcccaac cacacttaca cggttcctgc ggtggcttgt   1860
gtgacgcagg ttgtcaagga ggacacctgg cagtcgtaa                         1899

<210> SEQ ID NO 5
<211> LENGTH: 448
<212> TYPE: PRT
<213> ORGANISM: Aspergillus awamori

<400> SEQUENCE: 5

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Ile Lys Thr Leu Val
        50                  55                  60

Asp Leu Phe Arg Asn Gly Asp Thr Asp Leu Leu Ser Thr Ile Glu Asn
65                  70                  75                  80

Tyr Ile Ser Ser Gln Ala Ile Val Gln Gly Ile Ser Asn Pro Ser Gly
                85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Arg Gln Trp Leu Leu Asp Asn
    130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Gln Ile Leu Cys Tyr Leu Gln
    210                 215                 220
```

-continued

Ser Phe Trp Thr Gly Glu Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
            245                 250                 255

Pro Glu Ala Gly Cys Asp Asp Ser Thr Phe Gln Pro Cys Ser Pro Arg
        260                 265                 270

Ala Leu Ala Asn His Lys Glu Val Val Asp Ser Phe Arg Ser Ile Tyr
    275                 280                 285

Thr Leu Asn Asp Gly Leu Ser Asp Ser Glu Ala Val Ala Val Gly Arg
290                 295                 300

Tyr Pro Lys Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Gln Ala
            340                 345                 350

Leu Tyr Ser Asp Ala Ala Thr Gly Thr Tyr Ser Ser Ser Ser Ser Thr
        355                 360                 365

Tyr Ser Ser Ile Val Asp Ala Val Lys Thr Phe Ala Asp Gly Phe Val
370                 375                 380

Ser Ile Val Glu Thr His Ala Ala Ser Asn Gly Ser Leu Ser Glu Gln
385                 390                 395                 400

Tyr Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Met
            420                 425                 430

Pro Pro Ser Trp Gly Glu Thr Ser Ala Ser Ser Val Pro Gly Thr Cys
        435                 440                 445

<210> SEQ ID NO 6
<211> LENGTH: 449
<212> TYPE: PRT
<213> ORGANISM: Aspergillus niger

<400> SEQUENCE: 6

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Leu Lys Thr Leu Val
    50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110

Glu Thr Ala Tyr Thr Gly Ser Trp Gly Arg Pro Gln Arg Asp Gly Pro
        115                 120                 125

Ala Leu Arg Ala Thr Ala Met Ile Gly Phe Gly Gln Trp Leu Leu Asp
    130                 135                 140

Asn Gly Tyr Thr Ser Thr Ala Thr Asp Ile Val Trp Pro Leu Val Arg
145                 150                 155                 160

-continued

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
        180                 185                 190

His Arg Ala Leu Val Glu Gly Ser Ala Phe Ala Thr Ala Val Gly Ser
            195                 200                 205

Ser Cys Ser Trp Cys Asp Ser Gln Ala Pro Glu Ile Leu Cys Tyr Leu
    210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
            260                 265                 270

Arg Ala Leu Ala Asn His Lys Glu Val Asp Ser Phe Arg Ser Ile
                275                 280                 285

Tyr Thr Leu Asn Asp Gly Leu Ser Asp Ser Glu Ala Val Ala Val Gly
        290                 295                 300

Arg Tyr Pro Glu Asp Thr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
                325                 330                 335

Lys Gln Gly Ser Leu Glu Val Thr Asp Val Ser Leu Asp Phe Phe Lys
            340                 345                 350

Ala Leu Tyr Ser Asp Ala Ala Thr Gly Thr Tyr Ser Ser Ser Ser
        355                 360                 365

Thr Tyr Ser Ser Ile Val Asp Ala Val Lys Thr Phe Ala Asp Gly Phe
370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415

Trp Ser Tyr Ala Ala Leu Leu Thr Ala Asn Asn Arg Arg Asn Ser Val
            420                 425                 430

Val Pro Ala Ser Trp Gly Glu Thr Ser Ala Ser Ser Val Pro Gly Thr
        435                 440                 445

Cys

<210> SEQ ID NO 7
<211> LENGTH: 450
<212> TYPE: PRT
<213> ORGANISM: Aspergillus oryzae

<400> SEQUENCE: 7

Gln Ser Asp Leu Asn Ala Phe Ile Glu Ala Gln Thr Pro Ile Ala Lys
1               5                   10                  15

Gln Gly Tyr Leu Asn Asn Ile Gly Ala Asp Gly Lys Leu Val Glu Gly
            20                  25                  30

Ala Ala Ala Gly Ile Val Tyr Ala Ser Pro Ser Lys Ser Asn Pro Asp
        35                  40                  45

Tyr Phe Tyr Thr Trp Thr Arg Asp Ala Gly Leu Thr Met Glu Glu Tyr
    50                  55                  60

Ile Glu Gln Phe Ile Gly Gly Asp Ala Thr Leu Glu Ser Thr Ile Gln
65                  70                  75                  80

Asn Tyr Val Asp Ser Gln Ala Asn Glu Gln Ala Val Ser Asn Pro Ser

```
                     85                  90                  95
Gly Gly Leu Ser Asp Gly Ser Gly Leu Ala Glu Pro Lys Phe Tyr Tyr
                100                 105                 110
Asn Ile Ser Gln Phe Thr Asp Ser Trp Gly Arg Pro Gln Arg Asp Gly
                115                 120                 125
Pro Ala Leu Arg Ala Ser Ala Leu Ile Ala Tyr Gly Asn Ser Leu Ile
                130                 135                 140
Ser Ser Asp Lys Gln Ser Val Val Lys Ala Asn Ile Trp Pro Ile Tyr
145                 150                 155                 160
Gln Asn Asp Leu Ser Tyr Val Gly Gln Tyr Trp Asn Gln Thr Gly Phe
                165                 170                 175
Asp Leu Trp Glu Glu Val Gln Gly Ser Ser Phe Phe Thr Val Ala Val
                180                 185                 190
Gln His Lys Ala Leu Val Glu Gly Asp Ala Phe Ala Lys Ala Leu Gly
                195                 200                 205
Glu Glu Cys Gln Ala Cys Ser Val Ala Pro Gln Ile Leu Cys His Leu
                210                 215                 220
Gln Asp Phe Trp Asn Gly Ser Ala Val Leu Ser Asn Leu Pro Thr Asn
225                 230                 235                 240
Gly Arg Ser Gly Leu Asp Thr Asn Ser Leu Leu Gly Ser Ile His Thr
                245                 250                 255
Phe Asp Pro Ala Ala Cys Asp Thr Thr Phe Gln Pro Cys Ser
                260                 265                 270
Ser Arg Ala Leu Ser Asn His Lys Leu Val Val Asp Ser Phe Arg Ser
                275                 280                 285
Val Tyr Gly Ile Asn Asn Gly Arg Gly Ala Gly Lys Ala Ala Val
                290                 295                 300
Gly Pro Tyr Ala Glu Asp Thr Tyr Gln Gly Gly Asn Pro Trp Tyr Leu
305                 310                 315                 320
Thr Thr Leu Val Ala Ala Glu Leu Leu Tyr Asp Ala Leu Tyr Gln Trp
                325                 330                 335
Asp Lys Gln Gly Gln Val Asn Val Thr Glu Thr Ser Leu Pro Phe Phe
                340                 345                 350
Lys Asp Leu Ser Ser Asn Val Thr Thr Gly Ser Tyr Ala Lys Ser Ser
                355                 360                 365
Ser Ala Tyr Glu Ser Leu Thr Ser Ala Val Lys Thr Tyr Ala Asp Gly
                370                 375                 380
Phe Ile Ser Val Val Gln Glu Tyr Thr Pro Asp Gly Gly Ala Leu Ala
385                 390                 395                 400
Glu Gln Tyr Ser Arg Asp Gln Gly Thr Pro Val Ser Ala Ser Asp Leu
                405                 410                 415
Thr Trp Ser Tyr Ala Ala Phe Leu Ser Ala Val Gly Arg Arg Asn Gly
                420                 425                 430
Thr Val Pro Ala Ser Trp Gly Ser Thr Ala Asn Ala Val Pro Ser
                435                 440                 445
Gln Cys
    450

<210> SEQ ID NO 8
<211> LENGTH: 441
<212> TYPE: PRT
<213> ORGANISM: Humicola grisea

<400> SEQUENCE: 8

Ala Ala Val Asp Thr Phe Ile Asn Thr Glu Lys Pro Ile Ala Trp Asn
```

-continued

```
1               5                   10                  15
Lys Leu Leu Ala Asn Ile Gly Pro Asn Gly Lys Ala Ala Pro Gly Ala
                20                  25                  30

Ala Ala Gly Val Val Ile Ala Ser Pro Ser Arg Thr Asp Pro Pro Tyr
            35                  40                  45

Phe Phe Thr Trp Thr Pro Asp Ala Ala Leu Val Leu Thr Gly Ile Ile
    50                  55                  60

Glu Ser Leu Gly His Asn Tyr Asn Thr Thr Leu Gln Gln Val Ser Asn
65                  70                  75                  80

Pro Ser Gly Thr Phe Ala Asp Gly Ser Gly Leu Gly Glu Ala Lys Phe
                85                  90                  95

Asn Val Asp Leu Thr Ala Phe Thr Gly Glu Trp Gly Arg Pro Gln Arg
            100                 105                 110

Asp Gly Pro Pro Leu Arg Ala Ile Ala Leu Ile Gln Tyr Ala Lys Trp
            115                 120                 125

Leu Ile Ala Asn Gly Tyr Lys Ser Thr Ala Lys Ser Val Val Trp Pro
    130                 135                 140

Val Val Lys Asn Asp Leu Ala Tyr Thr Ala Gln Tyr Trp Asn Glu Thr
145                 150                 155                 160

Gly Phe Asp Leu Trp Glu Val Pro Gly Ser Ser Phe Phe Thr Ile
                165                 170                 175

Ala Ser Ser His Arg Ala Leu Thr Glu Gly Ala Tyr Leu Ala Ala Gln
            180                 185                 190

Leu Asp Thr Glu Cys Pro Pro Cys Thr Thr Val Ala Pro Gln Val Leu
            195                 200                 205

Cys Phe Gln Gln Ala Phe Trp Asn Ser Lys Gly Asn Tyr Val Val Ser
    210                 215                 220

Thr Ser Thr Ala Gly Glu Tyr Arg Ser Gly Lys Asp Ala Asn Ser Ile
225                 230                 235                 240

Leu Ala Ser Ile His Asn Phe Asp Pro Glu Ala Gly Cys Asp Asn Leu
                245                 250                 255

Thr Phe Gln Pro Cys Ser Glu Arg Ala Leu Ala Asn His Lys Ala Tyr
            260                 265                 270

Val Asp Ser Phe Arg Asn Leu Tyr Ala Ile Asn Lys Gly Ile Ala Gln
            275                 280                 285

Gly Lys Ala Val Ala Val Gly Arg Tyr Ser Glu Asp Val Tyr Tyr Asn
    290                 295                 300

Gly Asn Pro Trp Tyr Leu Ala Asn Phe Ala Ala Glu Gln Leu Tyr
305                 310                 315                 320

Asp Ala Ile Tyr Val Trp Asn Lys Gln Gly Ser Ile Thr Val Thr Ser
                325                 330                 335

Val Ser Leu Pro Phe Phe Arg Asp Leu Val Ser Ser Val Ser Thr Gly
            340                 345                 350

Thr Tyr Ser Lys Ser Ser Ser Thr Phe Thr Asn Ile Val Asn Ala Val
            355                 360                 365

Lys Ala Tyr Ala Asp Gly Phe Ile Glu Val Ala Ala Lys Tyr Thr Pro
    370                 375                 380

Ser Asn Gly Ala Leu Ala Glu Gln Tyr Asp Arg Asn Thr Gly Lys Pro
385                 390                 395                 400

Asp Ser Ala Ala Asp Leu Thr Trp Ser Tyr Ser Ala Phe Leu Ser Ala
                405                 410                 415

Ile Asp Arg Arg Ala Gly Leu Val Pro Pro Ser Trp Arg Ala Ser Val
            420                 425                 430
```

```
Ala Lys Ser Gln Leu Pro Ser Thr Cys
        435                 440

<210> SEQ ID NO 9
<211> LENGTH: 452
<212> TYPE: PRT
<213> ORGANISM: Hypocrea vinosa

<400> SEQUENCE: 9

Ser Val Asp Asp Phe Ile Asn Thr Gln Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Thr Asp Pro Asp Tyr Tyr
        35                  40                  45

Tyr Met Trp Thr Arg Asp Ser Ala Leu Val Phe Lys Asn Ile Val Asp
    50                  55                  60

Arg Phe Thr Gln Gln Tyr Asp Ala Gly Leu Gln Arg Arg Ile Glu Gln
65                  70                  75                  80

Tyr Ile Ser Ala Gln Val Thr Leu Gln Gly Ile Ser Asn Pro Ser Gly
                85                  90                  95

Ser Leu Ser Asp Gly Ser Gly Leu Gly Glu Pro Lys Phe Glu Leu Thr
            100                 105                 110

Leu Ser Gln Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Ser Phe
        275                 280                 285

Arg Ser Ile Tyr Gly Val Asn Lys Gly Ile Pro Ala Gly Ser Ala Val
    290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Ser Ala
            340                 345                 350

Phe Phe Gln Glu Leu Val Pro Gly Val Ala Ala Gly Thr Tyr Ser Ser
        355                 360                 365
```

```
Ser Gln Ser Thr Phe Thr Ser Ile Ile Asn Ala Ile Ser Thr Tyr Ala
    370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Arg Arg
                420                 425                 430

Ala Gly Val Val Pro Ser Trp Ala Ser Ser Gly Ala Asn Thr Val
        435                 440                 445

Pro Ser Ser Cys
    450

<210> SEQ ID NO 10
<211> LENGTH: 37
<212> TYPE: PRT
<213> ORGANISM: Trichoderma reesei

<400> SEQUENCE: 10

Ser Gly Ala Ser Val Val Gly Ser Tyr Ser Arg Pro Thr Ala Thr Ser
1               5                   10                  15

Phe Pro Pro Ser Gln Thr Pro Lys Pro Gly Val Pro Ser Gly Thr Pro
                20                  25                  30

Tyr Thr Pro Leu Pro
            35

<210> SEQ ID NO 11
<211> LENGTH: 109
<212> TYPE: PRT
<213> ORGANISM: Trichoderma reesei

<400> SEQUENCE: 11

Cys Ala Thr Pro Thr Ser Val Ala Val Thr Phe His Glu Leu Val Ser
1               5                   10                  15

Thr Gln Phe Gly Gln Thr Val Lys Val Ala Gly Asn Ala Ala Ala Leu
                20                  25                  30

Gly Asn Trp Ser Thr Ser Ala Ala Val Ala Leu Asp Ala Val Asn Tyr
            35                  40                  45

Ala Asp Asn His Pro Leu Trp Ile Gly Thr Val Asn Leu Glu Ala Gly
50                  55                  60

Asp Val Val Glu Tyr Lys Tyr Ile Asn Val Gly Gln Asp Gly Ser Val
65                  70                  75                  80

Thr Trp Glu Ser Asp Pro Asn His Thr Tyr Thr Val Pro Ala Val Ala
                85                  90                  95

Cys Val Thr Gln Val Val Lys Glu Asp Thr Trp Gln Ser
            100                 105

<210> SEQ ID NO 12
<211> LENGTH: 6
<212> TYPE: PRT
<213> ORGANISM: Trichoderma reesei

<400> SEQUENCE: 12

Ser Val Asp Asp Phe Ile
1               5

<210> SEQ ID NO 13
<211> LENGTH: 25
<212> TYPE: DNA
<213> ORGANISM: Artificial
```

```
<220> FEATURE:
<223> OTHER INFORMATION: synthetic primer

<400> SEQUENCE: 13
tcgcgttaac gctagcatgg atctc                                    25

<210> SEQ ID NO 14
<211> LENGTH: 25
<212> TYPE: DNA
<213> ORGANISM: Artificial
<220> FEATURE:
<223> OTHER INFORMATION: synthetic primer

<400> SEQUENCE: 14
tcgcgttaac gctagcatgg atctc                                    25

<210> SEQ ID NO 15
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 15
cgtcaccaag aggtctgttg acnnsttcat cagcaccgag acgcc              45

<210> SEQ ID NO 16
<211> LENGTH: 25
<212> TYPE: DNA
<213> ORGANISM: Artificial
<220> FEATURE:
<223> OTHER INFORMATION: synthetic primer

<400> SEQUENCE: 16
gtcaacagac ctcttggtga cgtcg                                    25

<210> SEQ ID NO 17
<211> LENGTH: 48
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 17
caccaagagg tctgttgacg acnnsatcag caccgagacg cctattgc           48

<210> SEQ ID NO 18
<211> LENGTH: 24
<212> TYPE: DNA
<213> ORGANISM: Artificial
<220> FEATURE:
<223> OTHER INFORMATION: synthetic primer

<400> SEQUENCE: 18
gtcgtcaaca gacctcttgg tgac                                     24

<210> SEQ ID NO 19
<211> LENGTH: 37
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 19
tgacgacttc atcagcaccg agnnscctat tgcactg                              37

<210> SEQ ID NO 20
<211> LENGTH: 21
<212> TYPE: DNA
<213> ORGANISM: Artificial
<220> FEATURE:
<223> OTHER INFORMATION: synthetic primer

<400> SEQUENCE: 20
ctcggtgctg atgaagtcgt c                                               21

<210> SEQ ID NO 21
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 21
tcatcagcac cgagacgcct nnsgcactga acaatcttct ttgca                     45

<210> SEQ ID NO 22
<211> LENGTH: 25
<212> TYPE: DNA
<213> ORGANISM: Artificial
<220> FEATURE:
<223> OTHER INFORMATION: synthetic primer

<400> SEQUENCE: 22
aggcgtctcg gtgctgatga agtcg                                           25

<210> SEQ ID NO 23
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 23
cagcaccgag acgcctattg cannsaacaa tcttctt                              37

<210> SEQ ID NO 24
<211> LENGTH: 21
<212> TYPE: DNA
<213> ORGANISM: Artificial
<220> FEATURE:
<223> OTHER INFORMATION: synthetic primer

<400> SEQUENCE: 24
tgcaataggc gtctcggtgc t                                               21
```

```
<210> SEQ ID NO 25
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 25
caccgagacg cctattgcac tgnnsaatct tctttgc                                37

<210> SEQ ID NO 26
<211> LENGTH: 21
<212> TYPE: DNA
<213> ORGANISM: Artificial
<220> FEATURE:
<223> OTHER INFORMATION: synthetic primer

<400> SEQUENCE: 26
cagtgcaata ggcgtctcgg t                                                 21

<210> SEQ ID NO 27
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 27
caatcttctt tgcaatgttg gtnnsgatgg atgccgt                                37

<210> SEQ ID NO 28
<211> LENGTH: 22
<212> TYPE: DNA
<213> ORGANISM: Artificial
<220> FEATURE:
<223> OTHER INFORMATION: synthetic primer

<400> SEQUENCE: 28
accaacattg caaagaagat tg                                                22

<210> SEQ ID NO 29
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 29
ttctttgcaa tgttggtcct nnsggatgcc gtgcattcgg cacat                       45

<210> SEQ ID NO 30
<211> LENGTH: 25
<212> TYPE: DNA
<213> ORGANISM: Artificial
<220> FEATURE:
<223> OTHER INFORMATION: synthetic primer

<400> SEQUENCE: 30
```
aggaccaaca ttgcaaagaa gattg                                             25

<210> SEQ ID NO 31
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 31
gtcctgatgg atgccgtgca nnsggcacat cagctggtgc ggtga                       45

<210> SEQ ID NO 32
<211> LENGTH: 25
<212> TYPE: DNA
<213> ORGANISM: Artificial
<220> FEATURE:
<223> OTHER INFORMATION: synthetic primer

<400> SEQUENCE: 32
tgcacggcat ccatcaggac caaca                                             25

<210> SEQ ID NO 33
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 33
tgcggtgatt gcatctccca gcnnsattga cccggac                                37

<210> SEQ ID NO 34
<211> LENGTH: 22
<212> TYPE: DNA
<213> ORGANISM: Artificial
<220> FEATURE:
<223> OTHER INFORMATION: synthetic primer

<400> SEQUENCE: 34
gctgggagat gcaatcaccg ca                                                22

<210> SEQ ID NO 35
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 35
tgattgcatc tcccagcaca nnsgacccgg actactatta catgt                       45

<210> SEQ ID NO 36
<211> LENGTH: 25
<212> TYPE: DNA
<213> ORGANISM: Artificial

-continued

```
<220> FEATURE:
<223> OTHER INFORMATION: synthetic primer

<400> SEQUENCE: 36
tgtgctggga gatgcaatca ccgca                                              25

<210> SEQ ID NO 37
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 37
ttgcatctcc cagcacaatt nnsccggact actattacat gtgga                        45

<210> SEQ ID NO 38
<211> LENGTH: 25
<212> TYPE: DNA
<213> ORGANISM: Artificial
<220> FEATURE:
<223> OTHER INFORMATION: synthetic primer

<400> SEQUENCE: 38
aattgtgctg ggagatgcaa tcacc                                              25

<210> SEQ ID NO 39
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 39
catctcccag cacaattgac nnsgactact attacatgtg gacgc                        45

<210> SEQ ID NO 40
<211> LENGTH: 25
<212> TYPE: DNA
<213> ORGANISM: Artificial
<220> FEATURE:
<223> OTHER INFORMATION: synthetic primer

<400> SEQUENCE: 40
gtcaattgtg ctgggagatg caatc                                              25

<210> SEQ ID NO 41
<211> LENGTH: 46
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 41
ctcccagcac aattgacccg nnstactatt acatgtggac gcgaga                       46
```

```
<210> SEQ ID NO 42
<211> LENGTH: 25
<212> TYPE: DNA
<213> ORGANISM: Artificial
<220> FEATURE:
<223> OTHER INFORMATION: synthetic primer

<400> SEQUENCE: 42
cgggtcaatt gtgctgggag atgca                                         25

<210> SEQ ID NO 43
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 43
ccagcacaat tgacccggac nnstattaca tgtggacgcg agata                   45

<210> SEQ ID NO 44
<211> LENGTH: 25
<212> TYPE: DNA
<213> ORGANISM: Artificial
<220> FEATURE:
<223> OTHER INFORMATION: synthetic primer

<400> SEQUENCE: 44
gtccgggtca attgtgctgg gagat                                         25

<210> SEQ ID NO 45
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 45
caattgaccc ggactactat nnsatgtgga cgcgagatag cgctc                   45

<210> SEQ ID NO 46
<211> LENGTH: 25
<212> TYPE: DNA
<213> ORGANISM: Artificial
<220> FEATURE:
<223> OTHER INFORMATION: synthetic primer

<400> SEQUENCE: 46
atagtagtcc gggtcaattg tgctg                                         25

<210> SEQ ID NO 47
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 47
```

-continued

```
acccggacta ctattacatg nnsacgcgag atagcgctct tgtct                45
```

<210> SEQ ID NO 48
<211> LENGTH: 25
<212> TYPE: DNA
<213> ORGANISM: Artificial
<220> FEATURE:
<223> OTHER INFORMATION: synthetic primer

<400> SEQUENCE: 48

```
catgtaatag tagtccgggt caatt                                      25
```

<210> SEQ ID NO 49
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 49

```
gacgcgagat agcgctcttg tcnnsaagaa cctcatc                         37
```

<210> SEQ ID NO 50
<211> LENGTH: 21
<212> TYPE: DNA
<213> ORGANISM: Artificial
<220> FEATURE:
<223> OTHER INFORMATION: synthetic primer

<400> SEQUENCE: 50

```
gacaagagcg ctatctcgcg t                                          21
```

<210> SEQ ID NO 51
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 51

```
gcgagatagc gctcttgtct tcnnsaacct catcgac                         37
```

<210> SEQ ID NO 52
<211> LENGTH: 21
<212> TYPE: DNA
<213> ORGANISM: Artificial
<220> FEATURE:
<223> OTHER INFORMATION: synthetic primer

<400> SEQUENCE: 52

```
gaagacaaga gcgctatctc g                                          21
```

<210> SEQ ID NO 53
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (23)..(24)
<223> OTHER INFORMATION: n is a, c, g, or t

<400> SEQUENCE: 53
agatagcgct cttgtcttca agnnsctcat cgaccgc                              37

<210> SEQ ID NO 54
<211> LENGTH: 21
<212> TYPE: DNA
<213> ORGANISM: Artificial
<220> FEATURE:
<223> OTHER INFORMATION: synthetic primer

<400> SEQUENCE: 54
cttgaagaca agagcgctat c                                              21

<210> SEQ ID NO 55
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 55
tgtcttcaag aacctcatcg acnnsttcac cgaaacg                             37

<210> SEQ ID NO 56
<211> LENGTH: 21
<212> TYPE: DNA
<213> ORGANISM: Artificial
<220> FEATURE:
<223> OTHER INFORMATION: synthetic primer

<400> SEQUENCE: 56
gtcgatgagg ttcttgaaga c                                              21

<210> SEQ ID NO 57
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 57
caagaacctc atcgaccgct tcnnsgaaac gtacgat                             37

<210> SEQ ID NO 58
<211> LENGTH: 21
<212> TYPE: DNA
<213> ORGANISM: Artificial
<220> FEATURE:
<223> OTHER INFORMATION: synthetic primer

<400> SEQUENCE: 58
gaagcggtcg atgaggttct t                                              21

<210> SEQ ID NO 59
<211> LENGTH: 37
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 59
gaacctcatc gaccgcttca ccnnsacgta cgatgcg                                37

<210> SEQ ID NO 60
<211> LENGTH: 21
<212> TYPE: DNA
<213> ORGANISM: Artificial
<220> FEATURE:
<223> OTHER INFORMATION: synthetic primer

<400> SEQUENCE: 60
ggtgaagcgg tcgatgaggt t                                                 21

<210> SEQ ID NO 61
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 61
tcgaccgctt caccgaaacg nnsgatgcgg gcctgcagcg ccgca                       45

<210> SEQ ID NO 62
<211> LENGTH: 25
<212> TYPE: DNA
<213> ORGANISM: Artificial
<220> FEATURE:
<223> OTHER INFORMATION: synthetic primer

<400> SEQUENCE: 62
cgtttcggtg aagcggtcga tgagg                                             25

<210> SEQ ID NO 63
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 63
ccgcttcacc gaaacgtacg atnnsggcct gcagcgc                                37

<210> SEQ ID NO 64
<211> LENGTH: 22
<212> TYPE: DNA
<213> ORGANISM: Artificial
<220> FEATURE:
<223> OTHER INFORMATION: synthetic primer

<400> SEQUENCE: 64
atcgtacgtt tcggtgaagc gg                                                22
```

```
<210> SEQ ID NO 65
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 65
cttcaccgaa acgtacgatg cgnnsctgca gcgccgc                              37

<210> SEQ ID NO 66
<211> LENGTH: 21
<212> TYPE: DNA
<213> ORGANISM: Artificial
<220> FEATURE:
<223> OTHER INFORMATION: synthetic primer

<400> SEQUENCE: 66
cgcatcgtac gtttcggtga a                                              21

<210> SEQ ID NO 67
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 67
aaacgtacga tgcgggcctg nnscgccgca tcgagcagta catta                    45

<210> SEQ ID NO 68
<211> LENGTH: 25
<212> TYPE: DNA
<213> ORGANISM: Artificial
<220> FEATURE:
<223> OTHER INFORMATION: synthetic primer

<400> SEQUENCE: 68
caggcccgca tcgtacgttt cggtg                                          25

<210> SEQ ID NO 69
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 69
cgtacgatgc gggcctgcag nnscgcatcg agcagtacat tactg                    45

<210> SEQ ID NO 70
<211> LENGTH: 25
<212> TYPE: DNA
<213> ORGANISM: Artificial
<220> FEATURE:
<223> OTHER INFORMATION: synthetic primer

<400> SEQUENCE: 70
```
ctgcaggccc gcatcgtacg tttcg                                          25

<210> SEQ ID NO 71
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 71
ctctccaggg cctctctaac nnstcgggct ccctcgcgga cggct              45

<210> SEQ ID NO 72
<211> LENGTH: 25
<212> TYPE: DNA
<213> ORGANISM: Artificial
<220> FEATURE:
<223> OTHER INFORMATION: synthetic primer

<400> SEQUENCE: 72
gttagagagg ccctggagag tgacc                                          25

<210> SEQ ID NO 73
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 73
gggcctctct aacccctcgg gcnnsctcgc ggacggc                       37

<210> SEQ ID NO 74
<211> LENGTH: 21
<212> TYPE: DNA
<213> ORGANISM: Artificial
<220> FEATURE:
<223> OTHER INFORMATION: synthetic primer

<400> SEQUENCE: 74
gcccgagggg ttagagaggc c                                              21

<210> SEQ ID NO 75
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 75
cctctctaac ccctcgggct ccnnsgcgga cggctct                       37

<210> SEQ ID NO 76
<211> LENGTH: 21
<212> TYPE: DNA
<213> ORGANISM: Artificial

```
<220> FEATURE:
<223> OTHER INFORMATION: synthetic primer

<400> SEQUENCE: 76
ggagcccgag gggttagaga g                                              21

<210> SEQ ID NO 77
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 77
ctctaacccc tcgggctccc tcnnsgacgg ctctggt                             37

<210> SEQ ID NO 78
<211> LENGTH: 21
<212> TYPE: DNA
<213> ORGANISM: Artificial
<220> FEATURE:
<223> OTHER INFORMATION: synthetic primer

<400> SEQUENCE: 78
gagggagccc gaggggttag a                                              21

<210> SEQ ID NO 79
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 79
acccctcggg ctccctcgcg nnsggctctg gtctcggcga gccca                    45

<210> SEQ ID NO 80
<211> LENGTH: 25
<212> TYPE: DNA
<213> ORGANISM: Artificial
<220> FEATURE:
<223> OTHER INFORMATION: synthetic primer

<400> SEQUENCE: 80
cgcgagggag cccgaggggt tagag                                          25

<210> SEQ ID NO 81
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 81
ctcgggctcc ctcgcggacg gcnnsggtct cggcgag                             37
```

```
<210> SEQ ID NO 82
<211> LENGTH: 21
<212> TYPE: DNA
<213> ORGANISM: Artificial
<220> FEATURE:
<223> OTHER INFORMATION: synthetic primer

<400> SEQUENCE: 82
gccgtccgcg agggagcccg a                                              21

<210> SEQ ID NO 83
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 83
tggtctcggc gagcccaagt ttnnsttgac cctgaag                             37

<210> SEQ ID NO 84
<211> LENGTH: 22
<212> TYPE: DNA
<213> ORGANISM: Artificial
<220> FEATURE:
<223> OTHER INFORMATION: synthetic primer

<400> SEQUENCE: 84
aaacttgggc tcgccgagac ca                                             22

<210> SEQ ID NO 85
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 85
tctcggcgag cccaagtttg agnnsaccct gaagcct                             37

<210> SEQ ID NO 86
<211> LENGTH: 21
<212> TYPE: DNA
<213> ORGANISM: Artificial
<220> FEATURE:
<223> OTHER INFORMATION: synthetic primer

<400> SEQUENCE: 86
ctcaaacttg ggctcgccga g                                              21

<210> SEQ ID NO 87
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 87
```

```
cgagcccaag tttgagttga ccnnsaagcc tttcacc                             37
```

<210> SEQ ID NO 88
<211> LENGTH: 21
<212> TYPE: DNA
<213> ORGANISM: Artificial
<220> FEATURE:
<223> OTHER INFORMATION: synthetic primer

<400> SEQUENCE: 88

```
ggtcaactca aacttgggct c                                              21
```

<210> SEQ ID NO 89
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 89

```
ccaagtttga gttgaccctg nnsccttca ccggcaactg gggtc                     45
```

<210> SEQ ID NO 90
<211> LENGTH: 25
<212> TYPE: DNA
<213> ORGANISM: Artificial
<220> FEATURE:
<223> OTHER INFORMATION: synthetic primer

<400> SEQUENCE: 90

```
cagggtcaac tcaaacttgg gctcg                                          25
```

<210> SEQ ID NO 91
<211> LENGTH: 46
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 91

```
ttgagttgac cctgaagcct nnsaccggca actggggtcg accgca                   46
```

<210> SEQ ID NO 92
<211> LENGTH: 25
<212> TYPE: DNA
<213> ORGANISM: Artificial
<220> FEATURE:
<223> OTHER INFORMATION: synthetic primer

<400> SEQUENCE: 92

```
aggcttcagg gtcaactcaa acttg                                          25
```

<210> SEQ ID NO 93
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 93
ccctgaagcc tttcaccggc nnstggggtc gaccgcagcg ggatg          45

<210> SEQ ID NO 94
<211> LENGTH: 25
<212> TYPE: DNA
<213> ORGANISM: Artificial
<220> FEATURE:
<223> OTHER INFORMATION: synthetic primer

<400> SEQUENCE: 94
gccggtgaaa ggcttcaggg tcaac                                25

<210> SEQ ID NO 95
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 95
ctttcaccgg caactggggt nnsccgcagc gggatggccc agctc          45

<210> SEQ ID NO 96
<211> LENGTH: 25
<212> TYPE: DNA
<213> ORGANISM: Artificial
<220> FEATURE:
<223> OTHER INFORMATION: synthetic primer

<400> SEQUENCE: 96
accccagttg ccggtgaaag gcttc                                25

<210> SEQ ID NO 97
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 97
gcaactgggg tcgaccgcag nnsgatggcc cagctctgcg agcca          45

<210> SEQ ID NO 98
<211> LENGTH: 25
<212> TYPE: DNA
<213> ORGANISM: Artificial
<220> FEATURE:
<223> OTHER INFORMATION: synthetic primer

<400> SEQUENCE: 98
ctgcggtcga ccccagttgc cggtg                                25

<210> SEQ ID NO 99
<211> LENGTH: 37
<212> TYPE: DNA
<213> ORGANISM: Artificial

```
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 99
ggatggccca gctctgcgag ccnnsgcctt gattgga                            37

<210> SEQ ID NO 100
<211> LENGTH: 22
<212> TYPE: DNA
<213> ORGANISM: Artificial
<220> FEATURE:
<223> OTHER INFORMATION: synthetic primer

<400> SEQUENCE: 100
ggctcgcaga gctgggccat cc                                           22

<210> SEQ ID NO 101
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 101
tgcgagccat tgccttgatt nnstactcaa agtggctcat caaca                  45

<210> SEQ ID NO 102
<211> LENGTH: 25
<212> TYPE: DNA
<213> ORGANISM: Artificial
<220> FEATURE:
<223> OTHER INFORMATION: synthetic primer

<400> SEQUENCE: 102
aatcaaggca atggctcgca gagct                                        25

<210> SEQ ID NO 103
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 103
cattgccttg attggatact cannstggct catcaac                           37

<210> SEQ ID NO 104
<211> LENGTH: 22
<212> TYPE: DNA
<213> ORGANISM: Artificial
<220> FEATURE:
<223> OTHER INFORMATION: synthetic primer

<400> SEQUENCE: 104
tgagtatcca atcaaggcaa tg                                           22
```

```
<210> SEQ ID NO 105
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 105
tggatactca aagtggctca tcnnsaacaa ctatcag                              37

<210> SEQ ID NO 106
<211> LENGTH: 21
<212> TYPE: DNA
<213> ORGANISM: Artificial
<220> FEATURE:
<223> OTHER INFORMATION: synthetic primer

<400> SEQUENCE: 106
gatgagccac tttgagtatc c                                               21

<210> SEQ ID NO 107
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 107
atactcaaag tggctcatca acnnsaacta tcagtcg                              37

<210> SEQ ID NO 108
<211> LENGTH: 21
<212> TYPE: DNA
<213> ORGANISM: Artificial
<220> FEATURE:
<223> OTHER INFORMATION: synthetic primer

<400> SEQUENCE: 108
gttgatgagc cactttgagt a                                               21

<210> SEQ ID NO 109
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 109
caaagtggct catcaacaac nnstatcagt cgactgtgtc caacg                     45

<210> SEQ ID NO 110
<211> LENGTH: 25
<212> TYPE: DNA
<213> ORGANISM: Artificial
<220> FEATURE:
<223> OTHER INFORMATION: synthetic primer

<400> SEQUENCE: 110
```
gttgttgatg agccactttg agtat                              25

<210> SEQ ID NO 111
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 111
aaagtggctc atcaacaaca acnnscagtc gactgtg                 37

<210> SEQ ID NO 112
<211> LENGTH: 21
<212> TYPE: DNA
<213> ORGANISM: Artificial
<220> FEATURE:
<223> OTHER INFORMATION: synthetic primer

<400> SEQUENCE: 112
gttgttgttg atgagccact t                                  21

<210> SEQ ID NO 113
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 113
ggctcatcaa caacaactat nnstcgactg tgtccaacgt catct        45

<210> SEQ ID NO 114
<211> LENGTH: 25
<212> TYPE: DNA
<213> ORGANISM: Artificial
<220> FEATURE:
<223> OTHER INFORMATION: synthetic primer

<400> SEQUENCE: 114
atagttgttg ttgatgagcc acttt                              25

<210> SEQ ID NO 115
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 115
caacaactat cagtcgactg tgnnsaacgt catctgg                 37

<210> SEQ ID NO 116
<211> LENGTH: 21
<212> TYPE: DNA
<213> ORGANISM: Artificial

```
<220> FEATURE:
<223> OTHER INFORMATION: synthetic primer

<400> SEQUENCE: 116
cacagtcgac tgatagttgt t                                              21

<210> SEQ ID NO 117
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 117
caactatcag tcgactgtgt ccnnsgtcat ctggcct                             37

<210> SEQ ID NO 118
<211> LENGTH: 21
<212> TYPE: DNA
<213> ORGANISM: Artificial
<220> FEATURE:
<223> OTHER INFORMATION: synthetic primer

<400> SEQUENCE: 118
ggacacagtc gactgatagt t                                              21

<210> SEQ ID NO 119
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 119
gcctattgtg cgcaacgacc tcnnstatgt tgcccagt                            38

<210> SEQ ID NO 120
<211> LENGTH: 21
<212> TYPE: DNA
<213> ORGANISM: Artificial
<220> FEATURE:
<223> OTHER INFORMATION: synthetic primer

<400> SEQUENCE: 120
gaggtcgttg cgcacaatag g                                              21

<210> SEQ ID NO 121
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 121
acctcaacta tgttgcccag nnstggaacc aaaccggctt tgacc                    45
```

```
<210> SEQ ID NO 122
<211> LENGTH: 25
<212> TYPE: DNA
<213> ORGANISM: Artificial
<220> FEATURE:
<223> OTHER INFORMATION: synthetic primer

<400> SEQUENCE: 122
ctgggcaaca tagttgaggt cgttg                                               25

<210> SEQ ID NO 123
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 123
atgttgccca gtactggaac nnsaccggct ttgacctctg ggaag                         45

<210> SEQ ID NO 124
<211> LENGTH: 25
<212> TYPE: DNA
<213> ORGANISM: Artificial
<220> FEATURE:
<223> OTHER INFORMATION: synthetic primer

<400> SEQUENCE: 124
gttccagtac tgggcaacat agttg                                               25

<210> SEQ ID NO 125
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 125
agtactggaa ccaaaccggc nnsgacctct gggaagaagt caatg                         45

<210> SEQ ID NO 126
<211> LENGTH: 25
<212> TYPE: DNA
<213> ORGANISM: Artificial
<220> FEATURE:
<223> OTHER INFORMATION: synthetic primer

<400> SEQUENCE: 126
gccggtttgg ttccagtact gggca                                               25

<210> SEQ ID NO 127
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 127
```
accaaaccgg ctttgacctc nnsgaagaag tcaatgggag ctcat        45

<210> SEQ ID NO 128
<211> LENGTH: 25
<212> TYPE: DNA
<213> ORGANISM: Artificial
<220> FEATURE:
<223> OTHER INFORMATION: synthetic primer

<400> SEQUENCE: 128
gaggtcaaag ccggtttggt tccag        25

<210> SEQ ID NO 129
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 129
ccggctttga cctctgggaa nnsgtcaatg ggagctcatt cttta        45

<210> SEQ ID NO 130
<211> LENGTH: 25
<212> TYPE: DNA
<213> ORGANISM: Artificial
<220> FEATURE:
<223> OTHER INFORMATION: synthetic primer

<400> SEQUENCE: 130
ttcccagagg tcaaagccgg tttgg        25

<210> SEQ ID NO 131
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 131
gctttgacct ctgggaagaa nnsaatggga gctcattctt tactg        45

<210> SEQ ID NO 132
<211> LENGTH: 25
<212> TYPE: DNA
<213> ORGANISM: Artificial
<220> FEATURE:
<223> OTHER INFORMATION: synthetic primer

<400> SEQUENCE: 132
ttcttcccag aggtcaaagc cggtt        25

<210> SEQ ID NO 133
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (23)..(24)
<223> OTHER INFORMATION: n is a, c, g, or t

<400> SEQUENCE: 133
ctttgacctc tgggaagaag tcnnsgggag ctcattc                              37

<210> SEQ ID NO 134
<211> LENGTH: 22
<212> TYPE: DNA
<213> ORGANISM: Artificial
<220> FEATURE:
<223> OTHER INFORMATION: synthetic primer

<400> SEQUENCE: 134
gacttcttcc cagaggtcaa ag                                             22

<210> SEQ ID NO 135
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 135
tgtcgagggc gccactcttg ctnnsactct tggccag                             37

<210> SEQ ID NO 136
<211> LENGTH: 21
<212> TYPE: DNA
<213> ORGANISM: Artificial
<220> FEATURE:
<223> OTHER INFORMATION: synthetic primer

<400> SEQUENCE: 136
agcaagagtg gcgccctcga c                                              21

<210> SEQ ID NO 137
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 137
cgagggcgcc actcttgctg ccnnscttgg ccagtcg                             37

<210> SEQ ID NO 138
<211> LENGTH: 21
<212> TYPE: DNA
<213> ORGANISM: Artificial
<220> FEATURE:
<223> OTHER INFORMATION: synthetic primer

<400> SEQUENCE: 138
ggcagcaaga gtggcgccct c                                              21

<210> SEQ ID NO 139
<211> LENGTH: 45
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 139
ctcttgctgc cactcttggc nnstcgggaa gcgcttattc atctg            45

<210> SEQ ID NO 140
<211> LENGTH: 25
<212> TYPE: DNA
<213> ORGANISM: Artificial
<220> FEATURE:
<223> OTHER INFORMATION: synthetic primer

<400> SEQUENCE: 140
gccaagagtg gcagcaagag tggcg                                  25

<210> SEQ ID NO 141
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 141
ccactcttgg ccagtcggga nnsgcttatt catctgttgc tcccc            45

<210> SEQ ID NO 142
<211> LENGTH: 25
<212> TYPE: DNA
<213> ORGANISM: Artificial
<220> FEATURE:
<223> OTHER INFORMATION: synthetic primer

<400> SEQUENCE: 142
tcccgactgg ccaagagtgg cagca                                  25

<210> SEQ ID NO 143
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 143
tggccagtcg ggaagcgctt atnnstctgt tgctccc                     37

<210> SEQ ID NO 144
<211> LENGTH: 21
<212> TYPE: DNA
<213> ORGANISM: Artificial
<220> FEATURE:
<223> OTHER INFORMATION: synthetic primer

<400> SEQUENCE: 144
ataagcgctt cccgactggc c                                      21
```

-continued

```
<210> SEQ ID NO 145
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 145
gtcgggaagc gcttattcat ctnnsgctcc ccaggtt                              37

<210> SEQ ID NO 146
<211> LENGTH: 21
<212> TYPE: DNA
<213> ORGANISM: Artificial
<220> FEATURE:
<223> OTHER INFORMATION: synthetic primer

<400> SEQUENCE: 146
agatgaataa gcgcttcccg a                                              21

<210> SEQ ID NO 147
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 147
cgcttattca tctgttgctc ccnnsgtttt gtgcttt                              37

<210> SEQ ID NO 148
<211> LENGTH: 21
<212> TYPE: DNA
<213> ORGANISM: Artificial
<220> FEATURE:
<223> OTHER INFORMATION: synthetic primer

<400> SEQUENCE: 148
gggagcaaca gatgaataag c                                              21

<210> SEQ ID NO 149
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 149
tgtgctttct ccaacgattc nnsgtgtcgt ctggtggata cgtcg                     45

<210> SEQ ID NO 150
<211> LENGTH: 26
<212> TYPE: DNA
<213> ORGANISM: Artificial
<220> FEATURE:
<223> OTHER INFORMATION: synthetic primer

<400> SEQUENCE: 150
```
gaatcgttgg agaaagcaca aaacct       26

<210> SEQ ID NO 151
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 151
gtgctttctc caacgattct ggnnstcgtc tggtgga       37

<210> SEQ ID NO 152
<211> LENGTH: 21
<212> TYPE: DNA
<213> ORGANISM: Artificial
<220> FEATURE:
<223> OTHER INFORMATION: synthetic primer

<400> SEQUENCE: 152
ccagaatcgt tggagaaagc a       21

<210> SEQ ID NO 153
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 153
ctttctccaa cgattctggg tgnnstctgg tggatacg       38

<210> SEQ ID NO 154
<211> LENGTH: 21
<212> TYPE: DNA
<213> ORGANISM: Artificial
<220> FEATURE:
<223> OTHER INFORMATION: synthetic primer

<400> SEQUENCE: 154
cacccagaat cgttggagaa a       21

<210> SEQ ID NO 155
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 155
tctccaacga ttctgggtgt cgnnsggtgg atacgtc       37

<210> SEQ ID NO 156
<211> LENGTH: 22
<212> TYPE: DNA
<213> ORGANISM: Artificial

```
<220> FEATURE:
<223> OTHER INFORMATION: synthetic primer

<400> SEQUENCE: 156
cgacacccag aatcgttgga ga                                              22

<210> SEQ ID NO 157
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 157
ggtgtcgtct ggtggatacg tcnnstccaa catcaacac                             39

<210> SEQ ID NO 158
<211> LENGTH: 21
<212> TYPE: DNA
<213> ORGANISM: Artificial
<220> FEATURE:
<223> OTHER INFORMATION: synthetic primer

<400> SEQUENCE: 158
gacgtatcca ccagacgaca c                                               21

<210> SEQ ID NO 159
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 159
tggtggatac gtcgactcca acnnsaacac caacgag                              37

<210> SEQ ID NO 160
<211> LENGTH: 21
<212> TYPE: DNA
<213> ORGANISM: Artificial
<220> FEATURE:
<223> OTHER INFORMATION: synthetic primer

<400> SEQUENCE: 160
gttggagtcg acgtatccac c                                               21

<210> SEQ ID NO 161
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 161
tggatacgtc gactccaaca tcnnsaccaa cgagggca                             38
```

```
<210> SEQ ID NO 162
<211> LENGTH: 22
<212> TYPE: DNA
<213> ORGANISM: Artificial
<220> FEATURE:
<223> OTHER INFORMATION: synthetic primer

<400> SEQUENCE: 162
gatgttggag tcgacgtatc ca                                              22

<210> SEQ ID NO 163
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 163
atacgtcgac tccaacatca acnnsaacga gggcaggac                            39

<210> SEQ ID NO 164
<211> LENGTH: 21
<212> TYPE: DNA
<213> ORGANISM: Artificial
<220> FEATURE:
<223> OTHER INFORMATION: synthetic primer

<400> SEQUENCE: 164
gttgatgttg gagtcgacgt a                                               21

<210> SEQ ID NO 165
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 165
tcgactccaa catcaacacc nnsgagggca ggactggcaa ggatg                     45

<210> SEQ ID NO 166
<211> LENGTH: 25
<212> TYPE: DNA
<213> ORGANISM: Artificial
<220> FEATURE:
<223> OTHER INFORMATION: synthetic primer

<400> SEQUENCE: 166
ggtgttgatg ttggagtcga cgtat                                           25

<210> SEQ ID NO 167
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 167
```
actccaacat caacaccaac nnsggcagga ctggcaagga tgtca        45

<210> SEQ ID NO 168
<211> LENGTH: 25
<212> TYPE: DNA
<213> ORGANISM: Artificial
<220> FEATURE:
<223> OTHER INFORMATION: synthetic primer

<400> SEQUENCE: 168
gttggtgttg atgttggagt cgacg        25

<210> SEQ ID NO 169
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 169
ctccaacatc aacaccaacg agnnsaggac tggcaag        37

<210> SEQ ID NO 170
<211> LENGTH: 23
<212> TYPE: DNA
<213> ORGANISM: Artificial
<220> FEATURE:
<223> OTHER INFORMATION: synthetic primer

<400> SEQUENCE: 170
ctcgttggtg ttgatgttgg agt        23

<210> SEQ ID NO 171
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 171
acatcaacac caacgagggc nnsactggca aggatgtcaa ctccg        45

<210> SEQ ID NO 172
<211> LENGTH: 26
<212> TYPE: DNA
<213> ORGANISM: Artificial
<220> FEATURE:
<223> OTHER INFORMATION: synthetic primer

<400> SEQUENCE: 172
gccctcgttg gtgttgatgt tggagt        26

<210> SEQ ID NO 173
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (23)..(24)
<223> OTHER INFORMATION: n is a, c, g, or t

<400> SEQUENCE: 173
ttccatccac accttcgatc ccnnscttgg ctgtgac                              37

<210> SEQ ID NO 174
<211> LENGTH: 21
<212> TYPE: DNA
<213> ORGANISM: Artificial
<220> FEATURE:
<223> OTHER INFORMATION: synthetic primer

<400> SEQUENCE: 174
gggatcgaag gtgtggatgg a                                              21

<210> SEQ ID NO 175
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 175
catccacacc ttcgatccca acnnsggctg tgacgca                              37

<210> SEQ ID NO 176
<211> LENGTH: 21
<212> TYPE: DNA
<213> ORGANISM: Artificial
<220> FEATURE:
<223> OTHER INFORMATION: synthetic primer

<400> SEQUENCE: 176
gttgggatcg aaggtgtgga t                                              21

<210> SEQ ID NO 177
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 177
ccacaccttc gatcccaacc ttnnstgtga cgcaggc                              37

<210> SEQ ID NO 178
<211> LENGTH: 21
<212> TYPE: DNA
<213> ORGANISM: Artificial
<220> FEATURE:
<223> OTHER INFORMATION: synthetic primer

<400> SEQUENCE: 178
aaggttggga tcgaaggtgt g                                              21

<210> SEQ ID NO 179
<211> LENGTH: 38
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 179
cgatcccaac cttggctgtg acnnsggcac cttccagc                             38

<210> SEQ ID NO 180
<211> LENGTH: 21
<212> TYPE: DNA
<213> ORGANISM: Artificial
<220> FEATURE:
<223> OTHER INFORMATION: synthetic primer

<400> SEQUENCE: 180
gtcacagcca aggttgggat c                                               21

<210> SEQ ID NO 181
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 181
tcccaacctt ggctgtgacg cannsacctt ccagcca                              37

<210> SEQ ID NO 182
<211> LENGTH: 21
<212> TYPE: DNA
<213> ORGANISM: Artificial
<220> FEATURE:
<223> OTHER INFORMATION: synthetic primer

<400> SEQUENCE: 182
tgcgtcacag ccaaggttgg g                                               21

<210> SEQ ID NO 183
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 183
aggcaccttc cagccatgca gtnnsaaagc gctctcc                              37

<210> SEQ ID NO 184
<211> LENGTH: 21
<212> TYPE: DNA
<213> ORGANISM: Artificial
<220> FEATURE:
<223> OTHER INFORMATION: synthetic primer

<400> SEQUENCE: 184
actgcatggc tggaaggtgc c                                               21
```

```
<210> SEQ ID NO 185
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 185
caaagcgctc tccaacctca agnnsgttgt cgactcct                    38

<210> SEQ ID NO 186
<211> LENGTH: 21
<212> TYPE: DNA
<213> ORGANISM: Artificial
<220> FEATURE:
<223> OTHER INFORMATION: synthetic primer

<400> SEQUENCE: 186
cttgaggttg gagagcgctt t                                      21

<210> SEQ ID NO 187
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 187
ggttgttgtc gactccttcc gcnnsatcta cggcgtg                     37

<210> SEQ ID NO 188
<211> LENGTH: 21
<212> TYPE: DNA
<213> ORGANISM: Artificial
<220> FEATURE:
<223> OTHER INFORMATION: synthetic primer

<400> SEQUENCE: 188
gcggaaggag tcgacaacaa c                                      21

<210> SEQ ID NO 189
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 189
ttgtcgactc cttccgctcc nnstacggcg tgaacaaggg cattc            45

<210> SEQ ID NO 190
<211> LENGTH: 25
<212> TYPE: DNA
<213> ORGANISM: Artificial
<220> FEATURE:
<223> OTHER INFORMATION: synthetic primer

<400> SEQUENCE: 190
```

```
ggagcggaag gagtcgacaa caacc                                          25

<210> SEQ ID NO 191
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 191
actccttccg ctccatctac nnsgtgaaca agggcattcc tgccg                    45

<210> SEQ ID NO 192
<211> LENGTH: 25
<212> TYPE: DNA
<213> ORGANISM: Artificial
<220> FEATURE:
<223> OTHER INFORMATION: synthetic primer

<400> SEQUENCE: 192
gtagatggag cggaaggagt cgaca                                          25

<210> SEQ ID NO 193
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 193
gctccatcta cggcgtgaac nnsggcattc ctgccggtgc tgccg                    45

<210> SEQ ID NO 194
<211> LENGTH: 25
<212> TYPE: DNA
<213> ORGANISM: Artificial
<220> FEATURE:
<223> OTHER INFORMATION: synthetic primer

<400> SEQUENCE: 194
gttcacgccg tagatggagc ggaag                                          25

<210> SEQ ID NO 195
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 195
ctacggcgtg aacaagggca ttnnsgccgg tgctgccg                            38

<210> SEQ ID NO 196
<211> LENGTH: 21
<212> TYPE: DNA
<213> ORGANISM: Artificial
```

```
<220> FEATURE:
<223> OTHER INFORMATION: synthetic primer

<400> SEQUENCE: 196
aatgcccttg ttcacgccgt a                                              21

<210> SEQ ID NO 197
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 197
cggcgtgaac aagggcattc ctnnsggtgc tgccgtc                             37

<210> SEQ ID NO 198
<211> LENGTH: 21
<212> TYPE: DNA
<213> ORGANISM: Artificial
<220> FEATURE:
<223> OTHER INFORMATION: synthetic primer

<400> SEQUENCE: 198
aggaatgccc ttgttcacgc c                                              21

<210> SEQ ID NO 199
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 199
gaacaagggc attcctgccg gtnnsgccgt cgccatt                             37

<210> SEQ ID NO 200
<211> LENGTH: 21
<212> TYPE: DNA
<213> ORGANISM: Artificial
<220> FEATURE:
<223> OTHER INFORMATION: synthetic primer

<400> SEQUENCE: 200
accggcagga atgcccttgt t                                              21

<210> SEQ ID NO 201
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 201
gtgctgccgt cgccattggc nnstatgcag aggatgtgta ctaca                    45
```

```
<210> SEQ ID NO 202
<211> LENGTH: 25
<212> TYPE: DNA
<213> ORGANISM: Artificial
<220> FEATURE:
<223> OTHER INFORMATION: synthetic primer

<400> SEQUENCE: 202
gccaatggcg acggcagcac cggca                                          25

<210> SEQ ID NO 203
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 203
ctgccgtcgc cattggccgg nnsgcagagg atgtgtacta caacg                    45

<210> SEQ ID NO 204
<211> LENGTH: 25
<212> TYPE: DNA
<213> ORGANISM: Artificial
<220> FEATURE:
<223> OTHER INFORMATION: synthetic primer

<400> SEQUENCE: 204
ccggccaatg gcgacggcag caccg                                          25

<210> SEQ ID NO 205
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 205
tgccgtcgcc attggccggt atnnsgagga tgtgtac                             37

<210> SEQ ID NO 206
<211> LENGTH: 21
<212> TYPE: DNA
<213> ORGANISM: Artificial
<220> FEATURE:
<223> OTHER INFORMATION: synthetic primer

<400> SEQUENCE: 206
ataccggcca atggcgacgg c                                              21

<210> SEQ ID NO 207
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 207
```

```
ccattggccg gtatgcagag nnsgtgtact acaacggcaa ccctt          45
```

<210> SEQ ID NO 208
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 208

```
ccattggccg gtatgcagag nnsgtgtact acaacggcaa ccctt          45
```

<210> SEQ ID NO 209
<211> LENGTH: 25
<212> TYPE: DNA
<213> ORGANISM: Artificial
<220> FEATURE:
<223> OTHER INFORMATION: synthetic primer

<400> SEQUENCE: 209

```
ctctgcatac cggccaatgg cgacg                                25
```

<210> SEQ ID NO 210
<211> LENGTH: 25
<212> TYPE: DNA
<213> ORGANISM: Artificial
<220> FEATURE:
<223> OTHER INFORMATION: synthetic primer

<400> SEQUENCE: 210

```
ctctgcatac cggccaatgg cgacg                                25
```

<210> SEQ ID NO 211
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 211

```
ttggccggta tgcagaggat nnstactaca acggcaaccc ttggt          45
```

<210> SEQ ID NO 212
<211> LENGTH: 25
<212> TYPE: DNA
<213> ORGANISM: Artificial
<220> FEATURE:
<223> OTHER INFORMATION: synthetic primer

<400> SEQUENCE: 212

```
atcctctgca taccggccaa tggcg                                25
```

<210> SEQ ID NO 213
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (21)..(22)
<223> OTHER INFORMATION: n is a, c, g, or t

<400> SEQUENCE: 213
gccggtatgc agaggatgtg nnstacaacg gcaacccttg gtatc              45

<210> SEQ ID NO 214
<211> LENGTH: 25
<212> TYPE: DNA
<213> ORGANISM: Artificial
<220> FEATURE:
<223> OTHER INFORMATION: synthetic primer

<400> SEQUENCE: 214
cacatcctct gcataccggc caatg                                    25

<210> SEQ ID NO 215
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 215
ggtatgcaga ggatgtgtac nnsaacggca acccttggta tcttg              45

<210> SEQ ID NO 216
<211> LENGTH: 27
<212> TYPE: DNA
<213> ORGANISM: Artificial
<220> FEATURE:
<223> OTHER INFORMATION: synthetic primer

<400> SEQUENCE: 216
gtacacatcc tctgcatacc ggccaat                                  27

<210> SEQ ID NO 217
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 217
atgcagagga tgtgtactac nnsggcaacc cttggtatct tgcta              45

<210> SEQ ID NO 218
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 218
atgcagagga tgtgtactac nnsggcaacc cttggtatct tgcta              45
```

```
<210> SEQ ID NO 219
<211> LENGTH: 26
<212> TYPE: DNA
<213> ORGANISM: Artificial
<220> FEATURE:
<223> OTHER INFORMATION: synthetic primer

<400> SEQUENCE: 219
gtagtacaca tcctctgcat accggc                                            26

<210> SEQ ID NO 220
<211> LENGTH: 26
<212> TYPE: DNA
<213> ORGANISM: Artificial
<220> FEATURE:
<223> OTHER INFORMATION: synthetic primer

<400> SEQUENCE: 220
gtagtacaca tcctctgcat accggc                                            26

<210> SEQ ID NO 221
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 221
tgtactacaa cggcaaccct nnstatcttg ctacatttgc tgctg                       45

<210> SEQ ID NO 222
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 222
tgtactacaa cggcaaccct nnstatcttg ctacatttgc tgctg                       45

<210> SEQ ID NO 223
<211> LENGTH: 25
<212> TYPE: DNA
<213> ORGANISM: Artificial
<220> FEATURE:
<223> OTHER INFORMATION: synthetic primer

<400> SEQUENCE: 223
agggttgccg ttgtagtaca catcc                                             25

<210> SEQ ID NO 224
<211> LENGTH: 25
<212> TYPE: DNA
<213> ORGANISM: Artificial
<220> FEATURE:
<223> OTHER INFORMATION: synthetic primer

<400> SEQUENCE: 224
agggttgccg ttgtagtaca catcc                                             25
```

```
<210> SEQ ID NO 225
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 225
gcagctgtac gatgccatct acnnstggaa gaagacg                              37

<210> SEQ ID NO 226
<211> LENGTH: 21
<212> TYPE: DNA
<213> ORGANISM: Artificial
<220> FEATURE:
<223> OTHER INFORMATION: synthetic primer

<400> SEQUENCE: 226
gtagatggca tcgtacagct g                                               21

<210> SEQ ID NO 227
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 227
acgatgccat ctacgtctgg nnsaagacgg gctccatcac ggtga                     45

<210> SEQ ID NO 228
<211> LENGTH: 25
<212> TYPE: DNA
<213> ORGANISM: Artificial
<220> FEATURE:
<223> OTHER INFORMATION: synthetic primer

<400> SEQUENCE: 228
ccagacgtag atggcatcgt acagc                                           25

<210> SEQ ID NO 229
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 229
atgccatcta cgtctggaag nnsacgggct ccatcacggt gaccg                     45

<210> SEQ ID NO 230
<211> LENGTH: 28
<212> TYPE: DNA
<213> ORGANISM: Artificial
<220> FEATURE:
<223> OTHER INFORMATION: synthetic primer

<400> SEQUENCE: 230
```
cttccagacg tagatggcat cgtacagc          28

<210> SEQ ID NO 231
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (24)..(25)
<223> OTHER INFORMATION: n is a, c, g, or t

<400> SEQUENCE: 231
atgccatcta cgtctggaag aagnnsggct ccatcacg          38

<210> SEQ ID NO 232
<211> LENGTH: 21
<212> TYPE: DNA
<213> ORGANISM: Artificial
<220> FEATURE:
<223> OTHER INFORMATION: synthetic primer

<400> SEQUENCE: 232
cttcttccag acgtagatgg c          21

<210> SEQ ID NO 233
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 233
ctacgtctgg aagaagacgg gcnnsatcac ggtgacc          37

<210> SEQ ID NO 234
<211> LENGTH: 22
<212> TYPE: DNA
<213> ORGANISM: Artificial
<220> FEATURE:
<223> OTHER INFORMATION: synthetic primer

<400> SEQUENCE: 234
gcccgtcttc ttccagacgt ag          22

<210> SEQ ID NO 235
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 235
ctggaagaag acgggctcca tcnnsgtgac cgccacctc          39

<210> SEQ ID NO 236
<211> LENGTH: 21
<212> TYPE: DNA
<213> ORGANISM: Artificial

```
<220> FEATURE:
<223> OTHER INFORMATION: synthetic primer

<400> SEQUENCE: 236
gatggagccc gtcttcttcc a                                          21

<210> SEQ ID NO 237
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 237
gacgggctcc atcacggtga ccnnsacctc cctggcc                         37

<210> SEQ ID NO 238
<211> LENGTH: 21
<212> TYPE: DNA
<213> ORGANISM: Artificial
<220> FEATURE:
<223> OTHER INFORMATION: synthetic primer

<400> SEQUENCE: 238
ggtcaccgtg atggagcccg t                                          21

<210> SEQ ID NO 239
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 239
gctccatcac ggtgaccgcc nnstccctgg ccttcttcca ggagc                45

<210> SEQ ID NO 240
<211> LENGTH: 25
<212> TYPE: DNA
<213> ORGANISM: Artificial
<220> FEATURE:
<223> OTHER INFORMATION: synthetic primer

<400> SEQUENCE: 240
ggcggtcacc gtgatggagc ccgtc                                      25

<210> SEQ ID NO 241
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 241
ccacctccct ggccttcttc nnsgagcttg ttcctggcgt gacgg                45
```

```
<210> SEQ ID NO 242
<211> LENGTH: 25
<212> TYPE: DNA
<213> ORGANISM: Artificial
<220> FEATURE:
<223> OTHER INFORMATION: synthetic primer

<400> SEQUENCE: 242
gaagaaggcc agggaggtgg cggtc                                              25

<210> SEQ ID NO 243
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 243
cctggccttc ttccaggagc ttnnscctgg cgtgacg                                 37

<210> SEQ ID NO 244
<211> LENGTH: 21
<212> TYPE: DNA
<213> ORGANISM: Artificial
<220> FEATURE:
<223> OTHER INFORMATION: synthetic primer

<400> SEQUENCE: 244
aagctcctgg aagaaggcca g                                                  21

<210> SEQ ID NO 245
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 245
cttcttccag gagcttgttc ctnnsgtgac ggccggg                                 37

<210> SEQ ID NO 246
<211> LENGTH: 21
<212> TYPE: DNA
<213> ORGANISM: Artificial
<220> FEATURE:
<223> OTHER INFORMATION: synthetic primer

<400> SEQUENCE: 246
aggaacaagc tcctggaaga a                                                  21

<210> SEQ ID NO 247
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 247
```

```
aggagcttgt tcctggcgtg nnsgccggga cctactccag cagct          45

<210> SEQ ID NO 248
<211> LENGTH: 25
<212> TYPE: DNA
<213> ORGANISM: Artificial
<220> FEATURE:
<223> OTHER INFORMATION: synthetic primer

<400> SEQUENCE: 248
cacgccagga acaagctcct ggaag                                25

<210> SEQ ID NO 249
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 249
ggagcttgtt cctggcgtga cgnnsgggac ctactcc                   37

<210> SEQ ID NO 250
<211> LENGTH: 21
<212> TYPE: DNA
<213> ORGANISM: Artificial
<220> FEATURE:
<223> OTHER INFORMATION: synthetic primer

<400> SEQUENCE: 250
cgtcacgcca ggaacaagct c                                    21

<210> SEQ ID NO 251
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 251
gcgtgacggc cgggacctac nnsagcagct cttcgacctt tacca          45

<210> SEQ ID NO 252
<211> LENGTH: 25
<212> TYPE: DNA
<213> ORGANISM: Artificial
<220> FEATURE:
<223> OTHER INFORMATION: synthetic primer

<400> SEQUENCE: 252
gtaggtcccg gccgtcacgc cagga                                25

<210> SEQ ID NO 253
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
```

```
<222> LOCATION: (21)..(22)
<223> OTHER INFORMATION: n is a, c, g, or t

<400> SEQUENCE: 253
tgacggccgg gacctactcc nnsagctctt cgacctttac caaca        45

<210> SEQ ID NO 254
<211> LENGTH: 25
<212> TYPE: DNA
<213> ORGANISM: Artificial
<220> FEATURE:
<223> OTHER INFORMATION: synthetic primer

<400> SEQUENCE: 254
ggagtaggtc ccggccgtca cgcca                              25

<210> SEQ ID NO 255
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 255
ctccagcagc tcttcgacct ttnnsaacat catcaacg                38

<210> SEQ ID NO 256
<211> LENGTH: 21
<212> TYPE: DNA
<213> ORGANISM: Artificial
<220> FEATURE:
<223> OTHER INFORMATION: synthetic primer

<400> SEQUENCE: 256
aaaggtcgaa gagctgctgg a                                  21

<210> SEQ ID NO 257
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 257
gcagctcttc gacctttacc nnsatcatca acgccgtctc gacat        45

<210> SEQ ID NO 258
<211> LENGTH: 25
<212> TYPE: DNA
<213> ORGANISM: Artificial
<220> FEATURE:
<223> OTHER INFORMATION: synthetic primer

<400> SEQUENCE: 258
ggtaaaggtc gaagagctgc tggag                              25

<210> SEQ ID NO 259
<211> LENGTH: 37
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 259
ttcgaccttt accaacatca tcnnsgccgt ctcgaca                             37

<210> SEQ ID NO 260
<211> LENGTH: 21
<212> TYPE: DNA
<213> ORGANISM: Artificial
<220> FEATURE:
<223> OTHER INFORMATION: synthetic primer

<400> SEQUENCE: 260
gatgatgttg gtaaaggtcg a                                              21

<210> SEQ ID NO 261
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 261
taccaacatc atcaacgccg tcnnsacata cgccgat                             37

<210> SEQ ID NO 262
<211> LENGTH: 21
<212> TYPE: DNA
<213> ORGANISM: Artificial
<220> FEATURE:
<223> OTHER INFORMATION: synthetic primer

<400> SEQUENCE: 262
gacggcgttg atgatgttgg t                                              21

<210> SEQ ID NO 263
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 263
gacatacgcc gatggcttcc tcnnsgaggc tgccaag                             37

<210> SEQ ID NO 264
<211> LENGTH: 21
<212> TYPE: DNA
<213> ORGANISM: Artificial
<220> FEATURE:
<223> OTHER INFORMATION: synthetic primer

<400> SEQUENCE: 264
gaggaagcca tcggcgtatg t                                              21
```

```
<210> SEQ ID NO 265
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 265
atacgccgat ggcttcctca gcnnsgctgc caagtac                              37

<210> SEQ ID NO 266
<211> LENGTH: 21
<212> TYPE: DNA
<213> ORGANISM: Artificial
<220> FEATURE:
<223> OTHER INFORMATION: synthetic primer

<400> SEQUENCE: 266
gctgaggaag ccatcggcgt a                                              21

<210> SEQ ID NO 267
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 267
cgatggcttc ctcagcgagg ctnnsaagta cgtcccc                              37

<210> SEQ ID NO 268
<211> LENGTH: 21
<212> TYPE: DNA
<213> ORGANISM: Artificial
<220> FEATURE:
<223> OTHER INFORMATION: synthetic primer

<400> SEQUENCE: 268
agcctcgctg aggaagccat c                                              21

<210> SEQ ID NO 269
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 269
tggcttcctc agcgaggctg ccnnstacgt ccccgcc                              37

<210> SEQ ID NO 270
<211> LENGTH: 21
<212> TYPE: DNA
<213> ORGANISM: Artificial
<220> FEATURE:
<223> OTHER INFORMATION: synthetic primer

<400> SEQUENCE: 270
```
ggcagcctcg ctgaggaagc c                                         21

<210> SEQ ID NO 271
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 271
tcctcagcga ggctgccaag nnsgtccccg ccgacggttc gctgg               45

<210> SEQ ID NO 272
<211> LENGTH: 25
<212> TYPE: DNA
<213> ORGANISM: Artificial
<220> FEATURE:
<223> OTHER INFORMATION: synthetic primer

<400> SEQUENCE: 272
cttggcagcc tcgctgagga agcca                                     25

<210> SEQ ID NO 273
<211> LENGTH: 46
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 273
aggctgccaa gtacgtcccc nnsgacggtt cgctggccga gcagtt              46

<210> SEQ ID NO 274
<211> LENGTH: 25
<212> TYPE: DNA
<213> ORGANISM: Artificial
<220> FEATURE:
<223> OTHER INFORMATION: synthetic primer

<400> SEQUENCE: 274
ggggacgtac ttggcagcct cgctg                                     25

<210> SEQ ID NO 275
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 275
agtacgtccc cgccgacggt nnsctggccg agcagtttga ccgca               45

<210> SEQ ID NO 276
<211> LENGTH: 26
<212> TYPE: DNA
<213> ORGANISM: Artificial

```
<220> FEATURE:
<223> OTHER INFORMATION: synthetic primer

<400> SEQUENCE: 276
accgtcggcg gggacgtact tggcag                                              26

<210> SEQ ID NO 277
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 277
cgctggccga gcagtttgac nnsaacagcg gcactccgct gtctg                         45

<210> SEQ ID NO 278
<211> LENGTH: 25
<212> TYPE: DNA
<213> ORGANISM: Artificial
<220> FEATURE:
<223> OTHER INFORMATION: synthetic primer

<400> SEQUENCE: 278
gtcaaactgc tcggccagcg aaccg                                               25

<210> SEQ ID NO 279
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 279
tggccgagca gtttgaccgc nnsagcggca ctccgctgtc tgcgc                         45

<210> SEQ ID NO 280
<211> LENGTH: 25
<212> TYPE: DNA
<213> ORGANISM: Artificial
<220> FEATURE:
<223> OTHER INFORMATION: synthetic primer

<400> SEQUENCE: 280
gcggtcaaac tgctcggcca gcgaa                                               25

<210> SEQ ID NO 281
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 281
ggccgagcag tttgaccgca acnnsggcac tccgctg                                  37
```

```
<210> SEQ ID NO 282
<211> LENGTH: 21
<212> TYPE: DNA
<213> ORGANISM: Artificial
<220> FEATURE:
<223> OTHER INFORMATION: synthetic primer

<400> SEQUENCE: 282
gttgcggtca aactgctcgg c                                              21

<210> SEQ ID NO 283
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 283
agtttgaccg caacagcggc nnsccgctgt ctgcgcttca cctga                    45

<210> SEQ ID NO 284
<211> LENGTH: 25
<212> TYPE: DNA
<213> ORGANISM: Artificial
<220> FEATURE:
<223> OTHER INFORMATION: synthetic primer

<400> SEQUENCE: 284
gccgctgttg cggtcaaact gctcg                                          25

<210> SEQ ID NO 285
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 285
gcaacagcgg cactccgctg nnsgcgcttc acctgacgtg gtcgt                    45

<210> SEQ ID NO 286
<211> LENGTH: 25
<212> TYPE: DNA
<213> ORGANISM: Artificial
<220> FEATURE:
<223> OTHER INFORMATION: synthetic primer

<400> SEQUENCE: 286
cagcggagtg ccgctgttgc ggtca                                          25

<210> SEQ ID NO 287
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 287
```
cagcggcact ccgctgtctg cgnnscacct gacgtggt                    38

<210> SEQ ID NO 288
<211> LENGTH: 21
<212> TYPE: DNA
<213> ORGANISM: Artificial
<220> FEATURE:
<223> OTHER INFORMATION: synthetic primer

<400> SEQUENCE: 288
cgcagacagc ggagtgccgc t                                      21

<210> SEQ ID NO 289
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 289
gcactccgct gtctgcgctt nnsctgacgt ggtcgtacgc ctcgt            45

<210> SEQ ID NO 290
<211> LENGTH: 25
<212> TYPE: DNA
<213> ORGANISM: Artificial
<220> FEATURE:
<223> OTHER INFORMATION: synthetic primer

<400> SEQUENCE: 290
aagcgcagac agcggagtgc cgctg                                  25

<210> SEQ ID NO 291
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 291
tgtctgcgct tcacctgacg nnstcgtacg cctcgttctt gacag            45

<210> SEQ ID NO 292
<211> LENGTH: 25
<212> TYPE: DNA
<213> ORGANISM: Artificial
<220> FEATURE:
<223> OTHER INFORMATION: synthetic primer

<400> SEQUENCE: 292
cgtcaggtga agcgcagaca gcgga                                  25

<210> SEQ ID NO 293
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (23)..(24)
<223> OTHER INFORMATION: n is a, c, g, or t

<400> SEQUENCE: 293
gtacgcctcg ttcttgacag ccnnsgcccg tcgggct                              37

<210> SEQ ID NO 294
<211> LENGTH: 21
<212> TYPE: DNA
<213> ORGANISM: Artificial
<220> FEATURE:
<223> OTHER INFORMATION: synthetic primer

<400> SEQUENCE: 294
ggctgtcaag aacgaggcgt a                                               21

<210> SEQ ID NO 295
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 295
cgcctcgttc ttgacagcca cgnnscgtcg gctggc                               37

<210> SEQ ID NO 296
<211> LENGTH: 21
<212> TYPE: DNA
<213> ORGANISM: Artificial
<220> FEATURE:
<223> OTHER INFORMATION: synthetic primer

<400> SEQUENCE: 296
cgtggctgtc aagaacgagg c                                               21

<210> SEQ ID NO 297
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 297
tcttgacagc cacggcccgt nnsgctggca tcgtgccccc ctcgt                     45

<210> SEQ ID NO 298
<211> LENGTH: 25
<212> TYPE: DNA
<213> ORGANISM: Artificial
<220> FEATURE:
<223> OTHER INFORMATION: synthetic primer

<400> SEQUENCE: 298
acgggccgtg gctgtcaaga acgag                                           25

<210> SEQ ID NO 299
<211> LENGTH: 45
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 299
ccacggcccg tcgggctggc nnsgtgcccc cctcgtgggc caaca            45

<210> SEQ ID NO 300
<211> LENGTH: 25
<212> TYPE: DNA
<213> ORGANISM: Artificial
<220> FEATURE:
<223> OTHER INFORMATION: synthetic primer

<400> SEQUENCE: 300
gccagcccga cgggccgtgg ctgtc                                  25

<210> SEQ ID NO 301
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 301
tggcatcgtg cccccctcgt ggnnsaacag cagcgct                     37

<210> SEQ ID NO 302
<211> LENGTH: 21
<212> TYPE: DNA
<213> ORGANISM: Artificial
<220> FEATURE:
<223> OTHER INFORMATION: synthetic primer

<400> SEQUENCE: 302
ccacgagggg ggcacgatgc c                                      21

<210> SEQ ID NO 303
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 303
catcgtgccc ccctcgtggg ccnnsagcag cgctagc                     37

<210> SEQ ID NO 304
<211> LENGTH: 21
<212> TYPE: DNA
<213> ORGANISM: Artificial
<220> FEATURE:
<223> OTHER INFORMATION: synthetic primer

<400> SEQUENCE: 304
ggcccacgag gggggcacga t                                      21
```

```
<210> SEQ ID NO 305
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 305 cgtgccccc tcgtgggcca acnnsagcgc tagcacg                          37

<210> SEQ ID NO 306
<211> LENGTH: 21
<212> TYPE: DNA
<213> ORGANISM: Artificial
<220> FEATURE:
<223> OTHER INFORMATION: synthetic primer

<400> SEQUENCE: 306
gttggcccac gagggggca c                                           21

<210> SEQ ID NO 307
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (23)..(24)
<223> OTHER INFORMATION: n is a, c, g, or t

<400> SEQUENCE: 307
gtgggccaac agcagcgcta gcnnsatccc ctcgacg                         37

<210> SEQ ID NO 308
<211> LENGTH: 588
<212> TYPE: PRT
<213> ORGANISM: Talaromyces sp.

<400> SEQUENCE: 308

Gly Ser Leu Asp Ser Phe Leu Ala Thr Glu Thr Pro Ile Ala Leu Gln
1               5                   10                  15

Gly Val Leu Asn Asn Ile Gly Pro Asn Gly Ala Asp Val Ala Gly Ala
            20                  25                  30

Ser Ala Gly Ile Val Val Ala Ser Pro Ser Arg Ser Asp Pro Asp Tyr
        35                  40                  45

Phe Tyr Ser Trp Thr Arg Asp Ala Ala Leu Thr Ala Lys Tyr Leu Val
    50                  55                  60

Asp Ala Phe Ile Ala Gly Asn Lys Asp Leu Glu Gln Thr Ile Gln Glu
65                  70                  75                  80

Tyr Ile Ser Ala Gln Ala Gln Val Gln Thr Ile Ser Asn Pro Ser Gly
                85                  90                  95

Asp Leu Ser Thr Gly Gly Leu Gly Glu Pro Lys Phe Asn Val Asn Glu
            100                 105                 110

Thr Ala Phe Thr Gly Pro Trp Gly Arg Pro Gln Arg Asp Gly Pro Ala
        115                 120                 125

Leu Arg Ala Thr Ala Leu Ile Ala Tyr Ala Asn Tyr Leu Ile Asp Asn
```

```
            130                 135                 140
Gly Gln Ala Ser Thr Ala Asp Glu Ile Ile Trp Pro Ile Val Gln Asn
145                 150                 155                 160

Asp Leu Ser Tyr Val Thr Gln Tyr Trp Asn Ser Ser Thr Phe Asp Leu
                165                 170                 175

Trp Glu Glu Val Glu Gly Ser Ser Phe Phe Thr Thr Ala Val Gln His
                180                 185                 190

Arg Ala Leu Val Glu Gly Asn Ala Leu Ala Thr Arg Leu Asn His Thr
                195                 200                 205

Cys Pro Asn Cys Val Ser Gln Ala Pro Gln Val Leu Cys Phe Leu Gln
210                 215                 220

Ser Tyr Trp Thr Gly Ser Tyr Val Leu Ala Asn Phe Gly Gly Ser Gly
225                 230                 235                 240

Arg Ser Gly Lys Asp Val Asn Ser Ile Leu Gly Ser Ile His Thr Phe
                245                 250                 255

Asp Pro Ala Gly Gly Cys Asp Asp Ser Thr Phe Gln Pro Cys Ser Ala
                260                 265                 270

Arg Ala Leu Ala Asn His Lys Val Val Thr Asp Ser Phe Arg Ser Val
                275                 280                 285

Tyr Ala Val Asn Ser Gly Ile Ala Glu Gly Ser Ala Val Ala Val Gly
                290                 295                 300

Arg Tyr Pro Glu Asp Val Tyr Gln Gly Gly Asn Pro Trp Tyr Leu Ala
305                 310                 315                 320

Thr Ala Ala Ala Glu Gln Leu Tyr Asp Ala Ile Tyr Gln Trp Asn
                325                 330                 335

Lys Ile Gly Ser Ile Ser Ile Thr Asp Val Ser Leu Ala Phe Phe Gln
                340                 345                 350

Asp Ile Tyr Pro Ser Ala Ala Val Gly Thr Tyr Asn Ser Gly Ser Ser
                355                 360                 365

Thr Phe Asn Asp Ile Ile Ser Ala Val Gln Thr Tyr Ala Asp Gly Tyr
                370                 375                 380

Leu Ser Ile Ile Glu Lys Tyr Thr Pro Ser Asp Gly Ser Leu Thr Glu
385                 390                 395                 400

Gln Phe Ser Arg Ser Asp Gly Thr Pro Leu Ser Ala Ser Gly Leu Thr
                405                 410                 415

Trp Ser Tyr Ala Ser Leu Leu Thr Ala Ala Ala Arg Arg Gln Ser Ile
                420                 425                 430

Val Pro Ala Ser Trp Gly Glu Ser Ser Ala Ser Ser Val Pro Ala Val
                435                 440                 445

Cys Ser Ala Thr Ser Ala Thr Gly Pro Tyr Ser Thr Ala Thr Asn Thr
450                 455                 460

Ala Trp Pro Ser Ser Gly Ser Gly Pro Ser Thr Thr Thr Ser Val Pro
465                 470                 475                 480

Cys Thr Thr Pro Thr Ser Val Ala Val Thr Phe Asp Glu Ile Val Ser
                485                 490                 495

Thr Thr Tyr Gly Glu Thr Ile Tyr Leu Ala Gly Ser Ile Pro Glu Leu
                500                 505                 510

Gly Asn Trp Ser Pro Ser Ser Ala Ile Pro Leu Arg Ala Asp Ala Tyr
                515                 520                 525

Thr Ser Ser Asn Pro Leu Trp Tyr Val Thr Leu Asn Leu Pro Ala Gly
                530                 535                 540

Thr Ser Phe Glu Tyr Lys Phe Phe Lys Lys Glu Thr Asp Gly Thr Ile
545                 550                 555                 560
```

-continued

```
Val Trp Glu Asp Asp Pro Asn Arg Ser Tyr Thr Val Pro Ala Tyr Cys
            565                 570                 575

Gly Gln Thr Thr Ala Ile Leu Asp Asp Ser Trp Gln
            580                 585
```

GLUCOAMYLASE VARIANTS WITH ALTERED PROPERTIES

CROSS-REFERENCE TO RELATED APPLICATIONS

This application claims priority to International patent application PCT/US07/21683, filed Oct. 9, 2007, which claims priority to U.S. Provisional application 60/850,431, filed Oct. 10, 2006, the contents of both are incorporated by reference in their entirety herein.

FIELD OF THE INVENTION

The present invention relates to variants of a parent glucoamylase having altered properties (e.g., improved thermostability and/or specific activity). In particular, the present invention provides compositions comprising the variant glucoamylases, including starch hydrolyzing compositions, animal feed compositions and cleaning compositions. The invention also relates to DNA constructs encoding the variants and methods of producing the glucoamylase variants in host cells.

BACKGROUND OF THE INVENTION

Glucoamylase enzymes (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin).

Glucoamylases are produced by numerous strains of bacteria, fungi, yeast and plants. Particularly interesting, and commercially important, glucoamylases are fungal enzymes that are extracellularly produced, for example from strains of *Aspergillus* (Svensson et al. (1983) *Carlsberg Res. Commun.* 48:529-544; Boel et al., (1984) *EMBO J.* 3:1097-1102; Hayashida et al., (1989) *Agric. Biol. Chem.* 53:923-929; U.S. Pat. No. 5,024,941; U.S. Pat. No. 4,794,175 and WO 88/09795); *Talaromyces* (U.S. Pat. No. 4,247,637; U.S. Pat. No. 6,255,084 and U.S. Pat. No. 6,620,924); *Rhizopus* (Ashikari et al., (1986) *Agric. Biol. Chem.* 50:957-964; Ashikari et al., (1989) *App. Microbiol. and Biotech.* 32:129-133 and U.S. Pat. No. 4,863,864); *Humicola* (WO 05/052148 and U.S. Pat. No. 4,618,579) and *Mucor* (Houghton-Larsen et al., (2003) *Appl. Microbiol. Biotechnol.* 62:210-217). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g. for producing glucose and other monosaccharides from starch). Glucoamylases are used to produce high fructose corn sweeteners, which comprise over 50% of the sweetener market in the United States. In general, glucoamylases may be, and commonly are, used with alpha amylases in starch hydrolyzing processes to hydrolyze starch to dextrins and then glucose. The glucose may then be converted to fructose by other enzymes (e.g. glucose isomerases); crystallized; or used in fermentations to produce numerous end products (e.g., ethanol, citric acid, lactic acid, succinate, ascorbic acid intermediates, glutamic acid, glycerol and 1,3-propanediol). Ethanol produced by using glucoamylases in the fermentation of starch and/or cellulose containing material may be used as a source of fuel or for alcoholic consumption.

Although glucoamylases have been used successfully in commercial applications for many years, a need still exists for new glucoamylases having altered properties.

SUMMARY OF THE INVENTION

In some aspects the present invention relates to isolated glucoamylase variants having one or more amino acid substitutions at a position corresponding to residue position: 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, 418, 430, 431, 433, 436, 442, 443, 444, 448 and 451 of SEQ ID NO: 2 or SEQ ID NO: 3 or an equivalent position in a parent glucoamylase. In some embodiments, the parent glucoamylase comprises the sequence of SEQ ID NOs: 1, 4, 5, 6, 7, 8, or 9. In some embodiments, a parent glucoamylase comprises SEQ ID NO: 2. In some embodiments, the parent glucoamylase is obtained from a *Trichoderma* spp., an *Aspergillus* spp., a *Humicola* spp., a *Penicillium* spp., a *Talaromyces* spp, or a *Schizosaccharmyces* spp. In further embodiments, the equivalent position in a parent is determined by sequence identity. In other embodiments, the parent glucoamylase has at least 80% sequence identity to SEQ ID NO: 2. In additional embodiments, the equivalent position in a parent is determined by structural identity to SEQ ID NOs: 2 or 3. In yet other embodiments of this aspect, the variant has a substitution in a position chosen from: T10D/F/G/K/L/M/P/R/S; L14E/H; N15D/N; P23A/G; F59A/G; K60F/H; N61D/I/L/V/N/W; R65A/C/G/I/K/M/S/V/Y; T67C/I/K/M/T; E68I/M/W; A72E/G/L/M/Q/R/W/Y; G73C/L/W; S97F/M/N/P/R/S/V/W/Y; L98H/M; A99C/L/M/N/P; S102A/C/I/L/M/N/R/V/W/Y; E110Q/S/W; L113E/N; K114C/D/E/L/M/Q/S/T/V; I133K/R/S/T; K140A/E/F/H/K/L/M/N/Q/R/S/V/W/Y; N144C/D/E/I/K; N145A/C/E/I/K/L/M/Q/R/V/W/Y; Y147A/M/R; S152H/M; N153C/D/K/L/W/Y; N164A/G; N182C/E/K/P/R; A204C/D/G/I/M/Q/T; T205A/D/H/I/K/M/N/P/Q/S/V/W/Y; S214P/T; V216C/G/H/K/N/Y; Q219D/G/H/N/P/S; W228A/F/G/H/I/L/M/Q/S/T/N/Y; V229E/I/M/N/Q; S230C/D/E/F/G/H/1/K/L/N/P/Q/R/T/V/Y; S231C/D/F/L/M/N/Q/R/S/V/Y; D236F/G/L/M/N/P/S/T/V; I239M/Q/S/V/W/Y; T241C/E/H/L/M/P/S/T/V; N242C/F/H/M/T/V/W; N263H/K/P; L264A/C/E/F/L/S; G265E/G/H/I/K/R/T; A268C/D/E/F/G/I/K/L/P/R/T/W; G269E; D276S; V284R/T/V/Y/A/E/F/H/K/N/P/W; P300K/R; A301E/K/L/P/S/W; A303C/D/F/H/I/K/L/N/R/T/V/W/Y; A311N/P/Q/S/Y; V338P/Q/S/Y; T342N/V; S344A/T; T346G/H/M/N/P/Q/Y; A349L/I/K/M/N/Q/R/W; G361H/L/R; A364M/W; N379A/C/D/G/I/M/P/S; S382A/N/P/V/W; S390A/Y; E391A/E/I/K/L/M/Q/R/V/W/Y; A393E/G/H/I/K/L/M/N/Q/R/S/T/V/W/Y; K394A/H/K/L/M/Q/R/S/T/V/W; S410E/H/N; L417A/D/E/F/G/I/K/Q/R/S/T/V/W/Y; H418E/M; T430A/E/F/G/H/I/K/M/N/Q/R/V; A431C/E/H/I/L/M/Q/R/S/W/Y; R433A/C/E/F/G/K/L/M/N/S/V/W/Y; I436E/F/G/H/K/P/R/S/T/V/Y; S444M/N/P/Q/R/T/V/W; T448F/G/I/P/Q/T/V; and S451E/H/K/L/Q/T of SEQ ID NO: 2 or SEQ ID NO:3 or an equivalent position in a parent glucoamylase.

In another aspect, the present invention relates to an isolated glucoamylase variant comprising one or more amino acid substitutions at a position corresponding to positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, 418, 430, 431, 433, 436, 442, 443, 444, 448 and 451 of SEQ ID NO: 2 or SEQ ID NO: 3. In one embodiment of this aspect, the glucoamylase variants comprise one or more amino acid substitutions corresponding to a position chosen from positions 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 300, 301, 303, 311, 338, 342, 344, 346, 349, 359, 361, 364, 379, 382, 390, 391, 393, 394, 410, 417, 418, 430, 431, 433, 442, 444, 448, and 451 of SEQ ID NO: 2 or 3. In other embodiments of this aspect, the glucoamylase variants comprise one or more amino acid substitutions at a position corresponding to positions 61, 67, 72, 97, 102, 133, 205, 219, 228, 230, 231, 239, 263, 268, 291, 342, 394, 430, 431 and 451 of SEQ ID NO: 2 or SEQ ID NO: 3. In yet further embodiments of this aspect, the glucoamylase variants have one or more amino acid substitutions corresponding to at least one of the following: T67M, A72Y, S97N, S102M, I133T, T205Q, Q219S, W228M, S230F, S230G, S230N, S230R, S231L, I239V, I239Y, N263P, A268C, A268G, A268K, S291A, T342V, K394S, T430K, A431Q, S451K of SEQ ID NO: 2 or SEQ ID NO:3.

In further aspects, the glucoamylase variants of the invention have an altered property compared to a parent glucoamylase. In some embodiments the altered property is an increase in specific activity compared to a glucoamylase comprising the sequence of SEQ ID NO: 2, SEQ ID NO: 3 or a parent glucoamylase having at least 80% sequence identity to SEQ ID NO: 2. In some embodiments, the glucoamylase variant has increased specific activity compared to the glucoamylase comprising SEQ ID NO: 2. In other embodiments of this aspect, the glucoamylase variants comprise one or more amino acid substitutions corresponding to a position chosen from positions: 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 300, 301, 303, 311, 338, 342, 344, 346, 349, 359, 361, 364, 379, 382, 390, 391, 393, 394, 410, 417, 418, 430, 431, 433, 442, 444, 448, and 451 of SEQ ID NO: 2 or 3.

In yet other aspects, the glucoamylase variants of the invention have increased thermo stability compared to a glucoamylase comprising the sequence of SEQ ID NO: 2, SEQ ID NO: 3 or a parent glucoamylase having at least 80% sequence identity to SEQ ID NO: 2. In some embodiments, the glucoamylase variant has increased thermo stability compared to the glucoamylase comprising SEQ ID NO: 2 or SEQ ID NO: 3. In some embodiments of this aspect, the glucoamylase variants of the invention comprise one or more amino acid substitutions corresponding to a position chosen from positions: 10, 15, 23, 42, 59, 60, 61, 68, 72, 73, 97, 98, 99, 102, 114, 133, 140, 144, 147, 152, 153, 164, 182, 204, 205, 214, 216, 228, 229, 230, 231, 236, 241, 242, 263, 264, 265, 268, 269, 276, 284, 291, 300, 301, 303, 311, 338, 342, 344, 346, 349, 359, 361, 364, 379, 382, 390, 391, 393, 394, 410, 417, 430, 431, 433, 436, 442, 443, 444, 448, and 451 of SEQ ID NO: 2 or SEQ ID NO: 3. In other embodiments of this aspect, the glucoamylase variants of the invention comprise one or more amino acid substitutions corresponding to a position chosen from positions: 10, 42, 68, 73, 97, 114, 153, 229, 231, 236, 264, 291, 301, 344, 361, 364, 417, and 433 of SEQ ID NO: 2 or SEQ ID NO: 3. In yet other embodiments of this aspect, the glucoamylase variants comprise one or more amino acid substitutions corresponding to a position chosen from positions 68, 73, 114, 153, 236, 344, 361, 364 and 433 of SEQ ID NO: 2 or SEQ ID NO: 3. In yet some embodiments of this aspect, the glucoamylase variants comprise one or more amino acid substitutions corresponding to at least one of the following: T10S, T42V, E68C, E68M, G73F, G73W, K114M, K114T, N153A, N153S, N153V, W228V, D236R, G361D, G361 E, G361P, G361Y, A364D, A364E, A364F, A364G, A364K, A365L, A365R, R433c, R433G, R433L, R433N, R433S, R433V, and I436H of SEQ ID NO: 2 or SEQ ID NO: 3.

In yet additional aspects, the glucoamylase variants of the invention have increased specific activity and increased thermostability compared to a glucoamylase comprising the sequence of SEQ ID NO: 2, SEQ ID NO: 3 or a parent glucoamylase having at least 80% sequence identity to SEQ ID NO: 2. In some embodiments of this aspect, the glucoamylase variants of the invention comprise one or more amino acid substitutions corresponding to a position chosen from positions: 10, 15, 59, 61, 68, 72, 73, 97, 99, 102, 133, 140, 153, 182, 204, 205, 214, 228, 229, 230, 231, 236, 241, 242, 264, 265, 268, 275, 284, 291, 300, 301, 303, 311, 338, 344, 346, 359, 361, 364, 370, 382, 391, 393, 394, 410, 417, 430, 431, 433, 444, 448, and 451 of SEQ ID NO: 2 or SEQ ID NO: 3. In further embodiments of this aspect, the glucoamylase variants comprise one or more amino acid substitutions corresponding to a position chosen from position 228, 230, 231, 268, 291, 417, 433, and 451 of SEQ ID NO: 2 or SEQ ID NO:3. In additional embodiments of this aspect, the glucoamylase variants have one or more amino acid substitutions corresponding to at least one of the following: W228A, W228F, W228H, W228M, S230F, S230G, S230R, S231L, A268C, A268G, S291A, L417R, R433Y, and S451K of SEQ ID NO: 2 or SEQ ID NO:3.

In a further aspect, the invention relates to an isolated polynucleotide encoding any one of the glucoamylase variants encompassed by the invention. In some embodiments, the invention relates to a host cell comprising a polynucleotide encoding a glucoamylase encompassed by the invention.

In other aspects, the invention is related to enzyme compositions comprising one or more glucoamylase variants encompassed by the invention. In some embodiments the enzyme compositions will include additional enzymes such as one or more alpha amylases. In some embodiments, the enzyme compositions will be used in a starch conversion process, an alcohol fermentation process and/or an animal feed formulation.

In some aspects the invention relates to a method of producing a variant glucoamylase encompassed by the invention comprising transforming a host cell with a polynucleotide encoding a glucoamylase variant of the invention; culturing the host cell under conditions suitable for the expression and production of said glucoamylase variant and producing said variant. In some embodiments the glucoamylase variant is recovered from the culture.

BRIEF DESCRIPTION OF THE DRAWINGS

FIG. 1A illustrates a *Trichoderma reesei* glucoamylase (TrGA) having 632 amino acids (SEQ ID NO: 1). The signal peptide is underlined, the catalytic region (SEQ ID NO:3) starting with amino acid residues SVDDFI (SEQ ID NO:12) and having 453 amino acid residues is in bold; the linker region is in italics and the starch binding domain (SBD) is both italics and underlined. The mature protein which includes the catalytic domain (SEQ ID NO:3), linker region (SEQ ID NO:10) and starch binding domain (SEQ ID NO:11)

is represented by SEQ ID NO:2. FIG. 1B illustrates the cDNA (SEQ ID NO:4) which codes for the TrGA.

FIGS. 5A-5B illustrate an alignment comparison of the catalytic domains of parent glucoamylases including glucoamylase derived from *Aspergillus awamori* (AaGA) (SEQ ID NO:5); *Aspergillus niger* (AnGA) (SEQ ID NO:6); *Aspergillus oryzae* (AoGA) (SEQ ID NO:7); *Trichoderma reesei* (TrGA) (SEQ ID NO:3); *Humicola grisea* (HgGA) (SEQ ID NO:8); and *Hypocrea vinosa* (HvGA) (SEQ ID NO:9). Identical amino acids are indicated by an asterisk (*).

FIG. 5C illustrates the *Talaromyces glucoamylase* (TeGA) mature protein sequence (SEQ ID NO:308).

DETAILED DESCRIPTION OF THE INVENTION

I. Definitions

Figure 1C:
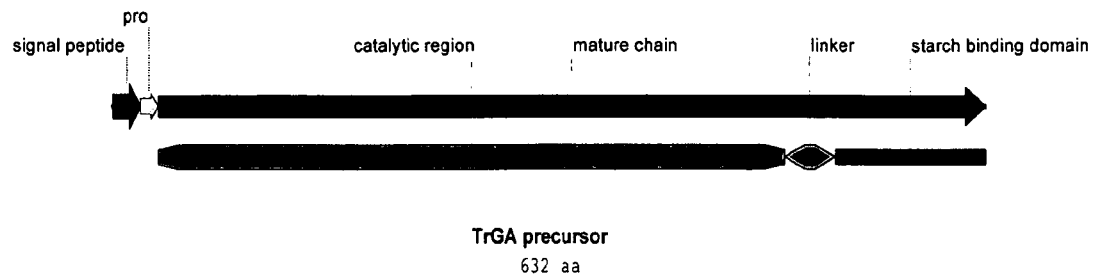
FIG. 1C illustrates the precursor and mature protein TrGA domains.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "glucoamylase (EC 3.2.1.3)" refers to an enzyme that catalyzes the release of D-glucose from the non-reducing ends of starch and related oligo- and polysaccharides.

As used herein, the term "parent" or "parent sequence" refers to a sequence that has sequence and/or structural identity with TrGA (e.g., SEQ ID NOs: 1, 2 and/or 3) and is a native or naturally occurring sequence in a host cell.

As used herein, the term "TrGA" refers to a *Trichoderma reesei* glucoamylase sequence having the mature protein sequence illustrated in SEQ ID NO:2, which includes the catalytic domain having the sequence illustrated in SEQ ID NO:3. The isolation, cloning and expression of the TrGA are described in WO 2006/060062 and U.S. Pat. Pub. No. 2006/0094080 published May 4, 2006 which are incorporated herein by reference. The TrGA is also considered a parent glucoamylase sequence. In some embodiments, the parent sequence refers to a TrGA that is the starting point for protein engineering. The numbering of the glucoamylase amino acids herein is based on the sequence of the TrGA glucoamylase sequence (SEQ ID NO: 2 and SEQ ID NO: 3).

The phrase "mature form of a protein or polypeptide" refers to the final functional form of the protein or polypeptide. To exemplify, a mature form of the TrGA includes the catalytic domain, linker region and starch binding domain having the amino acid sequence of SEQ ID NO:2.

The term "*Trichoderma* glucoamylase homologues" refers to parent glucoamylases having at least 80% amino acid sequence identity to the TrGA sequence (SEQ ID NO:1, SEQ ID NO:2 or SEQ ID NO:3) and which glucoamylases retain the functional characteristics of a glucoamylase.

As used herein, a "homologous sequence" means a nucleic acid or polypeptide sequence having at least 100%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to a nucleic acid sequence or polypeptide sequence when optimally aligned for comparison, wherein the function of the candidate nucleic acid sequence or polypeptide sequence is essentially the same as the nucleic acid sequence or polypeptide sequence said candidate homologous sequence is being compared with. In some embodiments, homologous sequences have between 85% and 100% sequence identity, while in other embodiments there is between 90% and 100% sequence identity, and in other embodiments, there is 95% and 100% sequence identity. In some embodiments, the candidate homologous sequence or parent is compared with the TrGA nucleic acid sequence or mature protein sequence. The sequence identity can be measured over the entire length of the parent or homologous sequence.

As used herein, the terms "glucoamylase variant", "variant" and "TrGA variant" are used in reference to glucoamylases that are similar to a parent glucoamylase sequence (e.g., the TrGA or *Trichoderma* glucoamylase homologues) but have at least one substitution, deletion or insertion in their amino acid sequence that makes them different in sequence from a parent glucoamylase. In some cases they have been manipulated/engineered to include at least one substitution, deletion or insertion in their amino acid sequence that makes them different in sequence from a parent glucoamylase.

As used herein the term "catalytic domain" refers to a structural region of a polypeptide, which contains the active site for substrate hydrolysis.

The term "linker" refers to a short amino acid sequence generally having between 3 and 40 amino acid residues that covalently bind an amino acid sequence comprising a starch binding domain with an amino acid sequence comprising a catalytic domain.

The term "starch binding domain" refers to an amino acid sequence that binds preferentially to a starch substrate.

As used herein, the terms "mutant sequence" and "mutant gene" are used interchangeably and refer to a polynucleotide sequence that has an alteration in at least one codon occurring in a host cell's parent sequence. The expression product of the mutant sequence is a variant protein with an altered amino acid sequence relative to the parent. The expression product may have an altered functional capacity (e.g., enhanced enzymatic activity).

The term "property" or grammatical equivalents thereof in the context of a polypeptide, as used herein, refers to any characteristic or attribute of a polypeptide that can be selected or detected. These properties include, but are not limited to oxidative stability, substrate specificity, catalytic activity, thermal stability, pH activity profile, resistance to proteolytic degradation, $K_M$, $K_{CAT}$, $K_{CAT}/K_M$ ratio, protein folding, ability to bind a substrate and ability to be secreted.

The term "property" or grammatical equivalent thereof in the context of a nucleic acid, as used herein, refers to any characteristic or attribute of a nucleic acid that can be selected or detected. These properties include, but are not limited to, a property affecting gene transcription (e.g., promoter strength or promoter recognition), a property affecting RNA processing (e.g., RNA splicing and RNA stability), a property affecting translation (e.g., regulation, binding of mRNA to ribosomal proteins).

The terms "thermally stable" and "thermostable" refer to glucoamylase variants of the present invention that retain a specified amount of enzymatic activity after exposure to identified temperatures over a given period of time under conditions prevailing during the hydrolysis of starch substrates, for example while exposed to altered temperatures.

The term "enhanced stability" in the context of a property such as thermostability refers to a higher retained starch hydrolytic activity over time as compared to another reference (e.g., parent) glucoamylase.

The term "diminished stability" in the context of a property such as thermostability refers to a lower retained starch hydrolytic activity over time as compared to another reference glucoamylase.

The term "specific activity" The specific activity is defined as the activity per mg of glucoamylase protein. In some embodiments, the activity for glucoamylase is determined by the ethanol assay described herein and expressed as the amount of glucose which is produced from the starch substrate. In some embodiments, the protein concentration can be determined using the Caliper assay described herein.

The terms "active" and "biologically active" refer to a biological activity associated with a particular protein. It follows that the biological activity of a given protein refers to any biological activity typically attributed to that protein by those skilled in the art. For example, an enzymatic activity associated with a glucoamylase is hydrolytic and, thus an active glucoamylase has hydrolytic activity.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction.

As used herein, the terms "transformed" and "stably transformed" refer to a cell that has a non-native (heterologous) polynucleotide sequence integrated into its genome or as an episomal plasmid that is maintained for at least two generations.

As used herein, the terms "selectable marker" and "selective marker" refer to a nucleic acid (e.g., a gene) capable of expression in host cells which allows for ease of selection of those hosts containing the vector. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "promoter" refers to a nucleic acid sequence that functions to direct transcription of a downstream gene. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, (1981) *Adv. Appl. Math.*, 2:482; Needleman and Wunsch, (1988) *J. Mol. Biol.*, 48:443; Pearson and Lipman, (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al., (1984) *Nucl. Acid Res.*, 12:387-395).

The "percent (%) nucleic acid sequence identity" or "percent (%) amino acid sequence identity" is defined as the percentage of nucleotide residues or amino acid residues in a candidate sequence that are identical with the nucleotide residues or amino acid residues of the starting sequence (i.e., TrGA). The sequence identity can be measured over the entire length of the starting sequence (i.e., TrGA SEQ ID NO:2 or 3).

Homologous sequences are determined by known methods of sequence alignment. A commonly used alignment method is BLAST described by Altschul et al., (Altschul et al., (1990) *J. Mol. Biol.*, 215:403-410; and Karlin et al., (1993) *Proc. Natl. Acad. Sci. USA* 90:5873-5787). A particularly useful BLAST program is the WU-BLAST-2 program (See, Altschul et al., (1996) *Meth. Enzymol.*, 266:460-480). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Other methods find use in aligning sequences. One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, (1987) *J. Mol. Evol.*, 35:351-360). The method is similar to that described by Higgins and Sharp (Higgins and Sharp, (1989) *CABIOS* 5:151-153). Useful PILEUP parameters including a default gap weight of 3.00, a default gap length weight of 0.10, and weighted end gaps.

The term "optimal alignment" refers to the alignment giving the highest percent identity score. An "equivalent position" refers to an optimal alignment between two sequences. For example using FIGS. 5D and 5E, position 491 in TrGA (SEQ ID NO: 2) is C491; the equivalent position for *Aspergillus niger* is position C509; and the equivalent position for *Aspergillus awamori* is position Q538. See FIG. 8 for an exemplary alignment of the three-dimensional sequence.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous or homologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

In some embodiments of the invention, mutated DNA sequences are generated with site saturation mutagenesis in at least one codon. In other embodiments, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, more than 98% or more than 99% homology with the parent sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, "heterologous protein" refers to a protein or polypeptide that does not naturally occur in the host cell.

As used herein, "homologous protein" refers to a protein or polypeptide native or naturally occurring in a cell and includes native proteins that are over-expressed in the cell whether by recombinant DNA technology or naturally.

An enzyme is "over-expressed" in a host cell if the enzyme is expressed in the cell at a higher level than the level at which it is expressed in a corresponding wild-type cell.

The terms "protein" and "polypeptide" are used interchangeably herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the invention are described by the following nomenclature: [original amino acid residue/position/substituted amino acid residue]. For example the substitution of leucine for arginine at position 76 is represented as R76L. When more than one amino acid is substituted at a given position, the substitution is represented as 1) Q172C, Q172D or Q172R; 2) Q172C, D, or R or c) Q172C/D/R. When a position suitable for substitution is identified herein without a specific amino acid suggested, it is to be understood that any amino acid residue may be substituted for the amino acid residue present in the position. Where a variant glucoamylase contains a deletion in comparison with other glucoamylases the deletion is indicated with "*". For example, a deletion at position R76 is represented as R76*. A deletion of two or more consecutive amino acids is indicated for example as (76-78)*.

A "prosequence" is an amino acid sequence between the signal sequence and mature protein that is necessary for the secretion of the protein. Cleavage of the pro sequence will result in a mature active protein.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., glucoamylase), or may be from a gene encoding another secreted protein.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polypeptides that are involved in post-translational activity (e.g., polypeptides cleaved therefrom to leave the mature form of a protein or peptide).

"Host strain" or "host cell" refers to a suitable host for an expression vector comprising DNA according to the present invention.

The terms "derived from" and "obtained from" refer to not only a glucoamylase produced or producible by a strain of the organism in question, but also a glucoamylase encoded by a DNA sequence isolated from such strain and produced in a host organism containing such DNA sequence. Additionally, the term refers to a glucoamylase which is encoded by a DNA sequence of synthetic and/or cDNA origin and which has the identifying characteristics of the glucoamylase in question.

A "derivative" within the scope of this definition generally retains the characteristic hydrolyzing activity observed in the wild-type, native or parent form to the extent that the derivative is useful for similar purposes as the wild-type, native or parent form. Functional derivatives of glucoamylases encompass naturally occurring, synthetically or recombinantly produced peptides or peptide fragments which have the general characteristics of the glucoamylases of the present invention.

The term "isolated" or "purified" refers to a material that is removed from its original environment (e.g., the natural environment if it is naturally occurring). In some embodiments, an isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. Pat. No. 6,582,914, hereby incorporated by reference. In alternative embodiments, combinatorial mutagenesis methods encompass commercially available kits (e.g., QUIKCHANGE® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein the term "dry solids content (DS or ds)" refers to the total solids of a slurry in % on a dry weight basis.

As used herein, the term "initial hit" refers to a variant that was identified by screening a combinatorial consensus mutagenesis library. In embodiments, initial hits have improved performance characteristics, as compared to the starting gene.

As used herein, the term "improved hit" refers to a variant that was identified by screening an enhanced combinatorial consensus mutagenesis library.

As used herein, the term "target property" refers to the property of the starting gene that is to be altered. It is not intended that the present invention be limited to any particular target property. However, in some embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention. Other definitions of terms may appear throughout the specification.

Before the exemplary embodiments are described in more detail, it is to be understood that this invention is not limited to particular embodiments described herein, as such may, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

As used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Detailed Embodiments

An objective of the present invention was to alter properties, such as thermal stability and/or specific activity of parent glucoamylases and in particular *Trichoderma reesei* glucoamylase (TrGA), to obtain glucoamylase variants having the altered properties which would be useful in various applications such as starch conversion or alcohol fermentation processes.

Parent Glucoamylases:

In some embodiments, the present invention provides a glucoamylase variant of a parent glucoamylase. The parent glucoamylase can comprise a sequence that has sequence and/or structural identity with TrGA (SEQ ID NOs:2 and/or 3). In some embodiments, the parent glucoamylase comprises an amino acid sequence as illustrated in SEQ ID NOs:1, 2, 3, 5, 6, 7, 8 or 9. In some embodiments, the parent glucoamylase is a homologue. In some embodiments the parent glucoamylase has at least 50% sequence identity, at least 60% sequence identity, at least 70% sequence identity, at least 80% sequence identity, at least 85% sequence identity, at least 88% sequence identity, at least 90% sequence identity, at least 93% sequence identity, at least 95% sequence identity, at least 96% sequence identity, at least 97% sequence identity, at least 98% sequence identity and also at least 99% sequence identity with the TrGA amino acid sequence of SEQ ID NO: 2.

In some embodiments, the parent glucoamylase comprises a catalytic domain having an amino acid sequence having at least 50% amino acid sequence identity, at least 60% amino acid sequence identity, at least 70% amino acid sequence identity, at least 80% amino acid sequence, at least 85% amino acid sequence identity, at least 90% amino acid sequence identity, at least 93% amino acid sequence identity, at least 95% amino acid identity, at least 97% amino acid sequence identity and at least 99% amino acid sequence identity with one or more of the amino acid sequences illustrated in SEQ ID NO:1, 2, 3, 5, 6, 7, or 8. In other embodiments, the parent glucoamylase will have at least 80% sequence identity, at least 85% sequence identity, at least 90% sequence identity, at least 95% sequence identity, at least 97% sequence identity and also at least 98% sequence identity with the catalytic domain of the TrGA amino acid sequence of SEQ ID NO:3.

The parent glucoamylase can be encoded by a DNA sequence which hybridizes under medium, high or stringent conditions with a DNA encoding a glucoamylase having one of the amino acid sequences of SEQ ID NO: 1, 2 or 3. In some embodiments, the parent glucoamylase with at least 50% sequence identity, at least 60% amino acid sequence identity, at least 70% amino acid sequence identity, at least 80% amino acid sequence identity, at least 90% amino acid sequence identity, at least 95% amino acid identity and at least 97% amino acid sequence identity also has structural identity with SEQ ID NOs:2 and/or 3. While the parent glucoamylase is a native or naturally occurring sequence in a host cell, in some embodiments, the parent glucoamylase is a naturally occurring variant. In some embodiments, the parent glucoamylase is a variant that has been engineered and/or a hybrid glucoamylase.

Predicted structures and known sequences of glucoamylases are conserved among fungal species (Coutinho et al., (1994) Protein Eng., 7:393-400 and Coutinho et al., (1994), Protein Eng., 7: 749-760). In some embodiments, the parent glucoamylase is a filamentous fungal glucoamylase. In some embodiments, the parent glucoamylase is obtained from a *Trichoderma* strain (e.g., *T. reesei, T. longibrachiatum, T. strictipilis, T. asperellum, T. konilangbra* and *T. hazianum*), an *Aspergillus* strain (e.g. *A. niger, A. nidulans, A. kawachi, A. awamori* and *A. orzyae*), a *Talaromyces* strain (e.g. *T. emersonii, T. thermophilus*, and *T. duponti*), a *Hypocrea* strain (e.g. *H. gelatinosa, H. orientalis, H. vinosa*, and *H. citrina*), a *Fusarium* strain (e.g., *F. oxysporum, F. roseum*, and *F. venenatum*), a *Neurospora* strain (e.g., *N. crassa*) and a *Humicola* strain (e.g., *H. grisea, H. insolens* and *H. lanuginosa*), a *Penicillium* strain (e.g. *P. notatum* or *P. chrysogenum*), or a *Saccharomycopsis* strain (e.g. *S. fibuligera*).

In some embodiments, the parent glucoamylase is a bacterial glucoamylase. For example, the polypeptide may be obtained from a gram positive bacterial strain such as *Bacillus* (e.g., *B. alkalophilus, B. amyloliquefaciens, B. lentus, B. licheniformis, B. stearothermophilus, B. subtilis* and *B. thuringiensis*) or a *Streptomyces* strain (e.g., *S. lividans*).

In some other embodiments, the parent glucoamylase will comprise an amino acid sequence having at least 90% sequence identity, at least 93% sequence identity, at least 95% sequence identity, at least 96% sequence identity, at least 97% sequence identity, at least 98% sequence identity and also at least 99% sequence identity with the catalytic domain of the *Aspergillus* parent glucoamylase of SEQ ID NO:5 or SEQ ID NO:6.

In other embodiments, the parent glucoamylase will comprise an amino acid sequence having at least 90% sequence identity, at least 95% sequence identity, at least 97% sequence identity and also at least 99% sequence identity with the catalytic domain of the *Humicola grisea* (HgGA) parent glucoamylase of SEQ ID NO:8.

In some embodiments, the parent glucoamylase has at least 50% sequence identity, at least 60% sequence identity, at least 70% sequence identity, at least 80% sequence identity, at least 85% sequence identity, at least 88% sequence identity, at least 90% sequence identity, at least 93% sequence identity, at least 95% sequence identity, at least 96% sequence identity, at least 97% sequence identity, at least 98% sequence identity and also at least 99% sequence identity with the TrGA amino acid sequence of SEQ ID NO: 2 or 3 and has structural identity to the glucoamylase of SEQ ID NO:2 or 3.

In further embodiments, a *Trichoderma* glucoamylase homologue will be obtained from a *Trichoderma* or *Hypocrea* strain. Some *Trichoderma* glucoamylase homologues are described in US Pat. Pub. No. 2006/0094080 and reference is made specifically to amino acid sequences set forth in SEQ ID NOs: 17-22 and 43-47 of said reference.

In some embodiments, the parent glucoamylase is TrGA comprising the amino acid sequence of SEQ ID NO:2 or a *Trichoderma* glucoamylase homologue having at least 80%, at least 85%, at least 88%, at least 90%, at least 93%, at least 95%, at least 96%, at least 97%, at least 98%, at least 99% sequence identity to the TrGA sequence.

A parent glucoamylase can be isolated and/or identified using standard recombinant DNA techniques. Any standard techniques can be used that are known to the skilled artisan. For example, probes and/or primers specific for conserved areas of the glucoamylase can be used to identify homologues in bacterial or fungal cells (the catalytic domain, the active site, etc.). Alternatively degenerate PCR can be used to identify homologues in bacterial or fungal cells. In some cases, known sequences, such as in a database, can be analyzed for sequence and/or structural homology to one of the known glucoamylases, including SEQ ID NOs: 1, 2 or 3. Functional assays can also be used to identify glucoamylase activity in a bacterial or fungal cell. Proteins having glucoamylase activity can be isolated and reverse sequenced to isolate the corresponding DNA sequence. Such methods are known to the skilled artisan.

Glucoamylase Structural Homology:

The central dogma of molecular biology is that the sequence of DNA encoding a gene for a particular enzyme, determines the amino acid sequence of the protein, this sequence in turn determines the three-dimensional folding of the enzyme. This folding brings together disparate residues that create a catalytic center and substrate binding surface and this results in the high specificity and activity of the enzymes in question.

Figure 6:
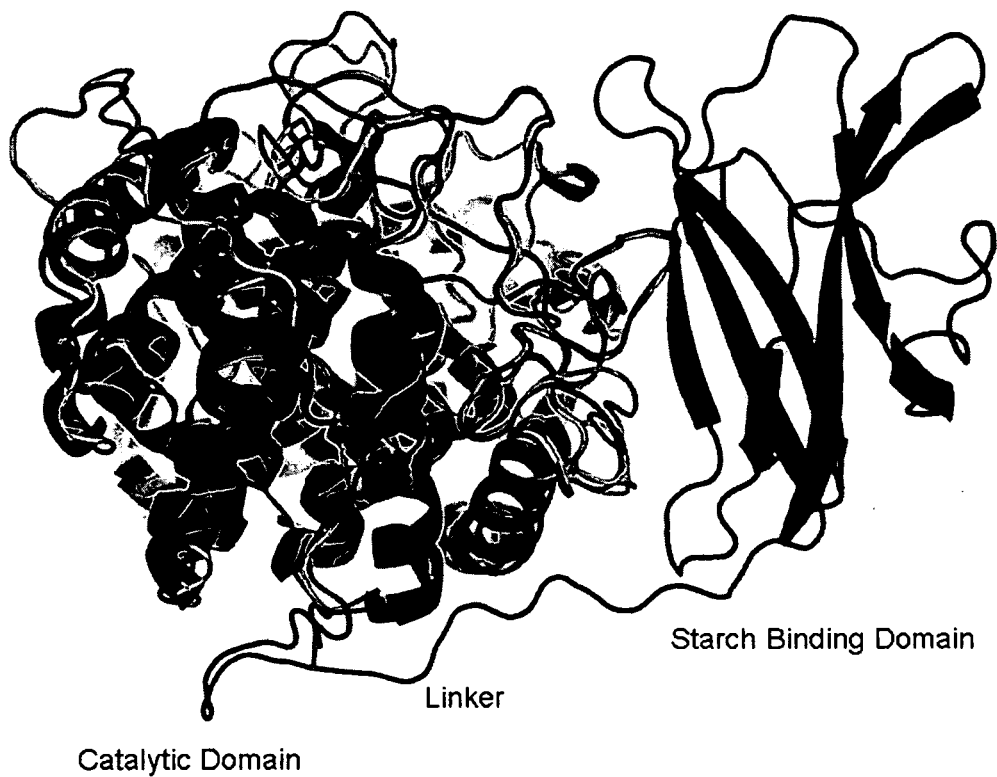
FIG. 6 is a comparison of the three dimensional structures of *Trichoderma* glucoamylase (black) (SEQ ID NO:2) and *Aspergillus awamori* glucoamylase (grey) viewed from the side. The side is measured in reference to the active site and the active site entrance is at the "top" of the molecule.
Figure 7:
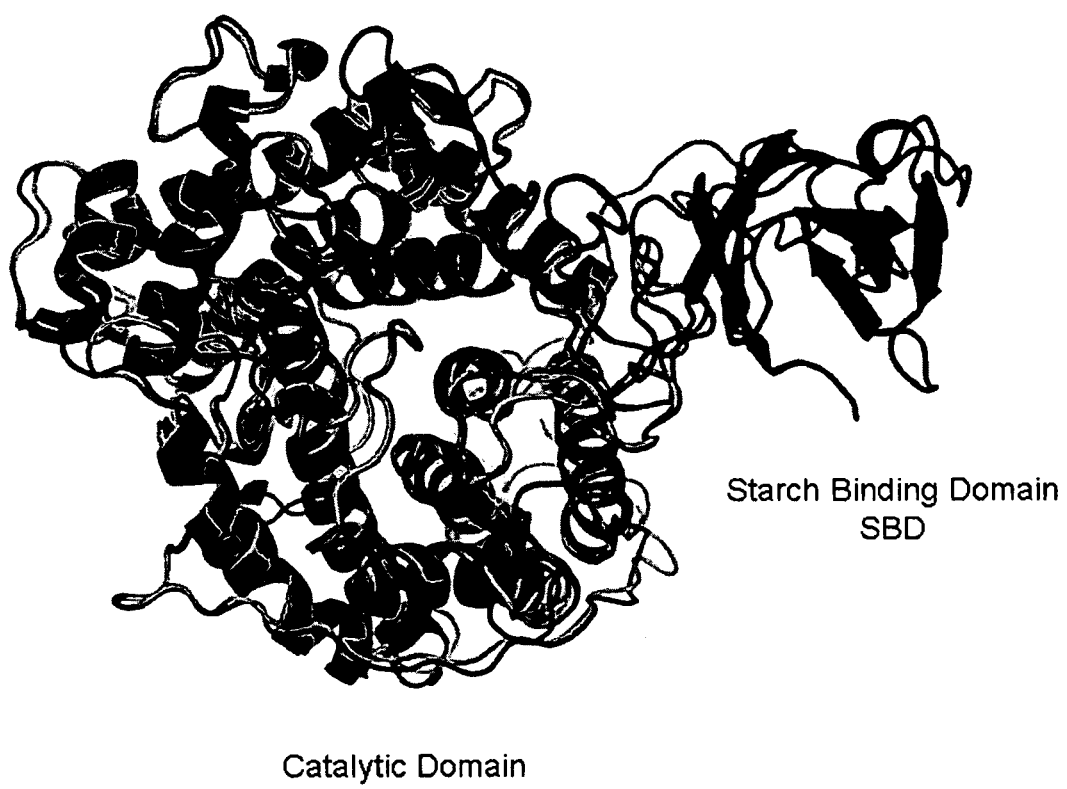
FIG. 7 is a comparison of the three dimensional structures of *Trichoderma glucoamylase* (black) and *Aspergillus awamori* glucoamylase (grey) viewed from the top. The active site entrance is at the "top" of the molecule.

Glucoamylases consist of as many as three distinct structural domains, a catalytic domain of approximately 450 residues which is structurally conserved, generally followed by a linker region consisting of between 30 and 80 residues which are connected to a starch binding domain of approximately 100 residues. The structure of the *Trichoderma reesei* glucoamylase with all three regions intact was determined to 1.8 Angstrom resolution herein (see Table 9 and Examples 8 and 9). Using the coordinates (see Table 9) the catalytic structure was aligned with the coordinates of the catalytic domain from *Aspergillus awamorii* strain X100 that was determined previously (Aleshin, et al (1994) *J Mol Biol* 238: 575-591). The *Aspergillus awamori* crystal structure only included the catalytic domain. As seen in FIGS. 6 and 7 the structure of the catalytic domains overlap very closely and it is possible to identify equivalent residues based on this structural superposition. The inventors believe that all glucoamylases share the basic structure depicted in FIGS. 6 and 7. The conservation of structure in the glucoamylase molecule correlates with the conservation of activity and a conserved mechanism of action for all glucoamylases. Given this high homology, site specific variants of the *Trichoderma* glucoamylase resulting in altered function would also have similar structural and therefore functional consequences in other glucoamylases.

The present invention, however, is not limited to the variants of the parent *Trichoderma* glucoamylase disclosed in FIG. 1, but extends to variants of parent glucoamylases comprising amino acid residues at positions which are "equivalent" to the particular identified residues in *Trichoderma reesei* glucoamylase (SEQ ID NO:2). In some embodiments, of the present invention, the parent glucoamylase is a *Talaromyces* GA and the substitutions are made at the equivalent amino acid residue positions in *Talaromyces* glucoamylase (see e.g. SEQ ID NO:308, FIG. 5C) as those described herein. In other embodiments, the parent glucoamylase comprises SEQ ID NO:5; SEQ ID NO:6; SEQ ID NO:7; SEQ ID NO:3; SEQ ID NO:8; and SEQ ID NO:9 (See FIGS. 5A-5B). In further embodiments, the parent glucoamylase is a *Penicillium* glucoamylase, such as *Penicillium chrysogenum*.

Structural identity determines whether the amino acid residues are equivalent. Structural identity is a one-to-one topological equivalent when the two structures (three dimensional and amino acid structures) are aligned. A residue (amino acid) position of a glucoamylase is equivalent to a residue of *T. reesei* glucoamylase if it is either homologous (i.e., corresponding in position in either primary or tertiary structure) or analogous to a specific residue or portion of that residue in *T. reesei* glucoamylase (having the same or similar functional capacity to combine, react, or interact chemically).

In order to establish identity to the primary structure, the amino acid sequence of a glucoamylase can be directly compared to *Trichoderma reesei* glucoamylase primary sequence and particularly to a set of residues known to be invariant in glucoamylases for which sequence is known. For example, FIGS. 5A and B herein shows the conserved residues between glucoamylases. After aligning the conserved residues, allowing for necessary insertions and deletions in order to maintain alignment (i.e. avoiding the elimination of conserved residues through arbitrary deletion and insertion), the residues equivalent to particular amino acids in the primary sequence of *Trichoderma reesei* glucoamylase are defined. Alignment of conserved residues can conserve 100% of such residues. However, alignment of greater than 75% or as little as 50% of conserved residues is also adequate to define equivalent residues, particularly when alignment based on structural identity is included.

For example, in FIG. 5, glucoamylases from six organisms are aligned to provide the maximum amount of homology between amino acid sequences. A comparison of these sequences shows that there are a number of conserved residues contained in each sequence as designated by an asterisk. These conserved residues, thus, may be used to define the corresponding equivalent amino acid residues of *Trichoderma reesei* glucoamylase in other glucoamylases such as glucoamylase from *Aspergillus niger*.

Structural identity involves the identification of equivalent residues between the two structures. "Equivalent residues" can be defined by determining homology at the level of tertiary structure (structural identity) for an enzyme whose tertiary structure has been determined by x-ray crystallography. Equivalent residues are defined as those for which the atomic coordinates of two or more of the main chain atoms of a particular amino acid residue of the *Trichoderma reesei* glucoamylase (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the glucoamylase in question to the *Trichoderma reesei* glucoamylase. The best model is the crystallographic model giving the lowest R factor for experimental $$R \text{ factor} = \frac{\sum_h |Fo(h)| - |Fc(h)|}{\sum_h |Fo(h)|}$$

diffraction data at the highest resolution available.

Equivalent residues which are functionally analogous to a specific residue of *Trichoderma reesei* glucoamylase are defined as those amino acids of the enzyme which may adopt a conformation such that they either alter, modify or contribute to protein structure, substrate binding or catalysis in a manner defined and attributed to a specific residue of the *Trichoderma reesei* glucoamylase. Further, they are those residues of the enzyme (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Trichoderma reesei* glucoamylase. The coordinates of the three dimensional structure of *Trichoderma reesei* glucoamylase are set forth in Table 9 and can be used as outlined above to determine equivalent residues on the level of tertiary structure.

Variants:

The variants according to the invention include at least one substitution, deletion or insertion in the amino acid sequence of a parent glucoamylase that makes the variant different in sequence from the parent glucoamylase. In some embodiments, the variants of the invention will have at least 20%, at least 40%, at least 50%, at least 60%, at least 70%, at least 80%, at least 85%, at least 90%, at least 95%, at least 97% and also at least 100% of the glucoamylase activity of TrGA (SEQ ID NO:2). In some embodiments, the variants according to the invention will comprise a substitution, deletion or insertion in at least one amino acid position of the parent TrGA (SEQ ID NO:2), or in an equivalent position in the sequence of another parent glucoamylase having at least 50%, at least 60%, at least 70%, at least 80%, at least 90% sequence identity to the TrGA sequence, including but not limited to; at least 93% sequence identity, at least 95%, at least 97%, and at least 99% sequence identity. In some embodiments, the parent glucoamylase will have structural identity to the TrGA sequence.

In other embodiments, the variant according to the invention will comprise a substitution, deletion or insertion in at least one amino acid position of a fragment of the parent TrGA, wherein the fragment comprises the catalytic domain of the TrGA sequence (SEQ ID NO:3) or in an equivalent position in a fragment comprising the catalytic domain of a parent glucoamylase having at least 50%, at least 60%, at least 70%, at least 80% sequence identity to the fragment of the TrGA sequence, at least 90%, at least 95%, at least 97%, and at least 99% sequence identity. In some embodiments, the fragment will comprise at least 400, 425, 450, and/or 500 amino acid residues. In some embodiments, when the parent glucoamylase includes a catalytic domain, linker region and starch binding domain, the fragment may include part of the linker region. In some embodiments, the variant will comprise a substitution, deletion or insertion in the amino acid sequence of a fragment of the TrGA sequence (SEQ ID NO: 2 or SEQ ID NO: 3). In some embodiments, the variant will have structural identity with the TrGA sequence (SEQ ID NOs: 2 or 3).

Structural identity with reference to an amino acid substitution, means that the substitution occurs at the equivalent amino acid position in the homologous glucoamylase or parent glucoamylase. The term equivalent position means a position that is common to two parent sequences which is based on an alignment of the amino acid sequence of the parent glucoamylase in question as well as alignment of the three-dimensional structure of the parent glucoamylase in question with the TrGA reference glucoamylase amino acid sequence and three-dimensional sequence. For example, with reference to FIG. 5, position 24 in TrGA (SEQ ID NO: 3) is D24 and the equivalent position for *Aspergillus niger* (SEQ ID NO. 6) is position D25 and the equivalent position for *Aspergillus oryzae* (SEQ ID NO: 7) is position D26. See FIGS. 6 and 7 for an exemplary alignment of the three-dimensional sequence.

In some embodiments, the glucoamylase variant will have more than one substitution (e.g. two, three or four substitutions) as compared to a corresponding parent glucoamylase.

In some embodiments, a glucoamylase variant comprises a substitution, deletion or insertion in at least one amino acid position in a position corresponding to the regions of non-conserved amino acids as illustrated in FIGS. 5A and 5B (e.g. amino acid positions corresponding to those positions which are not designated by"*" in FIGS. 5A and 5B). In some embodiments, the variant comprises a substitution in at least one amino acid position in a position corresponding to the regions of non-conserved amino acids as illustrated in FIGS. 5A and 5B.

While the variants can be in any position in the mature protein sequence (SEQ ID NOs: 2 or 3), in some embodiments, a glucoamylase variant comprises one or more substitutions in the following positions in the amino acid sequence set forth in SEQ ID NOs: 2 or 3: 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 236, 239, 240, 241, 242, 244, 263, 264, 265, 268, 269, 276, 284, 291, 300, 301, 303, 310, 311, 313, 316, 338, 342, 344, 346, 349, 359, 361, 364, 375, 379, 382, 390, 391, 393, 394, 408, 410, 415, 417, 418, 430, 431, 433, 436, 442, 443, 444, 448 and 451, or in an equivalent position in a parent glucoamylase. In some embodiments, the parent glucoamylase will have at least 50%, at least 60%, at least 70%, at least 80%, at least 90%, at least 95%, at least 96%, at least 97% at least 98%, and at least 99% sequence identity with SEQ ID NO: 2 or SEQ ID NO: 3. In other embodiments, the parent glucoamylase will be a *Trichoderma* glucoamylase homologue. In some embodiments, the variant will have altered properties. In some embodiments, the parent glucoamylase will have structural identity with the glucoamylase of SEQ ID NOs: 2 or 3.

In some embodiments, the glucoamylase variant comprises one or more substitutions in the following positions in the amino acid sequence set forth in SEQ ID NO: 2 or 3: T10, L14, N15, P23, T42, P45, D46, F59, K60, N61, T67, E68, A72, G73, S97, L98, A99, S102, K108, E110, L113, K114, R122, Q124, R125, I133, K140, N144, N145, Y147, S152, N153, N164, F175, N182, A204, T205, S214, V216, Q219, W228, V229, S230, S231, D236, I239, N240, T241, N242, G244, N263, L264, G265, A268, G269, D276, V284, S291, P300, A301, A303, Y310, A311, D313, Y316, V338, T342, S344, T346, A349, V359, G361, A364, T375, N379, S382, S390, E391, A393, K394, R408, S410, S415, L417, H418, T430, A431, R433, I436, A442, N443, S444, T448 and S451 or an equivalent position in parent glucoamylase (e.g. a *Trichoderma* glucoamylase homologue). In some embodiments, the variant will have altered properties as compared to the parent glucoamylase.

In other embodiments, the variant of a glucoamylase parent comprises one or more substitutions in the following positions in the amino acid sequence set forth in SEQ ID NO:2 or 3: 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 300, 301, 303, 311, 338, 342, 344, 346, 349, 359, 361, 364, 375, 379, 382, 390, 391, 393, 394, 410, 417, 418, 430, 431, 433, 442, 444, 448, and 451 or an equivalent position in a parent glucoamylase. In some embodiments, the parent glucoamylase will have 50%, at least 60%, at least 70%, at least 80%, at least 90%, at least 95%, at least 96%, at least 97% at least 98%, and at least 99% sequence identity with SEQ ID NO: 2 or SEQ ID NO: 3. In other embodiments the parent glucoamylase will be a *Trichoderma* glucoamylase homologue. In some embodiments, the variant will have at least one altered property as compared to the parent glucoamylase. In some embodiments, the at least one altered property is specific activity. In some embodiments, the variant has one or more substitutions corresponding to one of the following positions: 61, 67, 72, 97, 102, 133, 205, 219, 228, 230, 231, 239, 263, 268, 291, 342, 394, 430, 431 and 451 of SEQ ID NO: 2 and/or 3. In some embodiments, the substitution at these positions is chosen from: N61I, T67M, A72Y, S97N, S102M, I133T, T205Q, Q219S, W228H, W228M, S230F, S230G, S230N, S230R, S231L, I239V, I239Y, N263P, A268C, A268G, A268K, S291A, T342V, K394S, T430K, A431Q, and S451K of SEQ ID NO: 2 and/or 3. In some embodiments, the variant has one or more substitutions corresponding to one of the following positions: 72, 133, 219, 228, 230, 231, 239, 263, 268, and 451 of SEQ ID NO: 2 and/or 3. In some embodiments, the substitution at these positions is chosen from: A72Y, I133T, Q219S, W228H, W228M, S230R, S230F, S230G, S231L, I239V, N263P, A268C, A268G, and S451K of SEQ ID NO: 2 and/or 3. In some embodiments, the variant has at least one altered property and the at least one altered property is an increased specific activity as compared to the parent glucoamylase.

In further embodiments, the variant of a glucoamylase parent comprises at least one of the following substitutions in the following positions in an amino acid sequence set forth in SEQ ID NO:2 or 3: T10D/F/G/K/L/M/P/R/S; L14E/H; N15D/N; P23A/G; F59A/G; K60F/H; N61D/I/L/Q/V/W; R65A/C/G/I/K/M/S/V/Y; T67C/I/K/M/T; E68I/M/W; A72E/G/L/M/Q/R/W/Y; G73C/L/W; S97F/M/N/P/R/S/V/W/Y; L98H/M; A99C/L/M/N/P; S102A/C/I/L/M/N/R/V/W/Y; E110Q/S/W; L113E/N; K114C/D/E/L/M/Q/S/T/V; I133K/R/S/T; K140A/E/F/H/K/L/M/N/Q/R/S/V/W/Y; N144C/D/E/I/K; N145A/C/E/I/K/L/M/Q/R/V/W/Y; Y147A/M/R; S152H/M; N153C/D/K/L/W/Y; N164A/G; N182C/E/K/P/R; A204C/D/G/I/M/Q/T; T205A/D/H/UK/M/N/P/Q/S/V/W/Y; S214P/T; V216C/G/H/K/N/Y; Q219D/G/H/N/P/S; W228A/F/G/H/I/L/M/Q/S/T/V/Y; V229E/I/M/N/Q; S230C/D/E/F/G/H/I/K/L/N/P/Q/R/T/V/Y; S231C/D/F/L/M/N/Q/R/S/V/Y; D236F/G/L/M/N/P/S/T/V; I239M/Q/S/V/W/Y; T241C/E/H/L/M/P/S/T/V; N242C/F/H/M/T/V/W; N263H/K/P; L264A/C/E/F/L/S; G265E/G/H/I/K/R/T; A268C/D/E/F/G/I/K/L/P/R/T/W; G269E; D276S; V284R/T/V/Y/A/E/F/H/K/N/P/W; P300K/R; A301E/K/L/P/S/W; A303C/D/F/H/I/K/L/N/R/T/V/W/Y; A311N/P/Q/S/Y; V338P/Q/S/Y; T342N/V; S344A/T; T346G/H/M/N/P/Q/Y; A349L/I/K/M/N/Q/R/W; G361H/L/R; A364M/W; T375C/D/E/H/V/W/Y; N379A/C/D/G/I/M/P/S; S382A/N/P/V/W; S390A/Y; E391A/E/I/K/L/M/Q/R/V/W/Y; A393 E/G/H/I/K/L/M/N/Q/R/S/T/V/W/Y; K394A/H/K/L/M/Q/R/S/T/V/W; S410E/H/N; L417A/D/E/F/G/I/K/Q/R/S/T/V/W/Y; H418E/M; T430A/E/F/G/H/UK/M/N/Q/R/V; A431C/E/H/I/L/M/Q/R/S/W/Y; R433A/C/E/F/G/K/L/M/N/S/V/W/Y; I436E/F/G/H/K/P/R/S/T/V/Y; S444M/N/P/Q/R/T/V/W; T448F/G/I/P/Q/T/V; and S451E/H/K/L/Q/T or a substitution in an equivalent position in a parent glucoamylase.

In other embodiments, the variant of a glucoamylase parent comprises one or more substitutions in the following positions in the amino acid sequence set forth in SEQ ID NO:2 or 3: 10, 15, 23, 42, 59, 60, 61, 68, 72, 73, 97, 98, 99, 102, 114, 133, 140, 144, 147, 152, 153, 164, 182, 204, 205, 214, 216, 228, 229, 230, 231, 236, 241, 242, 263, 264, 265, 268, 269, 276, 284, 291, 300, 301, 303, 311, 338, 342, 344, 346, 349, 359, 361, 364, 375, 379, 382, 390, 391, 393, 394, 410, 417, 430, 431, 433, 436, 442, 443, 444, 448, and 451 or an equivalent position in a parent glucoamylase (e.g., *Trichoderma* glucoamylase homologue). In some embodiments, the parent glucoamylase will have at least 50%, at least 60%, at least 70%, at least 80%, at least 90%, at least 95%, at least 96%, at least 97% at least 98%, and at least 99% sequence identity with SEQ ID NO: 2 or SEQ ID NO: 3. In some embodiments, the parent glucoamylase also shows structural identity with the glucoamylase of SEQ ID NOs: 2 and/or 3. In other embodiments the parent glucoamylase will be a *Trichoderma* glucoamylase homologue. In some embodiments, the variant has one or more substitutions corresponding to one of the following positions: 10, 42, 68, 73, 97, 114, 153, 229, 231, 236, 264, 291, 301, 344, 361, 364, 375, 417, and 433 of SEQ ID NO: 2 and/or 3. In some embodiments, the substitution at these positions is chosen from: T10S, T42V, E68C, E68M, G73F, G73W, K114M, K114T, N153A, N153S, N153V, W228V, D236R, G361D, G361E, G361P, G361Y, A364D, A364E, A364F, A364G, A364K, A365L, A365R, R433C, R433G, R433L, R433N, R433S, R433V, and I436H of SEQ ID NO: 2 and/or 3. In some embodiments, the variant has one or more substitutions corresponding to one of the following positions: 42, 68, 73, 114, 153, 236, 361, and 364 of SEQ ID NOs: 2 and/or 3. In some embodiments, the substitution at these positions is chosen from: T42V, E68M, G73F, G73W, K114T, N153S, N153V, D236R, G361D, A364F, and A364L of SEQ ID NO: 2 and/or 3. In some embodiments, the variant has at least one altered property and the at least one altered property is an increased thermostability as compared to the parent glucoamylase.

In other embodiments, the variant of a glucoamylase parent comprises one or more substitutions in the following positions in the amino acid sequence set forth in SEQ ID NOs:2 or 3: 10, 15, 59, 61, 68, 72, 73, 97, 99, 102, 133, 140, 153, 182, 204, 205, 214, 228, 229, 230, 231, 236, 241, 242, 264, 265, 268, 275, 284, 291, 300, 301, 303, 311, 338, 344, 346, 359, 361, 364, 375, 370, 382, 391, 393, 394, 410, 417, 430, 431, 433, 444, 448, and 451 and/or an equivalent position in a parent glucoamylase (e.g., *Trichoderma* glucoamylase homologue). In some embodiments, the parent glucoamylase will have at least 50%, at least 60%, at least 70%, at least 80%, at least 90%, at least 95%, at least 96%, at least 97% at least 98%, and at least 99% sequence identity with SEQ ID NO: 2 or SEQ ID NO: 3. In some embodiments, the parent glucoamylase will also have structural identity with the glucoamylase of SEQ ID NOs: 2 and/or 3. In other embodiments the parent glucoamylase will be a *Trichoderma* glucoamylase homologue. In some embodiments, the variant will have at least one altered property as compared to the parent glucoamylase. In some embodiments, the variant has one or more substitutions corresponding to one of the following positions: 228, 230, 231, 268, 291, 417, 433, and 451 of SEQ ID NOs: 2 and/or 3. In some embodiments, the substitution at these positions is chosen from: W228H, W228M, S230F, S230G, S230R, S231L, A268C, A268G, S291A, L417R, R433Y, and S451K of SEQ ID NOs: 2 and/or 3. In some embodiments, the variant has at least one altered property and the at least one altered property is an increased thermostability or specific activity as compared to the parent glucoamylase. In some embodiments, the variant has both an increased thermostability and an increased specific activity as compared to the parent glucoamylase.

Glucoamylase variants of the invention may also include chimeric or hybrid glucoamylases with, for example a starch binding domain (SBD) from one glucoamylase and a catalytic domain and linker from another. For example, a hybrid glucoamylase can be made by swapping the SBD from AnGA with the SBD from TrGA, making a hybrid with the AnGA SBD and the TrGA catalytic domain and linker. Alternatively, the SBD and linker from AnGA can be swapped for the SBD and linker of TrGA.

In some aspects, the variant glucoamylase exhibits increased thermostability as compared to the parent glucoamylase. In some embodiments, the altered property is increased specific activity compared to the parent glucoamylase. In some embodiments, the altered property is increased thermostability at lower temperatures as compared to the parent glucoamylase. In some embodiments, the altered property is both increased specific activity and increased thermostability as compared to the parent glucoamylase.

A number of parent glucoamylases have been aligned with the amino acid sequence of TrGA. FIG. 5 includes the catalytic domain of the following parent glucoamylases *Aspergillus awamori* (AaGA) (SEQ ID NO:5); *Aspergillus niger* (AnGA) (SEQ ID NO:6); *Aspergillus orzyae* (AoGA) (SEQ ID NO:7), *Humicola grisea* (HgGA) (SEQ ID NO:8) and *Hypocrea vinosa* (HvGA) (SEQ ID NO:9). The % identity of the catalytic domains is represented in Table 1 below.

TABLE 1

|      | AaGA | AnGA | AoGA | HgGA | HvGA | TrGA |
|------|------|------|------|------|------|------|
| AaGA | 100  | 95   | 58   | 53   | 57   | 56   |
| AnGA |      | 100  | 59   | 53   | 57   | 56   |
| AoGA |      |      | 100  | 55   | 56   | 56   |
| HgGA |      |      |      | 100  | 61   | 63   |
| HvGA |      |      |      |      | 100  | 91   |
| TrGA |      |      |      |      |      | 100  |

In some embodiments, for example, the variant glucoamylase will be derived from a parent glucoamylase which is an *Aspergillus* glucoamylase and the variant will include at least one substitution in a position equivalent to a position set forth in SEQ ID NO:2 or SEQ ID NO:3 and particularly in a position corresponding to: T10, L14, N15, P23, T42, P45, D46, F59, K60, N61, R65, T67, E68, A72, G73, S97, L98, A99, S102, K108, E110, L113, K114, R122, Q124, R125, I133, K140, N144, N145, Y147, S152, N153, N164, F175, N182, A204, T205, S214, V216, Q219, W228, V229, S230, S231, D236, I239, N240, T241, N242, G244, N263, L264, G265, A268, G269, D276, V284, S291, P300, A301, A303, Y310, A311, D313, Y316, V338, T342, S344, T346, A349, V359, G361, A364, T375, N379, S382, S390, E391, A393, K394, R408, S410, S415, L417, H418, T430, A431, R433, I436, A442, N443, S444, T448 and S451.

Altered Properties

The present invention also provides glucoamylase variants having at least one altered property (e.g., improved property) as compared to a parent glucoamylase and particularly to the TrGA. In some embodiments, at least one altered property (e.g. improved property) is chosen from acid stability, thermal stability and specific activity. In some embodiments, the altered property is increased acid stability, increased thermal stability and/or increased specific activity. In some embodiments, the increased thermal stability is at higher temperatures. In some embodiments, the increased pH stability is at high pH. In further embodiments, the increased pH stability is at low pH.

The glucoamylase variants of the invention may also provide higher rates of starch hydrolysis at low substrate concentrations as compared to the parent glucoamylase. The variant may have a higher Vmax or lower Km than a parent glucoamylase when tested under the same conditions. For example the variant glucoamylase may have a higher Vmax at a temperature range of 25° C. to 70° C. (e.g. at 25° C. to 35° C.; 30° C.–35° C.; 40° C. to 50° C.; at 50° C. to 55° C. and at 55° C. to 62° C.). The Michaelis-Menten constant, Km and Vmax values can be easily determined using standard known procedures.

Thermal Stability (Thermostable Variants):

In some aspects, the invention relates to a variant glucoamylase having altered thermal stability as compared to a parent (wild type). Altered thermostability can be at increased temperatures or at decreased temperatures. Thermostability is measured as the % residual activity after incubation for 1 hour at 64 degree centigrade in NaAc buffer pH 4.5. Under these conditions TrGA has a residual activity of between about 15% and 44% due to day-to-day variation as compared to the initial activity before incubation. Thus, in some embodiments, variants with increased thermostability have a residual activity that is between at least 1% and at least 50% more than that of the parent (after incubation for 1 hour at 64 degrees centigrade in NaAc buffer pH 4.5), including 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, and 50% as compared to the initial activity before incubation. For example, when the parent residual activity is 15%, a variant with increased thermal stability may have a residual activity of between about 16% and about 75%. In some embodiments, the glucoamylase variant will have improved thermostability such as retaining at least 50%, 60%, 70%, 75%, 80%, 85%, 90%, 92%, 95%, 96%, 97%, 98% or 99% enzymatic activity after exposure to altered temperatures over a given time period, for example, at least 60 minutes, 120 minutes, 180 minutes, 240 minutes, 300 minutes, etc. In some embodiments, the variant has increased thermal stability compared to the parent glucoamylase at selected temperatures in the range of 40 to 80° C., also in the range of 50 to 75° C. and in the range of 60 to 70° C., and at a pH range of 4.0 to 6.0. In some embodiments, the thermostability is determined as described in the Examples. In some embodiments, the variant has increased thermal stability at lower temperature compared to the parent glucoamylase at selected temperature in the range of 20 to 50° C., including 35 to 45 and 30° C. to 40° C.

In some embodiments, variants having an improvement in thermostability include one or more deletions, substitutions or insertions and particularly substitutions in the following positions in the amino acid sequence set forth in SEQ ID NO:2 or SEQ ID NO:3: T10, N15, P23, T42, F59, K60, N61, E68, A72, G73, S97, L98, A99, S102, K114, I133, K140, N144, Y147, S152, N153, N164, N182, A204, T205, S214, V216, W228, V229, S230, S231, D236, T241, N242, N263, L264, G265, A268, G269, D276, V284, S291, P300, A301, A303, A311, V338, T342, S344, T346, A349, V359, G361, A364, T375, N379, S382, S390, E391, A393, K394, S410, L417, T430, A431, R433, I436, A442, N443, S444, T448 and S451 and/or an equivalent position in a parent glucoamylase. In some embodiments, the parent glucoamylase will be a *Trichoderma* glucoamylase homologue and in further embodiments, the parent glucoamylase will have at least 50%, at least 60%, at least 70%, at least 80%, at least 90%, at least 95% and at least 98% sequence identity to SEQ ID NOs:2 or 3. In some embodiments, the parent glucoamylase will also have structural identity to SEQ ID NOs: 2 and/or 3. In some embodiments, the variant having increased thermostability has a substitution in at least one of the positions: 10, 42, 68, 73, 97, 153, 229, 231, 236, 264, 291, 301, 344, 361, 364, 375, and/or 417 of SEQ ID NO: 2 and/or 3. In some embodiments, the variant having thermostability has a substitution in at least one of the positions: 42, 68, 73, 153, 236, 344, 361, 364, and 365 of SEQ ID NO: 2 or SEQ ID NO:3.

Specific Activity:

As used herein, specific activity is the activity of the glucoamylase per mg of protein. Activity was determined using the ethanol assay. The screening identified variants having a Performance Index (PI)>1.0 compared to the parent TrGA PI. The PI is calculated from the specific activities (activity/mg enzyme) of the wildtype (WT) and the variant enzymes. It is the quotient "Variant-specific activity/WT-specific activity" and can be a measure of the increase in specific activity of the variant. A PI of 2 should be about 2 fold better than WT In some aspects, the invention relates to a variant glucoamylase having altered specific activity as compared to a parent or wildtype glucoamylase. In some embodiments, the altered specific activity is increased specific activity. Increased specific activity can be defined as an increased performance index of greater than or equal to about 1, including greater than or equal to about 1.1, 1.2, 1.3, 1.4, 1.5, 1.6, 1.7, 1.8, 1.9, and 2. In some embodiments, the increased specific activity is from about 1.0 to about 5.0, including 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, and 4.9. In some embodiments, the variant has an at least 1 fold higher specific activity than the parent glucoamylase, including at least 1.1 fold, 1.2 fold, 1.3 fold, 1.4 fold, 1.5 fold, 1.6 fold, 1.7 fold, 1.8 fold, 1.9 fold, 2 fold, 2.2 fold, 2.5 fold, 2.7 fold, 2.9 fold, 3 fold, 4 fold, and 5 fold.

In some embodiments, variants having an improvement in specific activity include one or more deletions, substitutions or insertions in the following positions in the amino acid sequence set forth in SEQ ID NO:2 and/or 3: T10, L14, N15, P23, F59, K60, N61, T67, E68, A72, G73, S97, L98, A99, S102, E110, L113, I133, K140, N144, N145, Y147, S152, N153, N164, N182, A204, T205, S214, V216, Q219, W228, V229, S230, S231, D236, I239, T241, N242, N263, L264, G265, A268, G269, D276, V284, S291, P300, A301, A311, V338, T342, S344, T346, A349, V359, G361, A364, T375, N379, S382, S390, E391, A393, K394, S410, S415, L417, H418, T430, A431, R433, A442, S444, T448 and/or S451 and/or an equivalent position in a parent glucoamylase. In some embodiments, variants of the invention having improved specific activity include a substitution in the following positions in the amino acid sequence set forth in SEQ ID NO: 2 or 3: 61, 67, 72, 97, 102, 133, 205, 219, 228, 230, 231, 239, 263, 268, 291, 342, 394, 430, 431 and 451 and/or an equivalent position in a parent glucoamylase. In some embodiments, the parent glucoamylase will comprise a sequence having at least 50%, at least 60%, at least 70%, at least 80%, at least 90% or 95% sequence identity to the sequence of SEQ ID NO:2 or 3. In some embodiments, the parent glucoamylase will also have structural identity to SEQ ID NO: 2 and/or 3. In some embodiments, the variant having increased specific activity has a substitution in at least one of the positions: 72, 133, 219, 228, 230, 231, 239, 263, 268, and 451 of SEQ ID NO: 2 and/or 3.

Combined Thermostability and Specific Activity

In some aspects, the invention relates to a variant glucoamylase having both altered thermostability and altered specific activity as compared to a parent (e.g., wildtype). In some embodiments, the altered specific activity is an increased specific activity. In some embodiments, the altered thermostability is an increased thermostability at high temperatures (e.g., at temperatures above 80° C.) as compared to the parent glucoamylase.

In some embodiments, variants with an increased thermostability and increased specific activity include one or more deletions, substitutions or insertions and substitutions in the following positions in the amino acid sequence set forth in SEQ ID NOs:2 or 3: T10, N15, F59, N61, E68, A72, G73, S97, A99, S102, I133, K140, N153, N182, A204, T205, S214, W228, V229, S230, S231, D236, T241, N242, L264, G265, A268, D276, V284, S291, P300, A301, A303, A311, V338, S344, T346, V359, G361, A364, T375, N379, S382, E391, A393, K394, S410, L417, T430, A431, R433, S444, T448 and/or S451 and/or an equivalent position in a parent glucoamylase. In some embodiments, the parent glucoamylase will be a Trichoderma glucoamylase homologue and in further embodiments, the parent glucoamylase will have at least 50%, at least 60%, at least 70%, at least 80%, at least 90%, at least 95% and at least 98% sequence identity to SEQ ID NO:2 or 3. In some embodiments, the parent glucoamylase will also have structural identity to SEQ ID NO: 2 and/or 3. In some embodiments, the variant having increased thermostability and specific activity has a substitution in at least one of the positions: 228, 230, 231, 268, 291, 417, 433, and 451 of SEQ ID NO: 2 and/or 3.

Polynucleotides:

The present invention also relates to isolated polynucleotides encoding a variant glucoamylase of the invention. The polynucleotides may be prepared by established techniques known in the art. The polynucleotides may be prepared synthetically, such as by an automatic DNA synthesizer. The DNA sequence may be of mixed genomic (or cDNA) and synthetic origin prepared by ligating fragments together. The polynucleotides may also be prepared by polymerase chain reaction (PCR) using specific primers. In general, reference is made to Minshull J., et al., (2004), Engineered protein function by selective amino acid diversification, Methods 32(4): 416-427. DNA may also be synthesized by a number of commercial companies such as Geneart AG, Regensburg, Germany.

The present invention also provides isolated polynucleotides comprising a nucleotide sequence (i) having at least 50% identity to SEQ ID NO:4, including at least 60%, at least 70%, at least 80%, at least 90%, at least 95%, and at least 99%, or (ii) being capable of hybridizing to a probe derived from the nucleotide sequence set forth in SEQ ID NO:4, under conditions of intermediate to high stringency, or (iii) being complementary to a nucleotide sequence having at least 90% sequence identity to the sequence set forth in SEQ ID NO:4. Probes useful according to the invention may include at least 50, 100, 150, 200, 250, 300 or more contiguous nucleotides of SEQ ID NO:4. In some embodiments, the encoded polypeptide also has structural identity to SEQ ID NOs: 2 and/or 3.

The present invention further provides isolated polynucleotides that encode variant glucoamylases which comprise an amino acid sequence comprising at least 50%, at least 60%, at least 70%, at least 80%, at least 90%, at least 93%, at least 95%, at least 97%, at least 98%, or at least 99% amino acid sequence identity to SEQ ID NO:2. Additionally, the present invention provides expression vectors comprising any of the polynucleotides provided above.

The present invention also provides fragments (i.e., portions) of the DNA encoding the variant glucoamylases provided herein. These fragments find use in obtaining partial length DNA fragments capable of being used to isolate or identify polynucleotides encoding mature glucoamylase enzymes described herein from filamentous fungal cells (e.g., Trichoderma, Aspergillus, Fusarium, Penicillium, and Humicola), or a segment thereof having glucoamylase activity. In some embodiments, fragments of the DNA may comprise at least 50, 100, 150, 200, 250 300 or more contiguous nucleotides. In some embodiments, portions of the DNA provided in SEQ ID NO:4 find use in obtaining parent glucoamylase and particularly Trichoderma glucoamylase homologues from other species, such as filamentous fungi which encode a glucoamylase.

DNA Constructs and Vectors:

According to one embodiment of the invention, a DNA construct comprising a polynucleotide as described above encoding a variant glucoamylase encompassed by the invention and operably linked to a promoter sequence is assembled to transfer into a host cell.

The DNA construct may be introduced into a host cell using a vector. The vector may be any vector which when introduced into a host cell is stably introduced. In some embodiments, the vector is integrated into the host cell genome and is replicated. Vectors include cloning vectors, expression vectors, shuttle vectors, plasmids, phage particles, cassettes and the like. In some embodiments, the vector is an expression vector that comprises regulatory sequences operably linked to the glucoamylase coding sequence.

Examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. Reference is also made to the Fungal Genetics Stock Center Catalogue of Strains (FGSC, <www.fgsc.net>) for a list of vectors. Particularly useful vectors include vectors obtained from for example Invitrogen and Promega.

Suitable plasmids for use in bacterial cells include pBR322 and pUC19 permitting replication in *E. coli* and pE194 for example permitting replication in *Bacillus*. Other specific vectors suitable for use in *E. coli* host cells include vectors such as pFB6, pBR322, pUC18, pUC100, pDONR™201, pDONR™221, pENTR™, pGEM®3Z and pGEM®4Z.

Specific vectors suitable for use in fungal cells include pRAX, a general purpose expression vector useful in *Aspergillus*, pRAX with a glaA promoter, and in *Hypocrea/Trichoderma* includes pTrex3g with a cbh1 promoter.

In some embodiments, the promoter shows transcriptional activity in a bacterial or a fungal host cell and may be derived from genes encoding proteins either homologous or heterologous to the host cell. The promoter may be a mutant, a truncated and/or a hybrid promoter. The above-mentioned promoters are known in the art. Examples of suitable promoters useful in fungal cells and particularly filamentous fungal cells such as *Trichoderma* or *Aspergillus* cells include such exemplary promoters as the *T. reesei* promoters cbh1, cbh2, egl1, egl2, eg5, xln1 and xln2. Other examples of useful promoters include promoters from *A. awamori* and *A. niger* glucoamylase genes (glaA) (See, Nunberg et al., (1984) *Mol. Cell Biol.* 4:2306-2315 and Boel et al., (1984) *EMBO J.* 3:1581-1585), *A. oryzae* TAKA amylase promoter, the TPI (triose phosphate isomerase) promoter from *S. cerevisiae*, the promoter from *Aspergillus nidulans* acetamidase genes and *Rhizomucor miehei* lipase genes. Examples of suitable promoters useful in bacterial cells include those obtained from the *E. coli* lac operon; *Bacillus licheniformis* alpha amylase gene (amyL), *B. stearothermophilus* amylase gene (amyS); *Bacillus subtilis* xylA and xylB genes, the beta-lactamase gene, and the tac promoter. In some embodiments, the promoter is one that is native to the host cell. For example, when *T. reesei* is the host, the promoter is a native *T. reesei* promoter. In other embodiments, the promoter is one that is heterologous to the fungal host cell. In some embodiments, the promoter will be the promoter of a parent glucoamylase (e.g., the TrGA promoter).

In some embodiments, the DNA construct includes nucleic acids coding for a signal sequence, that is, an amino acid sequence linked to the amino terminus of the polypeptide which directs the encoded polypeptide into the cell's secretory pathway. The 5' end of the coding sequence of the nucleic acid sequence may naturally include a signal peptide coding region which is naturally linked in translation reading frame with the segment of the glucoamylase coding sequence which encodes the secreted glucoamylase or the 5' end of the coding sequence of the nucleic acid sequence may include a signal peptide which is foreign to the coding sequence. In some embodiments, the DNA construct includes a signal sequence that is naturally associated with a parent glucoamylase gene from which a variant glucoamylase has been obtained. In some embodiments the signal sequence will be the sequence depicted in SEQ ID NO:1 or a sequence having at least 90%, at least 94% and at least 98% sequence identity thereto. Effective signal sequences may include the signal sequences obtained from other filamentous fungal enzymes, such as from *Trichoderma* (*T. reesei* glucoamylase), *Humicola* (*H. insolens* cellulase or *H. grisea* glucoamylase), *Aspergillus* (*A. niger* glucoamylase and *A. oryzae* TAKA amylase), and *Rhizopus*.

In additional embodiments, a DNA construct or vector comprising a signal sequence and a promoter sequence to be introduced into a host cell are derived from the same source. In some embodiments, the native glucoamylase signal sequence of a *Trichoderma* glucoamylase homologue, such as a signal sequence from a *Hypocrea* strain may be used.

In some embodiments, the expression vector also includes a termination sequence. Any termination sequence functional in the host cell may be used in the present invention. In some embodiments, the termination sequence and the promoter sequence are derived from the same source. In another embodiment, the termination sequence is homologous to the host cell. Useful termination sequences include termination sequences obtained from the genes of *Trichoderma reesei* cbh1; *A. niger* or *A. awamori* glucoamylase (Nunberg et al. (1984) supra, and Boel et al., (1984) supra), *Aspergillus nidulans* anthranilate synthase, *Aspergillus oryzae* TAKA amylase, or *A. nidulans* trpC (Punt et al., (1987) *Gene* 56:117-124).

In some embodiments, an expression vector includes a selectable marker. Examples of selectable markers include ones which confer antimicrobial resistance (e.g., hygromycin and phleomycin). Nutritional selective markers also find use in the present invention including those markers known in the art as amdS (acetamidase), argB (ornithine carbamoyltransferase) and pyrG (orotidine-5' phosphate decarboxylase). Markers useful in vector systems for transformation of *Trichoderma* are known in the art (See, e.g., Finkelstein, chapter 6 in BIOTECHNOLOGY OF FILAMENTOUS FUNGI, Finkelstein et al. (1992) Eds. Butterworth-Heinemann, Boston, Mass.; Kinghorn et al. (1992) APPLIED MOLECULAR GENETICS OF FILAMENTOUS FUNGI, Blackie Academic and Professional, Chapman and Hall, London; Berges and Barreau (1991) *Curr. Genet.* 19:359-365; and van Hartingsveldt et al., (1987) *Mol. Gen. Genet.* 206:71-75). In some embodiments, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttilä et al., (1987) *Gene* 61:155-164.

Methods used to ligate the DNA construct comprising a nucleic acid sequence encoding a variant glucoamylase, a promoter, a termination and other sequences and to insert them into a suitable vector are well known in the art. Linking is generally accomplished by ligation at convenient restriction sites. If such sites do not exist, synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Host Cells:

The present invention also relates to host cells comprising a polynucleotide encoding a variant glucoamylase of the invention. In some embodiments, the host cells are chosen from bacterial, fungal, plant and yeast cells. The term host cell includes both the cells, progeny of the cells and protoplasts created from the cells which are used to produce a variant glucoamylase according to the invention.

In some embodiments, the host cells are fungal cells and preferably filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens, H. lanuginosa* and *H. grisea*); *Chrysosporium* sp. (e.g., *C. lucknowense*), *Gliocladium* sp., *Aspergillus* sp. (e.g., *A. oryzae, A. niger, A. sojae, A. japonicus, A. nidulans*, and *A. awamori*) (Ward et al., (1993) Appl. Microbiol. Biotechnol. 39:738-743 and Goedegebuur et al., (2002) Genet 41:89-98), *Fusarium* sp., (e.g. *F. roseum, F. graminum F. cerealis, F. oxysporum* and *F. venenatum*), *Neurospora* sp., (*N. crassa*), *Hypocrea* sp., *Mucor* sp., (*M. miehei*), *Rhizopus* sp. and *Emericella* sp. (See also, Innis et al., (1985) *Sci.* 228:21-26). The term "*Trichoderma*" or "*Trichoderma* sp." or "*Trichoderma* spp." refer to any fungal genus previously or currently classified as *Trichoderma*.

In some embodiments, the host cells will be gram-positive bacterial cells. Non-limiting examples include strains of *Streptomyces*, (e.g., *S. lividans, S. coelicolor* and *S. griseus*) and *Bacillus*. As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*."

In some embodiments, the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp.

In other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g. methods disclosed in U.S. Pat. No. 5,246,853, U.S. Pat. No. 5,475,101 and WO 92/06209). Gene inactivation may be accomplished by complete or partial deletion, by insertional inactivation or by any other means which renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or deleted. Exemplary *Trichoderma reesei* host cells having quad-deleted proteins are set forth and described in U.S. Pat. No. 5,847,276 and WO 05/001036. In other embodiments, the host cell is a protease deficient or protease minus strain.

Transformation of Host Cells:

Introduction of a DNA construct or vector into a host cell includes techniques such as transformation; electroporation; nuclear microinjection; transduction; transfection, (e.g., lipofection-mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56).

Transformation methods for *Bacillus* are disclosed in numerous references including Anagnostopoulos C and J. Spizizen (1961) J. Bacteriol. 81:741-746 and WO 02/14490.

Transformation methods for *Aspergillus* are described in Yelton et al (1984) *Proc. Natl. Acad. Sci. USA* 81:1470-1474; Berka et al., (1991) in Applications of Enzyme Biotechnology, Eds. Kelly and Baldwin, Plenum Press (NY); Cao et al., (2000) Sci. 9:991-1001; Campbell et al., (1989) *Curr. Genet.* 16:53-56 and EP 238 023. The expression of heterologous protein in *Trichoderma* is described in U.S. Pat. No. 6,022, 725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to WO96/00787 and Bajar et al., (1991) *Proc. Natl. Acad. Sci. USA* 88:8202-28212 for transformation of *Fusarium* strains.

In one specific embodiment, the preparation of *Trichoderma* sp. for transformation involves the preparation of protoplasts from fungal mycelia (See, Campbell et al., (1989) *Curr. Genet.* 16:53-56; Pentilla et al., (1987) Gene 61:155-164). *Agrobacterium tumefaciens*-mediated transformation of filamentous fungi is known (See, de Groot et al., (1998) *Nat. Biotechnol.* 16:839-842). Reference is also made to U.S. Pat. No. 6,022,725 and U.S. Pat. No. 6,268,328 for transformation procedures used with filamentous fungal hosts.

In some embodiments, genetically stable transformants are constructed with vector systems whereby the nucleic acid encoding the variant glucoamylase is stably integrated into a host strain chromosome. Transformants are then purified by known techniques.

In some further embodiments, the host cells are plant cells, such as cells from a monocot plant (e.g. corn, wheat and sorghum) or cells from a dicot plant (e.g. soybean). Methods for making DNA constructs useful in transformation of plants and methods for plant transformation are known. Some of these methods include *Agrobacterium tumefaciens* mediated gene transfer; microprojectile bombardment, PEG mediated transformation of protoplasts, electroporation and the like. Reference is made to U.S. Pat. No. 6,803,499, U.S. Pat. No. 6,777,589; Fromm et al (1990) *Biotechnol.* 8:833-839; Potrykus et al (1985) *Mol. Gen. Genet.* 199:169-177.

Production of Proteins:

The present invention further relates to methods of producing the variant glucoamylases, which comprises transforming a host cell with an expression vector comprising a polynucleotide encoding a variant glucoamylase according to the invention, culturing the host cell under conditions suitable for expression and production of the variant glucoamylase and optionally recovering the variant glucoamylase.

In the expression and production methods of the present invention the host cells are cultured under suitable conditions in shake flask cultivation, small scale or large scale fermentations (including continuous, batch and fed batch fermentations) in laboratory or industrial fermentors, with suitable medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) find use in the present invention. Culture conditions for bacterial and filamentous fungal cells are known in the art and may be found in the scientific literature and/or from the source of the fungi such as the American Type Culture Collection and Fungal Genetics Stock Center. In cases where a glucoamylase coding sequence is under the control of an inducible promoter, the inducing agent (e.g., a sugar, metal salt or antimicrobial), is added to the medium at a concentration effective to induce glucoamylase expression.

In some embodiments, the present invention relates to methods of producing the variant glucoamylase in a plant host comprising transforming a plant cell with a vector comprising a polynucleotide encoding a glucoamylase variant according to the invention and growing the plant cell under conditions suitable for the expression and production of the variant.

In some embodiments, assays are carried out to evaluate the expression of a variant glucoamylase by a cell line that has been transformed with a polynucleotide encoding a variant glucoamylase encompassed by the invention. The assays can be carried out at the protein level, the RNA level and/or by use of functional bioassays particular to glucoamylase activity and/or production. Some of these assays include Northern blotting, dot blotting (DNA or RNA analysis), RT-PCR (reverse transcriptase polymerase chain reaction), in situ hybridization using an appropriately labeled probe (based on the nucleic acid coding sequence) and conventional Southern blotting and autoradiography.

In addition, the production and/or expression of a variant glucoamylase may be measured in a sample directly, for example, by assays directly measuring reducing sugars such as glucose in the culture medium and by assays for measuring glucoamylase activity, expression and/or production. In particular, glucoamylase activity may be assayed by the 3,5-dinitrosalicylic acid (DNS) method (See, Goto et al., (1994) Biosci. Biotechnol. Biochem. 58:49-54). In additional embodiments, protein expression, is evaluated by immunological methods, such as immunohistochemical staining of cells, tissue sections or immunoassay of tissue culture medium, (e.g., by Western blot or ELISA). Such immunoassays can be used to qualitatively and quantitatively evaluate expression of a glucoamylase. The details of such methods are known to those of skill in the art and many reagents for practicing such methods are commercially available.

The glucoamylases of the present invention may be recovered or purified from culture media by a variety of procedures known in the art including centrifugation, filtration, extraction, precipitation and the like.

Compositions:

The variant glucoamylases of the invention may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions. Further the variant glucoamylases may be used in baking applications, such as bread and cake production, brewing, healthcare, textile, environmental waste conversion processes, biopulp processing, and biomass conversion applications.

In some embodiments, an enzyme composition comprising a variant glucoamylase encompassed by the invention will be optionally used in combination with any one or combination of the following enzymes—alpha amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzymes and other glucoamylases.

In some embodiments, the enzyme composition will include an alpha amylase such as fungal alpha amylases (e.g. *Aspergillus* sp.) or bacterial alpha amylases (e.g. *Bacillus* sp. such as *B. stearothermophilus*, *B. amyloliquefaciens* and *B. licheniformis*) and variants and hybrids thereof. In some embodiments, the alpha amylase is an acid stable alpha amylase. In some embodiments, the alpha amylase is *Aspergillus kawachi* alpha amylase (AkAA), see U.S. Pat. No. 7,037,704. Commercially available alpha amylases contemplated for use in the compositions of the invention are known and include GZYME G997, SPEZYME FRED, SPEZYME XTRA, (Danisco US, Inc, Genencor Division), TERMAMYL 120-L and SUPRA (Novozymes, Biotech.).

In some embodiments, the enzyme composition will include an acid fungal protease. In a further embodiment, the acid fungal protease is derived from a *Trichoderma* sp and may be any one of the proteases disclosed in US 2006/015342, published Jul. 13, 2006 (e.g. SEQ ID NO:10). In a further embodiment, the enzyme composition will include a phytase (e.g., a *Buttiauxiella* spp. or variant thereof (e.g., see PCT patent publication WO 2006/043178).

In other embodiments, the variant glucoamylases of the invention may be combined with other glucoamylases. In some embodiments, the glucoamylases of the invention will be combined with one or more glucoamylases derived from strains of *Aspergillus* or variants thereof, such as *A. oryzae*, *A. niger*, *A. kawachi*, and *A. awamori*; glucoamylases derived from strains of *Humicola* or variants thereof, particularly *H. grisea*, such as the glucoamylase having at least 90%, 93%, 95%, 96%, 97%, 98% and 99% sequence identity to SEQ ID NO: 3 disclosed in WO 05/052148; glucoamylases derived from strains of *Talaromyces* or variants thereof, particularly *T. emersonii*; glucoamylases derived from strains of *Athelia* and particularly *A. rolfsii*; glucoamylases derived from strains of *Penicillium*, particularly *P. chrysogenum*.

Uses:

In particular, the variant glucoamylases may be used for starch conversion processes, and particularly in the production of dextrose for fructose syrups, specialty sugars and in alcohol and other end-product (e.g. organic acid, ascorbic acid, and amino acids) production from fermentation of starch containing substrates (G. M. A van Beynum et al., Eds. (1985) STARCH CONVERSION TECHNOLOGY, Marcel Dekker Inc. NY). Dextrins produced using variant glucoamylase compositions of the invention may result in glucose yields of at least 80%, at least 85%, at least 90% and at least 95%. Production of alcohol from the fermentation of starch substrates using glucoamylases encompassed by the invention may include the production of fuel alcohol or potable alcohol. In some embodiments, the production of alcohol will be greater when the variant glucoamylase is used under the same conditions as the parent glucoamylase. In some embodiments, the production of alcohol will be between about 0.5% and 2.5% better, including but not limited to 0.6%, 0.7%, 0.8%, 0.9%, 1.0%, 1.1%, 1.2%, 1.3%, 1.4%, 1.5%, 1.6%. 1.7%, 1.8%, 1.9%, 2.0%, 2.1%, 2.2%, 2.3%, and 2.4% more alcohol than the parent glucoamylase.

In some embodiments, the variant glucoamylases of the invention will find use in the hydrolysis of starch from various plant-based substrates, which are used for alcohol production. In some embodiments, the plant-based substrates will include corn, wheat, barley, rye, milo, rice, sugar cane, potatoes and combinations thereof. In some embodiments, the plant-based substrate will be fractionated plant material, for example a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, $3^{rd}$ Ed., Eds K. A. Jacques et al., 1999, Nottingham University Press, UK. In certain embodiments, the alcohol will be ethanol. In particular, alcohol fermentation production processes are characterized as wet milling or dry milling processes. In some embodiments, the variant glucoamylase will be used in a wet milling fermentation process and in other embodiments the variant glucoamylase will find use in a dry milling process.

Dry grain milling involves a number of basic steps, which generally include: grinding, cooking, liquefaction, saccharification, fermentation and separation of liquid and solids to produce alcohol and other co-products. Plant material and particularly whole cereal grains, such as corn, wheat or rye are ground. In some cases the grain may be first fractionated into component parts. The ground plant material may be milled to obtain a coarse or fine particle. The ground plant material is mixed with liquid (e.g. water and/or thin stillage) in a slurry tank. The slurry is subjected to high temperatures (e.g. 90° C. to 105° C. or higher) in a jet cooker along with liquefying enzymes (e.g. alpha amylases) to solublize and hydrolyze the starch in the grain to dextrins. The mixture is cooled down and further treated with saccharifying enzymes, such as glucoamylases encompassed by the instant invention, to produce glucose. The mash containing glucose may then be fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the variant glucoamylase is used in a process for starch hydrolysis wherein the temperature of the process is between 30° C. and 75° C., in some embodiments, between 40° C. and 65° C. In some embodiments, the variant glucoamylase is used in a process for starch hydrolysis at a pH of between pH 3.0 and pH 6.5. The fermentation processes in some embodiments include milling of a cereal grain or fractionated grain and combining the ground cereal grain with liquid to form a slurry which is then mixed in a single vessel with a variant glucoamylase according to the invention and optionally other enzymes such as, but not limited to, alpha amylases, other glucoamylases, phytases, proteases, pullulanases, isoamylases or other enzymes having granular starch hydrolyzing activity and yeast to produce ethanol and other co-products (See e.g., U.S. Pat. No. 4,514,496, WO 04/081193 and WO 04/080923).

In some embodiments, the invention pertains to a method of saccharifying a liquid starch solution, which comprises an enzymatic saccharification step using a variant glucoamylase of the invention.

The present invention also provides an animal feed composition or formulation comprising at least one variant glucoamylase encompassed by the invention. Methods of using a glucoamylase enzyme in the production of feeds comprising starch are provided in WO 03/049550 (herein incorporated by reference in its entirety). Briefly, the glucoamylase variant is admixed with a feed comprising starch. The glucoamylase is capable of degrading resistant starch for use by the animal.

Other objects and advantages of the present invention are apparent from the present Specification.

Experimental

In the disclosure and experimental section which follows, the following abbreviations apply: GA (glucoamylase); GAU (glucoamylase unit); wt % (weight percent); ° C. (degrees Centigrade); rpm (revolutions per minute); $H_2O$ (water); $dH_2O$ (deionized water); $dIH_2O$ (deionized water, Milli-Q filtration); aa or AA (amino acid); by (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec(s) or s(s) (second/seconds); min(s) or m(s) (minute/minutes); hr(s) or h(s) (hour/hours); DO (dissolved oxygen); ABS (Absorbance); EtOH (ethanol); PSS (physiological salt solution); m/v (mass/volume); and MTP (microtiter plate); N (Normal); DP1 (monosaccharides); DP2 (disaccharides); DP>3 (oligosaccharides, sugars having a degree of polymerization greater than 3); ppm (parts per million).

Assays and methods used in the examples below are provided. However, it should be noted that different methods may be used to provide variants of a parent molecule and the invention is not limited to the methods used in the examples. It is intended that any suitable means for making variants and selection of variants may be used.

pNPG Glucoamylase Activity Assay for 96-Well Microtiter Plates:

The reagent solutions were: NaAc buffer (200 mM sodium acetate buffer pH 4.5); Substrate (50 mM p-nitrophenyl-α-D-glucopyranoside (Sigma N-1377) in NaAc buffer (0.3 g/20 ml)) and stop solution (800 mM glycine-NaOH buffer pH 10). 30 µl filtered supernatant was placed in a fresh 96-well flat bottom MTP. To each well 50 µl NaAc buffer and 120 µl substrate was added and incubated for 30 minutes at 50° C. (Thermolab systems iEMS Incubator/shaker HT). The reaction was terminated by adding 100 µl stop solution. The absorbance was measured at 405 nm in a MTP-reader (Molecular Devices Spectramax 384 plus) and the activity was calculated using a molar extinction coefficient of 0.011 µM/cm.

Thermal Stability Assay:

Crude supernatant (8 µl) was added to 280 µl 50 mM NaAc buffer pH 4.5. The diluted sample was equally divided over 2 MTPs. One MTP (initial plate) was incubated for 1 hr at 4° C. and the other MTP (residual plate) was incubated at 64° C. (Thermolab systems iEMS Incubator/Shaker HT) for 1 hr. The residual plate was chilled for 10 min on ice. Activity was measured of both plates using the ethanol screening assay described below. 60 µl of the initial plate or residual plate was added to 120 µl 4% soluble corn starch and incubated for 2 hrs at 32° C. 900 rpm (Thermolabsystems iEMS Incubator/Shaker HT).

Thermal stability was calculated as % residual activity as follows:

$$\frac{ABS(340) \text{ residual} - \text{blank}}{ABS(340) \text{ initial} - \text{blank}} \times 100\%.$$

The crude supernatant material was tested for remaining glucose in the culture medium after the growth period. If remaining glucose was found, the thermal stability was not calculated.

Based on the residual activity of WT and mutant the performance index (PI) for the thermal stability was calculated. The PI of a variant is the quotient "Variant-residual activity/WT-residual activity." The PI of WT is 1.0 and a variant with a PI>1.0 has a specific activity that is greater than WT.

Caliper Protein Determination

Data Analysis and Calculation of Performance Index of Ethanol Application Assay.

Protein levels were measured using a microfluidic electrophoresis instrument (Caliper Life Sciences, Hopkinton, Mass., USA). The microfluidic chip and protein samples were prepared according to the manufacturer's instructions (LABCHIP® HT Protein Express, P/N 760301). Culture supernatants were prepared and stored in 96-well microtiter plates at −20° C. until use, when they were thawed by warming in a 37° C. incubator for 30 minutes. After shaking briefly, 2 µl of each culture sample was transferred to a 96-well PCR plate (Bio-Rad, Hercules, Calif., USA) containing 7 µl samples buffer (Caliper) followed by heating the plate to 90° C. for 5 minutes on a thermostatically controlled plate heater. The plate was allowed to cool before adding 40 µl water to each sample. The plate was then placed in the instrument along with a protein standard supplied and calibrated by the manufacturer. As the proteins move past a focal point in the chip, the fluorescence signal was recorded and the protein concentration was determined by quantitating the signal relative to the signal generated by the calibrated set of protein standards.

After the Caliper protein determination the data was processed in the following way. The calibration ladders are checked for correctness of the peak pattern. If the calibration ladder which was associated with the run did not suffice, it was replaced by a calibration ladder of an adjacent run. For peak detection, the default settings of the global peak find option of the caliper software were used. The peak of interest was selected at 75 kDA+/−10%.

The result was exported to a spreadsheet program and the peak area was related to the corresponding activity (ABS340-blank measurement) in the ethanol application assay. With the area and activity numbers of 12 Wild Type samples, a calibration line was made using the "Enzyme Kinetics" equation of the program Grafit Version 5 (Erithacus Software, Horley, UK) in combination with a non-linear fit function. The default settings were used to calculate the Km and Vmax parameters. Based on these two parameters, a Michaelis-Menten reference line was made and the specific activity of each variant was calculated based on this reference line.

Based on the specific activity of WT and variants the performance index (PI) for the specific activity was calculated. The PI of a variant is the quotient "Variant-specific activity/WT-specific activity." The PI of WT is 1.0 and a variant with a PI>1.0 had a specific activity that is greater than WT.

Hexokinase Activity Assay:

Hexokinase cocktail: 10-15 minutes prior to use, 90 ml water was added to a BoatIL container glucose HK R1 (IL test glucose (HK) kit, Instrument Laboratory #182507-40) and gently mixed. 100 µl of Hexokinase cocktail was added to 85 µl of dH$_2$O. 15 µl of sample was added to the mixtures and incubated for 10 minutes in the dark at room temperature. Absorbance was read at 340 nm in a MTP-reader. Glucose concentrations were calculated according to a glucose (0-2 mg/ml) standard curve.

Assay Conditions Ethanol Screening Assay:

8% stock solution: 8 g of soluble corn starch (Sigma #S4180) was suspended in 40 ml dH$_2$O at room temperature. 50 ml of boiling dH$_2$O was added to the slurry in a 250 ml flask and cooked for 5 minutes. The starch solution was cooled to 25° C. and the volume adjusted to 100 ml with dH$_2$O.

Stop solution: 800 mM Glycine-NaOH buffer, pH 10.

4% (m/v) soluble starch working solution: stock solution was diluted (1:1) with 100 mM sodium acetate buffer pH 3.7.

5 µl crude supernatant was diluted with 175 µl 50 mM NaAc buffer pH 4.5 in a flat bottom 96-well MTP. 60 µl of this dilution was added to 120 µl 4% soluble corn starch and incubated for 2 hrs at 32° C. 900 rpm (Thermolabsystems iEMS Incubator/Shaker HT). The reaction was stopped by adding 90 µl 4° C.-cold Stop Solution. The sample was placed on ice. Starch was spun down at 1118×g at 15° C. for 5 minutes (SIGMA 6K15) and 15 µl supernatant was used in the Hexokinase activity assay described above to determine the glucose content.

The crude supernatant material was tested for remaining glucose in the culture medium after the growth period. If remaining glucose was found, the amount of glucose produced by the Glucoamylase was not calculated.

EXAMPLES

The following examples are provided in order to demonstrate and further illustrate certain embodiments and aspects of the present invention and are not to be construed as limiting the scope thereof.

Example 1

Construction of TrGA Site Evaluation Libraries (SELs) in the pTTT Vector for Expression in *Trichoderma reesei*

Figure 2:
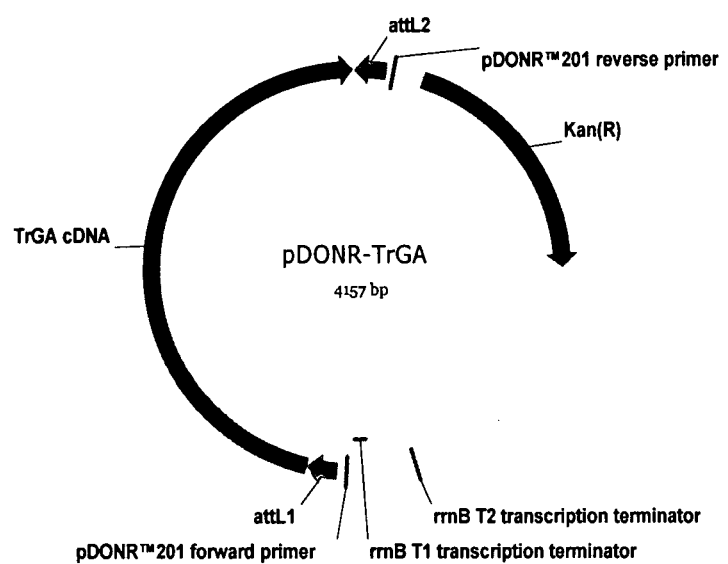
FIG. 2 illustrates the destination plasmid pDONR-TrGA which includes the cDNA (SEQ ID NO:4) of the TrGA.

A *Trichoderma reesei* cDNA sequence (SEQ ID NO: 4) was cloned into pDONR™201 via the Gateway® BP recombination reaction (Invitrogen, Carlsbad, Calif., USA) resulting in the entry vector pDONR-TrGA (FIG. 2). The cDNA sequence (SEQ ID NO:4) encodes the TrGA signal peptide, the pro-sequence, and the mature protein, including the catalytic domain, linker region and starch binding domain (SEQ ID NO:1). SEQ ID NO:4 and SEQ ID NO:1 are shown in FIGS. 1B and 1A. FIG. 1C illustrates the precursor and mature protein TrGA domains.

Figure 3:
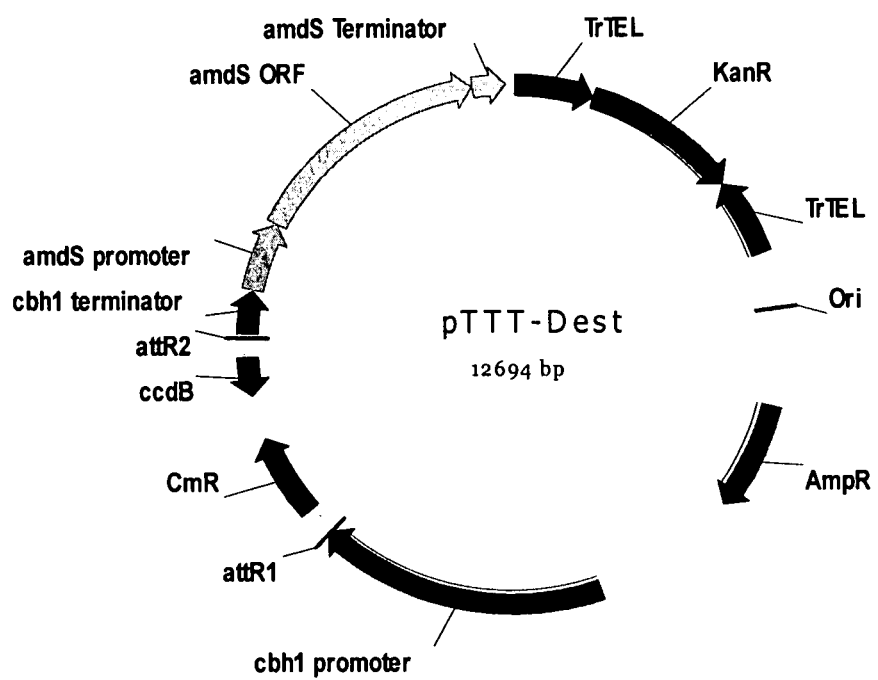
FIG. 3 illustrates the plasmid pTTT-Dest.
Figure 4:
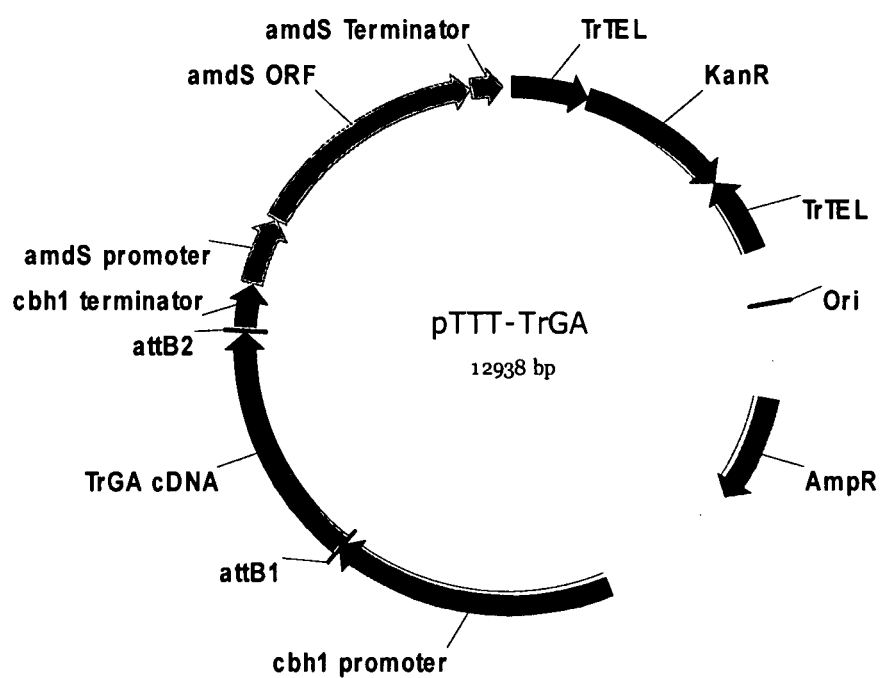
FIG. 4 illustrates the final expression vector pTTT-TrGA.

To express the TrGA protein in *Trichoderma reesei*, the TrGA coding sequence (SEQ ID NO:4) was cloned into the Gateway compatible destination vector pTTT-Dest (FIG. 3) via the GATEWAY® LR recombination reaction. The expression vector contained the *T. reesei* cbhI-derived promoter and terminator regions which allowed for strong inducible expression of a gene of interest. The vector also contained the *Aspergillus nidulans* amdS selective marker which allowed for growth of the transformants on acetamide as a sole nitrogen source. The expression vector also contained *T. reesei* telomere regions which allowed for non-chromosomal plasmid maintenance in a fungal cell. On the destination pTTT-Dest plasmid, the cbhI promoter and terminator regions were separated by the chloramphenicol resistance gene, Cm^R, and the lethal *E. coli* gene, ccdB, flanked by the bacteriophage lambda-based specific recombination sites attR1, attR2. This configuration allowed for direct selection of recombinants containing the TrGA gene under control of the cbhI regulatory elements in the right orientation via the GATEWAY® LR recombination reaction. The final expression vector pTTT-TrGA is shown in FIG. 4.

SELs were constructed using the pDONR-TrGA entry vector (FIG. 2) as a template and the primers listed in Table 2. All primers used in the mutagenesis experiments contained the triplet NNS (N=A, C, T, G and S=C or G) at the position that aligns with the codon of the TrGA sequence designed to be mutated (SEQ ID NO:1), allowing for a random incorporation of nucleotides at the preselected position. Construction of each SEL library started with two independent PCR amplifications on the pDONR-TrGA entry vector: one using the Gateway F (pDONR201-FW) and a specific mutagenesis primer R (Table 2), and the other—the Gateway primer R (pDONR201-RV) and a specific mutagenesis primer F (Table 2). High fidelity PHUSION DNA polymerase (Finnzymes OY, Espoo, Finland) was used in a PCR amplification reaction including 0.2 µM primers. The reactions were carried out for 25 cycles according to the protocol provided by Finnzymes. 1 µl aliquots of the PCR fragments obtained were used as templates for a subsequent fusion PCR reaction together with the Gateway FW and Gateway RV primers (Invitrogen). This PCR amplification, after 22 cycles, produced a population of the full-length linear TrGA DNA fragments randomly mutated at the specific codon position. The fragments were flanked by the Gateway-specific attL1, attL2 recombination sites on both ends. The DNA fragments were purified with a CHARGES WITCH® PCR clean-up kit (Invitrogen, Carlsbad USA) and then recombined with 100 ng of the pTTT-destination vector (FIG. 3) using the LR CLONASE™ II enzyme mix according to the protocol supplied by Invitrogen. The recombination products that were generated were transformed into *E. coli* Max Efficiency DH5α, as described by the supplier (Invitrogen). The final expression constructs pTTT-TrGA with mutations at the desired position were selected by plating bacteria on 2×YT agar plates (16 g/L Bacto Tryptone (Difco), 10 g/L Bacto Yeast Extract (Difco), 5 g/L NaCl, 16 g/L Bacto Agar (Difco)) with 100 µg/ml ampicillin.

96 single colonies from each library were grown for 24 hrs at 37° C. in MTP containing 200 µL, 2×YT medium with 100 µg/ml ampicillin. Cultures were used directly to amplify PCR fragments encompassing the region where a specific mutation was introduced. The specific PCR products obtained were sequenced using an ABI3100 sequence analyzer (Applied Biosystems). Each library contained from 15 to 19 different TrGA variants in the final expression vector. These variants were individually transformed into *T. reesei*, as described below. Libraries are numbered from 1 to 182 referencing the specific amino acid residue in the TrGA sequence which was randomly mutated.

TABLE 2

Primers used to generate TrGA SELs

| AA-position | F/R | DNA Sequence 5' to 3' |
|---|---|---|
| pDONR201- | F | TCGCGTTAACGCTAGCATGGATCTC (SEQ ID NO: 13) |
| pDONR201- | R | TCGCGTTAACGCTAGCATGGATCTC (SEQ ID NO: 14) |

TABLE 2-continued

Primers used to generate TrGA SELs

| AA-position | F/R | DNA Sequence 5' to 3' |
|---|---|---|
| 4 | F | CGTCACCAAGAGGTCTGTTGACNNSTTCATCAGCACCG AGACGCC (SEQ ID NO: 15) |
| 4 | R | GTCAACAGACCTCTTGGTGACGTCG (SEQ ID NO: 16) |
| 5 | F | CACCAAGAGGTCTGTTGACGACNNSATCAGCACCGAGA CGCCTATTGC (SEQ ID NO: 17) |
| 5 | R | GTCGTCAACAGACCTCTTGGTGAC (SEQ ID NO: 18) |
| 10 | F | TGACGACTTCATCAGCACCGAGNNSCCTATTGCACTG (SEQ ID NO: 19) |
| 10 | R | CTCGGTGCTGATGAAGTCGTC (SEQ ID NO: 20) |
| 12 | F | TCATCAGCACCGAGACGCCTNNSGCACTGAACAATCTT CTTTGCA (SEQ ID NO: 21) |
| 12 | R | AGGCGTCTCGGTGCTGATGAAGTCG (SEQ ID NO: 22) |
| 14 | F | CAGCACCGAGACGCCTATTGCANNSAACAATCTTCTT (SEQ ID NO: 23) |
| 14 | R | TGCAATAGGCGTCTCGGTGCT (SEQ ID NO: 24) |
| 15 | F | CACCGAGACGCCTATTGCACTGNNSAATCTTCTTTGC (SEQ ID NO: 25) |
| 15 | R | CAGTGCAATAGGCGTCTCGGT (SEQ ID NO: 26) |
| 23 | F | CAATCTTCTTTGCAATGTTGGTNNSGATGGATGCCGT (SEQ ID NO: 27) |
| 23 | R | ACCAACATTGCAAAGAAGATTG (SEQ ID NO: 28) |
| 24 | F | TTCTTTGCAATGTTGGTCCTNNSGGATGCCGTGCATT CGGCACAT (SEQ ID NO: 29) |
| 24 | R | AGGACCAACATTGCAAAGAAGATTG (SEQ ID NO: 30) |
| 29 | F | GTCCTGATGGATGCCGTGCANNSGGCACATCAGCTGG TGCGGTGA (SEQ ID NO: 31) |
| 29 | R | TGCACGGCATCCATCAGGACCAACA (SEQ ID NO: 32) |
| 42 | F | TGCGGTGATTGCATCTCCCAGCNNSATTGACCCGGAC (SEQ ID NO: 33) |
| 42 | R | GCTGGGAGATGCAATCACCGCA (SEQ ID NO: 34) |
| 43 | F | TGATTGCATCTCCCAGCACANNSGACCCGGACTACT ATTACATGT (SEQ ID NO: 35) |
| 43 | R | TGTGCTGGGAGATGCAATCACCGCA (SEQ ID NO: 36) |

TABLE 2-continued

Primers used to generate TrGA SELs

| AA-position | F/R | DNA Sequence 5' to 3' |
|---|---|---|
| 44 | F | TTGCATCTCCCAGCACAATTNNSCCGGACTACTATT<br>ACATGTGGA<br>(SEQ ID NO: 37) |
| 44 | R | AATTGTGCTGGGAGATGCAATCACC<br>(SEQ ID NO: 38) |
| 45 | F | CATCTCCCAGCACAATTGACNNSGACTACTATTACA<br>TGTGGACGC<br>(SEQ ID NO: 39) |
| 45 | R | GTCAATTGTGCTGGGAGATGCAATC<br>(SEQ ID NO: 40) |
| 46 | F | CTCCCAGCACAATTGACCCGNNSTACTATTACATGT<br>GGACGCGAGA<br>(SEQ ID NO: 41) |
| 46 | R | CGGGTCAATTGTGCTGGGAGATGCA<br>(SEQ ID NO: 42) |
| 47 | F | CCAGCACAATTGACCCGGACNNSTATTACATGTGGA<br>CGCGAGATA<br>(SEQ ID NO: 43) |
| 47 | R | GTCCGGGTCAATTGTGCTGGGAGAT<br>(SEQ ID NO: 44) |
| 49 | F | CAATTGACCCGGACTACTATNNSATGTGGACGCGAGA<br>TAGCGCTC<br>(SEQ ID NO: 45) |
| 49 | R | ATAGTAGTCCGGGTCAATTGTGCTG<br>(SEQ ID NO: 46) |
| 51 | F | ACCCGGACTACTATTACATGNNSACGCGAGATAGCGC<br>TCTTGTCT<br>(SEQ ID NO: 47) |
| 51 | R | CATGTAATAGTAGTCCGGGTCAATT<br>(SEQ ID NO: 48) |
| 59 | F | GACGCGAGATAGCGCTCTTGTCNNSAAGAACCTCATC<br>(SEQ ID NO: 49) |
| 59 | R | GACAAGAGCGCTATCTCGCGT<br>(SEQ ID NO: 50) |
| 60 | F | GCGAGATAGCGCTCTTGTCTTCNNSAACCTCATCGAC<br>(SEQ ID NO: 51) |
| 60 | R | GAAGACAAGAGCGCTATCTCG<br>(SEQ ID NO: 52) |
| 61 | F | AGATAGCGCTCTTGTCTTCAAGNNSCTCATCGACCGC<br>(SEQ ID NO: 53) |
| 61 | R | CTTGAAGACAAGAGCGCTATC<br>(SEQ ID NO: 54) |
| 65 | F | TGTCTTCAAGAACCTCATCGACNNSTTCACCGAAACG<br>(SEQ ID NO: 55) |
| 65 | R | GTCGATGAGGTTCTTGAAGAC<br>(SEQ ID NO: 56) |
| 67 | F | CAAGAACCTCATCGACCGCTTCNNSGAAACGTACGAT<br>(SEQ ID NO: 57) |
| 67 | R | GAAGCGGTCGATGAGGTTCTT<br>(SEQ ID NO: 58) |
| 68 | F | GAACCTCATCGACCGCTTCACCNNSACGTACGATGCG<br>(SEQ ID NO: 59) |
| 68 | R | GGTGAAGCGGTCGATGAGGTT<br>(SEQ ID NO: 60) |
| 70 | F | TCGACCGCTTCACCGAAACGNNSGATGCGGGCCTGCA<br>GCGCCGCA<br>(SEQ ID NO: 61) |
| 70 | R | CGTTTCGGTGAAGCGGTCGATGAGG<br>(SEQ ID NO: 62) |
| 72 | F | CCGCTTCACCGAAACGTACGATNNSGGCCTGCAGCGC<br>(SEQ ID NO: 63) |
| 72 | R | ATCGTACGTTTCGGTGAAGCGG<br>(SEQ ID NO: 64) |
| 73 | F | CTTCACCGAAACGTACGATGCGNNSCTGCAGCGCCGC<br>(SEQ ID NO: 65) |
| 73 | R | CGCATCGTACGTTTCGGTGAA<br>(SEQ ID NO: 66) |
| 75 | F | AAACGTACGATGCGGGCCTGNNSCGCCGCATCGAGCA<br>GTACATTA<br>(SEQ ID NO: 67) |
| 75 | R | CAGGCCCGCATCGTACGTTTCGGTG<br>(SEQ ID NO: 68) |
| 76 | F | CGTACGATGCGGGCCTGCAGNNSCGCATCGAGCAGTAC<br>ATTACTG<br>(SEQ ID NO: 69) |
| 76 | R | CTGCAGGCCCGCATCGTACGTTTCG<br>(SEQ ID NO: 70) |
| 94 | F | CTCTCCAGGGCCTCTCTAACNNSTCGGGCTCCCTCGCG<br>GACGGCT<br>(SEQ ID NO: 71) |
| 94 | R | GTTAGAGAGGCCCTGGAGAGTGACC<br>(SEQ ID NO: 72) |
| 97 | F | GGGCCTCTCTAACCCCTCGGGCNNSCTCGCGGACGGC<br>(SEQ ID NO: 73) |
| 97 | R | GCCCGAGGGGTTAGAGAGGCC<br>(SEQ ID NO: 74) |
| 98 | F | CCTCTCTAACCCCTCGGGCTCCNNSGCGGACGGCTCT<br>(SEQ ID NO: 75) |
| 98 | R | GGAGCCCGAGGGGTTAGAGAG<br>(SEQ ID NO: 76) |
| 99 | F | CTCTAACCCCTCGGGCTCCCTCNNSGACGGCTCTGGT<br>(SEQ ID NO: 77) |
| 99 | R | GAGGGAGCCCGAGGGGTTAGA<br>(SEQ ID NO: 78) |
| 100 | F | ACCCCTCGGGCTCCCTCGCGNNSGGCTCTGGTCTCGG<br>CGAGCCCA<br>(SEQ ID NO: 79) |
| 100 | R | CGCGAGGGAGCCCGAGGGGTTAGAG<br>(SEQ ID NO: 80) |
| 102 | F | CTCGGGCTCCCTCGCGGACGGCNNSGGTCTCGGCGAG<br>(SEQ ID NO: 81) |
| 102 | R | GCCGTCCGCGAGGGAGCCCGA<br>(SEQ ID NO: 82) |

TABLE 2-continued

Primers used to generate TrGA SELs

| AA-position | F/R | DNA Sequence 5' to 3' |
|---|---|---|
| 110 | F | TGGTCTCGGCGAGCCCAAGTTTNNSTTGACCCTGAAG (SEQ ID NO: 83) |
| 110 | R | AAACTTGGGCTCGCCGAGACCA (SEQ ID NO: 84) |
| 111 | F | TCTCGGCGAGCCCAAGTTTGAGNNSACCCTGAAGCCT (SEQ ID NO: 85) |
| 111 | R | CTCAAACTTGGGCTCGCCGAG (SEQ ID NO: 86) |
| 113 | F | CGAGCCCAAGTTTGAGTTGACCNNSAAGCCTTTCACC (SEQ ID NO: 87) |
| 113 | R | GGTCAACTCAAACTTGGGCTC (SEQ ID NO: 88) |
| 114 | F | CCAAGTTTGAGTTGACCCTGNNSCCTTTCACCGGCAACTGGGGTC (SEQ ID NO: 89) |
| 114 | R | CAGGGTCAACTCAAACTTGGGCTCG (SEQ ID NO: 90) |
| 116 | F | TTGAGTTGACCCTGAAGCCTNNSACCGGCAACTGGGGTCGACCGCA (SEQ ID NO: 91) |
| 116 | R | AGGCTTCAGGGTCAACTCAAACTTG (SEQ ID NO: 92) |
| 119 | F | CCCTGAAGCCTTTCACCGGCNNSTGGGGTCGACCGCAGCGGGATG (SEQ ID NO: 93) |
| 119 | R | GCCGGTGAAAGGCTTCAGGGTCAAC (SEQ ID NO: 94) |
| 122 | F | CTTTCACCGGCAACTGGGGTNNSCCGCAGCGGGATGGCCCAGCTC (SEQ ID NO: 95) |
| 122 | R | ACCCCAGTTGCCGGTGAAAGGCTTC (SEQ ID NO: 96) |
| 125 | F | GCAACTGGGGTCGACCGCAGNNSGATGGCCCAGCTCTGCGAGCCA (SEQ ID NO: 97) |
| 125 | R | CTGCGGTCGACCCCAGTTGCCGGTG (SEQ ID NO: 98) |
| 133 | F | GGATGGCCCAGCTCTGCGAGCCNNSGCCTTGATTGGA (SEQ ID NO: 99) |
| 133 | R | GGCTCGCAGAGCTGGGCCATCC (SEQ ID NO: 100) |
| 137 | F | TGCGAGCCATTGCCTTGATTNNSTACTCAAAGTGGCTCATCAACA (SEQ ID NO: 101) |
| 137 | R | AATCAAGGCAATGGCTCGCAGAGCT (SEQ ID NO: 102) |
| 140 | F | CATTGCCTTGATTGGATACTCNNSTGGCTCATCAAC (SEQ ID NO: 103) |
| 140 | R | TGAGTATCCAATCAAGGCAATG (SEQ ID NO: 104) |
| 144 | F | TGGATACTCAAAGTGGCTCATCNNSAACAACTATCAG (SEQ ID NO: 105) |
| 144 | R | GATGAGCCACTTTGAGTATCC (SEQ ID NO: 106) |
| 145 | F | ATACTCAAAGTGGCTCATCAACNNSAACTATCAGTCG (SEQ ID NO: 107) |
| 145 | R | GTTGATGAGCCACTTTGAGTA (SEQ ID NO: 108) |
| 146 | F | CAAAGTGGCTCATCAACAACNNSTATCAGTCGACTGTGTCCAACG (SEQ ID NO: 109) |
| 146 | R | GTTGTTGATGAGCCACTTTGAGTAT (SEQ ID NO: 110) |
| 147 | F | AAAGTGGCTCATCAACAACAACNNSCAGTCGACTGTG (SEQ ID NO: 111) |
| 147 | R | GTTGTTGTTGATGAGCCACTT (SEQ ID NO: 112) |
| 148 | F | GGCTCATCAACAACAACTATNNSTCGACTGTGTCCAACGTCATCT (SEQ ID NO: 113) |
| 148 | R | ATAGTTGTTGTTGATGAGCCACTTT (SEQ ID NO: 114) |
| 152 | F | CAACAACTATCAGTCGACTGTGNNSAACGTCATCTGG (SEQ ID NO: 115) |
| 152 | R | CACAGTCGACTGATAGTTGTT (SEQ ID NO: 116) |
| 153 | F | CAACTATCAGTCGACTGTGTCCNNSGTCATCTGGCCT (SEQ ID NO: 117) |
| 153 | R | GGACACAGTCGACTGATAGTT (SEQ ID NO: 118) |
| 164 | F | GCCTATTGTGCGCAACGACCTCNNSTATGTTGCCCAGT (SEQ ID NO: 119) |
| 164 | R | GAGGTCGTTGCGCACAATAGG (SEQ ID NO: 120) |
| 169 | F | ACCTCAACTATGTTGCCCAGNNSTGGAACCAAACCGGCTTTGACC (SEQ ID NO: 121) |
| 169 | R | CTGGGCAACATAGTTGAGGTCGTTG (SEQ ID NO: 122) |
| 172 | F | ATGTTGCCCAGTACTGGAACNNSACCGGCTTTGACCTCTGGGAAG (SEQ ID NO: 123) |
| 172 | R | GTTCCAGTACTGGGCAACATAGTTG (SEQ ID NO: 124) |
| 175 | F | AGTACTGGAACCAAACCGGCNNSGACCTCTGGGAAGAAGTCAATG (SEQ ID NO: 125) |
| 175 | R | GCCGGTTTGGTTCCAGTACTGGGCA (SEQ ID NO: 126) |
| 178 | F | ACCAAACCGGCTTTGACCTCNNSGAAGAAGTCAATGGGAGCTCAT (SEQ ID NO: 127) |
| 178 | R | GAGGTCAAAGCCGGTTTGGTTCCAG (SEQ ID NO: 128) |

TABLE 2-continued

Primers used to generate TrGA SELs

| AA-position | F/R | DNA Sequence 5' to 3' |
|---|---|---|
| 180 | F | CCGGCTTTGACCTCTGGGAANNSGTCAATGGGAGCTCATTCTTTA (SEQ ID NO: 129) |
| 180 | R | TTCCCAGAGGTCAAAGCCGGTTTGG (SEQ ID NO: 130) |
| 181 | F | GCTTTGACCTCTGGGAAGAANNSAATGGGAGCTCATTCTTTACTG (SEQ ID NO: 131) |
| 181 | R | TTCTTCCCAGAGGTCAAAGCCGGTT (SEQ ID NO: 132) |
| 182 | F | CTTTGACCTCTGGGAAGAAGTCNNSGGGAGCTCATTC (SEQ ID NO: 133) |
| 182 | R | GACTTCTTCCCAGAGGTCAAAG (SEQ ID NO: 134) |
| 204 | F | TGTCGAGGGCGCCACTCTTGCTNNSACTCTTGGCCAG (SEQ ID NO: 135) |
| 204 | R | AGCAAGAGTGGCGCCCTCGAC (SEQ ID NO: 136) |
| 205 | F | CGAGGGCGCCACTCTTGCTGCCNNSCTTGGCCAGTCG (SEQ ID NO: 137) |
| 205 | R | GGCAGCAAGAGTGGCGCCCTC (SEQ ID NO: 138) |
| 208 | F | CTCTTGCTGCCACTCTTGGCNNSTCGGGAAGCGCTTATTCATCTG (SEQ ID NO: 139) |
| 208 | R | GCCAAGAGTGGCAGCAAGAGTGGCG (SEQ ID NO: 140) |
| 211 | F | CCACTCTTGGCCAGTCGGGANNSGCTTATTCATCTGTTGCTCCCC (SEQ ID NO: 141) |
| 211 | R | TCCCGACTGGCCAAGAGTGGCAGCA (SEQ ID NO: 142) |
| 214 | F | TGGCCAGTCGGGAAGCGCTTATNNSTCTGTTGCTCCC (SEQ ID NO: 143) |
| 214 | R | ATAAGCGCTTCCCGACTGGCC (SEQ ID NO: 144) |
| 216 | F | GTCGGGAAGCGCTTATTCATCTNNSGCTCCCCAGGTT (SEQ ID NO: 145) |
| 216 | R | AGATGAATAAGCGCTTCCCGA (SEQ ID NO: 146) |
| 219 | F | CGCTTATTCATCTGTTGCTCCCNNSGTTTTGTGCTTT (SEQ ID NO: 147) |
| 219 | R | GGGAGCAACAGATGAATAAGC (SEQ ID NO: 148) |
| 228 | F | TGTGCTTTCTCCAACGATTCNNSGTGTCGTCTGGTGGATACGTCG (SEQ ID NO: 149) |
| 228 | R | GAATCGTTGGAGAAAGCACAAAACCT (SEQ ID NO: 150) |
| 229 | F | GTGCTTTCTCCAACGATTCTGGNNSTCGTCTGGTGGA (SEQ ID NO: 151) |
| 229 | R | CCAGAATCGTTGGAGAAAGCA (SEQ ID NO: 152) |
| 230 | F | CTTTCTCCAACGATTCTGGGTGNNSTCTGGTGGATACG (SEQ ID NO: 153) |
| 230 | R | CACCCAGAATCGTTGGAGAAA (SEQ ID NO: 154) |
| 231 | F | TCTCCAACGATTCTGGGTGTCGNNSGGTGGATACGTC (SEQ ID NO: 155) |
| 231 | R | CGACACCCAGAATCGTTGGAGA (SEQ ID NO: 156) |
| 236 | F | GGTGTCGTCTGGTGGATACGTCNNSTCCAACATCAACAC (SEQ ID NO: 157) |
| 236 | R | GACGTATCCACCAGACGACAC (SEQ ID NO: 158) |
| 239 | F | TGGTGGATACGTCGACTCCAACNNSAACACCAACGAG (SEQ ID NO: 159) |
| 239 | R | GTTGGAGTCGACGTATCCACC (SEQ ID NO: 160) |
| 240 | F | TGGATACGTCGACTCCAACATCNNSACCAACGAGGGCA (SEQ ID NO: 161) |
| 240 | R | GATGTTGGAGTCGACGTATCCA (SEQ ID NO: 162) |
| 241 | F | ATACGTCGACTCCAACATCAACNNSAACGAGGGCAGGAC (SEQ ID NO: 163) |
| 241 | R | GTTGATGTTGGAGTCGACGTA (SEQ ID NO: 164) |
| 242 | F | TCGACTCCAACATCAACACCNNSGAGGGCAGGACTGGCAAGGATG (SEQ ID NO: 165) |
| 242 | R | GGTGTTGATGTTGGAGTCGACGTAT (SEQ ID NO: 166) |
| 243 | F | ACTCCAACATCAACACCAACNNSGGCAGGACTGGCAAGGATGTCA (SEQ ID NO: 167) |
| 243 | R | GTTGGTGTTGATGTTGGAGTCGACG (SEQ ID NO: 168) |
| 244 | F | CTCCAACATCAACACCAACGAGNNSAGGACTGGCAAG (SEQ ID NO: 169) |
| 244 | R | CTCGTTGGTGTTGATGTTGGAGT (SEQ ID NO: 170) |
| 245 | F | ACATCAACACCAACGAGGGCNNSACTGGCAAGGATGTCAACTCCG (SEQ ID NO: 171) |
| 245 | R | GCCCTCGTTGGTGTTGATGTTGGAGT (SEQ ID NO: 172) |
| 263 | F | TTCCATCCACACCTTCGATCCCNNSCTTGGCTGTGAC (SEQ ID NO: 173) |
| 263 | R | GGGATCGAAGGTGTGGATGGA (SEQ ID NO: 174) |

TABLE 2-continued

Primers used to generate TrGA SELs

| AA-position | F/R | DNA Sequence 5' to 3' |
|---|---|---|
| 264 | F | CATCCACACCTTCGATCCCAACNNSGGCTGTGACGCA (SEQ ID NO: 175) |
| 264 | R | GTTGGGATCGAAGGTGTGGAT (SEQ ID NO: 176) |
| 265 | F | CCACACCTTCGATCCCAACCTTNNSTGTGACGCAGGC (SEQ ID NO: 177) |
| 265 | R | AAGGTTGGGATCGAAGGTGTG (SEQ ID NO: 178) |
| 268 | F | CGATCCCAACCTTGGCTGTGACNNSGGCACCTTCCAGC (SEQ ID NO: 179) |
| 268 | R | GTCACAGCCAAGGTTGGGATC (SEQ ID NO: 180) |
| 269 | F | TCCCAACCTTGGCTGTGACGCANNSACCTTCCAGCCA (SEQ ID NO: 181) |
| 269 | R | TGCGTCACAGCCAAGGTTGGG (SEQ ID NO: 182) |
| 276 | F | AGGCACCTTCCAGCCATGCAGTNNSAAAGCGCTCTCC (SEQ ID NO: 183) |
| 276 | R | ACTGCATGGCTGGAAGGTGCC (SEQ ID NO: 184) |
| 284 | F | CAAAGCGCTCTCCAACCTCAAGNNSGTTGTCGACTCCT (SEQ ID NO: 185) |
| 284 | R | CTTGAGGTTGGAGAGCGCTTT (SEQ ID NO: 186) |
| 291 | F | GGTTGTTGTCGACTCCTTCCGCNNSATCTACGGCGTG (SEQ ID NO: 187) |
| 291 | R | GCGGAAGGAGTCGACAACAAC (SEQ ID NO: 188) |
| 292 | F | TTGTCGACTCCTTCCGCTCCNNSTACGGCGTGAACAAGGGCATTC (SEQ ID NO: 189) |
| 292 | R | GGAGCGGAAGGAGTCGACAACAACC (SEQ ID NO: 190) |
| 294 | F | ACTCCTTCCGCTCCATCTACNNSGTGAACAAGGGCATTCCTGCCG (SEQ ID NO: 191) |
| 294 | R | GTAGATGGAGCGGAAGGAGTCGACA (SEQ ID NO: 192) |
| 297 | F | GCTCCATCTACGGCGTGAACNNSGGCATTCCTGCCGGTGCTGCCG (SEQ ID NO: 193) |
| 297 | R | GTTCACGCCGTAGATGGAGCGGAAG (SEQ ID NO: 194) |
| 300 | F | CTACGGCGTGAACAAGGGCATTNNSGCCGGTGCTGCCG (SEQ ID NO: 195) |
| 300 | R | AATGCCCTTGTTCACGCCGTA (SEQ ID NO: 196) |
| 301 | F | CGGCGTGAACAAGGGCATTCCTNNSGGTGCTGCCGTC (SEQ ID NO: 197) |
| 301 | R | AGGAATGCCCTTGTTCACGCC (SEQ ID NO: 198) |
| 303 | F | GAACAAGGGCATTCCTGCCGGTNNSGCCGTCGCCATT (SEQ ID NO: 199) |
| 303 | R | ACCGGCAGGAATGCCCTTGTT (SEQ ID NO: 200) |
| 309 | F | GTGCTGCCGTCGCCATTGGCNNSTATGCAGAGGATGTGTACTACA (SEQ ID NO: 201) |
| 309 | R | GCCAATGGCGACGGCAGCACCGGCA (SEQ ID NO: 202) |
| 310 | F | CTGCCGTCGCCATTGGCCGGNNSGCAGAGGATGTGTACTACAACG (SEQ ID NO: 203) |
| 310 | R | CCGGCCAATGGCGACGGCAGCACCG (SEQ ID NO: 204) |
| 311 | F | TGCCGTCGCCATTGGCCGGTATNNSGAGGATGTGTAC (SEQ ID NO: 205) |
| 311 | R | ATACCGGCCAATGGCGACGGC (SEQ ID NO: 206) |
| 313 | F | CCATTGGCCGGTATGCAGAGNNSGTGTACTACAACGGCAACCCTT (SEQ ID NO: 207) |
| 313 | F | CCATTGGCCGGTATGCAGAGNNSGTGTACTACAACGGCAACCCTT (SEQ ID NO: 208) |
| 313 | R | CTCTGCATACCGGCCAATGGCGACG (SEQ ID NO: 209) |
| 313 | R | CTCTGCATACCGGCCAATGGCGACG (SEQ ID NO: 210) |
| 314 | F | TTGGCCGGTATGCAGAGGATNNSTACTACAACGGCAACCCTTGGT (SEQ ID NO: 211) |
| 314 | R | ATCCTCTGCATACCGGCCAATGGCG (SEQ ID NO: 212) |
| 315 | F | GCCGGTATGCAGAGGATGTGNNSTACAACGGCAACCCTTGGTATC (SEQ ID NO: 213) |
| 315 | R | CACATCCTCTGCATACCGGCCAATG (SEQ ID NO: 214) |
| 316 | F | GGTATGCAGAGGATGTGTACNNSAACGGCAACCCTTGGTATCTTG (SEQ ID NO: 215) |
| 316 | R | GTACACATCCTCTGCATACCGGCCAAT (SEQ ID NO: 216) |
| 317 | F | ATGCAGAGGATGTGTACTACNNSGGCAACCCTTGGTATCTTGCTA (SEQ ID NO: 217) |
| 317 | F | ATGCAGAGGATGTGTACTACNNSGGCAACCCTTGGTATCTTGCTA (SEQ ID NO: 218) |
| 317 | R | GTAGTACACATCCTCTGCATACCGGC (SEQ ID NO: 219) |
| 317 | R | GTAGTACACATCCTCTGCATACCGGC (SEQ ID NO: 220) |

TABLE 2-continued

Primers used to generate TrGA SELs

| AA-position | F/R | DNA Sequence 5' to 3' |
|---|---|---|
| 321 | F | TGTACTACAACGGCAACCCTNNSTATCTTGCTACATTTGCTGCTG (SEQ ID NO: 221) |
| 321 | F | TGTACTACAACGGCAACCCTNNSTATCTTGCTACATTTGCTGCTG (SEQ ID NO: 222) |
| 321 | R | AGGGTTGCCGTTGTAGTACACATCC (SEQ ID NO: 223) |
| 321 | R | AGGGTTGCCGTTGTAGTACACATCC (SEQ ID NO: 224) |
| 338 | F | GCAGCTGTACGATGCCATCTACNNSTGGAAGAAGACG (SEQ ID NO: 225) |
| 338 | R | GTAGATGGCATCGTACAGCTG (SEQ ID NO: 226) |
| 340 | F | ACGATGCCATCTACGTCTGGNNSAAGACGGGCTCCATCACGGTGA (SEQ ID NO: 227) |
| 340 | R | CCAGACGTAGATGGCATCGTACAGC (SEQ ID NO: 228) |
| 341 | F | ATGCCATCTACGTCTGGAAGNNSACGGGCTCCATCACGGTGACCG (SEQ ID NO: 229) |
| 341 | R | CTTCCAGACGTAGATGGCATCGTACAGC (SEQ ID NO: 230) |
| 342 | F | ATGCCATCTACGTCTGGAAGAAGNNSGGCTCCATCACG (SEQ ID NO: 231) |
| 342 | R | CTTCTTCCAGACGTAGATGGC (SEQ ID NO: 232) |
| 344 | F | CTACGTCTGGAAGAAGACGGGCNNSATCACGGTGACC (SEQ ID NO: 233) |
| 344 | R | GCCCGTCTTCTTCCAGACGTAG (SEQ ID NO: 234) |
| 346 | F | CTGGAAGAAGACGGGCTCCATCNNSGTGACCGCCACCTC (SEQ ID NO: 235) |
| 346 | R | GATGGAGCCCGTCTTCTTCCA (SEQ ID NO: 236) |
| 349 | F | GACGGGCTCCATCACGGTGACCNNSACCTCCCTGGCC (SEQ ID NO: 237) |
| 349 | R | GGTCACCGTGATGGAGCCCGT (SEQ ID NO: 238) |
| 350 | F | GCTCCATCACGGTGACCGCCNNSTCCCTGGCCTTCTTCCAGGAGC (SEQ ID NO: 239) |
| 350 | R | GGCGGTCACCGTGATGGAGCCCGTC (SEQ ID NO: 240) |
| 356 | F | CCACCTCCCTGGCCTTCTTCNNSGAGCTTGTTCCTGGCGTGACGG (SEQ ID NO: 241) |
| 356 | R | GAAGAAGGCCAGGGAGGTGGCGGTC (SEQ ID NO: 242) |
| 359 | F | CCTGGCCTTCTTCCAGGAGCTTNNSCCTGGCGTGACG (SEQ ID NO: 243) |
| 359 | R | AAGCTCCTGGAAGAAGGCCAG (SEQ ID NO: 244) |
| 361 | F | CTTCTTCCAGGAGCTTGTTCCTNNSGTGACGGCCGGG (SEQ ID NO: 245) |
| 361 | R | AGGAACAAGCTCCTGGAAGAA (SEQ ID NO: 246) |
| 363 | F | AGGAGCTTGTTCCTGGCGTGNNSGCCGGGACCTACTCCAGCAGCT (SEQ ID NO: 247) |
| 363 | R | CACGCCAGGAACAAGCTCCTGGAAG (SEQ ID NO: 248) |
| 364 | F | GGAGCTTGTTCCTGGCGTGACGNNSGGGACCTACTCC (SEQ ID NO: 249) |
| 364 | R | CGTCACGCCAGGAACAAGCTC (SEQ ID NO: 250) |
| 368 | F | GCGTGACGGCCGGGACCTACNNSAGCAGCTCTTCGACCTTTACCA (SEQ ID NO: 251) |
| 368 | R | GTAGGTCCCGGCCGTCACGCCAGGA (SEQ ID NO: 252) |
| 369 | F | TGACGGCCGGGACCTACTCCNNSAGCTCTTCGACCTTTACCAACA (SEQ ID NO: 253) |
| 369 | R | GGAGTAGGTCCCGGCCGTCACGCCA (SEQ ID NO: 254) |
| 375 | F | CTCCAGCAGCTCTTCGACCTTTNNSAACATCATCAACG (SEQ ID NO: 255) |
| 375 | R | AAAGGTCGAAGAGCTGCTGGA (SEQ ID NO: 256) |
| 376 | F | GCAGCTCTTCGACCTTTACCNNSATCATCAACGCCGTCTCGACAT (SEQ ID NO: 257) |
| 376 | R | GGTAAAGGTCGAAGAGCTGCTGGAG (SEQ ID NO: 258) |
| 379 | F | TTCGACCTTTACCAACATCATCNNSGCCGTCTCGACA (SEQ ID NO: 259) |
| 379 | R | GATGATGTTGGTAAAGGTCGA (SEQ ID NO: 260) |
| 382 | F | TACCAACATCATCAACGCCGTCNNSACATACGCCGAT (SEQ ID NO: 261) |
| 382 | R | GACGGCGTTGATGATGTTGGT (SEQ ID NO: 262) |
| 390 | F | GACATACGCCGATGGCTTCCTCNNSGAGGCTGCCAAG (SEQ ID NO: 263) |
| 390 | R | GAGGAAGCCATCGGCGTATGT (SEQ ID NO: 264) |
| 391 | F | ATACGCCGATGGCTTCCTCAGCNNSGCTGCCAAGTAC (SEQ ID NO: 265) |
| 391 | R | GCTGAGGAAGCCATCGGCGTA (SEQ ID NO: 266) |

TABLE 2-continued

Primers used to generate TrGA SELs

| AA-position | F/R | DNA Sequence 5' to 3' |
|---|---|---|
| 393 | F | CGATGGCTTCCTCAGCGAGGCTNNSAAGTACGTCCCC (SEQ ID NO: 267) |
| 393 | R | AGCCTCGCTGAGGAAGCCATC (SEQ ID NO: 268) |
| 394 | F | TGGCTTCCTCAGCGAGGCTGCCNNSTACGTCCCCGCC (SEQ ID NO: 269) |
| 394 | R | GGCAGCCTCGCTGAGGAAGCC (SEQ ID NO: 270) |
| 395 | F | TCCTCAGCGAGGCTGCCAAGNNSGTCCCCGCCGACGGTTCGCTGG (SEQ ID NO: 271) |
| 395 | R | CTTGGCAGCCTCGCTGAGGAAGCCA (SEQ ID NO: 272) |
| 398 | F | AGGCTGCCAAGTACGTCCCCNNSGACGGTTCGCTGGCCGAGCAGTT (SEQ ID NO: 273) |
| 398 | R | GGGGACGTACTTGGCAGCCTCGCTG (SEQ ID NO: 274) |
| 401 | F | AGTACGTCCCCGCCGACGGTNNSCTGGCCGAGCAGTTTGACCGCA (SEQ ID NO: 275) |
| 401 | R | ACCGTCGGCGGGGACGTACTTGGCAG (SEQ ID NO: 276) |
| 408 | F | CGCTGGCCGAGCAGTTTGACNNSAACAGCGGCACTCCGCTGTCTG (SEQ ID NO: 277) |
| 408 | R | GTCAAACTGCTCGGCCAGCGAACCG (SEQ ID NO: 278) |
| 409 | F | TGGCCGAGCAGTTTGACCGCNNSAGCGGCACTCCGCTGTCTGCGC (SEQ ID NO: 279) |
| 409 | R | GCGGTCAAACTGCTCGGCCAGCGAA (SEQ ID NO: 280) |
| 410 | F | GGCCGAGCAGTTTGACCGCAACNNSGGCACTCCGCTG (SEQ ID NO: 281) |
| 410 | R | GTTGCGGTCAAACTGCTCGGC (SEQ ID NO: 282) |
| 412 | F | AGTTTGACCGCAACAGCGGCNNSCCGCTGTCTGCGCTTCACCTGA (SEQ ID NO: 283) |
| 412 | R | GCCGCTGTTGCGGTCAAACTGCTCG (SEQ ID NO: 284) |
| 415 | F | GCAACAGCGGCACTCCGCTGNNSGCGCTTCACCTGACGTGGTCGT (SEQ ID NO: 285) |
| 415 | R | CAGCGGAGTGCCGCTGTTGCGGTCA (SEQ ID NO: 286) |
| 417 | F | CAGCGGCACTCCGCTGTCTGCGNNSCACCTGACGTGGT (SEQ ID NO: 287) |
| 417 | R | CGCAGACAGCGGAGTGCCGCT (SEQ ID NO: 288) |
| 418 | F | GCACTCCGCTGTCTGCGCTTNNSCTGACGTGGTCGTACGCCTCGT (SEQ ID NO: 289) |
| 418 | R | AAGCGCAGACAGCGGAGTGCCGCTG (SEQ ID NO: 290) |
| 421 | F | TGTCTGCGCTTCACCTGACGNNSTCGTACGCCTCGTTCTTGACAG (SEQ ID NO: 291) |
| 421 | R | CGTCAGGTGAAGCGCAGACAGCGGA (SEQ ID NO: 292) |
| 430 | F | GTACGCCTCGTTCTTGACAGCCNNSGCCCGTCGGGCT (SEQ ID NO: 293) |
| 430 | R | GGCTGTCAAGAACGAGGCGTA (SEQ ID NO: 294) |
| 431 | F | CGCCTCGTTCTTGACAGCCACGNNSCGTCGGGCTGGC (SEQ ID NO: 295) |
| 431 | R | CGTGGCTGTCAAGAACGAGGC (SEQ ID NO: 296) |
| 433 | F | TCTTGACAGCCACGGCCCGTNNSGCTGGCATCGTGCCCCCCTCGT (SEQ ID NO: 297) |
| 433 | R | ACGGGCCGTGGCTGTCAAGAACGAG (SEQ ID NO: 298) |
| 436 | F | CCACGGCCCGTCGGGCTGGCNNSGTGCCCCCCTCGTGGGCCAACA (SEQ ID NO: 299) |
| 436 | R | GCCAGCCCGACGGGCCGTGGCTGTC (SEQ ID NO: 300) |
| 442 | F | TGGCATCGTGCCCCCCTCGTGGNNSAACAGCAGCGCT (SEQ ID NO: 301) |
| 442 | R | CCACGAGGGGGCACGATGCC (SEQ ID NO: 302) |
| 443 | F | CATCGTGCCCCCCTCGTGGGCCNNSAGCAGCGCTAGC (SEQ ID NO: 303) |
| 443 | R | GGCCCACGAGGGGGCACGAT (SEQ ID NO: 304) |
| 444 | F | CGTGCCCCCCTCGTGGGCCAACNNSAGCGCTAGCACG (SEQ ID NO: 305) |
| 444 | R | GTTGGCCCACGAGGGGGCAC (SEQ ID NO: 306) |
| 448 | F | GTGGGCCAACAGCAGCGCTAGCNNSATCCCCTCGACG (SEQ ID NO: 307) |

F = Forward; R = Reverse

Example 2

Transformation of TrGA SELs into *Trichoderma reesei*

The SELs were transformed into *T. reesei* using the PEG protoplast method. The *E. coli* clones of the SELs confirmed by sequence analysis were grown overnight at 37° C. in deep well microtiter plates (Greiner Art. No. 780271) containing 1.200 µl of 2×YT medium with ampicillin (100 µg/ml) and kanamycin (50 µg/ml). Plasmid DNAs were isolated from the cultures using CHEMAGIC® Plasmid Mini Kit (Chemagen—Biopolymer Technologie AG, Baesweiler, Germany) and were transformed individually into a *T. reesei* host strain derived from RL-P37 bearing four gene deletions (Δcbh1, Δcbh2, Δegl1, Δegl2, i.e., "quad-deleted"; see U.S. Pat. No. 5,847,276, WO 92/06184 and WO 05/001036) using the PEG-Protoplast method (Penttilä et al. (1987) Gene 61:155-164) with the following modifications. 1) For protoplast preparation, spores were grown for 16-24 hours at 24° C. in *Trichoderma* Minimal Medium (MM) (20 g/L glucose, 15 g/L $KH_2PO_4$, pH 4.5, 5 g/L $(NH_4)_2SO_4$, 0.6 g/L $MgSO_4 \times 7H_2O$, 0.6 g/L $CaCl_2 \times 2H_2O$, 1 ml of 1000× *T. reesei* Trace elements solution {5 g/L $FeSO_4 \times 7H_2O$, 1.4 g/L $ZnSO_4 \times 7H_2O$, 1.6 g/L $MnSO_4 \times H_2O$, 3.7 g/L $CoCl_2 \times 6H_2O$}) with shaking at 150 rpm. Germinating spores were harvested by centrifugation and treated with 15 mg/ml of β-D-glucanase-G (Interspex—Art. No. 0439-1) solution to lyse the fungal cell walls. Further preparation of protoplasts was performed by a standard method, as described by Penttilä et al. (1987 supra). 2) The transformation method was scaled down 10 fold. In general, transformation mixtures containing up to 600 ng of DNA and $1–5 \times 10^5$ protoplasts in a total volume of 25 µl were treated with 200 ml of 25% PEG solution, diluted with 2 volumes of 1.2M sorbitol solution, mixed with 3% selective top agarose MM with acetamide (the same Minimal Medium as mentioned above but $(NH_4)_2SO_4$ was substituted with 20 mM acetamide) and poured onto 2% selective agarose with acetamide either in 24 well microtiter plates or in a 20×20 cm Q-tray divided in 48 wells. The plates were incubated at 28° C. for 5 to 8 days. Spores from the total population of transformants regenerated on each individual well were harvested from the plates using a solution of 0.85% NaCl, 0.015% Tween 80. Spore suspensions were used to inoculate fermentations in 96 wells MTPs. In the case of 24 well MTPs, an additional plating step on a fresh 24 well MTP with selective acetamide MM was introduced in order to enrich the spore numbers.

Example 3

Fermentation of *T. reesei* Transformants Expressing TrGA Variants in a MTP Format The transformants were fermented and the supernatants containing the expressed variant TrGA proteins were tested for various properties. In brief, 96 well filter plates (Corning Art. No. 3505) containing 200 µl of LD-GSM medium (5.0 g/L $(NH_4)_2SO_4$, 33 g/L 1,4-Piperazinebis(propanesulfonic acid), pH 5.5, 9.0 g/L Casamino acids, 1.0 g/L $KH_2PO_4$, 1.0 g/L $CaCl_2 \times 2H_2O$, 1.0 g/L $MgSO_4 \times 7H_2O$, 2.5 ml/L of 1000× *T. reesei* trace elements, 20 g/L Glucose, 10 g/L Sophorose) were inoculated in quadruplicate with spore suspensions of *T. reesei* transformants expressing TrGA variants (more than $10^4$ spores per well). The plates were incubated at 28° C. with 230 rpm shaking and 80% humidity for 6 days. Culture supernatants were harvested by vacuum filtration. The supernatants were used in different assays for screening of variants with improved properties.

Example 4

Preparation of the Whole Broth Samples from GA-Producing Transformants

TrGA producing transformants were initially pregrown in 250 ml shake flasks containing 30 ml of Proflo medium. Proflo medium contained: 30 g/L α-lactose, 6.5 g/L $(NH_4)_2SO_4$, 2 g/L $KH_2PO_4$, 0.3 g/L $MgSO_4 \times 7H_2O$, 0.2 g/L $CaCl_2 \times 2H_2O$, 1 ml/L 1000× trace element salt solution as mentioned above, 2 ml/L 10% Tween 80, 22.5 g/L ProFlo cottonseed flour (Traders protein, Memphis, Tenn.), 0.72 g/L $CaCO_3$. After two days of growth at 28° C. and 140 rpm, 10% of the Proflo culture was transferred into a 250 ml shake flask containing 30 ml of Lactose Defined Medium. The composition of the Lactose Defined Medium was as follows: 5 g/L $(NH_4)_2SO_4$, 33 g/L 1,4-Piperazinebis (propanesulfonic acid) buffer, pH 5.5, 9 g/L casamino acids, 4.5 g/L $KH_2PO_4$, 1.0 g/L $MgSO_4 \times 7H_2O$, 5 ml/L Mazu DF60-P antifoam (Mazur Chemicals, IL), 1 ml/L of 1000× trace element solution. 40 ml/L of 40% (w/v) lactose solution was added to the medium after sterilization. Shake flasks with the Lactose Defined Medium were incubated at 28° C., 140 rpm for 4-5 days.

Mycelium was removed from the culture samples by centrifugation and the supernatant was analyzed for total protein content (BCA Protein Assay Kit, Pierce Cat. No. 23225) and GA activity, as described above in the Experimental section.

The protein profile of the whole broth samples was determined by SDS-PAGE electrophoresis. Samples of the culture supernatant were mixed with an equal volume of 2× sample loading buffer with reducing agent and separated on NUPAGE® Novex 10% Bis-Tris Gel with MES SDS Running Buffer (Invitrogen, Carlsbad, Calif., USA). Polypeptide bands were visualized in the SDS gel with SIMPLYBLUE SafeStain (Invitrogen, Carlsbad, Calif., USA).

Example 5

Variants with Improved Thermal Stability

The parent TrGA molecule had a residual activity between 15 and 44% (day-to-day variation) under the conditions described. The performance index was calculated based on the TrGA thermostability of the same batch. The performance indices are the quotients PI=(Variant residual activity)/(TrGA residual activity). A performance index>1 indicated an improved stability. Variants which had a thermal stability performance index (PD of more than 1.0 are shown in the following Table 3.

TABLE 3

Thermal stability screening

| Variant | Performance Index of Thermal Stability |
|---|---|
| T010F | 1.11 |
| T010G | 1.13 |
| T010M | 1.12 |
| T010Q | 1.06 |
| T010R | 1.06 |
| T010S | 1.24 |
| T042V | 1.31 |
| F059A | 1.03 |
| F059G | 1.07 |
| F059L | 1.06 |
| F059M | 1.12 |
| F059Q | 1.10 |
| F059V | 1.03 |
| N061V | 1.06 |
| E068C | 1.23 |
| E068F | 1.14 |
| E068G | 1.15 |
| E068I | 1.19 |
| E068K | 1.01 |
| E068M | 1.29 |
| E068N | 1.18 |

TABLE 3-continued

Thermal stability screening

| Variant | Performance Index of Thermal Stability |
|---|---|
| E068Q | 1.15 |
| E068W | 1.09 |
| A072E | 1.07 |
| A072Q | 1.02 |
| G073F | 1.44 |
| G073M | 1.01 |
| G073N | 1.10 |
| G073W | 1.36 |
| S097E | 1.08 |
| S097G | 1.03 |
| S097T | 1.17 |
| S097V | 1.03 |
| L098C | 1.07 |
| A099C | 1.07 |
| A099F | 1.02 |
| A099I | 1.14 |
| A099L | 1.09 |
| A099Q | 1.07 |
| A099R | 1.02 |
| A099S | 1.11 |
| A099T | 1.02 |
| S102A | 1.02 |
| K114C | 1.19 |
| K114D | 1.17 |
| K114E | 1.16 |
| K114L | 1.10 |
| K114M | 1.21 |
| K114Q | 1.25 |
| I133V | 1.21 |
| K140D | 1.09 |
| K140Q | 1.06 |
| K140S | 1.05 |
| K140W | 1.04 |
| N144A | 1.11 |
| N144F | 1.06 |
| S152C | 1.04 |
| S152G | 1.09 |
| S152I | 1.09 |
| S152N | 1.12 |
| N153A | 1.28 |
| N153D | 1.06 |
| N153E | 1.29 |
| N153F | 1.16 |
| N153H | 1.01 |
| N153L | 1.06 |
| N153M | 1.27 |
| N153S | 1.31 |
| N153V | 1.34 |
| N153W | 1.19 |
| N182R | 1.02 |
| A204D | 1.02 |
| A204M | 1.08 |
| T205C | 1.02 |
| T205D | 1.06 |
| T205N | 1.09 |
| T205P | 1.17 |
| T205S | 1.04 |
| T205V | 1.06 |
| T205Y | 1.07 |
| S214C | 1.02 |
| S214E | 1.03 |
| S214N | 1.07 |
| S214P | 1.04 |
| S214Q | 1.13 |
| S214T | 1.06 |
| S214V | 1.13 |
| S214W | 1.03 |
| S214Y | 1.04 |
| V216I | 1.13 |
| W228A | 1.01 |
| W228F | 1.12 |
| W228G | 1.06 |
| W228H | 1.05 |
| W228I | 1.06 |
| W228L | 1.14 |
| W228M | 1.04 |
| W228Q | 1.15 |
| W228S | 1.15 |
| W228T | 1.06 |
| W228V | 1.21 |
| W228Y | 1.10 |
| V229A | 1.16 |
| V229D | 1.18 |
| V229E | 1.16 |
| V229F | 1.17 |
| V229G | 1.18 |
| V229H | 1.13 |
| V229I | 1.21 |
| V229L | 1.20 |
| V229M | 1.11 |
| V229N | 1.07 |
| V229P | 1.13 |
| V229Q | 1.10 |
| V229R | 1.07 |
| V229S | 1.12 |
| V229T | 1.11 |
| V229W | 1.07 |
| V229Y | 1.08 |
| S230C | 1.09 |
| S230D | 1.08 |
| S230E | 1.11 |
| S230F | 1.08 |
| S230G | 1.09 |
| S230H | 1.03 |
| S230K | 1.02 |
| S230L | 1.02 |
| S230M | 1.08 |
| S230N | 1.16 |
| S230P | 1.12 |
| S230Q | 1.20 |
| S230R | 1.11 |
| S230T | 1.07 |
| S230V | 1.11 |
| S230Y | 1.05 |
| S231A | 1.06 |
| S231C | 1.07 |
| S231D | 1.18 |
| S231E | 1.10 |
| S231F | 1.14 |
| S231K | 1.09 |
| S231L | 1.15 |
| S231M | 1.09 |
| S231N | 1.13 |
| S231Q | 1.18 |
| S231R | 1.13 |
| S231T | 1.16 |
| S231V | 1.21 |
| S231W | 1.06 |
| S231Y | 1.10 |
| D236A | 1.10 |
| D236C | 1.16 |
| D236E | 1.06 |
| D236F | 1.11 |
| D236G | 1.07 |
| D236H | 1.16 |
| D236I | 1.14 |
| D236K | 1.13 |
| D236L | 1.08 |
| D236M | 1.15 |
| D236N | 1.15 |
| D236P | 1.06 |
| D236R | 1.29 |
| D236T | 1.16 |
| D236V | 1.18 |
| D236Y | 1.07 |
| T241V | 1.05 |
| N242F | 1.03 |
| N242H | 1.01 |
| N263A | 1.18 |
| N263C | 1.14 |

TABLE 3-continued

Thermal stability screening

| Variant | Performance Index of Thermal Stability |
|---|---|
| N263L | 1.02 |
| N263M | 1.10 |
| N263R | 1.04 |
| N263T | 1.07 |
| L264A | 1.03 |
| L264D | 1.20 |
| L264I | 1.14 |
| L264K | 1.24 |
| L264M | 1.15 |
| L264P | 1.02 |
| L264R | 1.02 |
| L264V | 1.04 |
| L264Y | 1.15 |
| G265D | 1.08 |
| G265E | 1.03 |
| G265F | 1.08 |
| G265H | 1.09 |
| G265I | 1.09 |
| G265K | 1.05 |
| G265L | 1.07 |
| G265N | 1.15 |
| G265P | 1.07 |
| G265Q | 1.15 |
| G265R | 1.12 |
| G265S | 1.13 |
| G265T | 1.17 |
| G265V | 1.15 |
| G265W | 1.11 |
| G265Y | 1.10 |
| A268C | 1.16 |
| A268D | 1.20 |
| A268E | 1.10 |
| A268F | 1.07 |
| A268G | 1.11 |
| A268I | 1.12 |
| A268K | 1.11 |
| A268L | 1.11 |
| A268M | 1.18 |
| A268N | 1.10 |
| A268P | 1.13 |
| A268R | 1.15 |
| A268S | 1.09 |
| A268T | 1.14 |
| A268W | 1.05 |
| G269K | 1.01 |
| G269N | 1.08 |
| G269P | 1.08 |
| G269Q | 1.02 |
| G269R | 1.06 |
| D276E | 1.03 |
| D276Q | 1.03 |
| D276S | 1.02 |
| D276V | 1.17 |
| V284C | 1.09 |
| V284E | 1.14 |
| V284G | 1.13 |
| V284I | 1.10 |
| V284Q | 1.08 |
| V284R | 1.09 |
| V284S | 1.06 |
| V284T | 1.08 |
| V284W | 1.08 |
| V284Y | 1.12 |
| S291A | 1.21 |
| S291D | 1.02 |
| S291E | 1.02 |
| S291F | 1.24 |
| S291G | 1.05 |
| S291H | 1.25 |
| S291I | 1.10 |
| S291K | 1.13 |
| S291M | 1.21 |
| S291N | 1.08 |
| S291P | 1.11 |
| S291Q | 1.08 |
| S291R | 1.07 |
| S291T | 1.21 |
| S291V | 1.06 |
| S291W | 1.15 |
| P300A | 1.10 |
| P300N | 1.06 |
| P300Q | 1.05 |
| P300R | 1.02 |
| P300T | 1.07 |
| P300V | 1.02 |
| P300W | 1.11 |
| P300Y | 1.04 |
| A301A | 1.13 |
| A301K | 1.11 |
| A301L | 1.07 |
| A301P | 1.22 |
| A301R | 1.21 |
| A301S | 1.12 |
| A301T | 1.14 |
| A301V | 1.07 |
| A301W | 1.14 |
| A301Y | 1.14 |
| A303E | 1.02 |
| A303I | 1.02 |
| A303L | 1.03 |
| A303Q | 1.01 |
| A311C | 1.05 |
| A311E | 1.06 |
| A311G | 1.11 |
| A311H | 1.09 |
| A311I | 1.04 |
| A311K | 1.13 |
| A311L | 1.07 |
| A311R | 1.07 |
| A311S | 1.01 |
| A311Y | 1.02 |
| V338H | 1.12 |
| V338I | 1.21 |
| V338L | 1.17 |
| V338M | 1.13 |
| V338N | 1.23 |
| V338P | 1.18 |
| V338Q | 1.20 |
| V338S | 1.19 |
| V338Y | 1.10 |
| T342C | 1.06 |
| T342I | 1.04 |
| T342L | 1.17 |
| T342P | 1.08 |
| S344A | 1.05 |
| S344C | 1.16 |
| S344D | 1.02 |
| S344F | 1.10 |
| S344K | 1.12 |
| S344M | 1.26 |
| S344N | 1.16 |
| S344P | 1.20 |
| S344Q | 1.22 |
| S344R | 1.22 |
| S344T | 1.19 |
| S344V | 1.20 |
| S344W | 1.03 |
| T346D | 1.03 |
| T346L | 1.02 |
| T346M | 1.07 |
| T346N | 1.15 |
| T346P | 1.13 |
| T346Q | 1.12 |
| T346S | 1.13 |
| T346V | 1.09 |
| T346W | 1.06 |
| T346Y | 1.07 |
| A349D | 1.15 |
| A349E | 1.13 |
| A349F | 1.09 |

TABLE 3-continued

Thermal stability screening

| Variant | Performance Index of Thermal Stability |
|---|---|
| A349G | 1.12 |
| A349H | 1.11 |
| A349K | 1.14 |
| A349L | 1.16 |
| A349M | 1.07 |
| A349N | 1.09 |
| A349P | 1.03 |
| A349Q | 1.09 |
| A349R | 1.04 |
| A349T | 1.09 |
| A349V | 1.08 |
| A349W | 1.04 |
| A349Y | 1.04 |
| V359Q | 1.02 |
| V359R | 1.13 |
| V359Y | 1.01 |
| G361A | 1.13 |
| G361C | 1.16 |
| G361D | 1.35 |
| G361E | 1.24 |
| G361F | 1.20 |
| G361H | 1.11 |
| G361I | 1.20 |
| G361K | 1.16 |
| G361L | 1.22 |
| G361M | 1.28 |
| G361P | 1.27 |
| G361R | 1.19 |
| G361S | 1.22 |
| G361T | 1.16 |
| G361V | 1.15 |
| G361W | 1.22 |
| G361Y | 1.26 |
| A364C | 1.18 |
| A364D | 1.25 |
| A364E | 1.27 |
| A364F | 1.33 |
| A364G | 1.25 |
| A364K | 1.27 |
| A364L | 1.31 |
| A364M | 1.21 |
| A364Q | 1.19 |
| A364R | 1.28 |
| A364S | 1.23 |
| A364T | 1.23 |
| A364V | 1.23 |
| A364W | 1.23 |
| T375A | 1.17 |
| T375E | 1.03 |
| T375F | 1.06 |
| T375G | 1.05 |
| T375H | 1.13 |
| T375K | 1.10 |
| T375L | 1.03 |
| T375M | 1.17 |
| T375N | 1.20 |
| T375P | 1.15 |
| T375V | 1.16 |
| T375W | 1.11 |
| T375Y | 1.17 |
| N379A | 1.11 |
| N379C | 1.03 |
| N379D | 1.06 |
| N379F | 1.07 |
| N379G | 1.09 |
| N379H | 1.07 |
| N379I | 1.04 |
| N379K | 1.04 |
| N379L | 1.04 |
| N379M | 1.08 |
| N379P | 1.17 |
| N379Q | 1.11 |
| N379R | 1.07 |
| N379T | 1.09 |
| N379V | 1.13 |
| N379W | 1.09 |
| N379Y | 1.06 |
| S382A | 1.06 |
| S382D | 1.04 |
| S382E | 1.05 |
| S382G | 1.06 |
| S382I | 1.07 |
| S382K | 1.03 |
| S382N | 1.07 |
| S382P | 1.10 |
| S382R | 1.05 |
| S382T | 1.02 |
| S382Y | 1.04 |
| S390M | 1.06 |
| S390Q | 1.02 |
| S390R | 1.02 |
| E391L | 1.04 |
| E391R | 1.02 |
| E391S | 1.02 |
| E391W | 1.04 |
| E391Y | 1.02 |
| A393D | 1.11 |
| A393E | 1.03 |
| A393F | 1.09 |
| A393G | 1.12 |
| A393H | 1.05 |
| A393I | 1.06 |
| A393K | 1.05 |
| A393L | 1.17 |
| A393M | 1.07 |
| A393N | 1.11 |
| A393Q | 1.02 |
| A393R | 1.03 |
| A393S | 1.13 |
| A393T | 1.08 |
| A393V | 1.09 |
| A393W | 1.10 |
| A393Y | 1.12 |
| K394A | 1.08 |
| K394C | 1.06 |
| K394E | 1.07 |
| K394F | 1.09 |
| K394G | 1.05 |
| K394H | 1.08 |
| K394L | 1.08 |
| K394M | 1.06 |
| K394Q | 1.07 |
| K394R | 1.06 |
| K394T | 1.03 |
| K394V | 1.02 |
| S410E | 1.05 |
| S410H | 1.11 |
| S410I | 1.06 |
| S410K | 1.11 |
| S410L | 1.05 |
| S410M | 1.02 |
| S410N | 1.10 |
| S410Q | 1.15 |
| S410R | 1.18 |
| S410T | 1.04 |
| S410V | 1.13 |
| L417I | 1.04 |
| L417K | 1.20 |
| L417M | 1.05 |
| L417Q | 1.04 |
| L417R | 1.20 |
| L417V | 1.07 |
| L417Y | 1.01 |
| T430A | 1.05 |
| T430E | 1.02 |
| T430F | 1.06 |
| T430H | 1.10 |
| T430I | 1.04 |
| T430K | 1.08 |
| T430M | 1.17 |

TABLE 3-continued

Thermal stability screening

| Variant | Performance Index of Thermal Stability |
|---|---|
| T430N | 1.13 |
| T430Q | 1.05 |
| T430R | 1.13 |
| T430S | 1.17 |
| T430V | 1.05 |
| A431I | 1.03 |
| A431N | 1.03 |
| A431P | 1.08 |
| A431R | 1.08 |
| A431V | 1.03 |
| R433A | 1.13 |
| R433C | 1.24 |
| R433E | 1.22 |
| R433F | 1.17 |
| R433G | 1.23 |
| R433K | 1.12 |
| R433L | 1.23 |
| R433M | 1.10 |
| R433N | 1.28 |
| R433S | 1.23 |
| R433V | 1.28 |
| R433W | 1.16 |
| R433Y | 1.18 |
| I436E | 1.07 |
| I436F | 1.02 |
| I436G | 1.09 |
| I436H | 1.20 |
| I436K | 1.14 |
| I436P | 1.15 |
| I436R | 1.16 |
| I436S | 1.17 |
| I436T | 1.18 |
| I436V | 1.12 |
| I436Y | 1.05 |
| A442N | 1.06 |
| A442R | 1.04 |
| A442T | 1.09 |
| S444E | 1.04 |
| S444K | 1.07 |
| S444M | 1.05 |
| S444Q | 1.04 |
| T448A | 1.02 |
| T448E | 1.09 |
| T448F | 1.12 |
| T448I | 1.12 |
| T448L | 1.09 |
| T448M | 1.11 |
| T448Q | 1.17 |
| T448R | 1.09 |
| T448S | 1.07 |
| T448V | 1.13 |
| T448W | 1.01 |
| T448Y | 1.08 |
| S451E | 1.04 |
| S451H | 1.18 |
| S451K | 1.08 |
| S451L | 1.01 |
| S451Q | 1.06 |
| S451T | 1.02 |

Table 3 includes those variants that, when tested, showed an increased performance index over the parent glucoamylase. These included the following sites: 10, 42, 59, 60, 61, 68, 72, 73, 97, 98, 99, 102, 114, 133, 140, 144, 147, 152, 153, 164, 182, 204, 205, 214, 216, 228, 229, 230, 231, 236, 241, 242, 263, 264, 265, 268, 269, 276, 284, 291, 300, 301, 303, 311, 338, 342, 344, 346, 349, 359, 361, 364, 375, 379, 382, 390, 391, 393, 394, 410, 417, 430, 431, 433, 436, 442, 443, 444, 448, and 451. The sites with substitutions showing the highest increase included: T10S, T42V, E68C, E68M, G73F, G73W, K114M, K114T, I133V, N153A, N153S, N153V, W228V, V229I, V229L, S231V, D236R, L264D, S291M, S291T, A301P, A301R, S344M, S344P, S344Q, S344V, G361D, G361E, G361F, G361I, G361L, G361M, G361P, G361S, G361W, G361Y, A364D, A364E, A364F, A364G, A364K, A364L, A354R, A364S, A364V, A364W, T375N, R433C, R433G, R433N, R433S, R433V, and I436H.

Example 6

Variants with Improved Specific Activity (SA) in an Ethanol Screening Assay

Variants were tested in an ethanol screening assay using the assays described above. Table 4 shows the results of the screening assay for variants with a Performance Index (PI)>1.0 compared to the parent TrGA PI. The PI is calculated from the specific activities (activity/mg enzyme) of the WT and the variant enzymes. It is the quotient "Variant-specific activity/WT-specific activity." The PI of the specific activity for the wildtype TrGA was 1.0 and a variant with a PI>1.0 had a specific activity that was greater than the parent TrGA. The specific activity was the activity measured by the ethanol screening assay divided by the results obtained in the Caliper assay described above.

TABLE 4

Ethanol Screening

| Variant | PI for Specific Activity |
|---|---|
| T010D | 1.09 |
| T010F | 1.06 |
| T010G | 1.12 |
| T010K | 1.05 |
| T010L | 1.07 |
| T010M | 1.05 |
| T010P | 1.05 |
| T010R | 1.08 |
| T010S | 1.09 |
| L014E | 1.03 |
| L014H | 1.05 |
| N015D | 1.02 |
| P023A | 1.16 |
| P023F | 1.13 |
| P023N | 1.05 |
| F059A | 1.17 |
| F059F | 1.05 |
| F059G | 1.05 |
| K060F | 1.06 |
| K060H | 1.03 |
| N061D | 1.05 |
| N061I | 1.21 |
| N061L | 1.18 |
| N061Q | 1.08 |
| N061V | 1.11 |
| N061W | 1.02 |
| R065A | 1.17 |
| R065C | 1.08 |
| R065G | 1.08 |
| R065I | 1.11 |
| R065K | 1.09 |
| R065M | 1.07 |
| R065S | 1.12 |
| R065V | 1.14 |
| R065Y | 1.01 |
| T067C | 1.14 |
| T067I | 1.13 |
| T067K | 1.05 |
| T067M | 1.22 |
| E068I | 1.06 |
| E068M | 1.10 |
| E068W | 1.03 |
| A072E | 1.11 |
| A072G | 1.02 |

TABLE 4-continued

Ethanol Screening

| Variant | PI for Specific Activity |
|---|---|
| A072L | 1.03 |
| A072M | 1.11 |
| A072Q | 1.10 |
| A072R | 1.10 |
| A072W | 1.06 |
| A072Y | 1.30 |
| G073C | 1.02 |
| G073L | 1.07 |
| G073W | 1.03 |
| S097F | 1.11 |
| S097M | 1.11 |
| S097N | 1.23 |
| S097P | 1.18 |
| S097R | 1.07 |
| S097V | 1.12 |
| S097W | 1.09 |
| S097Y | 1.18 |
| L098H | 1.04 |
| L098M | 1.09 |
| A099C | 1.07 |
| A099L | 1.01 |
| A099M | 1.03 |
| A099N | 1.11 |
| A099P | 1.08 |
| S102A | 1.20 |
| S102C | 1.04 |
| S102I | 1.04 |
| S102L | 1.05 |
| S102M | 1.25 |
| S102N | 1.19 |
| S102R | 1.21 |
| S102V | 1.07 |
| S102W | 1.06 |
| S102Y | 1.10 |
| E110Q | 1.02 |
| E110S | 1.07 |
| E110W | 1.11 |
| L113E | 1.15 |
| L113N | 1.08 |
| I133K | 1.04 |
| I133R | 1.16 |
| I133S | 1.08 |
| I133T | 1.29 |
| K140A | 1.04 |
| K140E | 1.04 |
| K140F | 1.03 |
| K140H | 1.14 |
| K140L | 1.10 |
| K140M | 1.11 |
| K140N | 1.15 |
| K140Q | 1.08 |
| K140R | 1.12 |
| K140S | 1.13 |
| K140V | 1.15 |
| K140W | 1.07 |
| K140Y | 1.06 |
| N144C | 1.05 |
| N144D | 1.15 |
| N144E | 1.16 |
| N144I | 1.13 |
| N144K | 1.05 |
| N145A | 1.07 |
| N145C | 1.09 |
| N145E | 1.03 |
| N145I | 1.20 |
| N145K | 1.05 |
| N145L | 1.03 |
| N145M | 1.07 |
| N145Q | 1.14 |
| N145R | 1.11 |
| N145V | 1.12 |
| N145W | 1.14 |
| N145Y | 1.05 |
| Y147A | 1.02 |
| Y147M | 1.02 |
| Y147R | 1.12 |
| S152H | 1.08 |
| S152M | 1.10 |
| N153C | 1.09 |
| N153D | 1.20 |
| N153K | 1.13 |
| N153L | 1.12 |
| N153W | 1.07 |
| N153Y | 1.13 |
| N164A | 1.02 |
| N164G | 1.03 |
| N182C | 1.12 |
| N182E | 1.13 |
| N182K | 1.07 |
| N182P | 1.01 |
| N182R | 1.03 |
| A204C | 1.04 |
| A204D | 1.09 |
| A204G | 1.02 |
| A204I | 1.06 |
| A204M | 1.09 |
| A204Q | 1.09 |
| A204T | 1.05 |
| T205A | 1.03 |
| T205D | 1.03 |
| T205H | 1.03 |
| T205I | 1.05 |
| T205K | 1.09 |
| T205M | 1.05 |
| T205N | 1.09 |
| T205P | 1.17 |
| T205Q | 1.25 |
| T205S | 1.10 |
| T205V | 1.06 |
| T205W | 1.05 |
| T205Y | 1.18 |
| S214P | 1.08 |
| S214T | 1.07 |
| V216C | 1.08 |
| V216G | 1.05 |
| V216H | 1.03 |
| V216K | 1.02 |
| V216N | 1.13 |
| V216Y | 1.09 |
| Q219D | 1.05 |
| Q219G | 1.06 |
| Q219H | 1.03 |
| Q219N | 1.08 |
| Q219P | 1.16 |
| Q219S | 1.29 |
| W228A | 1.20 |
| W228F | 1.22 |
| W228G | 1.17 |
| W228H | 1.33 |
| W228I | 1.18 |
| W228L | 1.12 |
| W228M | 1.35 |
| W228T | 1.19 |
| V229E | 1.01 |
| V229I | 1.02 |
| V229M | 1.03 |
| V229N | 1.01 |
| V229Q | 1.02 |
| S230C | 1.23 |
| S230D | 1.13 |
| S230E | 1.10 |
| S230F | 1.63 |
| S230G | 1.77 |
| S230H | 1.05 |
| S230I | 1.18 |
| S230K | 1.04 |
| S230L | 1.20 |
| S230N | 1.23 |

TABLE 4-continued

Ethanol Screening

| Variant | PI for Specific Activity |
|---|---|
| S230P | 1.13 |
| S230Q | 1.20 |
| S230R | 1.84 |
| S230T | 1.11 |
| S230V | 1.12 |
| S230Y | 1.08 |
| S231C | 1.13 |
| S231D | 1.08 |
| S231F | 1.17 |
| S231L | 1.29 |
| S231M | 1.08 |
| S231N | 1.04 |
| S231Q | 1.05 |
| S231R | 1.02 |
| S231V | 1.07 |
| S231Y | 1.07 |
| D236F | 1.14 |
| D236G | 1.05 |
| D236L | 1.11 |
| D236M | 1.07 |
| D236N | 1.03 |
| D236P | 1.06 |
| D236S | 1.03 |
| D236T | 1.14 |
| D236V | 1.04 |
| I239M | 1.04 |
| I239Q | 1.08 |
| I239S | 1.11 |
| I239V | 1.52 |
| I239W | 1.02 |
| I239Y | 1.25 |
| T241C | 1.07 |
| T241E | 1.03 |
| T241H | 1.10 |
| T241L | 1.04 |
| T241M | 1.05 |
| T241P | 1.02 |
| T241S | 1.08 |
| T241V | 1.05 |
| N242C | 1.08 |
| N242F | 1.06 |
| N242M | 1.04 |
| N242T | 1.08 |
| N242V | 1.03 |
| N242W | 1.05 |
| N263H | 1.05 |
| N263K | 1.02 |
| N263P | 1.40 |
| L264A | 1.04 |
| L264C | 1.08 |
| L264E | 1.16 |
| L264F | 1.03 |
| L264S | 1.05 |
| G265E | 1.10 |
| G265H | 1.12 |
| G265I | 1.06 |
| G265K | 1.03 |
| G265R | 1.06 |
| G265T | 1.10 |
| A268C | 1.50 |
| A268D | 1.14 |
| A268E | 1.18 |
| A268F | 1.15 |
| A268G | 1.35 |
| A268I | 1.15 |
| A268K | 1.23 |
| A268L | 1.06 |
| A268P | 1.08 |
| A268R | 1.14 |
| A268T | 1.18 |
| A268W | 1.05 |
| G269E | 1.01 |
| D276S | 1.01 |
| V284R | 1.06 |
| V284T | 1.05 |
| V284Y | 1.07 |
| S291A | 1.26 |
| S291E | 1.09 |
| S291F | 1.13 |
| S291H | 1.13 |
| S291K | 1.07 |
| S291N | 1.04 |
| S291P | 1.12 |
| S291W | 1.04 |
| P300K | 1.10 |
| P300P | 1.12 |
| P300R | 1.11 |
| A301A | 1.01 |
| A301E | 1.09 |
| A301K | 1.09 |
| A301L | 1.05 |
| A301P | 1.02 |
| A301S | 1.03 |
| A301W | 1.04 |
| A303C | 1.06 |
| A303D | 1.04 |
| A303F | 1.09 |
| A303H | 1.05 |
| A303I | 1.09 |
| A303K | 1.02 |
| A303L | 1.05 |
| A303N | 1.04 |
| A303R | 1.10 |
| A303T | 1.11 |
| A303V | 1.04 |
| A303W | 1.15 |
| A303Y | 1.07 |
| A311N | 1.04 |
| A311P | 1.09 |
| A311Q | 1.19 |
| A311S | 1.01 |
| A311Y | 1.06 |
| V338P | 1.04 |
| V338Q | 1.12 |
| V338S | 1.14 |
| V338Y | 1.05 |
| T342N | 1.06 |
| T342V | 1.23 |
| S344A | 1.05 |
| S344T | 1.01 |
| T346G | 1.14 |
| T346H | 1.07 |
| T346M | 1.06 |
| T346N | 1.09 |
| T346P | 1.07 |
| T346Q | 1.04 |
| T346Y | 1.06 |
| A349L | 1.02 |
| V359I | 1.14 |
| V359K | 1.08 |
| V359M | 1.09 |
| V359N | 1.02 |
| V359Q | 1.14 |
| V359R | 1.15 |
| V359W | 1.04 |
| G361H | 1.11 |
| G361L | 1.04 |
| G361R | 1.04 |
| A364M | 1.05 |
| A364W | 1.07 |
| T375C | 1.12 |
| T375D | 1.01 |
| T375E | 1.02 |
| T375H | 1.05 |
| T375V | 1.04 |
| T375W | 1.02 |
| T375Y | 1.05 |
| N379A | 1.05 |

TABLE 4-continued

Ethanol Screening

| Variant | PI for Specific Activity |
|---|---|
| N379C | 1.10 |
| N379D | 1.05 |
| N379G | 1.07 |
| N379I | 1.01 |
| N379M | 1.04 |
| N379P | 1.06 |
| N379S | 1.01 |
| S382A | 1.02 |
| S382N | 1.02 |
| S382P | 1.10 |
| S382S | 1.09 |
| S382V | 1.10 |
| S382W | 1.10 |
| S390A | 1.05 |
| S390Y | 1.03 |
| E391A | 1.17 |
| E391E | 1.10 |
| E391I | 1.13 |
| E391K | 1.18 |
| E391L | 1.18 |
| E391M | 1.05 |
| E391Q | 1.04 |
| E391R | 1.08 |
| E391V | 1.05 |
| E391W | 1.12 |
| E391Y | 1.08 |
| A393E | 1.05 |
| A393G | 1.14 |
| A393H | 1.10 |
| A393I | 1.07 |
| A393K | 1.09 |
| A393L | 1.12 |
| A393M | 1.07 |
| A393N | 1.18 |
| A393Q | 1.02 |
| A393R | 1.09 |
| A393S | 1.10 |
| A393T | 1.13 |
| A393V | 1.16 |
| A393W | 1.04 |
| A393Y | 1.03 |
| K394A | 1.11 |
| K394H | 1.11 |
| K394K | 1.08 |
| K394L | 1.01 |
| K394M | 1.14 |
| K394Q | 1.09 |
| K394R | 1.19 |
| K394S | 1.22 |
| K394T | 1.08 |
| K394V | 1.05 |
| K394W | 1.13 |
| S410E | 1.01 |
| S410H | 1.06 |
| S410N | 1.04 |
| L417A | 1.12 |
| L417D | 1.19 |
| L417E | 1.10 |
| L417F | 1.08 |
| L417G | 1.19 |
| L417I | 1.10 |
| L417K | 1.02 |
| L417Q | 1.04 |
| L417R | 1.30 |
| L417S | 1.05 |
| L417T | 1.10 |
| L417V | 1.21 |
| L417W | 1.05 |
| L417Y | 1.10 |
| H418E | 1.01 |
| H418M | 1.12 |
| T430A | 1.19 |
| T430E | 1.15 |
| T430F | 1.09 |
| T430G | 1.16 |
| T430H | 1.15 |
| T430I | 1.06 |
| T430K | 1.24 |
| T430M | 1.16 |
| T430N | 1.07 |
| T430Q | 1.15 |
| T430R | 1.04 |
| T430V | 1.09 |
| A431C | 1.04 |
| A431E | 1.08 |
| A431H | 1.11 |
| A431I | 1.20 |
| A431L | 1.21 |
| A431M | 1.12 |
| A431Q | 1.22 |
| A431R | 1.11 |
| A431S | 1.09 |
| A431W | 1.04 |
| A431Y | 1.13 |
| R433A | 1.09 |
| R433M | 1.17 |
| R433W | 1.06 |
| R433Y | 1.22 |
| A442A | 1.13 |
| S444K | 1.03 |
| S444M | 1.13 |
| S444N | 1.04 |
| S444P | 1.08 |
| S444Q | 1.08 |
| S444R | 1.03 |
| S444T | 1.15 |
| S444V | 1.14 |
| S444W | 1.16 |
| T448F | 1.02 |
| T448G | 1.08 |
| T448I | 1.10 |
| T448P | 1.08 |
| T448Q | 1.04 |
| T448V | 1.04 |
| T451K | 1.29 |

Table 4 provides the variants having a performance index of at least 1.0. These included the following sites: 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 236, 239, 241, 242, 263, 264, 265, 268, 269, 276, 284, 291, 300, 301, 303, 311, 338, 342, 344, 346, 349, 359, 361, 364, 375, 379, 382, 390, 391, 393, 394, 410, 417, 418, 430, 431, 433, 442, 444, 448, and 451. The sites showing the highest specific activity (having a performance index above 1.2), included: 61, 67, 72, 97, 102, 133, 145, 153, 205, 219, 228, 230, 231, 239, 263, 268, 291, 311, 342, 394, 430, 431 and 451.

Example 7

Combined Specific Activity and Thermostability Variants

Table 5 shows the variants that had a performance index of 1.0 or better as compared to the parent for both properties: specific activity and thermostability. These included the following sites: 10, 15, 59, 61, 68, 72, 73, 97, 99, 102, 133, 140, 153, 182, 204, 205, 214, 228, 229, 230, 231, 236, 241, 242, 264, 265, 268, 275, 284, 291, 300, 301, 303, 311, 338, 344, 346, 359, 361, 364, 375, 370, 382, 391, 393, 394, 410, 417, 430, 431, 433, 444, 448, and 451. The sites showing the highest specific activity and thermostability combined included: 228, 230, 231, 268, 291, 417, 433, and 451.

TABLE 5

Combined variants

| Variant | PI of Specific Activity | PI of Thermal Stability |
|---|---|---|
| T010F | 1.06 | 1.11 |
| T010G | 1.12 | 1.13 |
| T010M | 1.05 | 1.12 |
| T010R | 1.08 | 1.06 |
| T010S | 1.09 | 1.24 |
| N015N | 1.06 | 1.06 |
| F059A | 1.17 | 1.03 |
| F059G | 1.05 | 1.07 |
| N061V | 1.11 | 1.06 |
| E068I | 1.06 | 1.19 |
| E068M | 1.10 | 1.29 |
| E068W | 1.03 | 1.09 |
| A072E | 1.11 | 1.07 |
| A072Q | 1.10 | 1.02 |
| G073W | 1.03 | 1.36 |
| S097V | 1.12 | 1.03 |
| A099C | 1.07 | 1.07 |
| A099L | 1.01 | 1.09 |
| S102A | 1.20 | 1.02 |
| K140Q | 1.08 | 1.06 |
| K140S | 1.13 | 1.05 |
| K140W | 1.07 | 1.04 |
| N153D | 1.20 | 1.06 |
| N153L | 1.12 | 1.06 |
| N153W | 1.07 | 1.19 |
| N182R | 1.03 | 1.02 |
| A204D | 1.09 | 1.02 |
| A204M | 1.09 | 1.08 |
| T205D | 1.03 | 1.06 |
| T205N | 1.09 | 1.09 |
| T205P | 1.17 | 1.17 |
| T205S | 1.10 | 1.04 |
| T205V | 1.06 | 1.06 |
| T205Y | 1.18 | 1.07 |
| S214P | 1.08 | 1.04 |
| S214T | 1.07 | 1.06 |
| W228A | 1.20 | 1.01 |
| W228F | 1.22 | 1.12 |
| W228G | 1.17 | 1.06 |
| W228H | 1.33 | 1.05 |
| W228I | 1.18 | 1.06 |
| W228L | 1.12 | 1.14 |
| W228M | 1.35 | 1.04 |
| W228T | 1.19 | 1.06 |
| V229E | 1.01 | 1.16 |
| V229I | 1.02 | 1.21 |
| V229M | 1.03 | 1.11 |
| V229N | 1.01 | 1.07 |
| V229Q | 1.02 | 1.10 |
| S230C | 1.23 | 1.09 |
| S230D | 1.13 | 1.08 |
| S230E | 1.10 | 1.11 |
| S230F | 1.63 | 1.08 |
| S230G | 1.77 | 1.09 |
| S230H | 1.05 | 1.03 |
| S230K | 1.04 | 1.02 |
| S230L | 1.20 | 1.02 |
| S230N | 1.23 | 1.16 |
| S230P | 1.13 | 1.12 |
| S230Q | 1.20 | 1.20 |
| S230R | 1.84 | 1.11 |
| S230T | 1.11 | 1.07 |
| S230V | 1.12 | 1.11 |
| S230Y | 1.08 | 1.05 |
| S231C | 1.13 | 1.07 |
| S231D | 1.08 | 1.18 |
| S231F | 1.17 | 1.14 |
| S231L | 1.29 | 1.15 |
| S231M | 1.08 | 1.09 |
| S231N | 1.04 | 1.13 |
| S231Q | 1.05 | 1.18 |
| S231R | 1.02 | 1.13 |
| S231V | 1.07 | 1.21 |
| S231Y | 1.07 | 1.10 |
| D236F | 1.14 | 1.11 |
| D236G | 1.05 | 1.07 |
| D236L | 1.11 | 1.08 |
| D236M | 1.07 | 1.15 |
| D236N | 1.03 | 1.15 |
| D236P | 1.06 | 1.06 |
| D236T | 1.14 | 1.16 |
| D236V | 1.04 | 1.18 |
| T241V | 1.05 | 1.05 |
| N242F | 1.06 | 1.03 |
| L264A | 1.04 | 1.03 |
| G265E | 1.10 | 1.03 |
| G265H | 1.12 | 1.09 |
| G265I | 1.06 | 1.09 |
| G265K | 1.03 | 1.05 |
| G265R | 1.06 | 1.12 |
| G265T | 1.10 | 1.17 |
| A268C | 1.50 | 1.16 |
| A268D | 1.14 | 1.20 |
| A268E | 1.18 | 1.10 |
| A268F | 1.15 | 1.07 |
| A268G | 1.35 | 1.11 |
| A268I | 1.15 | 1.12 |
| A268K | 1.23 | 1.11 |
| A268L | 1.06 | 1.11 |
| A268P | 1.08 | 1.13 |
| A268R | 1.14 | 1.15 |
| A268T | 1.18 | 1.14 |
| A268W | 1.05 | 1.05 |
| D276S | 1.01 | 1.02 |
| V284R | 1.06 | 1.09 |
| V284T | 1.05 | 1.08 |
| V284Y | 1.07 | 1.12 |
| S291A | 1.26 | 1.21 |
| S291E | 1.09 | 1.02 |
| S291F | 1.13 | 1.24 |
| S291H | 1.13 | 1.25 |
| S291K | 1.07 | 1.13 |
| S291N | 1.04 | 1.08 |
| S291P | 1.12 | 1.11 |
| S291W | 1.04 | 1.15 |
| P300R | 1.11 | 1.02 |
| A301K | 1.09 | 1.11 |
| A301L | 1.05 | 1.07 |
| A301P | 1.02 | 1.22 |
| A301S | 1.03 | 1.12 |
| A301W | 1.04 | 1.14 |
| A303I | 1.09 | 1.02 |
| A303L | 1.05 | 1.03 |
| A311S | 1.01 | 1.01 |
| A311Y | 1.06 | 1.02 |
| V338P | 1.04 | 1.18 |
| V338Q | 1.12 | 1.20 |
| V338S | 1.14 | 1.19 |
| V338Y | 1.05 | 1.10 |
| S344A | 1.05 | 1.05 |
| S344T | 1.01 | 1.19 |
| T346M | 1.06 | 1.07 |
| T346N | 1.09 | 1.15 |
| T346P | 1.07 | 1.13 |
| T346Q | 1.04 | 1.12 |
| T346Y | 1.06 | 1.07 |
| A349L | 1.02 | 1.16 |
| V359Q | 1.14 | 1.02 |
| V359R | 1.15 | 1.13 |
| G361H | 1.11 | 1.11 |
| G361L | 1.04 | 1.22 |
| G361R | 1.04 | 1.19 |
| A364M | 1.05 | 1.21 |
| A364W | 1.07 | 1.23 |

TABLE 5-continued

Combined variants

| Variant | PI of Specific Activity | PI of Thermal Stability |
|---|---|---|
| T375E | 1.02 | 1.03 |
| T375H | 1.05 | 1.13 |
| T375V | 1.04 | 1.16 |
| T375W | 1.02 | 1.11 |
| T375Y | 1.05 | 1.17 |
| N379A | 1.05 | 1.11 |
| N379C | 1.10 | 1.03 |
| N379D | 1.05 | 1.06 |
| N379G | 1.07 | 1.09 |
| N379I | 1.01 | 1.04 |
| N379M | 1.04 | 1.08 |
| N379P | 1.06 | 1.17 |
| S382A | 1.02 | 1.06 |
| S382N | 1.02 | 1.07 |
| S382P | 1.10 | 1.10 |
| E391L | 1.18 | 1.04 |
| E391R | 1.08 | 1.02 |
| E391W | 1.12 | 1.04 |
| E391Y | 1.08 | 1.02 |
| A393E | 1.05 | 1.03 |
| A393G | 1.14 | 1.12 |
| A393H | 1.10 | 1.05 |
| A393I | 1.07 | 1.06 |
| A393K | 1.09 | 1.05 |
| A393L | 1.12 | 1.17 |
| A393M | 1.07 | 1.07 |
| A393N | 1.18 | 1.11 |
| A393Q | 1.02 | 1.02 |
| A393R | 1.09 | 1.03 |
| A393S | 1.10 | 1.13 |
| A393T | 1.13 | 1.08 |
| A393V | 1.16 | 1.09 |
| A393W | 1.04 | 1.10 |
| A393Y | 1.03 | 1.12 |
| K394A | 1.11 | 1.08 |
| K394H | 1.11 | 1.08 |
| K394L | 1.01 | 1.08 |
| K394M | 1.14 | 1.06 |
| K394Q | 1.09 | 1.07 |
| K394R | 1.19 | 1.06 |
| K394T | 1.08 | 1.03 |
| K394V | 1.05 | 1.02 |
| S410E | 1.01 | 1.05 |
| S410H | 1.06 | 1.11 |
| S410N | 1.04 | 1.10 |
| L417I | 1.10 | 1.04 |
| L417K | 1.02 | 1.20 |
| L417Q | 1.04 | 1.04 |
| L417R | 1.30 | 1.20 |
| L417V | 1.21 | 1.07 |
| L417Y | 1.10 | 1.01 |
| T430A | 1.19 | 1.05 |
| T430E | 1.15 | 1.02 |
| T430F | 1.09 | 1.06 |
| T430H | 1.15 | 1.10 |
| T430I | 1.06 | 1.04 |
| T430K | 1.24 | 1.08 |
| T430M | 1.16 | 1.17 |
| T430N | 1.07 | 1.13 |
| T430Q | 1.15 | 1.05 |
| T430R | 1.04 | 1.13 |
| T430V | 1.09 | 1.05 |
| A431I | 1.20 | 1.03 |
| A431R | 1.11 | 1.08 |
| R433A | 1.09 | 1.13 |
| R433M | 1.17 | 1.10 |
| R433W | 1.06 | 1.16 |
| R433Y | 1.22 | 1.18 |
| S444K | 1.03 | 1.07 |
| S444M | 1.13 | 1.05 |
| S444Q | 1.08 | 1.04 |
| T448F | 1.02 | 1.12 |
| T448I | 1.10 | 1.12 |
| T448Q | 1.04 | 1.17 |
| T448V | 1.04 | 1.13 |
| S451K | 1.29 | 1.08 |

Example 8

Crystal Structure of TrGA

The complete three dimensional structure of *Trichoderma reesei* (*Hypocrea jecorina*) glucoamylase (TrGA) was determined at 1.9 Å resolution. Table 6 shows the coordinates for the *Trichoderma* glucoamylase crystal structure. TrGA was crystallized in an intact form containing 599 residues and all post-translational modifications that would normally occur in the natural host. The crystal structure was produced and analyzed as follows:

Protein expression and purification—The gene encoding *H. jecorina* GA was cloned and expressed according to the protocols described in patent application publication no. US 2006/0094080 A1, by Dunn-Coleman et al. (May 4, 2006).

The TrGA protein material used for all crystallization experiments was initially purified in one step by anion exchange chromatography as follows: concentrated culture supernatants of expressed TrGA, consisting of 180 mg/ml total protein, were prepared by diluting sample 1:10 in a 25 mM Tris-HCl, pH 8.0 buffer. A HIPREP 16/10 Q Sepharose FF column (GE Healthcare) was employed for the anion exchange purification. The HIPREP column was equilibrated with 4 column volumes (CV) starting buffer (25 mM Tris-HCl, pH 8.0) followed by application of 10 ml of the diluted protein sample. An 8 CV linear gradient of 0 to 140 mM NaCl in the running buffer (25 mM Tris-HCl, pH 8.0) was applied to elute bound protein. Bound TrGA eluted from the HIPREP Q sepharose column at a salt concentration of approximately 80 mM NaCl. Fractions containing pure TrGA protein were pooled and concentrated to 50 mg/ml using a 25 ml VIVASPIN centrifugal concentration tube (Viva Science) with a molecular weight cutoff (MWCO) of 10 kD. Purified and concentrated TrGA material was buffer exchanged using a DG-10 desalting column (Bio-Rad) equilibrated with 50 mM sodium acetate buffer, pH 4.3. Protein concentrations were determined by measuring the absorbance at 280 nm. The initially purified and concentrated TrGA protein stock was thereafter stored at −20° C.

Two additional purification steps, one additional anion exchange purification, and a size exclusion purification, were introduced to enhance the TrGA protein material's propensity to form crystals. These two additional purification steps were performed as follows: In the first anion exchange purification step a 10 ml MONOQ column (GE Healthcare) was employed. A sample of 1 ml of the initially purified and frozen TrGA material (50 mg protein) was thawed and the buffer was changed to 20 mM Tris-HCl, pH 8.0, by repeated dilution of the sample to 6 ml in the new buffer, followed by a concentration of the sample again to 0.5 ml using a 6 ml 5 kD MWCO concentration tube. The TrGA sample was diluted after the last concentration step in distilled water until a conductivity of the protein sample was reached that corresponded to the conductivity of the starting buffer of the anion purification, i.e. 25 mM Tris-HCl, pH 8.0. The MONOQ column was first equilibrated with 4 column volumes (CV) starting buffer, followed by application of the diluted protein sample to the column. Bound protein was eluted from the MONOQ column by two different gradients. In the first a 4 CV linear pH gradient was applied where the pH of the starting buffer was decreased from 8.0 to 6.0. In the second gradient an 8 CV long salt gradient was applied in which the salt concentration was increased from 0 to 350 mM NaCl in the running buffer (25 mM Tris-HCl, pH 6.0). Bound TrGA was found to elute from the column during the second salt gradient at an approximate NaCl concentration of 150 mM. Fractions containing TrGA were pooled and concentrated to 2 ml using a 6 ml 5 kD MWCO VIVASPIN concentration tube. The concentrated TrGA sample was thereafter applied to a SUPERDEX 200 16/60 size exclusion column (GE Healthcare) equilibrated with 4 CV of 20 mM Tris-Cl, pH 8.0, and 50 mM NaCl, which also was used as running buffer. Fractions from the main elution peak after the size exclusion purification were pooled and concentrated to an approximate protein concentration of 7.5 mg/ml using a 6 ml 5 kD MWCO VIVASPIN concentration tube.

Protein crystallization—The protein sample that was used to find the initial TrGA crystallization conditions was a sample of the TrGA material that was purified once by anion exchange purification and thereafter stored at −20° C. The TrGA protein sample was thawed and diluted with 50 mM sodium acetate buffer, pH 4.3, to approximately 12 mg/ml, prior to the initial crystallization experiments. TrGA crystals were found to grow in solution consisting of 25% PEG 3350, 0.20M ammonium acetate, 0.10M Bis-Tris pH 5.5 (reservoir solution), using the vapor-diffusion method with hanging drops (McPherson 1982), at 20° C. Crystallization drops were prepared by mixing equal amounts of protein solution (12 mg/ml) and reservoir solution to a final volume of 10 µl. The TrGA crystals were found to belong to the orthorhombic space group P212121 with approximate cell dimensions: a=52.2 Å, b=99.2 Å, c=121.2 Å, and have a calculated $V_m$ of 2.3 (Matthews 1968) with one molecule in the asymmetric unit.

X-ray data collection—The two orthorhombic TrGA datasets were collected from single crystals mounted in sealed capillary tubes, at room temperature. The initial lo-resolution orthorhombic TrGA X-ray dataset used to solve the structure by molecular replacement methods (MR), was collected on a home X-ray source, an MSC/Rigaku (Molecular Structures Corp., The Woodlands, Tex.) Raxis IV++ image plate detector with focusing mirrors using Cu Kα radiation from a Rigaku RU200 rotating anode generator. This dataset was processed, scaled, and averaged using the d*trek software provided by MSC/Rigaku. The orthorhombic X-ray dataset was used to solve the TrGA structure by molecular replacement (MR) and the high resolution orthorhombic dataset was used for the final orthorhombic space group TrGA structure model. The C centered monoclinic dataset was collected from a single frozen TrGA crystal at 100K, equilibrated in a cryo-protective agent comprised of 25% PEG 3350, 15% Glycerol 50 mM $CaCl_2$ and 0.1 M Bis-Tris pH 5.5 as cryoprotectant, mounted in rayon-fiber loops, and plunge frozen in liquid nitrogen prior to transportation to the synchrotron. The high-resolution orthorhombic (1.9 Å) data set and the C centric monoclinic dataset (1.8 Å) were both collected at a synchrotron source, beam line 911:5 at MAX LAB in Lund, Sweden. Both datasets that were collected at a synchrotron source were processed with MOSFLM, and scaled with program SCALA included in the CCP4 program package (Collaborative Computational Project Number 4 1994). All subsequent data processing was performed using the CCP4 program package (Collaborative Computational Project Number 4 1994), unless otherwise stated. A set of 5% of the reflections from each data set was set aside and used for monitoring the R-free (Brunger, A (1992) Nature, 355: 472-475).

Structure solution—The TrGA structure was initially solved by MR with the automatic replacement program MOLREP (Collaborative Computational Project Number 4 1994), included in the CCP4 program package, using the initial lo-resolution orthorhombic dataset, and using the coordinates of *Aspergillus awamori* GA (AaGA) variant X100 (pdb entry 1GLM (Aleshin, et al (1994) *J. Mol. Biol.* 238: 575-591) as search model. The *A. awamori* GA search model was edited to remove all glycosylation moieties attached to the protein molecule as N- and O-glycosylations, and all solvent molecules before carrying out the MR experiments. All reflections between 36.8 and 2.8 Å resolution, from the initial low resolution TrGA dataset, was used for the MR solution. The MR program found a single rotation function solution, with a maxima of 11.1σ above background, the next highest maxima was 3.8σ above the background. The translation function solution gave an R-factor of 48.7% and had a contrast factor of 17.4. The MR solution was refined for 10 cycles of restrained least squares refinement using the program Refmac 5.0 (Murshudov, et al. (1997) Acta Crystallogr., D53:240-255). This lowered the crystallographic R-factor to 31.1% while the R-free value dropped from 42.2% to 41.1%.

Model fitting and refinement—The refined MR solution model was used to calculate an initial density map from the lo-resolution orthorhombic TrGA dataset. Electron density for a disulfide bridge between residues 19 and 26 of TrGA, a disulfide bridge not present in the *A. awamori* variant X100 structure model, could readily be identified in this electron density map. This was taken as an indication that the electron density map was of sufficient quality to be used to build a structure model of TrGA from its amino acid sequence. The initial TrGA structure model, based on the lo-resolution dataset, was refined with alternating cycles of model building using Coot (Emsley et al, (2004) Acta *Crystallogr D Biol Crystallogr* 60:2126-32), and maximum likelihood refinement using Refmac 5.0.

The resolution of the initial TrGA structure model was extended to the resolution of the high-resolution orthorhombic dataset (1.9 Å) by refining the initial TrGA structure model against the high-resolution dataset for 10 cycles of restrained refinement using the program Refmac 5.0. Most water molecules in the structure models were located automatically by using the water picking protocols in the refinement programs, and then manually selected or discarded by inspection by eye. All structural comparisons were made with either Coot (Emsley et al. (2004) supra) or O (Jones et al. (1991) *Acta Crystallogr.*, A47: 110-119), and figures were prepared with PyMOL (DeLano W. L. (2002) The PyMOL Molecular Graphics System. Palo Alto, Calif., USA; DeLano Scientific).

From these results, it can be seen that the TrGA catalytic core segment followed the same $(\alpha/\alpha)_6$-barrel topology described by Aleshin et al. (1992, supra) for the AaGA, consisting of a double barrel of alpha helices with the C-terminal of the outer helix leading into the N-terminus of an inner helix. It was possible to identify key differences in the electron density such as the disulfide bridge between residues 19 and 26 and ar insertion (residues 257-260) relative to AaGA. The segment comprising 80-100 also underwent extensive model rebuilding. One major glycosylation site was identified at Asn 171, which had up to four glycoside moieties attached. A similar glycosylation site was identified in AaGA. Additionally, the catalytic core containing three cis-peptides between residues 22-23, 44-45 and 122-123 were conserved between TrGA and AaGA. Overall there was an rms variation of 0.535 Å between 409 out of 453 Cα atoms when comparing the coordinates of the catalytic cores of TrGA and AaGA.

Example 9

Homology Between TrGA and *Aspergillus awamori* GA

The crystal structure of the TrGA identified in Example 8, was superposed on the previously identified crystal structure of the *Aspergillus awamori* GA (AaGA). The AaGA crystal structure was obtained from the protein database (PDB) and the form of AaGA that was crystallized was the form containing only a catalytic domain. The structure of the *Trichoderma reesei* glucoamylase with all three regions intact was determined to 1.8 Angstrom resolution herein (see Table 6 and Example 8). Using the coordinates (see Table 6) the structure was aligned with the coordinates of the catalytic domain from *Aspergillus awamori* strain X100 that was determined previously (Aleshin, A. E., Hoffman, C., Firsov, L. M., and Honzatko, R. B. (1994) *J Mol Biol* 238: 575-591 and the PDB). As seen in FIGS. 6 and 7 the structure of the catalytic domain overlapped very closely and allowed the identification of equivalent residues based on this structural superposition.

Based on this analysis, sites were identified that could be mutated in TrGA and result in increased stability and/or specific activity. These sites include 108, 124, 175 and 316 at the active site. Also identified were specific pairwise variants Y47W/Y315F and Y47F/Y315W. Other sites identified were I43, D44, P45, D46, R122, R125, V181, E242, Y310, D313, V314, N317, R408, and N409. Because of the high structural homology it is expected that beneficial variants found at sites in *Trichoderma reesei* GA would have similar consequences in *Aspergillus awamori* and other homologous glucoamylases.

Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art are intended to be within the scope of the following claims.

TABLE 6

| | | | | | | | | |
|---|---|---|---|---|---|---|---|---|
| CRYST1 | 52.185 | | 99.232 | 121.240 | 90.00 | 90.00 | 90.00 | |
| ORIGX1 | 1.000000 | | 0.000000 | 0.000000 | | 0.00000 | | |
| ORIGX2 | 0.000000 | | 1.000000 | 0.000000 | | 0.00000 | | |
| ORIGX3 | 0.000000 | | 0.000000 | 1.000000 | | 0.00000 | | |
| SCALE1 | 0.019163 | | −0.000001 | −0.000001 | | 0.00000 | | |
| SCALE2 | 0.000000 | | 0.010077 | 0.000000 | | 0.00000 | | |
| SCALE3 | 0.000000 | | 0.000000 | 0.008248 | | 0.00000 | | |
| ATOM | 1 | N | SER | A1 | −30.485 | 30.567 | −21.185 | 1.00 | 37.11 |
| ATOM | 2 | CA | SER | A1 | −30.568 | 29.350 | −20.326 | 1.00 | 37.00 |
| ATOM | 3 | CB | SER | A1 | −31.953 | 28.707 | −20.424 | 1.00 | 37.27 |
| ATOM | 4 | OG | SER | A1 | −32.137 | 28.089 | −21.695 | 1.00 | 40.11 |
| ATOM | 5 | C | SER | A1 | −29.519 | 28.345 | −20.772 | 1.00 | 35.91 |
| ATOM | 6 | O | SER | A1 | −29.043 | 28.415 | −21.911 | 1.00 | 35.46 |
| ATOM | 7 | N | VAL | A2 | −29.170 | 27.425 | −19.867 | 1.00 | 34.51 |
| ATOM | 8 | CA | VAL | A2 | −28.302 | 26.293 | −20.179 | 1.00 | 33.56 |
| ATOM | 9 | CB | VAL | A2 | −28.142 | 25.339 | −18.955 | 1.00 | 33.84 |
| ATOM | 10 | CG1 | VAL | A2 | −27.349 | 24.103 | −19.316 | 1.00 | 34.20 |
| ATOM | 11 | CG2 | VAL | A2 | −27.468 | 26.057 | −17.827 | 1.00 | 34.79 |
| ATOM | 12 | C | VAL | A2 | −28.846 | 25.506 | −21.363 | 1.00 | 32.48 |
| ATOM | 13 | O | VAL | A2 | −28.086 | 25.109 | −22.245 | 1.00 | 31.10 |
| ATOM | 14 | N | ASP | A3 | −30.160 | 25.286 | −21.381 | 1.00 | 31.43 |
| ATOM | 15 | CA | ASP | A3 | −30.791 | 24.530 | −22.457 | 1.00 | 31.38 |
| ATOM | 16 | CB | ASP | A3 | −32.283 | 24.323 | −22.190 | 1.00 | 32.17 |
| ATOM | 17 | CG | ASP | A3 | −32.522 | 23.492 | −20.943 | 1.00 | 35.28 |
| ATOM | 18 | OD1 | ASP | A3 | −32.413 | 22.251 | −21.028 | 1.00 | 36.80 |
| ATOM | 19 | OD2 | ASP | A3 | −32.786 | 24.092 | −19.870 | 1.00 | 40.63 |
| ATOM | 20 | C | ASP | A3 | −30.556 | 25.153 | −23.818 | 1.00 | 30.59 |
| ATOM | 21 | O | ASP | A3 | −30.282 | 24.446 | −24.778 | 1.00 | 30.19 |
| ATOM | 22 | N | ASP | A4 | −30.644 | 26.477 | −23.875 | 1.00 | 29.89 |
| ATOM | 23 | CA | ASP | A4 | −30.369 | 27.244 | −25.083 | 1.00 | 29.99 |
| ATOM | 24 | CB | ASP | A4 | −30.601 | 28.731 | −24.822 | 1.00 | 31.12 |
| ATOM | 25 | CG | ASP | A4 | −32.088 | 29.121 | −24.785 | 1.00 | 34.16 |
| ATOM | 26 | OD1 | ASP | A4 | −32.991 | 28.260 | −24.925 | 1.00 | 36.06 |
| ATOM | 27 | OD2 | ASP | A4 | −32.340 | 30.332 | −24.608 | 1.00 | 39.96 |
| ATOM | 28 | C | ASP | A4 | −28.925 | 27.049 | −25.579 | 1.00 | 28.65 |
| ATOM | 29 | O | ASP | A4 | −28.697 | 26.881 | −26.770 | 1.00 | 28.51 |
| ATOM | 30 | N | PHE | A5 | −27.961 | 27.096 | −24.660 | 1.00 | 26.74 |
| ATOM | 31 | CA | PHE | A5 | −26.553 | 26.860 | −24.994 | 1.00 | 25.21 |
| ATOM | 32 | CB | PHE | A5 | −25.666 | 27.110 | −23.764 | 1.00 | 25.59 |
| ATOM | 33 | CG | PHE | A5 | −24.244 | 26.646 | −23.931 | 1.00 | 26.03 |
| ATOM | 34 | CD1 | PHE | A5 | −23.395 | 27.259 | −24.854 | 1.00 | 27.29 |
| ATOM | 35 | CE1 | PHE | A5 | −22.063 | 26.823 | −25.009 | 1.00 | 27.33 |
| ATOM | 36 | CZ | PHE | A5 | −21.593 | 25.783 | −24.228 | 1.00 | 26.77 |
| ATOM | 37 | CE2 | PHE | A5 | −22.425 | 25.181 | −23.286 | 1.00 | 28.42 |
| ATOM | 38 | CD2 | PHE | A5 | −23.749 | 25.617 | −23.144 | 1.00 | 28.42 |
| ATOM | 39 | C | PHE | A5 | −26.352 | 25.438 | −25.539 | 1.00 | 24.23 |
| ATOM | 40 | O | PHE | A5 | −25.659 | 25.244 | −26.544 | 1.00 | 23.56 |
| ATOM | 41 | N | ILE | A6 | −26.974 | 24.458 | −24.892 | 1.00 | 22.71 |
| ATOM | 42 | CA | ILE | A6 | −26.835 | 23.065 | −25.312 | 1.00 | 22.36 |

TABLE 6-continued

| ATOM | 43 | CB | ILE | A | 6 | −27.491 | 22.106 | −24.299 | 1.00 | 21.86 |
| ATOM | 44 | CG1 | ILE | A | 6 | −26.744 | 22.181 | −22.956 | 1.00 | 22.27 |
| ATOM | 45 | CD1 | ILE | A | 6 | −27.384 | 21.347 | −21.834 | 1.00 | 22.36 |
| ATOM | 46 | CG2 | ILE | A | 6 | −27.571 | 20.669 | −24.848 | 1.00 | 21.69 |
| ATOM | 47 | C | ILE | A | 6 | −27.388 | 22.855 | −26.723 | 1.00 | 22.84 |
| ATOM | 48 | O | ILE | A | 6 | −26.753 | 22.216 | −27.573 | 1.00 | 21.76 |
| ATOM | 49 | N | SER | A | 7 | −28.556 | 23.420 | −26.996 | 1.00 | 23.10 |
| ATOM | 50 | CA | SER | A | 7 | −29.146 | 23.175 | −28.309 | 1.00 | 23.90 |
| ATOM | 51 | CB | SER | A | 7 | −30.627 | 23.570 | −28.320 | 1.00 | 25.04 |
| ATOM | 52 | OG | SER | A | 7 | −30.717 | 24.982 | −28.282 | 1.00 | 30.08 |
| ATOM | 53 | C | SER | A | 7 | −28.340 | 23.874 | −29.422 | 1.00 | 22.78 |
| ATOM | 54 | O | SER | A | 7 | −28.186 | 23.337 | −30.508 | 1.00 | 22.94 |
| ATOM | 55 | N | THR | A | 8 | −27.800 | 25.053 | −29.140 | 1.00 | 22.50 |
| ATOM | 56 | CA | THR | A | 8 | −26.984 | 25.780 | −30.115 | 1.00 | 23.05 |
| ATOM | 57 | CB | THR | A | 8 | −26.834 | 27.247 | −29.698 | 1.00 | 23.65 |
| ATOM | 58 | OG1 | THR | A | 8 | −28.138 | 27.839 | −29.700 | 1.00 | 27.60 |
| ATOM | 59 | CG2 | THR | A | 8 | −25.939 | 28.018 | −30.660 | 1.00 | 26.76 |
| ATOM | 60 | C | THR | A | 8 | −25.601 | 25.159 | −30.307 | 1.00 | 21.46 |
| ATOM | 61 | O | THR | A | 8 | −25.109 | 25.051 | −31.437 | 1.00 | 21.38 |
| ATOM | 62 | N | GLU | A | 9 | −24.978 | 24.768 | −29.200 | 1.00 | 19.11 |
| ATOM | 63 | CA | GLU | A | 9 | −23.596 | 24.269 | −29.243 | 1.00 | 18.01 |
| ATOM | 64 | CB | GLU | A | 9 | −22.959 | 24.334 | −27.847 | 1.00 | 17.76 |
| ATOM | 65 | CG | GLU | A | 9 | −21.449 | 23.945 | −27.794 | 1.00 | 17.71 |
| ATOM | 66 | CD | GLU | A | 9 | −20.536 | 24.892 | −28.609 | 1.00 | 20.86 |
| ATOM | 67 | OE1 | GLU | A | 9 | −20.949 | 26.010 | −28.971 | 1.00 | 19.89 |
| ATOM | 68 | OE2 | GLU | A | 9 | −19.389 | 24.500 | −28.909 | 1.00 | 19.22 |
| ATOM | 69 | C | GLU | A | 9 | −23.462 | 22.846 | −29.784 | 1.00 | 17.77 |
| ATOM | 70 | O | GLU | A | 9 | −22.423 | 22.505 | −30.368 | 1.00 | 18.05 |
| ATOM | 71 | N | THR | A | 10 | −24.485 | 22.020 | −29.593 | 1.00 | 15.87 |
| ATOM | 72 | CA | THR | A | 10 | −24.404 | 20.609 | −29.958 | 1.00 | 17.31 |
| ATOM | 73 | CB | THR | A | 10 | −25.677 | 19.823 | −29.525 | 1.00 | 17.46 |
| ATOM | 74 | OG1 | THR | A | 10 | −25.768 | 19.860 | −28.090 | 1.00 | 17.46 |
| ATOM | 75 | CG2 | THR | A | 10 | −25.616 | 18.374 | −30.037 | 1.00 | 18.42 |
| ATOM | 76 | C | THR | A | 10 | −24.026 | 20.346 | −31.430 | 1.00 | 17.40 |
| ATOM | 77 | O | THR | A | 10 | −23.073 | 19.615 | −31.682 | 1.00 | 17.22 |
| ATOM | 78 | N | PRO | A | 11 | −24.764 | 20.934 | −32.412 | 1.00 | 18.30 |
| ATOM | 79 | CA | PRO | A | 11 | −24.346 | 20.649 | −33.798 | 1.00 | 18.11 |
| ATOM | 80 | CB | PRO | A | 11 | −25.440 | 21.317 | −34.662 | 1.00 | 18.57 |
| ATOM | 81 | CG | PRO | A | 11 | −26.094 | 22.310 | −33.771 | 1.00 | 19.16 |
| ATOM | 82 | CD | PRO | A | 11 | −25.975 | 21.779 | −32.361 | 1.00 | 18.54 |
| ATOM | 83 | C | PRO | A | 11 | −22.963 | 21.231 | −34.142 | 1.00 | 17.81 |
| ATOM | 84 | O | PRO | A | 11 | −22.241 | 20.655 | −34.964 | 1.00 | 17.74 |
| ATOM | 85 | N | ILE | A | 12 | −22.601 | 22.353 | −33.520 | 1.00 | 16.85 |
| ATOM | 86 | CA | ILE | A | 12 | −21.279 | 22.936 | −33.731 | 1.00 | 16.66 |
| ATOM | 87 | CB | ILE | A | 12 | −21.161 | 24.319 | −33.112 | 1.00 | 17.25 |
| ATOM | 88 | CG1 | ILE | A | 12 | −22.194 | 25.267 | −33.751 | 1.00 | 19.25 |
| ATOM | 89 | CD1 | ILE | A | 12 | −22.289 | 26.635 | −33.101 | 1.00 | 21.45 |
| ATOM | 90 | CG2 | ILE | A | 12 | −19.714 | 24.855 | −33.270 | 1.00 | 18.75 |
| ATOM | 91 | C | ILE | A | 12 | −20.170 | 22.023 | −33.178 | 1.00 | 16.30 |
| ATOM | 92 | O | ILE | A | 12 | −19.155 | 21.798 | −33.848 | 1.00 | 14.64 |
| ATOM | 93 | N | ALA | A | 13 | −20.360 | 21.527 | −31.951 | 1.00 | 15.28 |
| ATOM | 94 | CA | ALA | A | 13 | −19.375 | 20.627 | −31.304 | 1.00 | 15.19 |
| ATOM | 95 | CB | ALA | A | 13 | −19.788 | 20.332 | −29.883 | 1.00 | 15.31 |
| ATOM | 96 | C | ALA | A | 13 | −19.204 | 19.326 | −32.092 | 1.00 | 15.37 |
| ATOM | 97 | O | ALA | A | 13 | −18.083 | 18.834 | −32.297 | 1.00 | 13.56 |
| ATOM | 98 | N | LEU | A | 14 | −20.320 | 18.743 | −32.531 | 1.00 | 15.13 |
| ATOM | 99 | CA | LEU | A | 14 | −20.225 | 17.503 | −33.285 | 1.00 | 16.06 |
| ATOM | 100 | CB | LEU | A | 14 | −21.630 | 16.921 | −33.510 | 1.00 | 17.33 |
| ATOM | 101 | CG | LEU | A | 14 | −21.689 | 15.563 | −34.212 | 1.00 | 20.02 |
| ATOM | 102 | CD1 | LEU | A | 14 | −20.946 | 14.460 | −33.471 | 1.00 | 23.09 |
| ATOM | 103 | CD2 | LEU | A | 14 | −23.150 | 15.225 | −34.390 | 1.00 | 21.86 |
| ATOM | 104 | C | LEU | A | 14 | −19.506 | 17.749 | −34.623 | 1.00 | 15.61 |
| ATOM | 105 | O | LEU | A | 14 | −18.651 | 16.947 | −35.039 | 1.00 | 14.82 |
| ATOM | 106 | N | ASN | A | 15 | −19.853 | 18.852 | −35.285 | 1.00 | 15.30 |
| ATOM | 107 | CA | ASN | A | 15 | −19.236 | 19.228 | −36.567 | 1.00 | 16.34 |
| ATOM | 108 | CB | ASN | A | 15 | −19.848 | 20.545 | −37.073 | 1.00 | 16.07 |
| ATOM | 109 | CG | ASN | A | 15 | −19.232 | 21.010 | −38.388 | 1.00 | 18.31 |
| ATOM | 110 | OD1 | ASN | A | 15 | −19.565 | 20.487 | −39.431 | 1.00 | 17.60 |
| ATOM | 111 | ND2 | ASN | A | 15 | −18.312 | 21.987 | −38.325 | 1.00 | 21.40 |
| ATOM | 112 | C | ASN | A | 15 | −17.736 | 19.450 | −36.405 | 1.00 | 15.35 |
| ATOM | 113 | O | ASN | A | 15 | −16.926 | 18.954 | −37.198 | 1.00 | 15.29 |
| ATOM | 114 | N | ASN | A | 16 | −17.385 | 20.180 | −35.355 | 1.00 | 14.82 |
| ATOM | 115 | CA | ASN | A | 16 | −15.992 | 20.555 | −35.144 | 1.00 | 15.27 |
| ATOM | 116 | CB | ASN | A | 16 | −15.872 | 21.693 | −34.148 | 1.00 | 15.41 |
| ATOM | 117 | CG | ASN | A | 16 | −16.276 | 23.023 | −34.737 | 1.00 | 16.53 |
| ATOM | 118 | OD1 | ASN | A | 16 | −16.517 | 23.136 | −35.954 | 1.00 | 18.08 |
| ATOM | 119 | ND2 | ASN | A | 16 | −16.326 | 24.050 | −33.896 | 1.00 | 16.35 |
| ATOM | 120 | C | ASN | A | 16 | −15.159 | 19.362 | −34.723 | 1.00 | 14.91 |
| ATOM | 121 | O | ASN | A | 16 | −13.975 | 19.261 | −35.099 | 1.00 | 15.34 |
| ATOM | 122 | N | LEU | A | 17 | −15.771 | 18.460 | −33.956 | 1.00 | 14.29 |

TABLE 6-continued

| | | | | | | | | | |
|---|---|---|---|---|---|---|---|---|---|
| ATOM | 123 | CA | LEU | A | 17 | −15.114 | 17.191 | −33.610 | 1.00 | 13.90 |
| ATOM | 124 | CB | LEU | A | 17 | −16.003 | 16.346 | −32.672 | 1.00 | 13.94 |
| ATOM | 125 | CG | LEU | A | 17 | −15.351 | 15.065 | −32.133 | 1.00 | 16.81 |
| ATOM | 126 | CD1 | LEU | A | 17 | −15.933 | 14.708 | −30.779 | 1.00 | 20.06 |
| ATOM | 127 | CD2 | LEU | A | 17 | −15.484 | 13.880 | −33.097 | 1.00 | 19.31 |
| ATOM | 128 | C | LEU | A | 17 | −14.763 | 16.409 | −34.880 | 1.00 | 14.06 |
| ATOM | 129 | O | LEU | A | 17 | −13.613 | 15.957 | −35.073 | 1.00 | 12.69 |
| ATOM | 130 | N | LEU | A | 18 | −15.774 | 16.215 | −35.730 | 1.00 | 13.19 |
| ATOM | 131 | CA | LEU | A | 18 | −15.589 | 15.441 | −36.957 | 1.00 | 14.25 |
| ATOM | 132 | CB | LEU | A | 18 | −16.952 | 15.027 | −37.545 | 1.00 | 13.56 |
| ATOM | 133 | CG | LEU | A | 18 | −17.717 | 14.013 | −36.684 | 1.00 | 16.49 |
| ATOM | 134 | CD1 | LEU | A | 18 | −19.171 | 13.874 | −37.165 | 1.00 | 16.33 |
| ATOM | 135 | CD2 | LEU | A | 18 | −17.020 | 12.647 | −36.655 | 1.00 | 18.51 |
| ATOM | 136 | C | LEU | A | 18 | −14.703 | 16.132 | −38.007 | 1.00 | 13.49 |
| ATOM | 137 | O | LEU | A | 18 | −14.083 | 15.435 | −38.820 | 1.00 | 14.69 |
| ATOM | 138 | N | CYS | A | 19 | −14.613 | 17.462 | −37.964 | 1.00 | 13.01 |
| ATOM | 139 | CA | CYS | A | 19 | −13.629 | 18.223 | −38.760 | 1.00 | 13.22 |
| ATOM | 140 | CB | CYS | A | 19 | −13.796 | 19.738 | −38.556 | 1.00 | 14.20 |
| ATOM | 141 | SG | CYS | A | 19 | −15.125 | 20.407 | −39.642 | 1.00 | 16.22 |
| ATOM | 142 | C | CYS | A | 19 | −12.182 | 17.808 | −38.450 | 1.00 | 13.86 |
| ATOM | 143 | O | CYS | A | 19 | −11.278 | 18.043 | −39.259 | 1.00 | 13.42 |
| ATOM | 144 | N | ASN | A | 20 | −11.968 | 17.219 | −37.272 | 1.00 | 13.21 |
| ATOM | 145 | CA | ASN | A | 20 | −10.594 | 16.850 | −36.830 | 1.00 | 13.62 |
| ATOM | 146 | CB | ASN | A | 20 | −10.394 | 17.184 | −35.324 | 1.00 | 13.52 |
| ATOM | 147 | CG | ASN | A | 20 | −10.242 | 18.687 | −35.055 | 1.00 | 16.17 |
| ATOM | 148 | OD1 | ASN | A | 20 | −10.035 | 19.119 | −33.897 | 1.00 | 17.34 |
| ATOM | 149 | ND2 | ASN | A | 20 | −10.343 | 19.486 | −36.090 | 1.00 | 11.87 |
| ATOM | 150 | C | ASN | A | 20 | −10.262 | 15.381 | −37.116 | 1.00 | 13.99 |
| ATOM | 151 | O | ASN | A | 20 | −9.238 | 14.857 | −36.646 | 1.00 | 14.28 |
| ATOM | 152 | N | VAL | A | 21 | −11.123 | 14.705 | −37.875 | 1.00 | 13.41 |
| ATOM | 153 | CA | VAL | A | 21 | −10.923 | 13.287 | −38.167 | 1.00 | 14.20 |
| ATOM | 154 | CB | VAL | A | 21 | −12.177 | 12.448 | −37.827 | 1.00 | 14.30 |
| ATOM | 155 | CG1 | VAL | A | 21 | −11.953 | 10.971 | −38.189 | 1.00 | 15.30 |
| ATOM | 156 | CG2 | VAL | A | 21 | −12.517 | 12.553 | −36.312 | 1.00 | 14.17 |
| ATOM | 157 | C | VAL | A | 21 | −10.551 | 13.136 | −39.644 | 1.00 | 14.35 |
| ATOM | 158 | O | VAL | A | 21 | −11.255 | 13.642 | −40.491 | 1.00 | 15.68 |
| ATOM | 159 | N | GLY | A | 22 | −9.461 | 12.449 | −39.953 | 1.00 | 15.67 |
| ATOM | 160 | CA | GLY | A | 22 | −9.061 | 12.300 | −41.377 | 1.00 | 15.70 |
| ATOM | 161 | C | GLY | A | 22 | −9.843 | 11.182 | −42.060 | 1.00 | 17.34 |
| ATOM | 162 | O | GLY | A | 22 | −10.453 | 10.358 | −41.397 | 1.00 | 17.15 |
| ATOM | 163 | N | PRO | A | 23 | −9.806 | 11.117 | −43.404 | 1.00 | 18.42 |
| ATOM | 164 | CA | PRO | A | 23 | −9.009 | 11.946 | −44.278 | 1.00 | 18.20 |
| ATOM | 165 | CB | PRO | A | 23 | −8.716 | 10.990 | −45.446 | 1.00 | 18.64 |
| ATOM | 166 | CG | PRO | A | 23 | −9.983 | 10.171 | −45.560 | 1.00 | 18.81 |
| ATOM | 167 | CD | PRO | A | 23 | −10.568 | 10.092 | −44.153 | 1.00 | 18.59 |
| ATOM | 168 | C | PRO | A | 23 | −9.761 | 13.182 | −44.753 | 1.00 | 19.05 |
| ATOM | 169 | O | PRO | A | 23 | −9.183 | 14.055 | −45.426 | 1.00 | 19.36 |
| ATOM | 170 | N | ASP | A | 24 | −11.034 | 13.288 | −44.385 | 1.00 | 18.76 |
| ATOM | 171 | CA | ASP | A | 24 | −11.878 | 14.305 | −44.996 | 1.00 | 19.39 |
| ATOM | 172 | CB | ASP | A | 24 | −13.015 | 13.636 | −45.781 | 1.00 | 20.87 |
| ATOM | 173 | CG | ASP | A | 24 | −13.920 | 12.784 | −44.913 | 1.00 | 24.34 |
| ATOM | 174 | OD1 | ASP | A | 24 | −13.502 | 12.291 | −43.839 | 1.00 | 27.70 |
| ATOM | 175 | OD2 | ASP | A | 24 | −15.079 | 12.580 | −45.330 | 1.00 | 28.83 |
| ATOM | 176 | C | ASP | A | 24 | −12.452 | 15.372 | −44.061 | 1.00 | 18.08 |
| ATOM | 177 | O | ASP | A | 24 | −13.208 | 16.245 | −44.509 | 1.00 | 17.78 |
| ATOM | 178 | N | GLY | A | 25 | −12.100 | 15.331 | −42.775 | 1.00 | 16.65 |
| ATOM | 179 | CA | GLY | A | 25 | −12.634 | 16.343 | −41.852 | 1.00 | 16.02 |
| ATOM | 180 | C | GLY | A | 25 | −12.152 | 17.718 | −42.292 | 1.00 | 15.70 |
| ATOM | 181 | O | GLY | A | 25 | −11.033 | 17.849 | −42.811 | 1.00 | 16.22 |
| ATOM | 182 | N | CYS | A | 26 | −12.979 | 18.752 | −42.086 | 1.00 | 15.10 |
| ATOM | 183 | CA | CYS | A | 26 | −12.698 | 20.078 | −42.637 | 1.00 | 15.46 |
| ATOM | 184 | CB | CYS | A | 26 | −13.899 | 21.037 | −42.475 | 1.00 | 15.47 |
| ATOM | 185 | SG | CYS | A | 26 | −14.147 | 21.739 | −40.786 | 1.00 | 16.91 |
| ATOM | 186 | C | CYS | A | 26 | −11.407 | 20.731 | −42.116 | 1.00 | 15.65 |
| ATOM | 187 | O | CYS | A | 26 | −10.896 | 21.643 | −42.763 | 1.00 | 15.80 |
| ATOM | 188 | N | ARG | A | 27 | −10.879 | 20.259 | −40.973 | 1.00 | 15.02 |
| ATOM | 189 | CA | ARG | A | 27 | −9.615 | 20.808 | −40.443 | 1.00 | 14.56 |
| ATOM | 190 | CB | ARG | A | 27 | −9.819 | 21.480 | −39.066 | 1.00 | 15.00 |
| ATOM | 191 | CG | ARG | A | 27 | −10.695 | 22.728 | −39.164 | 1.00 | 15.15 |
| ATOM | 192 | CD | ARG | A | 27 | −10.826 | 23.551 | −37.888 | 1.00 | 14.30 |
| ATOM | 193 | NE | ARG | A | 27 | −11.874 | 24.566 | −38.080 | 1.00 | 15.05 |
| ATOM | 194 | CZ | ARG | A | 27 | −13.160 | 24.420 | −37.761 | 1.00 | 17.96 |
| ATOM | 195 | NH1 | ARG | A | 27 | −13.623 | 23.293 | −37.211 | 1.00 | 17.37 |
| ATOM | 196 | NH2 | ARG | A | 27 | −14.009 | 25.415 | −38.025 | 1.00 | 19.55 |
| ATOM | 197 | C | ARG | A | 27 | −8.489 | 19.776 | −40.394 | 1.00 | 15.49 |
| ATOM | 198 | O | ARG | A | 27 | −7.389 | 20.079 | −39.888 | 1.00 | 15.40 |
| ATOM | 199 | N | ALA | A | 28 | −8.768 | 18.577 | −40.910 | 1.00 | 15.17 |
| ATOM | 200 | CA | ALA | A | 28 | −7.805 | 17.484 | −40.988 | 1.00 | 16.06 |
| ATOM | 201 | CB | ALA | A | 28 | −8.163 | 16.374 | −39.975 | 1.00 | 15.52 |
| ATOM | 202 | C | ALA | A | 28 | −7.744 | 16.913 | −42.394 | 1.00 | 16.96 |

TABLE 6-continued

| | | | | | | | | | |
|---|---|---|---|---|---|---|---|---|---|
| ATOM | 203 | O | ALA | A | 28 | −7.453 | 15.730 | −42.581 | 1.00 | 17.60 |
| ATOM | 204 | N | PHE | A | 29 | −8.028 | 17.756 | −43.380 | 1.00 | 17.45 |
| ATOM | 205 | CA | PHE | A | 29 | −8.188 | 17.272 | −44.744 | 1.00 | 18.68 |
| ATOM | 206 | CB | PHE | A | 29 | −8.728 | 18.376 | −45.636 | 1.00 | 19.45 |
| ATOM | 207 | CG | PHE | A | 29 | −9.299 | 17.864 | −46.919 | 1.00 | 20.86 |
| ATOM | 208 | CD1 | PHE | A | 29 | −8.515 | 17.827 | −48.071 | 1.00 | 23.76 |
| ATOM | 209 | CE1 | PHE | A | 29 | −9.042 | 17.343 | −49.267 | 1.00 | 25.46 |
| ATOM | 210 | CZ | PHE | A | 29 | −10.357 | 16.889 | −49.318 | 1.00 | 22.85 |
| ATOM | 211 | CE2 | PHE | A | 29 | −11.151 | 16.924 | −48.180 | 1.00 | 24.78 |
| ATOM | 212 | CD2 | PHE | A | 29 | −10.611 | 17.408 | −46.973 | 1.00 | 22.71 |
| ATOM | 213 | C | PHE | A | 29 | −6.853 | 16.783 | −45.296 | 1.00 | 19.10 |
| ATOM | 214 | O | PHE | A | 29 | −5.862 | 17.501 | −45.224 | 1.00 | 19.40 |
| ATOM | 215 | N | GLY | A | 30 | −6.830 | 15.558 | −45.816 | 1.00 | 18.73 |
| ATOM | 216 | CA | GLY | A | 30 | −5.603 | 15.008 | −46.398 | 1.00 | 19.00 |
| ATOM | 217 | C | GLY | A | 30 | −4.717 | 14.307 | −45.399 | 1.00 | 19.69 |
| ATOM | 218 | O | GLY | A | 30 | −3.657 | 13.809 | −45.768 | 1.00 | 19.61 |
| ATOM | 219 | N | THR | A | 31 | −5.133 | 14.255 | −44.123 | 1.00 | 18.86 |
| ATOM | 220 | CA | THR | A | 31 | −4.450 | 13.384 | −43.165 | 1.00 | 19.14 |
| ATOM | 221 | CB | THR | A | 31 | −4.846 | 13.689 | −41.689 | 1.00 | 18.79 |
| ATOM | 222 | OG1 | THR | A | 31 | −6.265 | 13.579 | −41.559 | 1.00 | 18.61 |
| ATOM | 223 | CG2 | THR | A | 31 | −4.410 | 15.106 | −41.262 | 1.00 | 16.47 |
| ATOM | 224 | C | THR | A | 31 | −4.812 | 11.925 | −43.498 | 1.00 | 19.11 |
| ATOM | 225 | O | THR | A | 31 | −5.713 | 11.661 | −44.313 | 1.00 | 19.69 |
| ATOM | 226 | N | SER | A | 32 | −4.107 | 10.982 | −42.881 | 1.00 | 19.74 |
| ATOM | 227 | CA | SER | A | 32 | −4.367 | 9.554 | −43.094 | 1.00 | 20.00 |
| ATOM | 228 | CB | SER | A | 32 | −3.411 | 8.722 | −42.248 | 1.00 | 20.73 |
| ATOM | 229 | OG | SER | A | 32 | −2.064 | 8.973 | −42.612 | 1.00 | 21.56 |
| ATOM | 230 | C | SER | A | 32 | −5.806 | 9.217 | −42.704 | 1.00 | 20.57 |
| ATOM | 231 | O | SER | A | 32 | −6.334 | 9.778 | −41.732 | 1.00 | 20.70 |
| ATOM | 232 | N | ALA | A | 33 | −6.443 | 8.319 | −43.452 | 1.00 | 19.94 |
| ATOM | 233 | CA | ALA | A | 33 | −7.768 | 7.823 | −43.068 | 1.00 | 19.61 |
| ATOM | 234 | CB | ALA | A | 33 | −8.232 | 6.729 | −44.035 | 1.00 | 19.31 |
| ATOM | 235 | C | ALA | A | 33 | −7.764 | 7.285 | −41.637 | 1.00 | 19.10 |
| ATOM | 236 | O | ALA | A | 33 | −6.906 | 6.482 | −41.264 | 1.00 | 19.49 |
| ATOM | 237 | N | GLY | A | 34 | −8.742 | 7.719 | −40.856 | 1.00 | 17.74 |
| ATOM | 238 | CA | GLY | A | 34 | −8.878 | 7.282 | −39.473 | 1.00 | 18.31 |
| ATOM | 239 | C | GLY | A | 34 | −7.988 | 8.020 | −38.473 | 1.00 | 18.48 |
| ATOM | 240 | O | GLY | A | 34 | −8.050 | 7.739 | −37.271 | 1.00 | 19.07 |
| ATOM | 241 | N | ALA | A | 35 | −7.173 | 8.959 | −38.937 | 1.00 | 17.05 |
| ATOM | 242 | CA | ALA | A | 35 | −6.329 | 9.723 | −38.000 | 1.00 | 17.17 |
| ATOM | 243 | CB | ALA | A | 35 | −5.167 | 10.376 | −38.730 | 1.00 | 17.10 |
| ATOM | 244 | C | ALA | A | 35 | −7.173 | 10.784 | −37.271 | 1.00 | 16.55 |
| ATOM | 245 | O | ALA | A | 35 | −8.174 | 11.271 | −37.808 | 1.00 | 17.35 |
| ATOM | 246 | N | VAL | A | 36 | −6.793 | 11.130 | −36.051 | 1.00 | 15.39 |
| ATOM | 247 | CA | VAL | A | 36 | −7.490 | 12.198 | −35.328 | 1.00 | 14.41 |
| ATOM | 248 | CB | VAL | A | 36 | −8.142 | 11.687 | −34.031 | 1.00 | 15.02 |
| ATOM | 249 | CG1 | VAL | A | 36 | −8.903 | 12.828 | −33.349 | 1.00 | 16.72 |
| ATOM | 250 | CG2 | VAL | A | 36 | −9.081 | 10.520 | −34.336 | 1.00 | 16.45 |
| ATOM | 251 | C | VAL | A | 36 | −6.407 | 13.201 | −34.944 | 1.00 | 14.36 |
| ATOM | 252 | O | VAL | A | 36 | −5.421 | 12.816 | −34.311 | 1.00 | 14.44 |
| ATOM | 253 | N | ILE | A | 37 | −6.566 | 14.454 | −35.331 | 1.00 | 13.68 |
| ATOM | 254 | CA | ILE | A | 37 | −5.614 | 15.470 | −34.893 | 1.00 | 13.67 |
| ATOM | 255 | CB | ILE | A | 37 | −5.528 | 16.687 | −35.849 | 1.00 | 13.66 |
| ATOM | 256 | CG1 | ILE | A | 37 | −6.847 | 17.486 | −35.901 | 1.00 | 14.31 |
| ATOM | 257 | CD1 | ILE | A | 37 | −6.773 | 18.712 | −36.864 | 1.00 | 14.21 |
| ATOM | 258 | CG2 | ILE | A | 37 | −5.158 | 16.214 | −37.260 | 1.00 | 14.62 |
| ATOM | 259 | C | ILE | A | 37 | −6.041 | 15.908 | −33.505 | 1.00 | 13.27 |
| ATOM | 260 | O | ILE | A | 37 | −7.235 | 16.011 | −33.224 | 1.00 | 12.99 |
| ATOM | 261 | N | ALA | A | 38 | −5.081 | 16.159 | −32.630 | 1.00 | 13.03 |
| ATOM | 262 | CA | ALA | A | 38 | −5.445 | 16.697 | −31.333 | 1.00 | 12.81 |
| ATOM | 263 | CB | ALA | A | 38 | −4.235 | 16.680 | −30.377 | 1.00 | 12.73 |
| ATOM | 264 | C | ALA | A | 38 | −6.046 | 18.122 | −31.497 | 1.00 | 12.45 |
| ATOM | 265 | O | ALA | A | 38 | −6.939 | 18.503 | −30.775 | 1.00 | 12.23 |
| ATOM | 266 | N | SER | A | 39 | −5.555 | 18.870 | −32.482 | 1.00 | 12.90 |
| ATOM | 267 | CA | SER | A | 39 | −5.973 | 20.246 | −32.769 | 1.00 | 12.85 |
| ATOM | 268 | CB | SER | A | 39 | −5.512 | 21.211 | −31.657 | 1.00 | 12.63 |
| ATOM | 269 | OG | SER | A | 39 | −5.312 | 22.563 | −32.108 | 1.00 | 12.57 |
| ATOM | 270 | C | SER | A | 39 | −5.281 | 20.593 | −34.090 | 1.00 | 13.33 |
| ATOM | 271 | O | SER | A | 39 | −4.215 | 20.043 | −34.376 | 1.00 | 13.48 |
| ATOM | 272 | N | PRO | A | 40 | −5.880 | 21.500 | −34.885 | 1.00 | 13.12 |
| ATOM | 273 | CA | PRO | A | 40 | −5.248 | 21.999 | −36.108 | 1.00 | 13.76 |
| ATOM | 274 | CB | PRO | A | 40 | −6.407 | 22.689 | −36.860 | 1.00 | 14.41 |
| ATOM | 275 | CG | PRO | A | 40 | −7.386 | 23.045 | −35.797 | 1.00 | 14.32 |
| ATOM | 276 | CD | PRO | A | 40 | −7.223 | 22.081 | −34.665 | 1.00 | 13.18 |
| ATOM | 277 | C | PRO | A | 40 | −4.126 | 23.010 | −35.860 | 1.00 | 14.27 |
| ATOM | 278 | O | PRO | A | 40 | −3.474 | 23.420 | −36.824 | 1.00 | 14.43 |
| ATOM | 279 | N | SER | A | 41 | −3.864 | 23.381 | −34.599 | 1.00 | 13.42 |
| ATOM | 280 | CA | SER | A | 41 | −2.799 | 24.336 | −34.318 | 1.00 | 14.56 |
| ATOM | 281 | CB | SER | A | 41 | −2.788 | 24.817 | −32.840 | 1.00 | 14.40 |
| ATOM | 282 | OG | SER | A | 41 | −3.962 | 25.574 | −32.534 | 1.00 | 16.91 |

TABLE 6-continued

| | | | | | | | | | |
|---|---|---|---|---|---|---|---|---|---|
| ATOM | 283 | C | SER | A | 41 | −1.446 | 23.713 | −34.676 | 1.00 | 14.51 |
| ATOM | 284 | O | SER | A | 41 | −1.123 | 22.626 | −34.218 | 1.00 | 13.96 |
| ATOM | 285 | N | THR | A | 42 | −0.650 | 24.433 | −35.470 | 1.00 | 15.63 |
| ATOM | 286 | CA | THR | A | 42 | 0.652 | 23.924 | −35.919 | 1.00 | 16.17 |
| ATOM | 287 | CB | THR | A | 42 | 0.750 | 23.997 | −37.458 | 1.00 | 17.02 |
| ATOM | 288 | OG1 | THR | A | 42 | 0.267 | 25.283 | −37.890 | 1.00 | 17.03 |
| ATOM | 289 | CG2 | THR | A | 42 | −0.110 | 22.906 | −38.078 | 1.00 | 16.03 |
| ATOM | 290 | C | THR | A | 42 | 1.814 | 24.732 | −35.322 | 1.00 | 17.44 |
| ATOM | 291 | O | THR | A | 42 | 2.967 | 24.297 | −35.382 | 1.00 | 17.10 |
| ATOM | 292 | N | ILE | A | 43 | 1.509 | 25.913 | −34.787 | 1.00 | 18.37 |
| ATOM | 293 | CA | ILE | A | 43 | 2.510 | 26.786 | −34.171 | 1.00 | 20.62 |
| ATOM | 294 | CB | ILE | A | 43 | 2.923 | 27.952 | −35.114 | 1.00 | 20.73 |
| ATOM | 295 | CG1 | ILE | A | 43 | 3.550 | 27.428 | −36.411 | 1.00 | 21.88 |
| ATOM | 296 | CD1 | ILE | A | 43 | 3.788 | 28.507 | −37.508 | 1.00 | 22.99 |
| ATOM | 297 | CG2 | ILE | A | 43 | 3.895 | 28.910 | −34.409 | 1.00 | 21.41 |
| ATOM | 298 | C | ILE | A | 43 | 1.908 | 27.395 | −32.935 | 1.00 | 21.00 |
| ATOM | 299 | O | ILE | A | 43 | 0.796 | 27.921 | −32.995 | 1.00 | 21.76 |
| ATOM | 300 | N | ASP | A | 44 | 2.683 | 27.470 | −31.874 | 1.00 | 21.61 |
| ATOM | 301 | CA | ASP | A | 44 | 2.237 | 27.975 | −30.572 | 1.00 | 23.04 |
| ATOM | 302 | CB | ASP | A | 44 | 2.408 | 29.506 | −30.492 | 1.00 | 24.75 |
| ATOM | 303 | CG | ASP | A | 44 | 2.170 | 30.064 | −29.098 | 1.00 | 31.28 |
| ATOM | 304 | OD1 | ASP | A | 44 | 2.362 | 29.340 | −28.094 | 1.00 | 37.92 |
| ATOM | 305 | OD2 | ASP | A | 44 | 1.766 | 31.260 | −28.997 | 1.00 | 40.00 |
| ATOM | 306 | C | ASP | A | 44 | 0.782 | 27.608 | −30.196 | 1.00 | 21.65 |
| ATOM | 307 | O | ASP | A | 44 | −0.046 | 28.502 | −29.981 | 1.00 | 22.69 |
| ATOM | 308 | N | PRO | A | 45 | 0.441 | 26.449 | −29.805 | 1.00 | 19.86 |
| ATOM | 309 | CA | PRO | A | 45 | 1.356 | 25.320 | −29.775 | 1.00 | 18.66 |
| ATOM | 310 | CB | PRO | A | 45 | 0.883 | 24.549 | −28.549 | 1.00 | 18.40 |
| ATOM | 311 | CG | PRO | A | 45 | −0.653 | 24.763 | −28.586 | 1.00 | 18.13 |
| ATOM | 312 | CD | PRO | A | 45 | −0.899 | 26.066 | −29.318 | 1.00 | 20.04 |
| ATOM | 313 | C | PRO | A | 45 | 1.253 | 24.454 | −31.026 | 1.00 | 17.74 |
| ATOM | 314 | O | PRO | A | 45 | 0.368 | 24.652 | −31.858 | 1.00 | 17.36 |
| ATOM | 315 | N | ASP | A | 46 | 2.178 | 23.512 | −31.160 | 1.00 | 15.95 |
| ATOM | 316 | CA | ASP | A | 46 | 2.124 | 22.573 | −32.275 | 1.00 | 14.75 |
| ATOM | 317 | CB | ASP | A | 46 | 3.551 | 22.255 | −32.738 | 1.00 | 14.59 |
| ATOM | 318 | CG | ASP | A | 46 | 3.601 | 21.161 | −33.818 | 1.00 | 16.17 |
| ATOM | 319 | OD1 | ASP | A | 46 | 2.543 | 20.787 | −34.389 | 1.00 | 15.61 |
| ATOM | 320 | OD2 | ASP | A | 46 | 4.712 | 20.641 | −34.054 | 1.00 | 20.18 |
| ATOM | 321 | C | ASP | A | 46 | 1.436 | 21.303 | −31.748 | 1.00 | 13.83 |
| ATOM | 322 | O | ASP | A | 46 | 2.081 | 20.489 | −31.089 | 1.00 | 13.59 |
| ATOM | 323 | N | TYR | A | 47 | 0.126 | 21.165 | −31.992 | 1.00 | 11.86 |
| ATOM | 324 | CA | TYR | A | 47 | −0.621 | 19.975 | −31.580 | 1.00 | 12.11 |
| ATOM | 325 | CB | TYR | A | 47 | −1.895 | 20.387 | −30.854 | 1.00 | 11.69 |
| ATOM | 326 | CG | TYR | A | 47 | −1.773 | 20.722 | −29.377 | 1.00 | 12.59 |
| ATOM | 327 | CD1 | TYR | A | 47 | −0.589 | 21.236 | −28.827 | 1.00 | 13.54 |
| ATOM | 328 | CE1 | TYR | A | 47 | −0.524 | 21.586 | −27.462 | 1.00 | 12.81 |
| ATOM | 329 | CZ | TYR | A | 47 | −1.652 | 21.407 | −26.673 | 1.00 | 13.40 |
| ATOM | 330 | OH | TYR | A | 47 | −1.620 | 21.755 | −25.354 | 1.00 | 13.08 |
| ATOM | 331 | CE2 | TYR | A | 47 | −2.825 | 20.887 | −27.208 | 1.00 | 12.02 |
| ATOM | 332 | CD2 | TYR | A | 47 | −2.876 | 20.540 | −28.532 | 1.00 | 12.76 |
| ATOM | 333 | C | TYR | A | 47 | −0.994 | 19.090 | −32.772 | 1.00 | 11.46 |
| ATOM | 334 | O | TYR | A | 47 | −1.885 | 18.239 | −32.692 | 1.00 | 11.66 |
| ATOM | 335 | N | TYR | A | 48 | −0.316 | 19.301 | −33.893 | 1.00 | 12.26 |
| ATOM | 336 | CA | TYR | A | 48 | −0.697 | 18.639 | −35.132 | 1.00 | 12.80 |
| ATOM | 337 | CB | TYR | A | 48 | −0.323 | 19.509 | −36.348 | 1.00 | 12.75 |
| ATOM | 338 | CG | TYR | A | 48 | −1.134 | 19.146 | −37.569 | 1.00 | 13.21 |
| ATOM | 339 | CD1 | TYR | A | 48 | −2.492 | 19.482 | −37.652 | 1.00 | 14.46 |
| ATOM | 340 | CE1 | TYR | A | 48 | −3.254 | 19.124 | −38.767 | 1.00 | 15.86 |
| ATOM | 341 | CZ | TYR | A | 48 | −2.643 | 18.453 | −39.823 | 1.00 | 14.62 |
| ATOM | 342 | OH | TYR | A | 48 | −3.390 | 18.106 | −40.936 | 1.00 | 16.20 |
| ATOM | 343 | CE2 | TYR | A | 48 | −1.295 | 18.086 | −39.756 | 1.00 | 15.86 |
| ATOM | 344 | CD2 | TYR | A | 48 | −0.543 | 18.456 | −38.638 | 1.00 | 13.44 |
| ATOM | 345 | C | TYR | A | 48 | −0.072 | 17.245 | −35.187 | 1.00 | 13.47 |
| ATOM | 346 | O | TYR | A | 48 | 0.877 | 16.986 | −35.940 | 1.00 | 13.95 |
| ATOM | 347 | N | TYR | A | 49 | −0.592 | 16.360 | −34.338 | 1.00 | 13.13 |
| ATOM | 348 | CA | TYR | A | 49 | −0.131 | 14.987 | −34.171 | 1.00 | 13.51 |
| ATOM | 349 | CB | TYR | A | 49 | 0.887 | 14.842 | −33.009 | 1.00 | 13.11 |
| ATOM | 350 | CG | TYR | A | 49 | 2.133 | 15.662 | −33.216 | 1.00 | 13.90 |
| ATOM | 351 | CD1 | TYR | A | 49 | 3.193 | 15.174 | −33.996 | 1.00 | 13.54 |
| ATOM | 352 | CE1 | TYR | A | 49 | 4.354 | 15.964 | −34.216 | 1.00 | 13.41 |
| ATOM | 353 | CZ | TYR | A | 49 | 4.419 | 17.225 | −33.665 | 1.00 | 14.69 |
| ATOM | 354 | OH | TYR | A | 49 | 5.511 | 18.016 | −33.883 | 1.00 | 17.21 |
| ATOM | 355 | CE2 | TYR | A | 49 | 3.365 | 17.737 | −32.906 | 1.00 | 13.49 |
| ATOM | 356 | CD2 | TYR | A | 49 | 2.227 | 16.952 | −32.698 | 1.00 | 13.78 |
| ATOM | 357 | C | TYR | A | 49 | −1.349 | 14.181 | −33.783 | 1.00 | 13.93 |
| ATOM | 358 | O | TYR | A | 49 | −2.390 | 14.759 | −33.406 | 1.00 | 13.00 |
| ATOM | 359 | N | MET | A | 50 | −1.203 | 12.857 | −33.839 | 1.00 | 13.66 |
| ATOM | 360 | CA | MET | A | 50 | −2.241 | 11.940 | −33.365 | 1.00 | 14.56 |
| ATOM | 361 | CB | MET | A | 50 | −2.447 | 10.822 | −34.381 | 1.00 | 15.21 |
| ATOM | 362 | CG | MET | A | 50 | −3.532 | 9.811 | −33.947 | 1.00 | 15.64 |

TABLE 6-continued

| ATOM | 363 | SD | MET | A | 50 | −3.996 | 8.804 | −35.361 | 1.00 | 19.52 |
| ATOM | 364 | CE | MET | A | 50 | −5.204 | 7.742 | −34.566 | 1.00 | 17.12 |
| ATOM | 365 | C | MET | A | 50 | −1.797 | 11.323 | −32.060 | 1.00 | 14.38 |
| ATOM | 366 | O | MET | A | 50 | −0.806 | 10.583 | −32.024 | 1.00 | 13.80 |
| ATOM | 367 | N | TRP | A | 51 | −2.528 | 11.608 | −30.984 | 1.00 | 13.47 |
| ATOM | 368 | CA | TRP | A | 51 | −2.265 | 10.965 | −29.720 | 1.00 | 13.13 |
| ATOM | 369 | CB | TRP | A | 51 | −2.598 | 11.930 | −28.585 | 1.00 | 12.85 |
| ATOM | 370 | CG | TRP | A | 51 | −1.478 | 12.809 | −28.116 | 1.00 | 13.64 |
| ATOM | 371 | CD1 | TRP | A | 51 | −0.671 | 12.604 | −27.011 | 1.00 | 13.49 |
| ATOM | 372 | NE1 | TRP | A | 51 | 0.211 | 13.657 | −26.864 | 1.00 | 12.36 |
| ATOM | 373 | CE2 | TRP | A | 51 | −0.023 | 14.573 | −27.858 | 1.00 | 11.83 |
| ATOM | 374 | CD2 | TRP | A | 51 | −1.076 | 14.065 | −28.674 | 1.00 | 13.12 |
| ATOM | 375 | CE3 | TRP | A | 51 | −1.506 | 14.825 | −29.772 | 1.00 | 11.07 |
| ATOM | 376 | CZ3 | TRP | A | 51 | −0.859 | 16.061 | −30.035 | 1.00 | 12.87 |
| ATOM | 377 | CH2 | TRP | A | 51 | 0.193 | 16.522 | −29.218 | 1.00 | 13.24 |
| ATOM | 378 | CZ2 | TRP | A | 51 | 0.618 | 15.806 | −28.127 | 1.00 | 12.61 |
| ATOM | 379 | C | TRP | A | 51 | −3.136 | 9.732 | −29.575 | 1.00 | 13.35 |
| ATOM | 380 | O | TRP | A | 51 | −4.322 | 9.769 | −29.907 | 1.00 | 12.89 |
| ATOM | 381 | N | THR | A | 52 | −2.576 | 8.652 | −29.024 | 1.00 | 13.20 |
| ATOM | 382 | CA | THR | A | 52 | −3.386 | 7.462 | −28.753 | 1.00 | 13.02 |
| ATOM | 383 | CB | THR | A | 52 | −2.520 | 6.300 | −28.235 | 1.00 | 13.66 |
| ATOM | 384 | OG1 | THR | A | 52 | −1.553 | 5.999 | −29.246 | 1.00 | 15.07 |
| ATOM | 385 | CG2 | THR | A | 52 | −3.341 | 5.026 | −27.952 | 1.00 | 12.21 |
| ATOM | 386 | C | THR | A | 52 | −4.533 | 7.807 | −27.800 | 1.00 | 12.48 |
| ATOM | 387 | O | THR | A | 52 | −5.670 | 7.402 | −28.034 | 1.00 | 12.78 |
| ATOM | 388 | N | ARG | A | 53 | −4.224 | 8.556 | −26.747 | 1.00 | 12.03 |
| ATOM | 389 | CA | ARG | A | 53 | −5.238 | 8.868 | −25.737 | 1.00 | 11.89 |
| ATOM | 390 | CB | ARG | A | 53 | −4.607 | 9.570 | −24.545 | 1.00 | 11.46 |
| ATOM | 391 | CG | ARG | A | 53 | −5.611 | 10.330 | −23.618 | 1.00 | 13.19 |
| ATOM | 392 | CD | ARG | A | 53 | −4.896 | 10.881 | −22.375 | 1.00 | 11.14 |
| ATOM | 393 | NE | ARG | A | 53 | −3.793 | 11.694 | −22.819 | 1.00 | 12.52 |
| ATOM | 394 | CZ | ARG | A | 53 | −2.509 | 11.330 | −22.769 | 1.00 | 13.67 |
| ATOM | 395 | NH1 | ARG | A | 53 | −2.148 | 10.182 | −22.180 | 1.00 | 13.97 |
| ATOM | 396 | NH2 | ARG | A | 53 | −1.590 | 12.151 | −23.270 | 1.00 | 13.05 |
| ATOM | 397 | C | ARG | A | 53 | −6.395 | 9.709 | −26.319 | 1.00 | 12.45 |
| ATOM | 398 | O | ARG | A | 53 | −7.558 | 9.289 | −26.244 | 1.00 | 11.74 |
| ATOM | 399 | N | ASP | A | 54 | −6.090 | 10.885 | −26.874 | 1.00 | 11.73 |
| ATOM | 400 | CA | ASP | A | 54 | −7.169 | 11.747 | −27.385 | 1.00 | 11.90 |
| ATOM | 401 | CB | ASP | A | 54 | −6.638 | 13.018 | −28.053 | 1.00 | 12.25 |
| ATOM | 402 | CG | ASP | A | 54 | −5.794 | 13.879 | −27.120 | 1.00 | 13.97 |
| ATOM | 403 | OD1 | ASP | A | 54 | −4.983 | 13.332 | −26.354 | 1.00 | 13.57 |
| ATOM | 404 | OD2 | ASP | A | 54 | −5.910 | 15.110 | −27.215 | 1.00 | 13.88 |
| ATOM | 405 | C | ASP | A | 54 | −8.002 | 11.005 | −28.420 | 1.00 | 12.00 |
| ATOM | 406 | O | ASP | A | 54 | −9.236 | 11.138 | −28.454 | 1.00 | 10.97 |
| ATOM | 407 | N | SER | A | 55 | −7.334 | 10.250 | −29.297 | 1.00 | 11.19 |
| ATOM | 408 | CA | SER | A | 55 | −8.034 | 9.544 | −30.388 | 1.00 | 12.36 |
| ATOM | 409 | CB | SER | A | 55 | −7.017 | 8.901 | −31.340 | 1.00 | 13.05 |
| ATOM | 410 | OG | SER | A | 55 | −6.171 | 9.930 | −31.882 | 1.00 | 14.23 |
| ATOM | 411 | C | SER | A | 55 | −8.996 | 8.489 | −29.838 | 1.00 | 12.57 |
| ATOM | 412 | O | SER | A | 55 | −10.130 | 8.348 | −30.327 | 1.00 | 12.76 |
| ATOM | 413 | N | ALA | A | 56 | −8.556 | 7.764 | −28.819 | 1.00 | 12.60 |
| ATOM | 414 | CA | ALA | A | 56 | −9.373 | 6.718 | −28.218 | 1.00 | 13.25 |
| ATOM | 415 | CB | ALA | A | 56 | −8.517 | 5.830 | −27.329 | 1.00 | 12.73 |
| ATOM | 416 | C | ALA | A | 56 | −10.551 | 7.301 | −27.415 | 1.00 | 13.85 |
| ATOM | 417 | O | ALA | A | 56 | −11.640 | 6.723 | −27.409 | 1.00 | 14.51 |
| ATOM | 418 | N | LEU | A | 57 | −10.328 | 8.420 | −26.723 | 1.00 | 14.23 |
| ATOM | 419 | CA | LEU | A | 57 | −11.417 | 9.059 | −25.954 | 1.00 | 13.95 |
| ATOM | 420 | CB | LEU | A | 57 | −10.891 | 10.186 | −25.060 | 1.00 | 14.45 |
| ATOM | 421 | CG | LEU | A | 57 | −10.088 | 9.751 | −23.834 | 1.00 | 14.89 |
| ATOM | 422 | CD1 | LEU | A | 57 | −9.507 | 11.013 | −23.161 | 1.00 | 16.19 |
| ATOM | 423 | CD2 | LEU | A | 57 | −10.919 | 8.911 | −22.867 | 1.00 | 16.02 |
| ATOM | 424 | C | LEU | A | 57 | −12.483 | 9.609 | −26.886 | 1.00 | 13.92 |
| ATOM | 425 | O | LEU | A | 57 | −13.685 | 9.488 | −26.627 | 1.00 | 13.70 |
| ATOM | 426 | N | VAL | A | 58 | −12.027 | 10.199 | −27.975 | 1.00 | 13.15 |
| ATOM | 427 | CA | VAL | A | 58 | −12.920 | 10.751 | −28.989 | 1.00 | 15.20 |
| ATOM | 428 | CB | VAL | A | 58 | −12.133 | 11.605 | −30.031 | 1.00 | 14.52 |
| ATOM | 429 | CG1 | VAL | A | 58 | −12.970 | 11.861 | −31.302 | 1.00 | 17.86 |
| ATOM | 430 | CG2 | VAL | A | 58 | −11.704 | 12.954 | −29.393 | 1.00 | 15.79 |
| ATOM | 431 | C | VAL | A | 58 | −13.704 | 9.624 | −29.655 | 1.00 | 15.20 |
| ATOM | 432 | O | VAL | A | 58 | −14.930 | 9.718 | −29.784 | 1.00 | 15.30 |
| ATOM | 433 | N | PHE | A | 59 | −13.026 | 8.553 | −30.058 | 1.00 | 15.02 |
| ATOM | 434 | CA | PHE | A | 59 | −13.766 | 7.477 | −30.713 | 1.00 | 15.23 |
| ATOM | 435 | CB | PHE | A | 59 | −12.882 | 6.601 | −31.582 | 1.00 | 15.78 |
| ATOM | 436 | CG | PHE | A | 59 | −12.859 | 7.058 | −33.003 | 1.00 | 15.10 |
| ATOM | 437 | CD1 | PHE | A | 59 | −11.872 | 7.927 | −33.444 | 1.00 | 16.45 |
| ATOM | 438 | CE1 | PHE | A | 59 | −11.861 | 8.401 | −34.768 | 1.00 | 19.37 |
| ATOM | 439 | CZ | PHE | A | 59 | −12.876 | 8.026 | −35.644 | 1.00 | 16.44 |
| ATOM | 440 | CE2 | PHE | A | 59 | −13.901 | 7.165 | −35.186 | 1.00 | 16.90 |
| ATOM | 441 | CD2 | PHE | A | 59 | −13.895 | 6.709 | −33.882 | 1.00 | 16.17 |
| ATOM | 442 | C | PHE | A | 59 | −14.674 | 6.681 | −29.785 | 1.00 | 15.69 |

TABLE 6-continued

| | | | | | | | | | |
|---|---|---|---|---|---|---|---|---|---|
| ATOM | 443 | O | PHE | A | 59 | −15.699 | 6.175 | −30.220 | 1.00 | 15.46 |
| ATOM | 444 | N | LYS | A | 60 | −14.321 | 6.586 | −28.510 | 1.00 | 15.65 |
| ATOM | 445 | CA | LYS | A | 60 | −15.257 | 5.994 | −27.552 | 1.00 | 16.61 |
| ATOM | 446 | CB | LYS | A | 60 | −14.661 | 5.954 | −26.144 | 1.00 | 16.44 |
| ATOM | 447 | CG | LYS | A | 60 | −15.626 | 5.363 | −25.059 | 1.00 | 17.65 |
| ATOM | 448 | CD | LYS | A | 60 | −16.174 | 3.992 | −25.433 | 1.00 | 18.35 |
| ATOM | 449 | CE | LYS | A | 60 | −16.738 | 3.234 | −24.199 | 1.00 | 19.79 |
| ATOM | 450 | NZ | LYS | A | 60 | −17.819 | 3.976 | −23.512 | 1.00 | 18.40 |
| ATOM | 451 | C | LYS | A | 60 | −16.577 | 6.779 | −27.579 | 1.00 | 16.72 |
| ATOM | 452 | O | LYS | A | 60 | −17.663 | 6.182 | −27.681 | 1.00 | 17.08 |
| ATOM | 453 | N | ASN | A | 61 | −16.487 | 8.101 | −27.508 | 1.00 | 16.77 |
| ATOM | 454 | CA | ASN | A | 61 | −17.680 | 8.948 | −27.628 | 1.00 | 18.06 |
| ATOM | 455 | CB | ASN | A | 61 | −17.278 | 10.424 | −27.573 | 1.00 | 19.41 |
| ATOM | 456 | CG | ASN | A | 61 | −18.465 | 11.375 | −27.643 | 1.00 | 22.93 |
| ATOM | 457 | OD1 | ASN | A | 61 | −19.585 | 11.057 | −27.231 | 1.00 | 30.05 |
| ATOM | 458 | ND2 | ASN | A | 61 | −18.206 | 12.568 | −28.130 | 1.00 | 29.54 |
| ATOM | 459 | C | ASN | A | 61 | −18.480 | 8.659 | −28.907 | 1.00 | 17.28 |
| ATOM | 460 | O | ASN | A | 61 | −19.697 | 8.475 | −28.852 | 1.00 | 18.11 |
| ATOM | 461 | N | LEU | A | 62 | −17.799 | 8.647 | −30.056 | 1.00 | 16.54 |
| ATOM | 462 | CA | LEU | A | 62 | −18.460 | 8.379 | −31.334 | 1.00 | 16.19 |
| ATOM | 463 | CB | LEU | A | 62 | −17.479 | 8.572 | −32.499 | 1.00 | 16.85 |
| ATOM | 464 | CG | LEU | A | 62 | −17.047 | 10.027 | −32.697 | 1.00 | 18.47 |
| ATOM | 465 | CD1 | LEU | A | 62 | −16.118 | 10.153 | −33.916 | 1.00 | 20.38 |
| ATOM | 466 | CD2 | LEU | A | 62 | −18.263 | 10.925 | −32.837 | 1.00 | 19.93 |
| ATOM | 467 | C | LEU | A | 62 | −19.089 | 6.991 | −31.371 | 1.00 | 16.01 |
| ATOM | 468 | O | LEU | A | 62 | −20.225 | 6.833 | −31.842 | 1.00 | 15.98 |
| ATOM | 469 | N | ILE | A | 63 | −18.387 | 5.998 | −30.831 | 1.00 | 15.67 |
| ATOM | 470 | CA | ILE | A | 63 | −18.910 | 4.628 | −30.810 | 1.00 | 15.86 |
| ATOM | 471 | CB | ILE | A | 63 | −17.803 | 3.610 | −30.372 | 1.00 | 15.88 |
| ATOM | 472 | CG1 | ILE | A | 63 | −16.756 | 3.466 | −31.478 | 1.00 | 14.98 |
| ATOM | 473 | CD1 | ILE | A | 63 | −15.375 | 2.976 | −30.966 | 1.00 | 15.62 |
| ATOM | 474 | CG2 | ILE | A | 63 | −18.398 | 2.251 | −30.016 | 1.00 | 15.96 |
| ATOM | 475 | C | ILE | A | 63 | −20.156 | 4.538 | −29.920 | 1.00 | 16.39 |
| ATOM | 476 | O | ILE | A | 63 | −21.137 | 3.854 | −30.272 | 1.00 | 16.90 |
| ATOM | 477 | N | ASP | A | 64 | −20.129 | 5.242 | −28.796 | 1.00 | 16.51 |
| ATOM | 478 | CA | ASP | A | 64 | −21.299 | 5.324 | −27.922 | 1.00 | 17.76 |
| ATOM | 479 | CB | ASP | A | 64 | −20.953 | 6.022 | −26.594 | 1.00 | 17.81 |
| ATOM | 480 | CG | ASP | A | 64 | −20.089 | 5.164 | −25.682 | 1.00 | 17.84 |
| ATOM | 481 | OD1 | ASP | A | 64 | −19.883 | 3.944 | −25.963 | 1.00 | 18.57 |
| ATOM | 482 | OD2 | ASP | A | 64 | −19.595 | 5.699 | −24.659 | 1.00 | 20.95 |
| ATOM | 483 | C | ASP | A | 64 | −22.492 | 5.982 | −28.617 | 1.00 | 18.64 |
| ATOM | 484 | O | ASP | A | 64 | −23.617 | 5.493 | −28.507 | 1.00 | 20.85 |
| ATOM | 485 | N | ARG | A | 65 | −22.262 | 7.070 | −29.348 | 1.00 | 19.57 |
| ATOM | 486 | CA | ARG | A | 65 | −23.341 | 7.750 | −30.097 | 1.00 | 20.59 |
| ATOM | 487 | CB | ARG | A | 65 | −22.823 | 9.046 | −30.733 | 1.00 | 20.62 |
| ATOM | 488 | CG | ARG | A | 65 | −22.465 | 10.083 | −29.693 | 1.00 | 25.00 |
| ATOM | 489 | CD | ARG | A | 65 | −22.010 | 11.385 | −30.324 | 1.00 | 28.44 |
| ATOM | 490 | NE | ARG | A | 65 | −23.106 | 12.071 | −30.990 | 1.00 | 31.14 |
| ATOM | 491 | CZ | ARG | A | 65 | −23.968 | 12.878 | −30.373 | 1.00 | 32.75 |
| ATOM | 492 | NH1 | ARG | A | 65 | −23.873 | 13.095 | −29.060 | 1.00 | 32.10 |
| ATOM | 493 | NH2 | ARG | A | 65 | −24.928 | 13.459 | −31.080 | 1.00 | 32.31 |
| ATOM | 494 | C | ARG | A | 65 | −23.907 | 6.841 | −31.184 | 1.00 | 20.83 |
| ATOM | 495 | O | ARG | A | 65 | −25.129 | 6.711 | −31.357 | 1.00 | 20.48 |
| ATOM | 496 | N | PHE | A | 66 | −22.998 | 6.213 | −31.910 | 1.00 | 20.52 |
| ATOM | 497 | CA | PHE | A | 66 | −23.340 | 5.271 | −32.966 | 1.00 | 21.42 |
| ATOM | 498 | CB | PHE | A | 66 | −22.046 | 4.778 | −33.604 | 1.00 | 21.97 |
| ATOM | 499 | CG | PHE | A | 66 | −22.224 | 3.603 | −34.520 | 1.00 | 21.97 |
| ATOM | 500 | CD1 | PHE | A | 66 | −22.601 | 3.791 | −35.844 | 1.00 | 23.23 |
| ATOM | 501 | CE1 | PHE | A | 66 | −22.768 | 2.690 | −36.699 | 1.00 | 22.87 |
| ATOM | 502 | CZ | PHE | A | 66 | −22.552 | 1.409 | −36.221 | 1.00 | 22.60 |
| ATOM | 503 | CE2 | PHE | A | 66 | −22.165 | 1.216 | −34.895 | 1.00 | 23.74 |
| ATOM | 504 | CD2 | PHE | A | 66 | −22.006 | 2.309 | −34.054 | 1.00 | 23.07 |
| ATOM | 505 | C | PHE | A | 66 | −24.152 | 4.084 | −32.415 | 1.00 | 21.98 |
| ATOM | 506 | O | PHE | A | 66 | −25.040 | 3.551 | −33.099 | 1.00 | 21.80 |
| ATOM | 507 | N | THR | A | 67 | −23.831 | 3.654 | −31.195 | 1.00 | 22.48 |
| ATOM | 508 | CA | THR | A | 67 | −24.546 | 2.537 | −30.576 | 1.00 | 23.79 |
| ATOM | 509 | CB | THR | A | 67 | −23.809 | 1.999 | −29.333 | 1.00 | 23.68 |
| ATOM | 510 | OG1 | THR | A | 67 | −22.551 | 1.439 | −29.745 | 1.00 | 23.93 |
| ATOM | 511 | CG2 | THR | A | 67 | −24.613 | 0.881 | −28.653 | 1.00 | 23.90 |
| ATOM | 512 | C | THR | A | 67 | −25.992 | 2.925 | −30.258 | 1.00 | 24.77 |
| ATOM | 513 | O | THR | A | 67 | −26.893 | 2.090 | −30.349 | 1.00 | 25.31 |
| ATOM | 514 | N | GLU | A | 68 | −26.207 | 4.189 | −29.916 | 1.00 | 25.62 |
| ATOM | 515 | CA | GLU | A | 68 | −27.540 | 4.688 | −29.616 | 1.00 | 27.41 |
| ATOM | 516 | CB | GLU | A | 68 | −27.466 | 6.038 | −28.894 | 1.00 | 28.13 |
| ATOM | 517 | CG | GLU | A | 68 | −26.997 | 5.951 | −27.446 | 1.00 | 32.86 |
| ATOM | 518 | CD | GLU | A | 68 | −28.095 | 5.487 | −26.468 | 1.00 | 38.33 |
| ATOM | 519 | OE1 | GLU | A | 68 | −29.241 | 5.982 | −26.542 | 1.00 | 40.42 |
| ATOM | 520 | OE2 | GLU | A | 68 | −27.799 | 4.633 | −25.607 | 1.00 | 42.48 |
| ATOM | 521 | C | GLU | A | 68 | −28.418 | 4.784 | −30.873 | 1.00 | 27.86 |
| ATOM | 522 | O | GLU | A | 68 | −29.602 | 4.429 | −30.845 | 1.00 | 28.00 |

TABLE 6-continued

| | | | | | | | | | |
|---|---|---|---|---|---|---|---|---|---|
| ATOM | 523 | N | THR | A | 69 | −27.833 | 5.260 | −31.968 | 1.00 | 27.32 |
| ATOM | 524 | CA | THR | A | 69 | −28.540 | 5.373 | −33.241 | 1.00 | 27.32 |
| ATOM | 525 | CB | THR | A | 69 | −29.113 | 6.792 | −33.451 | 1.00 | 27.49 |
| ATOM | 526 | OG1 | THR | A | 69 | −29.922 | 7.153 | −32.334 | 1.00 | 30.86 |
| ATOM | 527 | CG2 | THR | A | 69 | −29.945 | 6.843 | −34.719 | 1.00 | 29.06 |
| ATOM | 528 | C | THR | A | 69 | −27.563 | 5.133 | −34.359 | 1.00 | 26.07 |
| ATOM | 529 | O | THR | A | 69 | −26.619 | 5.905 | −34.523 | 1.00 | 25.25 |
| ATOM | 530 | N | TYR | A | 70 | −27.790 | 4.064 | −35.123 | 1.00 | 25.65 |
| ATOM | 531 | CA | TYR | A | 70 | −26.948 | 3.738 | −36.267 | 1.00 | 25.36 |
| ATOM | 532 | CB | TYR | A | 70 | −27.480 | 2.504 | −37.013 | 1.00 | 25.26 |
| ATOM | 533 | CG | TYR | A | 70 | −26.638 | 2.104 | −38.217 | 1.00 | 25.62 |
| ATOM | 534 | CD1 | TYR | A | 70 | −26.949 | 2.567 | −39.498 | 1.00 | 25.62 |
| ATOM | 535 | CE1 | TYR | A | 70 | −26.190 | 2.201 | −40.611 | 1.00 | 26.48 |
| ATOM | 536 | CZ | TYR | A | 70 | −25.099 | 1.360 | −40.437 | 1.00 | 25.36 |
| ATOM | 537 | OH | TYR | A | 70 | −24.354 | 0.995 | −41.520 | 1.00 | 24.80 |
| ATOM | 538 | CE2 | TYR | A | 70 | −24.770 | 0.883 | −39.175 | 1.00 | 25.59 |
| ATOM | 539 | CD2 | TYR | A | 70 | −25.538 | 1.259 | −38.071 | 1.00 | 25.36 |
| ATOM | 540 | C | TYR | A | 70 | −26.816 | 4.909 | −37.230 | 1.00 | 25.38 |
| ATOM | 541 | O | TYR | A | 70 | −27.802 | 5.573 | −37.583 | 1.00 | 24.87 |
| ATOM | 542 | N | ASP | A | 71 | −25.575 | 5.127 | −37.666 | 1.00 | 25.16 |
| ATOM | 543 | CA | ASP | A | 71 | −25.188 | 6.210 | −38.550 | 1.00 | 25.40 |
| ATOM | 544 | CB | ASP | A | 71 | −24.668 | 7.404 | −37.724 | 1.00 | 25.60 |
| ATOM | 545 | CG | ASP | A | 71 | −24.361 | 8.642 | −38.573 | 1.00 | 26.17 |
| ATOM | 546 | OD1 | ASP | A | 71 | −23.801 | 8.526 | −39.681 | 1.00 | 25.82 |
| ATOM | 547 | OD2 | ASP | A | 71 | −24.675 | 9.755 | −38.108 | 1.00 | 27.85 |
| ATOM | 548 | C | ASP | A | 71 | −24.061 | 5.619 | −39.386 | 1.00 | 25.64 |
| ATOM | 549 | O | ASP | A | 71 | −22.956 | 5.377 | −38.875 | 1.00 | 24.82 |
| ATOM | 550 | N | ALA | A | 72 | −24.347 | 5.379 | −40.665 | 1.00 | 24.95 |
| ATOM | 551 | CA | ALA | A | 72 | −23.380 | 4.764 | −41.586 | 1.00 | 24.24 |
| ATOM | 552 | CB | ALA | A | 72 | −24.047 | 4.434 | −42.921 | 1.00 | 24.35 |
| ATOM | 553 | C | ALA | A | 72 | −22.152 | 5.657 | −41.812 | 1.00 | 24.04 |
| ATOM | 554 | O | ALA | A | 72 | −21.054 | 5.159 | −42.086 | 1.00 | 23.21 |
| ATOM | 555 | N | GLY | A | 73 | −22.356 | 6.970 | −41.695 | 1.00 | 23.63 |
| ATOM | 556 | CA | GLY | A | 73 | −21.265 | 7.938 | −41.761 | 1.00 | 24.20 |
| ATOM | 557 | C | GLY | A | 73 | −20.285 | 7.809 | −40.596 | 1.00 | 23.85 |
| ATOM | 558 | O | GLY | A | 73 | −19.067 | 7.927 | −40.806 | 1.00 | 24.81 |
| ATOM | 559 | N | LEU | A | 74 | −20.798 | 7.588 | −39.376 | 1.00 | 22.78 |
| ATOM | 560 | CA | LEU | A | 74 | −19.927 | 7.347 | −38.232 | 1.00 | 22.21 |
| ATOM | 561 | CB | LEU | A | 74 | −20.662 | 7.449 | −36.879 | 1.00 | 22.58 |
| ATOM | 562 | CG | LEU | A | 74 | −21.132 | 8.846 | −36.434 | 1.00 | 24.06 |
| ATOM | 563 | CD1 | LEU | A | 74 | −21.732 | 8.793 | −35.019 | 1.00 | 22.31 |
| ATOM | 564 | CD2 | LEU | A | 74 | −20.002 | 9.869 | −36.503 | 1.00 | 26.04 |
| ATOM | 565 | C | LEU | A | 74 | −19.256 | 5.999 | −38.370 | 1.00 | 21.94 |
| ATOM | 566 | O | LEU | A | 74 | −18.060 | 5.872 | −38.098 | 1.00 | 20.62 |
| ATOM | 567 | N | GLN | A | 75 | −20.019 | 4.988 | −38.814 | 1.00 | 21.47 |
| ATOM | 568 | CA | GLN | A | 75 | −19.451 | 3.654 | −38.989 | 1.00 | 21.07 |
| ATOM | 569 | CB | GLN | A | 75 | −20.469 | 2.709 | −39.619 | 1.00 | 21.44 |
| ATOM | 570 | CG | GLN | A | 75 | −20.002 | 1.280 | −39.594 | 1.00 | 23.11 |
| ATOM | 571 | CD | GLN | A | 75 | −21.101 | 0.312 | −39.945 | 1.00 | 24.74 |
| ATOM | 572 | OE1 | GLN | A | 75 | −21.273 | −0.719 | −39.290 | 1.00 | 26.57 |
| ATOM | 573 | NE2 | GLN | A | 75 | −21.872 | 0.654 | −40.950 | 1.00 | 23.71 |
| ATOM | 574 | C | GLN | A | 75 | −18.219 | 3.704 | −39.889 | 1.00 | 21.05 |
| ATOM | 575 | O | GLN | A | 75 | −17.229 | 3.046 | −39.611 | 1.00 | 21.10 |
| ATOM | 576 | N | ARG | A | 76 | −18.294 | 4.466 | −40.975 | 1.00 | 20.73 |
| ATOM | 577 | CA | ARG | A | 76 | −17.184 | 4.551 | −41.910 | 1.00 | 21.56 |
| ATOM | 578 | CB | ARG | A | 76 | −17.544 | 5.460 | −43.101 | 1.00 | 22.06 |
| ATOM | 579 | CG | ARG | A | 76 | −16.452 | 5.627 | −44.168 | 1.00 | 24.00 |
| ATOM | 580 | CD | ARG | A | 76 | −15.586 | 6.895 | −43.934 | 1.00 | 27.60 |
| ATOM | 581 | NE | ARG | A | 76 | −16.275 | 8.150 | −44.280 | 1.00 | 30.93 |
| ATOM | 582 | CZ | ARG | A | 76 | −15.778 | 9.378 | −44.082 | 1.00 | 32.20 |
| ATOM | 583 | NH1 | ARG | A | 76 | −14.572 | 9.556 | −43.535 | 1.00 | 30.72 |
| ATOM | 584 | NH2 | ARG | A | 76 | −16.491 | 10.443 | −44.437 | 1.00 | 32.29 |
| ATOM | 585 | C | ARG | A | 76 | −15.942 | 5.063 | −41.162 | 1.00 | 20.85 |
| ATOM | 586 | O | ARG | A | 76 | −14.858 | 4.514 | −41.296 | 1.00 | 20.93 |
| ATOM | 587 | N | ARG | A | 77 | −16.116 | 6.119 | −40.378 | 1.00 | 20.17 |
| ATOM | 588 | CA | ARG | A | 77 | −14.990 | 6.723 | −39.631 | 1.00 | 19.61 |
| ATOM | 589 | CB | ARG | A | 77 | −15.419 | 8.058 | −39.009 | 1.00 | 19.11 |
| ATOM | 590 | CG | ARG | A | 77 | −15.719 | 9.106 | −40.075 | 1.00 | 20.18 |
| ATOM | 591 | CD | ARG | A | 77 | −16.379 | 10.299 | −39.459 | 1.00 | 22.42 |
| ATOM | 592 | NE | ARG | A | 77 | −16.489 | 11.411 | −40.396 | 1.00 | 24.06 |
| ATOM | 593 | CZ | ARG | A | 77 | −17.501 | 11.592 | −41.243 | 1.00 | 27.81 |
| ATOM | 594 | NH1 | ARG | A | 77 | −18.508 | 10.714 | −41.303 | 1.00 | 28.01 |
| ATOM | 595 | NH2 | ARG | A | 77 | −17.509 | 12.658 | −42.033 | 1.00 | 27.19 |
| ATOM | 596 | C | ARG | A | 77 | −14.425 | 5.789 | −38.570 | 1.00 | 18.77 |
| ATOM | 597 | O | ARG | A | 77 | −13.197 | 5.685 | −38.411 | 1.00 | 18.64 |
| ATOM | 598 | N | ILE | A | 78 | −15.320 | 5.117 | −37.852 | 1.00 | 17.79 |
| ATOM | 599 | CA | ILE | A | 78 | −14.931 | 4.125 | −36.857 | 1.00 | 18.13 |
| ATOM | 600 | CB | ILE | A | 78 | −16.165 | 3.514 | −36.151 | 1.00 | 17.88 |
| ATOM | 601 | CG1 | ILE | A | 78 | −16.862 | 4.564 | −35.282 | 1.00 | 18.78 |
| ATOM | 602 | CD1 | ILE | A | 78 | −18.274 | 4.154 | −34.879 | 1.00 | 19.16 |

TABLE 6-continued

| | | | | | | | | | |
|---|---|---|---|---|---|---|---|---|---|
| ATOM | 603 | CG2 | ILE | A | 78 | −15.772 | 2.279 | −35.308 | 1.00 | 18.15 |
| ATOM | 604 | C | ILE | A | 78 | −14.105 | 3.012 | −37.491 | 1.00 | 18.09 |
| ATOM | 605 | O | ILE | A | 78 | −13.088 | 2.612 | −36.949 | 1.00 | 17.42 |
| ATOM | 606 | N | GLU | A | 79 | −14.565 | 2.495 | −38.631 | 1.00 | 18.82 |
| ATOM | 607 | CA | GLU | A | 79 | −13.826 | 1.446 | −39.341 | 1.00 | 20.22 |
| ATOM | 608 | CB | GLU | A | 79 | −14.587 | 1.017 | −40.609 | 1.00 | 20.36 |
| ATOM | 609 | CG | GLU | A | 79 | −15.811 | 0.136 | −40.312 | 1.00 | 22.29 |
| ATOM | 610 | CD | GLU | A | 79 | −16.633 | −0.206 | −41.565 | 1.00 | 22.92 |
| ATOM | 611 | OE1 | GLU | A | 79 | −16.345 | 0.328 | −42.670 | 1.00 | 26.99 |
| ATOM | 612 | OE2 | GLU | A | 79 | −17.579 | −1.012 | −41.425 | 1.00 | 25.69 |
| ATOM | 613 | C | GLU | A | 79 | −12.418 | 1.918 | −39.704 | 1.00 | 18.80 |
| ATOM | 614 | O | GLU | A | 79 | −11.450 | 1.191 | −39.507 | 1.00 | 19.44 |
| ATOM | 615 | N | GLN | A | 80 | −12.301 | 3.147 | −40.211 | 1.00 | 18.84 |
| ATOM | 616 | CA | GLN | A | 80 | −10.998 | 3.661 | −40.636 | 1.00 | 17.90 |
| ATOM | 617 | CB | GLN | A | 80 | −11.149 | 4.921 | −41.482 | 1.00 | 18.92 |
| ATOM | 618 | CG | GLN | A | 80 | −11.794 | 4.593 | −42.844 | 1.00 | 21.99 |
| ATOM | 619 | CD | GLN | A | 80 | −12.040 | 5.799 | −43.707 | 1.00 | 27.48 |
| ATOM | 620 | OE1 | GLN | A | 80 | −12.265 | 6.898 | −43.223 | 1.00 | 30.45 |
| ATOM | 621 | NE2 | GLN | A | 80 | −12.037 | 5.586 | −45.013 | 1.00 | 32.63 |
| ATOM | 622 | C | GLN | A | 80 | −10.059 | 3.892 | −39.456 | 1.00 | 17.64 |
| ATOM | 623 | O | GLN | A | 80 | −8.862 | 3.612 | −39.535 | 1.00 | 17.21 |
| ATOM | 624 | N | TYR | A | 81 | −10.607 | 4.408 | −38.365 | 1.00 | 17.29 |
| ATOM | 625 | CA | TYR | A | 81 | −9.839 | 4.552 | −37.122 | 1.00 | 17.64 |
| ATOM | 626 | CB | TYR | A | 81 | −10.750 | 5.139 | −36.023 | 1.00 | 17.24 |
| ATOM | 627 | CG | TYR | A | 81 | −10.188 | 4.973 | −34.621 | 1.00 | 17.79 |
| ATOM | 628 | CD1 | TYR | A | 81 | −9.085 | 5.728 | −34.184 | 1.00 | 16.36 |
| ATOM | 629 | CE1 | TYR | A | 81 | −8.561 | 5.568 | −32.882 | 1.00 | 17.45 |
| ATOM | 630 | CZ | TYR | A | 81 | −9.146 | 4.646 | −32.009 | 1.00 | 16.35 |
| ATOM | 631 | OH | TYR | A | 81 | −8.654 | 4.457 | −30.724 | 1.00 | 17.06 |
| ATOM | 632 | CE2 | TYR | A | 81 | −10.238 | 3.890 | −32.423 | 1.00 | 17.51 |
| ATOM | 633 | CD2 | TYR | A | 81 | −10.754 | 4.055 | −33.729 | 1.00 | 17.00 |
| ATOM | 634 | C | TYR | A | 81 | −9.271 | 3.197 | −36.686 | 1.00 | 18.04 |
| ATOM | 635 | O | TYR | A | 81 | −8.098 | 3.083 | −36.321 | 1.00 | 17.85 |
| ATOM | 636 | N | ILE | A | 82 | −10.096 | 2.159 | −36.746 | 1.00 | 17.99 |
| ATOM | 637 | CA | ILE | A | 82 | −9.661 | 0.839 | −36.295 | 1.00 | 19.35 |
| ATOM | 638 | CB | ILE | A | 82 | −10.844 | −0.166 | −36.187 | 1.00 | 18.93 |
| ATOM | 639 | CG1 | ILE | A | 82 | −11.753 | 0.233 | −35.017 | 1.00 | 19.40 |
| ATOM | 640 | CD1 | ILE | A | 82 | −13.093 | −0.565 | −34.896 | 1.00 | 20.46 |
| ATOM | 641 | CG2 | ILE | A | 82 | −10.301 | −1.587 | −35.984 | 1.00 | 20.61 |
| ATOM | 642 | C | ILE | A | 82 | −8.547 | 0.292 | −37.194 | 1.00 | 19.92 |
| ATOM | 643 | O | ILE | A | 82 | −7.543 | −0.239 | −36.708 | 1.00 | 20.26 |
| ATOM | 644 | N | THR | A | 83 | −8.713 | 0.432 | −38.503 | 1.00 | 20.05 |
| ATOM | 645 | CA | THR | A | 83 | −7.709 | −0.100 | −39.406 | 1.00 | 21.11 |
| ATOM | 646 | CB | THR | A | 83 | −8.241 | −0.297 | −40.845 | 1.00 | 21.63 |
| ATOM | 647 | OG1 | THR | A | 83 | −8.830 | 0.902 | −41.306 | 1.00 | 25.88 |
| ATOM | 648 | CG2 | THR | A | 83 | −9.330 | −1.347 | −40.851 | 1.00 | 21.56 |
| ATOM | 649 | C | THR | A | 83 | −6.410 | 0.690 | −39.337 | 1.00 | 20.59 |
| ATOM | 650 | O | THR | A | 83 | −5.338 | 0.105 | −39.511 | 1.00 | 20.72 |
| ATOM | 651 | N | ALA | A | 84 | −6.494 | 1.997 | −39.050 | 1.00 | 19.51 |
| ATOM | 652 | CA | ALA | A | 84 | −5.292 | 2.809 | −38.777 | 1.00 | 19.37 |
| ATOM | 653 | CB | ALA | A | 84 | −5.652 | 4.290 | −38.507 | 1.00 | 19.42 |
| ATOM | 654 | C | ALA | A | 84 | −4.436 | 2.231 | −37.643 | 1.00 | 19.32 |
| ATOM | 655 | O | ALA | A | 84 | −3.208 | 2.370 | −37.649 | 1.00 | 19.47 |
| ATOM | 656 | N | GLN | A | 85 | −5.063 | 1.535 | −36.695 | 1.00 | 19.34 |
| ATOM | 657 | CA | GLN | A | 85 | −4.325 | 0.998 | −35.544 | 1.00 | 18.78 |
| ATOM | 658 | CB | GLN | A | 85 | −5.266 | 0.609 | −34.396 | 1.00 | 19.29 |
| ATOM | 659 | CG | GLN | A | 85 | −6.260 | 1.735 | −34.007 | 1.00 | 17.98 |
| ATOM | 660 | CD | GLN | A | 85 | −5.593 | 3.098 | −33.830 | 1.00 | 17.20 |
| ATOM | 661 | OE1 | GLN | A | 85 | −6.021 | 4.095 | −34.418 | 1.00 | 20.82 |
| ATOM | 662 | NE2 | GLN | A | 85 | −4.540 | 3.143 | −33.034 | 1.00 | 13.47 |
| ATOM | 663 | C | GLN | A | 85 | −3.447 | −0.178 | −35.932 | 1.00 | 19.08 |
| ATOM | 664 | O | GLN | A | 85 | −2.478 | −0.473 | −35.251 | 1.00 | 17.94 |
| ATOM | 665 | N | VAL | A | 86 | −3.808 | −0.838 | −37.032 | 1.00 | 19.32 |
| ATOM | 666 | CA | VAL | A | 86 | −2.999 | −1.928 | −37.588 | 1.00 | 20.79 |
| ATOM | 667 | CB | VAL | A | 86 | −3.670 | −2.581 | −38.823 | 1.00 | 21.18 |
| ATOM | 668 | CG1 | VAL | A | 86 | −2.712 | −3.615 | −39.454 | 1.00 | 22.66 |
| ATOM | 669 | CG2 | VAL | A | 86 | −4.980 | −3.250 | −38.400 | 1.00 | 21.47 |
| ATOM | 670 | C | VAL | A | 86 | −1.617 | −1.381 | −37.940 | 1.00 | 20.63 |
| ATOM | 671 | O | VAL | A | 86 | −0.602 | −1.930 | −37.520 | 1.00 | 21.41 |
| ATOM | 672 | N | THR | A | 87 | −1.604 | −0.251 | −38.641 | 1.00 | 20.67 |
| ATOM | 673 | CA | THR | A | 87 | −0.361 | 0.419 | −39.015 | 1.00 | 21.10 |
| ATOM | 674 | CB | THR | A | 87 | −0.659 | 1.583 | −39.986 | 1.00 | 21.59 |
| ATOM | 675 | OG1 | THR | A | 87 | −1.176 | 1.033 | −41.202 | 1.00 | 23.63 |
| ATOM | 676 | CG2 | THR | A | 87 | 0.585 | 2.370 | −40.305 | 1.00 | 22.02 |
| ATOM | 677 | C | THR | A | 87 | 0.412 | 0.881 | −37.795 | 1.00 | 20.28 |
| ATOM | 678 | O | THR | A | 87 | 1.620 | 0.641 | −37.679 | 1.00 | 20.22 |
| ATOM | 679 | N | LEU | A | 88 | −0.280 | 1.543 | −36.874 | 1.00 | 19.11 |
| ATOM | 680 | CA | LEU | A | 88 | 0.367 | 2.097 | −35.697 | 1.00 | 18.71 |
| ATOM | 681 | CB | LEU | A | 88 | −0.585 | 3.015 | −34.903 | 1.00 | 18.08 |
| ATOM | 682 | CG | LEU | A | 88 | −1.016 | 4.294 | −35.596 | 1.00 | 18.50 |

TABLE 6-continued

| | | | | | | | | | |
|---|---|---|---|---|---|---|---|---|---|
| ATOM | 683 | CD1 | LEU | A | 88 | −2.038 | 5.058 | −34.706 | 1.00 | 19.12 |
| ATOM | 684 | CD2 | LEU | A | 88 | 0.206 | 5.193 | −35.937 | 1.00 | 19.81 |
| ATOM | 685 | C | LEU | A | 88 | 0.976 | 1.057 | −34.780 | 1.00 | 18.33 |
| ATOM | 686 | O | LEU | A | 88 | 2.101 | 1.244 | −34.336 | 1.00 | 18.76 |
| ATOM | 687 | N | GLN | A | 89 | 0.255 | −0.029 | −34.492 | 1.00 | 18.75 |
| ATOM | 688 | CA | GLN | A | 89 | 0.809 | −1.085 | −33.623 | 1.00 | 19.67 |
| ATOM | 689 | CB | GLN | A | 89 | −0.199 | −2.201 | −33.373 | 1.00 | 19.69 |
| ATOM | 690 | CG | GLN | A | 89 | −1.397 | −1.775 | −32.564 | 1.00 | 19.25 |
| ATOM | 691 | CD | GLN | A | 89 | −2.140 | −2.951 | −32.004 | 1.00 | 20.83 |
| ATOM | 692 | OE1 | GLN | A | 89 | −2.121 | −4.037 | −32.580 | 1.00 | 19.26 |
| ATOM | 693 | NE2 | GLN | A | 89 | −2.802 | −2.751 | −30.861 | 1.00 | 19.61 |
| ATOM | 694 | C | GLN | A | 89 | 2.097 | −1.683 | −34.203 | 1.00 | 20.68 |
| ATOM | 695 | O | GLN | A | 89 | 3.013 | −2.026 | −33.461 | 1.00 | 21.21 |
| ATOM | 696 | N | GLY | A | 90 | 2.164 | −1.778 | −35.524 | 1.00 | 21.75 |
| ATOM | 697 | CA | GLY | A | 90 | 3.330 | −2.374 | −36.173 | 1.00 | 23.35 |
| ATOM | 698 | C | GLY | A | 90 | 4.604 | −1.552 | −36.096 | 1.00 | 24.79 |
| ATOM | 699 | O | GLY | A | 90 | 5.699 | −2.104 | −36.299 | 1.00 | 25.52 |
| ATOM | 700 | N | ASN | A | 91 | 4.477 | −0.252 | −35.796 | 1.00 | 25.17 |
| ATOM | 701 | CA | ASN | A | 91 | 5.596 | 0.714 | −35.870 | 1.00 | 26.14 |
| ATOM | 702 | CB | ASN | A | 91 | 5.108 | 2.161 | −35.653 | 1.00 | 26.83 |
| ATOM | 703 | CG | ASN | A | 91 | 4.615 | 2.849 | −36.919 | 1.00 | 29.67 |
| ATOM | 704 | OD1 | ASN | A | 91 | 4.869 | 2.414 | −38.051 | 1.00 | 34.53 |
| ATOM | 705 | ND2 | ASN | A | 91 | 3.927 | 3.981 | −36.724 | 1.00 | 32.76 |
| ATOM | 706 | C | ASN | A | 91 | 6.656 | 0.489 | −34.820 | 1.00 | 25.67 |
| ATOM | 707 | O | ASN | A | 91 | 6.346 | 0.385 | −33.644 | 1.00 | 25.70 |
| ATOM | 708 | N | SER | A | 92 | 7.918 | 0.472 | −35.227 | 1.00 | 25.32 |
| ATOM | 709 | CA | SER | A | 92 | 8.990 | 0.668 | −34.257 | 1.00 | 25.27 |
| ATOM | 710 | CB | SER | A | 92 | 10.314 | 0.107 | −34.775 | 1.00 | 26.03 |
| ATOM | 711 | OG | SER | A | 92 | 10.212 | −1.305 | −34.803 | 1.00 | 30.67 |
| ATOM | 712 | C | SER | A | 92 | 9.103 | 2.171 | −34.003 | 1.00 | 23.80 |
| ATOM | 713 | O | SER | A | 92 | 9.055 | 2.979 | −34.942 | 1.00 | 24.56 |
| ATOM | 714 | N | ASN | A | 93 | 9.246 | 2.544 | −32.743 | 1.00 | 22.30 |
| ATOM | 715 | CA | ASN | A | 93 | 9.236 | 3.953 | −32.383 | 1.00 | 21.23 |
| ATOM | 716 | CB | ASN | A | 93 | 7.769 | 4.423 | −32.201 | 1.00 | 21.41 |
| ATOM | 717 | CG | ASN | A | 93 | 7.075 | 3.704 | −31.051 | 1.00 | 19.23 |
| ATOM | 718 | OD1 | ASN | A | 93 | 7.564 | 3.736 | −29.927 | 1.00 | 17.81 |
| ATOM | 719 | ND2 | ASN | A | 93 | 5.974 | 3.024 | −31.335 | 1.00 | 19.43 |
| ATOM | 720 | C | ASN | A | 93 | 10.103 | 4.149 | −31.150 | 1.00 | 20.39 |
| ATOM | 721 | O | ASN | A | 93 | 10.625 | 3.154 | −30.607 | 1.00 | 19.46 |
| ATOM | 722 | N | PRO | A | 94 | 10.337 | 5.410 | −30.732 | 1.00 | 19.95 |
| ATOM | 723 | CA | PRO | A | 94 | 11.228 | 5.604 | −29.574 | 1.00 | 19.89 |
| ATOM | 724 | CB | PRO | A | 94 | 11.235 | 7.131 | −29.385 | 1.00 | 19.51 |
| ATOM | 725 | CG | PRO | A | 94 | 10.988 | 7.653 | −30.753 | 1.00 | 19.96 |
| ATOM | 726 | CD | PRO | A | 94 | 9.952 | 6.717 | −31.325 | 1.00 | 19.99 |
| ATOM | 727 | C | PRO | A | 94 | 10.870 | 4.898 | −28.263 | 1.00 | 20.64 |
| ATOM | 728 | O | PRO | A | 94 | 11.756 | 4.727 | −27.430 | 1.00 | 20.54 |
| ATOM | 729 | N | SER | A | 95 | 9.610 | 4.485 | −28.073 | 1.00 | 20.36 |
| ATOM | 730 | CA | SER | A | 95 | 9.264 | 3.674 | −26.902 | 1.00 | 21.00 |
| ATOM | 731 | CB | SER | A | 95 | 7.770 | 3.736 | −26.587 | 1.00 | 20.05 |
| ATOM | 732 | OG | SER | A | 95 | 7.413 | 5.036 | −26.147 | 1.00 | 19.97 |
| ATOM | 733 | C | SER | A | 95 | 9.679 | 2.204 | −27.066 | 1.00 | 21.73 |
| ATOM | 734 | O | SER | A | 95 | 9.809 | 1.499 | −26.072 | 1.00 | 22.10 |
| ATOM | 735 | N | GLY | A | 96 | 9.853 | 1.748 | −28.306 | 1.00 | 21.90 |
| ATOM | 736 | CA | GLY | A | 96 | 10.229 | 0.350 | −28.562 | 1.00 | 23.56 |
| ATOM | 737 | C | GLY | A | 96 | 9.506 | −0.196 | −29.774 | 1.00 | 24.14 |
| ATOM | 738 | O | GLY | A | 96 | 9.121 | 0.557 | −30.664 | 1.00 | 24.24 |
| ATOM | 739 | N | SER | A | 97 | 9.315 | −1.510 | −29.828 | 1.00 | 25.24 |
| ATOM | 740 | CA | SER | A | 97 | 8.703 | −2.116 | −31.000 | 1.00 | 25.77 |
| ATOM | 741 | CB | SER | A | 97 | 9.751 | −2.874 | −31.834 | 1.00 | 27.15 |
| ATOM | 742 | OG | SER | A | 97 | 10.120 | −4.086 | −31.189 | 1.00 | 30.57 |
| ATOM | 743 | C | SER | A | 97 | 7.590 | −3.042 | −30.571 | 1.00 | 25.27 |
| ATOM | 744 | O | SER | A | 97 | 7.346 | −3.199 | −29.376 | 1.00 | 24.85 |
| ATOM | 745 | N | LEU | A | 98 | 6.930 | −3.655 | −31.543 | 1.00 | 24.82 |
| ATOM | 746 | CA | LEU | A | 98 | 5.826 | −4.559 | −31.252 | 1.00 | 25.88 |
| ATOM | 747 | CB | LEU | A | 98 | 4.982 | −4.813 | −32.504 | 1.00 | 25.31 |
| ATOM | 748 | CG | LEU | A | 98 | 3.714 | −5.673 | −32.420 | 1.00 | 25.89 |
| ATOM | 749 | CD1 | LEU | A | 98 | 2.745 | −5.169 | −31.337 | 1.00 | 25.58 |
| ATOM | 750 | CD2 | LEU | A | 98 | 3.006 | −5.724 | −33.778 | 1.00 | 26.27 |
| ATOM | 751 | C | LEU | A | 98 | 6.310 | −5.866 | −30.604 | 1.00 | 26.75 |
| ATOM | 752 | O | LEU | A | 98 | 5.607 | −6.438 | −29.762 | 1.00 | 27.41 |
| ATOM | 753 | N | ALA | A | 99 | 7.528 | −6.290 | −30.950 | 1.00 | 27.23 |
| ATOM | 754 | CA | ALA | A | 99 | 8.074 | −7.590 | −30.533 | 1.00 | 27.89 |
| ATOM | 755 | CB | ALA | A | 99 | 9.566 | −7.700 | −30.935 | 1.00 | 27.68 |
| ATOM | 756 | C | ALA | A | 99 | 7.893 | −7.911 | −29.053 | 1.00 | 27.86 |
| ATOM | 757 | O | ALA | A | 99 | 7.450 | −9.007 | −28.711 | 1.00 | 28.77 |
| ATOM | 758 | N | ASP | A | 100 | 8.241 | −6.966 | −28.181 | 1.00 | 27.75 |
| ATOM | 759 | CA | ASP | A | 100 | 8.030 | −7.137 | −26.741 | 1.00 | 27.20 |
| ATOM | 760 | CB | ASP | A | 100 | 9.328 | −6.937 | −25.966 | 1.00 | 27.10 |
| ATOM | 761 | CG | ASP | A | 100 | 9.845 | −5.525 | −26.038 | 1.00 | 30.19 |
| ATOM | 762 | OD1 | ASP | A | 100 | 10.891 | −5.281 | −25.419 | 1.00 | 32.28 |

TABLE 6-continued

| | | | | | | | | | |
|---|---|---|---|---|---|---|---|---|---|
| ATOM | 763 | OD2 | ASP | A | 100 | 9.225 | −4.654 | −26.694 | 1.00 | 30.36 |
| ATOM | 764 | C | ASP | A | 100 | 6.905 | −6.256 | −26.173 | 1.00 | 25.74 |
| ATOM | 765 | O | ASP | A | 100 | 6.761 | −6.108 | −24.956 | 1.00 | 26.33 |
| ATOM | 766 | N | GLY | A | 101 | 6.118 | −5.683 | −27.075 | 1.00 | 24.93 |
| ATOM | 767 | CA | GLY | A | 101 | 4.982 | −4.853 | −26.707 | 1.00 | 23.22 |
| ATOM | 768 | C | GLY | A | 101 | 5.326 | −3.418 | −26.342 | 1.00 | 22.68 |
| ATOM | 769 | O | GLY | A | 101 | 4.419 | −2.580 | −26.287 | 1.00 | 21.48 |
| ATOM | 770 | N | SER | A | 102 | 6.609 | −3.117 | −26.126 | 1.00 | 21.53 |
| ATOM | 771 | CA | SER | A | 102 | 6.996 | −1.815 | −25.563 | 1.00 | 21.49 |
| ATOM | 772 | CB | SER | A | 102 | 8.483 | −1.739 | −25.199 | 1.00 | 22.07 |
| ATOM | 773 | OG | SER | A | 102 | 9.283 | −1.958 | −26.345 | 1.00 | 21.77 |
| ATOM | 774 | C | SER | A | 102 | 6.604 | −0.643 | −26.449 | 1.00 | 20.66 |
| ATOM | 775 | O | SER | A | 102 | 6.279 | 0.403 | −25.925 | 1.00 | 20.67 |
| ATOM | 776 | N | GLY | A | 103 | 6.636 | −0.819 | −27.771 | 1.00 | 19.97 |
| ATOM | 777 | CA | GLY | A | 103 | 6.257 | 0.255 | −28.707 | 1.00 | 19.46 |
| ATOM | 778 | C | GLY | A | 103 | 4.824 | 0.777 | −28.539 | 1.00 | 18.94 |
| ATOM | 779 | O | GLY | A | 103 | 4.525 | 1.903 | −28.945 | 1.00 | 18.13 |
| ATOM | 780 | N | LEU | A | 104 | 3.939 | −0.043 | −27.956 | 1.00 | 18.13 |
| ATOM | 781 | CA | LEU | A | 104 | 2.517 | 0.326 | −27.818 | 1.00 | 16.92 |
| ATOM | 782 | CB | LEU | A | 104 | 1.672 | −0.924 | −27.447 | 1.00 | 17.28 |
| ATOM | 783 | CG | LEU | A | 104 | 1.715 | −2.104 | −28.430 | 1.00 | 16.76 |
| ATOM | 784 | CD1 | LEU | A | 104 | 1.072 | −3.356 | −27.836 | 1.00 | 21.62 |
| ATOM | 785 | CD2 | LEU | A | 104 | 1.069 | −1.751 | −29.761 | 1.00 | 19.06 |
| ATOM | 786 | C | LEU | A | 104 | 2.283 | 1.464 | −26.798 | 1.00 | 16.57 |
| ATOM | 787 | O | LEU | A | 104 | 1.202 | 2.092 | −26.807 | 1.00 | 16.79 |
| ATOM | 788 | N | GLY | A | 105 | 3.279 | 1.713 | −25.936 | 1.00 | 14.86 |
| ATOM | 789 | CA | GLY | A | 105 | 3.255 | 2.802 | −24.938 | 1.00 | 15.94 |
| ATOM | 790 | C | GLY | A | 105 | 3.558 | 4.199 | −25.482 | 1.00 | 15.05 |
| ATOM | 791 | O | GLY | A | 105 | 3.481 | 5.179 | −24.755 | 1.00 | 15.93 |
| ATOM | 792 | N | GLU | A | 106 | 3.869 | 4.292 | −26.780 | 1.00 | 14.63 |
| ATOM | 793 | CA | GLU | A | 106 | 4.236 | 5.548 | −27.416 | 1.00 | 14.49 |
| ATOM | 794 | CB | GLU | A | 106 | 4.728 | 5.250 | −28.847 | 1.00 | 13.83 |
| ATOM | 795 | CG | GLU | A | 106 | 5.215 | 6.470 | −29.678 | 1.00 | 16.14 |
| ATOM | 796 | CD | GLU | A | 106 | 6.479 | 7.155 | −29.139 | 1.00 | 18.44 |
| ATOM | 797 | OE1 | GLU | A | 106 | 6.978 | 6.817 | −28.044 | 1.00 | 21.44 |
| ATOM | 798 | OE2 | GLU | A | 106 | 6.972 | 8.083 | −29.817 | 1.00 | 21.04 |
| ATOM | 799 | C | GLU | A | 106 | 3.012 | 6.484 | −27.413 | 1.00 | 14.32 |
| ATOM | 800 | O | GLU | A | 106 | 1.928 | 6.074 | −27.828 | 1.00 | 15.51 |
| ATOM | 801 | N | PRO | A | 107 | 3.164 | 7.706 | −26.890 | 1.00 | 15.21 |
| ATOM | 802 | CA | PRO | A | 107 | 2.025 | 8.645 | −26.772 | 1.00 | 14.90 |
| ATOM | 803 | CB | PRO | A | 107 | 2.598 | 9.809 | −25.951 | 1.00 | 15.27 |
| ATOM | 804 | CG | PRO | A | 107 | 3.833 | 9.290 | −25.310 | 1.00 | 17.25 |
| ATOM | 805 | CD | PRO | A | 107 | 4.385 | 8.238 | −26.243 | 1.00 | 14.35 |
| ATOM | 806 | C | PRO | A | 107 | 1.468 | 9.219 | −28.066 | 1.00 | 14.48 |
| ATOM | 807 | O | PRO | A | 107 | 0.263 | 9.371 | −28.172 | 1.00 | 13.94 |
| ATOM | 808 | N | LYS | A | 108 | 2.320 | 9.567 | −29.027 | 1.00 | 14.24 |
| ATOM | 809 | CA | LYS | A | 108 | 1.837 | 10.309 | −30.204 | 1.00 | 14.51 |
| ATOM | 810 | CB | LYS | A | 108 | 1.853 | 11.828 | −29.960 | 1.00 | 14.26 |
| ATOM | 811 | CG | LYS | A | 108 | 3.225 | 12.524 | −30.029 | 1.00 | 13.88 |
| ATOM | 812 | CD | LYS | A | 108 | 3.102 | 14.033 | −29.775 | 1.00 | 15.15 |
| ATOM | 813 | CE | LYS | A | 108 | 4.299 | 14.820 | −30.283 | 1.00 | 17.08 |
| ATOM | 814 | NZ | LYS | A | 108 | 4.341 | 16.279 | −29.836 | 1.00 | 15.57 |
| ATOM | 815 | C | LYS | A | 108 | 2.608 | 9.953 | −31.454 | 1.00 | 14.69 |
| ATOM | 816 | O | LYS | A | 108 | 3.734 | 9.442 | −31.377 | 1.00 | 14.67 |
| ATOM | 817 | N | PHE | A | 109 | 1.976 | 10.203 | −32.594 | 1.00 | 14.54 |
| ATOM | 818 | CA | PHE | A | 109 | 2.530 | 9.860 | −33.902 | 1.00 | 15.20 |
| ATOM | 819 | CB | PHE | A | 109 | 1.839 | 8.594 | −34.451 | 1.00 | 15.67 |
| ATOM | 820 | CG | PHE | A | 109 | 1.973 | 7.407 | −33.553 | 1.00 | 16.81 |
| ATOM | 821 | CD1 | PHE | A | 109 | 1.081 | 7.219 | −32.490 | 1.00 | 17.93 |
| ATOM | 822 | CE1 | PHE | A | 109 | 1.205 | 6.117 | −31.649 | 1.00 | 21.93 |
| ATOM | 823 | CZ | PHE | A | 109 | 2.241 | 5.210 | −31.834 | 1.00 | 19.06 |
| ATOM | 824 | CE2 | PHE | A | 109 | 3.141 | 5.384 | −32.883 | 1.00 | 20.27 |
| ATOM | 825 | CD2 | PHE | A | 109 | 3.003 | 6.492 | −33.737 | 1.00 | 19.44 |
| ATOM | 826 | C | PHE | A | 109 | 2.301 | 10.992 | −34.881 | 1.00 | 15.19 |
| ATOM | 827 | O | PHE | A | 109 | 1.450 | 11.861 | −34.655 | 1.00 | 14.41 |
| ATOM | 828 | N | GLU | A | 110 | 3.039 | 10.971 | −35.993 | 1.00 | 15.14 |
| ATOM | 829 | CA | GLU | A | 110 | 2.756 | 11.905 | −37.077 | 1.00 | 15.24 |
| ATOM | 830 | CB | GLU | A | 110 | 3.905 | 11.933 | −38.103 | 1.00 | 15.00 |
| ATOM | 831 | CG | GLU | A | 110 | 5.302 | 12.204 | −37.493 | 1.00 | 16.29 |
| ATOM | 832 | CD | GLU | A | 110 | 5.554 | 13.673 | −37.174 | 1.00 | 17.52 |
| ATOM | 833 | OE1 | GLU | A | 110 | 4.708 | 14.544 | −37.504 | 1.00 | 17.65 |
| ATOM | 834 | OE2 | GLU | A | 110 | 6.619 | 13.963 | −36.587 | 1.00 | 18.74 |
| ATOM | 835 | C | GLU | A | 110 | 1.462 | 11.476 | −37.762 | 1.00 | 15.32 |
| ATOM | 836 | O | GLU | A | 110 | 1.093 | 10.278 | −37.753 | 1.00 | 15.26 |
| ATOM | 837 | N | LEU | A | 111 | 0.776 | 12.445 | −38.360 | 1.00 | 15.59 |
| ATOM | 838 | CA | LEU | A | 111 | −0.522 | 12.186 | −39.009 | 1.00 | 16.33 |
| ATOM | 839 | CB | LEU | A | 111 | −1.265 | 13.510 | −39.163 | 1.00 | 16.57 |
| ATOM | 840 | CG | LEU | A | 111 | −1.770 | 13.908 | −37.756 | 1.00 | 18.11 |
| ATOM | 841 | CD1 | LEU | A | 111 | −1.819 | 15.405 | −37.574 | 1.00 | 21.43 |
| ATOM | 842 | CD2 | LEU | A | 111 | −3.151 | 13.204 | −37.506 | 1.00 | 18.74 |

TABLE 6-continued

| | | | | | | | | | |
|---|---|---|---|---|---|---|---|---|---|
| ATOM | 843 | C | LEU | A | 111 | −0.409 | 11.436 | −40.350 | 1.00 | 17.37 |
| ATOM | 844 | O | LEU | A | 111 | −1.426 | 11.023 | −40.944 | 1.00 | 17.23 |
| ATOM | 845 | N | THR | A | 112 | 0.833 | 11.258 | −40.815 | 1.00 | 17.42 |
| ATOM | 846 | CA | THR | A | 112 | 1.144 | 10.301 | −41.887 | 1.00 | 17.92 |
| ATOM | 847 | CB | THR | A | 112 | 2.512 | 10.619 | −42.499 | 1.00 | 17.98 |
| ATOM | 848 | OG1 | THR | A | 112 | 3.476 | 10.702 | −41.445 | 1.00 | 18.32 |
| ATOM | 849 | CG2 | THR | A | 112 | 2.486 | 11.945 | −43.228 | 1.00 | 19.47 |
| ATOM | 850 | C | THR | A | 112 | 1.215 | 8.846 | −41.356 | 1.00 | 18.90 |
| ATOM | 851 | O | THR | A | 112 | 1.535 | 7.917 | −42.117 | 1.00 | 17.68 |
| ATOM | 852 | N | LEU | A | 113 | 0.944 | 8.664 | −40.055 | 1.00 | 18.48 |
| ATOM | 853 | CA | LEU | A | 113 | 1.041 | 7.379 | −39.348 | 1.00 | 19.78 |
| ATOM | 854 | CB | LEU | A | 113 | 0.061 | 6.319 | −39.904 | 1.00 | 19.45 |
| ATOM | 855 | CG | LEU | A | 113 | −1.411 | 6.699 | −40.074 | 1.00 | 21.71 |
| ATOM | 856 | CD1 | LEU | A | 113 | −2.194 | 5.470 | −40.477 | 1.00 | 23.46 |
| ATOM | 857 | CD2 | LEU | A | 113 | −2.005 | 7.323 | −38.800 | 1.00 | 21.59 |
| ATOM | 858 | C | LEU | A | 113 | 2.481 | 6.866 | −39.338 | 1.00 | 20.43 |
| ATOM | 859 | O | LEU | A | 113 | 2.737 | 5.704 | −39.653 | 1.00 | 20.96 |
| ATOM | 860 | N | LYS | A | 114 | 3.406 | 7.769 | −39.024 | 1.00 | 20.07 |
| ATOM | 861 | CA | LYS | A | 114 | 4.826 | 7.460 | −38.863 | 1.00 | 20.25 |
| ATOM | 862 | CB | LYS | A | 114 | 5.662 | 8.209 | −39.899 | 1.00 | 20.95 |
| ATOM | 863 | CG | LYS | A | 114 | 5.432 | 7.725 | −41.314 | 1.00 | 25.23 |
| ATOM | 864 | CD | LYS | A | 114 | 6.636 | 8.059 | −42.184 | 1.00 | 33.76 |
| ATOM | 865 | CE | LYS | A | 114 | 6.551 | 7.360 | −43.537 | 1.00 | 38.31 |
| ATOM | 866 | NZ | LYS | A | 114 | 5.285 | 7.711 | −44.251 | 1.00 | 41.29 |
| ATOM | 867 | C | LYS | A | 114 | 5.252 | 7.874 | −37.471 | 1.00 | 19.64 |
| ATOM | 868 | O | LYS | A | 114 | 4.576 | 8.708 | −36.845 | 1.00 | 19.39 |
| ATOM | 869 | N | PRO | A | 115 | 6.376 | 7.318 | −36.973 | 1.00 | 19.06 |
| ATOM | 870 | CA | PRO | A | 115 | 6.750 | 7.626 | −35.601 | 1.00 | 18.72 |
| ATOM | 871 | CB | PRO | A | 115 | 7.963 | 6.712 | −35.326 | 1.00 | 19.82 |
| ATOM | 872 | CG | PRO | A | 115 | 8.101 | 5.814 | −36.500 | 1.00 | 20.93 |
| ATOM | 873 | CD | PRO | A | 115 | 7.339 | 6.412 | −37.639 | 1.00 | 19.08 |
| ATOM | 874 | C | PRO | A | 115 | 7.156 | 9.093 | −35.434 | 1.00 | 18.70 |
| ATOM | 875 | O | PRO | A | 115 | 7.694 | 9.724 | −36.375 | 1.00 | 17.25 |
| ATOM | 876 | N | PHE | A | 116 | 6.844 | 9.628 | −34.256 | 1.00 | 18.55 |
| ATOM | 877 | CA | PHE | A | 116 | 7.342 | 10.918 | −33.805 | 1.00 | 18.27 |
| ATOM | 878 | CB | PHE | A | 116 | 6.359 | 11.566 | −32.809 | 1.00 | 18.41 |
| ATOM | 879 | CG | PHE | A | 116 | 6.908 | 12.804 | −32.151 | 1.00 | 17.33 |
| ATOM | 880 | CD1 | PHE | A | 116 | 6.942 | 14.014 | −32.847 | 1.00 | 16.98 |
| ATOM | 881 | CE1 | PHE | A | 116 | 7.457 | 15.173 | −32.254 | 1.00 | 16.22 |
| ATOM | 882 | CZ | PHE | A | 116 | 7.950 | 15.138 | −30.935 | 1.00 | 15.88 |
| ATOM | 883 | CE2 | PHE | A | 116 | 7.902 | 13.917 | −30.216 | 1.00 | 16.74 |
| ATOM | 884 | CD2 | PHE | A | 116 | 7.380 | 12.767 | −30.825 | 1.00 | 16.05 |
| ATOM | 885 | C | PHE | A | 116 | 8.701 | 10.695 | −33.141 | 1.00 | 19.14 |
| ATOM | 886 | O | PHE | A | 116 | 8.808 | 9.987 | −32.134 | 1.00 | 19.66 |
| ATOM | 887 | N | THR | A | 117 | 9.746 | 11.299 | −33.713 | 1.00 | 19.53 |
| ATOM | 888 | CA | THR | A | 117 | 11.116 | 11.020 | −33.315 | 1.00 | 20.15 |
| ATOM | 889 | CB | THR | A | 117 | 12.042 | 10.999 | −34.567 | 1.00 | 20.83 |
| ATOM | 890 | OG1 | THR | A | 117 | 11.988 | 12.277 | −35.222 | 1.00 | 22.59 |
| ATOM | 891 | CG2 | THR | A | 117 | 11.576 | 9.895 | −35.557 | 1.00 | 21.40 |
| ATOM | 892 | C | THR | A | 117 | 11.685 | 11.969 | −32.263 | 1.00 | 20.34 |
| ATOM | 893 | O | THR | A | 117 | 12.813 | 11.768 | −31.774 | 1.00 | 21.13 |
| ATOM | 894 | N | GLY | A | 118 | 10.943 | 13.017 | −31.914 | 1.00 | 19.25 |
| ATOM | 895 | CA | GLY | A | 118 | 11.451 | 14.018 | −30.974 | 1.00 | 19.41 |
| ATOM | 896 | C | GLY | A | 118 | 11.431 | 13.498 | −29.541 | 1.00 | 19.75 |
| ATOM | 897 | O | GLY | A | 118 | 10.913 | 12.397 | −29.281 | 1.00 | 19.99 |
| ATOM | 898 | N | ASN | A | 119 | 11.998 | 14.279 | −28.622 | 1.00 | 19.56 |
| ATOM | 899 | CA | ASN | A | 119 | 11.958 | 13.954 | −27.198 | 1.00 | 20.41 |
| ATOM | 900 | CB | ASN | A | 119 | 12.961 | 14.801 | −26.419 | 1.00 | 21.50 |
| ATOM | 901 | CG | ASN | A | 119 | 14.377 | 14.612 | −26.930 | 1.00 | 25.14 |
| ATOM | 902 | OD1 | ASN | A | 119 | 14.779 | 13.500 | −27.294 | 1.00 | 30.77 |
| ATOM | 903 | ND2 | ASN | A | 119 | 15.131 | 15.693 | −26.987 | 1.00 | 31.23 |
| ATOM | 904 | C | ASN | A | 119 | 10.550 | 14.194 | −26.696 | 1.00 | 20.06 |
| ATOM | 905 | O | ASN | A | 119 | 9.881 | 15.089 | −27.167 | 1.00 | 19.00 |
| ATOM | 906 | N | TRP | A | 120 | 10.084 | 13.348 | −25.787 | 1.00 | 19.74 |
| ATOM | 907 | CA | TRP | A | 120 | 8.707 | 13.466 | −25.316 | 1.00 | 19.03 |
| ATOM | 908 | CB | TRP | A | 120 | 7.717 | 12.917 | −26.359 | 1.00 | 18.71 |
| ATOM | 909 | CG | TRP | A | 120 | 6.351 | 13.522 | −26.162 | 1.00 | 19.76 |
| ATOM | 910 | CD1 | TRP | A | 120 | 5.239 | 12.901 | −25.673 | 1.00 | 19.81 |
| ATOM | 911 | NE1 | TRP | A | 120 | 4.186 | 13.799 | −25.593 | 1.00 | 19.49 |
| ATOM | 912 | CE2 | TRP | A | 120 | 4.612 | 15.021 | −26.042 | 1.00 | 19.44 |
| ATOM | 913 | CD2 | TRP | A | 120 | 5.975 | 14.886 | −26.410 | 1.00 | 19.35 |
| ATOM | 914 | CE3 | TRP | A | 120 | 6.657 | 16.014 | −26.895 | 1.00 | 18.94 |
| ATOM | 915 | CZ3 | TRP | A | 120 | 5.959 | 17.220 | −27.010 | 1.00 | 20.22 |
| ATOM | 916 | CH2 | TRP | A | 120 | 4.602 | 17.315 | −26.628 | 1.00 | 20.15 |
| ATOM | 917 | CZ2 | TRP | A | 120 | 3.918 | 16.233 | −26.160 | 1.00 | 18.83 |
| ATOM | 918 | C | TRP | A | 120 | 8.602 | 12.685 | −24.001 | 1.00 | 18.80 |
| ATOM | 919 | O | TRP | A | 120 | 9.454 | 11.833 | −23.722 | 1.00 | 18.83 |
| ATOM | 920 | N | GLY | A | 121 | 7.593 | 12.990 | −23.189 | 1.00 | 17.91 |
| ATOM | 921 | CA | GLY | A | 121 | 7.314 | 12.189 | −21.988 | 1.00 | 17.64 |
| ATOM | 922 | C | GLY | A | 121 | 6.721 | 10.834 | −22.362 | 1.00 | 18.93 |

TABLE 6-continued

| | | | | | | | | | |
|---|---|---|---|---|---|---|---|---|---|
| ATOM | 923 | O | GLY | A | 121 | 5.499 | 10.704 | −22.487 | 1.00 | 18.99 |
| ATOM | 924 | N | ARG | A | 122 | 7.589 | 9.828 | −22.536 | 1.00 | 17.95 |
| ATOM | 925 | CA | ARG | A | 122 | 7.195 | 8.483 | −22.958 | 1.00 | 17.86 |
| ATOM | 926 | CB | ARG | A | 122 | 7.686 | 8.193 | −24.394 | 1.00 | 17.37 |
| ATOM | 927 | CG | ARG | A | 122 | 9.181 | 8.529 | −24.626 | 1.00 | 19.53 |
| ATOM | 928 | CD | ARG | A | 122 | 9.689 | 7.987 | −25.969 | 1.00 | 17.88 |
| ATOM | 929 | NE | ARG | A | 122 | 9.012 | 8.549 | −27.159 | 1.00 | 18.08 |
| ATOM | 930 | CZ | ARG | A | 122 | 9.425 | 9.645 | −27.807 | 1.00 | 18.06 |
| ATOM | 931 | NH1 | ARG | A | 122 | 10.477 | 10.326 | −27.366 | 1.00 | 16.88 |
| ATOM | 932 | NH2 | ARG | A | 122 | 8.784 | 10.074 | −28.892 | 1.00 | 17.35 |
| ATOM | 933 | C | ARG | A | 122 | 7.799 | 7.450 | −21.976 | 1.00 | 17.48 |
| ATOM | 934 | O | ARG | A | 122 | 8.848 | 7.697 | −21.396 | 1.00 | 17.69 |
| ATOM | 935 | N | PRO | A | 123 | 7.142 | 6.298 | −21.781 | 1.00 | 17.14 |
| ATOM | 936 | CA | PRO | A | 123 | 5.886 | 5.916 | −22.382 | 1.00 | 16.01 |
| ATOM | 937 | CB | PRO | A | 123 | 5.908 | 4.385 | −22.266 | 1.00 | 16.51 |
| ATOM | 938 | CG | PRO | A | 123 | 6.585 | 4.144 | −20.969 | 1.00 | 16.30 |
| ATOM | 939 | CD | PRO | A | 123 | 7.658 | 5.238 | −20.873 | 1.00 | 16.95 |
| ATOM | 940 | C | PRO | A | 123 | 4.716 | 6.494 | −21.581 | 1.00 | 15.29 |
| ATOM | 941 | O | PRO | A | 123 | 4.926 | 7.057 | −20.521 | 1.00 | 15.07 |
| ATOM | 942 | N | GLN | A | 124 | 3.504 | 6.362 | −22.120 | 1.00 | 14.60 |
| ATOM | 943 | CA | GLN | A | 124 | 2.289 | 6.675 | −21.386 | 1.00 | 14.40 |
| ATOM | 944 | CB | GLN | A | 124 | 1.602 | 7.889 | −22.001 | 1.00 | 14.71 |
| ATOM | 945 | CG | GLN | A | 124 | 2.442 | 9.186 | −21.711 | 1.00 | 11.93 |
| ATOM | 946 | CD | GLN | A | 124 | 1.993 | 10.407 | −22.472 | 1.00 | 15.67 |
| ATOM | 947 | OE1 | GLN | A | 124 | 2.807 | 11.310 | −22.758 | 1.00 | 15.75 |
| ATOM | 948 | NE2 | GLN | A | 124 | 0.718 | 10.450 | −22.822 | 1.00 | 9.85 |
| ATOM | 949 | C | GLN | A | 124 | 1.441 | 5.421 | −21.511 | 1.00 | 14.28 |
| ATOM | 950 | O | GLN | A | 124 | 0.988 | 5.095 | −22.604 | 1.00 | 14.63 |
| ATOM | 951 | N | ARG | A | 125 | 1.241 | 4.731 | −20.390 | 1.00 | 13.50 |
| ATOM | 952 | CA | ARG | A | 125 | 0.700 | 3.382 | −20.398 | 1.00 | 13.96 |
| ATOM | 953 | CB | ARG | A | 125 | 1.331 | 2.567 | −19.256 | 1.00 | 14.28 |
| ATOM | 954 | CG | ARG | A | 125 | 2.864 | 2.703 | −19.249 | 1.00 | 15.16 |
| ATOM | 955 | CD | ARG | A | 125 | 3.503 | 1.577 | −18.439 | 1.00 | 18.07 |
| ATOM | 956 | NE | ARG | A | 125 | 4.924 | 1.827 | −18.132 | 1.00 | 17.46 |
| ATOM | 957 | CZ | ARG | A | 125 | 5.944 | 1.334 | −18.833 | 1.00 | 19.43 |
| ATOM | 958 | NH1 | ARG | A | 125 | 5.728 | 0.601 | −19.925 | 1.00 | 20.02 |
| ATOM | 959 | NH2 | ARG | A | 125 | 7.197 | 1.596 | −18.453 | 1.00 | 18.94 |
| ATOM | 960 | C | ARG | A | 125 | −0.829 | 3.335 | −20.359 | 1.00 | 14.48 |
| ATOM | 961 | O | ARG | A | 125 | −1.424 | 2.262 | −20.343 | 1.00 | 14.40 |
| ATOM | 962 | N | ASP | A | 126 | −1.462 | 4.509 | −20.374 | 1.00 | 14.03 |
| ATOM | 963 | CA | ASP | A | 126 | −2.919 | 4.568 | −20.542 | 1.00 | 13.39 |
| ATOM | 964 | CB | ASP | A | 126 | −3.488 | 5.922 | −20.067 | 1.00 | 13.17 |
| ATOM | 965 | CG | ASP | A | 126 | −2.926 | 7.092 | −20.845 | 1.00 | 14.17 |
| ATOM | 966 | OD1 | ASP | A | 126 | −1.713 | 7.108 | −21.143 | 1.00 | 12.29 |
| ATOM | 967 | OD2 | ASP | A | 126 | −3.705 | 8.003 | −21.187 | 1.00 | 16.69 |
| ATOM | 968 | C | ASP | A | 126 | −3.350 | 4.306 | −21.974 | 1.00 | 13.60 |
| ATOM | 969 | O | ASP | A | 126 | −4.452 | 3.806 | −22.189 | 1.00 | 13.56 |
| ATOM | 970 | N | GLY | A | 127 | −2.491 | 4.634 | −22.948 | 1.00 | 12.78 |
| ATOM | 971 | CA | GLY | A | 127 | −2.886 | 4.558 | −24.358 | 1.00 | 13.20 |
| ATOM | 972 | C | GLY | A | 127 | −3.473 | 3.213 | −24.794 | 1.00 | 12.77 |
| ATOM | 973 | O | GLY | A | 127 | −4.579 | 3.150 | −25.327 | 1.00 | 12.56 |
| ATOM | 974 | N | PRO | A | 128 | −2.720 | 2.120 | −24.613 | 1.00 | 13.94 |
| ATOM | 975 | CA | PRO | A | 128 | −3.262 | 0.810 | −24.978 | 1.00 | 12.97 |
| ATOM | 976 | CB | PRO | A | 128 | −2.135 | −0.162 | −24.552 | 1.00 | 14.15 |
| ATOM | 977 | CG | PRO | A | 128 | −0.907 | 0.656 | −24.721 | 1.00 | 14.39 |
| ATOM | 978 | CD | PRO | A | 128 | −1.323 | 2.010 | −24.150 | 1.00 | 13.67 |
| ATOM | 979 | C | PRO | A | 128 | −4.571 | 0.455 | −24.255 | 1.00 | 13.30 |
| ATOM | 980 | O | PRO | A | 128 | −5.433 | −0.161 | −24.869 | 1.00 | 13.72 |
| ATOM | 981 | N | ALA | A | 129 | −4.718 | 0.852 | −22.985 | 1.00 | 12.95 |
| ATOM | 982 | CA | ALA | A | 129 | −5.963 | 0.611 | −22.258 | 1.00 | 13.49 |
| ATOM | 983 | CB | ALA | A | 129 | −5.806 | 1.016 | −20.808 | 1.00 | 13.00 |
| ATOM | 984 | C | ALA | A | 129 | −7.162 | 1.329 | −22.923 | 1.00 | 13.43 |
| ATOM | 985 | O | ALA | A | 129 | −8.217 | 0.721 | −23.159 | 1.00 | 13.26 |
| ATOM | 986 | N | LEU | A | 130 | −6.998 | 2.619 | −23.221 | 1.00 | 12.51 |
| ATOM | 987 | CA | LEU | A | 130 | −8.068 | 3.409 | −23.813 | 1.00 | 12.69 |
| ATOM | 988 | CB | LEU | A | 130 | −7.678 | 4.903 | −23.806 | 1.00 | 12.56 |
| ATOM | 989 | CG | LEU | A | 130 | −7.458 | 5.555 | −22.426 | 1.00 | 14.76 |
| ATOM | 990 | CD1 | LEU | A | 130 | −6.959 | 6.991 | −22.643 | 1.00 | 15.23 |
| ATOM | 991 | CD2 | LEU | A | 130 | −8.776 | 5.544 | −21.651 | 1.00 | 15.30 |
| ATOM | 992 | C | LEU | A | 130 | −8.410 | 2.934 | −25.228 | 1.00 | 12.78 |
| ATOM | 993 | O | LEU | A | 130 | −9.571 | 2.863 | −25.607 | 1.00 | 12.83 |
| ATOM | 994 | N | ARG | A | 131 | −7.386 | 2.601 | −26.015 | 1.00 | 13.70 |
| ATOM | 995 | CA | ARG | A | 131 | −7.630 | 2.070 | −27.351 | 1.00 | 14.52 |
| ATOM | 996 | CB | ARG | A | 131 | −6.316 | 1.925 | −28.135 | 1.00 | 14.04 |
| ATOM | 997 | CG | ARG | A | 131 | −6.550 | 1.438 | −29.566 | 1.00 | 15.60 |
| ATOM | 998 | CD | ARG | A | 131 | −5.278 | 1.522 | −30.428 | 1.00 | 15.59 |
| ATOM | 999 | NE | ARG | A | 131 | −4.118 | 0.915 | −29.779 | 1.00 | 16.77 |
| ATOM | 1000 | CZ | ARG | A | 131 | −2.860 | 1.205 | −30.098 | 1.00 | 16.26 |
| ATOM | 1001 | NH1 | ARG | A | 131 | −2.610 | 2.104 | −31.054 | 1.00 | 16.37 |
| ATOM | 1002 | NH2 | ARG | A | 131 | −1.856 | 0.618 | −29.448 | 1.00 | 15.96 |

TABLE 6-continued

| ATOM | 1003 | C | ARG | A | 131 | −8.408 | 0.729 | −27.283 | 1.00 | 14.44 |
|---|---|---|---|---|---|---|---|---|---|---|
| ATOM | 1004 | O | ARG | A | 131 | −9.350 | 0.533 | −28.050 | 1.00 | 15.71 |
| ATOM | 1005 | N | ALA | A | 132 | −8.025 | −0.164 | −26.364 | 1.00 | 14.50 |
| ATOM | 1006 | CA | ALA | A | 132 | −8.738 | −1.456 | −26.195 | 1.00 | 15.06 |
| ATOM | 1007 | CB | ALA | A | 132 | −8.069 | −2.348 | −25.112 | 1.00 | 15.02 |
| ATOM | 1008 | C | ALA | A | 132 | −10.194 | −1.197 | −25.846 | 1.00 | 15.43 |
| ATOM | 1009 | O | ALA | A | 132 | −11.101 | −1.808 | −26.416 | 1.00 | 15.57 |
| ATOM | 1010 | N | ILE | A | 133 | −10.418 | −0.270 | −24.915 | 1.00 | 15.70 |
| ATOM | 1011 | CA | ILE | A | 133 | −11.777 | 0.049 | −24.491 | 1.00 | 14.44 |
| ATOM | 1012 | CB | ILE | A | 133 | −11.775 | 1.056 | −23.335 | 1.00 | 14.07 |
| ATOM | 1013 | CG1 | ILE | A | 133 | −11.268 | 0.387 | −22.046 | 1.00 | 15.40 |
| ATOM | 1014 | CD1 | ILE | A | 133 | −10.751 | 1.388 | −21.017 | 1.00 | 16.66 |
| ATOM | 1015 | CG2 | ILE | A | 133 | −13.176 | 1.702 | −23.101 | 1.00 | 13.98 |
| ATOM | 1016 | C | ILE | A | 133 | −12.633 | 0.517 | −25.679 | 1.00 | 14.36 |
| ATOM | 1017 | O | ILE | A | 133 | −13.781 | 0.102 | −25.807 | 1.00 | 14.69 |
| ATOM | 1018 | N | ALA | A | 134 | −12.079 | 1.362 | −26.545 | 1.00 | 13.69 |
| ATOM | 1019 | CA | ALA | A | 134 | −12.819 | 1.832 | −27.720 | 1.00 | 13.81 |
| ATOM | 1020 | CB | ALA | A | 134 | −12.019 | 2.949 | −28.452 | 1.00 | 13.99 |
| ATOM | 1021 | C | ALA | A | 134 | −13.140 | 0.662 | −28.657 | 1.00 | 14.62 |
| ATOM | 1022 | O | ALA | A | 134 | −14.279 | 0.473 | −29.087 | 1.00 | 14.90 |
| ATOM | 1023 | N | LEU | A | 135 | −12.133 | −0.155 | −28.947 | 1.00 | 14.66 |
| ATOM | 1024 | CA | LEU | A | 135 | −12.328 | −1.251 | −29.901 | 1.00 | 15.75 |
| ATOM | 1025 | CB | LEU | A | 135 | −10.984 | −1.875 | −30.311 | 1.00 | 15.75 |
| ATOM | 1026 | CG | LEU | A | 135 | −10.348 | −1.231 | −31.557 | 1.00 | 16.40 |
| ATOM | 1027 | CD1 | LEU | A | 135 | −10.257 | 0.308 | −31.471 | 1.00 | 18.56 |
| ATOM | 1028 | CD2 | LEU | A | 135 | −8.980 | −1.852 | −31.804 | 1.00 | 17.85 |
| ATOM | 1029 | C | LEU | A | 135 | −13.277 | −2.306 | −29.340 | 1.00 | 15.13 |
| ATOM | 1030 | O | LEU | A | 135 | −14.079 | −2.845 | −30.087 | 1.00 | 15.84 |
| ATOM | 1031 | N | ILE | A | 136 | −13.192 | −2.573 | −28.039 | 1.00 | 15.22 |
| ATOM | 1032 | CA | ILE | A | 136 | −14.153 | −3.473 | −27.377 | 1.00 | 15.71 |
| ATOM | 1033 | CB | ILE | A | 136 | −13.734 | −3.829 | −25.918 | 1.00 | 15.92 |
| ATOM | 1034 | CG1 | ILE | A | 136 | −12.408 | −4.598 | −25.904 | 1.00 | 15.39 |
| ATOM | 1035 | CD1 | ILE | A | 136 | −11.742 | −4.679 | −24.497 | 1.00 | 15.63 |
| ATOM | 1036 | CG2 | ILE | A | 136 | −14.842 | −4.611 | −25.204 | 1.00 | 16.20 |
| ATOM | 1037 | C | ILE | A | 136 | −15.565 | −2.902 | −27.457 | 1.00 | 17.10 |
| ATOM | 1038 | O | ILE | A | 136 | −16.531 | −3.631 | −27.728 | 1.00 | 17.48 |
| ATOM | 1039 | N | GLY | A | 137 | −15.685 | −1.581 | −27.297 | 1.00 | 16.46 |
| ATOM | 1040 | CA | GLY | A | 137 | −16.979 | −0.902 | −27.484 | 1.00 | 16.59 |
| ATOM | 1041 | C | GLY | A | 137 | −17.600 | −1.206 | −28.833 | 1.00 | 17.13 |
| ATOM | 1042 | O | GLY | A | 137 | −18.778 | −1.605 | −28.920 | 1.00 | 16.92 |
| ATOM | 1043 | N | TYR | A | 138 | −16.817 | −1.056 | −29.898 | 1.00 | 16.61 |
| ATOM | 1044 | CA | TYR | A | 138 | −17.353 | −1.349 | −31.224 | 1.00 | 17.93 |
| ATOM | 1045 | CB | TYR | A | 138 | −16.446 | −0.838 | −32.341 | 1.00 | 17.46 |
| ATOM | 1046 | CG | TYR | A | 138 | −17.112 | −0.897 | −33.693 | 1.00 | 18.28 |
| ATOM | 1047 | CD1 | TYR | A | 138 | −18.350 | −0.268 | −33.914 | 1.00 | 18.85 |
| ATOM | 1048 | CE1 | TYR | A | 138 | −18.966 | −0.314 | −35.153 | 1.00 | 21.29 |
| ATOM | 1049 | CZ | TYR | A | 138 | −18.358 | −1.001 | −36.207 | 1.00 | 20.99 |
| ATOM | 1050 | OH | TYR | A | 138 | −18.994 | −1.055 | −37.433 | 1.00 | 20.06 |
| ATOM | 1051 | CE2 | TYR | A | 138 | −17.133 | −1.636 | −36.026 | 1.00 | 19.88 |
| ATOM | 1052 | CD2 | TYR | A | 138 | −16.512 | −1.583 | −34.766 | 1.00 | 18.25 |
| ATOM | 1053 | C | TYR | A | 138 | −17.643 | −2.844 | −31.406 | 1.00 | 18.67 |
| ATOM | 1054 | O | TYR | A | 138 | −18.654 | −3.207 | −32.037 | 1.00 | 20.06 |
| ATOM | 1055 | N | SER | A | 139 | −16.766 | −3.686 | −30.864 | 1.00 | 19.48 |
| ATOM | 1056 | CA | SER | A | 139 | −16.942 | −5.146 | −30.900 | 1.00 | 21.02 |
| ATOM | 1057 | CB | SER | A | 139 | −15.808 | −5.829 | −30.129 | 1.00 | 21.09 |
| ATOM | 1058 | OG | SER | A | 139 | −14.581 | −5.598 | −30.789 | 1.00 | 21.49 |
| ATOM | 1059 | C | SER | A | 139 | −18.298 | −5.557 | −30.325 | 1.00 | 22.24 |
| ATOM | 1060 | O | SER | A | 139 | −19.002 | −6.392 | −30.907 | 1.00 | 23.64 |
| ATOM | 1061 | N | LYS | A | 140 | −18.669 | −4.976 | −29.188 | 1.00 | 22.77 |
| ATOM | 1062 | CA | LYS | A | 140 | −19.987 | −5.225 | −28.595 | 1.00 | 24.29 |
| ATOM | 1063 | CB | LYS | A | 140 | −20.218 | −4.343 | −27.370 | 1.00 | 24.29 |
| ATOM | 1064 | CG | LYS | A | 140 | −19.384 | −4.695 | −26.170 | 1.00 | 26.62 |
| ATOM | 1065 | CD | LYS | A | 140 | −19.696 | −3.693 | −25.060 | 1.00 | 28.24 |
| ATOM | 1066 | CE | LYS | A | 140 | −18.589 | −3.635 | −24.056 | 1.00 | 28.19 |
| ATOM | 1067 | NZ | LYS | A | 140 | −18.940 | −2.725 | −22.954 | 1.00 | 26.78 |
| ATOM | 1068 | C | LYS | A | 140 | −21.126 | −5.001 | −29.584 | 1.00 | 24.17 |
| ATOM | 1069 | O | LYS | A | 140 | −22.053 | −5.823 | −29.670 | 1.00 | 24.94 |
| ATOM | 1070 | N | TRP | A | 141 | −21.062 | −3.898 | −30.321 | 1.00 | 23.60 |
| ATOM | 1071 | CA | TRP | A | 141 | −22.054 | −3.613 | −31.338 | 1.00 | 24.29 |
| ATOM | 1072 | CB | TRP | A | 141 | −21.847 | −2.226 | −31.953 | 1.00 | 24.36 |
| ATOM | 1073 | CG | TRP | A | 141 | −22.973 | −1.833 | −32.874 | 1.00 | 24.25 |
| ATOM | 1074 | CD1 | TRP | A | 141 | −24.113 | −1.170 | −32.531 | 1.00 | 25.06 |
| ATOM | 1075 | NE1 | TRP | A | 141 | −24.921 | −1.016 | −33.638 | 1.00 | 25.22 |
| ATOM | 1076 | CE2 | TRP | A | 141 | −24.302 | −1.575 | −34.722 | 1.00 | 24.07 |
| ATOM | 1077 | CD2 | TRP | A | 141 | −23.078 | −2.115 | −34.276 | 1.00 | 24.80 |
| ATOM | 1078 | CE3 | TRP | A | 141 | −22.248 | −2.766 | −35.203 | 1.00 | 25.40 |
| ATOM | 1079 | CZ3 | TRP | A | 141 | −22.669 | −2.858 | −36.532 | 1.00 | 25.72 |
| ATOM | 1080 | CH2 | TRP | A | 141 | −23.891 | −2.304 | −36.940 | 1.00 | 24.95 |
| ATOM | 1081 | CZ2 | TRP | A | 141 | −24.721 | −1.666 | −36.051 | 1.00 | 25.14 |
| ATOM | 1082 | C | TRP | A | 141 | −22.078 | −4.666 | −32.448 | 1.00 | 24.47 |

TABLE 6-continued

| ATOM | 1083 | O | TRP | A | 141 | −23.155 | −5.152 | −32.831 | 1.00 | 24.52 |
|------|------|-----|-----|---|-----|---------|--------|---------|------|-------|
| ATOM | 1084 | N | LEU | A | 142 | −20.904 | −4.991 | −32.985 | 1.00 | 24.39 |
| ATOM | 1085 | CA | LEU | A | 142 | −20.806 | −6.024 | −34.010 | 1.00 | 25.05 |
| ATOM | 1086 | CB | LEU | A | 142 | −19.361 | −6.199 | −34.473 | 1.00 | 24.56 |
| ATOM | 1087 | CG | LEU | A | 142 | −18.754 | −5.023 | −35.252 | 1.00 | 24.44 |
| ATOM | 1088 | CD1 | LEU | A | 142 | −17.274 | −5.304 | −35.441 | 1.00 | 23.72 |
| ATOM | 1089 | CD2 | LEU | A | 142 | −19.424 | −4.793 | −36.624 | 1.00 | 25.76 |
| ATOM | 1090 | C | LEU | A | 142 | −21.406 | −7.364 | −33.556 | 1.00 | 25.97 |
| ATOM | 1091 | O | LEU | A | 142 | −22.195 | −7.966 | −34.283 | 1.00 | 26.49 |
| ATOM | 1092 | N | ILE | A | 143 | −21.045 | −7.814 | −32.359 | 1.00 | 27.04 |
| ATOM | 1093 | CA | ILE | A | 143 | −21.596 | −9.040 | −31.792 | 1.00 | 28.46 |
| ATOM | 1094 | CB | ILE | A | 143 | −20.959 | −9.362 | −30.425 | 1.00 | 28.30 |
| ATOM | 1095 | CG1 | ILE | A | 143 | −19.474 | −9.722 | −30.609 | 1.00 | 27.97 |
| ATOM | 1096 | CD1 | ILE | A | 143 | −18.707 | −9.814 | −29.301 | 1.00 | 29.85 |
| ATOM | 1097 | CG2 | ILE | A | 143 | −21.720 | −10.494 | −29.717 | 1.00 | 29.57 |
| ATOM | 1098 | C | ILE | A | 143 | −23.124 | −8.992 | −31.682 | 1.00 | 29.52 |
| ATOM | 1099 | O | ILE | A | 143 | −23.813 | −9.928 | −32.118 | 1.00 | 30.10 |
| ATOM | 1100 | N | ASN | A | 144 | −23.655 | −7.916 | −31.111 | 1.00 | 30.37 |
| ATOM | 1101 | CA | ASN | A | 144 | −25.109 | −7.768 | −30.988 | 1.00 | 32.18 |
| ATOM | 1102 | CB | ASN | A | 144 | −25.479 | −6.522 | −30.186 | 1.00 | 32.73 |
| ATOM | 1103 | CG | ASN | A | 144 | −26.960 | −6.489 | −29.792 | 1.00 | 36.88 |
| ATOM | 1104 | OD1 | ASN | A | 144 | −27.444 | −7.350 | −29.041 | 1.00 | 42.25 |
| ATOM | 1105 | ND2 | ASN | A | 144 | −27.685 | −5.488 | −30.291 | 1.00 | 40.10 |
| ATOM | 1106 | C | ASN | A | 144 | −25.820 | −7.760 | −32.341 | 1.00 | 32.17 |
| ATOM | 1107 | O | ASN | A | 144 | −27.012 | −8.029 | −32.411 | 1.00 | 32.73 |
| ATOM | 1108 | N | ASN | A | 145 | −25.094 | −7.460 | −33.411 | 1.00 | 32.19 |
| ATOM | 1109 | CA | ASN | A | 145 | −25.705 | −7.403 | −34.726 | 1.00 | 32.78 |
| ATOM | 1110 | CB | ASN | A | 145 | −25.526 | −6.014 | −35.331 | 1.00 | 33.16 |
| ATOM | 1111 | CG | ASN | A | 145 | −26.397 | −4.986 | −34.639 | 1.00 | 34.32 |
| ATOM | 1112 | OD1 | ASN | A | 145 | −27.576 | −4.841 | −34.969 | 1.00 | 37.42 |
| ATOM | 1113 | ND2 | ASN | A | 145 | −25.834 | −4.289 | −33.647 | 1.00 | 34.31 |
| ATOM | 1114 | C | ASN | A | 145 | −25.285 | −8.533 | −35.671 | 1.00 | 33.13 |
| ATOM | 1115 | O | ASN | A | 145 | −25.412 | −8.415 | −36.902 | 1.00 | 33.03 |
| ATOM | 1116 | N | ASN | A | 146 | −24.789 | −9.618 | −35.065 | 1.00 | 33.43 |
| ATOM | 1117 | CA | ASN | A | 146 | −24.475 | −10.885 | −35.736 | 1.00 | 34.14 |
| ATOM | 1118 | CB | ASN | A | 146 | −25.710 | −11.459 | −36.461 | 1.00 | 34.85 |
| ATOM | 1119 | CG | ASN | A | 146 | −26.994 | −11.280 | −35.657 | 1.00 | 37.41 |
| ATOM | 1120 | OD1 | ASN | A | 146 | −27.033 | −11.543 | −34.450 | 1.00 | 41.43 |
| ATOM | 1121 | ND2 | ASN | A | 146 | −28.047 | −10.814 | −36.321 | 1.00 | 41.54 |
| ATOM | 1122 | C | ASN | A | 146 | −23.266 | −10.795 | −36.652 | 1.00 | 33.92 |
| ATOM | 1123 | O | ASN | A | 146 | −23.216 | −11.419 | −37.724 | 1.00 | 33.76 |
| ATOM | 1124 | N | TYR | A | 147 | −22.280 | −10.013 | −36.221 | 1.00 | 32.92 |
| ATOM | 1125 | CA | TYR | A | 147 | −21.049 | −9.870 | −36.974 | 1.00 | 32.90 |
| ATOM | 1126 | CB | TYR | A | 147 | −20.859 | −8.423 | −37.451 | 1.00 | 33.31 |
| ATOM | 1127 | CG | TYR | A | 147 | −21.966 | −7.893 | −38.339 | 1.00 | 33.29 |
| ATOM | 1128 | CD1 | TYR | A | 147 | −22.168 | −8.410 | −39.621 | 1.00 | 34.11 |
| ATOM | 1129 | CE1 | TYR | A | 147 | −23.177 | −7.924 | −40.438 | 1.00 | 34.19 |
| ATOM | 1130 | CZ | TYR | A | 147 | −23.986 | −6.888 | −39.983 | 1.00 | 34.10 |
| ATOM | 1131 | OH | TYR | A | 147 | −24.987 | −6.399 | −40.794 | 1.00 | 35.08 |
| ATOM | 1132 | CE2 | TYR | A | 147 | −23.798 | −6.345 | −38.722 | 1.00 | 32.48 |
| ATOM | 1133 | CD2 | TYR | A | 147 | −22.792 | −6.852 | −37.906 | 1.00 | 32.03 |
| ATOM | 1134 | C | TYR | A | 147 | −19.857 | −10.297 | −36.138 | 1.00 | 32.74 |
| ATOM | 1135 | O | TYR | A | 147 | −18.795 | −9.710 | −36.242 | 1.00 | 32.03 |
| ATOM | 1136 | N | GLN | A | 148 | −20.037 | −11.325 | −35.312 | 1.00 | 33.44 |
| ATOM | 1137 | CA | GLN | A | 148 | −18.977 | −11.807 | −34.427 | 1.00 | 34.39 |
| ATOM | 1138 | CB | GLN | A | 148 | −19.483 | −12.971 | −33.573 | 1.00 | 34.76 |
| ATOM | 1139 | CG | GLN | A | 148 | −18.523 | −13.445 | −32.481 | 1.00 | 35.56 |
| ATOM | 1140 | CD | GLN | A | 148 | −19.216 | −14.273 | −31.401 | 1.00 | 36.59 |
| ATOM | 1141 | OE1 | GLN | A | 148 | −20.296 | −13.913 | −30.916 | 1.00 | 41.20 |
| ATOM | 1142 | NE2 | GLN | A | 148 | −18.589 | −15.380 | −31.008 | 1.00 | 38.65 |
| ATOM | 1143 | C | GLN | A | 148 | −17.690 | −12.196 | −35.176 | 1.00 | 34.46 |
| ATOM | 1144 | O | GLN | A | 148 | −16.582 | −12.002 | −34.654 | 1.00 | 34.20 |
| ATOM | 1145 | N | PHE | A | 149 | −17.841 | −12.735 | −36.391 | 1.00 | 34.19 |
| ATOM | 1146 | CA | PHE | A | 149 | −16.696 | −13.131 | −37.217 | 1.00 | 34.10 |
| ATOM | 1147 | CB | PHE | A | 149 | −17.140 | −13.804 | −38.534 | 1.00 | 35.60 |
| ATOM | 1148 | CG | PHE | A | 149 | −18.346 | −13.168 | −39.193 | 1.00 | 38.70 |
| ATOM | 1149 | CD1 | PHE | A | 149 | −19.388 | −13.976 | −39.676 | 1.00 | 42.72 |
| ATOM | 1150 | CE1 | PHE | A | 149 | −20.518 | −13.417 | −40.295 | 1.00 | 43.69 |
| ATOM | 1151 | CZ | PHE | A | 149 | −20.615 | −12.019 | −40.437 | 1.00 | 43.12 |
| ATOM | 1152 | CE2 | PHE | A | 149 | −19.567 | −11.188 | −39.953 | 1.00 | 43.20 |
| ATOM | 1153 | CD2 | PHE | A | 149 | −18.451 | −11.772 | −39.341 | 1.00 | 42.33 |
| ATOM | 1154 | C | PHE | A | 149 | −15.746 | −11.960 | −37.517 | 1.00 | 32.49 |
| ATOM | 1155 | O | PHE | A | 149 | −14.528 | −12.132 | −37.548 | 1.00 | 32.23 |
| ATOM | 1156 | N | THR | A | 150 | −16.327 | −10.789 | −37.751 | 1.00 | 30.95 |
| ATOM | 1157 | CA | THR | A | 150 | −15.570 | −9.568 | −38.040 | 1.00 | 29.68 |
| ATOM | 1158 | CB | THR | A | 150 | −16.512 | −8.424 | −38.445 | 1.00 | 29.97 |
| ATOM | 1159 | OG1 | THR | A | 150 | −17.162 | −8.768 | −39.673 | 1.00 | 30.58 |
| ATOM | 1160 | CG2 | THR | A | 150 | −15.758 | −7.096 | −38.637 | 1.00 | 29.18 |
| ATOM | 1161 | C | THR | A | 150 | −14.727 | −9.203 | −36.822 | 1.00 | 28.54 |
| ATOM | 1162 | O | THR | A | 150 | −13.566 | −8.827 | −36.965 | 1.00 | 28.38 |

TABLE 6-continued

| | | | | | | | | | |
|---|---|---|---|---|---|---|---|---|---|
| ATOM | 1163 | N | VAL | A | 151 | −15.310 | −9.354 | −35.636 | 1.00 | 27.23 |
| ATOM | 1164 | CA | VAL | A | 151 | −14.597 | −9.146 | −34.374 | 1.00 | 26.78 |
| ATOM | 1165 | CB | VAL | A | 151 | −15.529 | −9.352 | −33.148 | 1.00 | 26.25 |
| ATOM | 1166 | CG1 | VAL | A | 151 | −14.752 | −9.213 | −31.832 | 1.00 | 26.50 |
| ATOM | 1167 | CG2 | VAL | A | 151 | −16.690 | −8.361 | −33.178 | 1.00 | 24.41 |
| ATOM | 1168 | C | VAL | A | 151 | −13.384 | −10.080 | −34.305 | 1.00 | 27.61 |
| ATOM | 1169 | O | VAL | A | 151 | −12.246 | −9.638 | −34.106 | 1.00 | 26.67 |
| ATOM | 1170 | N | SER | A | 152 | −13.625 | −11.375 | −34.505 | 1.00 | 28.53 |
| ATOM | 1171 | CA | SER | A | 152 | −12.551 | −12.369 | −34.470 | 1.00 | 30.01 |
| ATOM | 1172 | CB | SER | A | 152 | −13.102 | −13.759 | −34.773 | 1.00 | 30.18 |
| ATOM | 1173 | OG | SER | A | 152 | −13.612 | −14.300 | −33.586 | 1.00 | 32.28 |
| ATOM | 1174 | C | SER | A | 152 | −11.419 | −12.091 | −35.430 | 1.00 | 30.23 |
| ATOM | 1175 | O | SER | A | 152 | −10.250 | −12.250 | −35.090 | 1.00 | 30.95 |
| ATOM | 1176 | N | ASN | A | 153 | −11.762 | −11.705 | −36.641 | 1.00 | 31.46 |
| ATOM | 1177 | CA | ASN | A | 153 | −10.753 | −11.624 | −37.674 | 1.00 | 32.41 |
| ATOM | 1178 | CB | ASN | A | 153 | −11.333 | −12.118 | −38.997 | 1.00 | 33.62 |
| ATOM | 1179 | CG | ASN | A | 153 | −11.791 | −13.584 | −38.902 | 1.00 | 36.13 |
| ATOM | 1180 | OD1 | ASN | A | 153 | −12.931 | −13.918 | −39.231 | 1.00 | 40.99 |
| ATOM | 1181 | ND2 | ASN | A | 153 | −10.917 | −14.444 | −38.383 | 1.00 | 37.61 |
| ATOM | 1182 | C | ASN | A | 153 | −10.060 | −10.272 | −37.787 | 1.00 | 32.10 |
| ATOM | 1183 | O | ASN | A | 153 | −8.850 | −10.213 | −38.020 | 1.00 | 32.79 |
| ATOM | 1184 | N | VAL | A | 154 | −10.810 | −9.193 | −37.577 | 1.00 | 30.55 |
| ATOM | 1185 | CA | VAL | A | 154 | −10.251 | −7.854 | −37.750 | 1.00 | 28.93 |
| ATOM | 1186 | CB | VAL | A | 154 | −11.217 | −6.925 | −38.537 | 1.00 | 29.03 |
| ATOM | 1187 | CG1 | VAL | A | 154 | −10.565 | −5.577 | −38.827 | 1.00 | 29.23 |
| ATOM | 1188 | CG2 | VAL | A | 154 | −11.654 | −7.585 | −39.860 | 1.00 | 29.87 |
| ATOM | 1189 | C | VAL | A | 154 | −9.824 | −7.211 | −36.414 | 1.00 | 27.28 |
| ATOM | 1190 | O | VAL | A | 154 | −8.722 | −6.678 | −36.306 | 1.00 | 26.96 |
| ATOM | 1191 | N | ILE | A | 155 | −10.685 | −7.288 | −35.403 | 1.00 | 25.13 |
| ATOM | 1192 | CA | ILE | A | 155 | −10.525 | −6.459 | −34.197 | 1.00 | 23.05 |
| ATOM | 1193 | CB | ILE | A | 155 | −11.900 | −5.972 | −33.670 | 1.00 | 23.10 |
| ATOM | 1194 | CG1 | ILE | A | 155 | −12.596 | −5.128 | −34.741 | 1.00 | 22.49 |
| ATOM | 1195 | CD1 | ILE | A | 155 | −14.006 | −4.680 | −34.375 | 1.00 | 22.72 |
| ATOM | 1196 | CG2 | ILE | A | 155 | −11.731 | −5.144 | −32.399 | 1.00 | 23.05 |
| ATOM | 1197 | C | ILE | A | 155 | −9.710 | −7.136 | −33.092 | 1.00 | 22.44 |
| ATOM | 1198 | O | ILE | A | 155 | −8.789 | −6.537 | −32.533 | 1.00 | 21.14 |
| ATOM | 1199 | N | TRP | A | 156 | −10.006 | −8.409 | −32.822 | 1.00 | 21.48 |
| ATOM | 1200 | CA | TRP | A | 156 | −9.392 | −9.099 | −31.696 | 1.00 | 21.75 |
| ATOM | 1201 | CB | TRP | A | 156 | −9.958 | −10.520 | −31.511 | 1.00 | 22.50 |
| ATOM | 1202 | CG | TRP | A | 156 | −9.298 | −11.245 | −30.371 | 1.00 | 23.43 |
| ATOM | 1203 | CD1 | TRP | A | 156 | −8.420 | −12.298 | −30.461 | 1.00 | 24.92 |
| ATOM | 1204 | NE1 | TRP | A | 156 | −8.011 | −12.680 | −29.198 | 1.00 | 24.85 |
| ATOM | 1205 | CE2 | TRP | A | 156 | −8.600 | −11.863 | −28.269 | 1.00 | 26.38 |
| ATOM | 1206 | CD2 | TRP | A | 156 | −9.416 | −10.941 | −28.970 | 1.00 | 25.03 |
| ATOM | 1207 | CE3 | TRP | A | 156 | −10.139 | −9.983 | −28.236 | 1.00 | 25.01 |
| ATOM | 1208 | CZ3 | TRP | A | 156 | −10.024 | −9.982 | −26.844 | 1.00 | 24.30 |
| ATOM | 1209 | CH2 | TRP | A | 156 | −9.206 | −10.910 | −26.185 | 1.00 | 23.97 |
| ATOM | 1210 | CZ2 | TRP | A | 156 | −8.495 | −11.861 | −26.875 | 1.00 | 24.60 |
| ATOM | 1211 | C | TRP | A | 156 | −7.845 | −9.109 | −31.699 | 1.00 | 21.52 |
| ATOM | 1212 | O | TRP | A | 156 | −7.235 | −8.945 | −30.648 | 1.00 | 21.78 |
| ATOM | 1213 | N | PRO | A | 157 | −7.209 | −9.303 | −32.870 | 1.00 | 21.66 |
| ATOM | 1214 | CA | PRO | A | 157 | −5.726 | −9.258 | −32.878 | 1.00 | 21.40 |
| ATOM | 1215 | CB | PRO | A | 157 | −5.378 | −9.459 | −34.360 | 1.00 | 21.26 |
| ATOM | 1216 | CG | PRO | A | 157 | −6.583 | −10.172 | −34.955 | 1.00 | 22.82 |
| ATOM | 1217 | CD | PRO | A | 157 | −7.762 | −9.596 | −34.207 | 1.00 | 21.45 |
| ATOM | 1218 | C | PRO | A | 157 | −5.162 | −7.898 | −32.410 | 1.00 | 21.30 |
| ATOM | 1219 | O | PRO | A | 157 | −4.092 | −7.837 | −31.795 | 1.00 | 21.11 |
| ATOM | 1220 | N | ILE | A | 158 | −5.881 | −6.821 | −32.724 | 1.00 | 20.52 |
| ATOM | 1221 | CA | ILE | A | 158 | −5.457 | −5.467 | −32.318 | 1.00 | 19.93 |
| ATOM | 1222 | CB | ILE | A | 158 | −6.273 | −4.348 | −33.034 | 1.00 | 19.73 |
| ATOM | 1223 | CG1 | ILE | A | 158 | −6.261 | −4.527 | −34.559 | 1.00 | 21.25 |
| ATOM | 1224 | CD1 | ILE | A | 158 | −7.229 | −3.640 | −35.351 | 1.00 | 20.03 |
| ATOM | 1225 | CG2 | ILE | A | 158 | −5.686 | −2.971 | −32.670 | 1.00 | 20.16 |
| ATOM | 1226 | C | ILE | A | 158 | −5.632 | −5.366 | −30.816 | 1.00 | 19.58 |
| ATOM | 1227 | O | ILE | A | 158 | −4.701 | −5.023 | −30.081 | 1.00 | 19.04 |
| ATOM | 1228 | N | VAL | A | 159 | −6.840 | −5.704 | −30.359 | 1.00 | 19.39 |
| ATOM | 1229 | CA | VAL | A | 159 | −7.201 | −5.624 | −28.953 | 1.00 | 19.15 |
| ATOM | 1230 | CB | VAL | A | 159 | −8.687 | −6.026 | −28.744 | 1.00 | 19.06 |
| ATOM | 1231 | CG1 | VAL | A | 159 | −9.046 | −6.028 | −27.253 | 1.00 | 20.39 |
| ATOM | 1232 | CG2 | VAL | A | 159 | −9.604 | −5.090 | −29.511 | 1.00 | 20.08 |
| ATOM | 1233 | C | VAL | A | 159 | −6.280 | −6.501 | −28.105 | 1.00 | 19.39 |
| ATOM | 1234 | O | VAL | A | 159 | −5.794 | −6.089 | −27.036 | 1.00 | 18.63 |
| ATOM | 1235 | N | ARG | A | 160 | −6.022 | −7.721 | −28.585 | 1.00 | 18.93 |
| ATOM | 1236 | CA | ARG | A | 160 | −5.171 | −8.633 | −27.833 | 1.00 | 19.64 |
| ATOM | 1237 | CB | ARG | A | 160 | −5.078 | −10.005 | −28.513 | 1.00 | 19.17 |
| ATOM | 1238 | CG | ARG | A | 160 | −4.064 | −10.942 | −27.872 | 1.00 | 21.41 |
| ATOM | 1239 | CD | ARG | A | 160 | −3.978 | −12.278 | −28.637 | 1.00 | 23.47 |
| ATOM | 1240 | NE | ARG | A | 160 | −3.542 | −12.066 | −30.021 | 1.00 | 29.25 |
| ATOM | 1241 | CZ | ARG | A | 160 | −3.963 | −12.771 | −31.074 | 1.00 | 33.46 |
| ATOM | 1242 | NH1 | ARG | A | 160 | −4.839 | −13.764 | −30.929 | 1.00 | 36.48 |

TABLE 6-continued

| | | | | | | | | | |
|---|---|---|---|---|---|---|---|---|---|
| ATOM | 1243 | NH2 | ARG | A | 160 | −3.501 | −12.489 | −32.289 | 1.00 | 34.33 |
| ATOM | 1244 | C | ARG | A | 160 | −3.785 | −8.058 | −27.580 | 1.00 | 18.24 |
| ATOM | 1245 | O | ARG | A | 160 | −3.262 | −8.233 | −26.517 | 1.00 | 18.13 |
| ATOM | 1246 | N | ASN | A | 161 | −3.182 | −7.371 | −28.551 | 1.00 | 18.57 |
| ATOM | 1247 | CA | ASN | A | 161 | −1.875 | −6.717 | −28.289 | 1.00 | 18.40 |
| ATOM | 1248 | CB | ASN | A | 161 | −1.344 | −6.052 | −29.561 | 1.00 | 18.82 |
| ATOM | 1249 | CG | ASN | A | 161 | −0.772 | −7.055 | −30.549 | 1.00 | 20.68 |
| ATOM | 1250 | OD1 | ASN | A | 161 | −0.240 | −8.097 | −30.149 | 1.00 | 22.60 |
| ATOM | 1251 | ND2 | ASN | A | 161 | −0.883 | −6.751 | −31.837 | 1.00 | 19.81 |
| ATOM | 1252 | C | ASN | A | 161 | −1.946 | −5.656 | −27.182 | 1.00 | 18.36 |
| ATOM | 1253 | O | ASN | A | 161 | −1.078 | −5.581 | −26.313 | 1.00 | 17.42 |
| ATOM | 1254 | N | ASP | A | 162 | −2.982 | −4.816 | −27.233 | 1.00 | 17.86 |
| ATOM | 1255 | CA | ASP | A | 162 | −3.163 | −3.782 | −26.194 | 1.00 | 16.85 |
| ATOM | 1256 | CB | ASP | A | 162 | −4.293 | −2.821 | −26.586 | 1.00 | 16.71 |
| ATOM | 1257 | CG | ASP | A | 162 | −3.851 | −1.791 | −27.623 | 1.00 | 17.46 |
| ATOM | 1258 | OD1 | ASP | A | 162 | −2.648 | −1.440 | −27.681 | 1.00 | 16.98 |
| ATOM | 1259 | OD2 | ASP | A | 162 | −4.719 | −1.333 | −28.388 | 1.00 | 18.89 |
| ATOM | 1260 | C | ASP | A | 162 | −3.421 | −4.354 | −24.799 | 1.00 | 16.51 |
| ATOM | 1261 | O | ASP | A | 162 | −2.846 | −3.897 | −23.822 | 1.00 | 15.71 |
| ATOM | 1262 | N | LEU | A | 163 | −4.278 | −5.371 | −24.715 | 1.00 | 16.83 |
| ATOM | 1263 | CA | LEU | A | 163 | −4.532 | −6.071 | −23.459 | 1.00 | 16.55 |
| ATOM | 1264 | CB | LEU | A | 163 | −5.661 | −7.088 | −23.637 | 1.00 | 16.96 |
| ATOM | 1265 | CG | LEU | A | 163 | −7.030 | −6.506 | −23.975 | 1.00 | 19.29 |
| ATOM | 1266 | CD1 | LEU | A | 163 | −8.007 | −7.663 | −24.227 | 1.00 | 19.71 |
| ATOM | 1267 | CD2 | LEU | A | 163 | −7.484 | −5.631 | −22.818 | 1.00 | 21.19 |
| ATOM | 1268 | C | LEU | A | 163 | −3.279 | −6.750 | −22.883 | 1.00 | 16.19 |
| ATOM | 1269 | O | LEU | A | 163 | −3.035 | −6.690 | −21.688 | 1.00 | 15.47 |
| ATOM | 1270 | N | ASN | A | 164 | −2.495 | −7.401 | −23.748 | 1.00 | 16.85 |
| ATOM | 1271 | CA | ASN | A | 164 | −1.251 | −8.040 | −23.305 | 1.00 | 16.44 |
| ATOM | 1272 | CB | ASN | A | 164 | −0.602 | −8.836 | −24.450 | 1.00 | 17.06 |
| ATOM | 1273 | CG | ASN | A | 164 | −1.333 | −10.153 | −24.718 | 1.00 | 19.63 |
| ATOM | 1274 | OD1 | ASN | A | 164 | −2.274 | −10.513 | −23.982 | 1.00 | 20.97 |
| ATOM | 1275 | ND2 | ASN | A | 164 | −0.903 | −10.881 | −25.756 | 1.00 | 19.79 |
| ATOM | 1276 | C | ASN | A | 164 | −0.301 | −7.022 | −22.761 | 1.00 | 16.80 |
| ATOM | 1277 | O | ASN | A | 164 | 0.349 | −7.261 | −21.751 | 1.00 | 15.97 |
| ATOM | 1278 | N | TYR | A | 165 | −0.250 | −5.860 | −23.415 | 1.00 | 16.45 |
| ATOM | 1279 | CA | TYR | A | 165 | 0.573 | −4.744 | −22.930 | 1.00 | 16.15 |
| ATOM | 1280 | CB | TYR | A | 165 | 0.420 | −3.508 | −23.844 | 1.00 | 16.63 |
| ATOM | 1281 | CG | TYR | A | 165 | 1.286 | −2.356 | −23.391 | 1.00 | 16.41 |
| ATOM | 1282 | CD1 | TYR | A | 165 | 0.838 | −1.459 | −22.404 | 1.00 | 17.94 |
| ATOM | 1283 | CE1 | TYR | A | 165 | 1.651 | −0.402 | −21.958 | 1.00 | 17.84 |
| ATOM | 1284 | CZ | TYR | A | 165 | 2.916 | −0.223 | −22.517 | 1.00 | 18.36 |
| ATOM | 1285 | OH | TYR | A | 165 | 3.699 | 0.841 | −22.091 | 1.00 | 16.54 |
| ATOM | 1286 | CE2 | TYR | A | 165 | 3.383 | −1.105 | −23.502 | 1.00 | 16.73 |
| ATOM | 1287 | CD2 | TYR | A | 165 | 2.552 | −2.157 | −23.942 | 1.00 | 16.01 |
| ATOM | 1288 | C | TYR | A | 165 | 0.198 | −4.366 | −21.503 | 1.00 | 16.26 |
| ATOM | 1289 | O | TYR | A | 165 | 1.073 | −4.218 | −20.650 | 1.00 | 15.43 |
| ATOM | 1290 | N | VAL | A | 166 | −1.104 | −4.177 | −21.258 | 1.00 | 16.75 |
| ATOM | 1291 | CA | VAL | A | 166 | −1.600 | −3.786 | −19.933 | 1.00 | 17.39 |
| ATOM | 1292 | CB | VAL | A | 166 | −3.124 | −3.479 | −19.986 | 1.00 | 17.57 |
| ATOM | 1293 | CG1 | VAL | A | 166 | −3.712 | −3.197 | −18.582 | 1.00 | 19.25 |
| ATOM | 1294 | CG2 | VAL | A | 166 | −3.363 | −2.272 | −20.909 | 1.00 | 16.49 |
| ATOM | 1295 | C | VAL | A | 166 | −1.258 | −4.829 | −18.865 | 1.00 | 17.83 |
| ATOM | 1296 | O | VAL | A | 166 | −0.741 | −4.483 | −17.792 | 1.00 | 18.00 |
| ATOM | 1297 | N | ALA | A | 167 | −1.520 | −6.099 | −19.188 | 1.00 | 18.26 |
| ATOM | 1298 | CA | ALA | A | 167 | −1.233 | −7.218 | −18.285 | 1.00 | 18.92 |
| ATOM | 1299 | CB | ALA | A | 167 | −1.716 | −8.532 | −18.899 | 1.00 | 18.25 |
| ATOM | 1300 | C | ALA | A | 167 | 0.251 | −7.325 | −17.956 | 1.00 | 19.08 |
| ATOM | 1301 | O | ALA | A | 167 | 0.611 | −7.757 | −16.854 | 1.00 | 20.02 |
| ATOM | 1302 | N | GLN | A | 168 | 1.097 | −6.955 | −18.920 | 1.00 | 19.13 |
| ATOM | 1303 | CA | GLN | A | 168 | 2.558 | −7.022 | −18.749 | 1.00 | 19.21 |
| ATOM | 1304 | CB | GLN | A | 168 | 3.218 | −7.201 | −20.115 | 1.00 | 19.08 |
| ATOM | 1305 | CG | GLN | A | 168 | 4.739 | −7.373 | −20.053 | 1.00 | 20.55 |
| ATOM | 1306 | CD | GLN | A | 168 | 5.337 | −7.891 | −21.355 | 1.00 | 20.26 |
| ATOM | 1307 | OE1 | GLN | A | 168 | 4.634 | −8.378 | −22.238 | 1.00 | 22.69 |
| ATOM | 1308 | NE2 | GLN | A | 168 | 6.643 | −7.772 | −21.476 | 1.00 | 23.10 |
| ATOM | 1309 | C | GLN | A | 168 | 3.182 | −5.807 | −18.048 | 1.00 | 19.60 |
| ATOM | 1310 | O | GLN | A | 168 | 4.104 | −5.942 | −17.205 | 1.00 | 18.87 |
| ATOM | 1311 | N | TYR | A | 169 | 2.709 | −4.609 | −18.404 | 1.00 | 19.23 |
| ATOM | 1312 | CA | TYR | A | 169 | 3.399 | −3.377 | −18.011 | 1.00 | 19.45 |
| ATOM | 1313 | CB | TYR | A | 169 | 3.760 | −2.560 | −19.266 | 1.00 | 20.43 |
| ATOM | 1314 | CG | TYR | A | 169 | 4.773 | −3.203 | −20.203 | 1.00 | 21.30 |
| ATOM | 1315 | CD1 | TYR | A | 169 | 6.125 | −3.243 | −19.872 | 1.00 | 23.63 |
| ATOM | 1316 | CE1 | TYR | A | 169 | 7.065 | −3.822 | −20.723 | 1.00 | 24.59 |
| ATOM | 1317 | CZ | TYR | A | 169 | 6.651 | −4.359 | −21.926 | 1.00 | 23.11 |
| ATOM | 1318 | OH | TYR | A | 169 | 7.580 | −4.924 | −22.779 | 1.00 | 25.26 |
| ATOM | 1319 | CE2 | TYR | A | 169 | 5.309 | −4.330 | −22.288 | 1.00 | 22.49 |
| ATOM | 1320 | CD2 | TYR | A | 169 | 4.375 | −3.754 | −21.422 | 1.00 | 20.87 |
| ATOM | 1321 | C | TYR | A | 169 | 2.675 | −2.449 | −17.015 | 1.00 | 19.49 |
| ATOM | 1322 | O | TYR | A | 169 | 3.205 | −1.386 | −16.691 | 1.00 | 19.69 |

TABLE 6-continued

| ATOM | 1323 | N | TRP | A | 170 | 1.508 | −2.850 | −16.498 | 1.00 | 18.91 |
| ATOM | 1324 | CA | TRP | A | 170 | 0.735 | −1.981 | −15.588 | 1.00 | 19.29 |
| ATOM | 1325 | CB | TRP | A | 170 | −0.610 | −2.626 | −15.208 | 1.00 | 18.85 |
| ATOM | 1326 | CG | TRP | A | 170 | −0.489 | −3.743 | −14.215 | 1.00 | 21.04 |
| ATOM | 1327 | CD1 | TRP | A | 170 | −0.342 | −5.083 | −14.489 | 1.00 | 20.67 |
| ATOM | 1328 | NE1 | TRP | A | 170 | −0.259 | −5.793 | −13.317 | 1.00 | 22.09 |
| ATOM | 1329 | CE2 | TRP | A | 170 | −0.336 | −4.928 | −12.258 | 1.00 | 19.19 |
| ATOM | 1330 | CD2 | TRP | A | 170 | −0.481 | −3.621 | −12.789 | 1.00 | 20.35 |
| ATOM | 1331 | CE3 | TRP | A | 170 | −0.582 | −2.530 | −11.905 | 1.00 | 19.61 |
| ATOM | 1332 | CZ3 | TRP | A | 170 | −0.546 | −2.769 | −10.542 | 1.00 | 22.33 |
| ATOM | 1333 | CH2 | TRP | A | 170 | −0.404 | −4.090 | −10.038 | 1.00 | 21.08 |
| ATOM | 1334 | CZ2 | TRP | A | 170 | −0.297 | −5.179 | −10.884 | 1.00 | 20.76 |
| ATOM | 1335 | C | TRP | A | 170 | 1.526 | −1.592 | −14.336 | 1.00 | 19.20 |
| ATOM | 1336 | O | TRP | A | 170 | 1.395 | −0.475 | −13.808 | 1.00 | 19.24 |
| ATOM | 1337 | N | ASN | A | 171 | 2.371 | −2.504 | −13.858 | 1.00 | 19.13 |
| ATOM | 1338 | CA | ASN | A | 171 | 3.054 | −2.280 | −12.596 | 1.00 | 20.12 |
| ATOM | 1339 | CB | ASN | A | 171 | 3.178 | −3.603 | −11.820 | 1.00 | 20.59 |
| ATOM | 1340 | CG | ASN | A | 171 | 3.646 | −3.419 | −10.392 | 1.00 | 22.31 |
| ATOM | 1341 | OD1 | ASN | A | 171 | 4.531 | −4.155 | −9.938 | 1.00 | 23.68 |
| ATOM | 1342 | ND2 | ASN | A | 171 | 3.081 | −2.435 | −9.684 | 1.00 | 18.77 |
| ATOM | 1343 | C | ASN | A | 171 | 4.392 | −1.557 | −12.797 | 1.00 | 20.93 |
| ATOM | 1344 | O | ASN | A | 171 | 5.333 | −1.724 | −12.022 | 1.00 | 20.35 |
| ATOM | 1345 | N | GLN | A | 172 | 4.449 | −0.712 | −13.826 | 1.00 | 20.64 |
| ATOM | 1346 | CA | GLN | A | 172 | 5.644 | 0.061 | −14.156 | 1.00 | 22.31 |
| ATOM | 1347 | CB | GLN | A | 172 | 6.262 | −0.452 | −15.469 | 1.00 | 22.04 |
| ATOM | 1348 | CG | GLN | A | 172 | 6.784 | −1.895 | −15.312 | 1.00 | 25.79 |
| ATOM | 1349 | CD | GLN | A | 172 | 7.536 | −2.450 | −16.515 | 1.00 | 27.61 |
| ATOM | 1350 | OE1 | GLN | A | 172 | 8.276 | −1.735 | −17.214 | 1.00 | 35.65 |
| ATOM | 1351 | NE2 | GLN | A | 172 | 7.367 | −3.755 | −16.752 | 1.00 | 33.80 |
| ATOM | 1352 | C | GLN | A | 172 | 5.287 | 1.539 | −14.268 | 1.00 | 21.36 |
| ATOM | 1353 | O | GLN | A | 172 | 4.175 | 1.867 | −14.704 | 1.00 | 21.04 |
| ATOM | 1354 | N | THR | A | 173 | 6.209 | 2.417 | −13.871 | 1.00 | 19.73 |
| ATOM | 1355 | CA | THR | A | 173 | 5.948 | 3.871 | −13.928 | 1.00 | 20.07 |
| ATOM | 1356 | CB | THR | A | 173 | 7.001 | 4.703 | −13.168 | 1.00 | 19.48 |
| ATOM | 1357 | OG1 | THR | A | 173 | 8.300 | 4.427 | −13.707 | 1.00 | 21.56 |
| ATOM | 1358 | CG2 | THR | A | 173 | 6.988 | 4.375 | −11.690 | 1.00 | 20.86 |
| ATOM | 1359 | C | THR | A | 173 | 5.913 | 4.347 | −15.375 | 1.00 | 18.53 |
| ATOM | 1360 | O | THR | A | 173 | 6.395 | 3.665 | −16.292 | 1.00 | 18.48 |
| ATOM | 1361 | N | GLY | A | 174 | 5.345 | 5.528 | −15.582 | 1.00 | 18.38 |
| ATOM | 1362 | CA | GLY | A | 174 | 5.363 | 6.149 | −16.903 | 1.00 | 17.13 |
| ATOM | 1363 | C | GLY | A | 174 | 4.760 | 7.522 | −16.736 | 1.00 | 16.77 |
| ATOM | 1364 | O | GLY | A | 174 | 4.462 | 7.939 | −15.605 | 1.00 | 16.87 |
| ATOM | 1365 | N | PHE | A | 175 | 4.571 | 8.223 | −17.849 | 1.00 | 14.68 |
| ATOM | 1366 | CA | PHE | A | 175 | 4.004 | 9.577 | −17.776 | 1.00 | 14.68 |
| ATOM | 1367 | CB | PHE | A | 175 | 4.522 | 10.432 | −18.948 | 1.00 | 15.16 |
| ATOM | 1368 | CG | PHE | A | 175 | 5.943 | 10.847 | −18.756 | 1.00 | 15.28 |
| ATOM | 1369 | CD1 | PHE | A | 175 | 6.981 | 10.000 | −19.144 | 1.00 | 18.04 |
| ATOM | 1370 | CE1 | PHE | A | 175 | 8.313 | 10.359 | −18.915 | 1.00 | 19.53 |
| ATOM | 1371 | CZ | PHE | A | 175 | 8.609 | 11.582 | −18.278 | 1.00 | 19.12 |
| ATOM | 1372 | CE2 | PHE | A | 175 | 7.571 | 12.429 | −17.876 | 1.00 | 18.63 |
| ATOM | 1373 | CD2 | PHE | A | 175 | 6.247 | 12.054 | −18.113 | 1.00 | 17.67 |
| ATOM | 1374 | C | PHE | A | 175 | 2.483 | 9.584 | −17.655 | 1.00 | 14.11 |
| ATOM | 1375 | O | PHE | A | 175 | 1.799 | 8.683 | −18.175 | 1.00 | 14.32 |
| ATOM | 1376 | N | ASP | A | 176 | 1.972 | 10.591 | −16.938 | 1.00 | 14.79 |
| ATOM | 1377 | CA | ASP | A | 176 | 0.541 | 10.764 | −16.713 | 1.00 | 14.45 |
| ATOM | 1378 | CB | ASP | A | 176 | 0.297 | 11.661 | −15.506 | 1.00 | 13.51 |
| ATOM | 1379 | CG | ASP | A | 176 | 0.685 | 13.126 | −15.760 | 1.00 | 14.99 |
| ATOM | 1380 | OD1 | ASP | A | 176 | 1.774 | 13.399 | −16.329 | 1.00 | 14.32 |
| ATOM | 1381 | OD2 | ASP | A | 176 | −0.112 | 14.012 | −15.376 | 1.00 | 15.08 |
| ATOM | 1382 | C | ASP | A | 176 | −0.143 | 11.343 | −17.962 | 1.00 | 14.21 |
| ATOM | 1383 | O | ASP | A | 176 | 0.525 | 11.641 | −18.963 | 1.00 | 14.31 |
| ATOM | 1384 | N | LEU | A | 177 | −1.467 | 11.511 | −17.891 | 1.00 | 13.30 |
| ATOM | 1385 | CA | LEU | A | 177 | −2.235 | 11.981 | −19.048 | 1.00 | 13.44 |
| ATOM | 1386 | CB | LEU | A | 177 | −3.752 | 11.839 | −18.832 | 1.00 | 13.71 |
| ATOM | 1387 | CG | LEU | A | 177 | −4.483 | 12.896 | −18.012 | 1.00 | 14.11 |
| ATOM | 1388 | CD1 | LEU | A | 177 | −5.996 | 12.647 | −18.061 | 1.00 | 13.65 |
| ATOM | 1389 | CD2 | LEU | A | 177 | −4.007 | 12.922 | −16.553 | 1.00 | 14.74 |
| ATOM | 1390 | C | LEU | A | 177 | −1.884 | 13.424 | −19.452 | 1.00 | 13.51 |
| ATOM | 1391 | O | LEU | A | 177 | −2.131 | 13.813 | −20.600 | 1.00 | 13.74 |
| ATOM | 1392 | N | TRP | A | 178 | −1.319 | 14.206 | −18.521 | 1.00 | 12.53 |
| ATOM | 1393 | CA | TRP | A | 178 | −0.804 | 15.553 | −18.855 | 1.00 | 12.95 |
| ATOM | 1394 | CB | TRP | A | 178 | −0.890 | 16.507 | −17.660 | 1.00 | 12.67 |
| ATOM | 1395 | CG | TRP | A | 178 | −2.247 | 16.549 | −17.005 | 1.00 | 13.10 |
| ATOM | 1396 | CD1 | TRP | A | 178 | −2.504 | 16.508 | −15.662 | 1.00 | 13.10 |
| ATOM | 1397 | NE1 | TRP | A | 178 | −3.856 | 16.568 | −15.440 | 1.00 | 12.14 |
| ATOM | 1398 | CE2 | TRP | A | 178 | −4.501 | 16.646 | −16.646 | 1.00 | 13.00 |
| ATOM | 1399 | CD2 | TRP | A | 178 | −3.516 | 16.641 | −17.657 | 1.00 | 12.53 |
| ATOM | 1400 | CE3 | TRP | A | 178 | −3.919 | 16.715 | −19.002 | 1.00 | 12.38 |
| ATOM | 1401 | CZ3 | TRP | A | 178 | −5.309 | 16.813 | −19.290 | 1.00 | 13.91 |
| ATOM | 1402 | CH2 | TRP | A | 178 | −6.262 | 16.804 | −18.257 | 1.00 | 13.52 |

TABLE 6-continued

| ATOM | 1403 | CZ2 | TRP | A | 178 | −5.883 | 16.718 | −16.930 | 1.00 | 13.97 |
| ATOM | 1404 | C | TRP | A | 178 | 0.632 | 15.565 | −19.400 | 1.00 | 13.35 |
| ATOM | 1405 | O | TRP | A | 178 | 1.147 | 16.641 | −19.756 | 1.00 | 13.76 |
| ATOM | 1406 | N | GLU | A | 179 | 1.255 | 14.387 | −19.447 | 1.00 | 13.33 |
| ATOM | 1407 | CA | GLU | A | 179 | 2.532 | 14.151 | −20.117 | 1.00 | 13.32 |
| ATOM | 1408 | CB | GLU | A | 179 | 2.503 | 14.632 | −21.582 | 1.00 | 12.64 |
| ATOM | 1409 | CG | GLU | A | 179 | 1.165 | 14.344 | −22.280 | 1.00 | 13.03 |
| ATOM | 1410 | CD | GLU | A | 179 | 1.274 | 14.434 | −23.785 | 1.00 | 14.68 |
| ATOM | 1411 | OE1 | GLU | A | 179 | 0.895 | 15.478 | −24.340 | 1.00 | 15.98 |
| ATOM | 1412 | OE2 | GLU | A | 179 | 1.730 | 13.457 | −24.405 | 1.00 | 15.44 |
| ATOM | 1413 | C | GLU | A | 179 | 3.667 | 14.853 | −19.374 | 1.00 | 15.00 |
| ATOM | 1414 | O | GLU | A | 179 | 4.626 | 15.292 | −20.004 | 1.00 | 14.90 |
| ATOM | 1415 | N | GLU | A | 180 | 3.561 | 14.932 | −18.048 | 1.00 | 14.78 |
| ATOM | 1416 | CA | GLU | A | 180 | 4.476 | 15.745 | −17.246 | 1.00 | 16.76 |
| ATOM | 1417 | CB | GLU | A | 180 | 3.719 | 16.928 | −16.630 | 1.00 | 16.95 |
| ATOM | 1418 | CG | GLU | A | 180 | 3.282 | 17.972 | −17.654 | 1.00 | 18.69 |
| ATOM | 1419 | CD | GLU | A | 180 | 2.240 | 18.969 | −17.122 | 1.00 | 19.72 |
| ATOM | 1420 | OE1 | GLU | A | 180 | 1.587 | 18.715 | −16.077 | 1.00 | 19.00 |
| ATOM | 1421 | OE2 | GLU | A | 180 | 2.076 | 20.020 | −17.793 | 1.00 | 24.62 |
| ATOM | 1422 | C | GLU | A | 180 | 5.124 | 14.954 | −16.104 | 1.00 | 16.50 |
| ATOM | 1423 | O | GLU | A | 180 | 6.265 | 15.202 | −15.750 | 1.00 | 17.36 |
| ATOM | 1424 | N | VAL | A | 181 | 4.364 | 14.056 | −15.488 | 1.00 | 16.77 |
| ATOM | 1425 | CA | VAL | A | 181 | 4.775 | 13.426 | −14.218 | 1.00 | 16.87 |
| ATOM | 1426 | CB | VAL | A | 181 | 3.672 | 13.555 | −13.130 | 1.00 | 16.78 |
| ATOM | 1427 | CG1 | VAL | A | 181 | 4.030 | 12.732 | −11.893 | 1.00 | 18.56 |
| ATOM | 1428 | CG2 | VAL | A | 181 | 3.490 | 15.008 | −12.726 | 1.00 | 17.21 |
| ATOM | 1429 | C | VAL | A | 181 | 5.057 | 11.953 | −14.451 | 1.00 | 17.22 |
| ATOM | 1430 | O | VAL | A | 181 | 4.177 | 11.205 | −14.825 | 1.00 | 16.93 |
| ATOM | 1431 | N | ASN | A | 182 | 6.290 | 11.532 | −14.201 | 1.00 | 18.39 |
| ATOM | 1432 | CA | ASN | A | 182 | 6.674 | 10.123 | −14.394 | 1.00 | 18.57 |
| ATOM | 1433 | CB | ASN | A | 182 | 8.136 | 10.079 | −14.845 | 1.00 | 19.77 |
| ATOM | 1434 | CG | ASN | A | 182 | 8.665 | 8.669 | −15.056 | 1.00 | 23.96 |
| ATOM | 1435 | OD1 | ASN | A | 182 | 9.881 | 8.470 | −15.058 | 1.00 | 33.20 |
| ATOM | 1436 | ND2 | ASN | A | 182 | 7.794 | 7.706 | −15.258 | 1.00 | 23.63 |
| ATOM | 1437 | C | ASN | A | 182 | 6.440 | 9.375 | −13.073 | 1.00 | 18.31 |
| ATOM | 1438 | O | ASN | A | 182 | 7.132 | 9.621 | −12.087 | 1.00 | 18.80 |
| ATOM | 1439 | N | GLY | A | 183 | 5.436 | 8.508 | −13.034 | 1.00 | 16.83 |
| ATOM | 1440 | CA | GLY | A | 183 | 5.091 | 7.828 | −11.790 | 1.00 | 15.98 |
| ATOM | 1441 | C | GLY | A | 183 | 3.989 | 6.837 | −12.033 | 1.00 | 15.59 |
| ATOM | 1442 | O | GLY | A | 183 | 3.937 | 6.228 | −13.117 | 1.00 | 15.30 |
| ATOM | 1443 | N | SER | A | 184 | 3.119 | 6.670 | −11.035 | 1.00 | 14.95 |
| ATOM | 1444 | CA | SER | A | 184 | 1.927 | 5.823 | −11.151 | 1.00 | 15.45 |
| ATOM | 1445 | CB | SER | A | 184 | 1.844 | 4.792 | −10.017 | 1.00 | 15.76 |
| ATOM | 1446 | OG | SER | A | 184 | 2.998 | 3.935 | −10.027 | 1.00 | 17.33 |
| ATOM | 1447 | C | SER | A | 184 | 0.731 | 6.758 | −11.073 | 1.00 | 15.14 |
| ATOM | 1448 | O | SER | A | 184 | 0.646 | 7.546 | −10.148 | 1.00 | 15.83 |
| ATOM | 1449 | N | SER | A | 185 | −0.151 | 6.706 | −12.066 | 1.00 | 14.73 |
| ATOM | 1450 | CA | SER | A | 185 | −1.169 | 7.755 | −12.190 | 1.00 | 13.87 |
| ATOM | 1451 | CB | SER | A | 185 | −0.991 | 8.535 | −13.515 | 1.00 | 14.73 |
| ATOM | 1452 | OG | SER | A | 185 | −1.793 | 9.721 | −13.544 | 1.00 | 14.93 |
| ATOM | 1453 | C | SER | A | 185 | −2.551 | 7.140 | −12.127 | 1.00 | 13.49 |
| ATOM | 1454 | O | SER | A | 185 | −2.834 | 6.134 | −12.792 | 1.00 | 13.35 |
| ATOM | 1455 | N | PHE | A | 186 | −3.427 | 7.782 | −11.354 | 1.00 | 13.72 |
| ATOM | 1456 | CA | PHE | A | 186 | −4.764 | 7.275 | −11.092 | 1.00 | 13.43 |
| ATOM | 1457 | CB | PHE | A | 186 | −5.511 | 8.319 | −10.260 | 1.00 | 13.58 |
| ATOM | 1458 | CG | PHE | A | 186 | −6.807 | 7.839 | −9.662 | 1.00 | 13.52 |
| ATOM | 1459 | CD1 | PHE | A | 186 | −6.819 | 6.873 | −8.655 | 1.00 | 16.11 |
| ATOM | 1460 | CE1 | PHE | A | 186 | −8.004 | 6.489 | −8.036 | 1.00 | 17.80 |
| ATOM | 1461 | CZ | PHE | A | 186 | −9.214 | 7.062 | −8.442 | 1.00 | 16.18 |
| ATOM | 1462 | CE2 | PHE | A | 186 | −9.211 | 8.051 | −9.432 | 1.00 | 15.77 |
| ATOM | 1463 | CD2 | PHE | A | 186 | −8.003 | 8.435 | −10.030 | 1.00 | 14.62 |
| ATOM | 1464 | C | PHE | A | 186 | −5.552 | 6.946 | −12.372 | 1.00 | 13.57 |
| ATOM | 1465 | O | PHE | A | 186 | −6.053 | 5.839 | −12.524 | 1.00 | 13.36 |
| ATOM | 1466 | N | PHE | A | 187 | −5.693 | 7.927 | −13.267 | 1.00 | 12.53 |
| ATOM | 1467 | CA | PHE | A | 187 | −6.416 | 7.762 | −14.527 | 1.00 | 12.84 |
| ATOM | 1468 | CB | PHE | A | 187 | −6.284 | 9.056 | −15.356 | 1.00 | 11.69 |
| ATOM | 1469 | CG | PHE | A | 187 | −6.949 | 9.016 | −16.711 | 1.00 | 13.25 |
| ATOM | 1470 | CD1 | PHE | A | 187 | −8.284 | 9.338 | −16.855 | 1.00 | 12.86 |
| ATOM | 1471 | CE1 | PHE | A | 187 | −8.893 | 9.342 | −18.102 | 1.00 | 14.12 |
| ATOM | 1472 | CZ | PHE | A | 187 | −8.139 | 9.041 | −19.236 | 1.00 | 14.05 |
| ATOM | 1473 | CE2 | PHE | A | 187 | −6.806 | 8.721 | −19.111 | 1.00 | 14.30 |
| ATOM | 1474 | CD2 | PHE | A | 187 | −6.206 | 8.711 | −17.857 | 1.00 | 15.10 |
| ATOM | 1475 | C | PHE | A | 187 | −5.887 | 6.563 | −15.318 | 1.00 | 12.69 |
| ATOM | 1476 | O | PHE | A | 187 | −6.666 | 5.837 | −15.932 | 1.00 | 14.00 |
| ATOM | 1477 | N | THR | A | 188 | −4.571 | 6.357 | −15.294 | 1.00 | 12.97 |
| ATOM | 1478 | CA | THR | A | 188 | −3.938 | 5.302 | −16.084 | 1.00 | 13.65 |
| ATOM | 1479 | CB | THR | A | 188 | −2.411 | 5.541 | −16.104 | 1.00 | 13.69 |
| ATOM | 1480 | OG1 | THR | A | 188 | −2.158 | 6.789 | −16.753 | 1.00 | 15.37 |
| ATOM | 1481 | CG2 | THR | A | 188 | −1.648 | 4.432 | −16.833 | 1.00 | 13.24 |
| ATOM | 1482 | C | THR | A | 188 | −4.284 | 3.929 | −15.478 | 1.00 | 14.12 |

TABLE 6-continued

| | | | | | | | | | |
|---|---|---|---|---|---|---|---|---|---|
| ATOM | 1483 | O | THR | A | 188 | −4.766 | 3.039 | −16.173 | 1.00 | 14.40 |
| ATOM | 1484 | N | VAL | A | 189 | −4.066 | 3.798 | −14.173 | 1.00 | 13.34 |
| ATOM | 1485 | CA | VAL | A | 189 | −4.348 | 2.543 | −13.446 | 1.00 | 14.76 |
| ATOM | 1486 | CB | VAL | A | 189 | −3.893 | 2.612 | −11.958 | 1.00 | 14.90 |
| ATOM | 1487 | CG1 | VAL | A | 189 | −4.331 | 1.334 | −11.186 | 1.00 | 16.95 |
| ATOM | 1488 | CG2 | VAL | A | 189 | −2.374 | 2.799 | −11.865 | 1.00 | 15.31 |
| ATOM | 1489 | C | VAL | A | 189 | −5.836 | 2.167 | −13.560 | 1.00 | 14.48 |
| ATOM | 1490 | O | VAL | A | 189 | −6.159 | 1.024 | −13.853 | 1.00 | 14.65 |
| ATOM | 1491 | N | ALA | A | 190 | −6.732 | 3.146 | −13.372 | 1.00 | 13.77 |
| ATOM | 1492 | CA | ALA | A | 190 | −8.171 | 2.858 | −13.351 | 1.00 | 13.46 |
| ATOM | 1493 | CB | ALA | A | 190 | −8.996 | 4.128 | −12.922 | 1.00 | 12.74 |
| ATOM | 1494 | C | ALA | A | 190 | −8.614 | 2.388 | −14.706 | 1.00 | 13.27 |
| ATOM | 1495 | O | ALA | A | 190 | −9.432 | 1.479 | −14.815 | 1.00 | 13.24 |
| ATOM | 1496 | N | ASN | A | 191 | −8.093 | 3.017 | −15.760 | 1.00 | 12.50 |
| ATOM | 1497 | CA | ASN | A | 191 | −8.438 | 2.598 | −17.127 | 1.00 | 13.01 |
| ATOM | 1498 | CB | ASN | A | 191 | −8.122 | 3.707 | −18.137 | 1.00 | 12.65 |
| ATOM | 1499 | CG | ASN | A | 191 | −9.191 | 4.781 | −18.118 | 1.00 | 14.08 |
| ATOM | 1500 | OD1 | ASN | A | 191 | −10.319 | 4.541 | −18.554 | 1.00 | 16.39 |
| ATOM | 1501 | ND2 | ASN | A | 191 | −8.857 | 5.955 | −17.583 | 1.00 | 17.21 |
| ATOM | 1502 | C | ASN | A | 191 | −7.815 | 1.259 | −17.521 | 1.00 | 13.93 |
| ATOM | 1503 | O | ASN | A | 191 | −8.412 | 0.490 | −18.270 | 1.00 | 13.87 |
| ATOM | 1504 | N | GLN | A | 192 | −6.636 | 0.995 | −16.980 | 1.00 | 14.06 |
| ATOM | 1505 | CA | GLN | A | 192 | −5.988 | −0.311 | −17.139 | 1.00 | 14.96 |
| ATOM | 1506 | CB | GLN | A | 192 | −4.575 | −0.274 | −16.552 | 1.00 | 14.33 |
| ATOM | 1507 | CG | GLN | A | 192 | −3.555 | 0.435 | −17.500 | 1.00 | 13.64 |
| ATOM | 1508 | CD | GLN | A | 192 | −2.206 | 0.635 | −16.857 | 1.00 | 15.33 |
| ATOM | 1509 | OE1 | GLN | A | 192 | −2.074 | 0.568 | −15.646 | 1.00 | 15.48 |
| ATOM | 1510 | NE2 | GLN | A | 192 | −1.182 | 0.925 | −17.682 | 1.00 | 16.10 |
| ATOM | 1511 | C | GLN | A | 192 | −6.855 | −1.411 | −16.519 | 1.00 | 15.11 |
| ATOM | 1512 | O | GLN | A | 192 | −7.076 | −2.457 | −17.141 | 1.00 | 16.04 |
| ATOM | 1513 | N | HIS | A | 193 | −7.398 | −1.140 | −15.329 | 1.00 | 15.81 |
| ATOM | 1514 | CA | HIS | A | 193 | −8.314 | −2.069 | −14.668 | 1.00 | 16.01 |
| ATOM | 1515 | CB | HIS | A | 193 | −8.746 | −1.586 | −13.281 | 1.00 | 16.72 |
| ATOM | 1516 | CG | HIS | A | 193 | −9.806 | −2.454 | −12.669 | 1.00 | 17.39 |
| ATOM | 1517 | ND1 | HIS | A | 193 | −11.113 | −2.039 | −12.505 | 1.00 | 18.05 |
| ATOM | 1518 | CE1 | HIS | A | 193 | −11.821 | −3.028 | −11.983 | 1.00 | 18.70 |
| ATOM | 1519 | NE2 | HIS | A | 193 | −11.023 | −4.071 | −11.814 | 1.00 | 17.20 |
| ATOM | 1520 | CD2 | HIS | A | 193 | −9.758 | −3.739 | −12.242 | 1.00 | 18.04 |
| ATOM | 1521 | C | HIS | A | 193 | −9.536 | −2.343 | −15.521 | 1.00 | 15.85 |
| ATOM | 1522 | O | HIS | A | 193 | −9.898 | −3.501 | −15.732 | 1.00 | 15.70 |
| ATOM | 1523 | N | ARG | A | 194 | −10.185 | −1.285 | −15.995 | 1.00 | 15.27 |
| ATOM | 1524 | CA | ARG | A | 194 | −11.349 | −1.437 | −16.852 | 1.00 | 15.29 |
| ATOM | 1525 | CB | ARG | A | 194 | −11.922 | −0.073 | −17.234 | 1.00 | 14.30 |
| ATOM | 1526 | CG | ARG | A | 194 | −13.029 | −0.212 | −18.239 | 1.00 | 14.46 |
| ATOM | 1527 | CD | ARG | A | 194 | −13.614 | 1.102 | −18.723 | 1.00 | 15.43 |
| ATOM | 1528 | NE | ARG | A | 194 | −14.589 | 0.780 | −19.767 | 1.00 | 15.58 |
| ATOM | 1529 | CZ | ARG | A | 194 | −15.624 | 1.539 | −20.125 | 1.00 | 17.92 |
| ATOM | 1530 | NH1 | ARG | A | 194 | −15.815 | 2.744 | −19.576 | 1.00 | 14.60 |
| ATOM | 1531 | NH2 | ARG | A | 194 | −16.451 | 1.095 | −21.060 | 1.00 | 16.15 |
| ATOM | 1532 | C | ARG | A | 194 | −11.047 | −2.258 | −18.111 | 1.00 | 15.74 |
| ATOM | 1533 | O | ARG | A | 194 | −11.842 | −3.120 | −18.504 | 1.00 | 15.56 |
| ATOM | 1534 | N | ALA | A | 195 | −9.918 | −1.967 | −18.758 | 1.00 | 15.60 |
| ATOM | 1535 | CA | ALA | A | 195 | −9.562 | −2.638 | −20.004 | 1.00 | 15.90 |
| ATOM | 1536 | CB | ALA | A | 195 | −8.254 | −2.042 | −20.591 | 1.00 | 15.40 |
| ATOM | 1537 | C | ALA | A | 195 | −9.436 | −4.150 | −19.798 | 1.00 | 15.65 |
| ATOM | 1538 | O | ALA | A | 195 | −9.959 | −4.929 | −20.610 | 1.00 | 16.79 |
| ATOM | 1539 | N | LEU | A | 196 | −8.763 | −4.550 | −18.721 | 1.00 | 16.36 |
| ATOM | 1540 | CA | LEU | A | 196 | −8.552 | −5.976 | −18.423 | 1.00 | 17.02 |
| ATOM | 1541 | CB | LEU | A | 196 | −7.625 | −6.126 | −17.235 | 1.00 | 16.96 |
| ATOM | 1542 | CG | LEU | A | 196 | −6.167 | −5.744 | −17.532 | 1.00 | 16.96 |
| ATOM | 1543 | CD1 | LEU | A | 196 | −5.375 | −5.857 | −16.252 | 1.00 | 18.93 |
| ATOM | 1544 | CD2 | LEU | A | 196 | −5.590 | −6.636 | −18.630 | 1.00 | 20.38 |
| ATOM | 1545 | C | LEU | A | 196 | −9.877 | −6.685 | −18.167 | 1.00 | 17.92 |
| ATOM | 1546 | O | LEU | A | 196 | −10.102 | −7.795 | −18.643 | 1.00 | 18.98 |
| ATOM | 1547 | N | VAL | A | 197 | −10.779 | −6.014 | −17.454 | 1.00 | 18.51 |
| ATOM | 1548 | CA | VAL | A | 197 | −12.112 | −6.560 | −17.181 | 1.00 | 18.81 |
| ATOM | 1549 | CB | VAL | A | 197 | −12.875 | −5.702 | −16.130 | 1.00 | 18.26 |
| ATOM | 1550 | CG1 | VAL | A | 197 | −14.340 | −6.173 | −15.994 | 1.00 | 21.18 |
| ATOM | 1551 | CG2 | VAL | A | 197 | −12.149 | −5.784 | −14.778 | 1.00 | 19.79 |
| ATOM | 1552 | C | VAL | A | 197 | −12.924 | −6.779 | −18.462 | 1.00 | 19.05 |
| ATOM | 1553 | O | VAL | A | 197 | −13.456 | −7.884 | −18.693 | 1.00 | 18.62 |
| ATOM | 1554 | N | GLU | A | 198 | −13.010 | −5.752 | −19.308 | 1.00 | 18.43 |
| ATOM | 1555 | CA | GLU | A | 198 | −13.747 | −5.873 | −20.556 | 1.00 | 19.38 |
| ATOM | 1556 | CB | GLU | A | 198 | −13.849 | −4.517 | −21.241 | 1.00 | 19.38 |
| ATOM | 1557 | CG | GLU | A | 198 | −14.609 | −3.530 | −20.417 | 1.00 | 20.22 |
| ATOM | 1558 | CD | GLU | A | 198 | −15.334 | −2.537 | −21.298 | 1.00 | 22.66 |
| ATOM | 1559 | OE1 | GLU | A | 198 | −16.313 | −2.940 | −21.940 | 1.00 | 22.16 |
| ATOM | 1560 | OE2 | GLU | A | 198 | −14.924 | −1.369 | −21.342 | 1.00 | 22.92 |
| ATOM | 1561 | C | GLU | A | 198 | −13.094 | −6.861 | −21.509 | 1.00 | 19.78 |
| ATOM | 1562 | O | GLU | A | 198 | −13.780 | −7.506 | −22.303 | 1.00 | 20.29 |

TABLE 6-continued

| | | | | | | | | | |
|---|---|---|---|---|---|---|---|---|---|
| ATOM | 1563 | N | GLY | A | 199 | −11.770 | −6.944 | −21.435 | 1.00 | 19.78 |
| ATOM | 1564 | CA | GLY | A | 199 | −10.998 | −7.823 | −22.314 | 1.00 | 20.88 |
| ATOM | 1565 | C | GLY | A | 199 | −11.288 | −9.285 | −21.986 | 1.00 | 21.53 |
| ATOM | 1566 | O | GLY | A | 199 | −11.546 | −10.083 | −22.879 | 1.00 | 22.36 |
| ATOM | 1567 | N | ALA | A | 200 | −11.256 | −9.615 | −20.702 | 1.00 | 21.79 |
| ATOM | 1568 | CA | ALA | A | 200 | −11.605 | −10.956 | −20.234 | 1.00 | 22.44 |
| ATOM | 1569 | CB | ALA | A | 200 | −11.463 | −11.038 | −18.728 | 1.00 | 22.21 |
| ATOM | 1570 | C | ALA | A | 200 | −13.016 | −11.329 | −20.696 | 1.00 | 22.54 |
| ATOM | 1571 | O | ALA | A | 200 | −13.237 | −12.419 | −21.214 | 1.00 | 22.25 |
| ATOM | 1572 | N | THR | A | 201 | −13.965 | −10.403 | −20.573 | 1.00 | 22.56 |
| ATOM | 1573 | CA | THR | A | 201 | −15.345 | −10.671 | −20.989 | 1.00 | 22.77 |
| ATOM | 1574 | CB | THR | A | 201 | −16.302 | −9.527 | −20.551 | 1.00 | 22.83 |
| ATOM | 1575 | OG1 | THR | A | 201 | −16.219 | −9.387 | −19.134 | 1.00 | 24.92 |
| ATOM | 1576 | CG2 | THR | A | 201 | −17.756 | −9.819 | −20.929 | 1.00 | 23.76 |
| ATOM | 1577 | C | THR | A | 201 | −15.435 | −10.905 | −22.485 | 1.00 | 22.78 |
| ATOM | 1578 | O | THR | A | 201 | −16.099 | −11.851 | −22.925 | 1.00 | 22.95 |
| ATOM | 1579 | N | LEU | A | 202 | −14.760 | −10.069 | −23.275 | 1.00 | 21.78 |
| ATOM | 1580 | CA | LEU | A | 202 | −14.805 | −10.236 | −24.717 | 1.00 | 22.62 |
| ATOM | 1581 | CB | LEU | A | 202 | −14.149 | −9.055 | −25.434 | 1.00 | 22.14 |
| ATOM | 1582 | CG | LEU | A | 202 | −14.142 | −9.107 | −26.964 | 1.00 | 23.10 |
| ATOM | 1583 | CD1 | LEU | A | 202 | −15.544 | −9.198 | −27.564 | 1.00 | 24.20 |
| ATOM | 1584 | CD2 | LEU | A | 202 | −13.346 | −7.938 | −27.570 | 1.00 | 22.53 |
| ATOM | 1585 | C | LEU | A | 202 | −14.139 | −11.552 | −25.151 | 1.00 | 23.15 |
| ATOM | 1586 | O | LEU | A | 202 | −14.649 | −12.245 | −26.036 | 1.00 | 22.90 |
| ATOM | 1587 | N | ALA | A | 203 | −13.019 | −11.883 | −24.510 | 1.00 | 23.38 |
| ATOM | 1588 | CA | ALA | A | 203 | −12.300 | −13.129 | −24.787 | 1.00 | 24.07 |
| ATOM | 1589 | CB | ALA | A | 203 | −11.076 | −13.229 | −23.913 | 1.00 | 23.57 |
| ATOM | 1590 | C | ALA | A | 203 | −13.211 | −14.354 | −24.569 | 1.00 | 24.38 |
| ATOM | 1591 | O | ALA | A | 203 | −13.264 | −15.244 | −25.411 | 1.00 | 25.21 |
| ATOM | 1592 | N | ALA | A | 204 | −13.920 | −14.363 | −23.447 | 1.00 | 25.20 |
| ATOM | 1593 | CA | ALA | A | 204 | −14.849 | −15.442 | −23.093 | 1.00 | 26.63 |
| ATOM | 1594 | CB | ALA | A | 204 | −15.450 | −15.186 | −21.727 | 1.00 | 26.12 |
| ATOM | 1595 | C | ALA | A | 204 | −15.939 | −15.583 | −24.150 | 1.00 | 27.48 |
| ATOM | 1596 | O | ALA | A | 204 | −16.267 | −16.687 | −24.564 | 1.00 | 28.39 |
| ATOM | 1597 | N | THR | A | 205 | −16.494 | −14.461 | −24.593 | 1.00 | 27.71 |
| ATOM | 1598 | CA | THR | A | 205 | −17.497 | −14.470 | −25.652 | 1.00 | 28.39 |
| ATOM | 1599 | CB | THR | A | 205 | −18.088 | −13.051 | −25.855 | 1.00 | 28.42 |
| ATOM | 1600 | OG1 | THR | A | 205 | −18.669 | −12.631 | −24.622 | 1.00 | 29.32 |
| ATOM | 1601 | CG2 | THR | A | 205 | −19.150 | −13.051 | −26.932 | 1.00 | 27.32 |
| ATOM | 1602 | C | THR | A | 205 | −16.968 | −15.004 | −26.981 | 1.00 | 28.72 |
| ATOM | 1603 | O | THR | A | 205 | −17.697 | −15.690 | −27.719 | 1.00 | 29.06 |
| ATOM | 1604 | N | LEU | A | 206 | −15.712 | −14.698 | −27.288 | 1.00 | 28.58 |
| ATOM | 1605 | CA | LEU | A | 206 | −15.122 | −15.122 | −28.539 | 1.00 | 29.40 |
| ATOM | 1606 | CB | LEU | A | 206 | −14.034 | −14.144 | −29.001 | 1.00 | 29.40 |
| ATOM | 1607 | CG | LEU | A | 206 | −14.438 | −12.694 | −29.322 | 1.00 | 29.97 |
| ATOM | 1608 | CD1 | LEU | A | 206 | −13.212 | −11.899 | −29.755 | 1.00 | 30.30 |
| ATOM | 1609 | CD2 | LEU | A | 206 | −15.561 | −12.629 | −30.375 | 1.00 | 29.58 |
| ATOM | 1610 | C | LEU | A | 206 | −14.540 | −16.538 | −28.489 | 1.00 | 29.55 |
| ATOM | 1611 | O | LEU | A | 206 | −14.118 | −17.054 | −29.521 | 1.00 | 30.16 |
| ATOM | 1612 | N | GLY | A | 207 | −14.500 | −17.145 | −27.307 | 1.00 | 30.30 |
| ATOM | 1613 | CA | GLY | A | 207 | −13.786 | −18.419 | −27.122 | 1.00 | 30.91 |
| ATOM | 1614 | C | GLY | A | 207 | −12.294 | −18.274 | −27.375 | 1.00 | 31.55 |
| ATOM | 1615 | O | GLY | A | 207 | −11.654 | −19.173 | −27.935 | 1.00 | 31.31 |
| ATOM | 1616 | N | GLN | A | 208 | −11.746 | −17.115 | −26.989 | 1.00 | 31.08 |
| ATOM | 1617 | CA | GLN | A | 208 | −10.311 | −16.877 | −27.031 | 1.00 | 31.10 |
| ATOM | 1618 | CB | GLN | A | 208 | −9.999 | −15.540 | −27.703 | 1.00 | 31.08 |
| ATOM | 1619 | CG | GLN | A | 208 | −10.451 | −15.455 | −29.142 | 1.00 | 33.86 |
| ATOM | 1620 | CD | GLN | A | 208 | −9.469 | −16.059 | −30.126 | 1.00 | 38.19 |
| ATOM | 1621 | OE1 | GLN | A | 208 | −9.686 | −15.999 | −31.335 | 1.00 | 41.96 |
| ATOM | 1622 | NE2 | GLN | A | 208 | −8.386 | −16.633 | −29.626 | 1.00 | 38.96 |
| ATOM | 1623 | C | GLN | A | 208 | −9.765 | −16.909 | −25.611 | 1.00 | 30.45 |
| ATOM | 1624 | O | GLN | A | 208 | −10.516 | −17.048 | −24.658 | 1.00 | 30.63 |
| ATOM | 1625 | N | SER | A | 209 | −8.451 | −16.816 | −25.469 | 1.00 | 29.96 |
| ATOM | 1626 | CA | SER | A | 209 | −7.841 | −16.898 | −24.160 | 1.00 | 30.04 |
| ATOM | 1627 | CB | SER | A | 209 | −6.382 | −17.343 | −24.297 | 1.00 | 30.04 |
| ATOM | 1628 | OG | SER | A | 209 | −5.763 | −17.371 | −23.030 | 1.00 | 32.75 |
| ATOM | 1629 | C | SER | A | 209 | −7.948 | −15.564 | −23.409 | 1.00 | 29.53 |
| ATOM | 1630 | O | SER | A | 209 | −7.493 | −14.532 | −23.908 | 1.00 | 29.85 |
| ATOM | 1631 | N | GLY | A | 210 | −8.545 | −15.594 | −22.216 | 1.00 | 28.41 |
| ATOM | 1632 | CA | GLY | A | 210 | −8.745 | −14.388 | −21.401 | 1.00 | 27.16 |
| ATOM | 1633 | C | GLY | A | 210 | −8.344 | −14.480 | −19.938 | 1.00 | 26.83 |
| ATOM | 1634 | O | GLY | A | 210 | −8.425 | −13.498 | −19.203 | 1.00 | 26.61 |
| ATOM | 1635 | N | SER | A | 211 | −7.888 | −15.648 | −19.497 | 1.00 | 25.85 |
| ATOM | 1636 | CA | SER | A | 211 | −7.651 | −15.867 | −18.067 | 1.00 | 25.26 |
| ATOM | 1637 | CB | SER | A | 211 | −7.401 | −17.353 | −17.783 | 1.00 | 25.87 |
| ATOM | 1638 | OG | SER | A | 211 | −6.315 | −17.789 | −18.573 | 1.00 | 26.62 |
| ATOM | 1639 | C | SER | A | 211 | −6.509 | −15.026 | −17.498 | 1.00 | 24.55 |
| ATOM | 1640 | O | SER | A | 211 | −6.542 | −14.676 | −16.311 | 1.00 | 24.46 |
| ATOM | 1641 | N | ALA | A | 212 | −5.505 | −14.712 | −18.323 | 1.00 | 23.56 |
| ATOM | 1642 | CA | ALA | A | 212 | −4.423 | −13.816 | −17.906 | 1.00 | 23.42 |

TABLE 6-continued

| | | | | | | | | |
|---|---|---|---|---|---|---|---|---|
| ATOM | 1643 | CB | ALA | A | 212 | −3.417 | −13.622 | −19.031 | 1.00 | 23.66 |
| ATOM | 1644 | C | ALA | A | 212 | −4.999 | −12.450 | −17.496 | 1.00 | 23.54 |
| ATOM | 1645 | O | ALA | A | 212 | −4.566 | −11.848 | −16.513 | 1.00 | 24.00 |
| ATOM | 1646 | N | TYR | A | 213 | −5.970 | −11.979 | −18.271 | 1.00 | 22.79 |
| ATOM | 1647 | CA | TYR | A | 213 | −6.594 | −10.676 | −18.017 | 1.00 | 22.18 |
| ATOM | 1648 | CB | TYR | A | 213 | −7.453 | −10.241 | −19.193 | 1.00 | 21.74 |
| ATOM | 1649 | CG | TYR | A | 213 | −6.761 | −10.345 | −20.515 | 1.00 | 20.05 |
| ATOM | 1650 | CD1 | TYR | A | 213 | −7.461 | −10.761 | −21.637 | 1.00 | 20.58 |
| ATOM | 1651 | CE1 | TYR | A | 213 | −6.854 | −10.854 | −22.868 | 1.00 | 21.95 |
| ATOM | 1652 | CZ | TYR | A | 213 | −5.503 | −10.545 | −22.988 | 1.00 | 20.62 |
| ATOM | 1653 | OH | TYR | A | 213 | −4.930 | −10.668 | −24.220 | 1.00 | 21.72 |
| ATOM | 1654 | CE2 | TYR | A | 213 | −4.758 | −10.149 | −21.888 | 1.00 | 19.76 |
| ATOM | 1655 | CD2 | TYR | A | 213 | −5.400 | −10.038 | −20.647 | 1.00 | 20.61 |
| ATOM | 1656 | C | TYR | A | 213 | −7.423 | −10.710 | −16.758 | 1.00 | 23.06 |
| ATOM | 1657 | O | TYR | A | 213 | −7.320 | −9.804 | −15.939 | 1.00 | 22.56 |
| ATOM | 1658 | N | SER | A | 214 | −8.226 | −11.767 | −16.578 | 1.00 | 23.15 |
| ATOM | 1659 | CA | SER | A | 214 | −9.064 | −11.832 | −15.392 | 1.00 | 23.90 |
| ATOM | 1660 | CB | SER | A | 214 | −10.244 | −12.798 | −15.580 | 1.00 | 24.54 |
| ATOM | 1661 | OG | SER | A | 214 | −9.776 | −14.085 | −15.939 | 1.00 | 27.95 |
| ATOM | 1662 | C | SER | A | 214 | −8.259 | −12.122 | −14.122 | 1.00 | 23.64 |
| ATOM | 1663 | O | SER | A | 214 | −8.676 | −11.762 | −13.026 | 1.00 | 23.43 |
| ATOM | 1664 | N | SER | A | 215 | −7.095 | −12.743 | −14.248 | 1.00 | 23.82 |
| ATOM | 1665 | CA | SER | A | 215 | −6.295 | −12.970 | −13.050 | 1.00 | 24.66 |
| ATOM | 1666 | CB | SER | A | 215 | −5.390 | −14.205 | −13.200 | 1.00 | 25.70 |
| ATOM | 1667 | OG | SER | A | 215 | −4.267 | −13.914 | −14.004 | 1.00 | 29.15 |
| ATOM | 1668 | C | SER | A | 215 | −5.491 | −11.739 | −12.610 | 1.00 | 23.98 |
| ATOM | 1669 | O | SER | A | 215 | −5.217 | −11.561 | −11.421 | 1.00 | 24.09 |
| ATOM | 1670 | N | VAL | A | 216 | −5.115 | −10.894 | −13.566 | 1.00 | 22.89 |
| ATOM | 1671 | CA | VAL | A | 216 | −4.347 | −9.679 | −13.272 | 1.00 | 22.50 |
| ATOM | 1672 | CB | VAL | A | 216 | −3.442 | −9.296 | −14.493 | 1.00 | 22.52 |
| ATOM | 1673 | CG1 | VAL | A | 216 | −2.855 | −7.888 | −14.369 | 1.00 | 24.11 |
| ATOM | 1674 | CG2 | VAL | A | 216 | −2.296 | −10.317 | −14.652 | 1.00 | 22.49 |
| ATOM | 1675 | C | VAL | A | 216 | −5.256 | −8.520 | −12.801 | 1.00 | 21.88 |
| ATOM | 1676 | O | VAL | A | 216 | −4.869 | −7.745 | −11.936 | 1.00 | 21.84 |
| ATOM | 1677 | N | ALA | A | 217 | −6.475 | −8.440 | −13.332 | 1.00 | 21.86 |
| ATOM | 1678 | CA | ALA | A | 217 | −7.374 | −7.303 | −13.050 | 1.00 | 21.59 |
| ATOM | 1679 | CB | ALA | A | 217 | −8.721 | −7.479 | −13.760 | 1.00 | 21.26 |
| ATOM | 1680 | C | ALA | A | 217 | −7.571 | −6.968 | −11.558 | 1.00 | 21.55 |
| ATOM | 1681 | O | ALA | A | 217 | −7.447 | −5.804 | −11.165 | 1.00 | 21.20 |
| ATOM | 1682 | N | PRO | A | 218 | −7.842 | −7.988 | −10.701 | 1.00 | 21.95 |
| ATOM | 1683 | CA | PRO | A | 218 | −8.030 | −7.700 | −9.282 | 1.00 | 21.59 |
| ATOM | 1684 | CB | PRO | A | 218 | −8.283 | −9.104 | −8.670 | 1.00 | 22.29 |
| ATOM | 1685 | CG | PRO | A | 218 | −8.789 | −9.905 | −9.789 | 1.00 | 22.61 |
| ATOM | 1686 | CD | PRO | A | 218 | −7.966 | −9.435 | −10.963 | 1.00 | 22.11 |
| ATOM | 1687 | C | PRO | A | 218 | −6.798 | −7.065 | −8.634 | 1.00 | 21.27 |
| ATOM | 1688 | O | PRO | A | 218 | −6.928 | −6.299 | −7.680 | 1.00 | 20.92 |
| ATOM | 1689 | N | GLN | A | 219 | −5.608 | −7.386 | −9.141 | 1.00 | 21.17 |
| ATOM | 1690 | CA | GLN | A | 219 | −4.378 | −6.786 | −8.609 | 1.00 | 21.51 |
| ATOM | 1691 | CB | GLN | A | 219 | −3.149 | −7.569 | −9.084 | 1.00 | 22.72 |
| ATOM | 1692 | CG | GLN | A | 219 | −3.113 | −8.985 | −8.516 | 1.00 | 24.90 |
| ATOM | 1693 | CD | GLN | A | 219 | −3.323 | −8.982 | −7.015 | 1.00 | 29.57 |
| ATOM | 1694 | OE1 | GLN | A | 219 | −2.715 | −8.188 | −6.288 | 1.00 | 31.58 |
| ATOM | 1695 | NE2 | GLN | A | 219 | −4.207 | −9.843 | −6.545 | 1.00 | 33.22 |
| ATOM | 1696 | C | GLN | A | 219 | −4.240 | −5.301 | −8.996 | 1.00 | 21.04 |
| ATOM | 1697 | O | GLN | A | 219 | −3.687 | −4.490 | −8.229 | 1.00 | 21.07 |
| ATOM | 1698 | N | VAL | A | 220 | −4.728 | −4.973 | −10.187 | 1.00 | 20.00 |
| ATOM | 1699 | CA | VAL | A | 220 | −4.746 | −3.577 | −10.630 | 1.00 | 19.34 |
| ATOM | 1700 | CB | VAL | A | 220 | −5.098 | −3.456 | −12.128 | 1.00 | 19.63 |
| ATOM | 1701 | CG1 | VAL | A | 220 | −4.991 | −2.000 | −12.581 | 1.00 | 19.15 |
| ATOM | 1702 | CG2 | VAL | A | 220 | −4.162 | −4.342 | −12.974 | 1.00 | 17.97 |
| ATOM | 1703 | C | VAL | A | 220 | −5.730 | −2.809 | −9.737 | 1.00 | 19.65 |
| ATOM | 1704 | O | VAL | A | 220 | −5.419 | −1.728 | −9.257 | 1.00 | 18.97 |
| ATOM | 1705 | N | LEU | A | 221 | −6.903 | −3.391 | −9.490 | 1.00 | 20.12 |
| ATOM | 1706 | CA | LEU | A | 221 | −7.895 | −2.776 | −8.620 | 1.00 | 20.83 |
| ATOM | 1707 | CB | LEU | A | 221 | −9.180 | −3.602 | −8.599 | 1.00 | 20.48 |
| ATOM | 1708 | CG | LEU | A | 221 | −10.336 | −2.991 | −7.790 | 1.00 | 22.48 |
| ATOM | 1709 | CD1 | LEU | A | 221 | −10.857 | −1.726 | −8.458 | 1.00 | 22.33 |
| ATOM | 1710 | CD2 | LEU | A | 221 | −11.430 | −4.011 | −7.637 | 1.00 | 22.51 |
| ATOM | 1711 | C | LEU | A | 221 | −7.360 | −2.591 | −7.192 | 1.00 | 21.44 |
| ATOM | 1712 | O | LEU | A | 221 | −7.617 | −1.578 | −6.539 | 1.00 | 20.45 |
| ATOM | 1713 | N | CYS | A | 222 | −6.600 | −3.572 | −6.718 | 1.00 | 22.60 |
| ATOM | 1714 | CA | CYS | A | 222 | −5.957 | −3.477 | −5.415 | 1.00 | 22.10 |
| ATOM | 1715 | CB | CYS | A | 222 | −5.159 | −4.749 | −5.125 | 1.00 | 23.41 |
| ATOM | 1716 | SG | CYS | A | 222 | −4.975 | −5.000 | −3.356 | 1.00 | 28.49 |
| ATOM | 1717 | C | CYS | A | 222 | −5.035 | −2.270 | −5.317 | 1.00 | 21.22 |
| ATOM | 1718 | O | CYS | A | 222 | −5.060 | −1.531 | −4.331 | 1.00 | 21.24 |
| ATOM | 1719 | N | PHE | A | 223 | −4.210 | −2.070 | −6.347 | 1.00 | 20.11 |
| ATOM | 1720 | CA | PHE | A | 223 | −3.287 | −0.955 | −6.368 | 1.00 | 19.03 |
| ATOM | 1721 | CB | PHE | A | 223 | −2.334 | −1.108 | −7.558 | 1.00 | 19.15 |
| ATOM | 1722 | CG | PHE | A | 223 | −1.297 | −0.011 | −7.669 | 1.00 | 19.23 |

TABLE 6-continued

| | | | | | | | | |
|---|---|---|---|---|---|---|---|---|
| ATOM | 1723 | CD1 | PHE | A | 223 | −0.576 | 0.410 | −6.558 | 1.00 | 19.90 |
| ATOM | 1724 | CE1 | PHE | A | 223 | 0.380 | 1.417 | −6.661 | 1.00 | 20.91 |
| ATOM | 1725 | CZ | PHE | A | 223 | 0.645 | 2.017 | −7.902 | 1.00 | 21.07 |
| ATOM | 1726 | CE2 | PHE | A | 223 | −0.061 | 1.598 | −9.024 | 1.00 | 18.81 |
| ATOM | 1727 | CD2 | PHE | A | 223 | −1.022 | 0.581 | −8.909 | 1.00 | 18.23 |
| ATOM | 1728 | C | PHE | A | 223 | −4.032 | 0.397 | −6.423 | 1.00 | 18.38 |
| ATOM | 1729 | O | PHE | A | 223 | −3.597 | 1.376 | −5.818 | 1.00 | 18.27 |
| ATOM | 1730 | N | LEU | A | 224 | −5.148 | 0.428 | −7.142 | 1.00 | 18.45 |
| ATOM | 1731 | CA | LEU | A | 224 | −5.957 | 1.665 | −7.277 | 1.00 | 18.42 |
| ATOM | 1732 | CB | LEU | A | 224 | −7.208 | 1.403 | −8.127 | 1.00 | 17.70 |
| ATOM | 1733 | CG | LEU | A | 224 | −7.990 | 2.645 | −8.610 | 1.00 | 19.73 |
| ATOM | 1734 | CD1 | LEU | A | 224 | −7.133 | 3.427 | −9.584 | 1.00 | 20.37 |
| ATOM | 1735 | CD2 | LEU | A | 224 | −9.302 | 2.228 | −9.264 | 1.00 | 18.64 |
| ATOM | 1736 | C | LEU | A | 224 | −6.385 | 2.226 | −5.917 | 1.00 | 18.87 |
| ATOM | 1737 | O | LEU | A | 224 | −6.553 | 3.438 | −5.757 | 1.00 | 18.45 |
| ATOM | 1738 | N | GLN | A | 225 | −6.578 | 1.336 | −4.944 | 1.00 | 19.17 |
| ATOM | 1739 | CA | GLN | A | 225 | −6.984 | 1.743 | −3.585 | 1.00 | 20.00 |
| ATOM | 1740 | CB | GLN | A | 225 | −7.340 | 0.511 | −2.725 | 1.00 | 20.26 |
| ATOM | 1741 | CG | GLN | A | 225 | −8.295 | −0.463 | −3.409 | 1.00 | 21.22 |
| ATOM | 1742 | CD | GLN | A | 225 | −9.519 | 0.225 | −3.993 | 1.00 | 22.53 |
| ATOM | 1743 | OE1 | GLN | A | 225 | −10.280 | 0.870 | −3.262 | 1.00 | 23.09 |
| ATOM | 1744 | NE2 | GLN | A | 225 | −9.718 | 0.092 | −5.302 | 1.00 | 19.33 |
| ATOM | 1745 | C | GLN | A | 225 | −5.944 | 2.599 | −2.871 | 1.00 | 20.19 |
| ATOM | 1746 | O | GLN | A | 225 | −6.299 | 3.399 | −2.009 | 1.00 | 20.64 |
| ATOM | 1747 | N | ARG | A | 226 | −4.678 | 2.450 | −3.253 | 1.00 | 20.51 |
| ATOM | 1748 | CA | ARG | A | 226 | −3.564 | 3.144 | −2.608 | 1.00 | 21.40 |
| ATOM | 1749 | CB | ARG | A | 226 | −2.219 | 2.505 | −2.990 | 1.00 | 22.72 |
| ATOM | 1750 | CG | ARG | A | 226 | −2.081 | 1.010 | −2.683 | 1.00 | 26.14 |
| ATOM | 1751 | CD | ARG | A | 226 | −1.806 | 0.741 | −1.204 | 1.00 | 32.16 |
| ATOM | 1752 | NE | ARG | A | 226 | −3.035 | 0.843 | −0.432 | 1.00 | 37.77 |
| ATOM | 1753 | CZ | ARG | A | 226 | −3.997 | −0.079 | −0.413 | 1.00 | 41.09 |
| ATOM | 1754 | NH1 | ARG | A | 226 | −5.093 | 0.120 | 0.322 | 1.00 | 42.17 |
| ATOM | 1755 | NH2 | ARG | A | 226 | −3.874 | −1.196 | −1.127 | 1.00 | 42.78 |
| ATOM | 1756 | C | ARG | A | 226 | −3.499 | 4.645 | −2.915 | 1.00 | 21.23 |
| ATOM | 1757 | O | ARG | A | 226 | −2.723 | 5.358 | −2.288 | 1.00 | 20.95 |
| ATOM | 1758 | N | PHE | A | 227 | −4.298 | 5.123 | −3.869 | 1.00 | 20.28 |
| ATOM | 1759 | CA | PHE | A | 227 | −4.280 | 6.545 | −4.250 | 1.00 | 19.67 |
| ATOM | 1760 | CB | PHE | A | 227 | −4.777 | 6.704 | −5.693 | 1.00 | 19.40 |
| ATOM | 1761 | CG | PHE | A | 227 | −3.814 | 6.195 | −6.744 | 1.00 | 18.28 |
| ATOM | 1762 | CD1 | PHE | A | 227 | −3.733 | 4.831 | −7.040 | 1.00 | 18.14 |
| ATOM | 1763 | CE1 | PHE | A | 227 | −2.855 | 4.355 | −8.046 | 1.00 | 18.24 |
| ATOM | 1764 | CZ | PHE | A | 227 | −2.034 | 5.264 | −8.748 | 1.00 | 16.75 |
| ATOM | 1765 | CE2 | PHE | A | 227 | −2.113 | 6.641 | −8.456 | 1.00 | 18.79 |
| ATOM | 1766 | CD2 | PHE | A | 227 | −3.005 | 7.091 | −7.452 | 1.00 | 17.51 |
| ATOM | 1767 | C | PHE | A | 227 | −5.126 | 7.435 | −3.343 | 1.00 | 20.55 |
| ATOM | 1768 | O | PHE | A | 227 | −4.967 | 8.659 | −3.334 | 1.00 | 20.38 |
| ATOM | 1769 | N | TRP | A | 228 | −6.032 | 6.820 | −2.583 | 1.00 | 20.72 |
| ATOM | 1770 | CA | TRP | A | 228 | −6.924 | 7.545 | −1.671 | 1.00 | 20.71 |
| ATOM | 1771 | CB | TRP | A | 228 | −8.036 | 6.596 | −1.211 | 1.00 | 20.41 |
| ATOM | 1772 | CG | TRP | A | 228 | −9.030 | 7.228 | −0.283 | 1.00 | 20.59 |
| ATOM | 1773 | CD1 | TRP | A | 228 | −9.243 | 6.915 | 1.040 | 1.00 | 21.81 |
| ATOM | 1774 | NE1 | TRP | A | 228 | −10.255 | 7.722 | 1.557 | 1.00 | 22.69 |
| ATOM | 1775 | CE2 | TRP | A | 228 | −10.712 | 8.553 | 0.565 | 1.00 | 20.71 |
| ATOM | 1776 | CD2 | TRP | A | 228 | −9.958 | 8.280 | −0.607 | 1.00 | 18.88 |
| ATOM | 1777 | CE3 | TRP | A | 228 | −10.225 | 9.014 | −1.772 | 1.00 | 18.79 |
| ATOM | 1778 | CZ3 | TRP | A | 228 | −11.209 | 9.986 | −1.734 | 1.00 | 20.13 |
| ATOM | 1779 | CH2 | TRP | A | 228 | −11.937 | 10.242 | −0.552 | 1.00 | 21.18 |
| ATOM | 1780 | CZ2 | TRP | A | 228 | −11.710 | 9.537 | 0.601 | 1.00 | 21.65 |
| ATOM | 1781 | C | TRP | A | 228 | −6.193 | 8.120 | −0.463 | 1.00 | 21.38 |
| ATOM | 1782 | O | TRP | A | 228 | −5.479 | 7.394 | 0.236 | 1.00 | 21.50 |
| ATOM | 1783 | N | VAL | A | 229 | −6.379 | 9.416 | −0.209 | 1.00 | 21.95 |
| ATOM | 1784 | CA | VAL | A | 229 | −5.844 | 10.065 | 0.983 | 1.00 | 22.99 |
| ATOM | 1785 | CB | VAL | A | 229 | −5.205 | 11.436 | 0.654 | 1.00 | 22.81 |
| ATOM | 1786 | CG1 | VAL | A | 229 | −4.490 | 12.026 | 1.871 | 1.00 | 23.48 |
| ATOM | 1787 | CG2 | VAL | A | 229 | −4.226 | 11.292 | −0.493 | 1.00 | 23.28 |
| ATOM | 1788 | C | VAL | A | 229 | −6.984 | 10.206 | 2.000 | 1.00 | 24.08 |
| ATOM | 1789 | O | VAL | A | 229 | −7.803 | 11.119 | 1.899 | 1.00 | 23.70 |
| ATOM | 1790 | N | SER | A | 230 | −7.044 | 9.298 | 2.974 | 1.00 | 25.37 |
| ATOM | 1791 | CA | SER | A | 230 | −8.193 | 9.290 | 3.905 | 1.00 | 27.59 |
| ATOM | 1792 | CB | SER | A | 230 | −8.254 | 8.000 | 4.728 | 1.00 | 27.67 |
| ATOM | 1793 | OG | SER | A | 230 | −7.029 | 7.805 | 5.402 | 1.00 | 31.30 |
| ATOM | 1794 | C | SER | A | 230 | −8.241 | 10.513 | 4.820 | 1.00 | 27.93 |
| ATOM | 1795 | O | SER | A | 230 | −9.321 | 10.983 | 5.174 | 1.00 | 28.91 |
| ATOM | 1796 | N | SER | A | 231 | −7.088 | 11.059 | 5.165 | 1.00 | 28.76 |
| ATOM | 1797 | CA | SER | A | 231 | −7.059 | 12.237 | 6.030 | 1.00 | 29.72 |
| ATOM | 1798 | CB | SER | A | 231 | −5.671 | 12.461 | 6.639 | 1.00 | 30.39 |
| ATOM | 1799 | OG | SER | A | 231 | −4.703 | 12.713 | 5.635 | 1.00 | 34.43 |
| ATOM | 1800 | C | SER | A | 231 | −7.566 | 13.491 | 5.323 | 1.00 | 29.39 |
| ATOM | 1801 | O | SER | A | 231 | −8.154 | 14.364 | 5.966 | 1.00 | 30.97 |
| ATOM | 1802 | N | GLY | A | 232 | −7.373 | 13.579 | 4.005 | 1.00 | 27.59 |

TABLE 6-continued

| | | | | | | | | | |
|---|---|---|---|---|---|---|---|---|---|
| ATOM | 1803 | CA | GLY | A | 232 | −7.867 | 14.728 | 3.247 | 1.00 | 25.22 |
| ATOM | 1804 | C | GLY | A | 232 | −9.181 | 14.518 | 2.493 | 1.00 | 23.25 |
| ATOM | 1805 | O | GLY | A | 232 | −9.810 | 15.487 | 2.077 | 1.00 | 23.19 |
| ATOM | 1806 | N | GLY | A | 233 | −9.589 | 13.265 | 2.320 | 1.00 | 20.97 |
| ATOM | 1807 | CA | GLY | A | 233 | −10.809 | 12.937 | 1.578 | 1.00 | 19.35 |
| ATOM | 1808 | C | GLY | A | 233 | −10.673 | 13.226 | 0.094 | 1.00 | 18.83 |
| ATOM | 1809 | O | GLY | A | 233 | −11.636 | 13.655 | −0.561 | 1.00 | 19.20 |
| ATOM | 1810 | N | TYR | A | 234 | −9.487 | 12.977 | −0.463 | 1.00 | 17.56 |
| ATOM | 1811 | CA | TYR | A | 234 | −9.309 | 13.155 | −1.915 | 1.00 | 17.17 |
| ATOM | 1812 | CB | TYR | A | 234 | −8.851 | 14.584 | −2.232 | 1.00 | 18.33 |
| ATOM | 1813 | CG | TYR | A | 234 | −7.441 | 14.876 | −1.758 | 1.00 | 20.39 |
| ATOM | 1814 | CD1 | TYR | A | 234 | −7.203 | 15.340 | −0.454 | 1.00 | 20.72 |
| ATOM | 1815 | CE1 | TYR | A | 234 | −5.905 | 15.594 | −0.018 | 1.00 | 24.11 |
| ATOM | 1816 | CZ | TYR | A | 234 | −4.840 | 15.399 | −0.897 | 1.00 | 23.78 |
| ATOM | 1817 | OH | TYR | A | 234 | −3.556 | 15.663 | −0.483 | 1.00 | 26.50 |
| ATOM | 1818 | CE2 | TYR | A | 234 | −5.055 | 14.956 | −2.187 | 1.00 | 24.07 |
| ATOM | 1819 | CD2 | TYR | A | 234 | −6.353 | 14.699 | −2.611 | 1.00 | 20.58 |
| ATOM | 1820 | C | TYR | A | 234 | −8.318 | 12.141 | −2.482 | 1.00 | 16.60 |
| ATOM | 1821 | O | TYR | A | 234 | −7.615 | 11.465 | −1.735 | 1.00 | 16.29 |
| ATOM | 1822 | N | VAL | A | 235 | −8.260 | 12.059 | −3.805 | 1.00 | 15.36 |
| ATOM | 1823 | CA | VAL | A | 235 | −7.325 | 11.164 | −4.472 | 1.00 | 15.62 |
| ATOM | 1824 | CB | VAL | A | 235 | −7.948 | 10.638 | −5.798 | 1.00 | 15.96 |
| ATOM | 1825 | CG1 | VAL | A | 235 | −6.889 | 9.893 | −6.645 | 1.00 | 17.31 |
| ATOM | 1826 | CG2 | VAL | A | 235 | −9.134 | 9.723 | −5.506 | 1.00 | 15.87 |
| ATOM | 1827 | C | VAL | A | 235 | −6.011 | 11.904 | −4.742 | 1.00 | 15.54 |
| ATOM | 1828 | O | VAL | A | 235 | −6.006 | 12.998 | −5.320 | 1.00 | 15.39 |
| ATOM | 1829 | N | ASP | A | 236 | −4.886 | 11.316 | −4.325 | 1.00 | 15.24 |
| ATOM | 1830 | CA | ASP | A | 236 | −3.580 | 11.837 | −4.705 | 1.00 | 15.22 |
| ATOM | 1831 | CB | ASP | A | 236 | −2.533 | 11.431 | −3.652 | 1.00 | 16.45 |
| ATOM | 1832 | CG | ASP | A | 236 | −1.145 | 11.922 | −3.970 | 1.00 | 18.62 |
| ATOM | 1833 | OD1 | ASP | A | 236 | −0.937 | 12.617 | −4.992 | 1.00 | 17.17 |
| ATOM | 1834 | OD2 | ASP | A | 236 | −0.223 | 11.568 | −3.182 | 1.00 | 22.79 |
| ATOM | 1835 | C | ASP | A | 236 | −3.303 | 11.256 | −6.098 | 1.00 | 15.06 |
| ATOM | 1836 | O | ASP | A | 236 | −3.088 | 10.040 | −6.261 | 1.00 | 15.39 |
| ATOM | 1837 | N | SER | A | 237 | −3.384 | 12.104 | −7.125 | 1.00 | 14.24 |
| ATOM | 1838 | CA | SER | A | 237 | −3.518 | 11.587 | −8.503 | 1.00 | 14.09 |
| ATOM | 1839 | CB | SER | A | 237 | −4.000 | 12.697 | −9.446 | 1.00 | 13.76 |
| ATOM | 1840 | OG | SER | A | 237 | −5.312 | 13.094 | −9.070 | 1.00 | 14.52 |
| ATOM | 1841 | C | SER | A | 237 | −2.277 | 10.883 | −9.053 | 1.00 | 14.22 |
| ATOM | 1842 | O | SER | A | 237 | −2.376 | 10.067 | −9.965 | 1.00 | 13.80 |
| ATOM | 1843 | N | ASN | A | 238 | −1.099 | 11.219 | −8.521 | 1.00 | 14.70 |
| ATOM | 1844 | CA | ASN | A | 238 | 0.116 | 10.547 | −8.952 | 1.00 | 15.28 |
| ATOM | 1845 | CB | ASN | A | 238 | 0.968 | 11.439 | −9.856 | 1.00 | 14.84 |
| ATOM | 1846 | CG | ASN | A | 238 | 0.277 | 11.742 | −11.176 | 1.00 | 17.08 |
| ATOM | 1847 | OD1 | ASN | A | 238 | 0.244 | 10.901 | −12.072 | 1.00 | 16.61 |
| ATOM | 1848 | ND2 | ASN | A | 238 | −0.308 | 12.932 | −11.278 | 1.00 | 16.63 |
| ATOM | 1849 | C | ASN | A | 238 | 0.912 | 10.150 | −7.736 | 1.00 | 16.07 |
| ATOM | 1850 | O | ASN | A | 238 | 1.169 | 10.988 | −6.890 | 1.00 | 15.88 |
| ATOM | 1851 | N | ILE | A | 239 | 1.280 | 8.875 | −7.659 | 1.00 | 16.09 |
| ATOM | 1852 | CA | ILE | A | 239 | 2.125 | 8.410 | −6.567 | 1.00 | 18.07 |
| ATOM | 1853 | CB | ILE | A | 239 | 1.340 | 7.452 | −5.600 | 1.00 | 17.66 |
| ATOM | 1854 | CG1 | ILE | A | 239 | 0.893 | 6.180 | −6.336 | 1.00 | 18.85 |
| ATOM | 1855 | CD1 | ILE | A | 239 | 0.184 | 5.109 | −5.437 | 1.00 | 19.02 |
| ATOM | 1856 | CG2 | ILE | A | 239 | 0.116 | 8.194 | −4.974 | 1.00 | 16.96 |
| ATOM | 1857 | C | ILE | A | 239 | 3.381 | 7.760 | −7.169 | 1.00 | 19.32 |
| ATOM | 1858 | O | ILE | A | 239 | 3.571 | 7.797 | −8.392 | 1.00 | 19.19 |
| ATOM | 1859 | N | ASN | A | 240 | 4.242 | 7.170 | −6.329 | 1.00 | 20.56 |
| ATOM | 1860 | CA | ASN | A | 240 | 5.517 | 6.617 | −6.823 | 1.00 | 22.24 |
| ATOM | 1861 | CB | ASN | A | 240 | 5.275 | 5.385 | −7.717 | 1.00 | 21.93 |
| ATOM | 1862 | CG | ASN | A | 240 | 4.874 | 4.153 | −6.926 | 1.00 | 24.19 |
| ATOM | 1863 | OD1 | ASN | A | 240 | 5.269 | 3.995 | −5.772 | 1.00 | 25.98 |
| ATOM | 1864 | ND2 | ASN | A | 240 | 4.083 | 3.278 | −7.538 | 1.00 | 22.26 |
| ATOM | 1865 | C | ASN | A | 240 | 6.334 | 7.677 | −7.571 | 1.00 | 23.27 |
| ATOM | 1866 | O | ASN | A | 240 | 7.000 | 7.381 | −8.562 | 1.00 | 23.15 |
| ATOM | 1867 | N | THR | A | 241 | 6.261 | 8.919 | −7.096 | 1.00 | 25.02 |
| ATOM | 1868 | CA | THR | A | 241 | 6.939 | 10.038 | −7.729 | 1.00 | 28.12 |
| ATOM | 1869 | CB | THR | A | 241 | 6.044 | 10.720 | −8.817 | 1.00 | 28.09 |
| ATOM | 1870 | OG1 | THR | A | 241 | 6.741 | 11.836 | −9.369 | 1.00 | 28.75 |
| ATOM | 1871 | CG2 | THR | A | 241 | 4.727 | 11.208 | −8.231 | 1.00 | 28.30 |
| ATOM | 1872 | C | THR | A | 241 | 7.302 | 11.065 | −6.674 | 1.00 | 29.96 |
| ATOM | 1873 | O | THR | A | 241 | 6.749 | 11.037 | −5.589 | 1.00 | 30.58 |
| ATOM | 1874 | N | ASN | A | 242 | 8.209 | 11.984 | −6.991 | 1.00 | 33.17 |
| ATOM | 1875 | CA | ASN | A | 242 | 8.585 | 13.019 | −6.024 | 1.00 | 36.07 |
| ATOM | 1876 | CB | ASN | A | 242 | 10.059 | 12.880 | −5.616 | 1.00 | 37.13 |
| ATOM | 1877 | CG | ASN | A | 242 | 10.324 | 11.631 | −4.771 | 1.00 | 40.96 |
| ATOM | 1878 | OD1 | ASN | A | 242 | 9.509 | 11.235 | −3.921 | 1.00 | 45.33 |
| ATOM | 1879 | ND2 | ASN | A | 242 | 11.477 | 11.007 | −4.998 | 1.00 | 44.43 |
| ATOM | 1880 | C | ASN | A | 242 | 8.321 | 14.427 | −6.528 | 1.00 | 37.00 |
| ATOM | 1881 | O | ASN | A | 242 | 9.091 | 15.346 | −6.245 | 1.00 | 37.94 |
| ATOM | 1882 | N | GLU | A | 243 | 7.210 | 14.602 | −7.233 | 1.00 | 37.54 |

TABLE 6-continued

| | | | | | | | | | |
|---|---|---|---|---|---|---|---|---|---|
| ATOM | 1883 | CA | GLU | A | 243 | 6.895 | 15.869 | −7.907 | 1.00 | 38.05 |
| ATOM | 1884 | CB | GLU | A | 243 | 5.775 | 15.638 | −8.925 | 1.00 | 38.77 |
| ATOM | 1885 | CG | GLU | A | 243 | 5.650 | 16.732 | −9.977 | 1.00 | 42.65 |
| ATOM | 1886 | CD | GLU | A | 243 | 6.959 | 16.985 | −10.709 | 1.00 | 47.49 |
| ATOM | 1887 | OE1 | GLU | A | 243 | 7.424 | 16.084 | −11.453 | 1.00 | 49.14 |
| ATOM | 1888 | OE2 | GLU | A | 243 | 7.520 | 18.090 | −10.532 | 1.00 | 50.15 |
| ATOM | 1889 | C | GLU | A | 243 | 6.559 | 17.088 | −7.015 | 1.00 | 37.15 |
| ATOM | 1890 | O | GLU | A | 243 | 6.645 | 18.240 | −7.469 | 1.00 | 38.39 |
| ATOM | 1891 | N | GLY | A | 244 | 6.174 | 16.873 | −5.766 | 1.00 | 35.69 |
| ATOM | 1892 | CA | GLY | A | 244 | 5.858 | 18.019 | −4.911 | 1.00 | 33.51 |
| ATOM | 1893 | C | GLY | A | 244 | 4.609 | 18.775 | −5.369 | 1.00 | 31.80 |
| ATOM | 1894 | O | GLY | A | 244 | 4.634 | 19.999 | −5.535 | 1.00 | 33.32 |
| ATOM | 1895 | N | ARG | A | 245 | 3.529 | 18.036 | −5.612 | 1.00 | 27.92 |
| ATOM | 1896 | CA | ARG | A | 245 | 2.200 | 18.618 | −5.781 | 1.00 | 24.21 |
| ATOM | 1897 | CB | ARG | A | 245 | 1.638 | 18.224 | −7.130 | 1.00 | 24.30 |
| ATOM | 1898 | CG | ARG | A | 245 | 2.410 | 18.842 | −8.275 | 1.00 | 24.62 |
| ATOM | 1899 | CD | ARG | A | 245 | 1.625 | 18.681 | −9.532 | 1.00 | 22.11 |
| ATOM | 1900 | NE | ARG | A | 245 | 2.462 | 18.829 | −10.713 | 1.00 | 21.13 |
| ATOM | 1901 | CZ | ARG | A | 245 | 2.114 | 18.302 | −11.878 | 1.00 | 21.50 |
| ATOM | 1902 | NH1 | ARG | A | 245 | 0.982 | 17.621 | −11.945 | 1.00 | 18.57 |
| ATOM | 1903 | NH2 | ARG | A | 245 | 2.883 | 18.443 | −12.951 | 1.00 | 20.83 |
| ATOM | 1904 | C | ARG | A | 245 | 1.295 | 18.040 | −4.718 | 1.00 | 21.84 |
| ATOM | 1905 | O | ARG | A | 245 | 1.624 | 17.021 | −4.128 | 1.00 | 20.65 |
| ATOM | 1906 | N | THR | A | 246 | 0.140 | 18.652 | −4.483 | 1.00 | 19.15 |
| ATOM | 1907 | CA | THR | A | 246 | −0.824 | 18.058 | −3.540 | 1.00 | 17.46 |
| ATOM | 1908 | CB | THR | A | 246 | −1.989 | 18.997 | −3.238 | 1.00 | 17.87 |
| ATOM | 1909 | OG1 | THR | A | 246 | −2.752 | 19.155 | −4.440 | 1.00 | 15.85 |
| ATOM | 1910 | CG2 | THR | A | 246 | −1.495 | 20.370 | −2.730 | 1.00 | 17.50 |
| ATOM | 1911 | C | THR | A | 246 | −1.426 | 16.769 | −4.103 | 1.00 | 17.25 |
| ATOM | 1912 | O | THR | A | 246 | −1.884 | 15.914 | −3.351 | 1.00 | 17.57 |
| ATOM | 1913 | N | GLY | A | 247 | −1.482 | 16.646 | −5.430 | 1.00 | 15.60 |
| ATOM | 1914 | CA | GLY | A | 247 | −2.148 | 15.492 | −6.054 | 1.00 | 15.02 |
| ATOM | 1915 | C | GLY | A | 247 | −3.609 | 15.761 | −6.396 | 1.00 | 14.69 |
| ATOM | 1916 | O | GLY | A | 247 | −4.260 | 14.939 | −7.059 | 1.00 | 14.45 |
| ATOM | 1917 | N | LYS | A | 248 | −4.137 | 16.890 | −5.928 | 1.00 | 13.43 |
| ATOM | 1918 | CA | LYS | A | 248 | −5.508 | 17.286 | −6.259 | 1.00 | 13.00 |
| ATOM | 1919 | CB | LYS | A | 248 | −5.969 | 18.453 | −5.396 | 1.00 | 12.32 |
| ATOM | 1920 | CG | LYS | A | 248 | −5.965 | 18.179 | −3.881 | 1.00 | 13.12 |
| ATOM | 1921 | CD | LYS | A | 248 | −6.133 | 19.493 | −3.102 | 1.00 | 14.08 |
| ATOM | 1922 | CE | LYS | A | 248 | −5.985 | 19.253 | −1.584 | 1.00 | 17.84 |
| ATOM | 1923 | NZ | LYS | A | 248 | −6.335 | 20.492 | −0.835 | 1.00 | 16.74 |
| ATOM | 1924 | C | LYS | A | 248 | −5.490 | 17.713 | −7.736 | 1.00 | 12.73 |
| ATOM | 1925 | O | LYS | A | 248 | −4.866 | 18.707 | −8.104 | 1.00 | 12.75 |
| ATOM | 1926 | N | ASP | A | 249 | −6.185 | 16.964 | −8.580 | 1.00 | 11.92 |
| ATOM | 1927 | CA | ASP | A | 249 | −5.958 | 17.098 | −10.024 | 1.00 | 11.16 |
| ATOM | 1928 | CB | ASP | A | 249 | −4.761 | 16.199 | −10.385 | 1.00 | 10.83 |
| ATOM | 1929 | CG | ASP | A | 249 | −4.268 | 16.349 | −11.831 | 1.00 | 12.54 |
| ATOM | 1930 | OD1 | ASP | A | 249 | −5.078 | 16.422 | −12.785 | 1.00 | 11.42 |
| ATOM | 1931 | OD2 | ASP | A | 249 | −3.025 | 16.342 | −12.001 | 1.00 | 13.30 |
| ATOM | 1932 | C | ASP | A | 249 | −7.232 | 16.577 | −10.662 | 1.00 | 11.38 |
| ATOM | 1933 | O | ASP | A | 249 | −7.774 | 15.542 | −10.236 | 1.00 | 10.86 |
| ATOM | 1934 | N | VAL | A | 250 | −7.700 | 17.265 | −11.703 | 1.00 | 11.28 |
| ATOM | 1935 | CA | VAL | A | 250 | −8.885 | 16.793 | −12.438 | 1.00 | 11.59 |
| ATOM | 1936 | CB | VAL | A | 250 | −9.366 | 17.859 | −13.493 | 1.00 | 12.49 |
| ATOM | 1937 | CG1 | VAL | A | 250 | −8.480 | 17.815 | −14.728 | 1.00 | 13.03 |
| ATOM | 1938 | CG2 | VAL | A | 250 | −10.859 | 17.654 | −13.852 | 1.00 | 13.75 |
| ATOM | 1939 | C | VAL | A | 250 | −8.711 | 15.386 | −13.064 | 1.00 | 11.77 |
| ATOM | 1940 | O | VAL | A | 250 | −9.698 | 14.750 | −13.467 | 1.00 | 11.71 |
| ATOM | 1941 | N | ASN | A | 251 | −7.461 | 14.925 | −13.168 | 1.00 | 10.73 |
| ATOM | 1942 | CA | ASN | A | 251 | −7.131 | 13.491 | −13.378 | 1.00 | 11.20 |
| ATOM | 1943 | CB | ASN | A | 251 | −5.699 | 13.265 | −12.813 | 1.00 | 10.94 |
| ATOM | 1944 | CG | ASN | A | 251 | −5.221 | 11.810 | −12.892 | 1.00 | 11.58 |
| ATOM | 1945 | OD1 | ASN | A | 251 | −5.986 | 10.864 | −12.672 | 1.00 | 12.47 |
| ATOM | 1946 | ND2 | ASN | A | 251 | −3.898 | 11.639 | −13.164 | 1.00 | 14.40 |
| ATOM | 1947 | C | ASN | A | 251 | −8.151 | 12.560 | −12.706 | 1.00 | 10.99 |
| ATOM | 1948 | O | ASN | A | 251 | −8.755 | 11.706 | −13.355 | 1.00 | 11.49 |
| ATOM | 1949 | N | SER | A | 252 | −8.407 | 12.774 | −11.417 | 1.00 | 11.45 |
| ATOM | 1950 | CA | SER | A | 252 | −9.293 | 11.876 | −10.634 | 1.00 | 11.79 |
| ATOM | 1951 | CB | SER | A | 252 | −9.062 | 12.155 | −9.149 | 1.00 | 13.31 |
| ATOM | 1952 | OG | SER | A | 252 | −9.338 | 13.524 | −8.882 | 1.00 | 13.41 |
| ATOM | 1953 | C | SER | A | 252 | −10.784 | 12.002 | −10.996 | 1.00 | 11.39 |
| ATOM | 1954 | O | SER | A | 252 | −11.532 | 11.023 | −10.964 | 1.00 | 12.69 |
| ATOM | 1955 | N | VAL | A | 253 | −11.199 | 13.203 | −11.383 | 1.00 | 10.56 |
| ATOM | 1956 | CA | VAL | A | 253 | −12.582 | 13.459 | −11.821 | 1.00 | 10.70 |
| ATOM | 1957 | CB | VAL | A | 253 | −12.884 | 15.004 | −11.856 | 1.00 | 11.02 |
| ATOM | 1958 | CG1 | VAL | A | 253 | −14.335 | 15.262 | −12.345 | 1.00 | 11.24 |
| ATOM | 1959 | CG2 | VAL | A | 253 | −12.711 | 15.585 | −10.449 | 1.00 | 10.91 |
| ATOM | 1960 | C | VAL | A | 253 | −12.810 | 12.827 | −13.187 | 1.00 | 11.38 |
| ATOM | 1961 | O | VAL | A | 253 | −13.824 | 12.143 | −13.407 | 1.00 | 11.69 |
| ATOM | 1962 | N | LEU | A | 254 | −11.866 | 13.059 | −14.108 | 1.00 | 11.32 |

TABLE 6-continued

| | | | | | | | | |
|---|---|---|---|---|---|---|---|---|
| ATOM | 1963 | CA | LEU | A | 254 | −11.891 | 12.393 | −15.417 | 1.00 | 12.12 |
| ATOM | 1964 | CB | LEU | A | 254 | −10.635 | 12.759 | −16.238 | 1.00 | 11.95 |
| ATOM | 1965 | CG | LEU | A | 254 | −10.634 | 14.202 | −16.763 | 1.00 | 12.23 |
| ATOM | 1966 | CD1 | LEU | A | 254 | −9.266 | 14.564 | −17.330 | 1.00 | 12.77 |
| ATOM | 1967 | CD2 | LEU | A | 254 | −11.714 | 14.371 | −17.845 | 1.00 | 15.26 |
| ATOM | 1968 | C | LEU | A | 254 | −11.963 | 10.872 | −15.271 | 1.00 | 12.22 |
| ATOM | 1969 | O | LEU | A | 254 | −12.675 | 10.201 | −16.024 | 1.00 | 12.01 |
| ATOM | 1970 | N | THR | A | 255 | −11.208 | 10.338 | −14.315 | 1.00 | 11.58 |
| ATOM | 1971 | CA | THR | A | 255 | −11.219 | 8.913 | −14.042 | 1.00 | 12.53 |
| ATOM | 1972 | CB | THR | A | 255 | −10.267 | 8.552 | −12.890 | 1.00 | 12.83 |
| ATOM | 1973 | OG1 | THR | A | 255 | −8.935 | 8.933 | −13.240 | 1.00 | 13.00 |
| ATOM | 1974 | CG2 | THR | A | 255 | −10.300 | 7.035 | −12.634 | 1.00 | 15.06 |
| ATOM | 1975 | C | THR | A | 255 | −12.632 | 8.448 | −13.705 | 1.00 | 13.12 |
| ATOM | 1976 | O | THR | A | 255 | −13.131 | 7.467 | −14.285 | 1.00 | 13.49 |
| ATOM | 1977 | N | SER | A | 256 | −13.289 | 9.158 | −12.790 | 1.00 | 13.46 |
| ATOM | 1978 | CA | SER | A | 256 | −14.641 | 8.781 | −12.343 | 1.00 | 12.85 |
| ATOM | 1979 | CB | SER | A | 256 | −15.152 | 9.760 | −11.282 | 1.00 | 13.40 |
| ATOM | 1980 | OG | SER | A | 256 | −16.332 | 9.252 | −10.674 | 1.00 | 16.69 |
| ATOM | 1981 | C | SER | A | 256 | −15.610 | 8.705 | −13.518 | 1.00 | 13.13 |
| ATOM | 1982 | O | SER | A | 256 | −16.360 | 7.711 | −13.654 | 1.00 | 13.10 |
| ATOM | 1983 | N | ILE | A | 257 | −15.594 | 9.728 | −14.377 | 1.00 | 12.32 |
| ATOM | 1984 | CA | ILE | A | 257 | −16.523 | 9.784 | −15.513 | 1.00 | 12.32 |
| ATOM | 1985 | CB | ILE | A | 257 | −16.747 | 11.215 | −16.072 | 1.00 | 11.55 |
| ATOM | 1986 | CG1 | ILE | A | 257 | −15.482 | 11.773 | −16.764 | 1.00 | 11.38 |
| ATOM | 1987 | CD1 | ILE | A | 257 | −15.699 | 13.143 | −17.441 | 1.00 | 13.23 |
| ATOM | 1988 | CG2 | ILE | A | 257 | −17.257 | 12.166 | −14.942 | 1.00 | 13.70 |
| ATOM | 1989 | C | ILE | A | 257 | −16.220 | 8.795 | −16.653 | 1.00 | 12.79 |
| ATOM | 1990 | O | ILE | A | 257 | −17.150 | 8.319 | −17.338 | 1.00 | 13.25 |
| ATOM | 1991 | N | HIS | A | 258 | −14.941 | 8.487 | −16.855 | 1.00 | 12.71 |
| ATOM | 1992 | CA | HIS | A | 258 | −14.565 | 7.566 | −17.931 | 1.00 | 13.41 |
| ATOM | 1993 | CB | HIS | A | 258 | −13.194 | 7.947 | −18.498 | 1.00 | 12.06 |
| ATOM | 1994 | CG | HIS | A | 258 | −13.268 | 9.175 | −19.341 | 1.00 | 13.92 |
| ATOM | 1995 | ND1 | HIS | A | 258 | −13.942 | 9.196 | −20.547 | 1.00 | 16.01 |
| ATOM | 1996 | CE1 | HIS | A | 258 | −13.891 | 10.421 | −21.047 | 1.00 | 18.57 |
| ATOM | 1997 | NE2 | HIS | A | 258 | −13.256 | 11.199 | −20.189 | 1.00 | 14.08 |
| ATOM | 1998 | CD2 | HIS | A | 258 | −12.861 | 10.449 | −19.108 | 1.00 | 13.51 |
| ATOM | 1999 | C | HIS | A | 258 | −14.649 | 6.091 | −17.565 | 1.00 | 14.12 |
| ATOM | 2000 | O | HIS | A | 258 | −14.645 | 5.239 | −18.454 | 1.00 | 14.90 |
| ATOM | 2001 | N | THR | A | 259 | −14.752 | 5.801 | −16.274 | 1.00 | 13.93 |
| ATOM | 2002 | CA | THR | A | 259 | −15.034 | 4.420 | −15.807 | 1.00 | 14.91 |
| ATOM | 2003 | CB | THR | A | 259 | −13.933 | 3.856 | −14.899 | 1.00 | 14.46 |
| ATOM | 2004 | OG1 | THR | A | 259 | −13.788 | 4.647 | −13.705 | 1.00 | 15.66 |
| ATOM | 2005 | CG2 | THR | A | 259 | −12.589 | 3.802 | −15.677 | 1.00 | 15.81 |
| ATOM | 2006 | C | THR | A | 259 | −16.433 | 4.248 | −15.173 | 1.00 | 14.21 |
| ATOM | 2007 | O | THR | A | 259 | −16.709 | 3.235 | −14.546 | 1.00 | 14.95 |
| ATOM | 2008 | N | PHE | A | 260 | −17.290 | 5.238 | −15.367 | 1.00 | 14.76 |
| ATOM | 2009 | CA | PHE | A | 260 | −18.691 | 5.194 | −14.926 | 1.00 | 15.13 |
| ATOM | 2010 | CB | PHE | A | 260 | −19.377 | 6.492 | −15.379 | 1.00 | 15.81 |
| ATOM | 2011 | CG | PHE | A | 260 | −20.886 | 6.508 | −15.228 | 1.00 | 15.47 |
| ATOM | 2012 | CD1 | PHE | A | 260 | −21.505 | 6.188 | −14.015 | 1.00 | 17.59 |
| ATOM | 2013 | CE1 | PHE | A | 260 | −22.903 | 6.259 | −13.898 | 1.00 | 19.11 |
| ATOM | 2014 | CZ | PHE | A | 260 | −23.682 | 6.653 | −14.991 | 1.00 | 17.18 |
| ATOM | 2015 | CE2 | PHE | A | 260 | −23.082 | 6.994 | −16.178 | 1.00 | 18.04 |
| ATOM | 2016 | CD2 | PHE | A | 260 | −21.679 | 6.917 | −16.296 | 1.00 | 17.22 |
| ATOM | 2017 | C | PHE | A | 260 | −19.436 | 3.977 | −15.475 | 1.00 | 15.55 |
| ATOM | 2018 | O | PHE | A | 260 | −19.426 | 3.725 | −16.684 | 1.00 | 15.81 |
| ATOM | 2019 | N | ASP | A | 261 | −20.093 | 3.235 | −14.586 | 1.00 | 15.51 |
| ATOM | 2020 | CA | ASP | A | 261 | −21.008 | 2.176 | −15.006 | 1.00 | 16.05 |
| ATOM | 2021 | CB | ASP | A | 261 | −20.303 | 0.813 | −15.015 | 1.00 | 16.46 |
| ATOM | 2022 | CG | ASP | A | 261 | −21.205 | −0.321 | −15.490 | 1.00 | 17.60 |
| ATOM | 2023 | OD1 | ASP | A | 261 | −22.440 | −0.122 | −15.579 | 1.00 | 18.97 |
| ATOM | 2024 | OD2 | ASP | A | 261 | −20.656 | −1.404 | −15.810 | 1.00 | 18.29 |
| ATOM | 2025 | C | ASP | A | 261 | −22.117 | 2.185 | −13.972 | 1.00 | 16.30 |
| ATOM | 2026 | O | ASP | A | 261 | −21.882 | 1.809 | −12.840 | 1.00 | 15.53 |
| ATOM | 2027 | N | PRO | A | 262 | −23.320 | 2.610 | −14.374 | 1.00 | 18.21 |
| ATOM | 2028 | CA | PRO | A | 262 | −24.438 | 2.716 | −13.412 | 1.00 | 20.39 |
| ATOM | 2029 | CB | PRO | A | 262 | −25.589 | 3.308 | −14.247 | 1.00 | 20.43 |
| ATOM | 2030 | CG | PRO | A | 262 | −25.235 | 3.044 | −15.669 | 1.00 | 20.06 |
| ATOM | 2031 | CD | PRO | A | 262 | −23.709 | 2.994 | −15.734 | 1.00 | 17.40 |
| ATOM | 2032 | C | PRO | A | 262 | −24.815 | 1.382 | −12.753 | 1.00 | 22.31 |
| ATOM | 2033 | O | PRO | A | 262 | −25.356 | 1.374 | −11.622 | 1.00 | 22.24 |
| ATOM | 2034 | N | ASN | A | 263 | −24.508 | 0.267 | −13.421 | 1.00 | 22.99 |
| ATOM | 2035 | CA | ASN | A | 263 | −24.750 | −1.048 | −12.838 | 1.00 | 25.42 |
| ATOM | 2036 | CB | ASN | A | 263 | −24.574 | −2.149 | −13.890 | 1.00 | 26.62 |
| ATOM | 2037 | CG | ASN | A | 263 | −25.680 | −2.128 | −14.948 | 1.00 | 30.74 |
| ATOM | 2038 | OD1 | ASN | A | 263 | −26.688 | −1.419 | −14.814 | 1.00 | 35.92 |
| ATOM | 2039 | ND2 | ASN | A | 263 | −25.490 | −2.906 | −16.007 | 1.00 | 35.87 |
| ATOM | 2040 | C | ASN | A | 263 | −23.894 | −1.316 | −11.598 | 1.00 | 25.45 |
| ATOM | 2041 | O | ASN | A | 263 | −24.210 | −2.190 | −10.795 | 1.00 | 26.56 |
| ATOM | 2042 | N | LEU | A | 264 | −22.835 | −0.529 | −11.413 | 1.00 | 24.54 |

TABLE 6-continued

| | | | | | | | | | |
|---|---|---|---|---|---|---|---|---|---|
| ATOM | 2043 | CA | LEU | A | 264 | −22.022 | −0.616 | −10.213 | 1.00 | 24.27 |
| ATOM | 2044 | CB | LEU | A | 264 | −20.549 | −0.287 | −10.520 | 1.00 | 24.43 |
| ATOM | 2045 | CG | LEU | A | 264 | −19.752 | −1.346 | −11.288 | 1.00 | 25.38 |
| ATOM | 2046 | CD1 | LEU | A | 264 | −18.375 | −0.809 | −11.659 | 1.00 | 26.05 |
| ATOM | 2047 | CD2 | LEU | A | 264 | −19.619 | −2.672 | −10.523 | 1.00 | 26.24 |
| ATOM | 2048 | C | LEU | A | 264 | −22.542 | 0.273 | −9.066 | 1.00 | 23.47 |
| ATOM | 2049 | O | LEU | A | 264 | −21.956 | 0.292 | −7.988 | 1.00 | 23.97 |
| ATOM | 2050 | N | GLY | A | 265 | −23.631 | 1.000 | −9.292 | 1.00 | 23.32 |
| ATOM | 2051 | CA | GLY | A | 265 | −24.218 | 1.840 | −8.237 | 1.00 | 22.74 |
| ATOM | 2052 | C | GLY | A | 265 | −23.204 | 2.843 | −7.729 | 1.00 | 21.84 |
| ATOM | 2053 | O | GLY | A | 265 | −22.416 | 3.373 | −8.510 | 1.00 | 22.83 |
| ATOM | 2054 | N | CYS | A | 266 | −23.175 | 3.086 | −6.424 | 1.00 | 21.37 |
| ATOM | 2055 | CA | CYS | A | 266 | −22.233 | 4.073 | −5.883 | 1.00 | 21.00 |
| ATOM | 2056 | CB | CYS | A | 266 | −22.947 | 5.049 | −4.936 | 1.00 | 20.86 |
| ATOM | 2057 | SG | CYS | A | 266 | −24.347 | 5.912 | −5.711 | 1.00 | 20.96 |
| ATOM | 2058 | C | CYS | A | 266 | −20.992 | 3.427 | −5.275 | 1.00 | 20.98 |
| ATOM | 2059 | O | CYS | A | 266 | −20.513 | 3.814 | −4.203 | 1.00 | 21.01 |
| ATOM | 2060 | N | ASP | A | 267 | −20.462 | 2.443 | −6.002 | 1.00 | 20.39 |
| ATOM | 2061 | CA | ASP | A | 267 | −19.303 | 1.686 | −5.577 | 1.00 | 20.67 |
| ATOM | 2062 | CB | ASP | A | 267 | −18.961 | 0.621 | −6.618 | 1.00 | 20.84 |
| ATOM | 2063 | CG | ASP | A | 267 | −17.666 | −0.101 | −6.288 | 1.00 | 24.28 |
| ATOM | 2064 | OD1 | ASP | A | 267 | −16.852 | −0.322 | −7.200 | 1.00 | 25.84 |
| ATOM | 2065 | OD2 | ASP | A | 267 | −17.455 | −0.407 | −5.098 | 1.00 | 27.46 |
| ATOM | 2066 | C | ASP | A | 267 | −18.072 | 2.567 | −5.391 | 1.00 | 19.78 |
| ATOM | 2067 | O | ASP | A | 267 | −17.593 | 3.161 | −6.353 | 1.00 | 18.61 |
| ATOM | 2068 | N | ALA | A | 268 | −17.544 | 2.621 | −4.174 | 1.00 | 18.35 |
| ATOM | 2069 | CA | ALA | A | 268 | −16.315 | 3.395 | −3.944 | 1.00 | 19.35 |
| ATOM | 2070 | CB | ALA | A | 268 | −16.207 | 3.868 | −2.472 | 1.00 | 19.46 |
| ATOM | 2071 | C | ALA | A | 268 | −15.017 | 2.701 | −4.415 | 1.00 | 19.46 |
| ATOM | 2072 | O | ALA | A | 268 | −14.009 | 3.371 | −4.665 | 1.00 | 19.42 |
| ATOM | 2073 | N | GLY | A | 269 | −15.029 | 1.370 | −4.534 | 1.00 | 19.01 |
| ATOM | 2074 | CA | GLY | A | 269 | −13.826 | 0.644 | −4.936 | 1.00 | 19.17 |
| ATOM | 2075 | C | GLY | A | 269 | −13.370 | 1.032 | −6.343 | 1.00 | 18.75 |
| ATOM | 2076 | O | GLY | A | 269 | −12.175 | 1.134 | −6.624 | 1.00 | 19.54 |
| ATOM | 2077 | N | THR | A | 270 | −14.330 | 1.257 | −7.230 | 1.00 | 17.92 |
| ATOM | 2078 | CA | THR | A | 270 | −14.016 | 1.662 | −8.594 | 1.00 | 18.35 |
| ATOM | 2079 | CB | THR | A | 270 | −14.852 | 0.882 | −9.616 | 1.00 | 18.43 |
| ATOM | 2080 | OG1 | THR | A | 270 | −16.246 | 1.085 | −9.350 | 1.00 | 18.51 |
| ATOM | 2081 | CG2 | THR | A | 270 | −14.529 | −0.626 | −9.555 | 1.00 | 19.75 |
| ATOM | 2082 | C | THR | A | 270 | −14.261 | 3.172 | −8.771 | 1.00 | 18.25 |
| ATOM | 2083 | O | THR | A | 270 | −14.326 | 3.674 | −9.904 | 1.00 | 17.88 |
| ATOM | 2084 | N | PHE | A | 271 | −14.434 | 3.880 | −7.650 | 1.00 | 17.17 |
| ATOM | 2085 | CA | PHE | A | 271 | −14.531 | 5.359 | −7.656 | 1.00 | 17.38 |
| ATOM | 2086 | CB | PHE | A | 271 | −13.183 | 5.965 | −8.121 | 1.00 | 17.67 |
| ATOM | 2087 | CG | PHE | A | 271 | −12.946 | 7.376 | −7.673 | 1.00 | 21.97 |
| ATOM | 2088 | CD1 | PHE | A | 271 | −12.656 | 7.653 | −6.337 | 1.00 | 24.90 |
| ATOM | 2089 | CE1 | PHE | A | 271 | −12.447 | 8.981 | −5.923 | 1.00 | 24.46 |
| ATOM | 2090 | CZ | PHE | A | 271 | −12.474 | 10.043 | −6.863 | 1.00 | 23.20 |
| ATOM | 2091 | CE2 | PHE | A | 271 | −12.733 | 9.783 | −8.196 | 1.00 | 21.92 |
| ATOM | 2092 | CD2 | PHE | A | 271 | −12.956 | 8.436 | −8.599 | 1.00 | 24.30 |
| ATOM | 2093 | C | PHE | A | 271 | −15.677 | 5.856 | −8.551 | 1.00 | 16.63 |
| ATOM | 2094 | O | PHE | A | 271 | −15.479 | 6.764 | −9.358 | 1.00 | 15.93 |
| ATOM | 2095 | N | GLN | A | 272 | −16.861 | 5.249 | −8.439 | 1.00 | 15.21 |
| ATOM | 2096 | CA | GLN | A | 272 | −18.011 | 5.673 | −9.251 | 1.00 | 14.97 |
| ATOM | 2097 | CB | GLN | A | 272 | −19.227 | 4.755 | −9.013 | 1.00 | 14.93 |
| ATOM | 2098 | CG | GLN | A | 272 | −19.021 | 3.355 | −9.615 | 1.00 | 16.30 |
| ATOM | 2099 | CD | GLN | A | 272 | −18.755 | 3.413 | −11.102 | 1.00 | 15.81 |
| ATOM | 2100 | OE1 | GLN | A | 272 | −19.575 | 3.909 | −11.883 | 1.00 | 16.97 |
| ATOM | 2101 | NE2 | GLN | A | 272 | −17.617 | 2.861 | −11.512 | 1.00 | 18.50 |
| ATOM | 2102 | C | GLN | A | 272 | −18.402 | 7.118 | −8.929 | 1.00 | 14.73 |
| ATOM | 2103 | O | GLN | A | 272 | −18.194 | 7.555 | −7.800 | 1.00 | 15.60 |
| ATOM | 2104 | N | PRO | A | 273 | −18.955 | 7.859 | −9.914 | 1.00 | 14.45 |
| ATOM | 2105 | CA | PRO | A | 273 | −19.342 | 9.255 | −9.682 | 1.00 | 14.57 |
| ATOM | 2106 | CB | PRO | A | 273 | −20.157 | 9.597 | −10.927 | 1.00 | 14.64 |
| ATOM | 2107 | CG | PRO | A | 273 | −19.443 | 8.767 | −12.031 | 1.00 | 14.70 |
| ATOM | 2108 | CD | PRO | A | 273 | −19.156 | 7.458 | −11.326 | 1.00 | 14.10 |
| ATOM | 2109 | C | PRO | A | 273 | −20.162 | 9.542 | −8.407 | 1.00 | 15.22 |
| ATOM | 2110 | O | PRO | A | 273 | −19.910 | 10.562 | −7.752 | 1.00 | 15.03 |
| ATOM | 2111 | N | CYS | A | 274 | −21.130 | 8.682 | −8.075 | 1.00 | 15.76 |
| ATOM | 2112 | CA | CYS | A | 274 | −21.926 | 8.913 | −6.853 | 1.00 | 16.22 |
| ATOM | 2113 | CB | CYS | A | 274 | −23.389 | 8.489 | −7.039 | 1.00 | 16.57 |
| ATOM | 2114 | SG | CYS | A | 274 | −23.611 | 6.769 | −7.423 | 1.00 | 17.39 |
| ATOM | 2115 | C | CYS | A | 274 | −21.331 | 8.281 | −5.605 | 1.00 | 16.64 |
| ATOM | 2116 | O | CYS | A | 274 | −21.958 | 8.329 | −4.529 | 1.00 | 16.55 |
| ATOM | 2117 | N | SER | A | 275 | −20.137 | 7.681 | −5.715 | 1.00 | 15.61 |
| ATOM | 2118 | CA | SER | A | 275 | −19.476 | 7.117 | −4.528 | 1.00 | 15.81 |
| ATOM | 2119 | CB | SER | A | 275 | −18.244 | 6.253 | −4.877 | 1.00 | 15.06 |
| ATOM | 2120 | OG | SER | A | 275 | −17.144 | 7.041 | −5.315 | 1.00 | 14.92 |
| ATOM | 2121 | C | SER | A | 275 | −19.097 | 8.232 | −3.545 | 1.00 | 16.06 |
| ATOM | 2122 | O | SER | A | 275 | −18.818 | 9.366 | −3.949 | 1.00 | 14.39 |

TABLE 6-continued

| | | | | | | | | | |
|---|---|---|---|---|---|---|---|---|---|
| ATOM | 2123 | N | ASP | A | 276 | −19.103 | 7.919 | −2.248 | 1.00 | 16.42 |
| ATOM | 2124 | CA | ASP | A | 276 | −18.731 | 8.935 | −1.271 | 1.00 | 16.52 |
| ATOM | 2125 | CB | ASP | A | 276 | −19.020 | 8.511 | 0.189 | 1.00 | 16.27 |
| ATOM | 2126 | CG | ASP | A | 276 | −18.244 | 7.281 | 0.656 | 1.00 | 19.14 |
| ATOM | 2127 | OD1 | ASP | A | 276 | −18.371 | 7.001 | 1.873 | 1.00 | 19.62 |
| ATOM | 2128 | OD2 | ASP | A | 276 | −17.544 | 6.593 | −0.120 | 1.00 | 17.10 |
| ATOM | 2129 | C | ASP | A | 276 | −17.312 | 9.469 | −1.492 | 1.00 | 16.17 |
| ATOM | 2130 | O | ASP | A | 276 | −17.084 | 10.683 | −1.415 | 1.00 | 15.20 |
| ATOM | 2131 | N | LYS | A | 277 | −16.381 | 8.577 | −1.823 | 1.00 | 15.43 |
| ATOM | 2132 | CA | LYS | A | 277 | −14.994 | 8.982 | −2.115 | 1.00 | 15.34 |
| ATOM | 2133 | CB | LYS | A | 277 | −14.089 | 7.763 | −2.326 | 1.00 | 15.23 |
| ATOM | 2134 | CG | LYS | A | 277 | −13.924 | 6.905 | −1.059 | 1.00 | 17.01 |
| ATOM | 2135 | CD | LYS | A | 277 | −12.752 | 5.929 | −1.204 | 1.00 | 21.20 |
| ATOM | 2136 | CE | LYS | A | 277 | −12.662 | 5.017 | 0.015 | 1.00 | 22.94 |
| ATOM | 2137 | NZ | LYS | A | 277 | −11.533 | 4.067 | −0.165 | 1.00 | 29.19 |
| ATOM | 2138 | C | LYS | A | 277 | −14.900 | 9.915 | −3.324 | 1.00 | 14.30 |
| ATOM | 2139 | O | LYS | A | 277 | −14.152 | 10.887 | −3.288 | 1.00 | 14.70 |
| ATOM | 2140 | N | ALA | A | 278 | −15.644 | 9.620 | −4.393 | 1.00 | 14.45 |
| ATOM | 2141 | CA | ALA | A | 278 | −15.588 | 10.464 | −5.605 | 1.00 | 13.61 |
| ATOM | 2142 | CB | ALA | A | 278 | −16.250 | 9.775 | −6.783 | 1.00 | 13.30 |
| ATOM | 2143 | C | ALA | A | 278 | −16.210 | 11.827 | −5.357 | 1.00 | 13.50 |
| ATOM | 2144 | O | ALA | A | 278 | −15.730 | 12.840 | −5.864 | 1.00 | 13.02 |
| ATOM | 2145 | N | LEU | A | 279 | −17.283 | 11.855 | −4.565 | 1.00 | 13.22 |
| ATOM | 2146 | CA | LEU | A | 279 | −17.936 | 13.132 | −4.239 | 1.00 | 12.92 |
| ATOM | 2147 | CB | LEU | A | 279 | −19.323 | 12.893 | −3.625 | 1.00 | 13.21 |
| ATOM | 2148 | CG | LEU | A | 279 | −20.384 | 12.358 | −4.601 | 1.00 | 13.94 |
| ATOM | 2149 | CD1 | LEU | A | 279 | −21.707 | 11.969 | −3.887 | 1.00 | 17.68 |
| ATOM | 2150 | CD2 | LEU | A | 279 | −20.653 | 13.319 | −5.781 | 1.00 | 17.52 |
| ATOM | 2151 | C | LEU | A | 279 | −17.065 | 13.995 | −3.348 | 1.00 | 12.84 |
| ATOM | 2152 | O | LEU | A | 279 | −16.941 | 15.203 | −3.577 | 1.00 | 13.54 |
| ATOM | 2153 | N | SER | A | 280 | −16.463 | 13.390 | −2.315 | 1.00 | 12.45 |
| ATOM | 2154 | CA | SER | A | 280 | −15.502 | 14.106 | −1.459 | 1.00 | 13.53 |
| ATOM | 2155 | CB | SER | A | 280 | −14.951 | 13.168 | −0.364 | 1.00 | 13.65 |
| ATOM | 2156 | OG | SER | A | 280 | −14.008 | 13.863 | 0.468 | 1.00 | 15.07 |
| ATOM | 2157 | C | SER | A | 280 | −14.332 | 14.672 | −2.285 | 1.00 | 14.09 |
| ATOM | 2158 | O | SER | A | 280 | −13.925 | 15.856 | −2.130 | 1.00 | 13.43 |
| ATOM | 2159 | N | ASN | A | 281 | −13.795 | 13.830 | −3.166 | 1.00 | 13.27 |
| ATOM | 2160 | CA | ASN | A | 281 | −12.690 | 14.257 | −4.027 | 1.00 | 13.19 |
| ATOM | 2161 | CB | ASN | A | 281 | −12.239 | 13.078 | −4.888 | 1.00 | 12.05 |
| ATOM | 2162 | CG | ASN | A | 281 | −11.116 | 13.455 | −5.849 | 1.00 | 13.13 |
| ATOM | 2163 | OD1 | ASN | A | 281 | −9.989 | 13.637 | −5.446 | 1.00 | 13.26 |
| ATOM | 2164 | ND2 | ASN | A | 281 | −11.442 | 13.573 | −7.124 | 1.00 | 11.63 |
| ATOM | 2165 | C | ASN | A | 281 | −13.096 | 15.432 | −4.933 | 1.00 | 12.33 |
| ATOM | 2166 | O | ASN | A | 281 | −12.330 | 16.380 | −5.109 | 1.00 | 13.49 |
| ATOM | 2167 | N | LEU | A | 282 | −14.287 | 15.355 | −5.506 | 1.00 | 12.05 |
| ATOM | 2168 | CA | LEU | A | 282 | −14.760 | 16.422 | −6.376 | 1.00 | 13.21 |
| ATOM | 2169 | CB | LEU | A | 282 | −16.147 | 16.109 | −6.949 | 1.00 | 12.17 |
| ATOM | 2170 | CG | LEU | A | 282 | −16.791 | 17.216 | −7.820 | 1.00 | 14.57 |
| ATOM | 2171 | CD1 | LEU | A | 282 | −16.011 | 17.378 | −9.126 | 1.00 | 16.58 |
| ATOM | 2172 | CD2 | LEU | A | 282 | −18.241 | 16.863 | −8.170 | 1.00 | 15.68 |
| ATOM | 2173 | C | LEU | A | 282 | −14.739 | 17.754 | −5.638 | 1.00 | 12.69 |
| ATOM | 2174 | O | LEU | A | 282 | −14.201 | 18.735 | −6.153 | 1.00 | 13.45 |
| ATOM | 2175 | N | LYS | A | 283 | −15.283 | 17.791 | −4.415 | 1.00 | 12.75 |
| ATOM | 2176 | CA | LYS | A | 283 | −15.306 | 19.026 | −3.656 | 1.00 | 12.89 |
| ATOM | 2177 | CB | LYS | A | 283 | −16.079 | 18.860 | −2.334 | 1.00 | 12.90 |
| ATOM | 2178 | CG | LYS | A | 283 | −15.912 | 20.089 | −1.432 | 1.00 | 13.94 |
| ATOM | 2179 | CD | LYS | A | 283 | −16.909 | 20.076 | −0.252 | 1.00 | 14.67 |
| ATOM | 2180 | CE | LYS | A | 283 | −16.530 | 21.136 | 0.797 | 1.00 | 13.67 |
| ATOM | 2181 | NZ | LYS | A | 283 | −16.315 | 22.489 | 0.212 | 1.00 | 19.03 |
| ATOM | 2182 | C | LYS | A | 283 | −13.889 | 19.537 | −3.385 | 1.00 | 12.43 |
| ATOM | 2183 | O | LYS | A | 283 | −13.612 | 20.710 | −3.556 | 1.00 | 12.14 |
| ATOM | 2184 | N | VAL | A | 284 | −12.988 | 18.652 | −2.966 | 1.00 | 12.02 |
| ATOM | 2185 | CA | VAL | A | 284 | −11.624 | 19.055 | −2.633 | 1.00 | 12.77 |
| ATOM | 2186 | CB | VAL | A | 284 | −10.845 | 17.875 | −2.014 | 1.00 | 13.17 |
| ATOM | 2187 | CG1 | VAL | A | 284 | −9.320 | 18.169 | −1.936 | 1.00 | 13.21 |
| ATOM | 2188 | CG2 | VAL | A | 284 | −11.391 | 17.557 | −0.630 | 1.00 | 15.81 |
| ATOM | 2189 | C | VAL | A | 284 | −10.927 | 19.599 | −3.881 | 1.00 | 12.74 |
| ATOM | 2190 | O | VAL | A | 284 | −10.228 | 20.636 | −3.827 | 1.00 | 12.21 |
| ATOM | 2191 | N | VAL | A | 285 | −11.153 | 18.927 | −5.012 | 1.00 | 11.54 |
| ATOM | 2192 | CA | VAL | A | 285 | −10.560 | 19.389 | −6.287 | 1.00 | 12.35 |
| ATOM | 2193 | CB | VAL | A | 285 | −10.694 | 18.330 | −7.425 | 1.00 | 12.36 |
| ATOM | 2194 | CG1 | VAL | A | 285 | −10.316 | 18.944 | −8.813 | 1.00 | 12.25 |
| ATOM | 2195 | CG2 | VAL | A | 285 | −9.795 | 17.104 | −7.140 | 1.00 | 13.25 |
| ATOM | 2196 | C | VAL | A | 285 | −11.130 | 20.770 | −6.712 | 1.00 | 12.08 |
| ATOM | 2197 | O | VAL | A | 285 | −10.367 | 21.696 | −6.989 | 1.00 | 12.60 |
| ATOM | 2198 | N | VAL | A | 286 | −12.452 | 20.913 | −6.728 | 1.00 | 11.87 |
| ATOM | 2199 | CA | VAL | A | 286 | −13.089 | 22.196 | −7.074 | 1.00 | 12.87 |
| ATOM | 2200 | CB | VAL | A | 286 | −14.631 | 22.080 | −7.038 | 1.00 | 13.01 |
| ATOM | 2201 | CG1 | VAL | A | 286 | −15.300 | 23.468 | −7.140 | 1.00 | 14.31 |
| ATOM | 2202 | CG2 | VAL | A | 286 | −15.103 | 21.157 | −8.200 | 1.00 | 14.42 |

TABLE 6-continued

| | | | | | | | | |
|---|---|---|---|---|---|---|---|---|
| ATOM | 2203 | C | VAL | A | 286 | −12.586 | 23.324 | −6.164 | 1.00 | 12.84 |
| ATOM | 2204 | O | VAL | A | 286 | −12.206 | 24.402 | −6.635 | 1.00 | 13.75 |
| ATOM | 2205 | N | ASP | A | 287 | −12.552 | 23.064 | −4.853 | 1.00 | 12.85 |
| ATOM | 2206 | CA | ASP | A | 287 | −12.116 | 24.059 | −3.870 | 1.00 | 13.90 |
| ATOM | 2207 | CB | ASP | A | 287 | −12.199 | 23.506 | −2.440 | 1.00 | 13.12 |
| ATOM | 2208 | CG | ASP | A | 287 | −13.637 | 23.441 | −1.924 | 1.00 | 16.00 |
| ATOM | 2209 | OD1 | ASP | A | 287 | −14.541 | 24.002 | −2.583 | 1.00 | 16.20 |
| ATOM | 2210 | OD2 | ASP | A | 287 | −13.857 | 22.835 | −0.858 | 1.00 | 16.76 |
| ATOM | 2211 | C | ASP | A | 287 | −10.727 | 24.564 | −4.136 | 1.00 | 14.28 |
| ATOM | 2212 | O | ASP | A | 287 | −10.425 | 25.722 | −3.841 | 1.00 | 15.53 |
| ATOM | 2213 | N | SER | A | 288 | −9.862 | 23.709 | −4.677 | 1.00 | 14.50 |
| ATOM | 2214 | CA | SER | A | 288 | −8.478 | 24.093 | −4.949 | 1.00 | 14.58 |
| ATOM | 2215 | CB | SER | A | 288 | −7.625 | 22.843 | −5.229 | 1.00 | 14.15 |
| ATOM | 2216 | OG | SER | A | 288 | −7.758 | 22.417 | −6.565 | 1.00 | 13.73 |
| ATOM | 2217 | C | SER | A | 288 | −8.326 | 25.186 | −6.038 | 1.00 | 14.61 |
| ATOM | 2218 | O | SER | A | 288 | −7.274 | 25.847 | −6.143 | 1.00 | 14.59 |
| ATOM | 2219 | N | PHE | A | 289 | −9.392 | 25.416 | −6.809 | 1.00 | 13.99 |
| ATOM | 2220 | CA | PHE | A | 289 | −9.419 | 26.447 | −7.831 | 1.00 | 14.09 |
| ATOM | 2221 | CB | PHE | A | 289 | −9.994 | 25.882 | −9.135 | 1.00 | 13.52 |
| ATOM | 2222 | CG | PHE | A | 289 | −9.169 | 24.807 | −9.704 | 1.00 | 11.38 |
| ATOM | 2223 | CD1 | PHE | A | 289 | −7.976 | 25.114 | −10.367 | 1.00 | 12.17 |
| ATOM | 2224 | CE1 | PHE | A | 289 | −7.184 | 24.095 | −10.905 | 1.00 | 13.93 |
| ATOM | 2225 | CZ | PHE | A | 289 | −7.572 | 22.783 | −10.771 | 1.00 | 13.96 |
| ATOM | 2226 | CE2 | PHE | A | 289 | −8.756 | 22.452 | −10.097 | 1.00 | 11.77 |
| ATOM | 2227 | CD2 | PHE | A | 289 | −9.555 | 23.472 | −9.571 | 1.00 | 11.08 |
| ATOM | 2228 | C | PHE | A | 289 | −10.219 | 27.698 | −7.491 | 1.00 | 14.73 |
| ATOM | 2229 | O | PHE | A | 289 | −10.092 | 28.713 | −8.189 | 1.00 | 14.71 |
| ATOM | 2230 | N | ARG | A | 290 | −11.054 | 27.621 | −6.464 | 1.00 | 15.09 |
| ATOM | 2231 | CA | ARG | A | 290 | −11.953 | 28.740 | −6.140 | 1.00 | 16.64 |
| ATOM | 2232 | CB | ARG | A | 290 | −12.842 | 28.401 | −4.936 | 1.00 | 15.99 |
| ATOM | 2233 | CG | ARG | A | 290 | −13.913 | 27.375 | −5.230 | 1.00 | 15.65 |
| ATOM | 2234 | CD | ARG | A | 290 | −14.821 | 27.163 | −4.012 | 1.00 | 16.79 |
| ATOM | 2235 | NE | ARG | A | 290 | −15.843 | 26.172 | −4.330 | 1.00 | 15.04 |
| ATOM | 2236 | CZ | ARG | A | 290 | −16.986 | 26.470 | −4.933 | 1.00 | 17.22 |
| ATOM | 2237 | NH1 | ARG | A | 290 | −17.248 | 27.734 | −5.243 | 1.00 | 15.41 |
| ATOM | 2238 | NH2 | ARG | A | 290 | −17.855 | 25.511 | −5.239 | 1.00 | 15.94 |
| ATOM | 2239 | C | ARG | A | 290 | −11.240 | 30.046 | −5.864 | 1.00 | 18.04 |
| ATOM | 2240 | O | ARG | A | 290 | −11.690 | 31.125 | −6.279 | 1.00 | 19.61 |
| ATOM | 2241 | N | SER | A | 291 | −10.150 | 29.984 | −5.128 | 1.00 | 19.44 |
| ATOM | 2242 | CA | SER | A | 291 | −9.571 | 31.246 | −4.667 | 1.00 | 21.57 |
| ATOM | 2243 | CB | SER | A | 291 | −9.146 | 31.101 | −3.212 | 1.00 | 22.18 |
| ATOM | 2244 | OG | SER | A | 291 | −7.998 | 30.284 | −3.144 | 1.00 | 28.35 |
| ATOM | 2245 | C | SER | A | 291 | −8.423 | 31.762 | −5.534 | 1.00 | 20.65 |
| ATOM | 2246 | O | SER | A | 291 | −7.865 | 32.851 | −5.272 | 1.00 | 22.43 |
| ATOM | 2247 | N | ILE | A | 292 | −8.066 | 31.019 | −6.576 | 1.00 | 19.16 |
| ATOM | 2248 | CA | ILE | A | 292 | −6.855 | 31.367 | −7.330 | 1.00 | 17.65 |
| ATOM | 2249 | CB | ILE | A | 292 | −5.805 | 30.185 | −7.408 | 1.00 | 18.07 |
| ATOM | 2250 | CG1 | ILE | A | 292 | −6.379 | 28.972 | −8.194 | 1.00 | 17.67 |
| ATOM | 2251 | CD1 | ILE | A | 292 | −5.315 | 27.924 | −8.649 | 1.00 | 17.27 |
| ATOM | 2252 | CG2 | ILE | A | 292 | −5.341 | 29.795 | −5.994 | 1.00 | 18.29 |
| ATOM | 2253 | C | ILE | A | 292 | −7.065 | 31.973 | −8.708 | 1.00 | 17.20 |
| ATOM | 2254 | O | ILE | A | 292 | −6.136 | 32.563 | −9.251 | 1.00 | 16.35 |
| ATOM | 2255 | N | TYR | A | 293 | −8.252 | 31.797 | −9.290 | 1.00 | 15.85 |
| ATOM | 2256 | CA | TYR | A | 293 | −8.509 | 32.304 | −10.648 | 1.00 | 15.83 |
| ATOM | 2257 | CB | TYR | A | 293 | −9.301 | 31.270 | −11.474 | 1.00 | 15.43 |
| ATOM | 2258 | CG | TYR | A | 293 | −8.571 | 30.014 | −11.886 | 1.00 | 15.10 |
| ATOM | 2259 | CD1 | TYR | A | 293 | −7.183 | 29.960 | −11.965 | 1.00 | 14.38 |
| ATOM | 2260 | CE1 | TYR | A | 293 | −6.540 | 28.795 | −12.395 | 1.00 | 14.38 |
| ATOM | 2261 | CZ | TYR | A | 293 | −7.306 | 27.685 | −12.743 | 1.00 | 14.90 |
| ATOM | 2262 | OH | TYR | A | 293 | −6.700 | 26.522 | −13.158 | 1.00 | 15.55 |
| ATOM | 2263 | CE2 | TYR | A | 293 | −8.670 | 27.722 | −12.671 | 1.00 | 15.47 |
| ATOM | 2264 | CD2 | TYR | A | 293 | −9.298 | 28.875 | −12.255 | 1.00 | 13.91 |
| ATOM | 2265 | C | TYR | A | 293 | −9.351 | 33.581 | −10.591 | 1.00 | 15.69 |
| ATOM | 2266 | O | TYR | A | 293 | −10.404 | 33.594 | −9.942 | 1.00 | 15.47 |
| ATOM | 2267 | N | GLY | A | 294 | −8.892 | 34.629 | −11.276 | 1.00 | 14.83 |
| ATOM | 2268 | CA | GLY | A | 294 | −9.641 | 35.899 | −11.353 | 1.00 | 15.57 |
| ATOM | 2269 | C | GLY | A | 294 | −11.078 | 35.702 | −11.858 | 1.00 | 15.93 |
| ATOM | 2270 | O | GLY | A | 294 | −12.010 | 36.359 | −11.376 | 1.00 | 15.66 |
| ATOM | 2271 | N | VAL | A | 295 | −11.288 | 34.773 | −12.799 | 1.00 | 15.60 |
| ATOM | 2272 | CA | VAL | A | 295 | −12.651 | 34.520 | −13.270 | 1.00 | 16.24 |
| ATOM | 2273 | CB | VAL | A | 295 | −12.753 | 33.561 | −14.501 | 1.00 | 16.31 |
| ATOM | 2274 | CG1 | VAL | A | 295 | −12.170 | 34.195 | −15.740 | 1.00 | 16.26 |
| ATOM | 2275 | CG2 | VAL | A | 295 | −12.128 | 32.184 | −14.199 | 1.00 | 16.19 |
| ATOM | 2276 | C | VAL | A | 295 | −13.596 | 34.013 | −12.172 | 1.00 | 16.97 |
| ATOM | 2277 | O | VAL | A | 295 | −14.813 | 34.108 | −12.320 | 1.00 | 18.03 |
| ATOM | 2278 | N | ASN | A | 296 | −13.047 | 33.463 | −11.092 | 1.00 | 16.93 |
| ATOM | 2279 | CA | ASN | A | 296 | −13.878 | 32.920 | −10.020 | 1.00 | 17.69 |
| ATOM | 2280 | CB | ASN | A | 296 | −13.250 | 31.633 | −9.472 | 1.00 | 17.57 |
| ATOM | 2281 | CG | ASN | A | 296 | −13.296 | 30.493 | −10.482 | 1.00 | 16.44 |
| ATOM | 2282 | OD1 | ASN | A | 296 | −14.158 | 30.481 | −11.356 | 1.00 | 17.29 |

TABLE 6-continued

| | | | | | | | | |
|---|---|---|---|---|---|---|---|---|
| ATOM | 2283 | ND2 | ASN | A | 296 | −12.401 | 29.513 | −10.336 | 1.00 | 15.99 |
| ATOM | 2284 | C | ASN | A | 296 | −14.187 | 33.915 | −8.896 | 1.00 | 19.30 |
| ATOM | 2285 | O | ASN | A | 296 | −14.945 | 33.601 | −7.979 | 1.00 | 19.07 |
| ATOM | 2286 | N | LYS | A | 297 | −13.617 | 35.116 | −9.007 | 1.00 | 20.37 |
| ATOM | 2287 | CA | LYS | A | 297 | −13.811 | 36.203 | −8.038 | 1.00 | 22.43 |
| ATOM | 2288 | CB | LYS | A | 297 | −13.209 | 37.502 | −8.584 | 1.00 | 22.90 |
| ATOM | 2289 | CG | LYS | A | 297 | −11.741 | 37.680 | −8.316 | 1.00 | 30.03 |
| ATOM | 2290 | CD | LYS | A | 297 | −11.401 | 39.189 | −8.309 | 1.00 | 35.34 |
| ATOM | 2291 | CE | LYS | A | 297 | −12.247 | 39.913 | −7.255 | 1.00 | 39.86 |
| ATOM | 2292 | NZ | LYS | A | 297 | −11.995 | 41.386 | −7.178 | 1.00 | 42.72 |
| ATOM | 2293 | C | LYS | A | 297 | −15.275 | 36.453 | −7.782 | 1.00 | 21.89 |
| ATOM | 2294 | O | LYS | A | 297 | −16.061 | 36.585 | −8.712 | 1.00 | 21.96 |
| ATOM | 2295 | N | GLY | A | 298 | −15.659 | 36.537 | −6.517 | 1.00 | 22.72 |
| ATOM | 2296 | CA | GLY | A | 298 | −17.050 | 36.869 | −6.219 | 1.00 | 22.99 |
| ATOM | 2297 | C | GLY | A | 298 | −18.043 | 35.720 | −6.278 | 1.00 | 23.54 |
| ATOM | 2298 | O | GLY | A | 298 | −19.180 | 35.885 | −5.855 | 1.00 | 25.04 |
| ATOM | 2299 | N | ILE | A | 299 | −17.647 | 34.546 | −6.784 | 1.00 | 22.16 |
| ATOM | 2300 | CA | ILE | A | 299 | −18.574 | 33.393 | −6.763 | 1.00 | 21.47 |
| ATOM | 2301 | CB | ILE | A | 299 | −18.251 | 32.350 | −7.884 | 1.00 | 21.22 |
| ATOM | 2302 | CG1 | ILE | A | 299 | −18.356 | 32.985 | −9.274 | 1.00 | 19.64 |
| ATOM | 2303 | CD1 | ILE | A | 299 | −17.740 | 32.095 | −10.415 | 1.00 | 19.76 |
| ATOM | 2304 | CG2 | ILE | A | 299 | −19.163 | 31.091 | −7.762 | 1.00 | 20.54 |
| ATOM | 2305 | C | ILE | A | 299 | −18.562 | 32.740 | −5.375 | 1.00 | 22.34 |
| ATOM | 2306 | O | ILE | A | 299 | −17.486 | 32.395 | −4.861 | 1.00 | 22.29 |
| ATOM | 2307 | N | PRO | A | 300 | −19.743 | 32.580 | −4.751 | 1.00 | 23.04 |
| ATOM | 2308 | CA | PRO | A | 300 | −19.791 | 32.018 | −3.392 | 1.00 | 23.60 |
| ATOM | 2309 | CB | PRO | A | 300 | −21.217 | 32.364 | −2.922 | 1.00 | 24.19 |
| ATOM | 2310 | CG | PRO | A | 300 | −22.015 | 32.437 | −4.178 | 1.00 | 23.80 |
| ATOM | 2311 | CD | PRO | A | 300 | −21.085 | 32.934 | −5.253 | 1.00 | 23.06 |
| ATOM | 2312 | C | PRO | A | 300 | −19.584 | 30.500 | −3.322 | 1.00 | 23.50 |
| ATOM | 2313 | O | PRO | A | 300 | −19.664 | 29.810 | −4.347 | 1.00 | 22.46 |
| ATOM | 2314 | N | ALA | A | 301 | −19.325 | 29.985 | −2.116 | 1.00 | 22.68 |
| ATOM | 2315 | CA | ALA | A | 301 | −19.380 | 28.549 | −1.905 | 1.00 | 22.89 |
| ATOM | 2316 | CB | ALA | A | 301 | −18.988 | 28.185 | −0.465 | 1.00 | 23.54 |
| ATOM | 2317 | C | ALA | A | 301 | −20.788 | 28.074 | −2.236 | 1.00 | 21.91 |
| ATOM | 2318 | O | ALA | A | 301 | −21.759 | 28.834 | −2.108 | 1.00 | 23.09 |
| ATOM | 2319 | N | GLY | A | 302 | −20.898 | 26.838 | −2.698 | 1.00 | 20.96 |
| ATOM | 2320 | CA | GLY | A | 302 | −22.173 | 26.272 | −3.115 | 1.00 | 19.69 |
| ATOM | 2321 | C | GLY | A | 302 | −22.565 | 26.637 | −4.537 | 1.00 | 19.78 |
| ATOM | 2322 | O | GLY | A | 302 | −23.661 | 26.283 | −4.991 | 1.00 | 19.32 |
| ATOM | 2323 | N | ALA | A | 303 | −21.686 | 27.355 | −5.235 | 1.00 | 17.97 |
| ATOM | 2324 | CA | ALA | A | 303 | −21.948 | 27.708 | −6.635 | 1.00 | 17.13 |
| ATOM | 2325 | CB | ALA | A | 303 | −22.168 | 29.212 | −6.812 | 1.00 | 16.73 |
| ATOM | 2326 | C | ALA | A | 303 | −20.784 | 27.245 | −7.481 | 1.00 | 16.19 |
| ATOM | 2327 | O | ALA | A | 303 | −19.647 | 27.171 | −7.004 | 1.00 | 16.23 |
| ATOM | 2328 | N | ALA | A | 304 | −21.067 | 26.956 | −8.746 | 1.00 | 15.66 |
| ATOM | 2329 | CA | ALA | A | 304 | −20.069 | 26.378 | −9.640 | 1.00 | 15.10 |
| ATOM | 2330 | CB | ALA | A | 304 | −20.750 | 25.795 | −10.860 | 1.00 | 15.80 |
| ATOM | 2331 | C | ALA | A | 304 | −19.002 | 27.394 | −10.044 | 1.00 | 14.74 |
| ATOM | 2332 | O | ALA | A | 304 | −19.270 | 28.587 | −10.121 | 1.00 | 14.27 |
| ATOM | 2333 | N | VAL | A | 305 | −17.783 | 26.914 | −10.300 | 1.00 | 14.18 |
| ATOM | 2334 | CA | VAL | A | 305 | −16.680 | 27.783 | −10.698 | 1.00 | 13.54 |
| ATOM | 2335 | CB | VAL | A | 305 | −15.656 | 27.971 | −9.543 | 1.00 | 13.42 |
| ATOM | 2336 | CG1 | VAL | A | 305 | −16.224 | 28.881 | −8.418 | 1.00 | 14.25 |
| ATOM | 2337 | CG2 | VAL | A | 305 | −15.218 | 26.597 | −8.966 | 1.00 | 14.99 |
| ATOM | 2338 | C | VAL | A | 305 | −15.952 | 27.141 | −11.873 | 1.00 | 13.34 |
| ATOM | 2339 | O | VAL | A | 305 | −16.121 | 25.944 | −12.126 | 1.00 | 12.46 |
| ATOM | 2340 | N | ALA | A | 306 | −15.130 | 27.921 | −12.562 | 1.00 | 13.38 |
| ATOM | 2341 | CA | ALA | A | 306 | −14.233 | 27.376 | −13.573 | 1.00 | 14.37 |
| ATOM | 2342 | CB | ALA | A | 306 | −13.709 | 28.504 | −14.470 | 1.00 | 15.32 |
| ATOM | 2343 | C | ALA | A | 306 | −13.082 | 26.626 | −12.938 | 1.00 | 14.68 |
| ATOM | 2344 | O | ALA | A | 306 | −12.457 | 27.116 | −11.974 | 1.00 | 15.21 |
| ATOM | 2345 | N | ILE | A | 307 | −12.781 | 25.452 | −13.484 | 1.00 | 13.50 |
| ATOM | 2346 | CA | ILE | A | 307 | −11.667 | 24.668 | −12.975 | 1.00 | 13.67 |
| ATOM | 2347 | CB | ILE | A | 307 | −12.134 | 23.438 | −12.163 | 1.00 | 14.45 |
| ATOM | 2348 | CG1 | ILE | A | 307 | −12.756 | 22.386 | −13.072 | 1.00 | 15.37 |
| ATOM | 2349 | CD1 | ILE | A | 307 | −12.921 | 21.033 | −12.368 | 1.00 | 19.15 |
| ATOM | 2350 | CG2 | ILE | A | 307 | −13.119 | 23.848 | −11.005 | 1.00 | 15.52 |
| ATOM | 2351 | C | ILE | A | 307 | −10.646 | 24.290 | −14.059 | 1.00 | 12.52 |
| ATOM | 2352 | O | ILE | A | 307 | −10.974 | 24.232 | −15.264 | 1.00 | 12.22 |
| ATOM | 2353 | N | GLY | A | 308 | −9.405 | 24.095 | −13.604 | 1.00 | 11.71 |
| ATOM | 2354 | CA | GLY | A | 308 | −8.276 | 23.737 | −14.452 | 1.00 | 11.64 |
| ATOM | 2355 | C | GLY | A | 308 | −7.853 | 22.306 | −14.199 | 1.00 | 11.62 |
| ATOM | 2356 | O | GLY | A | 308 | −8.667 | 21.444 | −13.806 | 1.00 | 12.05 |
| ATOM | 2357 | N | ARG | A | 309 | −6.583 | 22.026 | −14.454 | 1.00 | 11.39 |
| ATOM | 2358 | CA | ARG | A | 309 | −6.091 | 20.661 | −14.337 | 1.00 | 11.23 |
| ATOM | 2359 | CB | ARG | A | 309 | −4.896 | 20.467 | −15.275 | 1.00 | 11.37 |
| ATOM | 2360 | CG | ARG | A | 309 | −5.220 | 20.697 | −16.791 | 1.00 | 11.29 |
| ATOM | 2361 | CD | ARG | A | 309 | −4.066 | 20.130 | −17.625 | 1.00 | 12.62 |
| ATOM | 2362 | NE | ARG | A | 309 | −2.845 | 20.919 | −17.425 | 1.00 | 12.15 |

TABLE 6-continued

| | | | | | | | | |
|---|---|---|---|---|---|---|---|---|
| ATOM | 2363 | CZ | ARG | A | 309 | −1.701 | 20.665 | −18.047 | 1.00 | 15.00 |
| ATOM | 2364 | NH1 | ARG | A | 309 | −1.630 | 19.633 | −18.910 | 1.00 | 12.05 |
| ATOM | 2365 | NH2 | ARG | A | 309 | −0.624 | 21.395 | −17.778 | 1.00 | 13.85 |
| ATOM | 2366 | C | ARG | A | 309 | −5.654 | 20.425 | −12.888 | 1.00 | 11.83 |
| ATOM | 2367 | O | ARG | A | 309 | −6.093 | 19.481 | −12.221 | 1.00 | 11.38 |
| ATOM | 2368 | N | TYR | A | 310 | −4.806 | 21.322 | −12.399 | 1.00 | 11.88 |
| ATOM | 2369 | CA | TYR | A | 310 | −4.293 | 21.215 | −11.022 | 1.00 | 11.17 |
| ATOM | 2370 | CB | TYR | A | 310 | −3.225 | 20.082 | −10.878 | 1.00 | 12.49 |
| ATOM | 2371 | CG | TYR | A | 310 | −2.065 | 20.201 | −11.844 | 1.00 | 13.10 |
| ATOM | 2372 | CD1 | TYR | A | 310 | −2.128 | 19.622 | −13.138 | 1.00 | 12.57 |
| ATOM | 2373 | CE1 | TYR | A | 310 | −1.069 | 19.772 | −14.039 | 1.00 | 15.63 |
| ATOM | 2374 | CZ | TYR | A | 310 | 0.065 | 20.475 | −13.649 | 1.00 | 14.31 |
| ATOM | 2375 | OH | TYR | A | 310 | 1.119 | 20.611 | −14.529 | 1.00 | 14.42 |
| ATOM | 2376 | CE2 | TYR | A | 310 | 0.159 | 21.030 | −12.379 | 1.00 | 12.68 |
| ATOM | 2377 | CD2 | TYR | A | 310 | −0.909 | 20.906 | −11.485 | 1.00 | 14.04 |
| ATOM | 2378 | C | TYR | A | 310 | −3.779 | 22.596 | −10.644 | 1.00 | 12.74 |
| ATOM | 2379 | O | TYR | A | 310 | −3.333 | 23.356 | −11.505 | 1.00 | 12.44 |
| ATOM | 2380 | N | ALA | A | 311 | −3.872 | 22.945 | −9.362 | 1.00 | 11.99 |
| ATOM | 2381 | CA | ALA | A | 311 | −3.618 | 24.337 | −8.975 | 1.00 | 13.33 |
| ATOM | 2382 | CB | ALA | A | 311 | −4.084 | 24.589 | −7.508 | 1.00 | 12.88 |
| ATOM | 2383 | C | ALA | A | 311 | −2.157 | 24.768 | −9.197 | 1.00 | 13.50 |
| ATOM | 2384 | O | ALA | A | 311 | −1.906 | 25.951 | −9.468 | 1.00 | 14.52 |
| ATOM | 2385 | N | GLU | A | 312 | −1.216 | 23.823 | −9.140 | 1.00 | 13.52 |
| ATOM | 2386 | CA | GLU | A | 312 | 0.219 | 24.134 | −9.332 | 1.00 | 14.23 |
| ATOM | 2387 | CB | GLU | A | 312 | 1.111 | 23.020 | −8.790 | 1.00 | 15.44 |
| ATOM | 2388 | CG | GLU | A | 312 | 0.933 | 22.802 | −7.303 | 1.00 | 16.54 |
| ATOM | 2389 | CD | GLU | A | 312 | −0.130 | 21.762 | −6.950 | 1.00 | 18.91 |
| ATOM | 2390 | OE1 | GLU | A | 312 | −0.941 | 21.338 | −7.808 | 1.00 | 16.89 |
| ATOM | 2391 | OE2 | GLU | A | 312 | −0.150 | 21.345 | −5.778 | 1.00 | 18.72 |
| ATOM | 2392 | C | GLU | A | 312 | 0.591 | 24.380 | −10.796 | 1.00 | 14.80 |
| ATOM | 2393 | O | GLU | A | 312 | 1.741 | 24.736 | −11.100 | 1.00 | 14.98 |
| ATOM | 2394 | N | ASP | A | 313 | −0.374 | 24.197 | −11.697 | 1.00 | 13.37 |
| ATOM | 2395 | CA | ASP | A | 313 | −0.112 | 24.258 | −13.155 | 1.00 | 13.71 |
| ATOM | 2396 | CB | ASP | A | 313 | −1.457 | 24.079 | −13.888 | 1.00 | 12.88 |
| ATOM | 2397 | CG | ASP | A | 313 | −1.320 | 23.671 | −15.343 | 1.00 | 14.44 |
| ATOM | 2398 | OD1 | ASP | A | 313 | −0.197 | 23.597 | −15.900 | 1.00 | 13.19 |
| ATOM | 2399 | OD2 | ASP | A | 313 | −2.400 | 23.406 | −15.923 | 1.00 | 13.61 |
| ATOM | 2400 | C | ASP | A | 313 | 0.512 | 25.589 | −13.587 | 1.00 | 14.00 |
| ATOM | 2401 | O | ASP | A | 313 | 0.007 | 26.662 | −13.219 | 1.00 | 14.35 |
| ATOM | 2402 | N | VAL | A | 314 | 1.577 | 25.530 | −14.399 | 1.00 | 13.84 |
| ATOM | 2403 | CA | VAL | A | 314 | 2.145 | 26.747 | −14.988 | 1.00 | 15.19 |
| ATOM | 2404 | CB | VAL | A | 314 | 3.602 | 27.016 | −14.520 | 1.00 | 16.70 |
| ATOM | 2405 | CG1 | VAL | A | 314 | 3.638 | 27.295 | −13.009 | 1.00 | 17.94 |
| ATOM | 2406 | CG2 | VAL | A | 314 | 4.551 | 25.857 | −14.915 | 1.00 | 16.69 |
| ATOM | 2407 | C | VAL | A | 314 | 2.123 | 26.729 | −16.528 | 1.00 | 15.30 |
| ATOM | 2408 | O | VAL | A | 314 | 2.712 | 27.598 | −17.165 | 1.00 | 15.13 |
| ATOM | 2409 | N | TYR | A | 315 | 1.441 | 25.743 | −17.111 | 1.00 | 14.51 |
| ATOM | 2410 | CA | TYR | A | 315 | 1.351 | 25.634 | −18.580 | 1.00 | 15.65 |
| ATOM | 2411 | CB | TYR | A | 315 | 0.768 | 24.264 | −18.957 | 1.00 | 15.82 |
| ATOM | 2412 | CG | TYR | A | 315 | 0.694 | 23.988 | −20.457 | 1.00 | 16.29 |
| ATOM | 2413 | CD1 | TYR | A | 315 | 1.824 | 24.124 | −21.265 | 1.00 | 17.01 |
| ATOM | 2414 | CE1 | TYR | A | 315 | 1.778 | 23.859 | −22.634 | 1.00 | 18.92 |
| ATOM | 2415 | CZ | TYR | A | 315 | 0.588 | 23.421 | −23.208 | 1.00 | 16.14 |
| ATOM | 2416 | OH | TYR | A | 315 | 0.557 | 23.164 | −24.577 | 1.00 | 16.95 |
| ATOM | 2417 | CE2 | TYR | A | 315 | −0.552 | 23.261 | −22.423 | 1.00 | 15.41 |
| ATOM | 2418 | CD2 | TYR | A | 315 | −0.492 | 23.539 | −21.044 | 1.00 | 14.48 |
| ATOM | 2419 | C | TYR | A | 315 | 0.489 | 26.777 | −19.107 | 1.00 | 15.56 |
| ATOM | 2420 | O | TYR | A | 315 | −0.688 | 26.888 | −18.748 | 1.00 | 16.36 |
| ATOM | 2421 | N | TYR | A | 316 | 1.072 | 27.645 | −19.944 | 1.00 | 16.61 |
| ATOM | 2422 | CA | TYR | A | 316 | 0.404 | 28.890 | −20.380 | 1.00 | 17.53 |
| ATOM | 2423 | CB | TYR | A | 316 | −0.778 | 28.603 | −21.337 | 1.00 | 18.31 |
| ATOM | 2424 | CG | TYR | A | 316 | −0.329 | 28.321 | −22.742 | 1.00 | 19.74 |
| ATOM | 2425 | CD1 | TYR | A | 316 | −0.071 | 27.026 | −23.169 | 1.00 | 18.95 |
| ATOM | 2426 | CE1 | TYR | A | 316 | 0.353 | 26.757 | −24.466 | 1.00 | 18.69 |
| ATOM | 2427 | CZ | TYR | A | 316 | 0.551 | 27.812 | −25.342 | 1.00 | 21.77 |
| ATOM | 2428 | OH | TYR | A | 316 | 1.002 | 27.557 | −26.617 | 1.00 | 23.75 |
| ATOM | 2429 | CE2 | TYR | A | 316 | 0.329 | 29.125 | −24.932 | 1.00 | 22.39 |
| ATOM | 2430 | CD2 | TYR | A | 316 | −0.111 | 29.369 | −23.639 | 1.00 | 21.90 |
| ATOM | 2431 | C | TYR | A | 316 | −0.037 | 29.730 | −19.173 | 1.00 | 17.87 |
| ATOM | 2432 | O | TYR | A | 316 | −0.968 | 30.517 | −19.266 | 1.00 | 17.06 |
| ATOM | 2433 | N | ASN | A | 317 | 0.689 | 29.555 | −18.066 | 1.00 | 18.34 |
| ATOM | 2434 | CA | ASN | A | 317 | 0.483 | 30.231 | −16.766 | 1.00 | 19.27 |
| ATOM | 2435 | CB | ASN | A | 317 | 0.106 | 31.699 | −16.921 | 1.00 | 20.01 |
| ATOM | 2436 | CG | ASN | A | 317 | 1.171 | 32.489 | −17.624 | 1.00 | 24.51 |
| ATOM | 2437 | OD1 | ASN | A | 317 | 2.363 | 32.384 | −17.305 | 1.00 | 29.46 |
| ATOM | 2438 | ND2 | ASN | A | 317 | 0.756 | 33.269 | −18.603 | 1.00 | 29.08 |
| ATOM | 2439 | C | ASN | A | 317 | −0.506 | 29.551 | −15.842 | 1.00 | 18.28 |
| ATOM | 2440 | O | ASN | A | 317 | −0.706 | 30.001 | −14.719 | 1.00 | 19.05 |
| ATOM | 2441 | N | GLY | A | 318 | −1.114 | 28.459 | −16.300 | 1.00 | 17.74 |
| ATOM | 2442 | CA | GLY | A | 318 | −2.086 | 27.721 | −15.475 | 1.00 | 15.34 |

TABLE 6-continued

| ATOM | 2443 | C | GLY | A | 318 | −3.458 | 28.356 | −15.550 | 1.00 | 15.47 |
| ATOM | 2444 | O | GLY | A | 318 | −3.700 | 29.390 | −14.932 | 1.00 | 15.75 |
| ATOM | 2445 | N | ASN | A | 319 | −4.369 | 27.733 | −16.306 | 1.00 | 13.16 |
| ATOM | 2446 | CA | ASN | A | 319 | −5.672 | 28.305 | −16.557 | 1.00 | 12.74 |
| ATOM | 2447 | CB | ASN | A | 319 | −5.693 | 28.883 | −17.980 | 1.00 | 12.31 |
| ATOM | 2448 | CG | ASN | A | 319 | −4.676 | 29.979 | −18.187 | 1.00 | 13.01 |
| ATOM | 2449 | OD1 | ASN | A | 319 | −4.832 | 31.117 | −17.699 | 1.00 | 14.18 |
| ATOM | 2450 | ND2 | ASN | A | 319 | −3.640 | 29.665 | −18.942 | 1.00 | 11.49 |
| ATOM | 2451 | C | ASN | A | 319 | −6.799 | 27.271 | −16.442 | 1.00 | 12.27 |
| ATOM | 2452 | O | ASN | A | 319 | −6.545 | 26.071 | −16.456 | 1.00 | 12.28 |
| ATOM | 2453 | N | PRO | A | 320 | −8.054 | 27.732 | −16.334 | 1.00 | 12.96 |
| ATOM | 2454 | CA | PRO | A | 320 | −9.113 | 26.759 | −16.472 | 1.00 | 12.58 |
| ATOM | 2455 | CB | PRO | A | 320 | −10.395 | 27.579 | −16.324 | 1.00 | 13.28 |
| ATOM | 2456 | CG | PRO | A | 320 | −10.007 | 29.011 | −16.183 | 1.00 | 14.34 |
| ATOM | 2457 | CD | PRO | A | 320 | −8.537 | 29.090 | −15.991 | 1.00 | 12.66 |
| ATOM | 2458 | C | PRO | A | 320 | −9.101 | 26.090 | −17.851 | 1.00 | 12.18 |
| ATOM | 2459 | O | PRO | A | 320 | −8.643 | 26.698 | −18.820 | 1.00 | 11.99 |
| ATOM | 2460 | N | TRP | A | 321 | −9.589 | 24.852 | −17.912 | 1.00 | 11.79 |
| ATOM | 2461 | CA | TRP | A | 321 | −9.739 | 24.116 | −19.154 | 1.00 | 11.97 |
| ATOM | 2462 | CB | TRP | A | 321 | −8.988 | 22.775 | −19.063 | 1.00 | 11.15 |
| ATOM | 2463 | CG | TRP | A | 321 | −7.469 | 22.900 | −19.200 | 1.00 | 12.16 |
| ATOM | 2464 | CD1 | TRP | A | 321 | −6.658 | 23.837 | −18.627 | 1.00 | 13.28 |
| ATOM | 2465 | NE1 | TRP | A | 321 | −5.347 | 23.636 | −19.016 | 1.00 | 13.24 |
| ATOM | 2466 | CE2 | TRP | A | 321 | −5.290 | 22.538 | −19.831 | 1.00 | 13.51 |
| ATOM | 2467 | CD2 | TRP | A | 321 | −6.617 | 22.054 | −19.978 | 1.00 | 12.68 |
| ATOM | 2468 | CE3 | TRP | A | 321 | −6.846 | 20.938 | −20.787 | 1.00 | 14.41 |
| ATOM | 2469 | CZ3 | TRP | A | 321 | −5.741 | 20.323 | −21.428 | 1.00 | 13.49 |
| ATOM | 2470 | CH2 | TRP | A | 321 | −4.436 | 20.819 | −21.250 | 1.00 | 13.43 |
| ATOM | 2471 | CZ2 | TRP | A | 321 | −4.193 | 21.948 | −20.479 | 1.00 | 14.69 |
| ATOM | 2472 | C | TRP | A | 321 | −11.202 | 23.797 | −19.342 | 1.00 | 11.99 |
| ATOM | 2473 | O | TRP | A | 321 | −11.875 | 23.448 | −18.388 | 1.00 | 11.51 |
| ATOM | 2474 | N | TYR | A | 322 | −11.696 | 23.896 | −20.579 | 1.00 | 11.47 |
| ATOM | 2475 | CA | TYR | A | 322 | −13.088 | 23.511 | −20.841 | 1.00 | 11.31 |
| ATOM | 2476 | CB | TYR | A | 322 | −13.433 | 23.691 | −22.322 | 1.00 | 12.14 |
| ATOM | 2477 | CG | TYR | A | 322 | −13.352 | 25.130 | −22.793 | 1.00 | 12.81 |
| ATOM | 2478 | CD1 | TYR | A | 322 | −12.260 | 25.574 | −23.509 | 1.00 | 11.43 |
| ATOM | 2479 | CE1 | TYR | A | 322 | −12.173 | 26.914 | −23.965 | 1.00 | 12.91 |
| ATOM | 2480 | CZ | TYR | A | 322 | −13.216 | 27.802 | −23.697 | 1.00 | 14.27 |
| ATOM | 2481 | OH | TYR | A | 322 | −13.127 | 29.104 | −24.146 | 1.00 | 15.10 |
| ATOM | 2482 | CE2 | TYR | A | 322 | −14.324 | 27.373 | −22.982 | 1.00 | 13.40 |
| ATOM | 2483 | CD2 | TYR | A | 322 | −14.378 | 26.031 | −22.522 | 1.00 | 11.58 |
| ATOM | 2484 | C | TYR | A | 322 | −13.367 | 22.082 | −20.433 | 1.00 | 11.31 |
| ATOM | 2485 | O | TYR | A | 322 | −14.380 | 21.795 | −19.771 | 1.00 | 11.08 |
| ATOM | 2486 | N | LEU | A | 323 | −12.480 | 21.169 | −20.814 | 1.00 | 10.96 |
| ATOM | 2487 | CA | LEU | A | 323 | −12.770 | 19.750 | −20.561 | 1.00 | 11.04 |
| ATOM | 2488 | CB | LEU | A | 323 | −11.787 | 18.844 | −21.315 | 1.00 | 11.26 |
| ATOM | 2489 | CG | LEU | A | 323 | −10.314 | 18.876 | −20.903 | 1.00 | 10.53 |
| ATOM | 2490 | CD1 | LEU | A | 323 | −10.074 | 17.902 | −19.745 | 1.00 | 14.57 |
| ATOM | 2491 | CD2 | LEU | A | 323 | −9.474 | 18.437 | −22.112 | 1.00 | 13.19 |
| ATOM | 2492 | C | LEU | A | 323 | −12.778 | 19.449 | −19.048 | 1.00 | 11.68 |
| ATOM | 2493 | O | LEU | A | 323 | −13.444 | 18.510 | −18.602 | 1.00 | 12.06 |
| ATOM | 2494 | N | ALA | A | 324 | −12.036 | 20.239 | −18.268 | 1.00 | 9.86 |
| ATOM | 2495 | CA | ALA | A | 324 | −11.969 | 20.017 | −16.812 | 1.00 | 10.09 |
| ATOM | 2496 | CB | ALA | A | 324 | −10.746 | 20.767 | −16.234 | 1.00 | 9.76 |
| ATOM | 2497 | C | ALA | A | 324 | −13.272 | 20.518 | −16.178 | 1.00 | 10.17 |
| ATOM | 2498 | O | ALA | A | 324 | −13.866 | 19.840 | −15.325 | 1.00 | 10.29 |
| ATOM | 2499 | N | THR | A | 325 | −13.758 | 21.662 | −16.665 | 1.00 | 9.84 |
| ATOM | 2500 | CA | THR | A | 325 | −15.000 | 22.267 | −16.172 | 1.00 | 11.14 |
| ATOM | 2501 | CB | THR | A | 325 | −15.102 | 23.765 | −16.623 | 1.00 | 12.15 |
| ATOM | 2502 | OG1 | THR | A | 325 | −14.002 | 24.498 | −16.063 | 1.00 | 13.16 |
| ATOM | 2503 | CG2 | THR | A | 325 | −16.402 | 24.411 | −16.152 | 1.00 | 11.83 |
| ATOM | 2504 | C | THR | A | 325 | −16.218 | 21.413 | −16.570 | 1.00 | 11.50 |
| ATOM | 2505 | O | THR | A | 325 | −17.086 | 21.126 | −15.727 | 1.00 | 10.79 |
| ATOM | 2506 | N | PHE | A | 326 | −16.234 | 20.925 | −17.816 | 1.00 | 10.79 |
| ATOM | 2507 | CA | PHE | A | 326 | −17.272 | 19.959 | −18.240 | 1.00 | 12.12 |
| ATOM | 2508 | CB | PHE | A | 326 | −17.194 | 19.652 | −19.746 | 1.00 | 12.14 |
| ATOM | 2509 | CG | PHE | A | 326 | −17.518 | 20.851 | −20.640 | 1.00 | 13.71 |
| ATOM | 2510 | CD1 | PHE | A | 326 | −16.777 | 21.077 | −21.804 | 1.00 | 15.21 |
| ATOM | 2511 | CE1 | PHE | A | 326 | −17.043 | 22.188 | −22.635 | 1.00 | 14.99 |
| ATOM | 2512 | CZ | PHE | A | 326 | −18.072 | 23.066 | −22.311 | 1.00 | 16.33 |
| ATOM | 2513 | CE2 | PHE | A | 326 | −18.851 | 22.832 | −21.160 | 1.00 | 20.12 |
| ATOM | 2514 | CD2 | PHE | A | 326 | −18.561 | 21.717 | −20.331 | 1.00 | 16.63 |
| ATOM | 2515 | C | PHE | A | 326 | −17.216 | 18.643 | −17.464 | 1.00 | 11.56 |
| ATOM | 2516 | O | PHE | A | 326 | −18.263 | 18.069 | −17.180 | 1.00 | 11.74 |
| ATOM | 2517 | N | ALA | A | 327 | −16.014 | 18.174 | −17.103 | 1.00 | 11.35 |
| ATOM | 2518 | CA | ALA | A | 327 | −15.889 | 16.909 | −16.346 | 1.00 | 11.41 |
| ATOM | 2519 | CB | ALA | A | 327 | −14.397 | 16.538 | −16.158 | 1.00 | 11.95 |
| ATOM | 2520 | C | ALA | A | 327 | −16.612 | 16.964 | −14.965 | 1.00 | 12.04 |
| ATOM | 2521 | O | ALA | A | 327 | −17.260 | 15.985 | −14.561 | 1.00 | 12.69 |
| ATOM | 2522 | N | ALA | A | 328 | −16.505 | 18.097 | −14.266 | 1.00 | 12.13 |

TABLE 6-continued

| | | | | | | | | | |
|---|---|---|---|---|---|---|---|---|---|
| ATOM | 2523 | CA | ALA | A | 328 | −17.207 | 18.293 | −12.985 | 1.00 | 12.24 |
| ATOM | 2524 | CB | ALA | A | 328 | −16.871 | 19.662 | −12.369 | 1.00 | 12.48 |
| ATOM | 2525 | C | ALA | A | 328 | −18.707 | 18.157 | −13.177 | 1.00 | 12.90 |
| ATOM | 2526 | O | ALA | A | 328 | −19.378 | 17.454 | −12.411 | 1.00 | 13.60 |
| ATOM | 2527 | N | ALA | A | 329 | −19.239 | 18.814 | −14.202 | 1.00 | 12.55 |
| ATOM | 2528 | CA | ALA | A | 329 | −20.669 | 18.682 | −14.504 | 1.00 | 12.31 |
| ATOM | 2529 | CB | ALA | A | 329 | −21.027 | 19.551 | −15.692 | 1.00 | 12.87 |
| ATOM | 2530 | C | ALA | A | 329 | −21.035 | 17.226 | −14.788 | 1.00 | 12.71 |
| ATOM | 2531 | O | ALA | A | 329 | −22.016 | 16.700 | −14.266 | 1.00 | 12.32 |
| ATOM | 2532 | N | GLU | A | 330 | −20.231 | 16.572 | −15.629 | 1.00 | 12.54 |
| ATOM | 2533 | CA | GLU | A | 330 | −20.500 | 15.187 | −16.003 | 1.00 | 12.84 |
| ATOM | 2534 | CB | GLU | A | 330 | −19.519 | 14.718 | −17.100 | 1.00 | 12.55 |
| ATOM | 2535 | CG | GLU | A | 330 | −19.850 | 13.303 | −17.626 | 1.00 | 13.80 |
| ATOM | 2536 | CD | GLU | A | 330 | −19.108 | 12.953 | −18.917 | 1.00 | 13.54 |
| ATOM | 2537 | OE1 | GLU | A | 330 | −18.650 | 13.889 | −19.604 | 1.00 | 12.29 |
| ATOM | 2538 | OE2 | GLU | A | 330 | −18.998 | 11.739 | −19.209 | 1.00 | 14.52 |
| ATOM | 2539 | C | GLU | A | 330 | −20.523 | 14.231 | −14.809 | 1.00 | 12.94 |
| ATOM | 2540 | O | GLU | A | 330 | −21.400 | 13.346 | −14.726 | 1.00 | 12.90 |
| ATOM | 2541 | N | GLN | A | 331 | −19.598 | 14.402 | −13.866 | 1.00 | 12.03 |
| ATOM | 2542 | CA | GLN | A | 331 | −19.589 | 13.502 | −12.726 | 1.00 | 12.38 |
| ATOM | 2543 | CB | GLN | A | 331 | −18.415 | 13.795 | −11.797 | 1.00 | 12.24 |
| ATOM | 2544 | CG | GLN | A | 331 | −18.357 | 12.759 | −10.670 | 1.00 | 13.61 |
| ATOM | 2545 | CD | GLN | A | 331 | −17.327 | 13.072 | −9.608 | 1.00 | 15.82 |
| ATOM | 2546 | OE1 | GLN | A | 331 | −16.263 | 13.617 | −9.895 | 1.00 | 15.39 |
| ATOM | 2547 | NE2 | GLN | A | 331 | −17.628 | 12.702 | −8.372 | 1.00 | 13.76 |
| ATOM | 2548 | C | GLN | A | 331 | −20.912 | 13.643 | −11.969 | 1.00 | 12.33 |
| ATOM | 2549 | O | GLN | A | 331 | −21.512 | 12.659 | −11.556 | 1.00 | 12.45 |
| ATOM | 2550 | N | LEU | A | 332 | −21.377 | 14.873 | −11.844 | 1.00 | 12.57 |
| ATOM | 2551 | CA | LEU | A | 332 | −22.628 | 15.138 | −11.134 | 1.00 | 13.59 |
| ATOM | 2552 | CB | LEU | A | 332 | −22.747 | 16.631 | −10.868 | 1.00 | 13.17 |
| ATOM | 2553 | CG | LEU | A | 332 | −21.681 | 17.142 | −9.867 | 1.00 | 16.56 |
| ATOM | 2554 | CD1 | LEU | A | 332 | −21.718 | 18.678 | −9.801 | 1.00 | 18.10 |
| ATOM | 2555 | CD2 | LEU | A | 332 | −21.851 | 16.476 | −8.492 | 1.00 | 19.47 |
| ATOM | 2556 | C | LEU | A | 332 | −23.861 | 14.600 | −11.864 | 1.00 | 13.57 |
| ATOM | 2557 | O | LEU | A | 332 | −24.770 | 14.053 | −11.239 | 1.00 | 13.24 |
| ATOM | 2558 | N | TYR | A | 333 | −23.909 | 14.766 | −13.179 | 1.00 | 13.90 |
| ATOM | 2559 | CA | TYR | A | 333 | −24.988 | 14.131 | −13.972 | 1.00 | 14.37 |
| ATOM | 2560 | CB | TYR | A | 333 | −24.901 | 14.523 | −15.468 | 1.00 | 14.48 |
| ATOM | 2561 | CG | TYR | A | 333 | −25.056 | 16.001 | −15.721 | 1.00 | 13.91 |
| ATOM | 2562 | CD1 | TYR | A | 333 | −26.086 | 16.738 | −15.118 | 1.00 | 14.64 |
| ATOM | 2563 | CE1 | TYR | A | 333 | −26.208 | 18.117 | −15.350 | 1.00 | 15.65 |
| ATOM | 2564 | CZ | TYR | A | 333 | −25.315 | 18.758 | −16.196 | 1.00 | 16.47 |
| ATOM | 2565 | OH | TYR | A | 333 | −25.431 | 20.101 | −16.442 | 1.00 | 17.22 |
| ATOM | 2566 | CE2 | TYR | A | 333 | −24.310 | 18.050 | −16.836 | 1.00 | 16.59 |
| ATOM | 2567 | CD2 | TYR | A | 333 | −24.192 | 16.669 | −16.601 | 1.00 | 11.27 |
| ATOM | 2568 | C | TYR | A | 333 | −25.022 | 12.613 | −13.843 | 1.00 | 15.03 |
| ATOM | 2569 | O | TYR | A | 333 | −26.108 | 12.012 | −13.824 | 1.00 | 14.78 |
| ATOM | 2570 | N | ASP | A | 334 | −23.836 | 11.998 | −13.807 | 1.00 | 14.06 |
| ATOM | 2571 | CA | ASP | A | 334 | −23.714 | 10.555 | −13.602 | 1.00 | 14.83 |
| ATOM | 2572 | CB | ASP | A | 334 | −22.239 | 10.114 | −13.714 | 1.00 | 13.83 |
| ATOM | 2573 | CG | ASP | A | 334 | −21.708 | 10.149 | −15.136 | 1.00 | 15.84 |
| ATOM | 2574 | OD1 | ASP | A | 334 | −22.495 | 10.373 | −16.081 | 1.00 | 13.95 |
| ATOM | 2575 | OD2 | ASP | A | 334 | −20.470 | 9.943 | −15.313 | 1.00 | 15.50 |
| ATOM | 2576 | C | ASP | A | 334 | −24.254 | 10.163 | −12.224 | 1.00 | 15.21 |
| ATOM | 2577 | O | ASP | A | 334 | −24.941 | 9.132 | −12.080 | 1.00 | 15.93 |
| ATOM | 2578 | N | ALA | A | 335 | −23.933 | 10.969 | −11.213 | 1.00 | 15.09 |
| ATOM | 2579 | CA | ALA | A | 335 | −24.454 | 10.735 | −9.855 | 1.00 | 16.00 |
| ATOM | 2580 | CB | ALA | A | 335 | −23.809 | 11.719 | −8.864 | 1.00 | 15.13 |
| ATOM | 2581 | C | ALA | A | 335 | −25.980 | 10.823 | −9.803 | 1.00 | 16.10 |
| ATOM | 2582 | O | ALA | A | 335 | −26.643 | 9.916 | −9.245 | 1.00 | 16.77 |
| ATOM | 2583 | N | ILE | A | 336 | −26.530 | 11.879 | −10.398 | 1.00 | 16.35 |
| ATOM | 2584 | CA | ILE | A | 336 | −27.987 | 12.087 | −10.470 | 1.00 | 18.39 |
| ATOM | 2585 | CB | ILE | A | 336 | −28.332 | 13.422 | −11.162 | 1.00 | 18.85 |
| ATOM | 2586 | CG1 | ILE | A | 336 | −27.891 | 14.596 | −10.279 | 1.00 | 19.14 |
| ATOM | 2587 | CD1 | ILE | A | 336 | −27.879 | 15.904 | −10.986 | 1.00 | 22.50 |
| ATOM | 2588 | CG2 | ILE | A | 336 | −29.839 | 13.539 | −11.506 | 1.00 | 20.14 |
| ATOM | 2589 | C | ILE | A | 336 | −28.681 | 10.902 | −11.156 | 1.00 | 18.83 |
| ATOM | 2590 | O | ILE | A | 336 | −29.707 | 10.404 | −10.675 | 1.00 | 18.06 |
| ATOM | 2591 | N | TYR | A | 337 | −28.102 | 10.443 | −12.267 | 1.00 | 18.50 |
| ATOM | 2592 | CA | TYR | A | 337 | −28.642 | 9.287 | −12.970 | 1.00 | 18.99 |
| ATOM | 2593 | CB | TYR | A | 337 | −27.753 | 8.908 | −14.169 | 1.00 | 19.80 |
| ATOM | 2594 | CG | TYR | A | 337 | −28.328 | 7.737 | −14.954 | 1.00 | 20.76 |
| ATOM | 2595 | CD1 | TYR | A | 337 | −27.988 | 6.429 | −14.620 | 1.00 | 20.95 |
| ATOM | 2596 | CE1 | TYR | A | 337 | −28.511 | 5.345 | −15.322 | 1.00 | 22.94 |
| ATOM | 2597 | CZ | TYR | A | 337 | −29.382 | 5.559 | −16.356 | 1.00 | 22.19 |
| ATOM | 2598 | OH | TYR | A | 337 | −29.877 | 4.447 | −17.018 | 1.00 | 24.87 |
| ATOM | 2599 | CE2 | TYR | A | 337 | −29.752 | 6.845 | −16.721 | 1.00 | 22.31 |
| ATOM | 2600 | CD2 | TYR | A | 337 | −29.220 | 7.942 | −16.009 | 1.00 | 21.58 |
| ATOM | 2601 | C | TYR | A | 337 | −28.839 | 8.083 | −12.057 | 1.00 | 18.60 |
| ATOM | 2602 | O | TYR | A | 337 | −29.918 | 7.476 | −12.041 | 1.00 | 18.61 |

TABLE 6-continued

| | | | | | | | | | |
|---|---|---|---|---|---|---|---|---|---|
| ATOM | 2603 | N | VAL | A | 338 | −27.802 | 7.737 | −11.297 | 1.00 | 18.67 |
| ATOM | 2604 | CA | VAL | A | 338 | −27.837 | 6.573 | −10.406 | 1.00 | 18.90 |
| ATOM | 2605 | CB | VAL | A | 338 | −26.424 | 6.195 | −9.919 | 1.00 | 18.99 |
| ATOM | 2606 | CG1 | VAL | A | 338 | −26.462 | 5.121 | −8.820 | 1.00 | 19.71 |
| ATOM | 2607 | CG2 | VAL | A | 338 | −25.600 | 5.698 | −11.111 | 1.00 | 18.75 |
| ATOM | 2608 | C | VAL | A | 338 | −28.810 | 6.788 | −9.234 | 1.00 | 19.41 |
| ATOM | 2609 | O | VAL | A | 338 | −29.565 | 5.871 | −8.869 | 1.00 | 19.45 |
| ATOM | 2610 | N | TRP | A | 339 | −28.797 | 7.987 | −8.654 | 1.00 | 19.81 |
| ATOM | 2611 | CA | TRP | A | 339 | −29.743 | 8.290 | −7.559 | 1.00 | 20.46 |
| ATOM | 2612 | CB | TRP | A | 339 | −29.514 | 9.705 | −7.029 | 1.00 | 20.35 |
| ATOM | 2613 | CG | TRP | A | 339 | −28.222 | 9.830 | −6.329 | 1.00 | 18.64 |
| ATOM | 2614 | CD1 | TRP | A | 339 | −27.540 | 8.846 | −5.676 | 1.00 | 16.51 |
| ATOM | 2615 | NE1 | TRP | A | 339 | −26.391 | 9.359 | −5.126 | 1.00 | 17.81 |
| ATOM | 2616 | CE2 | TRP | A | 339 | −26.312 | 10.693 | −5.423 | 1.00 | 17.12 |
| ATOM | 2617 | CD2 | TRP | A | 339 | −27.452 | 11.025 | −6.183 | 1.00 | 17.64 |
| ATOM | 2618 | CE3 | TRP | A | 339 | −27.624 | 12.343 | −6.614 | 1.00 | 17.59 |
| ATOM | 2619 | CZ3 | TRP | A | 339 | −26.637 | 13.283 | −6.284 | 1.00 | 19.24 |
| ATOM | 2620 | CH2 | TRP | A | 339 | −25.510 | 12.912 | −5.520 | 1.00 | 18.24 |
| ATOM | 2621 | CZ2 | TRP | A | 339 | −25.320 | 11.626 | −5.103 | 1.00 | 18.45 |
| ATOM | 2622 | C | TRP | A | 339 | −31.201 | 8.108 | −7.997 | 1.00 | 21.83 |
| ATOM | 2623 | O | TRP | A | 339 | −31.981 | 7.478 | −7.274 | 1.00 | 22.01 |
| ATOM | 2624 | N | LYS | A | 340 | −31.549 | 8.646 | −9.168 | 1.00 | 22.85 |
| ATOM | 2625 | CA | LYS | A | 340 | −32.904 | 8.541 | −9.721 | 1.00 | 25.61 |
| ATOM | 2626 | CB | LYS | A | 340 | −33.066 | 9.411 | −10.967 | 1.00 | 25.52 |
| ATOM | 2627 | CG | LYS | A | 340 | −33.174 | 10.905 | −10.689 | 1.00 | 28.19 |
| ATOM | 2628 | CD | LYS | A | 340 | −33.227 | 11.692 | −11.991 | 1.00 | 34.04 |
| ATOM | 2629 | CE | LYS | A | 340 | −33.966 | 13.011 | −11.805 | 1.00 | 38.04 |
| ATOM | 2630 | NZ | LYS | A | 340 | −33.868 | 13.876 | −13.017 | 1.00 | 41.83 |
| ATOM | 2631 | C | LYS | A | 340 | −33.276 | 7.108 | −10.062 | 1.00 | 27.14 |
| ATOM | 2632 | O | LYS | A | 340 | −34.413 | 6.686 | −9.830 | 1.00 | 27.56 |
| ATOM | 2633 | N | LYS | A | 341 | −32.317 | 6.358 | −10.604 | 1.00 | 28.13 |
| ATOM | 2634 | CA | LYS | A | 341 | −32.552 | 4.975 | −11.018 | 1.00 | 30.18 |
| ATOM | 2635 | CB | LYS | A | 341 | −31.358 | 4.428 | −11.800 | 1.00 | 29.83 |
| ATOM | 2636 | CG | LYS | A | 341 | −31.688 | 3.173 | −12.624 | 1.00 | 33.04 |
| ATOM | 2637 | CD | LYS | A | 341 | −30.472 | 2.624 | −13.395 | 1.00 | 33.62 |
| ATOM | 2638 | CE | LYS | A | 341 | −29.652 | 1.592 | −12.588 | 1.00 | 38.22 |
| ATOM | 2639 | NZ | LYS | A | 341 | −28.691 | 2.188 | −11.573 | 1.00 | 40.88 |
| ATOM | 2640 | C | LYS | A | 341 | −32.816 | 4.081 | −9.817 | 1.00 | 30.19 |
| ATOM | 2641 | O | LYS | A | 341 | −33.744 | 3.260 | −9.837 | 1.00 | 30.15 |
| ATOM | 2642 | N | THR | A | 342 | −31.999 | 4.246 | −8.777 | 1.00 | 29.52 |
| ATOM | 2643 | CA | THR | A | 342 | −32.074 | 3.400 | −7.595 | 1.00 | 29.75 |
| ATOM | 2644 | CB | THR | A | 342 | −30.687 | 3.221 | −6.916 | 1.00 | 29.68 |
| ATOM | 2645 | OG1 | THR | A | 342 | −30.254 | 4.458 | −6.333 | 1.00 | 32.01 |
| ATOM | 2646 | CG2 | THR | A | 342 | −29.628 | 2.735 | −7.929 | 1.00 | 31.40 |
| ATOM | 2647 | C | THR | A | 342 | −33.129 | 3.901 | −6.596 | 1.00 | 29.01 |
| ATOM | 2648 | O | THR | A | 342 | −33.572 | 3.148 | −5.734 | 1.00 | 29.92 |
| ATOM | 2649 | N | GLY | A | 343 | −33.534 | 5.158 | −6.732 | 1.00 | 28.20 |
| ATOM | 2650 | CA | GLY | A | 343 | −34.537 | 5.782 | −5.862 | 1.00 | 28.30 |
| ATOM | 2651 | C | GLY | A | 343 | −34.068 | 6.045 | −4.438 | 1.00 | 27.91 |
| ATOM | 2652 | O | GLY | A | 343 | −34.887 | 6.133 | −3.519 | 1.00 | 28.16 |
| ATOM | 2653 | N | SER | A | 344 | −32.760 | 6.226 | −4.260 | 1.00 | 27.22 |
| ATOM | 2654 | CA | SER | A | 344 | −32.142 | 6.306 | −2.939 | 1.00 | 26.60 |
| ATOM | 2655 | CB | SER | A | 344 | −31.870 | 4.880 | −2.462 | 1.00 | 27.28 |
| ATOM | 2656 | OG | SER | A | 344 | −31.354 | 4.855 | −1.161 | 1.00 | 29.50 |
| ATOM | 2657 | C | SER | A | 344 | −30.823 | 7.107 | −2.979 | 1.00 | 26.02 |
| ATOM | 2658 | O | SER | A | 344 | −30.068 | 6.992 | −3.944 | 1.00 | 25.80 |
| ATOM | 2659 | N | ILE | A | 345 | −30.557 | 7.900 | −1.936 | 1.00 | 24.20 |
| ATOM | 2660 | CA | ILE | A | 345 | −29.295 | 8.641 | −1.770 | 1.00 | 23.04 |
| ATOM | 2661 | CB | ILE | A | 345 | −29.477 | 10.171 | −1.954 | 1.00 | 23.03 |
| ATOM | 2662 | CG1 | ILE | A | 345 | −30.021 | 10.474 | −3.340 | 1.00 | 22.44 |
| ATOM | 2663 | CD1 | ILE | A | 345 | −30.399 | 11.918 | −3.599 | 1.00 | 23.24 |
| ATOM | 2664 | CG2 | ILE | A | 345 | −28.138 | 10.918 | −1.670 | 1.00 | 22.00 |
| ATOM | 2665 | C | ILE | A | 345 | −28.726 | 8.415 | −0.378 | 1.00 | 23.13 |
| ATOM | 2666 | O | ILE | A | 345 | −29.392 | 8.684 | 0.623 | 1.00 | 23.57 |
| ATOM | 2667 | N | THR | A | 346 | −27.490 | 7.943 | −0.307 | 1.00 | 22.23 |
| ATOM | 2668 | CA | THR | A | 346 | −26.820 | 7.765 | 0.963 | 1.00 | 23.25 |
| ATOM | 2669 | CB | THR | A | 346 | −26.246 | 6.338 | 1.101 | 1.00 | 23.78 |
| ATOM | 2670 | OG1 | THR | A | 346 | −27.327 | 5.396 | 1.020 | 1.00 | 27.42 |
| ATOM | 2671 | CG2 | THR | A | 346 | −25.507 | 6.129 | 2.443 | 1.00 | 24.74 |
| ATOM | 2672 | C | THR | A | 346 | −25.753 | 8.849 | 1.138 | 1.00 | 23.03 |
| ATOM | 2673 | O | THR | A | 346 | −24.916 | 9.067 | 0.260 | 1.00 | 23.47 |
| ATOM | 2674 | N | VAL | A | 347 | −25.848 | 9.561 | 2.255 | 1.00 | 21.33 |
| ATOM | 2675 | CA | VAL | A | 347 | −24.845 | 10.537 | 2.674 | 1.00 | 20.11 |
| ATOM | 2676 | CB | VAL | A | 347 | −25.522 | 11.844 | 3.212 | 1.00 | 19.06 |
| ATOM | 2677 | CG1 | VAL | A | 347 | −24.489 | 12.834 | 3.700 | 1.00 | 19.66 |
| ATOM | 2678 | CG2 | VAL | A | 347 | −26.418 | 12.465 | 2.137 | 1.00 | 20.32 |
| ATOM | 2679 | C | VAL | A | 347 | −24.066 | 9.865 | 3.785 | 1.00 | 20.14 |
| ATOM | 2680 | O | VAL | A | 347 | −24.667 | 9.340 | 4.728 | 1.00 | 19.79 |
| ATOM | 2681 | N | THR | A | 348 | −22.734 | 9.878 | 3.671 | 1.00 | 19.85 |
| ATOM | 2682 | CA | THR | A | 348 | −21.851 | 9.274 | 4.660 | 1.00 | 19.92 |

TABLE 6-continued

| | | | | | | | | | |
|---|---|---|---|---|---|---|---|---|---|
| ATOM | 2683 | CB | THR | A | 348 | −20.965 | 8.185 | 4.018 | 1.00 | 19.82 |
| ATOM | 2684 | OG1 | THR | A | 348 | −19.921 | 8.815 | 3.277 | 1.00 | 20.35 |
| ATOM | 2685 | CG2 | THR | A | 348 | −21.785 | 7.278 | 3.092 | 1.00 | 21.67 |
| ATOM | 2686 | C | THR | A | 348 | −20.964 | 10.354 | 5.256 | 1.00 | 19.60 |
| ATOM | 2687 | O | THR | A | 348 | −20.961 | 11.484 | 4.760 | 1.00 | 19.51 |
| ATOM | 2688 | N | ALA | A | 349 | −20.191 | 10.006 | 6.292 | 1.00 | 19.18 |
| ATOM | 2689 | CA | ALA | A | 349 | −19.243 | 10.932 | 6.885 | 1.00 | 20.02 |
| ATOM | 2690 | CB | ALA | A | 349 | −18.494 | 10.275 | 8.044 | 1.00 | 20.61 |
| ATOM | 2691 | C | ALA | A | 349 | −18.240 | 11.466 | 5.842 | 1.00 | 19.79 |
| ATOM | 2692 | O | ALA | A | 349 | −17.756 | 12.601 | 5.947 | 1.00 | 20.15 |
| ATOM | 2693 | N | THR | A | 350 | −17.906 | 10.619 | 4.873 | 1.00 | 18.87 |
| ATOM | 2694 | CA | THR | A | 350 | −16.911 | 10.971 | 3.850 | 1.00 | 18.30 |
| ATOM | 2695 | CB | THR | A | 350 | −16.435 | 9.717 | 3.093 | 1.00 | 18.67 |
| ATOM | 2696 | OG1 | THR | A | 350 | −15.780 | 8.850 | 4.027 | 1.00 | 19.82 |
| ATOM | 2697 | CG2 | THR | A | 350 | −15.426 | 10.097 | 1.974 | 1.00 | 17.73 |
| ATOM | 2698 | C | THR | A | 350 | −17.463 | 12.003 | 2.871 | 1.00 | 17.30 |
| ATOM | 2699 | O | THR | A | 350 | −16.747 | 12.930 | 2.487 | 1.00 | 17.99 |
| ATOM | 2700 | N | SER | A | 351 | −18.716 | 11.847 | 2.467 | 1.00 | 16.16 |
| ATOM | 2701 | CA | SER | A | 351 | −19.316 | 12.803 | 1.517 | 1.00 | 15.78 |
| ATOM | 2702 | CB | SER | A | 351 | −20.214 | 12.076 | 0.512 | 1.00 | 15.85 |
| ATOM | 2703 | OG | SER | A | 351 | −21.280 | 11.412 | 1.156 | 1.00 | 17.14 |
| ATOM | 2704 | C | SER | A | 351 | −20.087 | 13.941 | 2.193 | 1.00 | 15.63 |
| ATOM | 2705 | O | SER | A | 351 | −20.736 | 14.743 | 1.524 | 1.00 | 13.62 |
| ATOM | 2706 | N | LEU | A | 352 | −20.048 | 14.006 | 3.527 | 1.00 | 15.09 |
| ATOM | 2707 | CA | LEU | A | 352 | −20.901 | 14.985 | 4.212 | 1.00 | 16.29 |
| ATOM | 2708 | CB | LEU | A | 352 | −20.759 | 14.851 | 5.736 | 1.00 | 16.64 |
| ATOM | 2709 | CG | LEU | A | 352 | −21.713 | 15.734 | 6.570 | 1.00 | 17.22 |
| ATOM | 2710 | CD1 | LEU | A | 352 | −23.138 | 15.281 | 6.418 | 1.00 | 19.06 |
| ATOM | 2711 | CD2 | LEU | A | 352 | −21.263 | 15.636 | 8.032 | 1.00 | 20.02 |
| ATOM | 2712 | C | LEU | A | 352 | −20.592 | 16.427 | 3.787 | 1.00 | 16.09 |
| ATOM | 2713 | O | LEU | A | 352 | −21.499 | 17.219 | 3.601 | 1.00 | 16.35 |
| ATOM | 2714 | N | ALA | A | 353 | −19.311 | 16.763 | 3.643 | 1.00 | 16.19 |
| ATOM | 2715 | CA | ALA | A | 353 | −18.933 | 18.148 | 3.354 | 1.00 | 15.74 |
| ATOM | 2716 | CB | ALA | A | 353 | −17.460 | 18.314 | 3.424 | 1.00 | 16.30 |
| ATOM | 2717 | C | ALA | A | 353 | −19.459 | 18.544 | 1.972 | 1.00 | 16.11 |
| ATOM | 2718 | O | ALA | A | 353 | −19.957 | 19.668 | 1.781 | 1.00 | 15.44 |
| ATOM | 2719 | N | PHE | A | 354 | −19.367 | 17.607 | 1.021 | 1.00 | 16.10 |
| ATOM | 2720 | CA | PHE | A | 354 | −19.885 | 17.849 | −0.325 | 1.00 | 15.25 |
| ATOM | 2721 | CB | PHE | A | 354 | −19.718 | 16.618 | −1.220 | 1.00 | 16.59 |
| ATOM | 2722 | CG | PHE | A | 354 | −20.497 | 16.707 | −2.500 | 1.00 | 15.45 |
| ATOM | 2723 | CD1 | PHE | A | 354 | −19.959 | 17.375 | −3.603 | 1.00 | 16.95 |
| ATOM | 2724 | CE1 | PHE | A | 354 | −20.664 | 17.489 | −4.793 | 1.00 | 17.06 |
| ATOM | 2725 | CZ | PHE | A | 354 | −21.956 | 16.953 | −4.888 | 1.00 | 16.75 |
| ATOM | 2726 | CE2 | PHE | A | 354 | −22.517 | 16.276 | −3.791 | 1.00 | 16.91 |
| ATOM | 2727 | CD2 | PHE | A | 354 | −21.778 | 16.160 | −2.594 | 1.00 | 17.48 |
| ATOM | 2728 | C | PHE | A | 354 | −21.374 | 18.188 | −0.226 | 1.00 | 15.56 |
| ATOM | 2729 | O | PHE | A | 354 | −21.815 | 19.183 | −0.797 | 1.00 | 15.08 |
| ATOM | 2730 | N | PHE | A | 355 | −22.140 | 17.347 | 0.474 | 1.00 | 14.54 |
| ATOM | 2731 | CA | PHE | A | 355 | −23.588 | 17.544 | 0.517 | 1.00 | 15.29 |
| ATOM | 2732 | CB | PHE | A | 355 | −24.295 | 16.319 | 1.078 | 1.00 | 15.61 |
| ATOM | 2733 | CG | PHE | A | 355 | −24.386 | 15.176 | 0.112 | 1.00 | 15.51 |
| ATOM | 2734 | CD1 | PHE | A | 355 | −25.306 | 15.205 | −0.945 | 1.00 | 14.91 |
| ATOM | 2735 | CE1 | PHE | A | 355 | −25.404 | 14.131 | −1.832 | 1.00 | 16.52 |
| ATOM | 2736 | CZ | PHE | A | 355 | −24.567 | 13.033 | −1.676 | 1.00 | 16.12 |
| ATOM | 2737 | CE2 | PHE | A | 355 | −23.648 | 12.994 | −0.628 | 1.00 | 15.62 |
| ATOM | 2738 | CD2 | PHE | A | 355 | −23.562 | 14.071 | 0.255 | 1.00 | 13.62 |
| ATOM | 2739 | C | PHE | A | 355 | −23.988 | 18.789 | 1.303 | 1.00 | 15.19 |
| ATOM | 2740 | O | PHE | A | 355 | −24.920 | 19.477 | 0.902 | 1.00 | 15.69 |
| ATOM | 2741 | N | GLN | A | 356 | −23.283 | 19.084 | 2.398 | 1.00 | 15.78 |
| ATOM | 2742 | CA | GLN | A | 356 | −23.679 | 20.216 | 3.257 | 1.00 | 16.16 |
| ATOM | 2743 | CB | GLN | A | 356 | −22.987 | 20.165 | 4.627 | 1.00 | 16.84 |
| ATOM | 2744 | CG | GLN | A | 356 | −23.564 | 19.115 | 5.579 | 1.00 | 17.13 |
| ATOM | 2745 | CD | GLN | A | 356 | −22.907 | 19.170 | 6.973 | 1.00 | 18.06 |
| ATOM | 2746 | OE1 | GLN | A | 356 | −21.808 | 19.707 | 7.138 | 1.00 | 20.29 |
| ATOM | 2747 | NE2 | GLN | A | 356 | −23.569 | 18.589 | 7.965 | 1.00 | 20.95 |
| ATOM | 2748 | C | GLN | A | 356 | −23.444 | 21.546 | 2.584 | 1.00 | 16.08 |
| ATOM | 2749 | O | GLN | A | 356 | −24.142 | 22.507 | 2.868 | 1.00 | 15.59 |
| ATOM | 2750 | N | GLU | A | 357 | −22.482 | 21.599 | 1.661 | 1.00 | 16.07 |
| ATOM | 2751 | CA | GLU | A | 357 | −22.261 | 22.808 | 0.884 | 1.00 | 16.41 |
| ATOM | 2752 | CB | GLU | A | 357 | −20.994 | 22.683 | 0.005 | 1.00 | 16.33 |
| ATOM | 2753 | CG | GLU | A | 357 | −20.671 | 23.942 | −0.770 | 1.00 | 15.64 |
| ATOM | 2754 | CD | GLU | A | 357 | −19.326 | 23.894 | −1.516 | 1.00 | 17.67 |
| ATOM | 2755 | OE1 | GLU | A | 357 | −18.931 | 24.947 | −2.066 | 1.00 | 19.03 |
| ATOM | 2756 | OE2 | GLU | A | 357 | −18.685 | 22.822 | −1.575 | 1.00 | 14.75 |
| ATOM | 2757 | C | GLU | A | 357 | −23.492 | 23.105 | 0.019 | 1.00 | 15.84 |
| ATOM | 2758 | O | GLU | A | 357 | −23.786 | 24.237 | −0.224 | 1.00 | 18.07 |
| ATOM | 2759 | N | LEU | A | 358 | −24.213 | 22.084 | −0.420 | 1.00 | 14.72 |
| ATOM | 2760 | CA | LEU | A | 358 | −25.364 | 22.251 | −1.310 | 1.00 | 15.75 |
| ATOM | 2761 | CB | LEU | A | 358 | −25.368 | 21.147 | −2.369 | 1.00 | 16.49 |
| ATOM | 2762 | CG | LEU | A | 358 | −24.057 | 21.100 | −3.168 | 1.00 | 16.81 |

TABLE 6-continued

| | | | | | | | | | |
|---|---|---|---|---|---|---|---|---|---|
| ATOM | 2763 | CD1 | LEU | A | 358 | −24.087 | 19.977 | −4.182 | 1.00 | 19.73 |
| ATOM | 2764 | CD2 | LEU | A | 358 | −23.775 | 22.465 | −3.846 | 1.00 | 19.34 |
| ATOM | 2765 | C | LEU | A | 358 | −26.708 | 22.251 | −0.582 | 1.00 | 15.36 |
| ATOM | 2766 | O | LEU | A | 358 | −27.656 | 22.911 | −1.028 | 1.00 | 14.78 |
| ATOM | 2767 | N | VAL | A | 359 | −26.786 | 21.511 | 0.520 | 1.00 | 15.34 |
| ATOM | 2768 | CA | VAL | A | 359 | −28.001 | 21.404 | 1.321 | 1.00 | 15.00 |
| ATOM | 2769 | CB | VAL | A | 359 | −28.691 | 20.006 | 1.154 | 1.00 | 15.90 |
| ATOM | 2770 | CG1 | VAL | A | 359 | −29.999 | 19.917 | 1.962 | 1.00 | 15.16 |
| ATOM | 2771 | CG2 | VAL | A | 359 | −28.967 | 19.685 | −0.348 | 1.00 | 16.26 |
| ATOM | 2772 | C | VAL | A | 359 | −27.531 | 21.624 | 2.775 | 1.00 | 14.72 |
| ATOM | 2773 | O | VAL | A | 359 | −27.192 | 20.653 | 3.500 | 1.00 | 14.22 |
| ATOM | 2774 | N | PRO | A | 360 | −27.467 | 22.893 | 3.193 | 1.00 | 14.98 |
| ATOM | 2775 | CA | PRO | A | 360 | −26.937 | 23.179 | 4.539 | 1.00 | 15.45 |
| ATOM | 2776 | CB | PRO | A | 360 | −27.150 | 24.700 | 4.700 | 1.00 | 15.45 |
| ATOM | 2777 | CG | PRO | A | 360 | −27.188 | 25.219 | 3.274 | 1.00 | 16.15 |
| ATOM | 2778 | CD | PRO | A | 360 | −27.854 | 24.127 | 2.471 | 1.00 | 14.54 |
| ATOM | 2779 | C | PRO | A | 360 | −27.692 | 22.385 | 5.611 | 1.00 | 15.31 |
| ATOM | 2780 | O | PRO | A | 360 | −28.918 | 22.262 | 5.555 | 1.00 | 15.07 |
| ATOM | 2781 | N | GLY | A | 361 | −26.936 | 21.842 | 6.560 | 1.00 | 15.94 |
| ATOM | 2782 | CA | GLY | A | 361 | −27.512 | 21.143 | 7.709 | 1.00 | 16.53 |
| ATOM | 2783 | C | GLY | A | 361 | −27.870 | 19.680 | 7.488 | 1.00 | 17.03 |
| ATOM | 2784 | O | GLY | A | 361 | −28.268 | 18.997 | 8.429 | 1.00 | 17.68 |
| ATOM | 2785 | N | VAL | A | 362 | −27.762 | 19.176 | 6.261 | 1.00 | 16.13 |
| ATOM | 2786 | CA | VAL | A | 362 | −28.163 | 17.769 | 6.037 | 1.00 | 16.72 |
| ATOM | 2787 | CB | VAL | A | 362 | −28.217 | 17.416 | 4.525 | 1.00 | 16.47 |
| ATOM | 2788 | CG1 | VAL | A | 362 | −26.808 | 17.311 | 3.947 | 1.00 | 16.75 |
| ATOM | 2789 | CG2 | VAL | A | 362 | −29.054 | 16.142 | 4.280 | 1.00 | 17.21 |
| ATOM | 2790 | C | VAL | A | 362 | −27.208 | 16.849 | 6.811 | 1.00 | 17.24 |
| ATOM | 2791 | O | VAL | A | 362 | −26.044 | 17.187 | 7.006 | 1.00 | 17.07 |
| ATOM | 2792 | N | THR | A | 363 | −27.695 | 15.703 | 7.274 | 1.00 | 18.15 |
| ATOM | 2793 | CA | THR | A | 363 | −26.821 | 14.789 | 8.025 | 1.00 | 19.86 |
| ATOM | 2794 | CB | THR | A | 363 | −27.388 | 14.459 | 9.405 | 1.00 | 20.59 |
| ATOM | 2795 | OG1 | THR | A | 363 | −28.634 | 13.776 | 9.217 | 1.00 | 22.85 |
| ATOM | 2796 | CG2 | THR | A | 363 | −27.610 | 15.742 | 10.182 | 1.00 | 22.71 |
| ATOM | 2797 | C | THR | A | 363 | −26.660 | 13.476 | 7.310 | 1.00 | 19.18 |
| ATOM | 2798 | O | THR | A | 363 | −27.398 | 13.184 | 6.371 | 1.00 | 18.87 |
| ATOM | 2799 | N | ALA | A | 364 | −25.697 | 12.679 | 7.769 | 1.00 | 19.67 |
| ATOM | 2800 | CA | ALA | A | 364 | −25.495 | 11.342 | 7.222 | 1.00 | 20.19 |
| ATOM | 2801 | CB | ALA | A | 364 | −24.361 | 10.637 | 7.930 | 1.00 | 20.38 |
| ATOM | 2802 | C | ALA | A | 364 | −26.783 | 10.541 | 7.343 | 1.00 | 21.17 |
| ATOM | 2803 | O | ALA | A | 364 | −27.551 | 10.720 | 8.293 | 1.00 | 21.92 |
| ATOM | 2804 | N | GLY | A | 365 | −27.041 | 9.687 | 6.360 | 1.00 | 21.67 |
| ATOM | 2805 | CA | GLY | A | 365 | −28.207 | 8.823 | 6.371 | 1.00 | 22.35 |
| ATOM | 2806 | C | GLY | A | 365 | −28.584 | 8.415 | 4.968 | 1.00 | 23.66 |
| ATOM | 2807 | O | GLY | A | 365 | −27.924 | 8.804 | 3.991 | 1.00 | 23.66 |
| ATOM | 2808 | N | THR | A | 366 | −29.639 | 7.615 | 4.862 | 1.00 | 23.70 |
| ATOM | 2809 | CA | THR | A | 366 | −30.148 | 7.183 | 3.582 | 1.00 | 24.56 |
| ATOM | 2810 | CB | THR | A | 366 | −30.188 | 5.644 | 3.491 | 1.00 | 25.67 |
| ATOM | 2811 | OG1 | THR | A | 366 | −28.849 | 5.143 | 3.649 | 1.00 | 27.09 |
| ATOM | 2812 | CG2 | THR | A | 366 | −30.715 | 5.216 | 2.159 | 1.00 | 25.47 |
| ATOM | 2813 | C | THR | A | 366 | −31.520 | 7.769 | 3.344 | 1.00 | 25.15 |
| ATOM | 2814 | O | THR | A | 366 | −32.427 | 7.612 | 4.177 | 1.00 | 25.01 |
| ATOM | 2815 | N | TYR | A | 367 | −31.668 | 8.447 | 2.210 | 1.00 | 24.20 |
| ATOM | 2816 | CA | TYR | A | 367 | −32.900 | 9.146 | 1.883 | 1.00 | 24.30 |
| ATOM | 2817 | CB | TYR | A | 367 | −32.616 | 10.648 | 1.701 | 1.00 | 23.51 |
| ATOM | 2818 | CG | TYR | A | 367 | −31.924 | 11.238 | 2.907 | 1.00 | 22.68 |
| ATOM | 2819 | CD1 | TYR | A | 367 | −32.639 | 11.506 | 4.078 | 1.00 | 21.99 |
| ATOM | 2820 | CE1 | TYR | A | 367 | −32.012 | 12.019 | 5.199 | 1.00 | 20.27 |
| ATOM | 2821 | CZ | TYR | A | 367 | −30.650 | 12.263 | 5.176 | 1.00 | 22.67 |
| ATOM | 2822 | OH | TYR | A | 367 | −30.036 | 12.789 | 6.287 | 1.00 | 21.24 |
| ATOM | 2823 | CE2 | TYR | A | 367 | −29.897 | 11.994 | 4.023 | 1.00 | 20.71 |
| ATOM | 2824 | CD2 | TYR | A | 367 | −30.541 | 11.479 | 2.904 | 1.00 | 20.37 |
| ATOM | 2825 | C | TYR | A | 367 | −33.531 | 8.542 | 0.641 | 1.00 | 25.39 |
| ATOM | 2826 | O | TYR | A | 367 | −32.900 | 8.456 | −0.415 | 1.00 | 24.86 |
| ATOM | 2827 | N | SER | A | 368 | −34.782 | 8.109 | 0.758 | 1.00 | 25.82 |
| ATOM | 2828 | CA | SER | A | 368 | −35.416 | 7.454 | −0.374 | 1.00 | 27.29 |
| ATOM | 2829 | CB | SER | A | 368 | −36.339 | 6.332 | 0.107 | 1.00 | 27.90 |
| ATOM | 2830 | OG | SER | A | 368 | −37.519 | 6.895 | 0.634 | 1.00 | 30.69 |
| ATOM | 2831 | C | SER | A | 368 | −36.171 | 8.466 | −1.218 | 1.00 | 27.68 |
| ATOM | 2832 | O | SER | A | 368 | −36.361 | 9.612 | −0.805 | 1.00 | 26.96 |
| ATOM | 2833 | N | SER | A | 369 | −36.629 | 8.025 | −2.388 | 1.00 | 28.98 |
| ATOM | 2834 | CA | SER | A | 369 | −37.260 | 8.908 | −3.367 | 1.00 | 30.52 |
| ATOM | 2835 | CB | SER | A | 369 | −37.520 | 8.167 | −4.681 | 1.00 | 30.90 |
| ATOM | 2836 | OG | SER | A | 369 | −38.269 | 6.983 | −4.452 | 1.00 | 32.57 |
| ATOM | 2837 | C | SER | A | 369 | −38.536 | 9.583 | −2.871 | 1.00 | 31.50 |
| ATOM | 2838 | O | SER | A | 369 | −38.954 | 10.572 | −3.442 | 1.00 | 32.33 |
| ATOM | 2839 | N | SER | A | 370 | −39.150 | 9.067 | −1.809 | 1.00 | 32.18 |
| ATOM | 2840 | CA | SER | A | 370 | −40.365 | 9.712 | −1.279 | 1.00 | 32.96 |
| ATOM | 2841 | CB | SER | A | 370 | −41.313 | 8.692 | −0.624 | 1.00 | 33.18 |
| ATOM | 2842 | OG | SER | A | 370 | −40.610 | 7.847 | 0.273 | 1.00 | 34.18 |

TABLE 6-continued

| ATOM | 2843 | C | SER | A | 370 | −40.049 | 10.864 | −0.323 | 1.00 | 32.37 |
|---|---|---|---|---|---|---|---|---|---|---|
| ATOM | 2844 | O | SER | A | 370 | −40.901 | 11.729 | −0.078 | 1.00 | 33.26 |
| ATOM | 2845 | N | SER | A | 371 | −38.825 | 10.893 | 0.197 | 1.00 | 31.13 |
| ATOM | 2846 | CA | SER | A | 371 | −38.443 | 11.911 | 1.174 | 1.00 | 30.04 |
| ATOM | 2847 | CB | SER | A | 371 | −37.180 | 11.487 | 1.912 | 1.00 | 29.83 |
| ATOM | 2848 | OG | SER | A | 371 | −36.046 | 11.714 | 1.100 | 1.00 | 30.43 |
| ATOM | 2849 | C | SER | A | 371 | −38.247 | 13.295 | 0.553 | 1.00 | 29.13 |
| ATOM | 2850 | O | SER | A | 371 | −37.795 | 13.424 | −0.589 | 1.00 | 28.84 |
| ATOM | 2851 | N | SER | A | 372 | −38.571 | 14.340 | 1.312 | 1.00 | 27.84 |
| ATOM | 2852 | CA | SER | A | 372 | −38.300 | 15.689 | 0.845 | 1.00 | 27.18 |
| ATOM | 2853 | CB | SER | A | 372 | −38.896 | 16.737 | 1.789 | 1.00 | 27.36 |
| ATOM | 2854 | OG | SER | A | 372 | −38.331 | 16.609 | 3.080 | 1.00 | 28.50 |
| ATOM | 2855 | C | SER | A | 372 | −36.783 | 15.902 | 0.680 | 1.00 | 25.79 |
| ATOM | 2856 | O | SER | A | 372 | −36.358 | 16.690 | −0.173 | 1.00 | 26.29 |
| ATOM | 2857 | N | THR | A | 373 | −35.979 | 15.193 | 1.479 | 1.00 | 24.06 |
| ATOM | 2858 | CA | THR | A | 373 | −34.517 | 15.337 | 1.448 | 1.00 | 22.51 |
| ATOM | 2859 | CB | THR | A | 373 | −33.833 | 14.501 | 2.545 | 1.00 | 22.26 |
| ATOM | 2860 | OG1 | THR | A | 373 | −34.543 | 14.636 | 3.788 | 1.00 | 23.04 |
| ATOM | 2861 | CG2 | THR | A | 373 | −32.370 | 14.926 | 2.734 | 1.00 | 21.06 |
| ATOM | 2862 | C | THR | A | 373 | −33.984 | 14.906 | 0.076 | 1.00 | 21.61 |
| ATOM | 2863 | O | THR | A | 373 | −33.134 | 15.578 | −0.513 | 1.00 | 19.74 |
| ATOM | 2864 | N | PHE | A | 374 | −34.493 | 13.777 | −0.413 | 1.00 | 21.13 |
| ATOM | 2865 | CA | PHE | A | 374 | −34.137 | 13.280 | −1.749 | 1.00 | 22.10 |
| ATOM | 2866 | CB | PHE | A | 374 | −34.950 | 12.023 | −2.051 | 1.00 | 22.12 |
| ATOM | 2867 | CG | PHE | A | 374 | −34.624 | 11.380 | −3.366 | 1.00 | 22.90 |
| ATOM | 2868 | CD1 | PHE | A | 374 | −33.677 | 10.368 | −3.432 | 1.00 | 23.83 |
| ATOM | 2869 | CE1 | PHE | A | 374 | −33.381 | 9.749 | −4.649 | 1.00 | 22.56 |
| ATOM | 2870 | CZ | PHE | A | 374 | −34.041 | 10.162 | −5.802 | 1.00 | 23.24 |
| ATOM | 2871 | CE2 | PHE | A | 374 | −34.985 | 11.161 | −5.752 | 1.00 | 23.36 |
| ATOM | 2872 | CD2 | PHE | A | 374 | −35.280 | 11.769 | −4.523 | 1.00 | 23.73 |
| ATOM | 2873 | C | PHE | A | 374 | −34.343 | 14.349 | −2.818 | 1.00 | 22.24 |
| ATOM | 2874 | O | PHE | A | 374 | −33.413 | 14.681 | −3.548 | 1.00 | 22.63 |
| ATOM | 2875 | N | THR | A | 375 | −35.549 | 14.923 | −2.880 | 1.00 | 22.72 |
| ATOM | 2876 | CA | THR | A | 375 | −35.890 | 15.963 | −3.852 | 1.00 | 23.34 |
| ATOM | 2877 | CB | THR | A | 375 | −37.364 | 16.398 | −3.683 | 1.00 | 23.63 |
| ATOM | 2878 | OG1 | THR | A | 375 | −38.193 | 15.244 | −3.809 | 1.00 | 27.83 |
| ATOM | 2879 | CG2 | THR | A | 375 | −37.768 | 17.413 | −4.749 | 1.00 | 27.05 |
| ATOM | 2880 | C | THR | A | 375 | −35.003 | 17.203 | −3.746 | 1.00 | 22.66 |
| ATOM | 2881 | O | THR | A | 375 | −34.603 | 17.766 | −4.756 | 1.00 | 21.43 |
| ATOM | 2882 | N | ASN | A | 376 | −34.744 | 17.632 | −2.508 | 1.00 | 20.80 |
| ATOM | 2883 | CA | ASN | A | 376 | −33.880 | 18.766 | −2.207 | 1.00 | 21.33 |
| ATOM | 2884 | CB | ASN | A | 376 | −33.856 | 18.975 | −0.688 | 1.00 | 21.98 |
| ATOM | 2885 | CG | ASN | A | 376 | −33.343 | 20.354 | −0.278 | 1.00 | 27.01 |
| ATOM | 2886 | OD1 | ASN | A | 376 | −32.582 | 21.011 | −1.004 | 1.00 | 31.72 |
| ATOM | 2887 | ND2 | ASN | A | 376 | −33.748 | 20.793 | 0.913 | 1.00 | 30.14 |
| ATOM | 2888 | C | ASN | A | 376 | −32.465 | 18.527 | −2.733 | 1.00 | 19.80 |
| ATOM | 2889 | O | ASN | A | 376 | −31.898 | 19.389 | −3.415 | 1.00 | 19.75 |
| ATOM | 2890 | N | ILE | A | 377 | −31.915 | 17.354 | −2.431 | 1.00 | 19.00 |
| ATOM | 2891 | CA | ILE | A | 377 | −30.586 | 16.983 | −2.916 | 1.00 | 18.66 |
| ATOM | 2892 | CB | ILE | A | 377 | −30.081 | 15.651 | −2.319 | 1.00 | 18.56 |
| ATOM | 2893 | CG1 | ILE | A | 377 | −29.834 | 15.813 | −0.800 | 1.00 | 18.42 |
| ATOM | 2894 | CD1 | ILE | A | 377 | −29.634 | 14.481 | −0.028 | 1.00 | 19.35 |
| ATOM | 2895 | CG2 | ILE | A | 377 | −28.787 | 15.233 | −3.025 | 1.00 | 18.07 |
| ATOM | 2896 | C | ILE | A | 377 | −30.546 | 16.964 | −4.451 | 1.00 | 18.87 |
| ATOM | 2897 | O | ILE | A | 377 | −29.655 | 17.575 | −5.058 | 1.00 | 18.47 |
| ATOM | 2898 | N | ILE | A | 378 | −31.513 | 16.293 | −5.068 | 1.00 | 18.45 |
| ATOM | 2899 | CA | ILE | A | 378 | −31.556 | 16.216 | −6.539 | 1.00 | 19.78 |
| ATOM | 2900 | CB | ILE | A | 378 | −32.738 | 15.359 | −7.085 | 1.00 | 20.45 |
| ATOM | 2901 | CG1 | ILE | A | 378 | −32.593 | 13.891 | −6.650 | 1.00 | 22.32 |
| ATOM | 2902 | CD1 | ILE | A | 378 | −31.414 | 13.145 | −7.270 | 1.00 | 24.68 |
| ATOM | 2903 | CG2 | ILE | A | 378 | −32.829 | 15.472 | −8.646 | 1.00 | 21.27 |
| ATOM | 2904 | C | ILE | A | 378 | −31.561 | 17.588 | −7.177 | 1.00 | 19.82 |
| ATOM | 2905 | O | ILE | A | 378 | −30.760 | 17.849 | −8.101 | 1.00 | 19.62 |
| ATOM | 2906 | N | ASN | A | 379 | −32.441 | 18.470 | −6.689 | 1.00 | 18.68 |
| ATOM | 2907 | CA | ASN | A | 379 | −32.531 | 19.820 | −7.224 | 1.00 | 19.13 |
| ATOM | 2908 | CB | ASN | A | 379 | −33.738 | 20.578 | −6.658 | 1.00 | 20.08 |
| ATOM | 2909 | CG | ASN | A | 379 | −35.066 | 19.956 | −7.087 | 1.00 | 25.11 |
| ATOM | 2910 | OD1 | ASN | A | 379 | −35.121 | 19.173 | −8.044 | 1.00 | 29.37 |
| ATOM | 2911 | ND2 | ASN | A | 379 | −36.144 | 20.289 | −6.369 | 1.00 | 29.08 |
| ATOM | 2912 | C | ASN | A | 379 | −31.241 | 20.604 | −7.040 | 1.00 | 17.96 |
| ATOM | 2913 | O | ASN | A | 379 | −30.774 | 21.273 | −7.981 | 1.00 | 17.85 |
| ATOM | 2914 | N | ALA | A | 380 | −30.662 | 20.497 | −5.841 | 1.00 | 15.93 |
| ATOM | 2915 | CA | ALA | A | 380 | −29.458 | 21.241 | −5.509 | 1.00 | 16.08 |
| ATOM | 2916 | CB | ALA | A | 380 | −29.120 | 21.061 | −4.033 | 1.00 | 16.14 |
| ATOM | 2917 | C | ALA | A | 380 | −28.299 | 20.783 | −6.389 | 1.00 | 15.64 |
| ATOM | 2918 | O | ALA | A | 380 | −27.566 | 21.607 | −6.938 | 1.00 | 16.56 |
| ATOM | 2919 | N | VAL | A | 381 | −28.153 | 19.471 | −6.519 | 1.00 | 15.22 |
| ATOM | 2920 | CA | VAL | A | 381 | −27.039 | 18.912 | −7.302 | 1.00 | 15.77 |
| ATOM | 2921 | CB | VAL | A | 381 | −26.823 | 17.403 | −6.999 | 1.00 | 15.61 |
| ATOM | 2922 | CG1 | VAL | A | 381 | −25.747 | 16.777 | −7.940 | 1.00 | 14.83 |

TABLE 6-continued

| | | | | | | | | | |
|---|---|---|---|---|---|---|---|---|---|
| ATOM | 2923 | CG2 | VAL | A | 381 | −26.386 | 17.234 | −5.551 | 1.00 | 14.84 |
| ATOM | 2924 | C | VAL | A | 381 | −27.243 | 19.211 | −8.794 | 1.00 | 16.08 |
| ATOM | 2925 | O | VAL | A | 381 | −26.281 | 19.508 | −9.505 | 1.00 | 16.62 |
| ATOM | 2926 | N | SER | A | 382 | −28.482 | 19.112 | −9.278 | 1.00 | 16.66 |
| ATOM | 2927 | CA | SER | A | 382 | −28.772 | 19.453 | −10.690 | 1.00 | 18.67 |
| ATOM | 2928 | CB | SER | A | 382 | −30.246 | 19.212 | −11.043 | 1.00 | 18.26 |
| ATOM | 2929 | OG | SER | A | 382 | −30.538 | 17.855 | −10.893 | 1.00 | 24.56 |
| ATOM | 2930 | C | SER | A | 382 | −28.434 | 20.894 | −11.005 | 1.00 | 18.10 |
| ATOM | 2931 | O | SER | A | 382 | −27.815 | 21.183 | −12.027 | 1.00 | 18.05 |
| ATOM | 2932 | N | THR | A | 383 | −28.853 | 21.810 | −10.132 | 1.00 | 17.66 |
| ATOM | 2933 | CA | THR | A | 383 | −28.521 | 23.216 | −10.298 | 1.00 | 17.72 |
| ATOM | 2934 | CB | THR | A | 383 | −29.199 | 24.063 | −9.180 | 1.00 | 18.48 |
| ATOM | 2935 | OG1 | THR | A | 383 | −30.606 | 23.985 | −9.373 | 1.00 | 19.72 |
| ATOM | 2936 | CG2 | THR | A | 383 | −28.771 | 25.550 | −9.227 | 1.00 | 19.59 |
| ATOM | 2937 | C | THR | A | 383 | −27.017 | 23.470 | −10.314 | 1.00 | 17.09 |
| ATOM | 2938 | O | THR | A | 383 | −26.524 | 24.286 | −11.109 | 1.00 | 17.00 |
| ATOM | 2939 | N | TYR | A | 384 | −26.299 | 22.774 | −9.435 | 1.00 | 15.62 |
| ATOM | 2940 | CA | TYR | A | 384 | −24.858 | 22.925 | −9.312 | 1.00 | 15.37 |
| ATOM | 2941 | CB | TYR | A | 384 | −24.397 | 22.164 | −8.068 | 1.00 | 15.00 |
| ATOM | 2942 | CG | TYR | A | 384 | −22.958 | 22.345 | −7.630 | 1.00 | 15.08 |
| ATOM | 2943 | CD1 | TYR | A | 384 | −22.361 | 23.601 | −7.578 | 1.00 | 15.83 |
| ATOM | 2944 | CE1 | TYR | A | 384 | −21.049 | 23.752 | −7.131 | 1.00 | 16.33 |
| ATOM | 2945 | CZ | TYR | A | 384 | −20.321 | 22.623 | −6.737 | 1.00 | 16.13 |
| ATOM | 2946 | OH | TYR | A | 384 | −19.018 | 22.738 | −6.302 | 1.00 | 16.22 |
| ATOM | 2947 | CE2 | TYR | A | 384 | −20.890 | 21.386 | −6.778 | 1.00 | 13.72 |
| ATOM | 2948 | CD2 | TYR | A | 384 | −22.203 | 21.242 | −7.232 | 1.00 | 14.72 |
| ATOM | 2949 | C | TYR | A | 384 | −24.186 | 22.396 | −10.590 | 1.00 | 15.13 |
| ATOM | 2950 | O | TYR | A | 384 | −23.319 | 23.065 | −11.173 | 1.00 | 14.43 |
| ATOM | 2951 | N | ALA | A | 385 | −24.605 | 21.213 | −11.033 | 1.00 | 15.02 |
| ATOM | 2952 | CA | ALA | A | 385 | −24.045 | 20.639 | −12.263 | 1.00 | 15.60 |
| ATOM | 2953 | CB | ALA | A | 385 | −24.634 | 19.295 | −12.503 | 1.00 | 15.85 |
| ATOM | 2954 | C | ALA | A | 385 | −24.249 | 21.564 | −13.477 | 1.00 | 16.15 |
| ATOM | 2955 | O | ALA | A | 385 | −23.292 | 21.857 | −14.211 | 1.00 | 15.49 |
| ATOM | 2956 | N | ASP | A | 386 | −25.483 | 22.055 | −13.660 | 1.00 | 15.57 |
| ATOM | 2957 | CA | ASP | A | 386 | −25.782 | 23.058 | −14.694 | 1.00 | 16.09 |
| ATOM | 2958 | CB | ASP | A | 386 | −27.279 | 23.433 | −14.687 | 1.00 | 15.88 |
| ATOM | 2959 | CG | ASP | A | 386 | −28.158 | 22.379 | −15.349 | 1.00 | 18.85 |
| ATOM | 2960 | OD1 | ASP | A | 386 | −27.672 | 21.307 | −15.766 | 1.00 | 18.94 |
| ATOM | 2961 | OD2 | ASP | A | 386 | −29.365 | 22.624 | −15.461 | 1.00 | 23.88 |
| ATOM | 2962 | C | ASP | A | 386 | −24.938 | 24.322 | −14.526 | 1.00 | 15.81 |
| ATOM | 2963 | O | ASP | A | 386 | −24.594 | 24.998 | −15.501 | 1.00 | 16.29 |
| ATOM | 2964 | N | GLY | A | 387 | −24.591 | 24.640 | −13.290 | 1.00 | 15.76 |
| ATOM | 2965 | CA | GLY | A | 387 | −23.735 | 25.787 | −13.038 | 1.00 | 14.35 |
| ATOM | 2966 | C | GLY | A | 387 | −22.354 | 25.654 | −13.663 | 1.00 | 14.35 |
| ATOM | 2967 | O | GLY | A | 387 | −21.791 | 26.644 | −14.129 | 1.00 | 13.79 |
| ATOM | 2968 | N | PHE | A | 388 | −21.771 | 24.453 | −13.624 | 1.00 | 14.30 |
| ATOM | 2969 | CA | PHE | A | 388 | −20.479 | 24.217 | −14.312 | 1.00 | 14.69 |
| ATOM | 2970 | CB | PHE | A | 388 | −19.912 | 22.824 | −13.987 | 1.00 | 14.42 |
| ATOM | 2971 | CG | PHE | A | 388 | −19.359 | 22.730 | −12.584 | 1.00 | 13.79 |
| ATOM | 2972 | CD1 | PHE | A | 388 | −18.139 | 23.335 | −12.269 | 1.00 | 14.50 |
| ATOM | 2973 | CE1 | PHE | A | 388 | −17.621 | 23.261 | −10.947 | 1.00 | 16.38 |
| ATOM | 2974 | CZ | PHE | A | 388 | −18.377 | 22.627 | −9.951 | 1.00 | 14.77 |
| ATOM | 2975 | CE2 | PHE | A | 388 | −19.604 | 22.045 | −10.265 | 1.00 | 16.35 |
| ATOM | 2976 | CD2 | PHE | A | 388 | −20.088 | 22.100 | −11.578 | 1.00 | 14.00 |
| ATOM | 2977 | C | PHE | A | 388 | −20.601 | 24.428 | −15.821 | 1.00 | 15.31 |
| ATOM | 2978 | O | PHE | A | 388 | −19.740 | 25.078 | −16.440 | 1.00 | 15.55 |
| ATOM | 2979 | N | LEU | A | 389 | −21.669 | 23.913 | −16.415 | 1.00 | 16.52 |
| ATOM | 2980 | CA | LEU | A | 389 | −21.889 | 24.159 | −17.856 | 1.00 | 17.84 |
| ATOM | 2981 | CB | LEU | A | 389 | −23.137 | 23.431 | −18.382 | 1.00 | 17.83 |
| ATOM | 2982 | CG | LEU | A | 389 | −23.172 | 21.911 | −18.427 | 1.00 | 22.75 |
| ATOM | 2983 | CD1 | LEU | A | 389 | −24.247 | 21.418 | −19.401 | 1.00 | 22.55 |
| ATOM | 2984 | CD2 | LEU | A | 389 | −21.805 | 21.333 | −18.806 | 1.00 | 24.63 |
| ATOM | 2985 | C | LEU | A | 389 | −22.013 | 25.634 | −18.136 | 1.00 | 18.32 |
| ATOM | 2986 | O | LEU | A | 389 | −21.409 | 26.138 | −19.091 | 1.00 | 19.50 |
| ATOM | 2987 | N | SER | A | 390 | −22.775 | 26.341 | −17.295 | 1.00 | 18.55 |
| ATOM | 2988 | CA | SER | A | 390 | −23.021 | 27.767 | −17.469 | 1.00 | 19.33 |
| ATOM | 2989 | CB | SER | A | 390 | −24.090 | 28.246 | −16.491 | 1.00 | 19.89 |
| ATOM | 2990 | OG | SER | A | 390 | −25.325 | 27.693 | −16.891 | 1.00 | 24.07 |
| ATOM | 2991 | C | SER | A | 390 | −21.763 | 28.603 | −17.323 | 1.00 | 19.51 |
| ATOM | 2992 | O | SER | A | 390 | −21.575 | 29.585 | −18.055 | 1.00 | 19.69 |
| ATOM | 2993 | N | GLU | A | 391 | −20.893 | 28.200 | −16.399 | 1.00 | 18.87 |
| ATOM | 2994 | CA | GLU | A | 391 | −19.633 | 28.879 | −16.220 | 1.00 | 19.59 |
| ATOM | 2995 | CB | GLU | A | 391 | −18.901 | 28.393 | −14.952 | 1.00 | 20.02 |
| ATOM | 2996 | CG | GLU | A | 391 | −19.528 | 28.924 | −13.668 | 1.00 | 23.54 |
| ATOM | 2997 | CD | GLU | A | 391 | −19.590 | 30.448 | −13.634 | 1.00 | 26.61 |
| ATOM | 2998 | OE1 | GLU | A | 391 | −18.609 | 31.102 | −14.023 | 1.00 | 28.42 |
| ATOM | 2999 | OE2 | GLU | A | 391 | −20.637 | 30.994 | −13.227 | 1.00 | 29.52 |
| ATOM | 3000 | C | GLU | A | 391 | −18.738 | 28.729 | −17.457 | 1.00 | 19.12 |
| ATOM | 3001 | O | GLU | A | 391 | −18.123 | 29.709 | −17.906 | 1.00 | 19.40 |
| ATOM | 3002 | N | ALA | A | 392 | −18.654 | 27.516 | −17.991 | 1.00 | 18.81 |

TABLE 6-continued

| | | | | | | | | | |
|---|---|---|---|---|---|---|---|---|---|
| ATOM | 3003 | CA | ALA | A | 392 | −17.861 | 27.304 | −19.201 | 1.00 | 19.72 |
| ATOM | 3004 | CB | ALA | A | 392 | −17.758 | 25.815 | −19.526 | 1.00 | 19.45 |
| ATOM | 3005 | C | ALA | A | 392 | −18.478 | 28.098 | −20.363 | 1.00 | 19.59 |
| ATOM | 3006 | O | ALA | A | 392 | −17.764 | 28.724 | −21.157 | 1.00 | 18.65 |
| ATOM | 3007 | N | ALA | A | 393 | −19.808 | 28.117 | −20.425 | 1.00 | 20.40 |
| ATOM | 3008 | CA | ALA | A | 393 | −20.526 | 28.820 | −21.507 | 1.00 | 21.27 |
| ATOM | 3009 | CB | ALA | A | 393 | −22.035 | 28.524 | −21.421 | 1.00 | 21.83 |
| ATOM | 3010 | C | ALA | A | 393 | −20.266 | 30.334 | −21.574 | 1.00 | 21.79 |
| ATOM | 3011 | O | ALA | A | 393 | −20.283 | 30.920 | −22.664 | 1.00 | 21.96 |
| ATOM | 3012 | N | LYS | A | 394 | −19.976 | 30.971 | −20.435 | 1.00 | 21.37 |
| ATOM | 3013 | CA | LYS | A | 394 | −19.626 | 32.383 | −20.447 | 1.00 | 22.02 |
| ATOM | 3014 | CB | LYS | A | 394 | −19.289 | 32.916 | −19.043 | 1.00 | 23.11 |
| ATOM | 3015 | CG | LYS | A | 394 | −20.411 | 32.980 | −18.044 | 1.00 | 25.98 |
| ATOM | 3016 | CD | LYS | A | 394 | −19.782 | 33.341 | −16.700 | 1.00 | 28.89 |
| ATOM | 3017 | CE | LYS | A | 394 | −20.793 | 33.314 | −15.576 | 1.00 | 34.05 |
| ATOM | 3018 | NZ | LYS | A | 394 | −20.097 | 33.674 | −14.290 | 1.00 | 33.96 |
| ATOM | 3019 | C | LYS | A | 394 | −18.403 | 32.626 | −21.310 | 1.00 | 21.55 |
| ATOM | 3020 | O | LYS | A | 394 | −18.188 | 33.742 | −21.771 | 1.00 | 22.41 |
| ATOM | 3021 | N | TYR | A | 395 | −17.570 | 31.604 | −21.488 | 1.00 | 19.98 |
| ATOM | 3022 | CA | TYR | A | 395 | −16.287 | 31.824 | −22.132 | 1.00 | 19.46 |
| ATOM | 3023 | CB | TYR | A | 395 | −15.137 | 31.464 | −21.185 | 1.00 | 20.82 |
| ATOM | 3024 | CG | TYR | A | 395 | −15.291 | 32.165 | −19.872 | 1.00 | 22.04 |
| ATOM | 3025 | CD1 | TYR | A | 395 | −15.644 | 31.450 | −18.716 | 1.00 | 23.21 |
| ATOM | 3026 | CE1 | TYR | A | 395 | −15.806 | 32.097 | −17.508 | 1.00 | 23.70 |
| ATOM | 3027 | CZ | TYR | A | 395 | −15.661 | 33.473 | −17.460 | 1.00 | 23.93 |
| ATOM | 3028 | OH | TYR | A | 395 | −15.828 | 34.143 | −16.272 | 1.00 | 26.14 |
| ATOM | 3029 | CE2 | TYR | A | 395 | −15.327 | 34.202 | −18.593 | 1.00 | 24.38 |
| ATOM | 3030 | CD2 | TYR | A | 395 | −15.157 | 33.548 | −19.791 | 1.00 | 22.37 |
| ATOM | 3031 | C | TYR | A | 395 | −16.157 | 31.119 | −23.451 | 1.00 | 19.22 |
| ATOM | 3032 | O | TYR | A | 395 | −15.045 | 30.940 | −23.941 | 1.00 | 18.70 |
| ATOM | 3033 | N | VAL | A | 396 | −17.299 | 30.718 | −24.018 | 1.00 | 18.16 |
| ATOM | 3034 | CA | VAL | A | 396 | −17.331 | 30.135 | −25.352 | 1.00 | 19.03 |
| ATOM | 3035 | CB | VAL | A | 396 | −18.396 | 29.025 | −25.458 | 1.00 | 18.18 |
| ATOM | 3036 | CG1 | VAL | A | 396 | −18.469 | 28.465 | −26.898 | 1.00 | 18.63 |
| ATOM | 3037 | CG2 | VAL | A | 396 | −18.094 | 27.915 | −24.452 | 1.00 | 18.97 |
| ATOM | 3038 | C | VAL | A | 396 | −17.654 | 31.288 | −26.308 | 1.00 | 19.65 |
| ATOM | 3039 | O | VAL | A | 396 | −18.644 | 31.986 | −26.098 | 1.00 | 19.66 |
| ATOM | 3040 | N | PRO | A | 397 | −16.810 | 31.507 | −27.328 | 1.00 | 20.41 |
| ATOM | 3041 | CA | PRO | A | 397 | −17.016 | 32.626 | −28.256 | 1.00 | 20.82 |
| ATOM | 3042 | CB | PRO | A | 397 | −15.794 | 32.561 | −29.175 | 1.00 | 21.47 |
| ATOM | 3043 | CG | PRO | A | 397 | −14.819 | 31.725 | −28.475 | 1.00 | 21.69 |
| ATOM | 3044 | CD | PRO | A | 397 | −15.598 | 30.741 | −27.661 | 1.00 | 19.70 |
| ATOM | 3045 | C | PRO | A | 397 | −18.280 | 32.434 | −29.073 | 1.00 | 21.11 |
| ATOM | 3046 | O | PRO | A | 397 | −18.844 | 31.339 | −29.088 | 1.00 | 19.88 |
| ATOM | 3047 | N | ALA | A | 398 | −18.713 | 33.492 | −29.765 | 1.00 | 21.26 |
| ATOM | 3048 | CA | ALA | A | 398 | −19.951 | 33.424 | −30.559 | 1.00 | 21.44 |
| ATOM | 3049 | CB | ALA | A | 398 | −20.227 | 34.766 | −31.230 | 1.00 | 22.38 |
| ATOM | 3050 | C | ALA | A | 398 | −19.971 | 32.297 | −31.587 | 1.00 | 21.30 |
| ATOM | 3051 | O | ALA | A | 398 | −21.038 | 31.769 | −31.901 | 1.00 | 22.15 |
| ATOM | 3052 | N | ASP | A | 399 | −18.804 | 31.896 | −32.102 | 1.00 | 20.30 |
| ATOM | 3053 | CA | ASP | A | 399 | −18.780 | 30.858 | −33.133 | 1.00 | 19.40 |
| ATOM | 3054 | CB | ASP | A | 399 | −17.587 | 31.032 | −34.071 | 1.00 | 19.42 |
| ATOM | 3055 | CG | ASP | A | 399 | −16.233 | 30.835 | −33.381 | 1.00 | 21.84 |
| ATOM | 3056 | OD1 | ASP | A | 399 | −16.146 | 30.569 | −32.159 | 1.00 | 20.91 |
| ATOM | 3057 | OD2 | ASP | A | 399 | −15.229 | 30.950 | −34.104 | 1.00 | 24.62 |
| ATOM | 3058 | C | ASP | A | 399 | −18.834 | 29.435 | −32.579 | 1.00 | 18.14 |
| ATOM | 3059 | O | ASP | A | 399 | −18.802 | 28.465 | −33.350 | 1.00 | 16.78 |
| ATOM | 3060 | N | GLY | A | 400 | −18.891 | 29.322 | −31.245 | 1.00 | 16.82 |
| ATOM | 3061 | CA | GLY | A | 400 | −18.996 | 28.015 | −30.607 | 1.00 | 15.41 |
| ATOM | 3062 | C | GLY | A | 400 | −17.693 | 27.229 | −30.556 | 1.00 | 15.07 |
| ATOM | 3063 | O | GLY | A | 400 | −17.704 | 26.041 | −30.203 | 1.00 | 15.23 |
| ATOM | 3064 | N | SER | A | 401 | −16.572 | 27.861 | −30.882 | 1.00 | 14.21 |
| ATOM | 3065 | CA | SER | A | 401 | −15.312 | 27.119 | −30.893 | 1.00 | 14.76 |
| ATOM | 3066 | CB | SER | A | 401 | −14.241 | 27.840 | −31.718 | 1.00 | 14.71 |
| ATOM | 3067 | OG | SER | A | 401 | −14.059 | 29.160 | −31.257 | 1.00 | 16.86 |
| ATOM | 3068 | C | SER | A | 401 | −14.815 | 26.866 | −29.448 | 1.00 | 14.38 |
| ATOM | 3069 | O | SER | A | 401 | −14.992 | 27.717 | −28.562 | 1.00 | 14.58 |
| ATOM | 3070 | N | LEU | A | 402 | −14.169 | 25.720 | −29.249 | 1.00 | 13.54 |
| ATOM | 3071 | CA | LEU | A | 402 | −13.603 | 25.364 | −27.968 | 1.00 | 13.21 |
| ATOM | 3072 | CB | LEU | A | 402 | −14.271 | 24.080 | −27.450 | 1.00 | 13.42 |
| ATOM | 3073 | CG | LEU | A | 402 | −15.776 | 24.192 | −27.162 | 1.00 | 14.06 |
| ATOM | 3074 | CD1 | LEU | A | 402 | −16.289 | 22.834 | −26.668 | 1.00 | 13.87 |
| ATOM | 3075 | CD2 | LEU | A | 402 | −15.997 | 25.264 | −26.109 | 1.00 | 17.00 |
| ATOM | 3076 | C | LEU | A | 402 | −12.111 | 25.143 | −28.109 | 1.00 | 12.99 |
| ATOM | 3077 | O | LEU | A | 402 | −11.695 | 24.166 | −28.707 | 1.00 | 13.19 |
| ATOM | 3078 | N | ALA | A | 403 | −11.320 | 26.070 | −27.578 | 1.00 | 13.02 |
| ATOM | 3079 | CA | ALA | A | 403 | −9.884 | 25.870 | −27.454 | 1.00 | 12.06 |
| ATOM | 3080 | CB | ALA | A | 403 | −9.194 | 27.226 | −27.220 | 1.00 | 11.77 |
| ATOM | 3081 | C | ALA | A | 403 | −9.591 | 24.907 | −26.300 | 1.00 | 12.81 |
| ATOM | 3082 | O | ALA | A | 403 | −10.508 | 24.315 | −25.714 | 1.00 | 12.36 |

TABLE 6-continued

| ATOM | 3083 | N | GLU | A | 404 | −8.308 | 24.772 | −25.959 | 1.00 | 11.39 |
|------|------|-----|-----|---|-----|--------|--------|---------|------|-------|
| ATOM | 3084 | CA | GLU | A | 404 | −7.918 | 23.922 | −24.855 | 1.00 | 11.47 |
| ATOM | 3085 | CB | GLU | A | 404 | −6.412 | 23.689 | −24.931 | 1.00 | 11.02 |
| ATOM | 3086 | CG | GLU | A | 404 | −5.865 | 22.723 | −23.873 | 1.00 | 11.30 |
| ATOM | 3087 | CD | GLU | A | 404 | −4.363 | 22.669 | −23.954 | 1.00 | 12.25 |
| ATOM | 3088 | OE1 | GLU | A | 404 | −3.729 | 23.692 | −23.622 | 1.00 | 12.06 |
| ATOM | 3089 | OE2 | GLU | A | 404 | −3.818 | 21.624 | −24.390 | 1.00 | 12.60 |
| ATOM | 3090 | C | GLU | A | 404 | −8.246 | 24.635 | −23.538 | 1.00 | 11.77 |
| ATOM | 3091 | O | GLU | A | 404 | −8.755 | 24.006 | −22.590 | 1.00 | 11.08 |
| ATOM | 3092 | N | GLN | A | 405 | −7.890 | 25.924 | −23.453 | 1.00 | 12.07 |
| ATOM | 3093 | CA | GLN | A | 405 | −7.952 | 26.655 | −22.196 | 1.00 | 13.33 |
| ATOM | 3094 | CB | GLN | A | 405 | −6.539 | 26.986 | −21.678 | 1.00 | 13.24 |
| ATOM | 3095 | CG | GLN | A | 405 | −5.625 | 25.821 | −21.553 | 1.00 | 15.96 |
| ATOM | 3096 | CD | GLN | A | 405 | −4.229 | 26.213 | −21.051 | 1.00 | 14.97 |
| ATOM | 3097 | OE1 | GLN | A | 405 | −4.068 | 27.130 | −20.236 | 1.00 | 15.09 |
| ATOM | 3098 | NE2 | GLN | A | 405 | −3.236 | 25.475 | −21.496 | 1.00 | 15.87 |
| ATOM | 3099 | C | GLN | A | 405 | −8.687 | 27.985 | −22.356 | 1.00 | 13.51 |
| ATOM | 3100 | O | GLN | A | 405 | −8.870 | 28.475 | −23.489 | 1.00 | 13.74 |
| ATOM | 3101 | N | PHE | A | 406 | −9.041 | 28.587 | −21.226 | 1.00 | 12.60 |
| ATOM | 3102 | CA | PHE | A | 406 | −9.516 | 29.990 | −21.207 | 1.00 | 13.82 |
| ATOM | 3103 | CB | PHE | A | 406 | −11.058 | 30.104 | −21.232 | 1.00 | 13.56 |
| ATOM | 3104 | CG | PHE | A | 406 | −11.800 | 29.385 | −20.123 | 1.00 | 15.20 |
| ATOM | 3105 | CD1 | PHE | A | 406 | −12.155 | 28.026 | −20.242 | 1.00 | 16.33 |
| ATOM | 3106 | CE1 | PHE | A | 406 | −12.879 | 27.370 | −19.239 | 1.00 | 16.80 |
| ATOM | 3107 | CZ | PHE | A | 406 | −13.340 | 28.094 | −18.114 | 1.00 | 16.74 |
| ATOM | 3108 | CE2 | PHE | A | 406 | −13.020 | 29.453 | −17.993 | 1.00 | 15.37 |
| ATOM | 3109 | CD2 | PHE | A | 406 | −12.260 | 30.101 | −19.000 | 1.00 | 17.56 |
| ATOM | 3110 | C | PHE | A | 406 | −8.836 | 30.737 | −20.078 | 1.00 | 13.80 |
| ATOM | 3111 | O | PHE | A | 406 | −8.587 | 30.151 | −19.018 | 1.00 | 14.02 |
| ATOM | 3112 | N | ASP | A | 407 | −8.481 | 31.997 | −20.321 | 1.00 | 14.98 |
| ATOM | 3113 | CA | ASP | A | 407 | −7.547 | 32.726 | −19.438 | 1.00 | 15.04 |
| ATOM | 3114 | CB | ASP | A | 407 | −7.237 | 34.115 | −20.032 | 1.00 | 15.99 |
| ATOM | 3115 | CG | ASP | A | 407 | −6.159 | 34.829 | −19.293 | 1.00 | 18.17 |
| ATOM | 3116 | OD1 | ASP | A | 407 | −6.474 | 35.508 | −18.293 | 1.00 | 20.41 |
| ATOM | 3117 | OD2 | ASP | A | 407 | −4.993 | 34.683 | −19.685 | 1.00 | 20.75 |
| ATOM | 3118 | C | ASP | A | 407 | −8.100 | 32.829 | −18.005 | 1.00 | 14.54 |
| ATOM | 3119 | O | ASP | A | 407 | −9.257 | 33.185 | −17.800 | 1.00 | 15.12 |
| ATOM | 3120 | N | ARG | A | 408 | −7.248 | 32.548 | −17.018 | 1.00 | 14.63 |
| ATOM | 3121 | CA | ARG | A | 408 | −7.644 | 32.530 | −15.609 | 1.00 | 15.33 |
| ATOM | 3122 | CB | ARG | A | 408 | −6.453 | 32.095 | −14.753 | 1.00 | 15.32 |
| ATOM | 3123 | CG | ARG | A | 408 | −5.236 | 33.062 | −14.828 | 1.00 | 14.48 |
| ATOM | 3124 | CD | ARG | A | 408 | −4.009 | 32.479 | −14.122 | 1.00 | 16.22 |
| ATOM | 3125 | NE | ARG | A | 408 | −4.237 | 32.248 | −12.695 | 1.00 | 15.55 |
| ATOM | 3126 | CZ | ARG | A | 408 | −3.613 | 31.323 | −11.961 | 1.00 | 18.66 |
| ATOM | 3127 | NH1 | ARG | A | 408 | −3.878 | 31.231 | −10.658 | 1.00 | 17.51 |
| ATOM | 3128 | NH2 | ARG | A | 408 | −2.717 | 30.499 | −12.511 | 1.00 | 17.12 |
| ATOM | 3129 | C | ARG | A | 408 | −8.167 | 33.886 | −15.108 | 1.00 | 16.66 |
| ATOM | 3130 | O | ARG | A | 408 | −8.898 | 33.943 | −14.110 | 1.00 | 16.82 |
| ATOM | 3131 | N | ASN | A | 409 | −7.781 | 34.964 | −15.790 | 1.00 | 18.00 |
| ATOM | 3132 | CA | ASN | A | 409 | −8.252 | 36.316 | −15.421 | 1.00 | 20.06 |
| ATOM | 3133 | CB | ASN | A | 409 | −7.069 | 37.275 | −15.355 | 1.00 | 20.32 |
| ATOM | 3134 | CG | ASN | A | 409 | −6.119 | 36.937 | −14.224 | 1.00 | 21.65 |
| ATOM | 3135 | OD1 | ASN | A | 409 | −6.549 | 36.678 | −13.111 | 1.00 | 24.42 |
| ATOM | 3136 | ND2 | ASN | A | 409 | −4.830 | 36.914 | −14.516 | 1.00 | 23.96 |
| ATOM | 3137 | C | ASN | A | 409 | −9.320 | 36.903 | −16.336 | 1.00 | 21.43 |
| ATOM | 3138 | O | ASN | A | 409 | −10.272 | 37.524 | −15.857 | 1.00 | 22.03 |
| ATOM | 3139 | N | SER | A | 410 | −9.152 | 36.724 | −17.646 | 1.00 | 22.25 |
| ATOM | 3140 | CA | SER | A | 410 | −10.007 | 37.410 | −18.624 | 1.00 | 22.76 |
| ATOM | 3141 | CB | SER | A | 410 | −9.146 | 38.159 | −19.636 | 1.00 | 23.45 |
| ATOM | 3142 | OG | SER | A | 410 | −8.470 | 37.260 | −20.495 | 1.00 | 23.38 |
| ATOM | 3143 | C | SER | A | 410 | −10.971 | 36.472 | −19.343 | 1.00 | 22.82 |
| ATOM | 3144 | O | SER | A | 410 | −11.898 | 36.925 | −20.010 | 1.00 | 23.59 |
| ATOM | 3145 | N | GLY | A | 411 | −10.758 | 35.161 | −19.238 | 1.00 | 21.64 |
| ATOM | 3146 | CA | GLY | A | 411 | −11.668 | 34.221 | −19.877 | 1.00 | 20.39 |
| ATOM | 3147 | C | GLY | A | 411 | −11.476 | 34.087 | −21.379 | 1.00 | 19.99 |
| ATOM | 3148 | O | GLY | A | 411 | −12.223 | 33.368 | −22.029 | 1.00 | 20.85 |
| ATOM | 3149 | N | THR | A | 412 | −10.478 | 34.750 | −21.941 | 1.00 | 19.04 |
| ATOM | 3150 | CA | THR | A | 412 | −10.268 | 34.658 | −23.383 | 1.00 | 20.25 |
| ATOM | 3151 | CB | THR | A | 412 | −9.447 | 35.853 | −23.922 | 1.00 | 21.81 |
| ATOM | 3152 | OG1 | THR | A | 412 | −8.187 | 35.900 | −23.257 | 1.00 | 26.24 |
| ATOM | 3153 | CG2 | THR | A | 412 | −10.160 | 37.163 | −23.631 | 1.00 | 23.82 |
| ATOM | 3154 | C | THR | A | 412 | −9.615 | 33.294 | −23.732 | 1.00 | 19.17 |
| ATOM | 3155 | O | THR | A | 412 | −8.786 | 32.796 | −22.970 | 1.00 | 17.70 |
| ATOM | 3156 | N | PRO | A | 413 | −9.996 | 32.688 | −24.874 | 1.00 | 18.84 |
| ATOM | 3157 | CA | PRO | A | 413 | −9.466 | 31.348 | −25.234 | 1.00 | 18.32 |
| ATOM | 3158 | CB | PRO | A | 413 | −10.220 | 31.002 | −26.525 | 1.00 | 18.75 |
| ATOM | 3159 | CG | PRO | A | 413 | −11.513 | 31.928 | −26.451 | 1.00 | 19.42 |
| ATOM | 3160 | CD | PRO | A | 413 | −10.943 | 33.195 | −25.891 | 1.00 | 19.40 |
| ATOM | 3161 | C | PRO | A | 413 | −7.959 | 31.399 | −25.464 | 1.00 | 18.87 |
| ATOM | 3162 | O | PRO | A | 413 | −7.436 | 32.406 | −25.955 | 1.00 | 18.20 |

TABLE 6-continued

| ATOM | 3163 | N | LEU | A | 414 | −7.253 | 30.353 | −25.051 | 1.00 | 18.44 |
|---|---|---|---|---|---|---|---|---|---|---|
| ATOM | 3164 | CA | LEU | A | 414 | −5.822 | 30.275 | −25.305 | 1.00 | 18.90 |
| ATOM | 3165 | CB | LEU | A | 414 | −4.992 | 30.974 | −24.208 | 1.00 | 21.66 |
| ATOM | 3166 | CG | LEU | A | 414 | −5.019 | 30.574 | −22.754 | 1.00 | 24.35 |
| ATOM | 3167 | CD1 | LEU | A | 414 | −4.134 | 31.484 | −21.892 | 1.00 | 27.42 |
| ATOM | 3168 | CD2 | LEU | A | 414 | −6.406 | 30.669 | −22.224 | 1.00 | 30.77 |
| ATOM | 3169 | C | LEU | A | 414 | −5.362 | 28.854 | −25.518 | 1.00 | 17.24 |
| ATOM | 3170 | O | LEU | A | 414 | −6.138 | 27.913 | −25.406 | 1.00 | 15.97 |
| ATOM | 3171 | N | SER | A | 415 | −4.091 | 28.733 | −25.865 | 1.00 | 15.34 |
| ATOM | 3172 | CA | SER | A | 415 | −3.473 | 27.481 | −26.257 | 1.00 | 15.28 |
| ATOM | 3173 | CB | SER | A | 415 | −3.434 | 26.468 | −25.101 | 1.00 | 14.94 |
| ATOM | 3174 | OG | SER | A | 415 | −2.632 | 25.355 | −25.445 | 1.00 | 14.00 |
| ATOM | 3175 | C | SER | A | 415 | −4.141 | 26.932 | −27.528 | 1.00 | 15.13 |
| ATOM | 3176 | O | SER | A | 415 | −4.665 | 27.718 | −28.334 | 1.00 | 14.92 |
| ATOM | 3177 | N | ALA | A | 416 | −4.097 | 25.618 | −27.714 | 1.00 | 14.27 |
| ATOM | 3178 | CA | ALA | A | 416 | −4.540 | 24.977 | −28.976 | 1.00 | 14.25 |
| ATOM | 3179 | CB | ALA | A | 416 | −4.380 | 23.486 | −28.889 | 1.00 | 13.68 |
| ATOM | 3180 | C | ALA | A | 416 | −5.981 | 25.314 | −29.315 | 1.00 | 14.33 |
| ATOM | 3181 | O | ALA | A | 416 | −6.854 | 25.216 | −28.459 | 1.00 | 14.09 |
| ATOM | 3182 | N | LEU | A | 417 | −6.223 | 25.680 | −30.567 | 1.00 | 13.34 |
| ATOM | 3183 | CA | LEU | A | 417 | −7.584 | 25.985 | −31.006 | 1.00 | 14.22 |
| ATOM | 3184 | CB | LEU | A | 417 | −7.536 | 26.931 | −32.194 | 1.00 | 16.32 |
| ATOM | 3185 | CG | LEU | A | 417 | −6.841 | 28.283 | −31.942 | 1.00 | 18.75 |
| ATOM | 3186 | CD1 | LEU | A | 417 | −7.005 | 29.127 | −33.163 | 1.00 | 23.81 |
| ATOM | 3187 | CD2 | LEU | A | 417 | −7.419 | 28.991 | −30.712 | 1.00 | 21.76 |
| ATOM | 3188 | C | LEU | A | 417 | −8.279 | 24.687 | −31.413 | 1.00 | 13.18 |
| ATOM | 3189 | O | LEU | A | 417 | −7.610 | 23.712 | −31.775 | 1.00 | 13.19 |
| ATOM | 3190 | N | HIS | A | 418 | −9.609 | 24.658 | −31.311 | 1.00 | 12.26 |
| ATOM | 3191 | CA | HIS | A | 418 | −10.399 | 23.496 | −31.764 | 1.00 | 11.77 |
| ATOM | 3192 | CB | HIS | A | 418 | −10.487 | 23.454 | −33.303 | 1.00 | 13.41 |
| ATOM | 3193 | CG | HIS | A | 418 | −11.294 | 24.566 | −33.898 | 1.00 | 14.68 |
| ATOM | 3194 | ND1 | HIS | A | 418 | −12.646 | 24.717 | −33.660 | 1.00 | 16.00 |
| ATOM | 3195 | CE1 | HIS | A | 418 | −13.095 | 25.762 | −34.341 | 1.00 | 17.83 |
| ATOM | 3196 | NE2 | HIS | A | 418 | −12.085 | 26.290 | −35.015 | 1.00 | 17.38 |
| ATOM | 3197 | CD2 | HIS | A | 418 | −10.948 | 25.557 | −34.763 | 1.00 | 17.65 |
| ATOM | 3198 | C | HIS | A | 418 | −9.826 | 22.187 | −31.206 | 1.00 | 12.24 |
| ATOM | 3199 | O | HIS | A | 418 | −9.540 | 21.250 | −31.947 | 1.00 | 12.10 |
| ATOM | 3200 | N | LEU | A | 419 | −9.656 | 22.116 | −29.880 | 1.00 | 10.99 |
| ATOM | 3201 | CA | LEU | A | 419 | −9.152 | 20.881 | −29.301 | 1.00 | 10.46 |
| ATOM | 3202 | CB | LEU | A | 419 | −8.742 | 21.069 | −27.826 | 1.00 | 10.91 |
| ATOM | 3203 | CG | LEU | A | 419 | −7.983 | 19.883 | −27.220 | 1.00 | 10.16 |
| ATOM | 3204 | CD1 | LEU | A | 419 | −6.524 | 19.944 | −27.669 | 1.00 | 11.45 |
| ATOM | 3205 | CD2 | LEU | A | 419 | −8.080 | 19.960 | −25.657 | 1.00 | 10.73 |
| ATOM | 3206 | C | LEU | A | 419 | −10.215 | 19.812 | −29.398 | 1.00 | 10.49 |
| ATOM | 3207 | O | LEU | A | 419 | −11.312 | 19.973 | −28.863 | 1.00 | 10.67 |
| ATOM | 3208 | N | THR | A | 420 | −9.860 | 18.686 | −30.021 | 1.00 | 10.22 |
| ATOM | 3209 | CA | THR | A | 420 | −10.833 | 17.629 | −30.296 | 1.00 | 10.90 |
| ATOM | 3210 | CB | THR | A | 420 | −10.201 | 16.460 | −31.096 | 1.00 | 11.55 |
| ATOM | 3211 | OG1 | THR | A | 420 | −9.357 | 16.999 | −32.115 | 1.00 | 12.00 |
| ATOM | 3212 | CG2 | THR | A | 420 | −11.310 | 15.625 | −31.786 | 1.00 | 12.52 |
| ATOM | 3213 | C | THR | A | 420 | −11.426 | 17.135 | −28.995 | 1.00 | 11.43 |
| ATOM | 3214 | O | THR | A | 420 | −12.648 | 16.903 | −28.891 | 1.00 | 11.83 |
| ATOM | 3215 | N | TRP | A | 421 | −10.569 | 16.987 | −27.980 | 1.00 | 9.79 |
| ATOM | 3216 | CA | TRP | A | 421 | −11.052 | 16.511 | −26.688 | 1.00 | 11.67 |
| ATOM | 3217 | CB | TRP | A | 421 | −9.839 | 16.184 | −25.803 | 1.00 | 12.06 |
| ATOM | 3218 | CG | TRP | A | 421 | −10.075 | 15.476 | −24.508 | 1.00 | 11.94 |
| ATOM | 3219 | CD1 | TRP | A | 421 | −11.274 | 15.202 | −23.881 | 1.00 | 14.46 |
| ATOM | 3220 | NE1 | TRP | A | 421 | −11.044 | 14.590 | −22.663 | 1.00 | 14.38 |
| ATOM | 3221 | CE2 | TRP | A | 421 | −9.691 | 14.497 | −22.468 | 1.00 | 13.52 |
| ATOM | 3222 | CD2 | TRP | A | 421 | −9.053 | 15.039 | −23.616 | 1.00 | 13.01 |
| ATOM | 3223 | CE3 | TRP | A | 421 | −7.652 | 15.045 | −23.680 | 1.00 | 15.38 |
| ATOM | 3224 | CZ3 | TRP | A | 421 | −6.932 | 14.503 | −22.605 | 1.00 | 16.10 |
| ATOM | 3225 | CH2 | TRP | A | 421 | −7.603 | 13.973 | −21.475 | 1.00 | 14.87 |
| ATOM | 3226 | CZ2 | TRP | A | 421 | −8.973 | 13.945 | −21.398 | 1.00 | 14.27 |
| ATOM | 3227 | C | TRP | A | 421 | −12.035 | 17.514 | −26.032 | 1.00 | 10.89 |
| ATOM | 3228 | O | TRP | A | 421 | −12.966 | 17.092 | −25.357 | 1.00 | 10.96 |
| ATOM | 3229 | N | SER | A | 422 | −11.844 | 18.822 | −26.211 | 1.00 | 10.49 |
| ATOM | 3230 | CA | SER | A | 422 | −12.833 | 19.794 | −25.696 | 1.00 | 11.13 |
| ATOM | 3231 | CB | SER | A | 422 | −12.459 | 21.243 | −26.049 | 1.00 | 10.97 |
| ATOM | 3232 | OG | SER | A | 422 | −11.302 | 21.682 | −25.338 | 1.00 | 13.73 |
| ATOM | 3233 | C | SER | A | 422 | −14.229 | 19.496 | −26.257 | 1.00 | 11.40 |
| ATOM | 3234 | O | SER | A | 422 | −15.204 | 19.468 | −25.530 | 1.00 | 12.11 |
| ATOM | 3235 | N | TYR | A | 423 | −14.320 | 19.281 | −27.563 | 1.00 | 11.29 |
| ATOM | 3236 | CA | TYR | A | 423 | −15.617 | 18.990 | −28.170 | 1.00 | 11.29 |
| ATOM | 3237 | CB | TYR | A | 423 | −15.502 | 19.020 | −29.717 | 1.00 | 11.85 |
| ATOM | 3238 | CG | TYR | A | 423 | −15.132 | 20.389 | −30.274 | 1.00 | 12.18 |
| ATOM | 3239 | CD1 | TYR | A | 423 | −16.002 | 21.485 | −30.145 | 1.00 | 10.35 |
| ATOM | 3240 | CE1 | TYR | A | 423 | −15.668 | 22.741 | −30.643 | 1.00 | 11.83 |
| ATOM | 3241 | CZ | TYR | A | 423 | −14.468 | 22.912 | −31.316 | 1.00 | 12.29 |
| ATOM | 3242 | OH | TYR | A | 423 | −14.157 | 24.145 | −31.783 | 1.00 | 13.08 |

TABLE 6-continued

| ATOM | 3243 | CE2 | TYR | A | 423 | −13.588 | 21.845 | −31.496 | 1.00 | 13.57 |
| ATOM | 3244 | CD2 | TYR | A | 423 | −13.942 | 20.572 | −30.991 | 1.00 | 12.74 |
| ATOM | 3245 | C | TYR | A | 423 | −16.217 | 17.673 | −27.658 | 1.00 | 12.12 |
| ATOM | 3246 | O | TYR | A | 423 | −17.430 | 17.622 | −27.323 | 1.00 | 12.13 |
| ATOM | 3247 | N | ALA | A | 424 | −15.385 | 16.623 | −27.539 | 1.00 | 10.99 |
| ATOM | 3248 | CA | ALA | A | 424 | −15.853 | 15.337 | −26.986 | 1.00 | 11.26 |
| ATOM | 3249 | CB | ALA | A | 424 | −14.717 | 14.294 | −26.952 | 1.00 | 11.73 |
| ATOM | 3250 | C | ALA | A | 424 | −16.411 | 15.535 | −25.588 | 1.00 | 10.93 |
| ATOM | 3251 | O | ALA | A | 424 | −17.465 | 14.974 | −25.246 | 1.00 | 11.68 |
| ATOM | 3252 | N | SER | A | 425 | −15.696 | 16.308 | −24.770 | 1.00 | 9.74 |
| ATOM | 3253 | CA | SER | A | 425 | −16.077 | 16.519 | −23.379 | 1.00 | 10.92 |
| ATOM | 3254 | CB | SER | A | 425 | −14.948 | 17.228 | −22.602 | 1.00 | 11.59 |
| ATOM | 3255 | OG | SER | A | 425 | −14.817 | 18.604 | −22.957 | 1.00 | 13.86 |
| ATOM | 3256 | C | SER | A | 425 | −17.402 | 17.291 | −23.219 | 1.00 | 11.65 |
| ATOM | 3257 | O | SER | A | 425 | −18.132 | 17.043 | −22.276 | 1.00 | 11.86 |
| ATOM | 3258 | N | PHE | A | 426 | −17.683 | 18.220 | −24.133 | 1.00 | 12.13 |
| ATOM | 3259 | CA | PHE | A | 426 | −18.983 | 18.891 | −24.154 | 1.00 | 12.95 |
| ATOM | 3260 | CB | PHE | A | 426 | −19.018 | 20.053 | −25.173 | 1.00 | 13.14 |
| ATOM | 3261 | CG | PHE | A | 426 | −20.410 | 20.575 | −25.391 | 1.00 | 15.93 |
| ATOM | 3262 | CD1 | PHE | A | 426 | −20.951 | 21.522 | −24.516 | 1.00 | 17.76 |
| ATOM | 3263 | CE1 | PHE | A | 426 | −22.279 | 21.980 | −24.688 | 1.00 | 17.49 |
| ATOM | 3264 | CZ | PHE | A | 426 | −23.064 | 21.455 | −25.716 | 1.00 | 17.22 |
| ATOM | 3265 | CE2 | PHE | A | 426 | −22.561 | 20.496 | −26.558 | 1.00 | 17.04 |
| ATOM | 3266 | CD2 | PHE | A | 426 | −21.225 | 20.045 | −26.396 | 1.00 | 17.29 |
| ATOM | 3267 | C | PHE | A | 426 | −20.079 | 17.878 | −24.502 | 1.00 | 13.31 |
| ATOM | 3268 | O | PHE | A | 426 | −21.120 | 17.827 | −23.850 | 1.00 | 13.38 |
| ATOM | 3269 | N | LEU | A | 427 | −19.834 | 17.077 | −25.539 | 1.00 | 13.23 |
| ATOM | 3270 | CA | LEU | A | 427 | −20.811 | 16.090 | −25.996 | 1.00 | 14.41 |
| ATOM | 3271 | CB | LEU | A | 427 | −20.339 | 15.410 | −27.291 | 1.00 | 14.32 |
| ATOM | 3272 | CG | LEU | A | 427 | −20.363 | 16.336 | −28.506 | 1.00 | 15.96 |
| ATOM | 3273 | CD1 | LEU | A | 427 | −19.661 | 15.639 | −29.689 | 1.00 | 18.66 |
| ATOM | 3274 | CD2 | LEU | A | 427 | −21.773 | 16.800 | −28.876 | 1.00 | 16.20 |
| ATOM | 3275 | C | LEU | A | 427 | −21.137 | 15.045 | −24.959 | 1.00 | 14.86 |
| ATOM | 3276 | O | LEU | A | 427 | −22.307 | 14.667 | −24.833 | 1.00 | 16.01 |
| ATOM | 3277 | N | THR | A | 428 | −20.130 | 14.551 | −24.235 | 1.00 | 13.81 |
| ATOM | 3278 | CA | THR | A | 428 | −20.397 | 13.544 | −23.196 | 1.00 | 13.67 |
| ATOM | 3279 | CB | THR | A | 428 | −19.134 | 12.732 | −22.745 | 1.00 | 12.87 |
| ATOM | 3280 | OG1 | THR | A | 428 | −18.127 | 13.597 | −22.185 | 1.00 | 12.33 |
| ATOM | 3281 | CG2 | THR | A | 428 | −18.533 | 11.902 | −23.923 | 1.00 | 13.77 |
| ATOM | 3282 | C | THR | A | 428 | −21.146 | 14.133 | −21.980 | 1.00 | 13.66 |
| ATOM | 3283 | O | THR | A | 428 | −22.102 | 13.517 | −21.478 | 1.00 | 15.09 |
| ATOM | 3284 | N | ALA | A | 429 | −20.738 | 15.312 | −21.524 | 1.00 | 13.72 |
| ATOM | 3285 | CA | ALA | A | 429 | −21.367 | 15.942 | −20.355 | 1.00 | 14.65 |
| ATOM | 3286 | CB | ALA | A | 429 | −20.704 | 17.295 | −20.036 | 1.00 | 14.11 |
| ATOM | 3287 | C | ALA | A | 429 | −22.852 | 16.158 | −20.643 | 1.00 | 15.47 |
| ATOM | 3288 | O | ALA | A | 429 | −23.704 | 15.908 | −19.783 | 1.00 | 15.97 |
| ATOM | 3289 | N | THR | A | 430 | −23.151 | 16.622 | −21.854 | 1.00 | 15.48 |
| ATOM | 3290 | CA | THR | A | 430 | −24.554 | 16.940 | −22.208 | 1.00 | 15.64 |
| ATOM | 3291 | CB | THR | A | 430 | −24.675 | 17.968 | −23.353 | 1.00 | 16.50 |
| ATOM | 3292 | OG1 | THR | A | 430 | −23.980 | 17.494 | −24.514 | 1.00 | 16.24 |
| ATOM | 3293 | CG2 | THR | A | 430 | −24.101 | 19.317 | −22.916 | 1.00 | 16.43 |
| ATOM | 3294 | C | THR | A | 430 | −25.401 | 15.690 | −22.463 | 1.00 | 15.41 |
| ATOM | 3295 | O | THR | A | 430 | −26.611 | 15.674 | −22.158 | 1.00 | 15.67 |
| ATOM | 3296 | N | ALA | A | 431 | −24.772 | 14.632 | −22.968 | 1.00 | 15.22 |
| ATOM | 3297 | CA | ALA | A | 431 | −25.437 | 13.311 | −23.049 | 1.00 | 16.26 |
| ATOM | 3298 | CB | ALA | A | 431 | −24.560 | 12.300 | −23.762 | 1.00 | 16.39 |
| ATOM | 3299 | C | ALA | A | 431 | −25.842 | 12.797 | −21.673 | 1.00 | 16.53 |
| ATOM | 3300 | O | ALA | A | 431 | −26.985 | 12.319 | −21.485 | 1.00 | 16.61 |
| ATOM | 3301 | N | ARG | A | 432 | −24.937 | 12.895 | −20.689 | 1.00 | 15.66 |
| ATOM | 3302 | CA | ARG | A | 432 | −25.256 | 12.410 | −19.342 | 1.00 | 15.64 |
| ATOM | 3303 | CB | ARG | A | 432 | −24.022 | 12.413 | −18.432 | 1.00 | 15.83 |
| ATOM | 3304 | CG | ARG | A | 432 | −22.862 | 11.574 | −18.994 | 1.00 | 14.85 |
| ATOM | 3305 | CD | ARG | A | 432 | −23.174 | 10.051 | −19.154 | 1.00 | 17.10 |
| ATOM | 3306 | NE | ARG | A | 432 | −21.958 | 9.472 | −19.708 | 1.00 | 18.67 |
| ATOM | 3307 | CZ | ARG | A | 432 | −21.766 | 9.225 | −21.003 | 1.00 | 20.81 |
| ATOM | 3308 | NH1 | ARG | A | 432 | −22.769 | 9.372 | −21.868 | 1.00 | 17.45 |
| ATOM | 3309 | NH2 | ARG | A | 432 | −20.576 | 8.781 | −21.427 | 1.00 | 19.90 |
| ATOM | 3310 | C | ARG | A | 432 | −26.375 | 13.235 | −18.719 | 1.00 | 16.42 |
| ATOM | 3311 | O | ARG | A | 432 | −27.256 | 12.685 | −18.030 | 1.00 | 17.47 |
| ATOM | 3312 | N | ARG | A | 433 | −26.371 | 14.535 | −18.996 | 1.00 | 16.54 |
| ATOM | 3313 | CA | ARG | A | 433 | −27.425 | 15.418 | −18.493 | 1.00 | 17.60 |
| ATOM | 3314 | CB | ARG | A | 433 | −27.204 | 16.852 | −18.960 | 1.00 | 16.74 |
| ATOM | 3315 | CG | ARG | A | 433 | −28.287 | 17.833 | −18.461 | 1.00 | 18.39 |
| ATOM | 3316 | CD | ARG | A | 433 | −27.931 | 19.239 | −18.866 | 1.00 | 20.79 |
| ATOM | 3317 | NE | ARG | A | 433 | −28.739 | 20.260 | −18.166 | 1.00 | 23.05 |
| ATOM | 3318 | CZ | ARG | A | 433 | −29.859 | 20.799 | −18.654 | 1.00 | 26.97 |
| ATOM | 3319 | NH1 | ARG | A | 433 | −30.333 | 20.404 | −19.837 | 1.00 | 24.94 |
| ATOM | 3320 | NH2 | ARG | A | 433 | −30.506 | 21.738 | −17.954 | 1.00 | 25.73 |
| ATOM | 3321 | C | ARG | A | 433 | −28.793 | 14.943 | −18.956 | 1.00 | 17.90 |
| ATOM | 3322 | O | ARG | A | 433 | −29.761 | 14.984 | −18.184 | 1.00 | 18.50 |

TABLE 6-continued

| | | | | | | | | | |
|---|---|---|---|---|---|---|---|---|---|
| ATOM | 3323 | N | ALA | A | 434 | −28.861 | 14.502 | −20.210 | 1.00 | 18.06 |
| ATOM | 3324 | CA | ALA | A | 434 | −30.103 | 13.993 | −20.806 | 1.00 | 19.10 |
| ATOM | 3325 | CB | ALA | A | 434 | −30.067 | 14.202 | −22.318 | 1.00 | 19.95 |
| ATOM | 3326 | C | ALA | A | 434 | −30.399 | 12.532 | −20.475 | 1.00 | 20.48 |
| ATOM | 3327 | O | ALA | A | 434 | −31.371 | 11.975 | −20.980 | 1.00 | 21.63 |
| ATOM | 3328 | N | GLY | A | 435 | −29.594 | 11.904 | −19.620 | 1.00 | 19.94 |
| ATOM | 3329 | CA | GLY | A | 435 | −29.865 | 10.531 | −19.182 | 1.00 | 21.09 |
| ATOM | 3330 | C | GLY | A | 435 | −29.415 | 9.475 | −20.188 | 1.00 | 21.57 |
| ATOM | 3331 | O | GLY | A | 435 | −29.847 | 8.304 | −20.130 | 1.00 | 21.64 |
| ATOM | 3332 | N | ILE | A | 436 | −28.529 | 9.873 | −21.100 | 1.00 | 20.44 |
| ATOM | 3333 | CA | ILE | A | 436 | −27.951 | 8.937 | −22.060 | 1.00 | 20.81 |
| ATOM | 3334 | CB | ILE | A | 436 | −27.753 | 9.601 | −23.447 | 1.00 | 20.75 |
| ATOM | 3335 | CG1 | ILE | A | 436 | −29.132 | 9.977 | −24.027 | 1.00 | 23.03 |
| ATOM | 3336 | CD1 | ILE | A | 436 | −29.103 | 11.031 | −25.128 | 1.00 | 26.34 |
| ATOM | 3337 | CG2 | ILE | A | 436 | −27.031 | 8.643 | −24.395 | 1.00 | 21.35 |
| ATOM | 3338 | C | ILE | A | 436 | −26.634 | 8.412 | −21.485 | 1.00 | 20.99 |
| ATOM | 3339 | O | ILE | A | 436 | −25.666 | 9.171 | −21.339 | 1.00 | 20.46 |
| ATOM | 3340 | N | VAL | A | 437 | −26.616 | 7.120 | −21.162 | 1.00 | 20.70 |
| ATOM | 3341 | CA | VAL | A | 437 | −25.465 | 6.479 | −20.517 | 1.00 | 21.39 |
| ATOM | 3342 | CB | VAL | A | 437 | −25.848 | 5.826 | −19.160 | 1.00 | 21.74 |
| ATOM | 3343 | CG1 | VAL | A | 437 | −26.340 | 6.911 | −18.205 | 1.00 | 22.12 |
| ATOM | 3344 | CG2 | VAL | A | 437 | −26.909 | 4.703 | −19.334 | 1.00 | 21.83 |
| ATOM | 3345 | C | VAL | A | 437 | −24.802 | 5.459 | −21.444 | 1.00 | 21.79 |
| ATOM | 3346 | O | VAL | A | 437 | −25.459 | 4.901 | −22.312 | 1.00 | 22.18 |
| ATOM | 3347 | N | PRO | A | 438 | −23.497 | 5.208 | −21.255 | 1.00 | 22.28 |
| ATOM | 3348 | CA | PRO | A | 438 | −22.837 | 4.291 | −22.181 | 1.00 | 22.83 |
| ATOM | 3349 | CB | PRO | A | 438 | −21.365 | 4.642 | −22.009 | 1.00 | 22.45 |
| ATOM | 3350 | CG | PRO | A | 438 | −21.248 | 5.054 | −20.578 | 1.00 | 23.88 |
| ATOM | 3351 | CD | PRO | A | 438 | −22.575 | 5.707 | −20.214 | 1.00 | 22.50 |
| ATOM | 3352 | C | PRO | A | 438 | −23.093 | 2.840 | −21.753 | 1.00 | 22.80 |
| ATOM | 3353 | O | PRO | A | 438 | −23.580 | 2.604 | −20.626 | 1.00 | 23.06 |
| ATOM | 3354 | N | PRO | A | 439 | −22.796 | 1.878 | −22.639 | 1.00 | 22.65 |
| ATOM | 3355 | CA | PRO | A | 439 | −22.911 | 0.452 | −22.283 | 1.00 | 22.08 |
| ATOM | 3356 | CB | PRO | A | 439 | −22.300 | −0.269 | −23.499 | 1.00 | 21.30 |
| ATOM | 3357 | CG | PRO | A | 439 | −22.526 | 0.664 | −24.618 | 1.00 | 22.81 |
| ATOM | 3358 | CD | PRO | A | 439 | −22.391 | 2.062 | −24.050 | 1.00 | 22.29 |
| ATOM | 3359 | C | PRO | A | 439 | −22.122 | 0.129 | −21.037 | 1.00 | 21.88 |
| ATOM | 3360 | O | PRO | A | 439 | −21.075 | 0.750 | −20.776 | 1.00 | 20.95 |
| ATOM | 3361 | N | SER | A | 440 | −22.628 | −0.818 | −20.253 | 1.00 | 22.34 |
| ATOM | 3362 | CA | SER | A | 440 | −21.932 | −1.273 | −19.060 | 1.00 | 23.42 |
| ATOM | 3363 | CB | SER | A | 440 | −22.818 | −2.195 | −18.224 | 1.00 | 24.01 |
| ATOM | 3364 | OG | SER | A | 440 | −23.805 | −1.412 | −17.566 | 1.00 | 26.78 |
| ATOM | 3365 | C | SER | A | 440 | −20.654 | −1.992 | −19.430 | 1.00 | 23.78 |
| ATOM | 3366 | O | SER | A | 440 | −20.540 | −2.554 | −20.522 | 1.00 | 23.97 |
| ATOM | 3367 | N | TRP | A | 441 | −19.681 | −1.929 | −18.536 | 1.00 | 24.15 |
| ATOM | 3368 | CA | TRP | A | 441 | −18.431 | −2.646 | −18.718 | 1.00 | 24.63 |
| ATOM | 3369 | CB | TRP | A | 441 | −17.255 | −1.679 | −18.819 | 1.00 | 22.62 |
| ATOM | 3370 | CG | TRP | A | 441 | −16.963 | −0.837 | −17.583 | 1.00 | 19.24 |
| ATOM | 3371 | CD1 | TRP | A | 441 | −17.409 | 0.432 | −17.339 | 1.00 | 16.95 |
| ATOM | 3372 | NE1 | TRP | A | 441 | −16.909 | 0.878 | −16.138 | 1.00 | 17.89 |
| ATOM | 3373 | CE2 | TRP | A | 441 | −16.111 | −0.098 | −15.595 | 1.00 | 17.88 |
| ATOM | 3374 | CD2 | TRP | A | 441 | −16.130 | −1.194 | −16.476 | 1.00 | 18.22 |
| ATOM | 3375 | CE3 | TRP | A | 441 | −15.377 | −2.338 | −16.149 | 1.00 | 19.64 |
| ATOM | 3376 | CZ3 | TRP | A | 441 | −14.658 | −2.355 | −14.961 | 1.00 | 18.61 |
| ATOM | 3377 | CH2 | TRP | A | 441 | −14.670 | −1.246 | −14.094 | 1.00 | 20.62 |
| ATOM | 3378 | CZ2 | TRP | A | 441 | −15.400 | −0.114 | −14.391 | 1.00 | 19.39 |
| ATOM | 3379 | C | TRP | A | 441 | −18.179 | −3.661 | −17.625 | 1.00 | 26.71 |
| ATOM | 3380 | O | TRP | A | 441 | −17.410 | −4.592 | −17.813 | 1.00 | 25.60 |
| ATOM | 3381 | N | ALA | A | 442 | −18.798 | −3.471 | −16.468 | 1.00 | 29.78 |
| ATOM | 3382 | CA | ALA | A | 442 | −18.442 | −4.292 | −15.330 | 1.00 | 33.94 |
| ATOM | 3383 | CB | ALA | A | 442 | −18.347 | −3.447 | −14.082 | 1.00 | 33.18 |
| ATOM | 3384 | C | ALA | A | 442 | −19.447 | −5.412 | −15.136 | 1.00 | 37.28 |
| ATOM | 3385 | O | ALA | A | 442 | −20.383 | −5.561 | −15.915 | 1.00 | 38.51 |
| ATOM | 3386 | N | ASN | A | 443 | −19.201 | −6.222 | −14.116 | 1.00 | 41.45 |
| ATOM | 3387 | CA | ASN | A | 443 | −20.226 | −7.030 | −13.467 | 1.00 | 45.10 |
| ATOM | 3388 | CB | ASN | A | 443 | −20.135 | −8.490 | −13.914 | 1.00 | 45.75 |
| ATOM | 3389 | CG | ASN | A | 443 | −18.815 | −9.129 | −13.531 | 1.00 | 48.14 |
| ATOM | 3390 | OD1 | ASN | A | 443 | −18.620 | −9.524 | −12.380 | 1.00 | 50.51 |
| ATOM | 3391 | ND2 | ASN | A | 443 | −17.888 | −9.212 | −14.492 | 1.00 | 50.01 |
| ATOM | 3392 | C | ASN | A | 443 | −19.946 | −6.892 | −11.972 | 1.00 | 46.93 |
| ATOM | 3393 | O | ASN | A | 443 | −18.878 | −6.396 | −11.580 | 1.00 | 47.13 |
| ATOM | 3394 | N | SER | A | 444 | −20.873 | −7.343 | −11.135 | 1.00 | 49.21 |
| ATOM | 3395 | CA | SER | A | 444 | −20.719 | −7.201 | −9.684 | 1.00 | 51.08 |
| ATOM | 3396 | CB | SER | A | 444 | −21.713 | −8.096 | −8.936 | 1.00 | 51.21 |
| ATOM | 3397 | OG | SER | A | 444 | −21.738 | −7.735 | −7.563 | 1.00 | 52.90 |
| ATOM | 3398 | C | SER | A | 444 | −19.291 | −7.452 | −9.165 | 1.00 | 51.89 |
| ATOM | 3399 | O | SER | A | 444 | −18.743 | −6.610 | −8.433 | 1.00 | 52.46 |
| ATOM | 3400 | N | SER | A | 445 | −18.700 | −8.588 | −9.558 | 1.00 | 52.45 |
| ATOM | 3401 | CA | SER | A | 445 | −17.400 | −9.030 | −9.029 | 1.00 | 52.98 |
| ATOM | 3402 | CB | SER | A | 445 | −17.138 | −10.497 | −9.385 | 1.00 | 53.12 |

TABLE 6-continued

| ATOM | 3403 | OG | SER | A | 445 | −16.901 | −10.650 | −10.775 | 1.00 | 54.45 |
|------|------|-----|-----|---|-----|---------|---------|---------|------|-------|
| ATOM | 3404 | C | SER | A | 445 | −16.202 | −8.159 | −9.449 | 1.00 | 52.99 |
| ATOM | 3405 | O | SER | A | 445 | −15.184 | −8.112 | −8.738 | 1.00 | 53.28 |
| ATOM | 3406 | N | ALA | A | 446 | −16.328 | −7.472 | −10.588 | 1.00 | 52.67 |
| ATOM | 3407 | CA | ALA | A | 446 | −15.301 | −6.536 | −11.063 | 1.00 | 52.20 |
| ATOM | 3408 | CB | ALA | A | 446 | −15.695 | −5.960 | −12.425 | 1.00 | 52.45 |
| ATOM | 3409 | C | ALA | A | 446 | −14.996 | −5.406 | −10.059 | 1.00 | 51.92 |
| ATOM | 3410 | O | ALA | A | 446 | −14.144 | −4.553 | −10.322 | 1.00 | 51.77 |
| ATOM | 3411 | N | SER | A | 447 | −15.696 | −5.413 | −8.919 | 1.00 | 51.23 |
| ATOM | 3412 | CA | SER | A | 447 | −15.471 | −4.453 | −7.827 | 1.00 | 50.73 |
| ATOM | 3413 | CB | SER | A | 447 | −16.769 | −3.706 | −7.495 | 1.00 | 50.70 |
| ATOM | 3414 | OG | SER | A | 447 | −17.765 | −4.605 | −7.021 | 1.00 | 50.91 |
| ATOM | 3415 | C | SER | A | 447 | −14.886 | −5.072 | −6.537 | 1.00 | 50.31 |
| ATOM | 3416 | O | SER | A | 447 | −14.604 | −4.345 | −5.580 | 1.00 | 50.16 |
| ATOM | 3417 | N | THR | A | 448 | −14.704 | −6.394 | −6.508 | 1.00 | 49.55 |
| ATOM | 3418 | CA | THR | A | 448 | −14.165 | −7.070 | −5.314 | 1.00 | 49.05 |
| ATOM | 3419 | CB | THR | A | 448 | −14.579 | −8.561 | −5.233 | 1.00 | 49.15 |
| ATOM | 3420 | OG1 | THR | A | 448 | −14.076 | −9.255 | −6.378 | 1.00 | 49.97 |
| ATOM | 3421 | CG2 | THR | A | 448 | −16.096 | −8.705 | −5.180 | 1.00 | 49.11 |
| ATOM | 3422 | C | THR | A | 448 | −12.641 | −6.958 | −5.215 | 1.00 | 48.34 |
| ATOM | 3423 | O | THR | A | 448 | −11.911 | −7.325 | −6.135 | 1.00 | 47.84 |
| ATOM | 3424 | N | ILE | A | 449 | −12.174 | −6.444 | −4.084 | 1.00 | 47.93 |
| ATOM | 3425 | CA | ILE | A | 449 | −10.760 | −6.150 | −3.891 | 1.00 | 47.42 |
| ATOM | 3426 | CB | ILE | A | 449 | −10.577 | −4.798 | −3.142 | 1.00 | 47.53 |
| ATOM | 3427 | CG1 | ILE | A | 449 | −11.346 | −3.680 | −3.863 | 1.00 | 46.60 |
| ATOM | 3428 | CD1 | ILE | A | 449 | −11.727 | −2.523 | −2.981 | 1.00 | 45.49 |
| ATOM | 3429 | CG2 | ILE | A | 449 | −9.097 | −4.438 | −2.999 | 1.00 | 46.84 |
| ATOM | 3430 | C | ILE | A | 449 | −10.104 | −7.299 | −3.124 | 1.00 | 47.45 |
| ATOM | 3431 | O | ILE | A | 449 | −10.606 | −7.688 | −2.067 | 1.00 | 47.66 |
| ATOM | 3432 | N | PRO | A | 450 | −8.993 | −7.857 | −3.663 | 1.00 | 47.28 |
| ATOM | 3433 | CA | PRO | A | 450 | −8.202 | −8.926 | −3.036 | 1.00 | 47.25 |
| ATOM | 3434 | CB | PRO | A | 450 | −6.982 | −9.040 | −3.946 | 1.00 | 47.03 |
| ATOM | 3435 | CG | PRO | A | 450 | −7.430 | −8.535 | −5.237 | 1.00 | 47.02 |
| ATOM | 3436 | CD | PRO | A | 450 | −8.431 | −7.470 | −4.969 | 1.00 | 47.07 |
| ATOM | 3437 | C | PRO | A | 450 | −7.731 | −8.562 | −1.639 | 1.00 | 47.48 |
| ATOM | 3438 | O | PRO | A | 450 | −7.608 | −7.377 | −1.322 | 1.00 | 47.43 |
| ATOM | 3439 | N | SER | A | 451 | −7.452 | −9.587 | −0.832 | 1.00 | 47.94 |
| ATOM | 3440 | CA | SER | A | 451 | −7.020 | −9.436 | 0.568 | 1.00 | 48.19 |
| ATOM | 3441 | CB | SER | A | 451 | −7.017 | −10.801 | 1.277 | 1.00 | 48.52 |
| ATOM | 3442 | OG | SER | A | 451 | −8.297 | −11.414 | 1.235 | 1.00 | 49.64 |
| ATOM | 3443 | C | SER | A | 451 | −5.641 | −8.799 | 0.701 | 1.00 | 47.83 |
| ATOM | 3444 | O | SER | A | 451 | −5.415 | −7.963 | 1.575 | 1.00 | 48.39 |
| ATOM | 3445 | N | THR | A | 452 | −4.715 | −9.212 | −0.158 | 1.00 | 47.14 |
| ATOM | 3446 | CA | THR | A | 452 | −3.379 | −8.613 | −0.211 | 1.00 | 46.42 |
| ATOM | 3447 | CB | THR | A | 452 | −2.323 | −9.540 | 0.434 | 1.00 | 46.66 |
| ATOM | 3448 | OG1 | THR | A | 452 | −2.518 | −10.887 | −0.032 | 1.00 | 48.38 |
| ATOM | 3449 | CG2 | THR | A | 452 | −2.446 | −9.514 | 1.962 | 1.00 | 47.77 |
| ATOM | 3450 | C | THR | A | 452 | −3.011 | −8.323 | −1.673 | 1.00 | 44.81 |
| ATOM | 3451 | O | THR | A | 452 | −3.348 | −9.107 | −2.558 | 1.00 | 44.97 |
| ATOM | 3452 | N | CYS | A | 453 | −2.363 | −7.187 | −1.931 | 1.00 | 43.37 |
| ATOM | 3453 | CA | CYS | A | 453 | −1.971 | −6.854 | −3.306 | 1.00 | 41.40 |
| ATOM | 3454 | CB | CYS | A | 453 | −1.918 | −5.339 | −3.574 | 1.00 | 41.01 |
| ATOM | 3455 | SG | CYS | A | 453 | −3.187 | −4.199 | −2.908 | 1.00 | 40.58 |
| ATOM | 3456 | C | CYS | A | 453 | −0.591 | −7.408 | −3.602 | 1.00 | 40.33 |
| ATOM | 3457 | O | CYS | A | 453 | 0.293 | −7.370 | −2.753 | 1.00 | 39.88 |
| ATOM | 3458 | N | SER | A | 454 | −0.405 | −7.911 | −4.812 | 1.00 | 39.25 |
| ATOM | 3459 | CA | SER | A | 454 | 0.937 | −8.142 | −5.336 | 1.00 | 38.68 |
| ATOM | 3460 | CB | SER | A | 454 | 1.222 | −9.638 | −5.484 | 1.00 | 38.56 |
| ATOM | 3461 | OG | SER | A | 454 | 0.276 | −10.251 | −6.349 | 1.00 | 40.44 |
| ATOM | 3462 | C | SER | A | 454 | 1.047 | −7.450 | −6.690 | 1.00 | 37.78 |
| ATOM | 3463 | O | SER | A | 454 | 0.030 | −7.187 | −7.347 | 1.00 | 36.71 |
| ATOM | 3464 | N | GLY | A | 455 | 2.275 | −7.175 | −7.111 | 1.00 | 37.06 |
| ATOM | 3465 | CA | GLY | A | 455 | 2.514 | −6.613 | −8.431 | 1.00 | 36.79 |
| ATOM | 3466 | C | GLY | A | 455 | 2.493 | −7.658 | −9.539 | 1.00 | 36.18 |
| ATOM | 3467 | O | GLY | A | 455 | 3.410 | −7.708 | −10.367 | 1.00 | 36.73 |
| ATOM | 3468 | N | ALA | A | 456 | 1.445 | −8.480 | −9.562 | 1.00 | 35.26 |
| ATOM | 3469 | CA | ALA | A | 456 | 1.321 | −9.584 | −10.512 | 1.00 | 34.46 |
| ATOM | 3470 | CB | ALA | A | 456 | 0.125 | −10.454 | −10.158 | 1.00 | 34.50 |
| ATOM | 3471 | C | ALA | A | 456 | 1.195 | −9.111 | −11.963 | 1.00 | 34.16 |
| ATOM | 3472 | O | ALA | A | 456 | 0.283 | −8.353 | −12.301 | 1.00 | 33.56 |
| ATOM | 3473 | N | SER | A | 457 | 2.097 | −9.588 | −12.817 | 1.00 | 33.11 |
| ATOM | 3474 | CA | SER | A | 457 | 2.013 | −9.302 | −14.241 | 1.00 | 32.60 |
| ATOM | 3475 | CB | SER | A | 457 | 3.022 | −8.219 | −14.635 | 1.00 | 32.50 |
| ATOM | 3476 | OG | SER | A | 457 | 4.352 | −8.691 | −14.519 | 1.00 | 33.28 |
| ATOM | 3477 | C | SER | A | 457 | 2.228 | −10.575 | −15.044 | 1.00 | 32.31 |
| ATOM | 3478 | O | SER | A | 457 | 2.641 | −11.605 | −14.494 | 1.00 | 32.32 |
| ATOM | 3479 | N | VAL | A | 458 | 1.908 | −10.511 | −16.330 | 1.00 | 31.12 |
| ATOM | 3480 | CA | VAL | A | 458 | 2.063 | −11.629 | −17.246 | 1.00 | 31.09 |
| ATOM | 3481 | CB | VAL | A | 458 | 0.682 | −12.199 | −17.659 | 1.00 | 31.00 |
| ATOM | 3482 | CG1 | VAL | A | 458 | 0.806 | −13.173 | −18.830 | 1.00 | 30.72 |

TABLE 6-continued

| | | | | | | | | | |
|---|---|---|---|---|---|---|---|---|---|
| ATOM | 3483 | CG2 | VAL | A | 458 | −0.014 | −12.847 | −16.459 | 1.00 | 31.08 |
| ATOM | 3484 | C | VAL | A | 458 | 2.817 | −11.144 | −18.480 | 1.00 | 30.88 |
| ATOM | 3485 | O | VAL | A | 458 | 2.401 | −10.177 | −19.126 | 1.00 | 29.70 |
| ATOM | 3486 | N | VAL | A | 459 | 3.924 | −11.811 | −18.805 | 1.00 | 30.81 |
| ATOM | 3487 | CA | VAL | A | 459 | 4.643 | −11.525 | −20.051 | 1.00 | 30.95 |
| ATOM | 3488 | CB | VAL | A | 459 | 6.046 | −12.172 | −20.071 | 1.00 | 31.34 |
| ATOM | 3489 | CG1 | VAL | A | 459 | 6.664 | −12.102 | −21.492 | 1.00 | 30.45 |
| ATOM | 3490 | CG2 | VAL | A | 459 | 6.947 | −11.522 | −19.030 | 1.00 | 32.03 |
| ATOM | 3491 | C | VAL | A | 459 | 3.805 | −12.032 | −21.227 | 1.00 | 31.37 |
| ATOM | 3492 | O | VAL | A | 459 | 3.443 | −13.214 | −21.288 | 1.00 | 31.84 |
| ATOM | 3493 | N | GLY | A | 460 | 3.480 | −11.137 | −22.154 | 1.00 | 30.71 |
| ATOM | 3494 | CA | GLY | A | 460 | 2.596 | −11.495 | −23.258 | 1.00 | 30.77 |
| ATOM | 3495 | C | GLY | A | 460 | 3.349 | −11.799 | −24.536 | 1.00 | 30.66 |
| ATOM | 3496 | O | GLY | A | 460 | 4.585 | −11.773 | −24.582 | 1.00 | 30.90 |
| ATOM | 3497 | N | SER | A | 461 | 2.606 | −12.094 | −25.584 | 1.00 | 30.44 |
| ATOM | 3498 | CA | SER | A | 461 | 3.219 | −12.227 | −26.877 | 1.00 | 31.06 |
| ATOM | 3499 | CB | SER | A | 461 | 3.301 | −13.695 | −27.308 | 1.00 | 31.44 |
| ATOM | 3500 | OG | SER | A | 461 | 2.018 | −14.278 | −27.419 | 1.00 | 34.77 |
| ATOM | 3501 | C | SER | A | 461 | 2.463 | −11.357 | −27.864 | 1.00 | 30.21 |
| ATOM | 3502 | O | SER | A | 461 | 1.246 | −11.156 | −27.736 | 1.00 | 30.87 |
| ATOM | 3503 | N | TYR | A | 462 | 3.192 | −10.822 | −28.836 | 1.00 | 28.84 |
| ATOM | 3504 | CA | TYR | A | 462 | 2.651 | −9.797 | −29.712 | 1.00 | 28.13 |
| ATOM | 3505 | CB | TYR | A | 462 | 3.365 | −8.471 | −29.426 | 1.00 | 26.74 |
| ATOM | 3506 | CG | TYR | A | 462 | 3.264 | −8.098 | −27.976 | 1.00 | 25.28 |
| ATOM | 3507 | CD1 | TYR | A | 462 | 2.184 | −7.335 | −27.508 | 1.00 | 23.75 |
| ATOM | 3508 | CE1 | TYR | A | 462 | 2.066 | −7.022 | −26.162 | 1.00 | 23.41 |
| ATOM | 3509 | CZ | TYR | A | 462 | 3.030 | −7.458 | −25.268 | 1.00 | 23.32 |
| ATOM | 3510 | OH | TYR | A | 462 | 2.907 | −7.155 | −23.941 | 1.00 | 23.50 |
| ATOM | 3511 | CE2 | TYR | A | 462 | 4.113 | −8.226 | −25.698 | 1.00 | 22.57 |
| ATOM | 3512 | CD2 | TYR | A | 462 | 4.223 | −8.537 | −27.050 | 1.00 | 24.71 |
| ATOM | 3513 | C | TYR | A | 462 | 2.844 | −10.191 | −31.152 | 1.00 | 28.83 |
| ATOM | 3514 | O | TYR | A | 462 | 3.898 | −10.697 | −31.529 | 1.00 | 29.33 |
| ATOM | 3515 | N | SER | A | 463 | 1.828 | −9.973 | −31.961 | 1.00 | 29.66 |
| ATOM | 3516 | CA | SER | A | 463 | 1.970 | −10.202 | −33.388 | 1.00 | 30.77 |
| ATOM | 3517 | CB | SER | A | 463 | 1.424 | −11.574 | −33.784 | 1.00 | 30.99 |
| ATOM | 3518 | OG | SER | A | 463 | 0.168 | −11.815 | −33.192 | 1.00 | 33.22 |
| ATOM | 3519 | C | SER | A | 463 | 1.311 | −9.082 | −34.170 | 1.00 | 31.28 |
| ATOM | 3520 | O | SER | A | 463 | 0.329 | −8.481 | −33.723 | 1.00 | 30.40 |
| ATOM | 3521 | N | ARG | A | 464 | 1.886 | −8.789 | −35.330 | 1.00 | 31.94 |
| ATOM | 3522 | CA | ARG | A | 464 | 1.377 | −7.775 | −36.225 | 1.00 | 32.97 |
| ATOM | 3523 | CB | ARG | A | 464 | 2.362 | −7.620 | −37.385 | 1.00 | 33.68 |
| ATOM | 3524 | CG | ARG | A | 464 | 2.353 | −6.274 | −38.061 | 1.00 | 36.94 |
| ATOM | 3525 | CD | ARG | A | 464 | 3.502 | −6.206 | −39.088 | 1.00 | 42.45 |
| ATOM | 3526 | NE | ARG | A | 464 | 4.794 | −6.065 | −38.415 | 1.00 | 45.53 |
| ATOM | 3527 | CZ | ARG | A | 464 | 5.416 | −4.903 | −38.227 | 1.00 | 47.50 |
| ATOM | 3528 | NH1 | ARG | A | 464 | 4.882 | −3.775 | −38.688 | 1.00 | 49.50 |
| ATOM | 3529 | NH2 | ARG | A | 464 | 6.580 | −4.863 | −37.592 | 1.00 | 48.59 |
| ATOM | 3530 | C | ARG | A | 464 | −0.017 | −8.171 | −36.741 | 1.00 | 33.03 |
| ATOM | 3531 | O | ARG | A | 464 | −0.166 | −9.228 | −37.358 | 1.00 | 33.00 |
| ATOM | 3532 | N | PRO | A | 465 | −1.053 | −7.333 | −36.479 | 1.00 | 32.72 |
| ATOM | 3533 | CA | PRO | A | 465 | −2.344 | −7.593 | −37.131 | 1.00 | 32.69 |
| ATOM | 3534 | CB | PRO | A | 465 | −3.274 | −6.504 | −36.558 | 1.00 | 32.50 |
| ATOM | 3535 | CG | PRO | A | 465 | −2.581 | −5.981 | −35.345 | 1.00 | 32.47 |
| ATOM | 3536 | CD | PRO | A | 465 | −1.102 | −6.134 | −35.618 | 1.00 | 32.83 |
| ATOM | 3537 | C | PRO | A | 465 | −2.189 | −7.421 | −38.642 | 1.00 | 33.30 |
| ATOM | 3538 | O | PRO | A | 465 | −1.332 | −6.661 | −39.097 | 1.00 | 33.20 |
| ATOM | 3539 | N | THR | A | 466 | −2.990 | −8.136 | −39.412 | 1.00 | 34.26 |
| ATOM | 3540 | CA | THR | A | 466 | −2.810 | −8.131 | −40.855 | 1.00 | 35.62 |
| ATOM | 3541 | CB | THR | A | 466 | −2.264 | −9.486 | −41.370 | 1.00 | 35.33 |
| ATOM | 3542 | OG1 | THR | A | 466 | −3.225 | −10.512 | −41.136 | 1.00 | 36.81 |
| ATOM | 3543 | CG2 | THR | A | 466 | −0.965 | −9.848 | −40.656 | 1.00 | 35.91 |
| ATOM | 3544 | C | THR | A | 466 | −4.076 | −7.711 | −41.600 | 1.00 | 36.15 |
| ATOM | 3545 | O | THR | A | 466 | −3.983 | −7.077 | −42.648 | 1.00 | 36.93 |
| ATOM | 3546 | N | ALA | A | 467 | −5.242 | −8.051 | −41.048 | 1.00 | 36.82 |
| ATOM | 3547 | CA | ALA | A | 467 | −6.540 | −7.648 | −41.609 | 1.00 | 37.30 |
| ATOM | 3548 | CB | ALA | A | 467 | −7.663 | −8.403 | −40.930 | 1.00 | 37.04 |
| ATOM | 3549 | C | ALA | A | 467 | −6.767 | −6.136 | −41.509 | 1.00 | 38.13 |
| ATOM | 3550 | O | ALA | A | 467 | −6.715 | −5.556 | −40.417 | 1.00 | 37.96 |
| ATOM | 3551 | N | THR | A | 468 | −7.011 | −5.502 | −42.653 | 1.00 | 38.66 |
| ATOM | 3552 | CA | THR | A | 468 | −7.146 | −4.050 | −42.702 | 1.00 | 39.18 |
| ATOM | 3553 | CB | THR | A | 468 | −5.970 | −3.406 | −43.428 | 1.00 | 39.43 |
| ATOM | 3554 | OG1 | THR | A | 468 | −5.955 | −3.879 | −44.778 | 1.00 | 40.06 |
| ATOM | 3555 | CG2 | THR | A | 468 | −4.637 | −3.717 | −42.734 | 1.00 | 39.67 |
| ATOM | 3556 | C | THR | A | 468 | −8.405 | −3.591 | −43.427 | 1.00 | 39.33 |
| ATOM | 3557 | O | THR | A | 468 | −8.468 | −2.451 | −43.890 | 1.00 | 39.79 |
| ATOM | 3558 | N | SER | A | 469 | −9.403 | −4.457 | −43.529 | 1.00 | 39.12 |
| ATOM | 3559 | CA | SER | A | 469 | −10.651 | −4.065 | −44.176 | 1.00 | 39.41 |
| ATOM | 3560 | CB | SER | A | 469 | −10.624 | −4.369 | −45.684 | 1.00 | 39.77 |
| ATOM | 3561 | OG | SER | A | 469 | −10.476 | −5.763 | −45.916 | 1.00 | 41.02 |
| ATOM | 3562 | C | SER | A | 469 | −11.850 | −4.732 | −43.537 | 1.00 | 38.54 |

TABLE 6-continued

| | | | | | | | | | |
|---|---|---|---|---|---|---|---|---|---|
| ATOM | 3563 | O | SER | A | 469 | −11.771 | −5.856 | −43.046 | 1.00 | 38.85 |
| ATOM | 3564 | N | PHE | A | 470 | −12.962 | −4.014 | −43.558 | 1.00 | 38.00 |
| ATOM | 3565 | CA | PHE | A | 470 | −14.216 | −4.507 | −43.031 | 1.00 | 37.29 |
| ATOM | 3566 | CB | PHE | A | 470 | −14.880 | −3.406 | −42.220 | 1.00 | 36.87 |
| ATOM | 3567 | CG | PHE | A | 470 | −14.277 | −3.212 | −40.865 | 1.00 | 35.43 |
| ATOM | 3568 | CD1 | PHE | A | 470 | −13.146 | −2.428 | −40.696 | 1.00 | 35.15 |
| ATOM | 3569 | CE1 | PHE | A | 470 | −12.589 | −2.252 | −39.437 | 1.00 | 33.73 |
| ATOM | 3570 | CZ | PHE | A | 470 | −13.159 | −2.852 | −38.332 | 1.00 | 35.04 |
| ATOM | 3571 | CE2 | PHE | A | 470 | −14.292 | −3.638 | −38.479 | 1.00 | 36.26 |
| ATOM | 3572 | CD2 | PHE | A | 470 | −14.844 | −3.816 | −39.751 | 1.00 | 35.71 |
| ATOM | 3573 | C | PHE | A | 470 | −15.128 | −4.923 | −44.181 | 1.00 | 37.34 |
| ATOM | 3574 | O | PHE | A | 470 | −15.059 | −4.337 | −45.258 | 1.00 | 37.21 |
| ATOM | 3575 | N | PRO | A | 471 | −15.987 | −5.931 | −43.959 | 1.00 | 37.46 |
| ATOM | 3576 | CA | PRO | A | 471 | −16.983 | −6.243 | −44.985 | 1.00 | 38.04 |
| ATOM | 3577 | CB | PRO | A | 471 | −17.790 | −7.383 | −44.361 | 1.00 | 37.60 |
| ATOM | 3578 | CG | PRO | A | 471 | −16.877 | −7.986 | −43.337 | 1.00 | 38.09 |
| ATOM | 3579 | CD | PRO | A | 471 | −16.093 | −6.828 | −42.795 | 1.00 | 37.31 |
| ATOM | 3580 | C | PRO | A | 471 | −17.879 | −5.033 | −45.231 | 1.00 | 38.96 |
| ATOM | 3581 | O | PRO | A | 471 | −18.108 | −4.245 | −44.306 | 1.00 | 38.78 |
| ATOM | 3582 | N | PRO | A | 472 | −18.378 | −4.869 | −46.471 | 1.00 | 39.78 |
| ATOM | 3583 | CA | PRO | A | 472 | −19.238 | −3.723 | −46.771 | 1.00 | 39.87 |
| ATOM | 3584 | CB | PRO | A | 472 | −19.378 | −3.780 | −48.293 | 1.00 | 40.09 |
| ATOM | 3585 | CG | PRO | A | 472 | −19.171 | −5.225 | −48.635 | 1.00 | 40.28 |
| ATOM | 3586 | CD | PRO | A | 472 | −18.171 | −5.740 | −47.649 | 1.00 | 40.02 |
| ATOM | 3587 | C | PRO | A | 472 | −20.604 | −3.864 | −46.114 | 1.00 | 39.75 |
| ATOM | 3588 | O | PRO | A | 472 | −21.017 | −4.980 | −45.798 | 1.00 | 40.10 |
| ATOM | 3589 | N | SER | A | 473 | −21.268 | −2.734 | −45.881 | 1.00 | 39.71 |
| ATOM | 3590 | CA | SER | A | 473 | −22.675 | −2.696 | −45.467 | 1.00 | 39.61 |
| ATOM | 3591 | CB | SER | A | 473 | −23.571 | −3.070 | −46.651 | 1.00 | 40.16 |
| ATOM | 3592 | OG | SER | A | 473 | −23.468 | −2.074 | −47.658 | 1.00 | 42.55 |
| ATOM | 3593 | C | SER | A | 473 | −23.043 | −3.509 | −44.221 | 1.00 | 38.94 |
| ATOM | 3594 | O | SER | A | 473 | −24.041 | −4.258 | −44.210 | 1.00 | 39.07 |
| ATOM | 3595 | N | GLN | A | 474 | −22.257 | −3.340 | −43.159 | 1.00 | 37.75 |
| ATOM | 3596 | CA | GLN | A | 474 | −22.558 | −3.993 | −41.888 | 1.00 | 36.60 |
| ATOM | 3597 | CB | GLN | A | 474 | −21.291 | −4.205 | −41.057 | 1.00 | 36.41 |
| ATOM | 3598 | CG | GLN | A | 474 | −20.331 | −5.169 | −41.732 | 1.00 | 36.24 |
| ATOM | 3599 | CD | GLN | A | 474 | −19.295 | −5.757 | −40.795 | 1.00 | 36.45 |
| ATOM | 3600 | OE1 | GLN | A | 474 | −18.478 | −5.040 | −40.211 | 1.00 | 35.30 |
| ATOM | 3601 | NE2 | GLN | A | 474 | −19.304 | −7.077 | −40.671 | 1.00 | 36.85 |
| ATOM | 3602 | C | GLN | A | 474 | −23.620 | −3.191 | −41.149 | 1.00 | 36.40 |
| ATOM | 3603 | O | GLN | A | 474 | −23.329 | −2.444 | −40.208 | 1.00 | 35.99 |
| ATOM | 3604 | N | THR | A | 475 | −24.859 | −3.350 | −41.616 | 1.00 | 35.59 |
| ATOM | 3605 | CA | THR | A | 475 | −26.012 | −2.595 | −41.148 | 1.00 | 35.20 |
| ATOM | 3606 | CB | THR | A | 475 | −27.051 | −2.478 | −42.287 | 1.00 | 35.73 |
| ATOM | 3607 | OG1 | THR | A | 475 | −27.120 | −3.737 | −42.959 | 1.00 | 36.85 |
| ATOM | 3608 | CG2 | THR | A | 475 | −26.642 | −1.418 | −43.310 | 1.00 | 34.51 |
| ATOM | 3609 | C | THR | A | 475 | −26.635 | −3.256 | −39.910 | 1.00 | 35.16 |
| ATOM | 3610 | O | THR | A | 475 | −26.363 | −4.420 | −39.622 | 1.00 | 34.47 |
| ATOM | 3611 | N | PRO | A | 476 | −27.453 | −2.510 | −39.148 | 1.00 | 35.36 |
| ATOM | 3612 | CA | PRO | A | 476 | −27.990 | −3.111 | −37.923 | 1.00 | 36.40 |
| ATOM | 3613 | CB | PRO | A | 476 | −28.567 | −1.910 | −37.167 | 1.00 | 36.04 |
| ATOM | 3614 | CG | PRO | A | 476 | −28.890 | −0.912 | −38.230 | 1.00 | 35.98 |
| ATOM | 3615 | CD | PRO | A | 476 | −27.907 | −1.119 | −39.339 | 1.00 | 35.70 |
| ATOM | 3616 | C | PRO | A | 476 | −29.085 | −4.171 | −38.158 | 1.00 | 37.45 |
| ATOM | 3617 | O | PRO | A | 476 | −29.654 | −4.244 | −39.254 | 1.00 | 36.95 |
| ATOM | 3618 | N | LYS | A | 477 | −29.342 | −4.984 | −37.133 | 1.00 | 39.01 |
| ATOM | 3619 | CA | LYS | A | 477 | −30.472 | −5.911 | −37.111 | 1.00 | 41.20 |
| ATOM | 3620 | CB | LYS | A | 477 | −30.541 | −6.641 | −35.774 | 1.00 | 41.46 |
| ATOM | 3621 | CG | LYS | A | 477 | −29.665 | −7.850 | −35.604 | 1.00 | 41.87 |
| ATOM | 3622 | CD | LYS | A | 477 | −29.939 | −8.517 | −34.237 | 1.00 | 42.36 |
| ATOM | 3623 | CE | LYS | A | 477 | −29.996 | −7.497 | −33.076 | 1.00 | 44.55 |
| ATOM | 3624 | NZ | LYS | A | 477 | −29.705 | −8.110 | −31.718 | 1.00 | 44.56 |
| ATOM | 3625 | C | LYS | A | 477 | −31.766 | −5.118 | −37.230 | 1.00 | 42.27 |
| ATOM | 3626 | O | LYS | A | 477 | −31.818 | −3.960 | −36.798 | 1.00 | 42.18 |
| ATOM | 3627 | N | PRO | A | 478 | −32.831 | −5.743 | −37.780 | 1.00 | 43.46 |
| ATOM | 3628 | CA | PRO | A | 478 | −34.150 | −5.106 | −37.669 | 1.00 | 44.02 |
| ATOM | 3629 | CB | PRO | A | 478 | −35.106 | −6.144 | −38.267 | 1.00 | 43.89 |
| ATOM | 3630 | CG | PRO | A | 478 | −34.255 | −7.033 | −39.105 | 1.00 | 44.08 |
| ATOM | 3631 | CD | PRO | A | 478 | −32.885 | −7.034 | −38.493 | 1.00 | 43.41 |
| ATOM | 3632 | C | PRO | A | 478 | −34.480 | −4.892 | −36.194 | 1.00 | 44.52 |
| ATOM | 3633 | O | PRO | A | 478 | −34.197 | −5.769 | −35.364 | 1.00 | 44.73 |
| ATOM | 3634 | N | GLY | A | 479 | −35.043 | −3.728 | −35.874 | 1.00 | 45.20 |
| ATOM | 3635 | CA | GLY | A | 479 | −35.421 | −3.395 | −34.494 | 1.00 | 45.90 |
| ATOM | 3636 | C | GLY | A | 479 | −34.386 | −2.601 | −33.711 | 1.00 | 46.37 |
| ATOM | 3637 | O | GLY | A | 479 | −34.576 | −2.331 | −32.520 | 1.00 | 46.98 |
| ATOM | 3638 | N | VAL | A | 480 | −33.282 | −2.244 | −34.367 | 1.00 | 46.28 |
| ATOM | 3639 | CA | VAL | A | 480 | −32.261 | −1.383 | −33.760 | 1.00 | 46.15 |
| ATOM | 3640 | CB | VAL | A | 480 | −30.820 | −1.863 | −34.121 | 1.00 | 46.20 |
| ATOM | 3641 | CG1 | VAL | A | 480 | −29.755 | −0.899 | −33.584 | 1.00 | 45.85 |
| ATOM | 3642 | CG2 | VAL | A | 480 | −30.569 | −3.281 | −33.603 | 1.00 | 46.25 |

TABLE 6-continued

| ATOM | 3643 | C | VAL | A | 480 | −32.498 | 0.046 | −34.260 | 1.00 | 45.93 |
| ATOM | 3644 | O | VAL | A | 480 | −32.673 | 0.240 | −35.465 | 1.00 | 46.15 |
| ATOM | 3645 | N | PRO | A | 481 | −32.534 | 1.049 | −33.344 | 1.00 | 45.70 |
| ATOM | 3646 | CA | PRO | A | 481 | −32.648 | 2.443 | −33.804 | 1.00 | 45.36 |
| ATOM | 3647 | CB | PRO | A | 481 | −32.388 | 3.266 | −32.542 | 1.00 | 45.39 |
| ATOM | 3648 | CG | PRO | A | 481 | −32.778 | 2.375 | −31.427 | 1.00 | 45.52 |
| ATOM | 3649 | CD | PRO | A | 481 | −32.481 | 0.962 | −31.873 | 1.00 | 45.83 |
| ATOM | 3650 | C | PRO | A | 481 | −31.609 | 2.762 | −34.877 | 1.00 | 45.08 |
| ATOM | 3651 | O | PRO | A | 481 | −30.405 | 2.555 | −34.681 | 1.00 | 44.45 |
| ATOM | 3652 | N | SER | A | 482 | −32.100 | 3.241 | −36.011 | 1.00 | 44.83 |
| ATOM | 3653 | CA | SER | A | 482 | −31.281 | 3.485 | −37.180 | 1.00 | 44.52 |
| ATOM | 3654 | CB | SER | A | 482 | −31.502 | 2.375 | −38.211 | 1.00 | 44.74 |
| ATOM | 3655 | OG | SER | A | 482 | −30.769 | 2.622 | −39.399 | 1.00 | 45.89 |
| ATOM | 3656 | C | SER | A | 482 | −31.661 | 4.836 | −37.765 | 1.00 | 43.84 |
| ATOM | 3657 | O | SER | A | 482 | −32.836 | 5.219 | −37.741 | 1.00 | 44.07 |
| ATOM | 3658 | N | GLY | A | 483 | −30.667 | 5.550 | −38.282 | 1.00 | 42.68 |
| ATOM | 3659 | CA | GLY | A | 483 | −30.872 | 6.872 | −38.853 | 1.00 | 41.64 |
| ATOM | 3660 | C | GLY | A | 483 | −30.085 | 7.095 | −40.130 | 1.00 | 41.05 |
| ATOM | 3661 | O | GLY | A | 483 | −29.430 | 6.179 | −40.647 | 1.00 | 41.09 |
| ATOM | 3662 | N | THR | A | 484 | −30.155 | 8.317 | −40.647 | 1.00 | 40.22 |
| ATOM | 3663 | CA | THR | A | 484 | −29.461 | 8.677 | −41.888 | 1.00 | 39.91 |
| ATOM | 3664 | CB | THR | A | 484 | −30.148 | 9.876 | −42.619 | 1.00 | 40.21 |
| ATOM | 3665 | OG1 | THR | A | 484 | −30.115 | 11.040 | −41.780 | 1.00 | 41.48 |
| ATOM | 3666 | CG2 | THR | A | 484 | −31.604 | 9.541 | −43.000 | 1.00 | 40.86 |
| ATOM | 3667 | C | THR | A | 484 | −27.995 | 9.033 | −41.603 | 1.00 | 38.43 |
| ATOM | 3668 | O | THR | A | 484 | −27.669 | 9.421 | −40.483 | 1.00 | 38.52 |
| ATOM | 3669 | N | PRO | A | 485 | −27.109 | 8.893 | −42.612 | 1.00 | 37.36 |
| ATOM | 3670 | CA | PRO | A | 485 | −25.695 | 9.226 | −42.413 | 1.00 | 36.29 |
| ATOM | 3671 | CB | PRO | A | 485 | −25.077 | 8.974 | −43.795 | 1.00 | 36.75 |
| ATOM | 3672 | CG | PRO | A | 485 | −25.997 | 7.985 | −44.442 | 1.00 | 37.04 |
| ATOM | 3673 | CD | PRO | A | 485 | −27.359 | 8.393 | −43.976 | 1.00 | 37.30 |
| ATOM | 3674 | C | PRO | A | 485 | −25.460 | 10.684 | −41.988 | 1.00 | 35.20 |
| ATOM | 3675 | O | PRO | A | 485 | −26.201 | 11.599 | −42.396 | 1.00 | 34.39 |
| ATOM | 3676 | N | TYR | A | 486 | −24.428 | 10.887 | −41.174 | 1.00 | 33.60 |
| ATOM | 3677 | CA | TYR | A | 486 | −24.025 | 12.233 | −40.782 | 1.00 | 32.74 |
| ATOM | 3678 | CB | TYR | A | 486 | −22.821 | 12.180 | −39.826 | 1.00 | 32.31 |
| ATOM | 3679 | CG | TYR | A | 486 | −22.348 | 13.564 | −39.452 | 1.00 | 32.79 |
| ATOM | 3680 | CD1 | TYR | A | 486 | −21.243 | 14.146 | −40.083 | 1.00 | 31.74 |
| ATOM | 3681 | CE1 | TYR | A | 486 | −20.827 | 15.430 | −39.742 | 1.00 | 30.85 |
| ATOM | 3682 | CZ | TYR | A | 486 | −21.527 | 16.141 | −38.778 | 1.00 | 31.99 |
| ATOM | 3683 | OH | TYR | A | 486 | −21.143 | 17.423 | −38.427 | 1.00 | 32.20 |
| ATOM | 3684 | CE2 | TYR | A | 486 | −22.629 | 15.588 | −38.160 | 1.00 | 31.88 |
| ATOM | 3685 | CD2 | TYR | A | 486 | −23.036 | 14.311 | −38.500 | 1.00 | 32.49 |
| ATOM | 3686 | C | TYR | A | 486 | −23.652 | 13.082 | −41.999 | 1.00 | 31.99 |
| ATOM | 3687 | O | TYR | A | 486 | −22.949 | 12.602 | −42.900 | 1.00 | 31.62 |
| ATOM | 3688 | N | THR | A | 487 | −24.106 | 14.336 | −42.004 | 1.00 | 31.14 |
| ATOM | 3689 | CA | THR | A | 487 | −23.676 | 15.336 | −42.986 | 1.00 | 31.43 |
| ATOM | 3690 | CB | THR | A | 487 | −24.879 | 15.785 | −43.869 | 1.00 | 31.94 |
| ATOM | 3691 | OG1 | THR | A | 487 | −25.321 | 14.665 | −44.644 | 1.00 | 35.19 |
| ATOM | 3692 | CG2 | THR | A | 487 | −24.489 | 16.904 | −44.810 | 1.00 | 32.95 |
| ATOM | 3693 | C | THR | A | 487 | −23.110 | 16.561 | −42.261 | 1.00 | 29.79 |
| ATOM | 3694 | O | THR | A | 487 | −23.761 | 17.078 | −41.363 | 1.00 | 29.20 |
| ATOM | 3695 | N | PRO | A | 488 | −21.901 | 17.027 | −42.644 | 1.00 | 29.20 |
| ATOM | 3696 | CA | PRO | A | 488 | −21.309 | 18.228 | −42.005 | 1.00 | 28.77 |
| ATOM | 3697 | CB | PRO | A | 488 | −19.988 | 18.435 | −42.763 | 1.00 | 28.75 |
| ATOM | 3698 | CG | PRO | A | 488 | −19.684 | 17.126 | −43.408 | 1.00 | 29.52 |
| ATOM | 3699 | CD | PRO | A | 488 | −21.010 | 16.448 | −43.667 | 1.00 | 29.41 |
| ATOM | 3700 | C | PRO | A | 488 | −22.175 | 19.463 | −42.194 | 1.00 | 28.44 |
| ATOM | 3701 | O | PRO | A | 488 | −23.003 | 19.499 | −43.116 | 1.00 | 28.51 |
| ATOM | 3702 | N | LEU | A | 489 | −21.971 | 20.469 | −41.345 | 1.00 | 27.28 |
| ATOM | 3703 | CA | LEU | A | 489 | −22.606 | 21.775 | −41.522 | 1.00 | 26.52 |
| ATOM | 3704 | CB | LEU | A | 489 | −22.269 | 22.708 | −40.365 | 1.00 | 27.19 |
| ATOM | 3705 | CG | LEU | A | 489 | −22.805 | 22.303 | −38.987 | 1.00 | 27.53 |
| ATOM | 3706 | CD1 | LEU | A | 489 | −22.233 | 23.242 | −37.929 | 1.00 | 26.81 |
| ATOM | 3707 | CD2 | LEU | A | 489 | −24.332 | 22.323 | −38.970 | 1.00 | 28.98 |
| ATOM | 3708 | C | LEU | A | 489 | −22.137 | 22.402 | −42.833 | 1.00 | 26.65 |
| ATOM | 3709 | O | LEU | A | 489 | −20.983 | 22.210 | −43.245 | 1.00 | 25.40 |
| ATOM | 3710 | N | PRO | A | 490 | −23.030 | 23.153 | −43.503 | 1.00 | 26.84 |
| ATOM | 3711 | CA | PRO | A | 490 | −22.636 | 23.745 | −44.786 | 1.00 | 26.44 |
| ATOM | 3712 | CB | PRO | A | 490 | −23.983 | 24.107 | −45.432 | 1.00 | 27.00 |
| ATOM | 3713 | CG | PRO | A | 490 | −24.900 | 24.341 | −44.289 | 1.00 | 27.68 |
| ATOM | 3714 | CD | PRO | A | 490 | −24.425 | 23.475 | −43.137 | 1.00 | 26.91 |
| ATOM | 3715 | C | PRO | A | 490 | −21.737 | 24.982 | −44.668 | 1.00 | 26.22 |
| ATOM | 3716 | O | PRO | A | 490 | −21.826 | 25.729 | −43.698 | 1.00 | 25.74 |
| ATOM | 3717 | N | CYS | A | 491 | −20.858 | 25.182 | −45.650 | 1.00 | 26.06 |
| ATOM | 3718 | CA | CYS | A | 491 | −20.079 | 26.412 | −45.754 | 1.00 | 26.88 |
| ATOM | 3719 | CB | CYS | A | 491 | −18.630 | 26.194 | −45.302 | 1.00 | 27.00 |
| ATOM | 3720 | SG | CYS | A | 491 | −18.450 | 25.196 | −43.819 | 1.00 | 27.23 |
| ATOM | 3721 | C | CYS | A | 491 | −20.032 | 26.822 | −47.217 | 1.00 | 27.27 |
| ATOM | 3722 | O | CYS | A | 491 | −20.369 | 26.026 | −48.083 | 1.00 | 27.34 |

TABLE 6-continued

| | | | | | | | | | |
|---|---|---|---|---|---|---|---|---|---|
| ATOM | 3723 | N | ALA | A | 492 | −19.577 | 28.045 | −47.484 | 1.00 | 28.05 |
| ATOM | 3724 | CA | ALA | A | 492 | −19.205 | 28.449 | −48.845 | 1.00 | 29.40 |
| ATOM | 3725 | CB | ALA | A | 492 | −18.837 | 29.928 | −48.866 | 1.00 | 29.49 |
| ATOM | 3726 | C | ALA | A | 492 | −18.023 | 27.599 | −49.320 | 1.00 | 30.37 |
| ATOM | 3727 | O | ALA | A | 492 | −17.310 | 26.998 | −48.497 | 1.00 | 30.36 |
| ATOM | 3728 | N | THR | A | 493 | −17.828 | 27.508 | −50.633 | 1.00 | 31.27 |
| ATOM | 3729 | CA | THR | A | 493 | −16.612 | 26.883 | −51.163 | 1.00 | 32.43 |
| ATOM | 3730 | CB | THR | A | 493 | −16.845 | 26.234 | −52.533 | 1.00 | 33.22 |
| ATOM | 3731 | OG1 | THR | A | 493 | −17.944 | 25.324 | −52.431 | 1.00 | 38.55 |
| ATOM | 3732 | CG2 | THR | A | 493 | −15.590 | 25.464 | −52.996 | 1.00 | 33.71 |
| ATOM | 3733 | C | THR | A | 493 | −15.596 | 28.006 | −51.254 | 1.00 | 31.35 |
| ATOM | 3734 | O | THR | A | 493 | −15.916 | 29.068 | −51.795 | 1.00 | 31.58 |
| ATOM | 3735 | N | PRO | A | 494 | −14.390 | 27.815 | −50.682 | 1.00 | 30.44 |
| ATOM | 3736 | CA | PRO | A | 494 | −13.464 | 28.947 | −50.696 | 1.00 | 30.01 |
| ATOM | 3737 | CB | PRO | A | 494 | −12.414 | 28.555 | −49.645 | 1.00 | 30.26 |
| ATOM | 3738 | CG | PRO | A | 494 | −12.416 | 27.077 | −49.658 | 1.00 | 30.56 |
| ATOM | 3739 | CD | PRO | A | 494 | −13.815 | 26.635 | −49.997 | 1.00 | 30.85 |
| ATOM | 3740 | C | PRO | A | 494 | −12.809 | 29.089 | −52.060 | 1.00 | 28.81 |
| ATOM | 3741 | O | PRO | A | 494 | −12.801 | 28.137 | −52.834 | 1.00 | 28.82 |
| ATOM | 3742 | N | THR | A | 495 | −12.260 | 30.258 | −52.352 | 1.00 | 28.43 |
| ATOM | 3743 | CA | THR | A | 495 | −11.551 | 30.419 | −53.623 | 1.00 | 28.44 |
| ATOM | 3744 | CB | THR | A | 495 | −11.885 | 31.748 | −54.319 | 1.00 | 28.68 |
| ATOM | 3745 | OG1 | THR | A | 495 | −11.449 | 32.839 | −53.500 | 1.00 | 30.39 |
| ATOM | 3746 | CG2 | THR | A | 495 | −13.383 | 31.858 | −54.564 | 1.00 | 29.85 |
| ATOM | 3747 | C | THR | A | 495 | −10.057 | 30.335 | −53.404 | 1.00 | 27.94 |
| ATOM | 3748 | O | THR | A | 495 | −9.289 | 30.159 | −54.352 | 1.00 | 27.63 |
| ATOM | 3749 | N | SER | A | 496 | −9.671 | 30.463 | −52.139 | 1.00 | 27.51 |
| ATOM | 3750 | CA | SER | A | 496 | −8.279 | 30.492 | −51.722 | 1.00 | 27.18 |
| ATOM | 3751 | CB | SER | A | 496 | −7.928 | 31.916 | −51.329 | 1.00 | 27.72 |
| ATOM | 3752 | OG | SER | A | 496 | −6.531 | 32.076 | −51.240 | 1.00 | 32.60 |
| ATOM | 3753 | C | SER | A | 496 | −8.134 | 29.583 | −50.501 | 1.00 | 25.85 |
| ATOM | 3754 | O | SER | A | 496 | −9.024 | 29.548 | −49.634 | 1.00 | 25.10 |
| ATOM | 3755 | N | VAL | A | 497 | −7.039 | 28.824 | −50.430 | 1.00 | 24.43 |
| ATOM | 3756 | CA | VAL | A | 497 | −6.801 | 28.032 | −49.209 | 1.00 | 22.17 |
| ATOM | 3757 | CB | VAL | A | 497 | −7.281 | 26.511 | −49.290 | 1.00 | 23.00 |
| ATOM | 3758 | CG1 | VAL | A | 497 | −6.224 | 25.445 | −48.881 | 1.00 | 22.48 |
| ATOM | 3759 | CG2 | VAL | A | 497 | −8.049 | 26.161 | −50.578 | 1.00 | 22.62 |
| ATOM | 3760 | C | VAL | A | 497 | −5.388 | 28.251 | −48.672 | 1.00 | 21.13 |
| ATOM | 3761 | O | VAL | A | 497 | −4.419 | 28.359 | −49.439 | 1.00 | 20.38 |
| ATOM | 3762 | N | ALA | A | 498 | −5.302 | 28.395 | −47.355 | 1.00 | 19.70 |
| ATOM | 3763 | CA | ALA | A | 498 | −4.020 | 28.576 | −46.702 | 1.00 | 18.92 |
| ATOM | 3764 | CB | ALA | A | 498 | −4.226 | 29.126 | −45.290 | 1.00 | 19.31 |
| ATOM | 3765 | C | ALA | A | 498 | −3.396 | 27.185 | −46.655 | 1.00 | 18.67 |
| ATOM | 3766 | O | ALA | A | 498 | −3.966 | 26.266 | −46.047 | 1.00 | 19.29 |
| ATOM | 3767 | N | VAL | A | 499 | −2.252 | 27.021 | −47.319 | 1.00 | 17.23 |
| ATOM | 3768 | CA | VAL | A | 499 | −1.551 | 25.735 | −47.361 | 1.00 | 16.09 |
| ATOM | 3769 | CB | VAL | A | 499 | −1.165 | 25.347 | −48.814 | 1.00 | 16.97 |
| ATOM | 3770 | CG1 | VAL | A | 499 | −0.403 | 23.984 | −48.863 | 1.00 | 16.08 |
| ATOM | 3771 | CG2 | VAL | A | 499 | −2.413 | 25.291 | −49.696 | 1.00 | 17.03 |
| ATOM | 3772 | C | VAL | A | 499 | −0.306 | 25.841 | −46.491 | 1.00 | 15.95 |
| ATOM | 3773 | O | VAL | A | 499 | 0.604 | 26.607 | −46.791 | 1.00 | 16.15 |
| ATOM | 3774 | N | THR | A | 500 | −0.279 | 25.085 | −45.404 | 1.00 | 15.16 |
| ATOM | 3775 | CA | THR | A | 500 | 0.863 | 25.116 | −44.505 | 1.00 | 14.85 |
| ATOM | 3776 | CB | THR | A | 500 | 0.415 | 24.916 | −43.035 | 1.00 | 14.76 |
| ATOM | 3777 | OG1 | THR | A | 500 | −0.403 | 26.022 | −42.635 | 1.00 | 16.00 |
| ATOM | 3778 | CG2 | THR | A | 500 | 1.639 | 24.856 | −42.136 | 1.00 | 15.39 |
| ATOM | 3779 | C | THR | A | 500 | 1.796 | 23.993 | −44.932 | 1.00 | 14.99 |
| ATOM | 3780 | O | THR | A | 500 | 1.480 | 22.804 | −44.792 | 1.00 | 14.81 |
| ATOM | 3781 | N | PHE | A | 501 | 2.941 | 24.370 | −45.481 | 1.00 | 14.71 |
| ATOM | 3782 | CA | PHE | A | 501 | 3.981 | 23.411 | −45.793 | 1.00 | 15.64 |
| ATOM | 3783 | CB | PHE | A | 501 | 4.943 | 23.964 | −46.832 | 1.00 | 15.86 |
| ATOM | 3784 | CG | PHE | A | 501 | 4.289 | 24.172 | −48.168 | 1.00 | 18.38 |
| ATOM | 3785 | CD1 | PHE | A | 501 | 3.676 | 25.388 | −48.469 | 1.00 | 19.85 |
| ATOM | 3786 | CE1 | PHE | A | 501 | 3.052 | 25.581 | −49.709 | 1.00 | 21.58 |
| ATOM | 3787 | CZ | PHE | A | 501 | 3.015 | 24.547 | −50.642 | 1.00 | 19.80 |
| ATOM | 3788 | CE2 | PHE | A | 501 | 3.607 | 23.324 | −50.356 | 1.00 | 21.69 |
| ATOM | 3789 | CD2 | PHE | A | 501 | 4.231 | 23.134 | −49.095 | 1.00 | 21.96 |
| ATOM | 3790 | C | PHE | A | 501 | 4.711 | 23.009 | −44.536 | 1.00 | 15.81 |
| ATOM | 3791 | O | PHE | A | 501 | 5.207 | 23.852 | −43.804 | 1.00 | 16.78 |
| ATOM | 3792 | N | HIS | A | 502 | 4.789 | 21.698 | −44.317 | 1.00 | 14.85 |
| ATOM | 3793 | CA | HIS | A | 502 | 5.239 | 21.175 | −43.027 | 1.00 | 14.17 |
| ATOM | 3794 | CB | HIS | A | 502 | 3.987 | 20.565 | −42.356 | 1.00 | 14.85 |
| ATOM | 3795 | CG | HIS | A | 502 | 4.221 | 19.875 | −41.054 | 1.00 | 13.69 |
| ATOM | 3796 | ND1 | HIS | A | 502 | 4.819 | 18.637 | −40.966 | 1.00 | 12.55 |
| ATOM | 3797 | CE1 | HIS | A | 502 | 4.816 | 18.241 | −39.702 | 1.00 | 15.76 |
| ATOM | 3798 | NE2 | HIS | A | 502 | 4.191 | 19.155 | −38.980 | 1.00 | 14.42 |
| ATOM | 3799 | CD2 | HIS | A | 502 | 3.797 | 20.183 | −39.804 | 1.00 | 14.92 |
| ATOM | 3800 | C | HIS | A | 502 | 6.317 | 20.161 | −43.412 | 1.00 | 14.16 |
| ATOM | 3801 | O | HIS | A | 502 | 6.013 | 19.043 | −43.824 | 1.00 | 13.85 |
| ATOM | 3802 | N | GLU | A | 503 | 7.577 | 20.590 | −43.352 | 1.00 | 13.63 |

TABLE 6-continued

| | | | | | | | | | |
|---|---|---|---|---|---|---|---|---|---|
| ATOM | 3803 | CA | GLU | A | 503 | 8.678 | 19.821 | −43.968 | 1.00 | 14.46 |
| ATOM | 3804 | CB | GLU | A | 503 | 9.434 | 20.712 | −44.996 | 1.00 | 14.22 |
| ATOM | 3805 | CG | GLU | A | 503 | 10.782 | 20.121 | −45.524 | 1.00 | 16.31 |
| ATOM | 3806 | CD | GLU | A | 503 | 10.620 | 18.973 | −46.539 | 1.00 | 21.32 |
| ATOM | 3807 | OE1 | GLU | A | 503 | 11.523 | 18.819 | −47.393 | 1.00 | 21.21 |
| ATOM | 3808 | OE2 | GLU | A | 503 | 9.609 | 18.230 | −46.510 | 1.00 | 20.10 |
| ATOM | 3809 | C | GLU | A | 503 | 9.657 | 19.322 | −42.917 | 1.00 | 14.22 |
| ATOM | 3810 | O | GLU | A | 503 | 10.175 | 20.121 | −42.131 | 1.00 | 15.31 |
| ATOM | 3811 | N | LEU | A | 504 | 9.960 | 18.027 | −42.927 | 1.00 | 14.92 |
| ATOM | 3812 | CA | LEU | A | 504 | 11.026 | 17.518 | −42.052 | 1.00 | 15.49 |
| ATOM | 3813 | CB | LEU | A | 504 | 10.658 | 16.147 | −41.489 | 1.00 | 16.33 |
| ATOM | 3814 | CG | LEU | A | 504 | 9.479 | 16.178 | −40.498 | 1.00 | 17.19 |
| ATOM | 3815 | CD1 | LEU | A | 504 | 8.922 | 14.753 | −40.320 | 1.00 | 19.08 |
| ATOM | 3816 | CD2 | LEU | A | 504 | 9.953 | 16.723 | −39.198 | 1.00 | 17.28 |
| ATOM | 3817 | C | LEU | A | 504 | 12.318 | 17.428 | −42.846 | 1.00 | 16.59 |
| ATOM | 3818 | O | LEU | A | 504 | 12.403 | 16.656 | −43.785 | 1.00 | 16.72 |
| ATOM | 3819 | N | VAL | A | 505 | 13.317 | 18.201 | −42.444 | 1.00 | 17.20 |
| ATOM | 3820 | CA | VAL | A | 505 | 14.592 | 18.235 | −43.154 | 1.00 | 19.16 |
| ATOM | 3821 | CB | VAL | A | 505 | 14.548 | 19.141 | −44.418 | 1.00 | 18.88 |
| ATOM | 3822 | CG1 | VAL | A | 505 | 14.028 | 20.539 | −44.090 | 1.00 | 19.28 |
| ATOM | 3823 | CG2 | VAL | A | 505 | 15.948 | 19.219 | −45.095 | 1.00 | 21.65 |
| ATOM | 3824 | C | VAL | A | 505 | 15.674 | 18.705 | −42.188 | 1.00 | 20.00 |
| ATOM | 3825 | O | VAL | A | 505 | 15.595 | 19.785 | −41.595 | 1.00 | 19.92 |
| ATOM | 3826 | N | SER | A | 506 | 16.685 | 17.868 | −42.011 | 1.00 | 21.73 |
| ATOM | 3827 | CA | SER | A | 506 | 17.761 | 18.216 | −41.104 | 1.00 | 23.33 |
| ATOM | 3828 | CB | SER | A | 506 | 18.570 | 16.974 | −40.771 | 1.00 | 23.74 |
| ATOM | 3829 | OG | SER | A | 506 | 19.583 | 17.320 | −39.847 | 1.00 | 28.30 |
| ATOM | 3830 | C | SER | A | 506 | 18.646 | 19.284 | −41.759 | 1.00 | 23.03 |
| ATOM | 3831 | O | SER | A | 506 | 19.070 | 19.139 | −42.908 | 1.00 | 23.20 |
| ATOM | 3832 | N | THR | A | 507 | 18.888 | 20.371 | −41.049 | 1.00 | 24.01 |
| ATOM | 3833 | CA | THR | A | 507 | 19.685 | 21.464 | −41.600 | 1.00 | 25.15 |
| ATOM | 3834 | CB | THR | A | 507 | 18.845 | 22.725 | −41.833 | 1.00 | 25.01 |
| ATOM | 3835 | OG1 | THR | A | 507 | 18.104 | 23.015 | −40.650 | 1.00 | 24.43 |
| ATOM | 3836 | CG2 | THR | A | 507 | 17.891 | 22.536 | −43.000 | 1.00 | 24.71 |
| ATOM | 3837 | C | THR | A | 507 | 20.795 | 21.812 | −40.623 | 1.00 | 27.09 |
| ATOM | 3838 | O | THR | A | 507 | 20.729 | 21.448 | −39.451 | 1.00 | 26.15 |
| ATOM | 3839 | N | GLN | A | 508 | 21.798 | 22.536 | −41.113 | 1.00 | 29.34 |
| ATOM | 3840 | CA | GLN | A | 508 | 22.912 | 22.986 | −40.272 | 1.00 | 32.54 |
| ATOM | 3841 | CB | GLN | A | 508 | 24.239 | 22.542 | −40.897 | 1.00 | 32.54 |
| ATOM | 3842 | CG | GLN | A | 508 | 24.369 | 21.010 | −40.972 | 1.00 | 34.32 |
| ATOM | 3843 | CD | GLN | A | 508 | 25.400 | 20.515 | −41.991 | 1.00 | 36.23 |
| ATOM | 3844 | OE1 | GLN | A | 508 | 26.283 | 19.700 | −41.660 | 1.00 | 41.79 |
| ATOM | 3845 | NE2 | GLN | A | 508 | 25.279 | 20.977 | −43.242 | 1.00 | 40.42 |
| ATOM | 3846 | C | GLN | A | 508 | 22.827 | 24.502 | −40.100 | 1.00 | 33.06 |
| ATOM | 3847 | O | GLN | A | 508 | 22.136 | 25.178 | −40.873 | 1.00 | 32.49 |
| ATOM | 3848 | N | PHE | A | 509 | 23.494 | 25.037 | −39.075 | 1.00 | 33.80 |
| ATOM | 3849 | CA | PHE | A | 509 | 23.432 | 26.476 | −38.782 | 1.00 | 35.03 |
| ATOM | 3850 | CB | PHE | A | 509 | 24.413 | 26.837 | −37.651 | 1.00 | 36.75 |
| ATOM | 3851 | CG | PHE | A | 509 | 24.481 | 28.315 | −37.340 | 1.00 | 39.07 |
| ATOM | 3852 | CD1 | PHE | A | 509 | 23.592 | 28.893 | −36.428 | 1.00 | 41.58 |
| ATOM | 3853 | CE1 | PHE | A | 509 | 23.642 | 30.265 | −36.140 | 1.00 | 42.61 |
| ATOM | 3854 | CZ | PHE | A | 509 | 24.603 | 31.073 | −36.766 | 1.00 | 41.78 |
| ATOM | 3855 | CE2 | PHE | A | 509 | 25.507 | 30.503 | −37.678 | 1.00 | 42.48 |
| ATOM | 3856 | CD2 | PHE | A | 509 | 25.441 | 29.127 | −37.955 | 1.00 | 41.46 |
| ATOM | 3857 | C | PHE | A | 509 | 23.712 | 27.311 | −40.040 | 1.00 | 34.58 |
| ATOM | 3858 | O | PHE | A | 509 | 24.614 | 26.990 | −40.815 | 1.00 | 34.58 |
| ATOM | 3859 | N | GLY | A | 510 | 22.912 | 28.355 | −40.256 | 1.00 | 33.85 |
| ATOM | 3860 | CA | GLY | A | 510 | 23.101 | 29.241 | −41.407 | 1.00 | 33.22 |
| ATOM | 3861 | C | GLY | A | 510 | 22.352 | 28.826 | −42.671 | 1.00 | 32.36 |
| ATOM | 3862 | O | GLY | A | 510 | 22.369 | 29.545 | −43.679 | 1.00 | 32.97 |
| ATOM | 3863 | N | GLN | A | 511 | 21.705 | 27.663 | −42.628 | 1.00 | 30.50 |
| ATOM | 3864 | CA | GLN | A | 511 | 20.885 | 27.217 | −43.745 | 1.00 | 29.02 |
| ATOM | 3865 | CB | GLN | A | 511 | 21.026 | 25.712 | −43.931 | 1.00 | 28.92 |
| ATOM | 3866 | CG | GLN | A | 511 | 22.436 | 25.276 | −44.349 | 1.00 | 29.91 |
| ATOM | 3867 | CD | GLN | A | 511 | 22.571 | 23.776 | −44.439 | 1.00 | 31.36 |
| ATOM | 3868 | OE1 | GLN | A | 511 | 21.760 | 23.036 | −43.879 | 1.00 | 31.69 |
| ATOM | 3869 | NE2 | GLN | A | 511 | 23.590 | 23.309 | −45.160 | 1.00 | 30.72 |
| ATOM | 3870 | C | GLN | A | 511 | 19.418 | 27.619 | −43.543 | 1.00 | 27.82 |
| ATOM | 3871 | O | GLN | A | 511 | 18.928 | 27.695 | −42.399 | 1.00 | 27.36 |
| ATOM | 3872 | N | THR | A | 512 | 18.727 | 27.895 | −44.650 | 1.00 | 25.92 |
| ATOM | 3873 | CA | THR | A | 512 | 17.305 | 28.271 | −44.613 | 1.00 | 24.51 |
| ATOM | 3874 | CB | THR | A | 512 | 17.126 | 29.763 | −44.994 | 1.00 | 24.95 |
| ATOM | 3875 | OG1 | THR | A | 512 | 17.769 | 30.580 | −44.004 | 1.00 | 27.43 |
| ATOM | 3876 | CG2 | THR | A | 512 | 15.653 | 30.151 | −45.069 | 1.00 | 25.94 |
| ATOM | 3877 | C | THR | A | 512 | 16.536 | 27.384 | −45.600 | 1.00 | 23.09 |
| ATOM | 3878 | O | THR | A | 512 | 16.994 | 27.152 | −46.717 | 1.00 | 22.75 |
| ATOM | 3879 | N | VAL | A | 513 | 15.376 | 26.877 | −45.200 | 1.00 | 20.62 |
| ATOM | 3880 | CA | VAL | A | 513 | 14.593 | 26.074 | −46.136 | 1.00 | 19.05 |
| ATOM | 3881 | CB | VAL | A | 513 | 13.946 | 24.855 | −45.428 | 1.00 | 19.18 |
| ATOM | 3882 | CG1 | VAL | A | 513 | 13.041 | 24.064 | −46.397 | 1.00 | 18.87 |

TABLE 6-continued

| | | | | | | | | | |
|---|---|---|---|---|---|---|---|---|---|
| ATOM | 3883 | CG2 | VAL | A | 513 | 15.042 | 23.938 | −44.895 | 1.00 | 20.56 |
| ATOM | 3884 | C | VAL | A | 513 | 13.536 | 26.979 | −46.748 | 1.00 | 17.98 |
| ATOM | 3885 | O | VAL | A | 513 | 12.910 | 27.768 | −46.029 | 1.00 | 16.65 |
| ATOM | 3886 | N | LYS | A | 514 | 13.346 | 26.857 | −48.063 | 1.00 | 17.91 |
| ATOM | 3887 | CA | LYS | A | 514 | 12.279 | 27.583 | −48.757 | 1.00 | 18.14 |
| ATOM | 3888 | CB | LYS | A | 514 | 12.845 | 28.712 | −49.638 | 1.00 | 17.66 |
| ATOM | 3889 | CG | LYS | A | 514 | 13.867 | 29.576 | −48.945 | 1.00 | 19.26 |
| ATOM | 3890 | CD | LYS | A | 514 | 14.197 | 30.839 | −49.765 | 1.00 | 21.27 |
| ATOM | 3891 | CE | LYS | A | 514 | 15.224 | 31.675 | −49.001 | 1.00 | 26.06 |
| ATOM | 3892 | NZ | LYS | A | 514 | 15.461 | 33.022 | −49.626 | 1.00 | 28.70 |
| ATOM | 3893 | C | LYS | A | 514 | 11.494 | 26.621 | −49.625 | 1.00 | 18.22 |
| ATOM | 3894 | O | LYS | A | 514 | 11.949 | 25.502 | −49.912 | 1.00 | 18.39 |
| ATOM | 3895 | N | VAL | A | 515 | 10.304 | 27.037 | −50.045 | 1.00 | 18.20 |
| ATOM | 3896 | CA | VAL | A | 515 | 9.546 | 26.212 | −50.980 | 1.00 | 19.00 |
| ATOM | 3897 | CB | VAL | A | 515 | 8.198 | 25.731 | −50.404 | 1.00 | 20.00 |
| ATOM | 3898 | CG1 | VAL | A | 515 | 7.403 | 26.904 | −49.879 | 1.00 | 21.01 |
| ATOM | 3899 | CG2 | VAL | A | 515 | 7.417 | 24.903 | −51.447 | 1.00 | 20.10 |
| ATOM | 3900 | C | VAL | A | 515 | 9.421 | 26.973 | −52.302 | 1.00 | 18.89 |
| ATOM | 3901 | O | VAL | A | 515 | 9.079 | 28.159 | −52.317 | 1.00 | 18.67 |
| ATOM | 3902 | N | ALA | A | 516 | 9.781 | 26.295 | −53.390 | 1.00 | 19.87 |
| ATOM | 3903 | CA | ALA | A | 516 | 9.796 | 26.898 | −54.732 | 1.00 | 20.38 |
| ATOM | 3904 | CB | ALA | A | 516 | 11.177 | 26.768 | −55.356 | 1.00 | 20.58 |
| ATOM | 3905 | C | ALA | A | 516 | 8.789 | 26.110 | −55.525 | 1.00 | 20.65 |
| ATOM | 3906 | O | ALA | A | 516 | 8.638 | 24.910 | −55.303 | 1.00 | 20.40 |
| ATOM | 3907 | N | GLY | A | 517 | 8.075 | 26.765 | −56.430 | 1.00 | 20.80 |
| ATOM | 3908 | CA | GLY | A | 517 | 7.092 | 26.039 | −57.214 | 1.00 | 22.32 |
| ATOM | 3909 | C | GLY | A | 517 | 6.536 | 26.853 | −58.352 | 1.00 | 22.86 |
| ATOM | 3910 | O | GLY | A | 517 | 6.902 | 28.024 | −58.527 | 1.00 | 22.58 |
| ATOM | 3911 | N | ASN | A | 518 | 5.642 | 26.233 | −59.116 | 1.00 | 24.66 |
| ATOM | 3912 | CA | ASN | A | 518 | 5.201 | 26.817 | −60.390 | 1.00 | 26.74 |
| ATOM | 3913 | CB | ASN | A | 518 | 4.670 | 25.754 | −61.354 | 1.00 | 26.97 |
| ATOM | 3914 | CG | ASN | A | 518 | 3.386 | 25.117 | −60.872 | 1.00 | 31.69 |
| ATOM | 3915 | OD1 | ASN | A | 518 | 3.004 | 25.226 | −59.677 | 1.00 | 28.89 |
| ATOM | 3916 | ND2 | ASN | A | 518 | 2.707 | 24.419 | −61.786 | 1.00 | 31.65 |
| ATOM | 3917 | C | ASN | A | 518 | 4.199 | 27.937 | −60.232 | 1.00 | 27.20 |
| ATOM | 3918 | O | ASN | A | 518 | 4.154 | 28.822 | −61.079 | 1.00 | 28.68 |
| ATOM | 3919 | N | ALA | A | 519 | 3.399 | 27.907 | −59.163 | 1.00 | 27.04 |
| ATOM | 3920 | CA | ALA | A | 519 | 2.424 | 28.978 | −58.898 | 1.00 | 26.47 |
| ATOM | 3921 | CB | ALA | A | 519 | 1.473 | 28.598 | −57.747 | 1.00 | 27.02 |
| ATOM | 3922 | C | ALA | A | 519 | 3.090 | 30.322 | −58.629 | 1.00 | 26.35 |
| ATOM | 3923 | O | ALA | A | 519 | 4.226 | 30.394 | −58.135 | 1.00 | 25.27 |
| ATOM | 3924 | N | ALA | A | 520 | 2.369 | 31.394 | −58.954 | 1.00 | 26.25 |
| ATOM | 3925 | CA | ALA | A | 520 | 2.887 | 32.741 | −58.784 | 1.00 | 26.77 |
| ATOM | 3926 | CB | ALA | A | 520 | 1.872 | 33.775 | −59.298 | 1.00 | 27.50 |
| ATOM | 3927 | C | ALA | A | 520 | 3.250 | 33.004 | −57.317 | 1.00 | 26.68 |
| ATOM | 3928 | O | ALA | A | 520 | 4.301 | 33.560 | −57.030 | 1.00 | 26.01 |
| ATOM | 3929 | N | ALA | A | 521 | 2.395 | 32.548 | −56.399 | 1.00 | 26.75 |
| ATOM | 3930 | CA | ALA | A | 521 | 2.628 | 32.712 | −54.963 | 1.00 | 26.82 |
| ATOM | 3931 | CB | ALA | A | 521 | 1.395 | 32.251 | −54.167 | 1.00 | 26.85 |
| ATOM | 3932 | C | ALA | A | 521 | 3.876 | 31.950 | −54.504 | 1.00 | 26.51 |
| ATOM | 3933 | O | ALA | A | 521 | 4.485 | 32.305 | −53.494 | 1.00 | 26.63 |
| ATOM | 3934 | N | LEU | A | 522 | 4.261 | 30.919 | −55.259 | 1.00 | 26.79 |
| ATOM | 3935 | CA | LEU | A | 522 | 5.452 | 30.113 | −54.932 | 1.00 | 26.50 |
| ATOM | 3936 | CB | LEU | A | 522 | 5.185 | 28.626 | −55.155 | 1.00 | 26.64 |
| ATOM | 3937 | CG | LEU | A | 522 | 4.224 | 27.946 | −54.169 | 1.00 | 26.58 |
| ATOM | 3938 | CD1 | LEU | A | 522 | 4.049 | 26.489 | −54.533 | 1.00 | 27.59 |
| ATOM | 3939 | CD2 | LEU | A | 522 | 4.718 | 28.092 | −52.730 | 1.00 | 28.08 |
| ATOM | 3940 | C | LEU | A | 522 | 6.696 | 30.559 | −55.709 | 1.00 | 26.54 |
| ATOM | 3941 | O | LEU | A | 522 | 7.779 | 29.987 | −55.547 | 1.00 | 25.56 |
| ATOM | 3942 | N | GLY | A | 523 | 6.518 | 31.575 | −56.552 | 1.00 | 26.25 |
| ATOM | 3943 | CA | GLY | A | 523 | 7.637 | 32.267 | −57.199 | 1.00 | 26.16 |
| ATOM | 3944 | C | GLY | A | 523 | 7.996 | 31.809 | −58.607 | 1.00 | 26.84 |
| ATOM | 3945 | O | GLY | A | 523 | 9.029 | 32.227 | −59.152 | 1.00 | 25.81 |
| ATOM | 3946 | N | ASN | A | 524 | 7.162 | 30.946 | −59.193 | 1.00 | 27.13 |
| ATOM | 3947 | CA | ASN | A | 524 | 7.413 | 30.419 | −60.539 | 1.00 | 27.74 |
| ATOM | 3948 | CB | ASN | A | 524 | 7.046 | 31.484 | −61.591 | 1.00 | 28.43 |
| ATOM | 3949 | CG | ASN | A | 524 | 7.123 | 30.960 | −63.015 | 1.00 | 30.79 |
| ATOM | 3950 | OD1 | ASN | A | 524 | 6.856 | 29.780 | −63.285 | 1.00 | 30.80 |
| ATOM | 3951 | ND2 | ASN | A | 524 | 7.515 | 31.838 | −63.936 | 1.00 | 33.61 |
| ATOM | 3952 | C | ASN | A | 524 | 8.845 | 29.857 | −60.710 | 1.00 | 28.44 |
| ATOM | 3953 | O | ASN | A | 524 | 9.531 | 30.104 | −61.720 | 1.00 | 27.82 |
| ATOM | 3954 | N | TRP | A | 525 | 9.280 | 29.111 | −59.693 | 1.00 | 27.99 |
| ATOM | 3955 | CA | TRP | A | 525 | 10.573 | 28.398 | −59.659 | 1.00 | 28.92 |
| ATOM | 3956 | CB | TRP | A | 525 | 10.787 | 27.507 | −60.896 | 1.00 | 28.31 |
| ATOM | 3957 | CG | TRP | A | 525 | 9.803 | 26.394 | −61.060 | 1.00 | 27.68 |
| ATOM | 3958 | CD1 | TRP | A | 525 | 8.902 | 26.247 | −62.078 | 1.00 | 27.96 |
| ATOM | 3959 | NE1 | TRP | A | 525 | 8.166 | 25.106 | −61.907 | 1.00 | 27.55 |
| ATOM | 3960 | CE2 | TRP | A | 525 | 8.589 | 24.471 | −60.762 | 1.00 | 30.58 |
| ATOM | 3961 | CD2 | TRP | A | 525 | 9.609 | 25.277 | −60.184 | 1.00 | 27.84 |
| ATOM | 3962 | CE3 | TRP | A | 525 | 10.230 | 24.842 | −59.001 | 1.00 | 26.50 |

TABLE 6-continued

| | | | | | | | | | |
|---|---|---|---|---|---|---|---|---|---|
| ATOM | 3963 | CZ3 | TRP | A | 525 | 9.787 | 23.655 | −58.411 | 1.00 | 27.55 |
| ATOM | 3964 | CH2 | TRP | A | 525 | 8.752 | 22.889 | −58.998 | 1.00 | 27.90 |
| ATOM | 3965 | CZ2 | TRP | A | 525 | 8.144 | 23.279 | −60.168 | 1.00 | 26.22 |
| ATOM | 3966 | C | TRP | A | 525 | 11.790 | 29.301 | −59.452 | 1.00 | 29.66 |
| ATOM | 3967 | O | TRP | A | 525 | 12.921 | 28.804 | −59.346 | 1.00 | 30.61 |
| ATOM | 3968 | N | SER | A | 526 | 11.570 | 30.613 | −59.380 | 1.00 | 30.33 |
| ATOM | 3969 | CA | SER | A | 526 | 12.645 | 31.536 | −59.004 | 1.00 | 31.13 |
| ATOM | 3970 | CB | SER | A | 526 | 12.213 | 32.993 | −59.187 | 1.00 | 31.02 |
| ATOM | 3971 | OG | SER | A | 526 | 13.166 | 33.838 | −58.562 | 1.00 | 33.69 |
| ATOM | 3972 | C | SER | A | 526 | 13.086 | 31.312 | −57.560 | 1.00 | 31.29 |
| ATOM | 3973 | O | SER | A | 526 | 12.271 | 31.381 | −56.627 | 1.00 | 31.21 |
| ATOM | 3974 | N | THR | A | 527 | 14.373 | 31.049 | −57.367 | 1.00 | 31.34 |
| ATOM | 3975 | CA | THR | A | 527 | 14.880 | 30.794 | −56.021 | 1.00 | 31.64 |
| ATOM | 3976 | CB | THR | A | 527 | 16.259 | 30.098 | −56.024 | 1.00 | 31.79 |
| ATOM | 3977 | OG1 | THR | A | 527 | 17.217 | 30.931 | −56.682 | 1.00 | 31.43 |
| ATOM | 3978 | CG2 | THR | A | 527 | 16.169 | 28.739 | −56.724 | 1.00 | 32.27 |
| ATOM | 3979 | C | THR | A | 527 | 14.911 | 32.045 | −55.152 | 1.00 | 31.99 |
| ATOM | 3980 | O | THR | A | 527 | 14.847 | 31.959 | −53.922 | 1.00 | 32.36 |
| ATOM | 3981 | N | SER | A | 528 | 14.986 | 33.209 | −55.787 | 1.00 | 31.79 |
| ATOM | 3982 | CA | SER | A | 528 | 14.928 | 34.463 | −55.054 | 1.00 | 32.02 |
| ATOM | 3983 | CB | SER | A | 528 | 15.517 | 35.615 | −55.885 | 1.00 | 32.70 |
| ATOM | 3984 | OG | SER | A | 528 | 14.712 | 35.882 | −57.031 | 1.00 | 34.94 |
| ATOM | 3985 | C | SER | A | 528 | 13.497 | 34.784 | −54.579 | 1.00 | 31.23 |
| ATOM | 3986 | O | SER | A | 528 | 13.330 | 35.435 | −53.550 | 1.00 | 32.02 |
| ATOM | 3987 | N | ALA | A | 529 | 12.479 | 34.314 | −55.306 | 1.00 | 29.33 |
| ATOM | 3988 | CA | ALA | A | 529 | 11.093 | 34.506 | −54.893 | 1.00 | 27.60 |
| ATOM | 3989 | CB | ALA | A | 529 | 10.211 | 34.864 | −56.086 | 1.00 | 27.34 |
| ATOM | 3990 | C | ALA | A | 529 | 10.482 | 33.328 | −54.112 | 1.00 | 26.40 |
| ATOM | 3991 | O | ALA | A | 529 | 9.311 | 33.382 | −53.754 | 1.00 | 26.54 |
| ATOM | 3992 | N | ALA | A | 530 | 11.268 | 32.286 | −53.842 | 1.00 | 25.12 |
| ATOM | 3993 | CA | ALA | A | 530 | 10.777 | 31.114 | −53.096 | 1.00 | 24.19 |
| ATOM | 3994 | CB | ALA | A | 530 | 11.855 | 30.063 | −52.991 | 1.00 | 23.88 |
| ATOM | 3995 | C | ALA | A | 530 | 10.336 | 31.555 | −51.706 | 1.00 | 23.55 |
| ATOM | 3996 | O | ALA | A | 530 | 10.848 | 32.540 | −51.182 | 1.00 | 23.61 |
| ATOM | 3997 | N | VAL | A | 531 | 9.396 | 30.833 | −51.110 | 1.00 | 22.18 |
| ATOM | 3998 | CA | VAL | A | 531 | 8.851 | 31.248 | −49.821 | 1.00 | 22.62 |
| ATOM | 3999 | CB | VAL | A | 531 | 7.380 | 30.821 | −49.677 | 1.00 | 22.81 |
| ATOM | 4000 | CG1 | VAL | A | 531 | 6.815 | 31.335 | −48.346 | 1.00 | 25.06 |
| ATOM | 4001 | CG2 | VAL | A | 531 | 6.551 | 31.353 | −50.886 | 1.00 | 25.38 |
| ATOM | 4002 | C | VAL | A | 531 | 9.659 | 30.646 | −48.674 | 1.00 | 21.29 |
| ATOM | 4003 | O | VAL | A | 531 | 9.768 | 29.425 | −48.564 | 1.00 | 20.72 |
| ATOM | 4004 | N | ALA | A | 532 | 10.215 | 31.493 | −47.819 | 1.00 | 20.86 |
| ATOM | 4005 | CA | ALA | A | 532 | 11.008 | 30.999 | −46.698 | 1.00 | 20.26 |
| ATOM | 4006 | CB | ALA | A | 532 | 11.850 | 32.128 | −46.084 | 1.00 | 21.02 |
| ATOM | 4007 | C | ALA | A | 532 | 10.093 | 30.356 | −45.646 | 1.00 | 20.51 |
| ATOM | 4008 | O | ALA | A | 532 | 9.019 | 30.884 | −45.337 | 1.00 | 20.05 |
| ATOM | 4009 | N | LEU | A | 533 | 10.514 | 29.200 | −45.129 | 1.00 | 19.00 |
| ATOM | 4010 | CA | LEU | A | 533 | 9.855 | 28.565 | −43.999 | 1.00 | 18.65 |
| ATOM | 4011 | CB | LEU | A | 533 | 9.901 | 27.029 | −44.148 | 1.00 | 18.14 |
| ATOM | 4012 | CG | LEU | A | 533 | 9.395 | 26.450 | −45.483 | 1.00 | 19.25 |
| ATOM | 4013 | CD1 | LEU | A | 533 | 9.385 | 24.923 | −45.427 | 1.00 | 21.28 |
| ATOM | 4014 | CD2 | LEU | A | 533 | 8.030 | 26.980 | −45.894 | 1.00 | 18.58 |
| ATOM | 4015 | C | LEU | A | 533 | 10.541 | 29.014 | −42.702 | 1.00 | 18.95 |
| ATOM | 4016 | O | LEU | A | 533 | 11.622 | 29.648 | −42.744 | 1.00 | 18.94 |
| ATOM | 4017 | N | ASP | A | 534 | 9.905 | 28.715 | −41.570 | 1.00 | 18.56 |
| ATOM | 4018 | CA | ASP | A | 534 | 10.381 | 29.096 | −40.238 | 1.00 | 18.36 |
| ATOM | 4019 | CB | ASP | A | 534 | 9.220 | 29.634 | −39.374 | 1.00 | 19.76 |
| ATOM | 4020 | CG | ASP | A | 534 | 8.757 | 30.992 | −39.798 | 1.00 | 23.55 |
| ATOM | 4021 | OD1 | ASP | A | 534 | 7.548 | 31.264 | −39.659 | 1.00 | 26.14 |
| ATOM | 4022 | OD2 | ASP | A | 534 | 9.600 | 31.774 | −40.283 | 1.00 | 27.39 |
| ATOM | 4023 | C | ASP | A | 534 | 10.877 | 27.867 | −39.504 | 1.00 | 17.68 |
| ATOM | 4024 | O | ASP | A | 534 | 10.310 | 26.780 | −39.667 | 1.00 | 16.10 |
| ATOM | 4025 | N | ALA | A | 535 | 11.883 | 28.057 | −38.654 | 1.00 | 17.05 |
| ATOM | 4026 | CA | ALA | A | 535 | 12.405 | 26.950 | −37.835 | 1.00 | 17.76 |
| ATOM | 4027 | CB | ALA | A | 535 | 13.926 | 26.952 | −37.832 | 1.00 | 17.96 |
| ATOM | 4028 | C | ALA | A | 535 | 11.872 | 27.027 | −36.403 | 1.00 | 17.82 |
| ATOM | 4029 | O | ALA | A | 535 | 12.482 | 26.490 | −35.474 | 1.00 | 18.36 |
| ATOM | 4030 | N | VAL | A | 536 | 10.745 | 27.706 | −36.225 | 1.00 | 17.68 |
| ATOM | 4031 | CA | VAL | A | 536 | 10.138 | 27.861 | −34.898 | 1.00 | 18.65 |
| ATOM | 4032 | CB | VAL | A | 536 | 8.824 | 28.719 | −34.975 | 1.00 | 18.66 |
| ATOM | 4033 | CG1 | VAL | A | 536 | 7.805 | 28.123 | −35.971 | 1.00 | 19.98 |
| ATOM | 4034 | CG2 | VAL | A | 536 | 8.208 | 28.962 | −33.570 | 1.00 | 20.19 |
| ATOM | 4035 | C | VAL | A | 536 | 9.938 | 26.514 | −34.155 | 1.00 | 18.51 |
| ATOM | 4036 | O | VAL | A | 536 | 10.124 | 26.437 | −32.923 | 1.00 | 19.61 |
| ATOM | 4037 | N | ASN | A | 537 | 9.570 | 25.468 | −34.883 | 1.00 | 18.59 |
| ATOM | 4038 | CA | ASN | A | 537 | 9.344 | 24.154 | −34.261 | 1.00 | 19.07 |
| ATOM | 4039 | CB | ASN | A | 537 | 8.074 | 23.498 | −34.816 | 1.00 | 19.28 |
| ATOM | 4040 | CG | ASN | A | 537 | 6.800 | 24.252 | −34.448 | 1.00 | 21.02 |
| ATOM | 4041 | OD1 | ASN | A | 537 | 6.742 | 24.940 | −33.435 | 1.00 | 24.12 |
| ATOM | 4042 | ND2 | ASN | A | 537 | 5.762 | 24.089 | −35.265 | 1.00 | 20.99 |

TABLE 6-continued

| | | | | | | | | | |
|---|---|---|---|---|---|---|---|---|---|
| ATOM | 4043 | C | ASN | A | 537 | 10.518 | 23.182 | −34.445 | 1.00 | 19.15 |
| ATOM | 4044 | O | ASN | A | 537 | 10.394 | 21.971 | −34.196 | 1.00 | 18.60 |
| ATOM | 4045 | N | TYR | A | 538 | 11.653 | 23.699 | −34.897 | 1.00 | 19.05 |
| ATOM | 4046 | CA | TYR | A | 538 | 12.767 | 22.830 | −35.234 | 1.00 | 20.32 |
| ATOM | 4047 | CB | TYR | A | 538 | 13.816 | 23.618 | −36.026 | 1.00 | 20.37 |
| ATOM | 4048 | CG | TYR | A | 538 | 14.916 | 22.747 | −36.588 | 1.00 | 20.37 |
| ATOM | 4049 | CD1 | TYR | A | 538 | 14.822 | 22.238 | −37.886 | 1.00 | 20.39 |
| ATOM | 4050 | CE1 | TYR | A | 538 | 15.853 | 21.436 | −38.437 | 1.00 | 20.49 |
| ATOM | 4051 | CZ | TYR | A | 538 | 16.961 | 21.137 | −37.670 | 1.00 | 20.65 |
| ATOM | 4052 | OH | TYR | A | 538 | 17.946 | 20.341 | −38.218 | 1.00 | 21.53 |
| ATOM | 4053 | CE2 | TYR | A | 538 | 17.066 | 21.602 | −36.361 | 1.00 | 22.05 |
| ATOM | 4054 | CD2 | TYR | A | 538 | 16.043 | 22.418 | −35.825 | 1.00 | 21.95 |
| ATOM | 4055 | C | TYR | A | 538 | 13.436 | 22.209 | −33.981 | 1.00 | 21.29 |
| ATOM | 4056 | O | TYR | A | 538 | 13.733 | 22.919 | −33.036 | 1.00 | 21.89 |
| ATOM | 4057 | N | ALA | A | 539 | 13.695 | 20.902 | −34.014 | 1.00 | 22.15 |
| ATOM | 4058 | CA | ALA | A | 539 | 14.646 | 20.258 | −33.083 | 1.00 | 23.67 |
| ATOM | 4059 | CB | ALA | A | 539 | 13.909 | 19.536 | −31.976 | 1.00 | 23.94 |
| ATOM | 4060 | C | ALA | A | 539 | 15.545 | 19.289 | −33.849 | 1.00 | 24.35 |
| ATOM | 4061 | O | ALA | A | 539 | 15.117 | 18.698 | −34.833 | 1.00 | 23.63 |
| ATOM | 4062 | N | ASP | A | 540 | 16.793 | 19.118 | −33.405 | 1.00 | 25.69 |
| ATOM | 4063 | CA | ASP | A | 540 | 17.722 | 18.196 | −34.099 | 1.00 | 27.42 |
| ATOM | 4064 | CB | ASP | A | 540 | 19.044 | 18.051 | −33.339 | 1.00 | 28.62 |
| ATOM | 4065 | CG | ASP | A | 540 | 19.724 | 19.368 | −33.140 | 1.00 | 33.80 |
| ATOM | 4066 | OD1 | ASP | A | 540 | 19.875 | 20.115 | −34.147 | 1.00 | 36.83 |
| ATOM | 4067 | OD2 | ASP | A | 540 | 20.080 | 19.663 | −31.970 | 1.00 | 40.32 |
| ATOM | 4068 | C | ASP | A | 540 | 17.150 | 16.818 | −34.400 | 1.00 | 26.63 |
| ATOM | 4069 | O | ASP | A | 540 | 17.386 | 16.277 | −35.485 | 1.00 | 27.28 |
| ATOM | 4070 | N | ASN | A | 541 | 16.403 | 16.247 | −33.458 | 1.00 | 25.08 |
| ATOM | 4071 | CA | ASN | A | 541 | 15.827 | 14.922 | −33.687 | 1.00 | 24.03 |
| ATOM | 4072 | CB | ASN | A | 541 | 15.988 | 14.032 | −32.441 | 1.00 | 25.14 |
| ATOM | 4073 | CG | ASN | A | 541 | 15.337 | 14.623 | −31.191 | 1.00 | 27.81 |
| ATOM | 4074 | OD1 | ASN | A | 541 | 15.366 | 14.001 | −30.118 | 1.00 | 31.57 |
| ATOM | 4075 | ND2 | ASN | A | 541 | 14.771 | 15.824 | −31.306 | 1.00 | 28.81 |
| ATOM | 4076 | C | ASN | A | 541 | 14.349 | 14.991 | −34.118 | 1.00 | 22.46 |
| ATOM | 4077 | O | ASN | A | 541 | 13.660 | 13.979 | −34.172 | 1.00 | 22.35 |
| ATOM | 4078 | N | HIS | A | 542 | 13.871 | 16.197 | −34.403 | 1.00 | 19.85 |
| ATOM | 4079 | CA | HIS | A | 542 | 12.580 | 16.354 | −35.083 | 1.00 | 18.22 |
| ATOM | 4080 | CB | HIS | A | 542 | 11.426 | 16.392 | −34.062 | 1.00 | 16.89 |
| ATOM | 4081 | CG | HIS | A | 542 | 10.071 | 16.341 | −34.699 | 1.00 | 17.32 |
| ATOM | 4082 | ND1 | HIS | A | 542 | 9.211 | 17.417 | −34.711 | 1.00 | 16.28 |
| ATOM | 4083 | CE1 | HIS | A | 542 | 8.111 | 17.088 | −35.371 | 1.00 | 14.64 |
| ATOM | 4084 | NE2 | HIS | A | 542 | 8.217 | 15.834 | −35.765 | 1.00 | 15.41 |
| ATOM | 4085 | CD2 | HIS | A | 542 | 9.435 | 15.340 | −35.358 | 1.00 | 15.14 |
| ATOM | 4086 | C | HIS | A | 542 | 12.662 | 17.650 | −35.902 | 1.00 | 17.48 |
| ATOM | 4087 | O | HIS | A | 542 | 12.198 | 18.698 | −35.446 | 1.00 | 17.79 |
| ATOM | 4088 | N | PRO | A | 543 | 13.324 | 17.584 | −37.083 | 1.00 | 17.00 |
| ATOM | 4089 | CA | PRO | A | 543 | 13.797 | 18.752 | −37.832 | 1.00 | 17.09 |
| ATOM | 4090 | CB | PRO | A | 543 | 14.948 | 18.164 | −38.677 | 1.00 | 16.57 |
| ATOM | 4091 | CG | PRO | A | 543 | 14.472 | 16.759 | −38.994 | 1.00 | 18.22 |
| ATOM | 4092 | CD | PRO | A | 543 | 13.676 | 16.321 | −37.764 | 1.00 | 17.39 |
| ATOM | 4093 | C | PRO | A | 543 | 12.718 | 19.435 | −38.691 | 1.00 | 16.46 |
| ATOM | 4094 | O | PRO | A | 543 | 12.811 | 19.497 | −39.922 | 1.00 | 17.09 |
| ATOM | 4095 | N | LEU | A | 544 | 11.726 | 19.987 | −38.009 | 1.00 | 15.36 |
| ATOM | 4096 | CA | LEU | A | 544 | 10.534 | 20.535 | −38.636 | 1.00 | 15.10 |
| ATOM | 4097 | CB | LEU | A | 544 | 9.341 | 20.376 | −37.672 | 1.00 | 15.29 |
| ATOM | 4098 | CG | LEU | A | 544 | 7.968 | 20.927 | −38.134 | 1.00 | 16.53 |
| ATOM | 4099 | CD1 | LEU | A | 544 | 7.524 | 20.364 | −39.494 | 1.00 | 15.92 |
| ATOM | 4100 | CD2 | LEU | A | 544 | 6.900 | 20.700 | −37.062 | 1.00 | 14.59 |
| ATOM | 4101 | C | LEU | A | 544 | 10.694 | 22.018 | −39.025 | 1.00 | 15.09 |
| ATOM | 4102 | O | LEU | A | 544 | 11.037 | 22.851 | −38.197 | 1.00 | 15.34 |
| ATOM | 4103 | N | TRP | A | 545 | 10.456 | 22.298 | −40.303 | 1.00 | 15.03 |
| ATOM | 4104 | CA | TRP | A | 545 | 10.327 | 23.637 | −40.843 | 1.00 | 15.36 |
| ATOM | 4105 | CB | TRP | A | 545 | 11.288 | 23.790 | −42.023 | 1.00 | 15.40 |
| ATOM | 4106 | CG | TRP | A | 545 | 12.758 | 23.921 | −41.663 | 1.00 | 15.62 |
| ATOM | 4107 | CD1 | TRP | A | 545 | 13.653 | 22.903 | −41.384 | 1.00 | 16.85 |
| ATOM | 4108 | NE1 | TRP | A | 545 | 14.906 | 23.437 | −41.129 | 1.00 | 18.69 |
| ATOM | 4109 | CE2 | TRP | A | 545 | 14.837 | 24.803 | −41.246 | 1.00 | 17.78 |
| ATOM | 4110 | CD2 | TRP | A | 545 | 13.498 | 25.140 | −41.584 | 1.00 | 17.01 |
| ATOM | 4111 | CE3 | TRP | A | 545 | 13.163 | 26.488 | −41.777 | 1.00 | 17.17 |
| ATOM | 4112 | CZ3 | TRP | A | 545 | 14.165 | 27.456 | −41.637 | 1.00 | 18.29 |
| ATOM | 4113 | CH2 | TRP | A | 545 | 15.483 | 27.085 | −41.295 | 1.00 | 17.22 |
| ATOM | 4114 | CZ2 | TRP | A | 545 | 15.835 | 25.767 | −41.111 | 1.00 | 19.09 |
| ATOM | 4115 | C | TRP | A | 545 | 8.907 | 23.832 | −41.359 | 1.00 | 15.14 |
| ATOM | 4116 | O | TRP | A | 545 | 8.327 | 22.933 | −41.986 | 1.00 | 14.45 |
| ATOM | 4117 | N | ILE | A | 546 | 8.362 | 25.025 | −41.149 | 1.00 | 15.19 |
| ATOM | 4118 | CA | ILE | A | 546 | 6.938 | 25.244 | −41.428 | 1.00 | 16.51 |
| ATOM | 4119 | CB | ILE | A | 546 | 6.107 | 24.988 | −40.130 | 1.00 | 17.39 |
| ATOM | 4120 | CG1 | ILE | A | 546 | 4.615 | 24.852 | −40.420 | 1.00 | 20.44 |
| ATOM | 4121 | CD1 | ILE | A | 546 | 3.882 | 23.992 | −39.392 | 1.00 | 23.59 |
| ATOM | 4122 | CG2 | ILE | A | 546 | 6.391 | 26.064 | −39.050 | 1.00 | 17.70 |

TABLE 6-continued

| ATOM | 4123 | C   | ILE | A | 546 | 6.674  | 26.635 | −42.006 | 1.00 | 16.75 |
| ATOM | 4124 | O   | ILE | A | 546 | 7.352  | 27.593 | −41.647 | 1.00 | 15.81 |
| ATOM | 4125 | N   | ALA | A | 547 | 5.716  | 26.743 | −42.925 | 1.00 | 16.88 |
| ATOM | 4126 | CA  | ALA | A | 547 | 5.197  | 28.057 | −43.279 | 1.00 | 17.94 |
| ATOM | 4127 | CB  | ALA | A | 547 | 6.222  | 28.893 | −43.931 | 1.00 | 21.49 |
| ATOM | 4128 | C   | ALA | A | 547 | 4.009  | 27.919 | −44.167 | 1.00 | 18.29 |
| ATOM | 4129 | O   | ALA | A | 547 | 3.727  | 26.828 | −44.655 | 1.00 | 18.52 |
| ATOM | 4130 | N   | THR | A | 548 | 3.316  | 29.031 | −44.362 | 1.00 | 17.99 |
| ATOM | 4131 | CA  | THR | A | 548 | 1.970  | 29.017 | −44.919 | 1.00 | 18.72 |
| ATOM | 4132 | CB  | THR | A | 548 | 0.929  | 29.419 | −43.855 | 1.00 | 18.65 |
| ATOM | 4133 | OG1 | THR | A | 548 | 1.000  | 28.500 | −42.751 | 1.00 | 19.46 |
| ATOM | 4134 | CG2 | THR | A | 548 | −0.491 | 29.379 | −44.438 | 1.00 | 18.79 |
| ATOM | 4135 | C   | THR | A | 548 | 1.865  | 29.960 | −46.104 | 1.00 | 19.60 |
| ATOM | 4136 | O   | THR | A | 548 | 2.347  | 31.090 | −46.040 | 1.00 | 19.83 |
| ATOM | 4137 | N   | VAL | A | 549 | 1.227  | 29.485 | −47.164 | 1.00 | 20.41 |
| ATOM | 4138 | CA  | VAL | A | 549 | 1.048  | 30.280 | −48.389 | 1.00 | 22.36 |
| ATOM | 4139 | CB  | VAL | A | 549 | 1.944  | 29.722 | −49.537 | 1.00 | 22.77 |
| ATOM | 4140 | CG1 | VAL | A | 549 | 1.717  | 30.491 | −50.845 | 1.00 | 25.80 |
| ATOM | 4141 | CG2 | VAL | A | 549 | 3.429  | 29.781 | −49.148 | 1.00 | 24.78 |
| ATOM | 4142 | C   | VAL | A | 549 | −0.399 | 30.119 | −48.800 | 1.00 | 22.21 |
| ATOM | 4143 | O   | VAL | A | 549 | −0.943 | 29.018 | −48.719 | 1.00 | 21.56 |
| ATOM | 4144 | N   | ASN | A | 550 | −1.028 | 31.211 | −49.240 | 1.00 | 22.80 |
| ATOM | 4145 | CA  | ASN | A | 550 | −2.356 | 31.107 | −49.831 | 1.00 | 23.95 |
| ATOM | 4146 | CB  | ASN | A | 550 | −3.114 | 32.411 | −49.649 | 1.00 | 24.39 |
| ATOM | 4147 | CG  | ASN | A | 550 | −3.367 | 32.706 | −48.201 | 1.00 | 27.42 |
| ATOM | 4148 | OD1 | ASN | A | 550 | −3.811 | 31.838 | −47.462 | 1.00 | 28.69 |
| ATOM | 4149 | ND2 | ASN | A | 550 | −3.041 | 33.911 | −47.771 | 1.00 | 31.89 |
| ATOM | 4150 | C   | ASN | A | 550 | −2.278 | 30.733 | −51.294 | 1.00 | 23.98 |
| ATOM | 4151 | O   | ASN | A | 550 | −1.598 | 31.400 | −52.065 | 1.00 | 24.73 |
| ATOM | 4152 | N   | LEU | A | 551 | −2.973 | 29.667 | −51.662 | 1.00 | 24.24 |
| ATOM | 4153 | CA  | LEU | A | 551 | −3.016 | 29.180 | −53.020 | 1.00 | 24.78 |
| ATOM | 4154 | CB  | LEU | A | 551 | −2.348 | 27.797 | −53.135 | 1.00 | 25.00 |
| ATOM | 4155 | CG  | LEU | A | 551 | −0.858 | 27.721 | −52.787 | 1.00 | 25.19 |
| ATOM | 4156 | CD1 | LEU | A | 551 | −0.356 | 26.284 | −52.803 | 1.00 | 27.45 |
| ATOM | 4157 | CD2 | LEU | A | 551 | −0.018 | 28.613 | −53.718 | 1.00 | 26.73 |
| ATOM | 4158 | C   | LEU | A | 551 | −4.471 | 29.104 | −53.488 | 1.00 | 25.46 |
| ATOM | 4159 | O   | LEU | A | 551 | −5.393 | 29.018 | −52.675 | 1.00 | 24.27 |
| ATOM | 4160 | N   | GLU | A | 552 | −4.661 | 29.148 | −54.804 | 1.00 | 26.15 |
| ATOM | 4161 | CA  | GLU | A | 552 | −6.004 | 29.165 | −55.366 | 1.00 | 28.20 |
| ATOM | 4162 | CB  | GLU | A | 552 | −5.955 | 29.639 | −56.823 | 1.00 | 28.30 |
| ATOM | 4163 | CG  | GLU | A | 552 | −7.326 | 29.739 | −57.494 | 1.00 | 32.28 |
| ATOM | 4164 | CD  | GLU | A | 552 | −7.250 | 30.281 | −58.926 | 1.00 | 33.44 |
| ATOM | 4165 | OE1 | GLU | A | 552 | −8.110 | 31.126 | −59.274 | 1.00 | 41.80 |
| ATOM | 4166 | OE2 | GLU | A | 552 | −6.340 | 29.873 | −59.695 | 1.00 | 39.14 |
| ATOM | 4167 | C   | GLU | A | 552 | −6.610 | 27.768 | −55.253 | 1.00 | 26.97 |
| ATOM | 4168 | O   | GLU | A | 552 | −5.979 | 26.783 | −55.622 | 1.00 | 26.49 |
| ATOM | 4169 | N   | ALA | A | 553 | −7.822 | 27.684 | −54.723 | 1.00 | 27.21 |
| ATOM | 4170 | CA  | ALA | A | 553 | −8.502 | 26.399 | −54.603 | 1.00 | 27.89 |
| ATOM | 4171 | CB  | ALA | A | 553 | −9.876 | 26.574 | −53.953 | 1.00 | 28.37 |
| ATOM | 4172 | C   | ALA | A | 553 | −8.637 | 25.773 | −55.979 | 1.00 | 28.57 |
| ATOM | 4173 | O   | ALA | A | 553 | −8.900 | 26.477 | −56.952 | 1.00 | 28.83 |
| ATOM | 4174 | N   | GLY | A | 554 | −8.438 | 24.465 | −56.064 | 1.00 | 28.44 |
| ATOM | 4175 | CA  | GLY | A | 554 | −8.556 | 23.753 | −57.330 | 1.00 | 29.66 |
| ATOM | 4176 | C   | GLY | A | 554 | −7.274 | 23.693 | −58.145 | 1.00 | 30.04 |
| ATOM | 4177 | O   | GLY | A | 554 | −7.122 | 22.814 | −59.000 | 1.00 | 30.33 |
| ATOM | 4178 | N   | ASP | A | 555 | −6.347 | 24.606 | −57.869 | 1.00 | 30.23 |
| ATOM | 4179 | CA  | ASP | A | 555 | −5.098 | 24.716 | −58.630 | 1.00 | 30.61 |
| ATOM | 4180 | CB  | ASP | A | 555 | −4.313 | 25.939 | −58.161 | 1.00 | 30.85 |
| ATOM | 4181 | CG  | ASP | A | 555 | −3.382 | 26.503 | −59.236 | 1.00 | 34.49 |
| ATOM | 4182 | OD1 | ASP | A | 555 | −3.441 | 26.053 | −60.407 | 1.00 | 37.19 |
| ATOM | 4183 | OD2 | ASP | A | 555 | −2.572 | 27.408 | −58.901 | 1.00 | 36.59 |
| ATOM | 4184 | C   | ASP | A | 555 | −4.238 | 23.467 | −58.486 | 1.00 | 30.14 |
| ATOM | 4185 | O   | ASP | A | 555 | −4.156 | 22.882 | −57.419 | 1.00 | 30.07 |
| ATOM | 4186 | N   | VAL | A | 556 | −3.602 | 23.046 | −59.572 | 1.00 | 29.55 |
| ATOM | 4187 | CA  | VAL | A | 556 | −2.628 | 21.963 | −59.492 | 1.00 | 28.74 |
| ATOM | 4188 | CB  | VAL | A | 556 | −2.732 | 20.987 | −60.680 | 1.00 | 29.35 |
| ATOM | 4189 | CG1 | VAL | A | 556 | −1.666 | 19.877 | −60.569 | 1.00 | 28.99 |
| ATOM | 4190 | CG2 | VAL | A | 556 | −4.125 | 20.365 | −60.720 | 1.00 | 30.44 |
| ATOM | 4191 | C   | VAL | A | 556 | −1.261 | 22.623 | −59.448 | 1.00 | 28.04 |
| ATOM | 4192 | O   | VAL | A | 556 | −0.869 | 23.336 | −60.384 | 1.00 | 27.25 |
| ATOM | 4193 | N   | VAL | A | 557 | −0.544 | 22.389 | −58.352 | 1.00 | 26.81 |
| ATOM | 4194 | CA  | VAL | A | 557 | 0.739  | 23.040 | −58.100 | 1.00 | 26.14 |
| ATOM | 4195 | CB  | VAL | A | 557 | 0.690  | 23.859 | −56.759 | 1.00 | 26.71 |
| ATOM | 4196 | CG1 | VAL | A | 557 | 2.073  | 24.140 | −56.219 | 1.00 | 27.82 |
| ATOM | 4197 | CG2 | VAL | A | 557 | −0.088 | 25.175 | −56.952 | 1.00 | 27.34 |
| ATOM | 4198 | C   | VAL | A | 557 | 1.856  | 21.999 | −58.092 | 1.00 | 25.64 |
| ATOM | 4199 | O   | VAL | A | 557 | 1.646  | 20.845 | −57.693 | 1.00 | 25.24 |
| ATOM | 4200 | N   | GLU | A | 558 | 3.035  | 22.409 | −58.553 | 1.00 | 24.16 |
| ATOM | 4201 | CA  | GLU | A | 558 | 4.223  | 21.579 | −58.516 | 1.00 | 24.38 |
| ATOM | 4202 | CB  | GLU | A | 558 | 4.737  | 21.296 | −59.933 | 1.00 | 24.86 |

TABLE 6-continued

| | | | | | | | | | |
|---|---|---|---|---|---|---|---|---|---|
| ATOM | 4203 | CG | GLU | A | 558 | 4.064 | 20.108 | −60.606 | 1.00 | 26.34 |
| ATOM | 4204 | CD | GLU | A | 558 | 4.670 | 19.790 | −61.962 | 1.00 | 27.68 |
| ATOM | 4205 | OE1 | GLU | A | 558 | 5.917 | 19.684 | −62.065 | 1.00 | 30.56 |
| ATOM | 4206 | OE2 | GLU | A | 558 | 3.883 | 19.638 | −62.915 | 1.00 | 32.45 |
| ATOM | 4207 | C | GLU | A | 558 | 5.262 | 22.337 | −57.730 | 1.00 | 22.54 |
| ATOM | 4208 | O | GLU | A | 558 | 5.389 | 23.550 | −57.883 | 1.00 | 22.93 |
| ATOM | 4209 | N | TYR | A | 559 | 5.992 | 21.640 | −56.867 | 1.00 | 21.45 |
| ATOM | 4210 | CA | TYR | A | 559 | 6.927 | 22.346 | −55.995 | 1.00 | 19.96 |
| ATOM | 4211 | CB | TYR | A | 559 | 6.188 | 22.972 | −54.784 | 1.00 | 19.42 |
| ATOM | 4212 | CG | TYR | A | 559 | 5.624 | 21.952 | −53.796 | 1.00 | 18.65 |
| ATOM | 4213 | CD1 | TYR | A | 559 | 6.383 | 21.524 | −52.703 | 1.00 | 18.64 |
| ATOM | 4214 | CE1 | TYR | A | 559 | 5.887 | 20.595 | −51.794 | 1.00 | 19.09 |
| ATOM | 4215 | CZ | TYR | A | 559 | 4.614 | 20.090 | −51.955 | 1.00 | 18.58 |
| ATOM | 4216 | OH | TYR | A | 559 | 4.135 | 19.160 | −51.056 | 1.00 | 20.55 |
| ATOM | 4217 | CE2 | TYR | A | 559 | 3.819 | 20.493 | −53.024 | 1.00 | 18.22 |
| ATOM | 4218 | CD2 | TYR | A | 559 | 4.335 | 21.438 | −53.946 | 1.00 | 18.82 |
| ATOM | 4219 | C | TYR | A | 559 | 8.066 | 21.445 | −55.541 | 1.00 | 20.13 |
| ATOM | 4220 | O | TYR | A | 559 | 8.008 | 20.215 | −55.679 | 1.00 | 20.26 |
| ATOM | 4221 | N | LYS | A | 560 | 9.098 | 22.079 | −54.995 | 1.00 | 19.51 |
| ATOM | 4222 | CA | LYS | A | 560 | 10.208 | 21.379 | −54.349 | 1.00 | 19.72 |
| ATOM | 4223 | CB | LYS | A | 560 | 11.410 | 21.175 | −55.282 | 1.00 | 19.66 |
| ATOM | 4224 | CG | LYS | A | 560 | 11.390 | 19.870 | −56.058 | 1.00 | 22.20 |
| ATOM | 4225 | CD | LYS | A | 560 | 12.767 | 19.633 | −56.714 | 1.00 | 24.46 |
| ATOM | 4226 | CE | LYS | A | 560 | 12.781 | 18.341 | −57.531 | 1.00 | 26.96 |
| ATOM | 4227 | NZ | LYS | A | 560 | 14.189 | 18.050 | −57.980 | 1.00 | 26.97 |
| ATOM | 4228 | C | LYS | A | 560 | 10.680 | 22.257 | −53.234 | 1.00 | 18.68 |
| ATOM | 4229 | O | LYS | A | 560 | 10.583 | 23.484 | −53.318 | 1.00 | 19.68 |
| ATOM | 4230 | N | TYR | A | 561 | 11.240 | 21.640 | −52.206 | 1.00 | 17.87 |
| ATOM | 4231 | CA | TYR | A | 561 | 11.927 | 22.420 | −51.187 | 1.00 | 17.82 |
| ATOM | 4232 | CB | TYR | A | 561 | 11.921 | 21.690 | −49.840 | 1.00 | 17.42 |
| ATOM | 4233 | CG | TYR | A | 561 | 10.518 | 21.449 | −49.346 | 1.00 | 16.12 |
| ATOM | 4234 | CD1 | TYR | A | 561 | 9.831 | 20.276 | −49.661 | 1.00 | 15.94 |
| ATOM | 4235 | CE1 | TYR | A | 561 | 8.511 | 20.062 | −49.199 | 1.00 | 15.79 |
| ATOM | 4236 | CZ | TYR | A | 561 | 7.897 | 21.050 | −48.456 | 1.00 | 15.89 |
| ATOM | 4237 | OH | TYR | A | 561 | 6.614 | 20.889 | −47.981 | 1.00 | 17.17 |
| ATOM | 4238 | CE2 | TYR | A | 561 | 8.557 | 22.224 | −48.164 | 1.00 | 16.19 |
| ATOM | 4239 | CD2 | TYR | A | 561 | 9.856 | 22.430 | −48.625 | 1.00 | 17.57 |
| ATOM | 4240 | C | TYR | A | 561 | 13.360 | 22.650 | −51.607 | 1.00 | 18.63 |
| ATOM | 4241 | O | TYR | A | 561 | 13.963 | 21.786 | −52.265 | 1.00 | 18.40 |
| ATOM | 4242 | N | ILE | A | 562 | 13.904 | 23.792 | −51.201 | 1.00 | 18.56 |
| ATOM | 4243 | CA | ILE | A | 562 | 15.322 | 24.085 | −51.434 | 1.00 | 20.18 |
| ATOM | 4244 | CB | ILE | A | 562 | 15.524 | 25.247 | −52.419 | 1.00 | 19.65 |
| ATOM | 4245 | CG1 | ILE | A | 562 | 14.837 | 26.520 | −51.896 | 1.00 | 21.64 |
| ATOM | 4246 | CD1 | ILE | A | 562 | 15.074 | 27.789 | −52.741 | 1.00 | 21.24 |
| ATOM | 4247 | CG2 | ILE | A | 562 | 15.017 | 24.829 | −53.797 | 1.00 | 20.44 |
| ATOM | 4248 | C | ILE | A | 562 | 15.971 | 24.446 | −50.128 | 1.00 | 20.56 |
| ATOM | 4249 | O | ILE | A | 562 | 15.316 | 24.956 | −49.229 | 1.00 | 19.84 |
| ATOM | 4250 | N | ASN | A | 563 | 17.254 | 24.134 | −50.029 | 1.00 | 21.41 |
| ATOM | 4251 | CA | ASN | A | 563 | 18.076 | 24.467 | −48.886 | 1.00 | 22.99 |
| ATOM | 4252 | CB | ASN | A | 563 | 18.833 | 23.209 | −48.435 | 1.00 | 22.69 |
| ATOM | 4253 | CG | ASN | A | 563 | 19.629 | 23.433 | −47.156 | 1.00 | 25.48 |
| ATOM | 4254 | OD1 | ASN | A | 563 | 20.203 | 24.492 | −46.965 | 1.00 | 28.81 |
| ATOM | 4255 | ND2 | ASN | A | 563 | 19.669 | 22.436 | −46.285 | 1.00 | 25.82 |
| ATOM | 4256 | C | ASN | A | 563 | 19.039 | 25.561 | −49.372 | 1.00 | 24.66 |
| ATOM | 4257 | O | ASN | A | 563 | 19.794 | 25.326 | −50.323 | 1.00 | 24.16 |
| ATOM | 4258 | N | VAL | A | 564 | 18.977 | 26.749 | −48.780 | 1.00 | 26.20 |
| ATOM | 4259 | CA | VAL | A | 564 | 19.877 | 27.837 | −49.206 | 1.00 | 28.74 |
| ATOM | 4260 | CB | VAL | A | 564 | 19.156 | 29.091 | −49.832 | 1.00 | 28.91 |
| ATOM | 4261 | CG1 | VAL | A | 564 | 19.461 | 30.408 | −49.087 | 1.00 | 31.10 |
| ATOM | 4262 | CG2 | VAL | A | 564 | 17.655 | 28.836 | −50.079 | 1.00 | 28.92 |
| ATOM | 4263 | C | VAL | A | 564 | 20.886 | 28.181 | −48.122 | 1.00 | 29.56 |
| ATOM | 4264 | O | VAL | A | 564 | 20.538 | 28.320 | −46.954 | 1.00 | 29.10 |
| ATOM | 4265 | N | GLY | A | 565 | 22.150 | 28.266 | −48.527 | 1.00 | 32.02 |
| ATOM | 4266 | CA | GLY | A | 565 | 23.252 | 28.423 | −47.577 | 1.00 | 34.92 |
| ATOM | 4267 | C | GLY | A | 565 | 23.539 | 29.876 | −47.248 | 1.00 | 37.47 |
| ATOM | 4268 | O | GLY | A | 565 | 22.969 | 30.788 | −47.871 | 1.00 | 37.66 |
| ATOM | 4269 | N | GLN | A | 566 | 24.419 | 30.098 | −46.267 | 1.00 | 39.85 |
| ATOM | 4270 | CA | GLN | A | 566 | 24.897 | 31.456 | −45.926 | 1.00 | 42.75 |
| ATOM | 4271 | CB | GLN | A | 566 | 26.054 | 31.398 | −44.918 | 1.00 | 42.83 |
| ATOM | 4272 | CG | GLN | A | 566 | 25.727 | 30.761 | −43.565 | 1.00 | 44.99 |
| ATOM | 4273 | CD | GLN | A | 566 | 26.940 | 30.689 | −42.626 | 1.00 | 44.88 |
| ATOM | 4274 | OE1 | GLN | A | 566 | 27.972 | 30.089 | −42.958 | 1.00 | 47.67 |
| ATOM | 4275 | NE2 | GLN | A | 566 | 26.810 | 31.293 | −41.441 | 1.00 | 47.62 |
| ATOM | 4276 | C | GLN | A | 566 | 25.373 | 32.195 | −47.181 | 1.00 | 43.30 |
| ATOM | 4277 | O | GLN | A | 566 | 25.052 | 33.365 | −47.389 | 1.00 | 44.01 |
| ATOM | 4278 | N | ASP | A | 567 | 26.118 | 31.479 | −48.023 | 1.00 | 44.30 |
| ATOM | 4279 | CA | ASP | A | 567 | 26.739 | 32.029 | −49.236 | 1.00 | 44.62 |
| ATOM | 4280 | CB | ASP | A | 567 | 27.916 | 31.139 | −49.650 | 1.00 | 45.13 |
| ATOM | 4281 | CG | ASP | A | 567 | 27.492 | 29.702 | −49.966 | 1.00 | 47.62 |
| ATOM | 4282 | OD1 | ASP | A | 567 | 26.421 | 29.255 | −49.485 | 1.00 | 48.73 |

TABLE 6-continued

| | | | | | | | | | |
|---|---|---|---|---|---|---|---|---|---|
| ATOM | 4283 | OD2 | ASP | A | 567 | 28.245 | 29.010 | −50.693 | 1.00 | 50.47 |
| ATOM | 4284 | C | ASP | A | 567 | 25.776 | 32.197 | −50.421 | 1.00 | 44.04 |
| ATOM | 4285 | O | ASP | A | 567 | 26.196 | 32.575 | −51.522 | 1.00 | 44.36 |
| ATOM | 4286 | N | GLY | A | 568 | 24.497 | 31.899 | −50.205 | 1.00 | 42.85 |
| ATOM | 4287 | CA | GLY | A | 568 | 23.488 | 32.045 | −51.247 | 1.00 | 41.38 |
| ATOM | 4288 | C | GLY | A | 568 | 23.359 | 30.851 | −52.177 | 1.00 | 40.41 |
| ATOM | 4289 | O | GLY | A | 568 | 22.496 | 30.854 | −53.054 | 1.00 | 40.62 |
| ATOM | 4290 | N | SER | A | 569 | 24.195 | 29.827 | −51.990 | 1.00 | 39.02 |
| ATOM | 4291 | CA | SER | A | 569 | 24.137 | 28.623 | −52.827 | 1.00 | 37.72 |
| ATOM | 4292 | CB | SER | A | 569 | 25.365 | 27.746 | −52.600 | 1.00 | 38.07 |
| ATOM | 4293 | OG | SER | A | 569 | 25.454 | 27.359 | −51.238 | 1.00 | 39.18 |
| ATOM | 4294 | C | SER | A | 569 | 22.868 | 27.819 | −52.540 | 1.00 | 36.72 |
| ATOM | 4295 | O | SER | A | 569 | 22.474 | 27.672 | −51.382 | 1.00 | 36.47 |
| ATOM | 4296 | N | VAL | A | 570 | 22.222 | 27.313 | −53.583 | 1.00 | 35.25 |
| ATOM | 4297 | CA | VAL | A | 570 | 20.988 | 26.558 | −53.365 | 1.00 | 34.26 |
| ATOM | 4298 | CB | VAL | A | 570 | 19.709 | 27.243 | −53.987 | 1.00 | 34.42 |
| ATOM | 4299 | CG1 | VAL | A | 570 | 18.992 | 26.358 | −55.020 | 1.00 | 35.11 |
| ATOM | 4300 | CG2 | VAL | A | 570 | 20.010 | 28.651 | −54.506 | 1.00 | 35.12 |
| ATOM | 4301 | C | VAL | A | 570 | 21.113 | 25.080 | −53.718 | 1.00 | 33.29 |
| ATOM | 4302 | O | VAL | A | 570 | 21.735 | 24.694 | −54.714 | 1.00 | 32.88 |
| ATOM | 4303 | N | THR | A | 571 | 20.515 | 24.261 | −52.864 | 1.00 | 31.66 |
| ATOM | 4304 | CA | THR | A | 571 | 20.480 | 22.825 | −53.021 | 1.00 | 30.87 |
| ATOM | 4305 | CB | THR | A | 571 | 21.016 | 22.146 | −51.752 | 1.00 | 30.96 |
| ATOM | 4306 | OG1 | THR | A | 571 | 22.311 | 22.686 | −51.442 | 1.00 | 33.18 |
| ATOM | 4307 | CG2 | THR | A | 571 | 21.117 | 20.637 | −51.935 | 1.00 | 30.95 |
| ATOM | 4308 | C | THR | A | 571 | 19.018 | 22.473 | −53.210 | 1.00 | 29.72 |
| ATOM | 4309 | O | THR | A | 571 | 18.186 | 22.832 | −52.373 | 1.00 | 28.84 |
| ATOM | 4310 | N | TRP | A | 572 | 18.697 | 21.846 | −54.337 | 1.00 | 29.01 |
| ATOM | 4311 | CA | TRP | A | 572 | 17.331 | 21.388 | −54.589 | 1.00 | 28.49 |
| ATOM | 4312 | CB | TRP | A | 572 | 17.004 | 21.367 | −56.086 | 1.00 | 28.99 |
| ATOM | 4313 | CG | TRP | A | 572 | 16.950 | 22.690 | −56.739 | 1.00 | 29.65 |
| ATOM | 4314 | CD1 | TRP | A | 572 | 18.014 | 23.419 | −57.217 | 1.00 | 30.67 |
| ATOM | 4315 | NE1 | TRP | A | 572 | 17.564 | 24.603 | −57.769 | 1.00 | 31.84 |
| ATOM | 4316 | CE2 | TRP | A | 572 | 16.196 | 24.655 | −57.668 | 1.00 | 30.45 |
| ATOM | 4317 | CD2 | TRP | A | 572 | 15.770 | 23.464 | −57.028 | 1.00 | 30.30 |
| ATOM | 4318 | CE3 | TRP | A | 572 | 14.398 | 23.274 | −56.791 | 1.00 | 29.43 |
| ATOM | 4319 | CZ3 | TRP | A | 572 | 13.502 | 24.266 | −57.205 | 1.00 | 30.24 |
| ATOM | 4320 | CH2 | TRP | A | 572 | 13.959 | 25.437 | −57.846 | 1.00 | 30.31 |
| ATOM | 4321 | CZ2 | TRP | A | 572 | 15.298 | 25.649 | −58.083 | 1.00 | 29.71 |
| ATOM | 4322 | C | TRP | A | 572 | 17.205 | 19.991 | −54.031 | 1.00 | 28.21 |
| ATOM | 4323 | O | TRP | A | 572 | 18.168 | 19.212 | −54.060 | 1.00 | 27.50 |
| ATOM | 4324 | N | GLU | A | 573 | 16.033 | 19.647 | −53.499 | 1.00 | 27.69 |
| ATOM | 4325 | CA | GLU | A | 573 | 15.819 | 18.251 | −53.123 | 1.00 | 27.17 |
| ATOM | 4326 | CB | GLU | A | 573 | 14.586 | 18.074 | −52.222 | 1.00 | 27.18 |
| ATOM | 4327 | CG | GLU | A | 573 | 13.287 | 18.406 | −52.901 | 1.00 | 26.04 |
| ATOM | 4328 | CD | GLU | A | 573 | 12.059 | 18.111 | −52.028 | 1.00 | 26.20 |
| ATOM | 4329 | OE1 | GLU | A | 573 | 12.112 | 17.224 | −51.141 | 1.00 | 25.84 |
| ATOM | 4330 | OE2 | GLU | A | 573 | 11.032 | 18.764 | −52.264 | 1.00 | 22.24 |
| ATOM | 4331 | C | GLU | A | 573 | 15.725 | 17.419 | −54.405 | 1.00 | 27.91 |
| ATOM | 4332 | O | GLU | A | 573 | 15.498 | 17.957 | −55.497 | 1.00 | 26.94 |
| ATOM | 4333 | N | SER | A | 574 | 15.907 | 16.108 | −54.267 | 1.00 | 28.48 |
| ATOM | 4334 | CA | SER | A | 574 | 15.880 | 15.201 | −55.410 | 1.00 | 29.59 |
| ATOM | 4335 | CB | SER | A | 574 | 16.296 | 13.805 | −54.975 | 1.00 | 29.73 |
| ATOM | 4336 | OG | SER | A | 574 | 17.609 | 13.875 | −54.449 | 1.00 | 32.74 |
| ATOM | 4337 | C | SER | A | 574 | 14.526 | 15.134 | −56.095 | 1.00 | 29.70 |
| ATOM | 4338 | O | SER | A | 574 | 13.500 | 15.482 | −55.513 | 1.00 | 29.12 |
| ATOM | 4339 | N | ASP | A | 575 | 14.544 | 14.669 | −57.339 | 1.00 | 29.54 |
| ATOM | 4340 | CA | ASP | A | 575 | 13.337 | 14.435 | −58.109 | 1.00 | 29.98 |
| ATOM | 4341 | CB | ASP | A | 575 | 13.705 | 14.000 | −59.534 | 1.00 | 30.69 |
| ATOM | 4342 | CG | ASP | A | 575 | 14.324 | 15.125 | −60.331 | 1.00 | 33.96 |
| ATOM | 4343 | OD1 | ASP | A | 575 | 14.056 | 16.299 | −59.997 | 1.00 | 36.25 |
| ATOM | 4344 | OD2 | ASP | A | 575 | 15.083 | 14.846 | −61.290 | 1.00 | 37.94 |
| ATOM | 4345 | C | ASP | A | 575 | 12.519 | 13.358 | −57.428 | 1.00 | 28.93 |
| ATOM | 4346 | O | ASP | A | 575 | 13.050 | 12.633 | −56.600 | 1.00 | 28.34 |
| ATOM | 4347 | N | PRO | A | 576 | 11.217 | 13.267 | −57.760 | 1.00 | 28.58 |
| ATOM | 4348 | CA | PRO | A | 576 | 10.469 | 14.173 | −58.650 | 1.00 | 27.92 |
| ATOM | 4349 | CB | PRO | A | 576 | 9.319 | 13.294 | −59.131 | 1.00 | 28.52 |
| ATOM | 4350 | CG | PRO | A | 576 | 9.053 | 12.378 | −57.954 | 1.00 | 28.29 |
| ATOM | 4351 | CD | PRO | A | 576 | 10.377 | 12.159 | −57.267 | 1.00 | 28.76 |
| ATOM | 4352 | C | PRO | A | 576 | 9.894 | 15.397 | −57.938 | 1.00 | 27.25 |
| ATOM | 4353 | O | PRO | A | 576 | 9.887 | 15.452 | −56.703 | 1.00 | 28.13 |
| ATOM | 4354 | N | ASN | A | 577 | 9.394 | 16.360 | −58.707 | 1.00 | 25.62 |
| ATOM | 4355 | CA | ASN | A | 577 | 8.612 | 17.449 | −58.129 | 1.00 | 24.83 |
| ATOM | 4356 | CB | ASN | A | 577 | 8.013 | 18.336 | −59.224 | 1.00 | 24.90 |
| ATOM | 4357 | CG | ASN | A | 577 | 9.055 | 19.184 | −59.913 | 1.00 | 25.61 |
| ATOM | 4358 | OD1 | ASN | A | 577 | 10.176 | 19.321 | −59.423 | 1.00 | 25.83 |
| ATOM | 4359 | ND2 | ASN | A | 577 | 8.693 | 19.756 | −61.060 | 1.00 | 25.07 |
| ATOM | 4360 | C | ASN | A | 577 | 7.466 | 16.868 | −57.322 | 1.00 | 24.22 |
| ATOM | 4361 | O | ASN | A | 577 | 6.949 | 15.798 | −57.672 | 1.00 | 23.69 |
| ATOM | 4362 | N | HIS | A | 578 | 7.057 | 17.562 | −56.259 | 1.00 | 23.20 |

TABLE 6-continued

| | | | | | | | | | |
|---|---|---|---|---|---|---|---|---|---|
| ATOM | 4363 | CA | HIS | A | 578 | 5.830 | 17.179 | −55.570 | 1.00 | 22.96 |
| ATOM | 4364 | CB | HIS | A | 578 | 5.734 | 17.844 | −54.200 | 1.00 | 22.09 |
| ATOM | 4365 | CG | HIS | A | 578 | 6.874 | 17.538 | −53.285 | 1.00 | 21.80 |
| ATOM | 4366 | ND1 | HIS | A | 578 | 6.809 | 16.558 | −52.318 | 1.00 | 21.62 |
| ATOM | 4367 | CE1 | HIS | A | 578 | 7.948 | 16.530 | −51.645 | 1.00 | 21.36 |
| ATOM | 4368 | NE2 | HIS | A | 578 | 8.743 | 17.465 | −52.133 | 1.00 | 20.16 |
| ATOM | 4369 | CD2 | HIS | A | 578 | 8.096 | 18.109 | −53.160 | 1.00 | 19.78 |
| ATOM | 4370 | C | HIS | A | 578 | 4.697 | 17.707 | −56.429 | 1.00 | 23.58 |
| ATOM | 4371 | O | HIS | A | 578 | 4.814 | 18.794 | −56.976 | 1.00 | 23.64 |
| ATOM | 4372 | N | THR | A | 579 | 3.603 | 16.955 | −56.534 | 1.00 | 23.98 |
| ATOM | 4373 | CA | THR | A | 579 | 2.426 | 17.448 | −57.254 | 1.00 | 25.34 |
| ATOM | 4374 | CB | THR | A | 579 | 2.092 | 16.568 | −58.477 | 1.00 | 26.08 |
| ATOM | 4375 | OG1 | THR | A | 579 | 3.162 | 16.672 | −59.429 | 1.00 | 29.14 |
| ATOM | 4376 | CG2 | THR | A | 579 | 0.749 | 16.979 | −59.126 | 1.00 | 26.14 |
| ATOM | 4377 | C | THR | A | 579 | 1.259 | 17.480 | −56.291 | 1.00 | 25.05 |
| ATOM | 4378 | O | THR | A | 579 | 0.977 | 16.487 | −55.629 | 1.00 | 25.73 |
| ATOM | 4379 | N | TYR | A | 580 | 0.591 | 18.619 | −56.213 | 1.00 | 25.23 |
| ATOM | 4380 | CA | TYR | A | 580 | −0.450 | 18.802 | −55.211 | 1.00 | 25.68 |
| ATOM | 4381 | CB | TYR | A | 580 | 0.098 | 19.556 | −53.976 | 1.00 | 25.88 |
| ATOM | 4382 | CG | TYR | A | 580 | −0.931 | 19.763 | −52.866 | 1.00 | 26.21 |
| ATOM | 4383 | CD1 | TYR | A | 580 | −1.284 | 21.048 | −52.429 | 1.00 | 26.22 |
| ATOM | 4384 | CE1 | TYR | A | 580 | −2.256 | 21.233 | −51.399 | 1.00 | 27.53 |
| ATOM | 4385 | CZ | TYR | A | 580 | −2.860 | 20.111 | −50.841 | 1.00 | 27.08 |
| ATOM | 4386 | OH | TYR | A | 580 | −3.806 | 20.207 | −49.844 | 1.00 | 27.88 |
| ATOM | 4387 | CE2 | TYR | A | 580 | −2.510 | 18.841 | −51.264 | 1.00 | 26.97 |
| ATOM | 4388 | CD2 | TYR | A | 580 | −1.562 | 18.671 | −52.276 | 1.00 | 26.29 |
| ATOM | 4389 | C | TYR | A | 580 | −1.634 | 19.523 | −55.828 | 1.00 | 25.65 |
| ATOM | 4390 | O | TYR | A | 580 | −1.490 | 20.596 | −56.403 | 1.00 | 25.29 |
| ATOM | 4391 | N | THR | A | 581 | −2.813 | 18.915 | −55.732 | 1.00 | 25.95 |
| ATOM | 4392 | CA | THR | A | 581 | −4.015 | 19.629 | −56.117 | 1.00 | 25.78 |
| ATOM | 4393 | CB | THR | A | 581 | −5.016 | 18.700 | −56.806 | 1.00 | 26.75 |
| ATOM | 4394 | OG1 | THR | A | 581 | −4.332 | 18.000 | −57.855 | 1.00 | 26.57 |
| ATOM | 4395 | CG2 | THR | A | 581 | −6.189 | 19.498 | −57.397 | 1.00 | 27.62 |
| ATOM | 4396 | C | THR | A | 581 | −4.627 | 20.285 | −54.874 | 1.00 | 25.36 |
| ATOM | 4397 | O | THR | A | 581 | −5.024 | 19.595 | −53.935 | 1.00 | 25.22 |
| ATOM | 4398 | N | VAL | A | 582 | −4.685 | 21.615 | −54.880 | 1.00 | 24.54 |
| ATOM | 4399 | CA | VAL | A | 582 | −5.255 | 22.382 | −53.777 | 1.00 | 24.15 |
| ATOM | 4400 | CB | VAL | A | 582 | −5.006 | 23.915 | −53.953 | 1.00 | 24.21 |
| ATOM | 4401 | CG1 | VAL | A | 582 | −5.472 | 24.700 | −52.744 | 1.00 | 23.87 |
| ATOM | 4402 | CG2 | VAL | A | 582 | −3.514 | 24.218 | −54.219 | 1.00 | 25.33 |
| ATOM | 4403 | C | VAL | A | 582 | −6.759 | 22.063 | −53.706 | 1.00 | 24.32 |
| ATOM | 4404 | O | VAL | A | 582 | −7.478 | 22.204 | −54.700 | 1.00 | 23.26 |
| ATOM | 4405 | N | PRO | A | 583 | −7.236 | 21.587 | −52.546 | 1.00 | 24.10 |
| ATOM | 4406 | CA | PRO | A | 583 | −8.665 | 21.230 | −52.476 | 1.00 | 24.34 |
| ATOM | 4407 | CB | PRO | A | 583 | −8.865 | 20.763 | −51.022 | 1.00 | 24.33 |
| ATOM | 4408 | CG | PRO | A | 583 | −7.516 | 20.538 | −50.468 | 1.00 | 25.16 |
| ATOM | 4409 | CD | PRO | A | 583 | −6.508 | 21.310 | −51.294 | 1.00 | 24.72 |
| ATOM | 4410 | C | PRO | A | 583 | −9.597 | 22.404 | −52.768 | 1.00 | 24.50 |
| ATOM | 4411 | O | PRO | A | 583 | −9.262 | 23.558 | −52.487 | 1.00 | 23.93 |
| ATOM | 4412 | N | ALA | A | 584 | −10.756 | 22.104 | −53.350 | 1.00 | 24.61 |
| ATOM | 4413 | CA | ALA | A | 584 | −11.817 | 23.084 | −53.477 | 1.00 | 24.77 |
| ATOM | 4414 | CB | ALA | A | 584 | −12.065 | 23.439 | −54.943 | 1.00 | 25.29 |
| ATOM | 4415 | C | ALA | A | 584 | −13.036 | 22.434 | −52.847 | 1.00 | 24.94 |
| ATOM | 4416 | O | ALA | A | 584 | −13.922 | 21.932 | −53.537 | 1.00 | 25.03 |
| ATOM | 4417 | N | VAL | A | 585 | −13.052 | 22.406 | −51.517 | 1.00 | 24.24 |
| ATOM | 4418 | CA | VAL | A | 585 | −14.075 | 21.673 | −50.776 | 1.00 | 23.75 |
| ATOM | 4419 | CB | VAL | A | 585 | −13.465 | 20.452 | −50.029 | 1.00 | 24.50 |
| ATOM | 4420 | CG1 | VAL | A | 585 | −14.515 | 19.770 | −49.151 | 1.00 | 24.48 |
| ATOM | 4421 | CG2 | VAL | A | 585 | −12.863 | 19.447 | −51.026 | 1.00 | 25.32 |
| ATOM | 4422 | C | VAL | A | 585 | −14.707 | 22.639 | −49.781 | 1.00 | 23.20 |
| ATOM | 4423 | O | VAL | A | 585 | −13.999 | 23.347 | −49.065 | 1.00 | 22.13 |
| ATOM | 4424 | N | ALA | A | 586 | −16.044 | 22.679 | −49.739 | 1.00 | 22.43 |
| ATOM | 4425 | CA | ALA | A | 586 | −16.749 | 23.546 | −48.804 | 1.00 | 21.79 |
| ATOM | 4426 | CB | ALA | A | 586 | −18.240 | 23.212 | −48.820 | 1.00 | 22.19 |
| ATOM | 4427 | C | ALA | A | 586 | −16.160 | 23.324 | −47.389 | 1.00 | 21.57 |
| ATOM | 4428 | O | ALA | A | 586 | −15.954 | 22.180 | −46.990 | 1.00 | 20.89 |
| ATOM | 4429 | N | CYS | A | 587 | −15.872 | 24.414 | −46.679 | 1.00 | 21.59 |
| ATOM | 4430 | CA | CYS | A | 587 | −15.388 | 24.379 | −45.268 | 1.00 | 21.68 |
| ATOM | 4431 | CB | CYS | A | 587 | −16.131 | 23.323 | −44.441 | 1.00 | 22.08 |
| ATOM | 4432 | SG | CYS | A | 587 | −17.952 | 23.374 | −44.507 | 1.00 | 23.60 |
| ATOM | 4433 | C | CYS | A | 587 | −13.886 | 24.129 | −45.094 | 1.00 | 21.27 |
| ATOM | 4434 | O | CYS | A | 587 | −13.386 | 24.225 | −43.980 | 1.00 | 21.08 |
| ATOM | 4435 | N | VAL | A | 588 | −13.178 | 23.780 | −46.170 | 1.00 | 20.53 |
| ATOM | 4436 | CA | VAL | A | 588 | −11.742 | 23.499 | −46.085 | 1.00 | 20.52 |
| ATOM | 4437 | CB | VAL | A | 588 | −11.351 | 22.268 | −46.958 | 1.00 | 20.47 |
| ATOM | 4438 | CG1 | VAL | A | 588 | −9.846 | 21.959 | −46.844 | 1.00 | 20.87 |
| ATOM | 4439 | CG2 | VAL | A | 588 | −12.163 | 21.042 | −46.549 | 1.00 | 20.51 |
| ATOM | 4440 | C | VAL | A | 588 | −10.949 | 24.731 | −46.504 | 1.00 | 20.59 |
| ATOM | 4441 | O | VAL | A | 588 | −10.699 | 24.950 | −47.705 | 1.00 | 21.88 |
| ATOM | 4442 | N | THR | A | 589 | −10.533 | 25.522 | −45.528 | 1.00 | 19.56 |

TABLE 6-continued

| | | | | | | | | | |
|---|---|---|---|---|---|---|---|---|---|
| ATOM | 4443 | CA | THR | A | 589 | −9.903 | 26.807 | −45.795 | 1.00 | 19.48 |
| ATOM | 4444 | CB | THR | A | 589 | −10.595 | 27.914 | −44.988 | 1.00 | 20.13 |
| ATOM | 4445 | OG1 | THR | A | 589 | −10.527 | 27.565 | −43.592 | 1.00 | 21.49 |
| ATOM | 4446 | CG2 | THR | A | 589 | −12.085 | 28.018 | −45.410 | 1.00 | 20.03 |
| ATOM | 4447 | C | THR | A | 589 | −8.424 | 26.819 | −45.427 | 1.00 | 19.42 |
| ATOM | 4448 | O | THR | A | 589 | −7.694 | 27.767 | −45.743 | 1.00 | 18.66 |
| ATOM | 4449 | N | GLN | A | 590 | −7.995 | 25.772 | −44.734 | 1.00 | 19.62 |
| ATOM | 4450 | CA | GLN | A | 590 | −6.606 | 25.629 | −44.317 | 1.00 | 20.20 |
| ATOM | 4451 | CB | GLN | A | 590 | −6.359 | 26.261 | −42.939 | 1.00 | 21.06 |
| ATOM | 4452 | CG | GLN | A | 590 | −4.950 | 25.956 | −42.410 | 1.00 | 27.00 |
| ATOM | 4453 | CD | GLN | A | 590 | −4.184 | 27.189 | −41.989 | 1.00 | 33.74 |
| ATOM | 4454 | OE1 | GLN | A | 590 | −4.771 | 28.196 | −41.611 | 1.00 | 37.22 |
| ATOM | 4455 | NE2 | GLN | A | 590 | −2.855 | 27.118 | −42.066 | 1.00 | 36.77 |
| ATOM | 4456 | C | GLN | A | 590 | −6.247 | 24.159 | −44.295 | 1.00 | 19.00 |
| ATOM | 4457 | O | GLN | A | 590 | −7.004 | 23.335 | −43.771 | 1.00 | 18.70 |
| ATOM | 4458 | N | VAL | A | 591 | −5.113 | 23.811 | −44.904 | 1.00 | 17.70 |
| ATOM | 4459 | CA | VAL | A | 591 | −4.682 | 22.404 | −44.940 | 1.00 | 17.15 |
| ATOM | 4460 | CB | VAL | A | 591 | −4.843 | 21.750 | −46.330 | 1.00 | 17.82 |
| ATOM | 4461 | CG1 | VAL | A | 591 | −6.316 | 21.701 | −46.744 | 1.00 | 18.11 |
| ATOM | 4462 | CG2 | VAL | A | 591 | −3.970 | 22.470 | −47.390 | 1.00 | 17.60 |
| ATOM | 4463 | C | VAL | A | 591 | −3.213 | 22.360 | −44.551 | 1.00 | 17.42 |
| ATOM | 4464 | O | VAL | A | 591 | −2.531 | 23.377 | −44.638 | 1.00 | 17.32 |
| ATOM | 4465 | N | VAL | A | 592 | −2.731 | 21.206 | −44.090 | 1.00 | 17.26 |
| ATOM | 4466 | CA | VAL | A | 592 | −1.291 | 21.092 | −43.887 | 1.00 | 17.03 |
| ATOM | 4467 | CB | VAL | A | 592 | −0.762 | 21.198 | −42.365 | 1.00 | 18.70 |
| ATOM | 4468 | CG1 | VAL | A | 592 | 0.335 | 20.217 | −41.930 | 1.00 | 18.75 |
| ATOM | 4469 | CG2 | VAL | A | 592 | −1.810 | 21.731 | −41.315 | 1.00 | 15.36 |
| ATOM | 4470 | C | VAL | A | 592 | −0.736 | 19.951 | −44.730 | 1.00 | 16.99 |
| ATOM | 4471 | O | VAL | A | 592 | −1.318 | 18.862 | −44.828 | 1.00 | 16.23 |
| ATOM | 4472 | N | LYS | A | 593 | 0.357 | 20.253 | −45.403 | 1.00 | 15.38 |
| ATOM | 4473 | CA | LYS | A | 593 | 0.953 | 19.302 | −46.293 | 1.00 | 16.27 |
| ATOM | 4474 | CB | LYS | A | 593 | 1.301 | 20.010 | −47.616 | 1.00 | 16.69 |
| ATOM | 4475 | CG | LYS | A | 593 | 1.835 | 19.096 | −48.694 | 1.00 | 20.55 |
| ATOM | 4476 | CD | LYS | A | 593 | 0.791 | 18.101 | −49.203 | 1.00 | 24.73 |
| ATOM | 4477 | CE | LYS | A | 593 | 1.330 | 17.311 | −50.409 | 1.00 | 27.26 |
| ATOM | 4478 | NZ | LYS | A | 593 | 2.395 | 16.299 | −50.074 | 1.00 | 28.37 |
| ATOM | 4479 | C | LYS | A | 593 | 2.209 | 18.783 | −45.588 | 1.00 | 16.01 |
| ATOM | 4480 | O | LYS | A | 593 | 3.175 | 19.525 | −45.427 | 1.00 | 15.12 |
| ATOM | 4481 | N | GLU | A | 594 | 2.195 | 17.519 | −45.175 | 1.00 | 15.82 |
| ATOM | 4482 | CA | GLU | A | 594 | 3.308 | 16.969 | −44.407 | 1.00 | 16.23 |
| ATOM | 4483 | CB | GLU | A | 594 | 2.798 | 16.017 | −43.317 | 1.00 | 16.26 |
| ATOM | 4484 | CG | GLU | A | 594 | 1.866 | 16.732 | −42.299 | 1.00 | 16.62 |
| ATOM | 4485 | CD | GLU | A | 594 | 1.727 | 15.949 | −40.991 | 1.00 | 18.94 |
| ATOM | 4486 | OE1 | GLU | A | 594 | 1.267 | 14.778 | −41.024 | 1.00 | 21.31 |
| ATOM | 4487 | OE2 | GLU | A | 594 | 2.107 | 16.507 | −39.940 | 1.00 | 16.43 |
| ATOM | 4488 | C | GLU | A | 594 | 4.286 | 16.245 | −45.323 | 1.00 | 17.34 |
| ATOM | 4489 | O | GLU | A | 594 | 3.973 | 15.177 | −45.852 | 1.00 | 17.78 |
| ATOM | 4490 | N | ASP | A | 595 | 5.463 | 16.833 | −45.487 | 1.00 | 17.05 |
| ATOM | 4491 | CA | ASP | A | 595 | 6.481 | 16.326 | −46.405 | 1.00 | 17.21 |
| ATOM | 4492 | CB | ASP | A | 595 | 6.823 | 17.379 | −47.475 | 1.00 | 16.63 |
| ATOM | 4493 | CG | ASP | A | 595 | 5.678 | 17.619 | −48.455 | 1.00 | 17.91 |
| ATOM | 4494 | OD1 | ASP | A | 595 | 5.023 | 16.631 | −48.857 | 1.00 | 20.73 |
| ATOM | 4495 | OD2 | ASP | A | 595 | 5.434 | 18.795 | −48.844 | 1.00 | 18.08 |
| ATOM | 4496 | C | ASP | A | 595 | 7.734 | 15.955 | −45.631 | 1.00 | 17.47 |
| ATOM | 4497 | O | ASP | A | 595 | 7.915 | 16.375 | −44.492 | 1.00 | 16.44 |
| ATOM | 4498 | N | THR | A | 596 | 8.598 | 15.162 | −46.277 | 1.00 | 18.11 |
| ATOM | 4499 | CA | THR | A | 596 | 9.917 | 14.835 | −45.747 | 1.00 | 18.85 |
| ATOM | 4500 | CB | THR | A | 596 | 9.991 | 13.390 | −45.188 | 1.00 | 19.58 |
| ATOM | 4501 | OG1 | THR | A | 596 | 9.057 | 13.248 | −44.116 | 1.00 | 20.97 |
| ATOM | 4502 | CG2 | THR | A | 596 | 11.385 | 13.124 | −44.598 | 1.00 | 20.94 |
| ATOM | 4503 | C | THR | A | 596 | 10.895 | 14.978 | −46.914 | 1.00 | 19.34 |
| ATOM | 4504 | O | THR | A | 596 | 10.588 | 14.531 | −48.024 | 1.00 | 19.05 |
| ATOM | 4505 | N | TRP | A | 597 | 12.050 | 15.581 | −46.631 | 1.00 | 20.24 |
| ATOM | 4506 | CA | TRP | A | 597 | 13.074 | 15.921 | −47.633 | 1.00 | 21.94 |
| ATOM | 4507 | CB | TRP | A | 597 | 14.325 | 16.453 | −46.940 | 1.00 | 22.34 |
| ATOM | 4508 | CG | TRP | A | 597 | 15.445 | 16.854 | −47.882 | 1.00 | 23.75 |
| ATOM | 4509 | CD1 | TRP | A | 597 | 16.509 | 16.079 | −48.275 | 1.00 | 25.08 |
| ATOM | 4510 | NE1 | TRP | A | 597 | 17.327 | 16.801 | −49.138 | 1.00 | 24.85 |
| ATOM | 4511 | CE2 | TRP | A | 597 | 16.802 | 18.059 | −49.300 | 1.00 | 25.25 |
| ATOM | 4512 | CD2 | TRP | A | 597 | 15.611 | 18.128 | −48.527 | 1.00 | 24.09 |
| ATOM | 4513 | CE3 | TRP | A | 597 | 14.875 | 19.325 | −48.519 | 1.00 | 24.91 |
| ATOM | 4514 | CZ3 | TRP | A | 597 | 15.334 | 20.401 | −49.262 | 1.00 | 23.38 |
| ATOM | 4515 | CH2 | TRP | A | 597 | 16.520 | 20.299 | −50.028 | 1.00 | 25.14 |
| ATOM | 4516 | CZ2 | TRP | A | 597 | 17.265 | 19.137 | −50.053 | 1.00 | 22.49 |
| ATOM | 4517 | C | TRP | A | 597 | 13.424 | 14.708 | −48.473 | 1.00 | 23.42 |
| ATOM | 4518 | O | TRP | A | 597 | 13.675 | 13.635 | −47.939 | 1.00 | 22.37 |
| ATOM | 4519 | N | GLN | A | 598 | 13.409 | 14.904 | −49.788 | 1.00 | 25.26 |
| ATOM | 4520 | CA | GLN | A | 598 | 13.698 | 13.850 | −50.755 | 1.00 | 27.05 |
| ATOM | 4521 | CB | GLN | A | 598 | 12.936 | 14.124 | −52.052 | 1.00 | 26.51 |
| ATOM | 4522 | CG | GLN | A | 598 | 11.418 | 13.948 | −51.895 | 1.00 | 26.10 |

TABLE 6-continued

| | | | | | | | | | |
|---|---|---|---|---|---|---|---|---|---|
| ATOM | 4523 | CD | GLN | A | 598 | 10.642 | 14.209 | −53.156 | 1.00 | 26.76 |
| ATOM | 4524 | OE1 | GLN | A | 598 | 11.194 | 14.620 | −54.175 | 1.00 | 27.68 |
| ATOM | 4525 | NE2 | GLN | A | 598 | 9.340 | 13.990 | −53.095 | 1.00 | 25.96 |
| ATOM | 4526 | C | GLN | A | 598 | 15.204 | 13.787 | −50.977 | 1.00 | 29.21 |
| ATOM | 4527 | O | GLN | A | 598 | 15.794 | 14.694 | −51.574 | 1.00 | 28.61 |
| ATOM | 4528 | N | SER | A | 599 | 15.818 | 12.722 | −50.453 | 1.00 | 32.41 |
| ATOM | 4529 | CA | SER | A | 599 | 17.273 | 12.530 | −50.498 | 1.00 | 35.70 |
| ATOM | 4530 | CB | SER | A | 599 | 17.747 | 11.698 | −49.302 | 1.00 | 35.61 |
| ATOM | 4531 | OG | SER | A | 599 | 17.374 | 12.296 | −48.072 | 1.00 | 39.62 |
| ATOM | 4532 | C | SER | A | 599 | 17.703 | 11.831 | −51.785 | 1.00 | 36.66 |
| ATOM | 4533 | O | SER | A | 599 | 16.916 | 11.145 | −52.433 | 1.00 | 37.44 |
| ATOM | 4534 | OXT | SER | A | 599 | 18.863 | 11.922 | −52.194 | 1.00 | 38.18 |
| ATOM | 4535 | C1 | MAN | A | 601 | −3.602 | −3.018 | −46.412 | 1.00 | 102.64 |
| ATOM | 4536 | C2 | MAN | A | 601 | −4.584 | −2.109 | −47.156 | 1.00 | 102.73 |
| ATOM | 4537 | O2 | MAN | A | 601 | −3.951 | −1.548 | −48.288 | 1.00 | 102.91 |
| ATOM | 4538 | C3 | MAN | A | 601 | −5.867 | −2.845 | −47.570 | 1.00 | 102.38 |
| ATOM | 4539 | O3 | MAN | A | 601 | −6.544 | −2.112 | −48.566 | 1.00 | 102.32 |
| ATOM | 4540 | C4 | MAN | A | 601 | −5.640 | −4.269 | −48.082 | 1.00 | 102.18 |
| ATOM | 4541 | O4 | MAN | A | 601 | −6.860 | −4.967 | −47.984 | 1.00 | 101.76 |
| ATOM | 4542 | C5 | MAN | A | 601 | −4.561 | −5.018 | −47.298 | 1.00 | 102.40 |
| ATOM | 4543 | C6 | MAN | A | 601 | −4.172 | −6.307 | −48.010 | 1.00 | 102.48 |
| ATOM | 4544 | O6 | MAN | A | 601 | −3.156 | −6.957 | −47.280 | 1.00 | 102.80 |
| ATOM | 4545 | O5 | MAN | A | 601 | −3.400 | −4.222 | −47.131 | 1.00 | 102.71 |
| ATOM | 4546 | C1 | MAN | A | 602 | −29.428 | −4.974 | −42.477 | 1.00 | 77.32 |
| ATOM | 4547 | C2 | MAN | A | 602 | −28.973 | −6.434 | −42.405 | 1.00 | 77.44 |
| ATOM | 4548 | O2 | MAN | A | 602 | −30.120 | −7.253 | −42.347 | 1.00 | 77.72 |
| ATOM | 4549 | C3 | MAN | A | 602 | −28.044 | −6.835 | −43.565 | 1.00 | 77.20 |
| ATOM | 4550 | O3 | MAN | A | 602 | −27.940 | −8.239 | −43.664 | 1.00 | 76.96 |
| ATOM | 4551 | C4 | MAN | A | 602 | −28.487 | −6.260 | −44.909 | 1.00 | 77.22 |
| ATOM | 4552 | O4 | MAN | A | 602 | −27.471 | −6.474 | −45.862 | 1.00 | 76.90 |
| ATOM | 4553 | C5 | MAN | A | 602 | −28.766 | −4.766 | −44.768 | 1.00 | 77.47 |
| ATOM | 4554 | C6 | MAN | A | 602 | −29.185 | −4.115 | −46.081 | 1.00 | 77.84 |
| ATOM | 4555 | O6 | MAN | A | 602 | −28.163 | −3.228 | −46.483 | 1.00 | 78.24 |
| ATOM | 4556 | O5 | MAN | A | 602 | −29.768 | −4.562 | −43.790 | 1.00 | 77.46 |
| ATOM | 4557 | C1 | MAN | A | 603 | −18.689 | 25.235 | −53.677 | 1.00 | 47.04 |
| ATOM | 4558 | C2 | MAN | A | 603 | −20.074 | 24.872 | −53.114 | 1.00 | 51.09 |
| ATOM | 4559 | O2 | MAN | A | 603 | −21.044 | 25.065 | −54.120 | 1.00 | 52.42 |
| ATOM | 4560 | C3 | MAN | A | 603 | −20.141 | 23.420 | −52.620 | 1.00 | 51.78 |
| ATOM | 4561 | O3 | MAN | A | 603 | −21.465 | 23.079 | −52.262 | 1.00 | 53.36 |
| ATOM | 4562 | C4 | MAN | A | 603 | −19.602 | 22.466 | −53.686 | 1.00 | 51.72 |
| ATOM | 4563 | O4 | MAN | A | 603 | −19.615 | 21.142 | −53.209 | 1.00 | 51.94 |
| ATOM | 4564 | C5 | MAN | A | 603 | −18.179 | 22.911 | −54.021 | 1.00 | 51.66 |
| ATOM | 4565 | C6 | MAN | A | 603 | −17.421 | 21.906 | −54.892 | 1.00 | 53.80 |
| ATOM | 4566 | O6 | MAN | A | 603 | −17.915 | 21.885 | −56.214 | 1.00 | 55.49 |
| ATOM | 4567 | O5 | MAN | A | 603 | −18.217 | 24.223 | −54.581 | 1.00 | 49.62 |
| ATOM | 4568 | C1 | MAN | A | 605 | −4.678 | 15.117 | −57.896 | 1.00 | 58.79 |
| ATOM | 4569 | C2 | MAN | A | 605 | −3.360 | 15.555 | −58.538 | 1.00 | 58.65 |
| ATOM | 4570 | O2 | MAN | A | 605 | −2.564 | 14.412 | −58.722 | 1.00 | 59.38 |
| ATOM | 4571 | C3 | MAN | A | 605 | −3.570 | 16.269 | −59.878 | 1.00 | 58.70 |
| ATOM | 4572 | O3 | MAN | A | 605 | −2.523 | 15.985 | −60.778 | 1.00 | 59.27 |
| ATOM | 4573 | C4 | MAN | A | 605 | −4.915 | 15.892 | −60.491 | 1.00 | 58.73 |
| ATOM | 4574 | O4 | MAN | A | 605 | −5.084 | 16.538 | −61.730 | 1.00 | 59.62 |
| ATOM | 4575 | C5 | MAN | A | 605 | −6.054 | 16.284 | −59.547 | 1.00 | 58.90 |
| ATOM | 4576 | C6 | MAN | A | 605 | −7.370 | 15.612 | −59.932 | 1.00 | 58.75 |
| ATOM | 4577 | O6 | MAN | A | 605 | −7.255 | 14.219 | −59.738 | 1.00 | 59.42 |
| ATOM | 4578 | O5 | MAN | A | 605 | −5.730 | 16.034 | −58.173 | 1.00 | 58.30 |
| ATOM | 4579 | C1 | MAN | A | 606 | −10.273 | 28.688 | −42.727 | 1.00 | 25.90 |
| ATOM | 4580 | C2 | MAN | A | 606 | −9.839 | 27.944 | −41.452 | 1.00 | 28.64 |
| ATOM | 4581 | O2 | MAN | A | 606 | −9.245 | 28.909 | −40.620 | 1.00 | 28.84 |
| ATOM | 4582 | C3 | MAN | A | 606 | −10.999 | 27.249 | −40.710 | 1.00 | 29.65 |
| ATOM | 4583 | O3 | MAN | A | 606 | −10.568 | 26.763 | −39.441 | 1.00 | 28.85 |
| ATOM | 4584 | C4 | MAN | A | 606 | −12.203 | 28.177 | −40.551 | 1.00 | 30.36 |
| ATOM | 4585 | O4 | MAN | A | 606 | −13.330 | 27.463 | −40.084 | 1.00 | 30.29 |
| ATOM | 4586 | C5 | MAN | A | 606 | −12.553 | 28.769 | −41.914 | 1.00 | 30.72 |
| ATOM | 4587 | C6 | MAN | A | 606 | −13.730 | 29.731 | −41.778 | 1.00 | 33.97 |
| ATOM | 4588 | O6 | MAN | A | 606 | −13.624 | 30.732 | −42.762 | 1.00 | 36.82 |
| ATOM | 4589 | O5 | MAN | A | 606 | −11.434 | 29.464 | −42.435 | 1.00 | 28.12 |
| ATOM | 4590 | C1 | MAN | A | 607 | −31.396 | 1.963 | −40.521 | 1.00 | 50.29 |
| ATOM | 4591 | C2 | MAN | A | 607 | −30.220 | 1.790 | −41.485 | 1.00 | 52.65 |
| ATOM | 4592 | O2 | MAN | A | 607 | −30.541 | 0.785 | −42.419 | 1.00 | 54.93 |
| ATOM | 4593 | C3 | MAN | A | 607 | −29.845 | 3.092 | −42.208 | 1.00 | 52.48 |
| ATOM | 4594 | O3 | MAN | A | 607 | −28.932 | 2.836 | −43.251 | 1.00 | 53.01 |
| ATOM | 4595 | C4 | MAN | A | 607 | −31.068 | 3.818 | −42.766 | 1.00 | 52.78 |
| ATOM | 4596 | O4 | MAN | A | 607 | −30.672 | 5.070 | −43.297 | 1.00 | 52.92 |
| ATOM | 4597 | C5 | MAN | A | 607 | −32.103 | 3.985 | −41.652 | 1.00 | 52.23 |
| ATOM | 4598 | C6 | MAN | A | 607 | −33.331 | 4.749 | −42.153 | 1.00 | 52.96 |
| ATOM | 4599 | O6 | MAN | A | 607 | −34.520 | 4.076 | −41.791 | 1.00 | 52.95 |
| ATOM | 4600 | O5 | MAN | A | 607 | −32.451 | 2.702 | −41.127 | 1.00 | 51.79 |
| ATOM | 4601 | C1 | MAN | A | 608 | 3.870 | 15.416 | −59.489 | 1.00 | 37.21 |
| ATOM | 4602 | C2 | MAN | A | 608 | 5.134 | 15.938 | −60.168 | 1.00 | 40.45 |

TABLE 6-continued

| | | | | | | | | | |
|---|---|---|---|---|---|---|---|---|---|
| ATOM | 4603 | O2 | MAN | A | 608 | 6.091 | 14.903 | −60.120 | 1.00 | 38.47 |
| ATOM | 4604 | C3 | MAN | A | 608 | 4.872 | 16.381 | −61.608 | 1.00 | 42.66 |
| ATOM | 4605 | O3 | MAN | A | 608 | 6.071 | 16.726 | −62.263 | 1.00 | 44.20 |
| ATOM | 4606 | C4 | MAN | A | 608 | 4.122 | 15.321 | −62.401 | 1.00 | 44.80 |
| ATOM | 4607 | O4 | MAN | A | 608 | 3.708 | 15.907 | −63.612 | 1.00 | 47.73 |
| ATOM | 4608 | C5 | MAN | A | 608 | 2.893 | 14.887 | −61.597 | 1.00 | 44.80 |
| ATOM | 4609 | C6 | MAN | A | 608 | 2.042 | 13.861 | −62.342 | 1.00 | 47.55 |
| ATOM | 4610 | O6 | MAN | A | 608 | 1.085 | 14.582 | −63.104 | 1.00 | 49.87 |
| ATOM | 4611 | O5 | MAN | A | 608 | 3.262 | 14.423 | −60.302 | 1.00 | 42.18 |
| ATOM | 4612 | C1 | NAG | A | 611 | 3.450 | −2.354 | −8.282 | 1.00 | 23.44 |
| ATOM | 4613 | C2 | NAG | A | 611 | 3.474 | −0.875 | −7.878 | 1.00 | 24.51 |
| ATOM | 4614 | N2 | NAG | A | 611 | 4.425 | −0.077 | −8.630 | 1.00 | 21.95 |
| ATOM | 4615 | C7 | NAG | A | 611 | 4.123 | 0.454 | −9.818 | 1.00 | 22.94 |
| ATOM | 4616 | O7 | NAG | A | 611 | 3.030 | 0.322 | −10.367 | 1.00 | 20.93 |
| ATOM | 4617 | C8 | NAG | A | 611 | 5.216 | 1.232 | −10.481 | 1.00 | 21.54 |
| ATOM | 4618 | C3 | NAG | A | 611 | 3.741 | −0.713 | −6.380 | 1.00 | 25.60 |
| ATOM | 4619 | O3 | NAG | A | 611 | 3.676 | 0.655 | −6.047 | 1.00 | 24.91 |
| ATOM | 4620 | C4 | NAG | A | 611 | 2.741 | −1.528 | −5.554 | 1.00 | 25.70 |
| ATOM | 4621 | O4 | NAG | A | 611 | 3.196 | −1.598 | −4.227 | 1.00 | 28.27 |
| ATOM | 4622 | C5 | NAG | A | 611 | 2.648 | −2.952 | −6.086 | 1.00 | 26.18 |
| ATOM | 4623 | C6 | NAG | A | 611 | 1.524 | −3.738 | −5.397 | 1.00 | 26.64 |
| ATOM | 4624 | O6 | NAG | A | 611 | 0.278 | −3.081 | −5.497 | 1.00 | 25.38 |
| ATOM | 4625 | O5 | NAG | A | 611 | 2.437 | −2.975 | −7.488 | 1.00 | 24.34 |
| ATOM | 4626 | C1 | NAG | A | 612 | 2.499 | −0.713 | −3.326 | 1.00 | 32.04 |
| ATOM | 4627 | C2 | NAG | A | 612 | 2.710 | −1.192 | −1.879 | 1.00 | 35.81 |
| ATOM | 4628 | N2 | NAG | A | 612 | 2.254 | −2.556 | −1.666 | 1.00 | 37.89 |
| ATOM | 4629 | C7 | NAG | A | 612 | 3.072 | −3.605 | −1.753 | 1.00 | 39.19 |
| ATOM | 4630 | O7 | NAG | A | 612 | 4.277 | −3.517 | −2.031 | 1.00 | 40.58 |
| ATOM | 4631 | C8 | NAG | A | 612 | 2.439 | −4.947 | −1.507 | 1.00 | 38.98 |
| ATOM | 4632 | C3 | NAG | A | 612 | 2.012 | −0.256 | −0.899 | 1.00 | 37.96 |
| ATOM | 4633 | O3 | NAG | A | 612 | 2.352 | −0.666 | 0.403 | 1.00 | 41.23 |
| ATOM | 4634 | C4 | NAG | A | 612 | 2.491 | 1.176 | −1.129 | 1.00 | 37.63 |
| ATOM | 4635 | O4 | NAG | A | 612 | 1.789 | 2.053 | −0.278 | 1.00 | 40.85 |
| ATOM | 4636 | C5 | NAG | A | 612 | 2.294 | 1.565 | −2.604 | 1.00 | 35.10 |
| ATOM | 4637 | C6 | NAG | A | 612 | 2.785 | 2.982 | −2.903 | 1.00 | 31.93 |
| ATOM | 4638 | O6 | NAG | A | 612 | 4.188 | 2.994 | −3.008 | 0.58 | 32.70 |
| ATOM | 4639 | O5 | NAG | A | 612 | 2.974 | 0.625 | −3.425 | 1.00 | 31.95 |
| ATOM | 4640 | O8 | BTB | A | 620 | −1.213 | 18.638 | −21.639 | 1.00 | 23.78 |
| ATOM | 4641 | C8 | BTB | A | 620 | −1.255 | 19.440 | −22.838 | 1.00 | 17.50 |
| ATOM | 4642 | C7 | BTB | A | 620 | −2.257 | 18.851 | −23.831 | 1.00 | 15.39 |
| ATOM | 4643 | N | BTB | A | 620 | −1.808 | 17.505 | −24.294 | 1.00 | 13.88 |
| ATOM | 4644 | C5 | BTB | A | 620 | −1.274 | 17.600 | −25.684 | 1.00 | 12.99 |
| ATOM | 4645 | C6 | BTB | A | 620 | 0.017 | 18.399 | −25.786 | 1.00 | 14.67 |
| ATOM | 4646 | O6 | BTB | A | 620 | 0.949 | 18.004 | −24.768 | 1.00 | 16.93 |
| ATOM | 4647 | C2 | BTB | A | 620 | −2.926 | 16.495 | −24.191 | 1.00 | 13.33 |
| ATOM | 4648 | C4 | BTB | A | 620 | −4.238 | 16.972 | −24.835 | 1.00 | 13.45 |
| ATOM | 4649 | O4 | BTB | A | 620 | −4.167 | 17.018 | −26.265 | 1.00 | 14.77 |
| ATOM | 4650 | C3 | BTB | A | 620 | −3.213 | 16.295 | −22.703 | 1.00 | 13.18 |
| ATOM | 4651 | O3 | BTB | A | 620 | −1.984 | 15.920 | −22.059 | 1.00 | 12.74 |
| ATOM | 4652 | C1 | BTB | A | 620 | −2.501 | 15.161 | −24.845 | 1.00 | 13.57 |
| ATOM | 4653 | O1 | BTB | A | 620 | −3.463 | 14.138 | −24.525 | 1.00 | 13.07 |
| ATOM | 4654 | O | WAT | W | 1 | −7.741 | 16.530 | −28.587 | 1.00 | 12.90 |
| ATOM | 4655 | O | WAT | W | 2 | −1.955 | 18.721 | −7.814 | 1.00 | 11.77 |
| ATOM | 4656 | O | WAT | W | 3 | −17.101 | 16.033 | −19.836 | 1.00 | 15.26 |
| ATOM | 4657 | O | WAT | W | 4 | −1.389 | 7.464 | −24.070 | 1.00 | 15.86 |
| ATOM | 4658 | O | WAT | W | 5 | −8.070 | 20.758 | −43.462 | 1.00 | 19.56 |
| ATOM | 4659 | O | WAT | W | 6 | −12.959 | 28.534 | −26.860 | 1.00 | 16.12 |
| ATOM | 4660 | O | WAT | W | 7 | −0.502 | 31.488 | −57.004 | 1.00 | 33.06 |
| ATOM | 4661 | O | WAT | W | 8 | 2.095 | 5.710 | −17.808 | 1.00 | 18.68 |
| ATOM | 4662 | O | WAT | W | 9 | −7.601 | 14.567 | −6.827 | 1.00 | 14.97 |
| ATOM | 4663 | O | WAT | W | 10 | 24.863 | 23.325 | −37.431 | 1.00 | 32.31 |
| ATOM | 4664 | O | WAT | W | 11 | −22.569 | 7.289 | −10.357 | 1.00 | 17.52 |
| ATOM | 4665 | O | WAT | W | 12 | −18.987 | 1.758 | −22.078 | 1.00 | 23.03 |
| ATOM | 4666 | O | WAT | W | 13 | −3.226 | 16.264 | −54.338 | 1.00 | 32.98 |
| ATOM | 4667 | O | WAT | W | 14 | 6.141 | 16.546 | −42.196 | 1.00 | 16.00 |
| ATOM | 4668 | O | WAT | W | 15 | −10.356 | 21.827 | −22.675 | 1.00 | 13.52 |
| ATOM | 4669 | O | WAT | W | 16 | −3.130 | 25.355 | −17.925 | 1.00 | 14.01 |
| ATOM | 4670 | O | WAT | W | 17 | −11.823 | 29.479 | −29.411 | 1.00 | 17.50 |
| ATOM | 4671 | O | WAT | W | 18 | −14.383 | 15.964 | −19.553 | 1.00 | 13.02 |
| ATOM | 4672 | O | WAT | W | 19 | −1.180 | 16.935 | −10.101 | 1.00 | 18.86 |
| ATOM | 4673 | O | WAT | W | 20 | −31.133 | 23.501 | 4.462 | 1.00 | 16.66 |
| ATOM | 4674 | O | WAT | W | 21 | −4.819 | 24.193 | −15.023 | 1.00 | 14.31 |
| ATOM | 4675 | O | WAT | W | 22 | 1.709 | 22.276 | −4.126 | 1.00 | 21.96 |
| ATOM | 4676 | O | WAT | W | 23 | −5.339 | 21.386 | −7.463 | 1.00 | 15.78 |
| ATOM | 4677 | O | WAT | W | 24 | −17.232 | 15.476 | 1.374 | 1.00 | 17.64 |
| ATOM | 4678 | O | WAT | W | 25 | −11.449 | 4.860 | −24.929 | 1.00 | 17.45 |
| ATOM | 4679 | O | WAT | W | 26 | −17.555 | 17.679 | −39.815 | 1.00 | 23.23 |
| ATOM | 4680 | O | WAT | W | 27 | 10.075 | 17.015 | −49.295 | 1.00 | 24.05 |
| ATOM | 4681 | O | WAT | W | 28 | −16.018 | −0.740 | −24.205 | 1.00 | 18.07 |
| ATOM | 4682 | O | WAT | W | 29 | 9.446 | 24.991 | −37.612 | 1.00 | 19.20 |

TABLE 6-continued

| ATOM | 4683 | O | WAT | W | 30 | −4.165 | 26.137 | −12.642 | 1.00 | 18.33 |
|---|---|---|---|---|---|---|---|---|---|---|
| ATOM | 4684 | O | WAT | W | 31 | 2.771 | 22.947 | −14.916 | 1.00 | 25.80 |
| ATOM | 4685 | O | WAT | W | 32 | −12.297 | 21.394 | −35.680 | 1.00 | 14.89 |
| ATOM | 4686 | O | WAT | W | 33 | −24.061 | 13.570 | 10.081 | 1.00 | 24.96 |
| ATOM | 4687 | O | WAT | W | 34 | 10.032 | 29.725 | −56.684 | 1.00 | 26.97 |
| ATOM | 4688 | O | WAT | W | 35 | 0.231 | 4.133 | −28.595 | 1.00 | 17.67 |
| ATOM | 4689 | O | WAT | W | 36 | 0.335 | 2.173 | −30.650 | 1.00 | 18.32 |
| ATOM | 4690 | O | WAT | W | 37 | −10.199 | 24.315 | −42.717 | 1.00 | 22.38 |
| ATOM | 4691 | O | WAT | W | 38 | −14.151 | 12.872 | −8.204 | 1.00 | 16.16 |
| ATOM | 4692 | O | WAT | W | 39 | −2.710 | 9.564 | −16.092 | 1.00 | 14.10 |
| ATOM | 4693 | O | WAT | W | 40 | 5.954 | 7.990 | −32.401 | 1.00 | 16.59 |
| ATOM | 4694 | O | WAT | W | 41 | 0.294 | 5.561 | −25.249 | 1.00 | 17.87 |
| ATOM | 4695 | O | WAT | W | 42 | 2.102 | 15.148 | −37.718 | 1.00 | 14.64 |
| ATOM | 4696 | O | WAT | W | 43 | −19.351 | 1.384 | −26.295 | 1.00 | 20.27 |
| ATOM | 4697 | O | WAT | W | 44 | −19.623 | 9.533 | −17.751 | 1.00 | 14.67 |
| ATOM | 4698 | O | WAT | W | 45 | 3.117 | 18.767 | −36.336 | 1.00 | 12.66 |
| ATOM | 4699 | O | WAT | W | 46 | −15.016 | 16.950 | 0.662 | 1.00 | 20.14 |
| ATOM | 4700 | O | WAT | W | 47 | −22.261 | 4.600 | −10.993 | 1.00 | 16.38 |
| ATOM | 4701 | O | WAT | W | 48 | −12.926 | 5.474 | −22.680 | 1.00 | 19.85 |
| ATOM | 4702 | O | WAT | W | 49 | 5.564 | 17.071 | −37.018 | 1.00 | 16.82 |
| ATOM | 4703 | O | WAT | W | 50 | −19.848 | 20.552 | −2.718 | 1.00 | 19.38 |
| ATOM | 4704 | O | WAT | W | 51 | −15.859 | 17.744 | −41.901 | 1.00 | 19.69 |
| ATOM | 4705 | O | WAT | W | 52 | −16.430 | 25.522 | −1.123 | 1.00 | 19.97 |
| ATOM | 4706 | O | WAT | W | 53 | −15.978 | 5.366 | −12.193 | 1.00 | 26.02 |
| ATOM | 4707 | O | WAT | W | 54 | −1.637 | 9.365 | −26.035 | 1.00 | 14.42 |
| ATOM | 4708 | O | WAT | W | 55 | −10.759 | 27.212 | −30.898 | 1.00 | 17.28 |
| ATOM | 4709 | O | WAT | W | 56 | −11.509 | 0.756 | −13.101 | 1.00 | 20.70 |
| ATOM | 4710 | O | WAT | W | 57 | −16.950 | 15.108 | 4.727 | 1.00 | 23.86 |
| ATOM | 4711 | O | WAT | W | 58 | −25.368 | 26.009 | −7.106 | 1.00 | 25.08 |
| ATOM | 4712 | O | WAT | W | 59 | −16.870 | 22.937 | −3.651 | 1.00 | 17.56 |
| ATOM | 4713 | O | WAT | W | 60 | −14.388 | 13.258 | −40.897 | 1.00 | 27.90 |
| ATOM | 4714 | O | WAT | W | 61 | −1.509 | −4.779 | −6.723 | 1.00 | 31.01 |
| ATOM | 4715 | O | WAT | W | 62 | −1.973 | 27.723 | −11.521 | 1.00 | 21.99 |
| ATOM | 4716 | O | WAT | W | 63 | −1.159 | −10.623 | −29.592 | 1.00 | 36.68 |
| ATOM | 4717 | O | WAT | W | 64 | −1.943 | 16.930 | −42.957 | 1.00 | 21.57 |
| ATOM | 4718 | O | WAT | W | 65 | −1.507 | 25.238 | −40.032 | 1.00 | 31.36 |
| ATOM | 4719 | O | WAT | W | 66 | −4.023 | 5.499 | −31.787 | 1.00 | 20.03 |
| ATOM | 4720 | O | WAT | W | 67 | −13.383 | 13.873 | −21.065 | 1.00 | 12.01 |
| ATOM | 4721 | O | WAT | W | 68 | −15.098 | 10.726 | −24.467 | 1.00 | 24.34 |
| ATOM | 4722 | O | WAT | W | 69 | −2.122 | 13.975 | −13.435 | 1.00 | 12.51 |
| ATOM | 4723 | O | WAT | W | 70 | −4.807 | 19.360 | −43.270 | 1.00 | 20.93 |
| ATOM | 4724 | O | WAT | W | 71 | −26.028 | 26.143 | −33.768 | 1.00 | 28.78 |
| ATOM | 4725 | O | WAT | W | 72 | −19.347 | 21.638 | 3.482 | 1.00 | 19.92 |
| ATOM | 4726 | O | WAT | W | 73 | −27.299 | 24.219 | −6.045 | 1.00 | 20.97 |
| ATOM | 4727 | O | WAT | W | 74 | −21.114 | −0.343 | −28.050 | 1.00 | 22.38 |
| ATOM | 4728 | O | WAT | W | 75 | −5.818 | 34.483 | −11.645 | 1.00 | 20.61 |
| ATOM | 4729 | O | WAT | W | 76 | 6.048 | 1.098 | −23.393 | 1.00 | 16.77 |
| ATOM | 4730 | O | WAT | W | 77 | −3.946 | 23.711 | −39.552 | 1.00 | 25.07 |
| ATOM | 4731 | O | WAT | W | 78 | −18.572 | 21.631 | −41.884 | 1.00 | 25.98 |
| ATOM | 4732 | O | WAT | W | 79 | 5.239 | 26.273 | −31.646 | 1.00 | 27.95 |
| ATOM | 4733 | O | WAT | W | 80 | 0.054 | 15.597 | −45.905 | 1.00 | 28.45 |
| ATOM | 4734 | O | WAT | W | 81 | −3.130 | 21.534 | −5.652 | 1.00 | 20.95 |
| ATOM | 4735 | O | WAT | W | 82 | −12.534 | 4.331 | −20.095 | 1.00 | 17.49 |
| ATOM | 4736 | O | WAT | W | 83 | 0.785 | 16.541 | −14.558 | 1.00 | 14.65 |
| ATOM | 4737 | O | WAT | W | 84 | −5.197 | 12.827 | −31.553 | 1.00 | 14.10 |
| ATOM | 4738 | O | WAT | W | 85 | −16.738 | 26.994 | −34.463 | 1.00 | 23.74 |
| ATOM | 4739 | O | WAT | W | 86 | 3.596 | 22.076 | −36.828 | 1.00 | 22.68 |
| ATOM | 4740 | O | WAT | W | 87 | 5.170 | 14.460 | −40.572 | 1.00 | 26.56 |
| ATOM | 4741 | O | WAT | W | 88 | −12.322 | 21.050 | 0.328 | 1.00 | 30.36 |
| ATOM | 4742 | O | WAT | W | 89 | 7.426 | 14.327 | −48.857 | 1.00 | 26.44 |
| ATOM | 4743 | O | WAT | W | 90 | −13.702 | 19.025 | 1.863 | 1.00 | 28.28 |
| ATOM | 4744 | O | WAT | W | 91 | 8.794 | 2.010 | −23.444 | 1.00 | 34.69 |
| ATOM | 4745 | O | WAT | W | 92 | −6.185 | 5.529 | −30.210 | 1.00 | 17.03 |
| ATOM | 4746 | O | WAT | W | 93 | −18.081 | 20.709 | −4.839 | 1.00 | 17.61 |
| ATOM | 4747 | O | WAT | W | 94 | −15.469 | 13.082 | −22.717 | 1.00 | 15.55 |
| ATOM | 4748 | O | WAT | W | 95 | 13.101 | 16.811 | −29.771 | 1.00 | 29.16 |
| ATOM | 4749 | O | WAT | W | 96 | −25.944 | 7.031 | −2.628 | 1.00 | 27.42 |
| ATOM | 4750 | O | WAT | W | 97 | −4.552 | 34.207 | −7.388 | 1.00 | 22.19 |
| ATOM | 4751 | O | WAT | W | 98 | −2.231 | −9.858 | −32.291 | 1.00 | 26.28 |
| ATOM | 4752 | O | WAT | W | 99 | 5.314 | 10.271 | −28.762 | 1.00 | 29.39 |
| ATOM | 4753 | O | WAT | W | 100 | −15.379 | 27.478 | −46.620 | 1.00 | 37.77 |
| ATOM | 4754 | O | WAT | W | 101 | 26.815 | 24.874 | −36.295 | 1.00 | 31.11 |
| ATOM | 4755 | O | WAT | W | 102 | −18.489 | −0.112 | −24.256 | 1.00 | 23.63 |
| ATOM | 4756 | O | WAT | W | 103 | −23.763 | 26.890 | −9.454 | 1.00 | 20.50 |
| ATOM | 4757 | O | WAT | W | 104 | −10.933 | 23.904 | −50.315 | 1.00 | 25.63 |
| ATOM | 4758 | O | WAT | W | 105 | 5.864 | 12.071 | −41.668 | 1.00 | 29.27 |
| ATOM | 4759 | O | WAT | W | 106 | 2.526 | 9.409 | −13.116 | 1.00 | 20.75 |
| ATOM | 4760 | O | WAT | W | 107 | −11.557 | −6.653 | −10.981 | 1.00 | 30.68 |
| ATOM | 4761 | O | WAT | W | 108 | −14.882 | 7.238 | −22.254 | 1.00 | 24.81 |
| ATOM | 4762 | O | WAT | W | 109 | −5.331 | −13.390 | −25.293 | 1.00 | 35.63 |

TABLE 6-continued

| ATOM | 4763 | O | WAT | W | 110 | −8.068 | 24.248 | −40.534 | 1.00 | 39.14 |
|---|---|---|---|---|---|---|---|---|---|---|
| ATOM | 4764 | O | WAT | W | 111 | −0.779 | 14.419 | −43.060 | 1.00 | 24.01 |
| ATOM | 4765 | O | WAT | W | 112 | −22.279 | 12.054 | −26.750 | 1.00 | 32.13 |
| ATOM | 4766 | O | WAT | W | 113 | −26.829 | 1.352 | −33.787 | 1.00 | 26.97 |
| ATOM | 4767 | O | WAT | W | 114 | −14.120 | 14.116 | 3.214 | 1.00 | 36.89 |
| ATOM | 4768 | O | WAT | W | 115 | 0.582 | −9.914 | −21.103 | 1.00 | 23.30 |
| ATOM | 4769 | O | WAT | W | 116 | −24.305 | 22.723 | 6.995 | 1.00 | 21.67 |
| ATOM | 4770 | O | WAT | W | 117 | −28.275 | 12.468 | −15.419 | 1.00 | 21.87 |
| ATOM | 4771 | O | WAT | W | 118 | 3.699 | 27.669 | −20.781 | 1.00 | 34.08 |
| ATOM | 4772 | O | WAT | W | 119 | −30.428 | 26.452 | 3.757 | 1.00 | 24.51 |
| ATOM | 4773 | O | WAT | W | 120 | 19.168 | 26.858 | −59.022 | 1.00 | 33.45 |
| ATOM | 4774 | O | WAT | W | 121 | −8.803 | 21.729 | −1.693 | 1.00 | 18.30 |
| ATOM | 4775 | O | WAT | W | 122 | 2.863 | 1.621 | −31.755 | 1.00 | 19.96 |
| ATOM | 4776 | O | WAT | W | 123 | −2.357 | 28.930 | −56.725 | 1.00 | 35.51 |
| ATOM | 4777 | O | WAT | W | 124 | −16.780 | 5.504 | −21.523 | 1.00 | 31.34 |
| ATOM | 4778 | O | WAT | W | 125 | 6.216 | 18.141 | −30.592 | 1.00 | 20.87 |
| ATOM | 4779 | O | WAT | W | 126 | 11.789 | 32.722 | −38.773 | 1.00 | 40.41 |
| ATOM | 4780 | O | WAT | W | 127 | −5.001 | 7.195 | −45.656 | 1.00 | 35.03 |
| ATOM | 4781 | O | WAT | W | 128 | −18.743 | 1.608 | −1.861 | 1.00 | 32.49 |
| ATOM | 4782 | O | WAT | W | 129 | −25.089 | −1.945 | −20.935 | 1.00 | 35.17 |
| ATOM | 4783 | O | WAT | W | 130 | −7.097 | −2.177 | −28.928 | 1.00 | 30.93 |
| ATOM | 4784 | O | WAT | W | 131 | −12.591 | 2.907 | −11.929 | 1.00 | 18.60 |
| ATOM | 4785 | O | WAT | W | 132 | −17.913 | −2.374 | −39.429 | 1.00 | 29.36 |
| ATOM | 4786 | O | WAT | W | 133 | −6.507 | −7.038 | −37.710 | 1.00 | 37.27 |
| ATOM | 4787 | O | WAT | W | 134 | −0.628 | 7.596 | −18.660 | 1.00 | 20.01 |
| ATOM | 4788 | O | WAT | W | 135 | −11.683 | 28.527 | −37.016 | 1.00 | 36.45 |
| ATOM | 4789 | O | WAT | W | 136 | −3.169 | 33.267 | −18.049 | 1.00 | 24.89 |
| ATOM | 4790 | O | WAT | W | 137 | −16.742 | 8.938 | −23.161 | 1.00 | 26.79 |
| ATOM | 4791 | O | WAT | W | 138 | −28.456 | 17.726 | −22.449 | 1.00 | 32.61 |
| ATOM | 4792 | O | WAT | W | 139 | 25.559 | 27.237 | −45.392 | 1.00 | 43.21 |
| ATOM | 4793 | O | WAT | W | 140 | −26.925 | 5.789 | −41.722 | 1.00 | 26.97 |
| ATOM | 4794 | O | WAT | W | 141 | −16.907 | 20.013 | −43.283 | 1.00 | 29.68 |
| ATOM | 4795 | O | WAT | W | 142 | −20.029 | 5.119 | −1.799 | 1.00 | 24.76 |
| ATOM | 4796 | O | WAT | W | 143 | 8.706 | 1.050 | −13.115 | 1.00 | 32.81 |
| ATOM | 4797 | O | WAT | W | 144 | −4.353 | 22.506 | −1.252 | 1.00 | 24.86 |
| ATOM | 4798 | O | WAT | W | 145 | −29.660 | 14.750 | −15.295 | 1.00 | 32.62 |
| ATOM | 4799 | O | WAT | W | 146 | 2.173 | 2.240 | −12.124 | 1.00 | 26.38 |
| ATOM | 4800 | O | WAT | W | 147 | 4.174 | −4.659 | −14.794 | 1.00 | 25.20 |
| ATOM | 4801 | O | WAT | W | 148 | −10.913 | 29.083 | −33.130 | 1.00 | 27.78 |
| ATOM | 4802 | O | WAT | W | 149 | −21.448 | 30.157 | −10.670 | 1.00 | 25.07 |
| ATOM | 4803 | O | WAT | W | 150 | −23.296 | 18.641 | −36.646 | 1.00 | 27.11 |
| ATOM | 4804 | O | WAT | W | 151 | −19.426 | 8.262 | −24.240 | 1.00 | 25.11 |
| ATOM | 4805 | O | WAT | W | 152 | 4.729 | −0.512 | −31.679 | 1.00 | 23.50 |
| ATOM | 4806 | O | WAT | W | 153 | 9.247 | 19.703 | −33.306 | 1.00 | 23.44 |
| ATOM | 4807 | O | WAT | W | 154 | 6.024 | 15.401 | −22.768 | 1.00 | 27.11 |
| ATOM | 4808 | O | WAT | W | 155 | −16.077 | 30.180 | −4.530 | 1.00 | 23.52 |
| ATOM | 4809 | O | WAT | W | 156 | −0.038 | 14.751 | −8.812 | 1.00 | 25.64 |
| ATOM | 4810 | O | WAT | W | 157 | 2.962 | 18.631 | −29.190 | 1.00 | 18.13 |
| ATOM | 4811 | O | WAT | W | 158 | 8.793 | 12.371 | −36.745 | 1.00 | 23.77 |
| ATOM | 4812 | O | WAT | W | 159 | −22.406 | 9.468 | −0.415 | 1.00 | 21.66 |
| ATOM | 4813 | O | WAT | W | 160 | −10.961 | 33.685 | −7.076 | 1.00 | 25.30 |
| ATOM | 4814 | O | WAT | W | 161 | −8.504 | 27.891 | −3.964 | 1.00 | 33.88 |
| ATOM | 4815 | O | WAT | W | 162 | 6.836 | 20.663 | −32.439 | 1.00 | 24.97 |
| ATOM | 4816 | O | WAT | W | 163 | 4.292 | 23.232 | −29.206 | 1.00 | 32.74 |
| ATOM | 4817 | O | WAT | W | 164 | 2.350 | 3.656 | −15.645 | 1.00 | 23.29 |
| ATOM | 4818 | O | WAT | W | 165 | −17.377 | 10.190 | −20.605 | 1.00 | 25.21 |
| ATOM | 4819 | O | WAT | W | 166 | −23.426 | 24.714 | 4.551 | 1.00 | 26.12 |
| ATOM | 4820 | O | WAT | W | 167 | 0.338 | 1.730 | −14.995 | 1.00 | 31.29 |
| ATOM | 4821 | O | WAT | W | 168 | −3.303 | 17.836 | −46.350 | 1.00 | 28.34 |
| ATOM | 4822 | O | WAT | W | 169 | 1.465 | 6.514 | −14.840 | 1.00 | 22.81 |
| ATOM | 4823 | O | WAT | W | 170 | 2.409 | 11.466 | −4.481 | 1.00 | 29.82 |
| ATOM | 4824 | O | WAT | W | 171 | 0.998 | 19.313 | −20.348 | 1.00 | 31.57 |
| ATOM | 4825 | O | WAT | W | 172 | 7.556 | −3.076 | −34.213 | 1.00 | 31.62 |
| ATOM | 4826 | O | WAT | W | 173 | −25.163 | 1.132 | −18.852 | 1.00 | 33.45 |
| ATOM | 4827 | O | WAT | W | 174 | −25.606 | 17.471 | −26.509 | 1.00 | 27.89 |
| ATOM | 4828 | O | WAT | W | 175 | 5.952 | 32.621 | −65.955 | 1.00 | 42.20 |
| ATOM | 4829 | O | WAT | W | 176 | −27.397 | 26.421 | −12.489 | 1.00 | 29.06 |
| ATOM | 4830 | O | WAT | W | 177 | −17.506 | 35.918 | −29.284 | 1.00 | 36.40 |
| ATOM | 4831 | O | WAT | W | 178 | −18.298 | 7.055 | −19.628 | 1.00 | 30.04 |
| ATOM | 4832 | O | WAT | W | 179 | −24.383 | 14.811 | −26.605 | 1.00 | 29.51 |
| ATOM | 4833 | O | WAT | W | 180 | −1.204 | 27.462 | −35.328 | 1.00 | 29.93 |
| ATOM | 4834 | O | WAT | W | 181 | −14.112 | 33.822 | −23.916 | 1.00 | 34.66 |
| ATOM | 4835 | O | WAT | W | 182 | 2.887 | 26.714 | −9.619 | 1.00 | 34.18 |
| ATOM | 4836 | O | WAT | W | 183 | −16.062 | 4.698 | 1.046 | 1.00 | 32.44 |
| ATOM | 4837 | O | WAT | W | 184 | −13.340 | 36.111 | −4.359 | 1.00 | 39.14 |
| ATOM | 4838 | O | WAT | W | 185 | 9.661 | 34.457 | −47.977 | 1.00 | 37.66 |
| ATOM | 4839 | O | WAT | W | 186 | −8.465 | 24.284 | −1.237 | 1.00 | 33.71 |
| ATOM | 4840 | O | WAT | W | 187 | 16.971 | 15.520 | −43.951 | 1.00 | 42.49 |
| ATOM | 4841 | O | WAT | W | 188 | −12.038 | −14.614 | −20.299 | 1.00 | 34.37 |
| ATOM | 4842 | O | WAT | W | 189 | −5.887 | 22.387 | −40.784 | 1.00 | 33.70 |

TABLE 6-continued

| ATOM | 4843 | O | WAT | W | 190 | −3.962 | −18.100 | −17.720 | 1.00 | 31.33 |
|---|---|---|---|---|---|---|---|---|---|---|
| ATOM | 4844 | O | WAT | W | 191 | −30.888 | 11.643 | −15.288 | 1.00 | 36.84 |
| ATOM | 4845 | O | WAT | W | 192 | 11.576 | 13.142 | −37.752 | 1.00 | 32.89 |
| ATOM | 4846 | O | WAT | W | 193 | −7.856 | 3.348 | −41.927 | 1.00 | 34.02 |
| ATOM | 4847 | O | WAT | W | 194 | −20.849 | 7.518 | 7.652 | 1.00 | 32.37 |
| ATOM | 4848 | O | WAT | W | 195 | 16.954 | 13.938 | −58.514 | 1.00 | 42.65 |
| ATOM | 4849 | O | WAT | W | 196 | −31.884 | 7.593 | −13.893 | 1.00 | 37.54 |
| ATOM | 4850 | O | WAT | W | 197 | 4.560 | −14.190 | −17.137 | 1.00 | 36.09 |
| ATOM | 4851 | O | WAT | W | 198 | 1.116 | 27.617 | −39.051 | 1.00 | 37.08 |
| ATOM | 4852 | O | WAT | W | 199 | −1.019 | −12.134 | −21.800 | 1.00 | 36.12 |
| ATOM | 4853 | O | WAT | W | 200 | 8.350 | 0.111 | −21.198 | 1.00 | 36.56 |
| ATOM | 4854 | O | WAT | W | 201 | −2.691 | 31.235 | −26.910 | 1.00 | 32.08 |
| ATOM | 4855 | O | WAT | W | 202 | 13.222 | 30.530 | −38.626 | 1.00 | 36.46 |
| ATOM | 4856 | O | WAT | W | 203 | −11.218 | 19.535 | −54.549 | 1.00 | 35.12 |
| ATOM | 4857 | O | WAT | W | 204 | −5.623 | 10.865 | −46.910 | 1.00 | 35.48 |
| ATOM | 4858 | O | WAT | W | 205 | −18.073 | 1.743 | −43.946 | 1.00 | 40.62 |
| ATOM | 4859 | O | WAT | W | 206 | −32.195 | 23.231 | 2.102 | 1.00 | 34.73 |
| ATOM | 4860 | O | WAT | W | 207 | −24.204 | 8.994 | −2.941 | 1.00 | 30.29 |
| ATOM | 4861 | O | WAT | W | 208 | −4.771 | 18.292 | −48.610 | 1.00 | 31.87 |
| ATOM | 4862 | O | WAT | W | 209 | −17.156 | 23.843 | −40.674 | 1.00 | 35.73 |
| ATOM | 4863 | O | WAT | W | 210 | 8.319 | 13.422 | −13.297 | 1.00 | 37.43 |
| ATOM | 4864 | O | WAT | W | 211 | −25.962 | 8.559 | −33.791 | 1.00 | 33.46 |
| ATOM | 4865 | O | WAT | W | 212 | −36.129 | 8.276 | 3.147 | 1.00 | 40.24 |
| ATOM | 4866 | O | WAT | W | 213 | 20.833 | 21.074 | −56.185 | 1.00 | 39.11 |
| ATOM | 4867 | O | WAT | W | 214 | −17.726 | 14.087 | 8.330 | 1.00 | 39.10 |
| ATOM | 4868 | O | WAT | W | 215 | 8.944 | 8.011 | −10.493 | 1.00 | 41.24 |
| ATOM | 4869 | O | WAT | W | 216 | −16.566 | 35.858 | −11.282 | 1.00 | 38.90 |
| ATOM | 4870 | O | WAT | W | 217 | −20.560 | 11.198 | −43.128 | 1.00 | 34.83 |
| ATOM | 4871 | O | WAT | W | 218 | 3.261 | −0.833 | −39.177 | 1.00 | 32.67 |
| ATOM | 4872 | O | WAT | W | 219 | −22.370 | −13.152 | −34.412 | 1.00 | 59.42 |
| ATOM | 4873 | O | WAT | W | 220 | −24.775 | 6.925 | 5.968 | 1.00 | 34.28 |
| ATOM | 4874 | O | WAT | W | 221 | −20.357 | 21.098 | −45.702 | 1.00 | 36.83 |
| ATOM | 4875 | O | WAT | W | 222 | 2.502 | 28.932 | −40.686 | 1.00 | 36.85 |
| ATOM | 4876 | O | WAT | W | 223 | −17.630 | −5.533 | −21.334 | 1.00 | 35.08 |
| ATOM | 4877 | O | WAT | W | 224 | −19.358 | −1.912 | −43.190 | 1.00 | 35.83 |
| ATOM | 4878 | O | WAT | W | 225 | −14.632 | 25.995 | −42.094 | 1.00 | 41.12 |
| ATOM | 4879 | O | WAT | W | 226 | −28.967 | 5.606 | −22.103 | 1.00 | 45.63 |
| ATOM | 4880 | O | WAT | W | 227 | −4.326 | 9.934 | 5.097 | 1.00 | 44.46 |
| ATOM | 4881 | O | WAT | W | 228 | 3.983 | 22.711 | −17.336 | 1.00 | 46.21 |
| ATOM | 4882 | O | WAT | W | 229 | −17.238 | 16.931 | 6.949 | 1.00 | 42.44 |
| ATOM | 4883 | O | WAT | W | 230 | −25.871 | 18.809 | 10.364 | 1.00 | 36.15 |
| ATOM | 4884 | O | WAT | W | 231 | −23.524 | 31.294 | −19.082 | 1.00 | 35.99 |
| ATOM | 4885 | O | WAT | W | 232 | −5.261 | −9.321 | −38.277 | 1.00 | 43.42 |
| ATOM | 4886 | O | WAT | W | 233 | −22.757 | 28.188 | −29.173 | 1.00 | 39.56 |
| ATOM | 4887 | O | WAT | W | 234 | −25.699 | 26.238 | −0.299 | 1.00 | 40.26 |
| ATOM | 4888 | O | WAT | W | 235 | −21.884 | −4.007 | −22.294 | 1.00 | 38.01 |
| ATOM | 4889 | O | WAT | W | 236 | −6.696 | −17.346 | −27.753 | 1.00 | 39.83 |
| ATOM | 4890 | O | WAT | W | 237 | −18.052 | 5.515 | 3.888 | 1.00 | 37.82 |
| ATOM | 4891 | O | WAT | W | 238 | −6.073 | 35.708 | −9.057 | 1.00 | 36.25 |
| ATOM | 4892 | O | WAT | W | 239 | −8.876 | 2.984 | −44.368 | 1.00 | 45.85 |
| ATOM | 4893 | O | WAT | W | 240 | 9.232 | 31.613 | −65.496 | 1.00 | 45.82 |
| ATOM | 4894 | O | WAT | W | 241 | −28.246 | 26.806 | −0.118 | 1.00 | 36.45 |
| ATOM | 4895 | O | WAT | W | 242 | −27.793 | 14.675 | −45.312 | 1.00 | 52.10 |
| ATOM | 4896 | O | WAT | W | 243 | 7.463 | 14.079 | −55.045 | 1.00 | 36.97 |
| ATOM | 4897 | O | WAT | W | 244 | −28.572 | 4.769 | −1.130 | 1.00 | 36.20 |
| ATOM | 4898 | O | WAT | W | 245 | 8.221 | 12.936 | −50.870 | 1.00 | 38.81 |
| ATOM | 4899 | O | WAT | W | 246 | −23.302 | −2.082 | −27.191 | 1.00 | 32.98 |
| ATOM | 4900 | O | WAT | W | 247 | −13.035 | 8.248 | −46.620 | 1.00 | 51.73 |
| ATOM | 4901 | O | WAT | W | 248 | −11.869 | 31.852 | −50.157 | 1.00 | 56.13 |
| ATOM | 4902 | O | WAT | W | 249 | 0.898 | 13.920 | −6.521 | 1.00 | 27.38 |
| ATOM | 4903 | O | WAT | W | 250 | 20.427 | 30.852 | −45.446 | 1.00 | 35.54 |
| ATOM | 4904 | O | WAT | W | 251 | −1.397 | 12.400 | −44.617 | 1.00 | 39.33 |
| ATOM | 4905 | O | WAT | W | 252 | −27.354 | 24.696 | −3.162 | 1.00 | 35.38 |
| ATOM | 4906 | O | WAT | W | 253 | 17.587 | 20.557 | −31.069 | 1.00 | 41.51 |
| ATOM | 4907 | O | WAT | W | 254 | −7.936 | 35.055 | −7.354 | 1.00 | 39.02 |
| ATOM | 4908 | O | WAT | W | 255 | −22.469 | 7.215 | −2.044 | 1.00 | 38.25 |
| ATOM | 4909 | O | WAT | W | 256 | 2.038 | 15.474 | −52.963 | 1.00 | 50.04 |
| ATOM | 4910 | O | WAT | W | 257 | 10.889 | 10.184 | −21.700 | 1.00 | 44.84 |
| ATOM | 4911 | O | WAT | W | 258 | −11.714 | 10.583 | 4.136 | 1.00 | 42.70 |
| ATOM | 4912 | O | WAT | W | 259 | −14.719 | 6.574 | 2.959 | 1.00 | 43.18 |
| ATOM | 4913 | O | WAT | W | 260 | −16.694 | 25.390 | −37.688 | 1.00 | 36.77 |
| ATOM | 4914 | O | WAT | W | 261 | −9.212 | 13.388 | −48.363 | 1.00 | 38.05 |
| ATOM | 4915 | O | WAT | W | 264 | −0.611 | −1.965 | −3.253 | 1.00 | 37.95 |
| ATOM | 4916 | O | WAT | W | 265 | −16.380 | 30.998 | −14.262 | 1.00 | 32.44 |
| ATOM | 4917 | O | WAT | W | 266 | 9.420 | 16.012 | −61.368 | 1.00 | 35.22 |
| ATOM | 4918 | O | WAT | W | 267 | −4.976 | −15.180 | −21.223 | 1.00 | 45.50 |
| ATOM | 4919 | O | WAT | W | 268 | −16.631 | 33.287 | −14.201 | 1.00 | 34.50 |
| ATOM | 4920 | O | WAT | W | 269 | −16.883 | 34.052 | −32.249 | 1.00 | 36.88 |
| ATOM | 4921 | O | WAT | W | 270 | −8.293 | −16.006 | −14.535 | 1.00 | 34.80 |
| ATOM | 4922 | O | WAT | W | 273 | 0.240 | 4.589 | −13.868 | 1.00 | 32.34 |

TABLE 6-continued

| | | | | | | | | | |
|---|---|---|---|---|---|---|---|---|---|
| ATOM | 4923 | O | WAT | W | 275 | 3.657 | 14.447 | −55.516 | 1.00 | 43.54 |
| ATOM | 4924 | O | WAT | W | 276 | −17.602 | 20.784 | −51.471 | 1.00 | 38.88 |
| ATOM | 4925 | O | WAT | W | 277 | −10.479 | 31.683 | −30.513 | 1.00 | 40.35 |
| ATOM | 4926 | O | WAT | W | 278 | −10.974 | 4.308 | −5.745 | 1.00 | 40.30 |
| ATOM | 4927 | O | WAT | W | 280 | −4.336 | 36.908 | −17.666 | 1.00 | 34.01 |
| ATOM | 4928 | O | WAT | W | 281 | 6.720 | 33.970 | −53.572 | 1.00 | 38.81 |
| ATOM | 4929 | O | WAT | W | 282 | −30.457 | 23.527 | −0.621 | 1.00 | 34.61 |
| ATOM | 4930 | O | WAT | W | 283 | 16.969 | 17.394 | −30.816 | 1.00 | 55.74 |
| ATOM | 4931 | O | WAT | W | 284 | −24.391 | 5.834 | −24.909 | 1.00 | 37.92 |
| ATOM | 4932 | O | WAT | W | 285 | 4.567 | 9.814 | −4.438 | 1.00 | 44.83 |
| ATOM | 4933 | O | WAT | W | 286 | −24.370 | −7.328 | −27.875 | 1.00 | 56.18 |
| ATOM | 4934 | O | WAT | W | 287 | −21.605 | 11.887 | 9.715 | 1.00 | 43.15 |
| ATOM | 4935 | O | WAT | W | 288 | 8.603 | 0.412 | −37.887 | 1.00 | 40.47 |
| ATOM | 4936 | O | WAT | W | 290 | −20.056 | 21.495 | 6.073 | 1.00 | 41.68 |
| ATOM | 4937 | O | WAT | W | 291 | −3.221 | 28.158 | −33.448 | 1.00 | 44.24 |
| ATOM | 4938 | O | WAT | W | 292 | 9.171 | 9.103 | −38.735 | 1.00 | 34.30 |
| ATOM | 4939 | O | WAT | W | 293 | 2.894 | 22.763 | −25.829 | 1.00 | 38.57 |
| ATOM | 4940 | O | WAT | W | 294 | −29.901 | 19.604 | −14.929 | 1.00 | 37.66 |
| ATOM | 4941 | O | WAT | W | 296 | −4.579 | 30.229 | −29.110 | 1.00 | 40.57 |
| ATOM | 4942 | O | WAT | W | 297 | −23.821 | 11.441 | −33.187 | 1.00 | 42.81 |
| ATOM | 4943 | O | WAT | W | 298 | −26.753 | −3.087 | −31.243 | 1.00 | 39.08 |
| ATOM | 4944 | O | WAT | W | 300 | −10.820 | 35.024 | −53.050 | 1.00 | 55.39 |
| ATOM | 4945 | O | WAT | W | 302 | −1.992 | 7.169 | −31.692 | 1.00 | 39.12 |
| ATOM | 4946 | O | WAT | W | 303 | −15.282 | −19.000 | −23.770 | 1.00 | 34.62 |
| ATOM | 4947 | O | WAT | W | 304 | 12.106 | 10.568 | −25.112 | 1.00 | 39.04 |
| ATOM | 4948 | O | WAT | W | 305 | 2.585 | 2.766 | 1.880 | 1.00 | 53.88 |
| ATOM | 4949 | O | WAT | W | 306 | 3.680 | 21.122 | −19.818 | 1.00 | 46.35 |
| ATOM | 4950 | O | WAT | W | 307 | 22.759 | 24.721 | −48.099 | 1.00 | 40.35 |
| ATOM | 4951 | O | WAT | W | 309 | −17.062 | −6.726 | −19.202 | 1.00 | 41.54 |
| ATOM | 4952 | O | WAT | W | 311 | 12.594 | 1.109 | −31.461 | 1.00 | 47.85 |
| ATOM | 4953 | O | WAT | W | 312 | 23.347 | 25.060 | −50.638 | 1.00 | 49.64 |
| ATOM | 4954 | O | WAT | W | 314 | −18.291 | 4.422 | −19.151 | 1.00 | 39.17 |
| ATOM | 4955 | O | WAT | W | 315 | −11.815 | −7.807 | −8.676 | 1.00 | 37.74 |
| ATOM | 4956 | O | WAT | W | 316 | −25.147 | 1.885 | −4.649 | 1.00 | 44.72 |
| ATOM | 4957 | O | WAT | W | 317 | −36.473 | 13.592 | 5.315 | 1.00 | 44.38 |
| ATOM | 4958 | O | WAT | W | 318 | −17.587 | 20.023 | −46.231 | 1.00 | 48.30 |
| ATOM | 4959 | O | WAT | W | 319 | −16.081 | 29.024 | −54.668 | 1.00 | 39.40 |
| ATOM | 4960 | O | WAT | W | 320 | −14.210 | 32.143 | −5.494 | 1.00 | 42.73 |
| ATOM | 4961 | O | WAT | W | 321 | −15.274 | 28.830 | −38.916 | 1.00 | 46.47 |
| ATOM | 4962 | O | WAT | W | 322 | −32.792 | 22.221 | −3.433 | 1.00 | 41.52 |
| ATOM | 4963 | O | WAT | W | 323 | −32.475 | 16.905 | −12.401 | 1.00 | 46.29 |
| ATOM | 4964 | O | WAT | W | 325 | 15.341 | 22.212 | −60.490 | 1.00 | 34.67 |
| ATOM | 4965 | O | WAT | W | 326 | −12.668 | 8.518 | −41.723 | 1.00 | 36.26 |
| ATOM | 4966 | O | WAT | W | 327 | 4.709 | 20.490 | −10.568 | 1.00 | 38.04 |
| ATOM | 4967 | O | WAT | W | 328 | 13.937 | 10.625 | −29.312 | 1.00 | 38.32 |
| ATOM | 4968 | O | WAT | W | 329 | −21.964 | 9.615 | −24.896 | 1.00 | 40.43 |
| ATOM | 4969 | O | WAT | W | 330 | 19.325 | 25.925 | −40.199 | 1.00 | 51.36 |
| ATOM | 4970 | O | WAT | W | 331 | −19.010 | 8.073 | −45.255 | 1.00 | 46.06 |
| ATOM | 4971 | O | WAT | W | 332 | −25.024 | −2.892 | −29.306 | 1.00 | 41.74 |
| ATOM | 4972 | O | WAT | W | 333 | −16.593 | −7.067 | −23.297 | 1.00 | 38.54 |
| ATOM | 4973 | O | WAT | W | 334 | −17.517 | 24.078 | 2.157 | 1.00 | 45.82 |
| ATOM | 4974 | O | WAT | W | 335 | −19.123 | 31.941 | 0.010 | 1.00 | 38.91 |
| ATOM | 4975 | O | WAT | W | 337 | 10.677 | 21.901 | −62.740 | 1.00 | 44.31 |
| ATOM | 4976 | O | WAT | W | 338 | 4.510 | 15.230 | −51.810 | 1.00 | 42.12 |
| ATOM | 4977 | O | WAT | W | 339 | 13.979 | 14.161 | −43.380 | 1.00 | 46.42 |
| ATOM | 4978 | O | WAT | W | 341 | 5.979 | −11.625 | −28.739 | 1.00 | 43.09 |
| ATOM | 4979 | O | WAT | W | 342 | −19.453 | 13.347 | 10.394 | 1.00 | 42.44 |
| ATOM | 4980 | O | WAT | W | 343 | 7.085 | 23.050 | −30.796 | 1.00 | 34.94 |
| ATOM | 4981 | O | WAT | W | 345 | 6.471 | 24.087 | −63.943 | 1.00 | 45.16 |
| ATOM | 4982 | O | WAT | W | 347 | 3.734 | 22.842 | −12.031 | 1.00 | 43.85 |
| ATOM | 4983 | O | WAT | W | 348 | −17.739 | 7.564 | 5.723 | 1.00 | 43.77 |
| ATOM | 4984 | O | WAT | W | 351 | −22.014 | 31.372 | −24.708 | 1.00 | 42.69 |
| ATOM | 4985 | O | WAT | W | 352 | 25.016 | 25.103 | −46.967 | 1.00 | 40.51 |
| ATOM | 4986 | O | WAT | W | 353 | 7.969 | 32.464 | −67.637 | 1.00 | 57.78 |
| ATOM | 4987 | O | WAT | W | 354 | −27.444 | 5.101 | 5.861 | 1.00 | 48.31 |
| ATOM | 4988 | O | WAT | W | 356 | 8.012 | 11.087 | −40.867 | 1.00 | 47.51 |
| ATOM | 4989 | O | WAT | W | 357 | 4.974 | 29.116 | −17.433 | 1.00 | 43.72 |
| ATOM | 4990 | O | WAT | W | 358 | −0.457 | 9.488 | −45.288 | 1.00 | 45.63 |
| ATOM | 4991 | O | WAT | W | 360 | −3.090 | 36.536 | −12.138 | 1.00 | 46.29 |
| ATOM | 4992 | O | WAT | W | 361 | 20.072 | 19.772 | −36.896 | 1.00 | 38.73 |
| ATOM | 4993 | O | WAT | W | 363 | −26.217 | 15.345 | −28.735 | 1.00 | 49.07 |
| ATOM | 4994 | O | WAT | W | 365 | −25.308 | 0.100 | −48.602 | 1.00 | 60.01 |
| ATOM | 4995 | O | WAT | W | 367 | 19.369 | 29.586 | −58.438 | 1.00 | 48.19 |
| ATOM | 4996 | O | WAT | W | 369 | 12.808 | 11.144 | −54.427 | 1.00 | 48.48 |
| ATOM | 4997 | O | WAT | W | 370 | 9.410 | 2.674 | −16.115 | 1.00 | 44.59 |
| ATOM | 4998 | O | WAT | W | 372 | −10.249 | 38.564 | −13.215 | 1.00 | 48.60 |
| ATOM | 4999 | O | WAT | W | 373 | −24.151 | 16.211 | 10.617 | 1.00 | 42.16 |
| ATOM | 5000 | O | WAT | W | 375 | −6.459 | 31.697 | −48.106 | 1.00 | 46.03 |
| ATOM | 5001 | O | WAT | W | 376 | −11.605 | 27.116 | −1.562 | 1.00 | 44.58 |
| ATOM | 5002 | O | WAT | W | 377 | −4.703 | 24.150 | −62.673 | 1.00 | 48.70 |

TABLE 6-continued

| ATOM | 5003 | O | WAT | W | 379 | 6.889 | 0.036 | −7.530 | 1.00 | 45.35 |
|---|---|---|---|---|---|---|---|---|---|---|
| ATOM | 5004 | O | WAT | W | 381 | −13.601 | 32.742 | −32.002 | 1.00 | 51.37 |
| ATOM | 5005 | O | WAT | W | 383 | −28.077 | 5.243 | −4.688 | 1.00 | 37.46 |

What is claimed is:

1. An isolated glucoamylase variant comprising one or more amino acid substitutions at a position corresponding to residue position: 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 239, 240, 241, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, 418, 430, 431, 433, 436, 442, 443, 444, 448 and 451 of SEQ ID NO: 2 or SEQ ID NO: 3 or an equivalent position in a parent glucoamylase; wherein the equivalent position in a parent glucoamylase is determined by sequence identity and said parent glucoamylase has at least 80% amino acid sequence identity with the sequence of SEQ ID NO: 2, and wherein said parent glucoamylase comprises the sequence of SEQ ID NOs: 1, 4, 5, 6, 7, 8, or 9.

2. The glucoamylase variant of claim 1, wherein said parent glucoamylase has at least 90% sequence identity with the sequence of SEQ ID NO:2.

3. The glucoamylase variant of claim 1, wherein the one or more amino acid substitutions corresponds to a position chosen from positions 10, 14, 15, 23, 42, 45, 46, 59, 60, 61, 67, 68, 72, 73, 97, 98, 99, 102, 108, 110, 113, 114, 122, 124, 125, 133, 140, 144, 145, 147, 152, 153, 164, 175, 182, 204, 205, 214, 216, 219, 228, 229, 230, 231, 239, 240, 241, 244, 263, 264, 265, 268, 269, 276, 284, 291, 300, 301, 303, 310, 311, 313, 316, 338, 342, 344, 346, 349, 359, 361, 364, 379, 382, 390, 391, 393, 394, 408, 410, 415, 417, 418, 430, 431, 433, 436, 442, 443, 444, 448 and 451 of SEQ ID NO: 2.

4. The glucoamylase variant of claim 1, wherein the variant comprises a substitution in a position chosen from: T10D/F/G/K/L/M/P/R/S; L14E/H; N15D/N; P23A/G; F59A/G; K60F/H; N61D/I/L/Q/V/W; R65A/C/G/I/K/M/S/V/Y; T67C/I/K/M/T; E68I/M/W; A72E/G/L/M/Q/R/W/Y; G73C/L/W; S97F/M/N/P/R/S/V/W/Y; L98H/M; A99C/L/M/N/P; S102A/C/I/L/M/N/RN/W/Y; E110Q/S/W; L113E/N; K114C/D/E/L/M/Q/S/T/V; I133K/R/S/T; K140A/E/F/H/K/L/M/N/Q/R/S/V/W/Y; N144C/D/E/I/K; N145A/C/E/I/K/L/M/Q/R/V/W/Y; Y147A/M/R; S152H/M; N153C/D/K/L/W/Y; N164A/G; N182C/E/K/P/R; A204C/D/G/I/M/Q/T; T205A/D/H/1/K/M/N/P/Q/S/V/W/Y; S214P/T; V216C/G/H/K/N/Y; Q219D/G/H/N/P/S; W228A/F/G/H/I/L/M/Q/S/T/V/Y; V229E/I/M/N/Q; S230C/D/E/F/G/H/I/K/L/N/P/Q/R/T/V/Y; S231C/D/F/L/M/N/Q/R/S/V/Y; I239M/Q/S/V/W/Y; T241C/E/H/L/M/P/S/T/V; N263H/K/P; L264A/C/E/F/L/S; G265E/G/H/I/K/R/T; A268C/D/E/F/G/I/K/L/P/R/T/W; G269E; D276S; V284R/TN/Y/A/E/F/H/K/N/P/W; P300K/R; A301E/K/L/P/S/W; A303C/D/F/H/I/K/L/N/R/T/V/W/Y; A311N/P/Q/S/Y; V338P/Q/S/Y; T342N/V; S344A/T; T346G/H/M/N/P/Q/Y; A349L/I/K/M/N/Q/R/W; G361H/L/R; A364M/W; N379A/C/D/G/I/M/P/S; S382A/N/P/V/W; S390A/Y; E391A/E/I/K/L/M/Q/R/V/W/Y; A393E/G/H/I/K/L/M/N/Q/R/S/T/V/W/Y; K394A/H/K/L/M/Q/R/S/T/V/W; S410E/H/N; L417A/D/E/F/G/I/K/Q/R/S/TN/W/Y; H418E/M; T430A/E/F/G/H/I/K/M/N/Q/RN; A431C/E/H/I/L/M/Q/R/S/W/Y; R433A/C/E/F/G/K/L/M/N/S/V/W/Y; I436E/F/G/H/K/P/R/S/T/V/Y; S444M/N/P/Q/R/T/V/W; T448F/G/I/P/Q/T/V; and S451E/H/K/L/Q/T of SEQ ID NO: 2 or SEQ ID NO:3 or an equivalent position in a parent glucoamylase.

5. The glucoamylase variant of claim 1, wherein the variant has increased specific activity compared to the glucoamylase comprising the sequence of SEQ ID NO: 2, SEQ ID NO: 3 or a parent glucoamylase having at least 80% sequence identity to SEQ ID NO: 2.

6. The glucoamylase variant of claim 5, wherein the variant has increased specific activity compared to the glucoamylase comprising SEQ ID NO: 2.

7. The glucoamylase variant of claim 1, wherein the one or more amino acid substitutions corresponds to a position chosen from positions 10, 14, 15, 23, 59, 60, 61, 65, 67, 68, 72, 73, 97, 98, 99, 102, 110, 113, 133, 140, 144, 145, 147, 152, 153, 164, 182, 204, 205, 214, 216, 219, 228, 229, 230, 231, 239, 241, 263, 264, 265, 268, 269, 276, 284, 291, 300, 301, 303, 311, 338, 342, 344, 346, 349, 359, 361, 364, 379, 382, 390, 391, 393, 394, 410, 417, 418, 430, 431, 433, 442, 444, 448, and 451 of SEQ ID NO: 2 or 3.

8. The glucoamylase variant of claim 7, wherein the one or more amino acid substitutions correspond to a position chosen from position 61, 67, 72, 97, 102, 133, 205, 219, 228, 230, 231, 239, 263, 268, 291, 342, 394, 430, 431 and 451.

9. The glucoamylase variant of claim 8, wherein the one or more amino acid substitutions correspond to at least one of the following: T67M, A72Y, S97N, S102M, I133T, T205Q, Q219S, W228M, S230F, S230G, S230N, S230R, S231L, I239V, I239Y, N263P, A268C, A268G, A268K, S291A, T342V, K394S, T430K, A431Q, S451K.

10. The glucoamylase variant of claim 1, wherein the variant has increased thermo stability compared to the glucoamylase comprising the sequence of SEQ ID NO: 2, SEQ ID NO: 3 or a parent glucoamylase having at least 80% sequence identity to SEQ ID NO: 2.

11. The glucoamylase variant of claim 10, wherein the variant has increased thermo stability compared to the glucoamylase comprising the sequence of SEQ ID NO: 2 or SEQ ID NO: 3.

12. The glucoamylase variant of claim 10, wherein the one or more amino acid substitutions corresponds to a position chosen from positions 10, 15, 23, 42, 59, 60, 61, 68, 72, 73, 97, 98, 99, 102, 114, 133, 140, 144, 147, 152, 153, 164, 182, 204, 205, 214, 216, 228, 229, 230, 231, 241, 263, 264, 265, 268, 269, 276, 284, 291, 300, 301, 303, 311, 338, 342, 344, 346, 349, 359, 361, 364, 379, 382, 390, 391, 393, 394, 410, 417, 430, 431, 433, 436, 442, 443, 444, 448, and 451 of SEQ ID NO: 2 or SEQ ID NO: 3.

13. The glucoamylase variant of claim 12, wherein the one or more amino acid substitutions correspond to a position chosen from positions 10, 42, 68, 73, 97, 114, 153, 229, 231, 264, 291, 301, 344, 361, 364, 417, and 433 of SEQ ID NO: 2 or SEQ ID NO: 3.

14. The glucoamylase variant of claim 13, wherein the one or more amino acid substitutions correspond to a position chosen from positions 68, 73, 114, 153, 344, 361, 364 and 433.

15. The glucoamylase variant of claim 13, wherein the one or more amino acid substitutions correspond to at least one of the following: T10S, T42V, E68C, E68M, G73F, G73W, K114M, K114T, N153A, N153S, N153V, W228V, G361D, G361E, G361P, G361Y, A364D, A364E, A364F, A364G, A364K, A365L, A365R, R433C, R433G, R433L, R433N, R433S, R433V, and I436H.

16. The glucoamylase variant of claim 1, wherein said variant has increased specific activity and increased thermo stability compared to the glucoamylase comprising SEQ ID NO: 2, SEQ ID NO: 3 or a parent glucoamylase having at least 80% sequence identity to the sequence of SEQ ID NO: 2.

17. The glucoamylase variant of claim 16, wherein the one or more amino acid substitutions correspond to a position chosen from position 10, 15, 59, 61, 68, 72, 73, 97, 99, 102, 133, 140, 153, 182, 204, 205, 214, 228, 229, 230, 231, 241, 264, 265, 268, 275, 284, 291, 300, 301, 303, 311, 338, 344, 346, 359, 361, 364, 370, 382, 391, 393, 394, 410, 417, 430, 431, 433, 444, 448, and 451 of SEQ ID NO: 2 or SEQ ID NO: 3.

18. The glucoamylase variant of claim 17, wherein the one or more amino acid substitutions correspond to a position chosen from position 228, 230, 231, 268, 291, 417, 433, and 451 of SEQ ID NO: 2 or SEQ ID NO:3.

19. The glucoamylase variant of claim 18, wherein the one or more amino acid substitutions correspond to at least one of the following: W228A, W228F, W228H, W228M, S230F, S230G, S230R, S231L, A268C, A268G, S291A, L417R, R433Y, and S451K of SEQ ID NO: 2 or SEQ ID NO:3.

20. A polynucleotide encoding the variant of claim 1.

21. A host cell comprising a polynucleotide of claim 20.

22. An enzyme composition comprising the glucoamylase variant of claim 1.

23. The enzyme composition of claim 22 further comprising an alpha amylase.

24. The enzyme composition of claim 22, wherein said composition is used in a starch conversion process.

25. The enzyme composition of claim 22, wherein said composition is used in an animal feed formulation.

26. The enzyme composition of claim 22, wherein said composition is used in an alcohol fermentation process.

27. A method of producing a variant glucoamylase in a host cell comprising transforming a host cell with a DNA construct comprising a polynucleotide of claim 20; culturing the host cell under conditions suitable for the expression and production of said glucoamylase variant and producing said variant.

28. The method according to claim 27 further comprising recovering the glucoamylase variant from said culture.

* * * * *